(12) United States Patent
Kato et al.

(10) Patent No.: US 8,318,323 B2
(45) Date of Patent: Nov. 27, 2012

(54) POLYCYCLIC COMPOUNDS AND ORGANIC ELECTROLUMINESCENCE DEVICE EMPLOYING THE SAME

(75) Inventors: Tomoki Kato, Sodegaura (JP); Masaki Numata, Sodegaura (JP); Kazuki Nishimura, Sodegaura (JP); Toshihiro Iwakuma, Sodegaura (JP); Chishio Hosokawa, Sodegaura (JP); Kei Yoshida, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 320 days.

(21) Appl. No.: 12/552,421

(22) Filed: Sep. 2, 2009

(65) Prior Publication Data

US 2010/0012931 A1   Jan. 21, 2010

Related U.S. Application Data

(63) Continuation of application No. 12/414,050, filed on Mar. 30, 2009, now abandoned.

(30) Foreign Application Priority Data

Jun. 5, 2008   (JP) ................. 2008-148532
Jun. 5, 2008   (JP) ................. 2008-148533
Jun. 5, 2008   (JP) ................. 2008-148534

(51) Int. Cl.
  *H01L 51/54*   (2006.01)
  *C09K 11/06*   (2006.01)
(52) U.S. Cl. ........ 428/690; 428/917; 548/418; 548/440; 549/43; 549/456; 313/504; 313/506; 252/301.16; 257/40; 257/103; 257/E51.047; 257/E51.051
(58) Field of Classification Search .................. None
  See application file for complete search history.

(56) References Cited

U.S. PATENT DOCUMENTS

| 5,942,340 | A | 8/1999 | Hu et al. | |
| 2006/0125009 | A1 | 6/2006 | Wu et al. | |
| 2007/0224446 | A1* | 9/2007 | Nakano et al. | 428/690 |
| 2008/0091025 | A1 | 4/2008 | Morishita et al. | |
| 2008/0145708 | A1 | 6/2008 | Heil et al. | |
| 2008/0220285 | A1 | 9/2008 | Vestweber et al. | |
| 2009/0302742 | A1* | 12/2009 | Komori et al. | 313/504 |
| 2009/0302743 | A1* | 12/2009 | Kato et al. | 313/504 |

FOREIGN PATENT DOCUMENTS

| EP | 1 962 354 A1 | 8/2008 |
| JP | 11-176578 | 7/1999 |
| JP | 2008-69120 | 3/2008 |
| WO | WO 2006/108497 A1 | 10/2006 |
| WO | WO 2006/122630 A1 | 11/2006 |
| WO | WO 2007/063754 A1 * | 6/2007 |
| WO | WO 2007/069569 A1 | 6/2007 |

* cited by examiner

*Primary Examiner* — Jennifer Chriss
*Assistant Examiner* — Michael H Wilson
(74) *Attorney, Agent, or Firm* — Oblon, Spivak, McClelland, Maier & Neustadt, L.L.P.

(57) ABSTRACT

Provided are a polycyclic compound of a compound having such a structure that two benzene rings bond to a central benzene ring each other to form a fused ring and another fused ring bonds to a terminal thereof, and an organic electroluminescence device including one or more organic thin film layers containing a light emitting layer between a cathode and an anode, in which at least one of the organic thin film layers includes the polycyclic compound of the present invention. The organic electroluminescence device has high luminous efficiency, no defect in pixels, and long lifetime. In addition, provided is a polycyclic compound realizing the organic electroluminescence device.

24 Claims, No Drawings

POLYCYCLIC COMPOUNDS AND ORGANIC ELECTROLUMINESCENCE DEVICE EMPLOYING THE SAME

This is a continuation application of U.S. application Ser. No. 12/414,050, filed Mar. 30, 2009.

TECHNICAL FIELD

The present invention relates to a polycyclic compound and an organic electroluminescence device using the polycyclic compound, in particular, an organic electroluminescence device, which shows high luminous efficiency and has a long lifetime, and a polycyclic compound for realizing the device.

BACKGROUND ART

An organic electroluminescence device (hereinafter, "electroluminescence" may be abbreviated as "EL") is a spontaneous light emitting device which utilizes the principle that a fluorescent substance emits light by energy of recombination of holes injected from an anode and electrons injected from a cathode when an electric field is applied. Since a laminate type organic EL device driven under a low electric voltage was reported, many studies have been conducted on organic EL devices using organic materials as the constituent materials. The devices of the laminate type use tris(8-quinolinolato) aluminum for a light emitting layer and a triphenyl-diamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato) aluminum complexes, light emitting materials such as coumarin derivatives, tetraphenylbutadiene derivatives, distyrylarylene derivatives, and oxadiazole derivatives are known. It is reported that light in the visible region ranging from blue light to red light can be obtained by using these light emitting materials, and realization of a device exhibiting color images is expected.

In addition, it has been recently proposed that a phosphorescent material as well as a fluorescent material be utilized in the light emitting layer of an organic EL device. High luminous efficiency is achieved by utilizing the singlet and triplet states of an excited state of an organic phosphorescent material in the light emitting layer of an organic EL device. Upon recombination of an electron and a hole in an organic EL device, singlet excitons and triplet excitons may be produced at a ratio of 1:3 owing to a difference in spin multiplicity between the singlet and triplet excitons, so the use of a phosphorescent material may achieve luminous efficiency three to four times as high as that of a device using fluorescence alone.

Patent Documents 1 to 4 are exemplary inventions each describing such materials for an organic EL device.

Patent Document 1 describes a compound using, as a mother skeleton, a structure obtained by crosslinking a ter-phenylene skeleton with, for example, a carbon atom, nitrogen atom, or oxygen atom. The document, which mainly discloses data indicative of the potential of the compound to serve as a hole transporting material, describes that the compound is used as a host material for a phosphorescent material in a light emitting layer. However, the description is limited to a red phosphorescent device, and the luminous efficiency of the device is not high enough for practical use.

Patent Document 2 describes an indolocarbazole compound having a substituent on a nitrogen atom or on an aromatic ring. The document recommends that the compound be used as a hole transporting material, and describes that a thermally and morphologically stable, thin hole transporting layer can be prepared from the compound. However, the document does not describe data indicative of the usefulness of the compound as a host material or electron transporting material to be used together with a phosphorescent material.

Patent Document 3 describes indolocarbazole compounds each having a substituent on a nitrogen atom or on an aromatic ring. The document discloses data on a green light emitting device using any one of those compounds as a host material for a phosphorescent material in its light emitting layer. However, a high voltage must be applied to the device to drive the device, and the device shows low luminous efficiency, so the device cannot be sufficiently put into practical use.

Patent Document 4 describes indolocarbazole compounds each having a substituent. The document describes that each of the compounds functions as a host material for a phosphorescent material in a light emitting layer. However, each of those compounds is characterized in that the compound has a dimer or trimer structure through a linking group, and each of the compounds tends to have a large molecular weight. The document discloses data on a green phosphorescent device using any one of those compounds, but all the compounds used each have a large molecular weight of 800 or more. The efficiency with which a material having a large molecular weight is deposited in a vacuum is poor, and the material may decompose owing to heating for a long time period, so the material may be insufficient in terms of practical use.

Patent Document 1: WO 2006/122630
Patent Document 2: EP 0908787
Patent Document 3: WO 2007/063796
Patent Document 4: WO 2007/063754
Non-patent Document 1: Applied Physics letters Vol. 74 No. 3, pp 442-444
Non-patent Document 2: Applied Physics letters Vol. 75 No. 1, pp 4-6

DISCLOSURE OF THE INVENTION

Problems to be Solved by the Invention

The present invention has been made with a view to solving the above problems, and an object of the present invention is to provide an organic EL device which shows high luminous efficiency and has a long lifetime, and a polycyclic compound for realizing the device.

Means for Solving the Problems

The inventors of the present invention have extensively studied in order to achieve the above object. As a result, the inventors found that the above object could be achieved by using, as a material for an organic EL device, a polycyclic compound represented by the following formula (1) or (2) and having such a structure that two benzene rings bonds to the ortho, meta, or para position of the central benzene ring to form a fused ring, and another fused ring represented by the following general formula (4) bonds to the terminal thereof, thereby completing the present invention.

That is, the present invention provides a polycyclic compound represented by the following formulae (1) or (2):

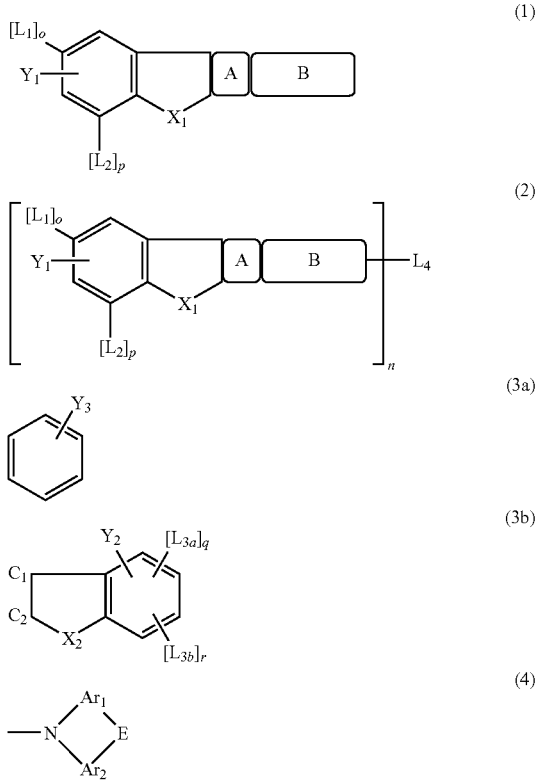

[In the general formulae (1) and (2), a ring A represents a benzene ring represented by the above formula (3a) which is fused to two adjacent rings at arbitrary positions and a structure B represents a structure represented by the above formula (3b) which is fused to the ring A to share a ring-forming carbons $C_1$ and $C_2$.

In the general formulae (1) and (2), $X_1$ and $X_2$ each independently represent oxygen (O), sulfur (S), N—$R_1$, or $CR_2R_3$, and $R_1$, $R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_1$ and $X_2$ represent N—$R_1$, at least one $R_1$ represents a substituted or unsubstituted monovalent fused aromatic heterocyclic group having 8 to 24 atoms forming the aromatic ring.

In the general formulae (1) and (2), o, p, q, and r each independently represent 0 or 1, provided that o+p is 1 or more.

In the general formula (2), n represents 2, 3, or 4.

In the general formulae (1) and (2), $L_1$, $L_2$, $L_{3a}$, and $L_{3b}$ each independently represent a structure represented by the general formula (4), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring, E represents a single bond, oxygen (O), sulfur (S), N—$R_4$, or $CR_5R_6$, and $R_4$, $R_5$, and $R_6$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring.

In the general formula (2), when n represents 2, $L_4$ represents a single bond, oxygen (O), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, when n represents 3, $L_4$ represents N, a substituted or unsubstituted alkanetriyl group having 1 to 20 carbon atoms, a substituted or unsubstituted cycloalkanetriyl group having 3 to 20 carbon atoms forming the ring, a substituted or unsubstituted trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group having 3 to 24 atoms forming the aromatic ring, and when n represents 4, $L_4$ represents a substituted or unsubstituted alkane tetrayl group having 1 to 20 carbon atoms, a substituted or unsubstituted cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formula (1) or (2), $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, or a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring which is bonded with a carbon atom, the number of $Y_1$'s is 0, 1, 2, or 3, the number of $Y_2$'s is 0, 1, 2, 3, or 4, and the number of $Y_3$'s is 0, 1, or 2;

provided that: there is no case where the general formula (1) has a structure represented by the following general formula (5):

[Chem 2]

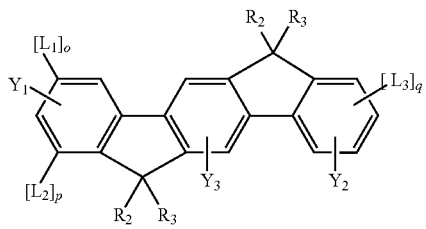

(5)

where $R_2, R_3, L_1, L_2, L_3, Y_1, Y_2, Y_3$, o, p, and q each have the same meanings as $R_2, R_3, L_1, L_2, L_{3a}, Y_1, Y_2, Y_3$, o, p, and q in the formula (1); and there is no case where the general formula (2) has a structure represented by the following general formula (6):

[Chem 3]

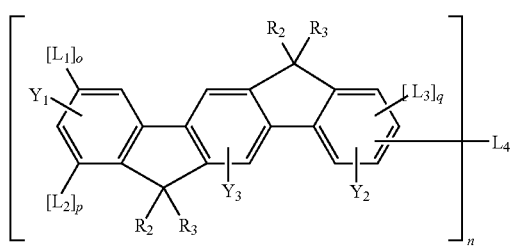

(6)

where $R_2, R_3, L_1, L_2, L_3, L_4, Y_1, Y_2, Y_3$, o, p, q, and n each have the same meanings as $R_2, R_3, L_1, L_2, L_{3a}, L_4, Y_1, Y_2, Y_3$, a, p, q, and n in the formula (2).]

In addition, the present invention provides an organic EL device having one or more organic thin film layers including a light emitting layer between a cathode and an anode in which at least one layer of the organic thin film layers contains the polycyclic compound.

Further, the polycyclic compound can be used also as an organic solar cell, organic semiconductor laser, a sensor using organic matter, or a material for an organic electron device used in an organic TFT.

Effects of the Invention

According to the present invention, there can be provided an organic EL device which shows high luminous efficiency and has a long lifetime, and a polycyclic compound for realizing the device.

BEST MODE FOR CARRYING OUT THE INVENTION

The polycyclic compound of the present invention is represented by the following formula (1) or (2):

[Chem 4]

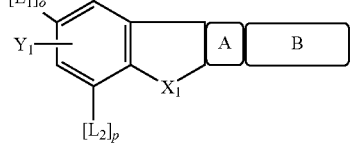

(1)

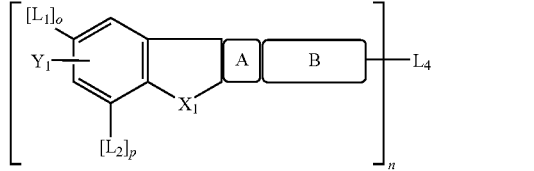

(2)

(3a)

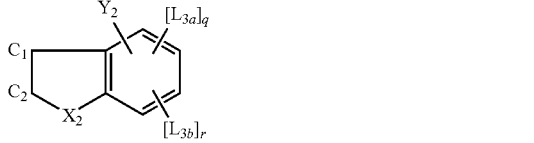

(3b)

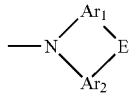

(4)

[In the general formulae (1) and (2), a ring A represents a benzene ring represented by the above formula (3a) which is fused to two adjacent rings at arbitrary positions and a structure B represents a structure represented by the above formula (3b) which is fused to the ring A to share a ring-forming carbons $C_1$ and $C_2$.

In the general formulae (1) and (2), $X_1$ and $X_2$ each independently represent oxygen (O), sulfur (S), N—$R_1$, or $CR_2R_3$, and $R_1, R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_1$ and $X_2$ represent N—$R_1$, at least one $R_1$ represents a substituted or unsubstituted monovalent fused aromatic heterocyclic group having 8 to 24 atoms forming the aromatic ring.

In the general formulae (1) and (2), o, p, q, and r each independently represent 0 or 1, provided that o+p is 1 or more. In addition, the case where q+r is 1 or less is preferred from the viewpoint of practical use, because the molecular weight of the polycyclic compound becomes small, the efficiency of the vacuum vapor deposition is improved, and decomposition due to long-time heating is suppressed.

In the general formula (2), n represents 2, 3, or 4.

In the general formulae (1) and (2), $L_1, L_2, L_{3a}$, and $L_{3b}$ each independently represent a structure represented by the general formula (4), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring, E represents a single bond, oxygen (O), sulfur (S), N—$R_4$, or $CR_5R_6$, and $R_4$, $R_5$, and $R_6$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring.

In the general formula (2), when n represents 2, $L_4$ represents a single bond, oxygen (O), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, further, when n represents 3, $L_4$ represents N, a substituted or unsubstituted alkanetriyl group having 1 to 20 carbon atoms, a substituted or unsubstituted cycloalkanetriyl group having 3 to 20 carbon atoms forming the ring, a substituted or unsubstituted trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group having 3 to 24 atoms forming the aromatic ring, and when n represents 4, $L_4$ represents a substituted or unsubstituted alkane tetrayl group having 1 to 20 carbon atoms, a substituted or unsubstituted cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formula (1) or (2), $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, or a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, which is bonded with a carbon atom, the number of $Y_1$'s is 0, 1, 2, or 3, the number of $Y_2$'s is 0, 1, 2, 3, or 4, and the number of $Y_3$'s is 0, 1, or 2;

provided that: there is no case where the general formula (1) has a structure represented by the following general formula (5):

[Chem 5]

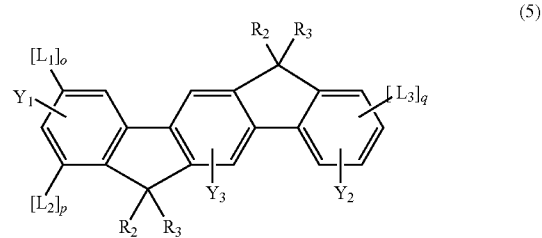

(5)

where $R_2$, $R_3$, $L_1$, $L_2$, $L_3$, $Y_1$, $Y_2$, $Y_3$, o, p, and q each have the same meanings as $R_2$, $R_3$, $L_1$, $L_2$, $L_{3a}$, $Y_1$, $Y_2$, $Y_3$, o, p, and q in the formula (1); and there is no case where the general formula (2) has a structure represented by the following general formula (6):

[Chem 6]

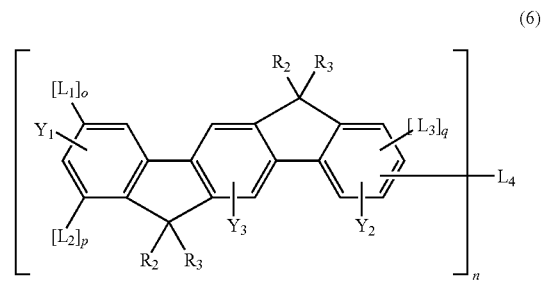

(6)

where $R_2$, $R_3$, $L_1$ $L_2$, $L_3$, $L_4$, $Y_1$, $Y_2$, $Y_3$, o, p, q, and n each have the same meanings as $R_2$, $R_3$, $L_1$ $L_2$, $L_{3a}$, $L_4$, $Y_1$, $Y_2$, $Y_3$, o, p, q, and n in the formula (2).]

The polycyclic compound of the present invention represented by the general formula (1) or (2) has as a substituent a fused ring such as carbazole so that the polycyclic compound can increase Tg and improve thin film stability in the case of being formed into a device compared to the case of a compound having a substituent formed of a single ring. In addition, because the binding positions of the fused rings such as carbazole represented by $L_1$ and $L_2$ are the meta position, expansion of the conjugate system can be prevented and the triplet energy gap can be enlarged. On the contrary, when the binding positions of the fused rings such as carbazole are the para position, the conjugate system is expanded and the triplet energy gap may be reduced.

The case where the polycyclic compound of the present invention has the structure B represented by the following general formula (3c) or the general formulae (7-1) to (18-1) below is preferred, because the triplet energy gap can be enlarged as described above so that the binding positions of the fused rings such as carbazole represented by $L_3$, $L_{3a}$, and $L_{3b}$ are the meta position.

[Chem 7]

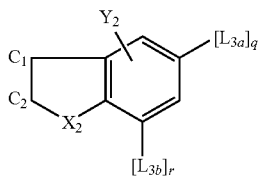

(3c)

The polycyclic compound of the present invention is preferably represented by any one of the following general formulae (7) to (18):

[Chem 8]

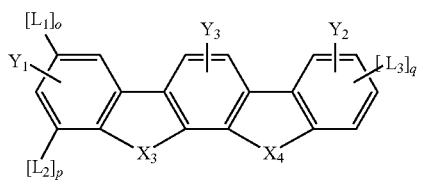

(7)

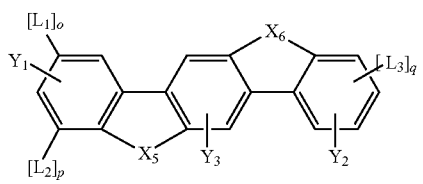

(8)

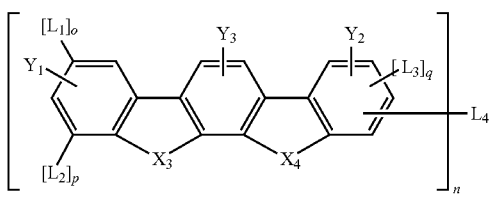

(9)

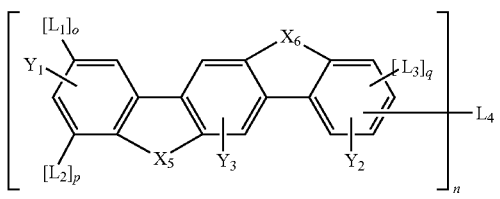

(10)

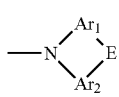

(4)

[In the general formulae (7) to (10), $X_3$, $X_4$, $X_5$, and $X_6$ each independently represent oxygen (O), sulfur (S), N—$R_1$, or $CR_2R_3$, and $R_1$, $R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_3$ and $X_4$ or both $X_5$ and $X_6$ represent N—$R_1$, at least one $R_1$ represents a substituted or unsubstituted monovalent fused aromatic heterocyclic group having 8 to 24 atoms forming the aromatic ring.

In the general formulae (7) to (10), o, p, and q each independently represent 0 or 1, provided that o+p is 1 or more.

In the general formulae (9) and (10), n represents 2, 3, or 4.

In the general formulae (7) to (10), $L_1$, $L_2$, and $L_3$ each independently represent a structure represented by the general formula (4), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring, E represents a single bond, oxygen (O), sulfur (S), N—$R_4$, or $CR_5R_6$, $R_4$, $R_5$, and $R_6$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring.

In the general formulae (9) and (10), when n represents 2, $L_4$ represents a single bond, oxygen (C), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, when n represents 3, $L_4$ represents N, a substituted or unsubstituted alkanetriyl group having 1 to 20 carbon atoms, a substituted or unsubstituted cycloalkanetriyl group having 3 to 20 carbon atoms forming the ring, a substituted or unsubstituted trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group having 3 to 24 atoms forming the aromatic ring, and when n represents 4, $L_4$ represents a substituted or unsubstituted alkane tetrayl group having 1 to 20 carbon atoms, a substituted or unsubstituted cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formulae (7) to (10), $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having a 1 to 20 carbon atoms, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, which is bonded with a carbon atom, the number of $Y_1$'s is 0, 1, 2, or 3, the number of $Y_2$'s is 0, 1, 2, 3, or 4, and the number of $Y_3$'s is 0, 1, or 2.]

As the polycyclic compounds represented by the above general formulae (7) to (10), the compound represented by any one of the following formulae (7-1), (7-2), (8-1), (8-2), (9-1), (9-2), (10-1), and (10-2) is preferred.

[Chem 9]

(7-1)
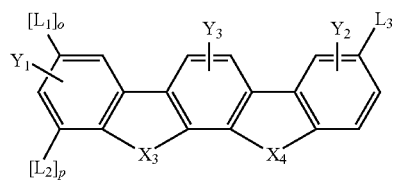

(7-2)
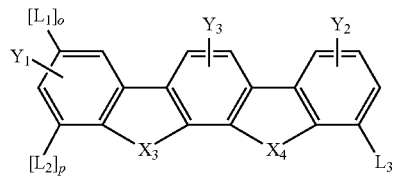

(8-1)
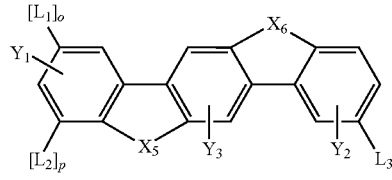

(8-2)
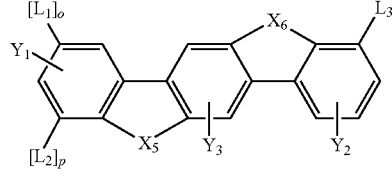

(9-1)
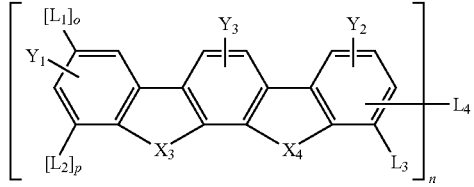

(9-2)
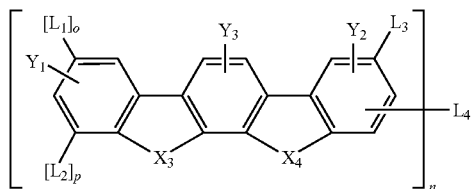

-continued (10-1)
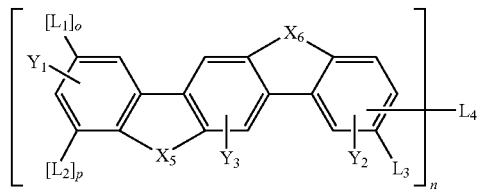

(10-2)
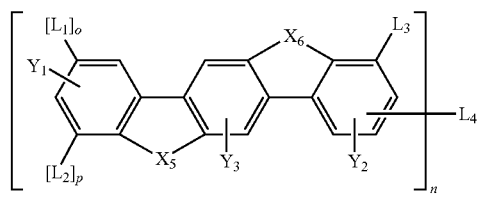

[Chem 10]

(11)
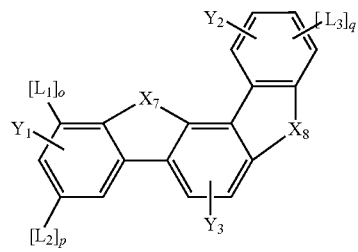

(12)
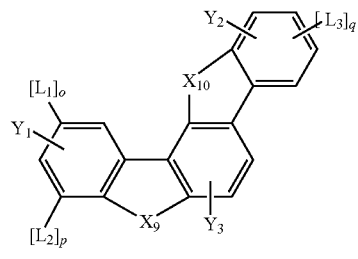

(13)
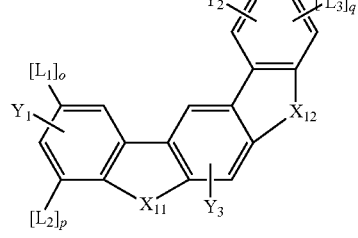

(14)
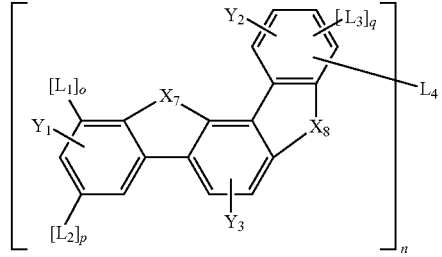

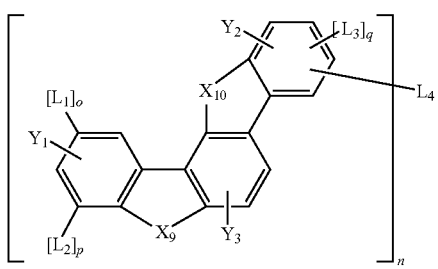

(15)

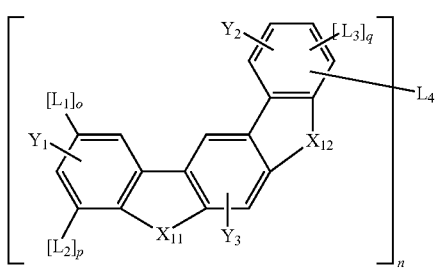

(16)

(4)

[In the general formulae (11) to (16), $X_7$, $X_8$, $X_9$, $X_{10}$, $X_{11}$, and $X_{12}$ each independently represent oxygen (O), sulfur (S), N—$R_1$, or $CR_2R_3$, $R_1$, $R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_7$ and $X_8$, both $X_9$ and $X_{10}$, or both $X_{11}$ and $X_{12}$ represent N—$R_1$, at least one $R_1$ represents a substituted or unsubstituted monovalent fused aromatic heterocyclic group having 8 to 24 atoms forming the aromatic ring.

In the general formulae (11) to (16), o, p, and q each independently represent 0 or 1, provided that o+p is 1 or more.

In the general formulae (14) to (16), n represents 2, 3, or 4.

In the general formulae (11) to (16), $L_1$, $L_2$, and $L_3$ each independently represent a structure represented by the general formula (7), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring, E represents a single bond, oxygen (O), sulfur (S), N—$R_4$, or $CR_5R_6$, and $R_4$, $R_5$, and $R_6$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring.

In the general formulae (14) to (16), when n represents 2, $L_4$ represents a single bond, oxygen (O), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, when n represents 3, $L_4$ represents N, a substituted or unsubstituted alkanetriyl group having 1 to 20 carbon atoms, a substituted or unsubstituted cycloalkanetriyl group having 3 to 20 carbon atoms forming the ring, a substituted or unsubstituted trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group having 3 to 24 atoms forming the aromatic ring, and when n represents 4, $L_4$ represents a substituted or unsubstituted alkane tetrayl group having 1 to 20 carbon atoms, a substituted or unsubstituted cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formulae (11) to (16), $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, which is bonded with a carbon atom, the number of $Y_1$'s is 0, 1, 2, or 3, the number of $Y_2$'s is 0, 1, 2, 3, or 4, and the number of $Y_3$'s is 0, 1, or 2.]

As the polycyclic compounds represented by the above general formulae (11) to (16), the compound represented by any one of the following general formulae (11-1), (11-2), (12-1), (12-2), (13-1), (13-2), (14-1), (14-2), (15-1), (15-2), (16-1), and (16-2) is preferred.

[Chem 11]
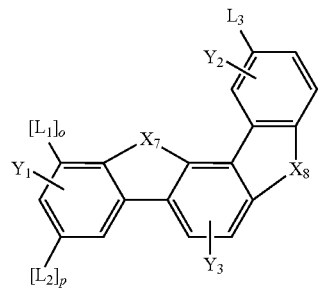
(11-1)
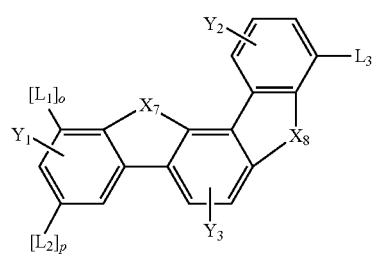
(11-2)
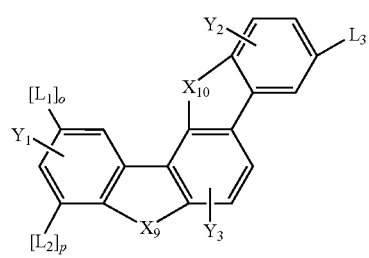
(12-1)
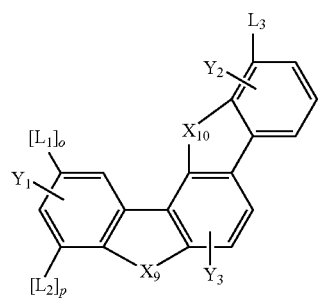
(12-2)
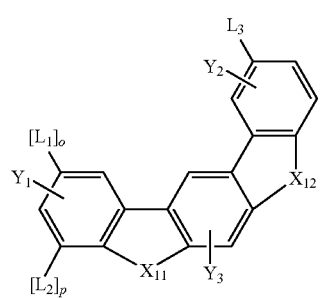
(13-1)
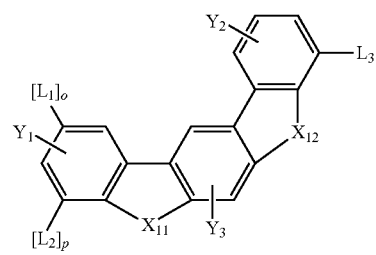
(13-2)
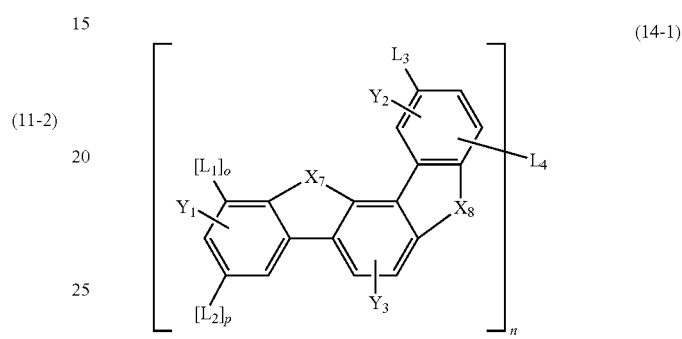
(14-1)
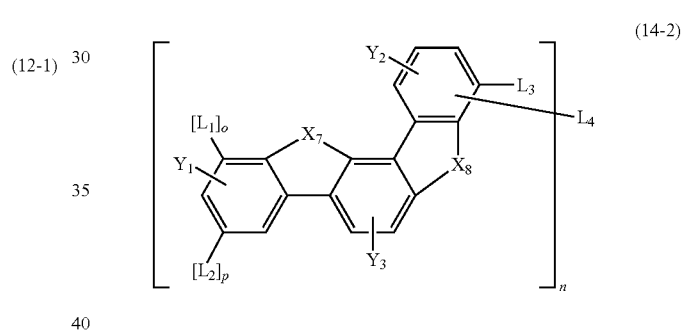
(14-2)
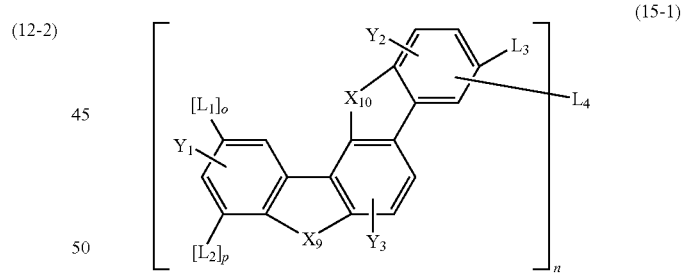
(15-1)
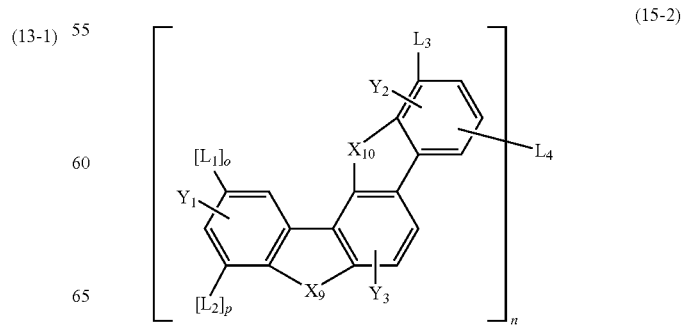
(15-2)

-continued

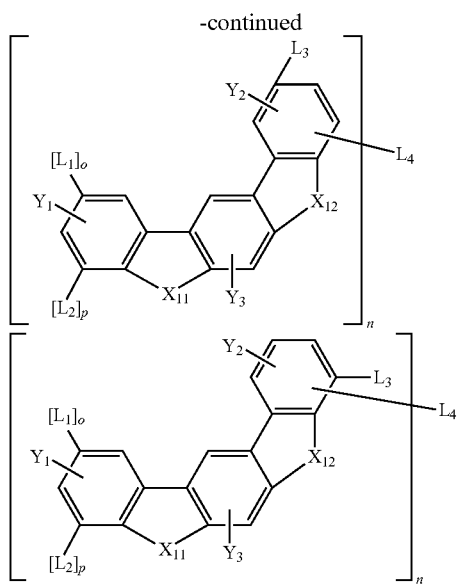

[Chem 13]

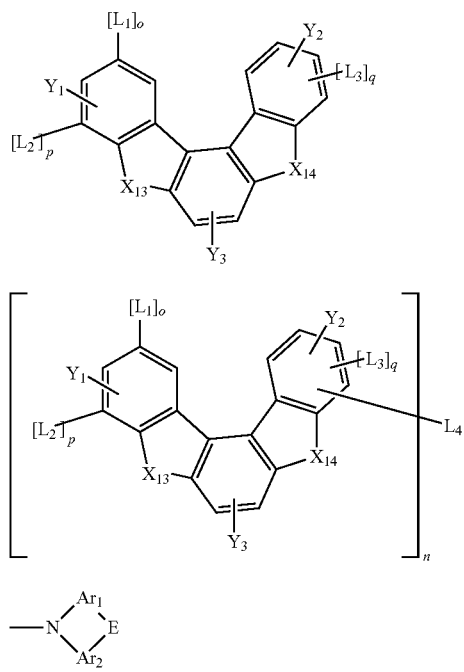

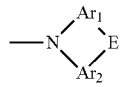
(4)

[In the general formulae (17) and (18), $X_{13}$ and $X_{14}$ each independently represent oxygen (O), sulfur (S), N—$R_1$, or $CR_2R_3$, $R_1$, $R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_{13}$ and $X_{14}$ represent N—$R_1$, at least one $R_1$ represents a substituted or unsubstituted monovalent fused aromatic heterocyclic group having 8 to 24 atoms forming the aromatic ring.

In the general formulae (17) and (18), o, p, and q each independently represent 0 or 1, provided that o+p is 1 or more.

In the general formula (18), n represents 2, 3, or 4.

In the general formulae (17) and (18), $L_1$, $L_2$, and $L_3$ each independently represent a structure represented by the general formula (3), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring, E represents a single bond, oxygen (O), sulfur (S), N—$R_4$, or $CR_5R_6$, $R_4$, $R_5$, and $R_6$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring;

In the general formula (18), when n represents 2, $L_4$ represents a single bond, oxygen (C), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, when n represents 3, $L_4$ represents N, a substituted or unsubstituted alkanetriyl group having 1 to 20 carbon atoms, a substituted or unsubstituted cycloalkanetriyl group having 3 to 20 carbon atoms forming the ring, a substituted or unsubstituted trivalent organosilyl group having 1 to 20 carbon atoms which is bonded with a silicon atom, a substituted or unsubstituted trivalent aromatic hydrocarbon group having 6 to 24 carbon atoms forming the aromatic ring, a substituted or unsubstituted trivalent aromatic heterocyclic group having 3 to 24 atoms forming the aromatic ring, and when n represents 4, $L_4$ represents a substituted or unsubstituted alkane tetrayl group having 1 to 20 carbon atoms, a substituted or unsubstituted cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formulae (17) and (18), $Y_1$, $Y_2$, and $Y_3$ each independently represent an alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms which is bonded with a carbon atom forming the aromatic ring, the number of $Y_1$'s is 0, 1, 2, or 3, the number of $Y_2$'s is 0, 1, 2, 3, or 4, and the number of $Y_3$'s is 0, 1, or 2.]

As the polycyclic compounds represented by the above general formulae (17) and (18), the compound represented by any one of the following formulae (17-1), (17-2), (18-1), and (18-2) is preferred.

[Chem 14]

(17-1)
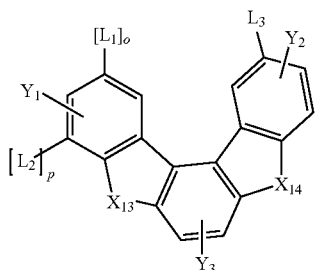

(17-2)
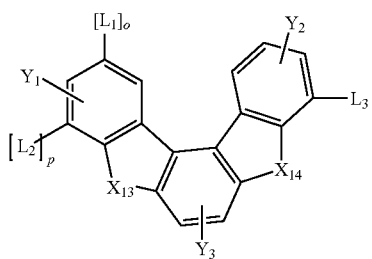

(18-1)
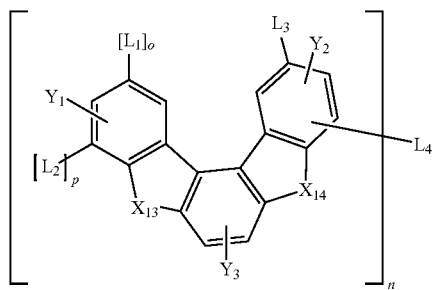

(18-2)
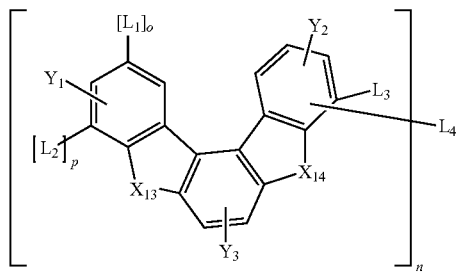

In addition, the polycyclic compound represented by the above general formula (8) is preferably the polycyclic compound represented by the following general formula (19). The polycyclic compound represented by the above general formula (10) is preferably the compound represented by the following general formula (20).

[Chem 15]

(19)
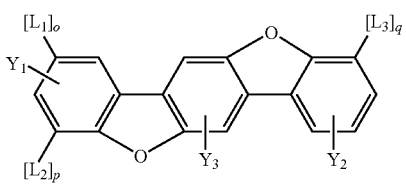

(20)
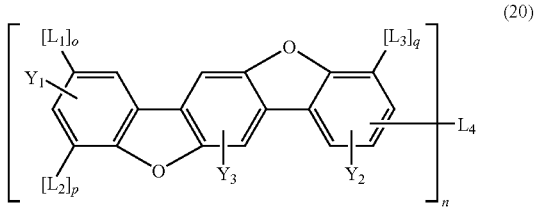

In the general formulae (1), (2), (3b), and (7) to (18) $X_1$ to $X_{14}$ each independently represent oxygen (O), sulfur (S), N—$R_1$, or $CR_2R_3$ (N—$R_1$ or $CR_2R_3$ bonds to the benzene ring to which the N atom or the C atom is adjacent).

In the general formulae (1), (2), and (7) to (18), $R_1$, $R_2$, and $R_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_1$ and $X_2$ represent N—$R_1$, when both $X_3$ and $X_4$ represent N—$R_1$, when both $X_5$ and $X_6$ represent N—$R_1$, when both $X_7$ and $X_8$ represent N—$R_1$, when both $X_9$ and $X_{10}$ represent N—$R_1$, when both $X_{11}$ and $X_{12}$ represent N—$R_1$, and when both $X_{13}$ and $X_{14}$ represent N—$R_1$, at least one $R_1$ represents a substituted or unsubstituted monovalent fused aromatic heterocyclic group having 8 to 24 atoms forming the aromatic ring.

In the general formulae (1), (2), and (7) to (18), $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 carbon atoms forming the aromatic ring, the number of $Y_1$'s is 0, 1, 2, or 3, the number of $Y_2$'s is 0, 1, 2, or 3, or 4, and the number of $Y_3$'s is 0, 1, or 2.

In the general formulae (1), (2), and (7) to (18), $L_1$, $L_2$, $L_3$, $L_{3a}$, and $L_{3b}$ each independently represent a structure represented by the general formula (4).

In the general formula (4), $Ar_1$ and $Ar_2$ each independently represent a substituted or unsubstituted divalent aromatic hydrocarbon group having 6 to 24 carbon atoms forming the aromatic ring or a substituted or unsubstituted divalent aromatic heterocyclic group having 3 to 24 atoms forming the aromatic ring.

In the general formula (4), E represents a single bond, oxygen (O), sulfur (S), N—$R_4$, or $CR_5R_6$, and $R_4$, $R_5$, and $R_6$ each independently a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring (N—$R_4$ or $CR_5R_6$ bonds to the benzene ring to which the N atom or the C atom is adjacent).

In the general formulae (2), (9), (10), (14) to (16), (18), and (20), n represents 2, 3, or 4.

In the general formulae (2), (9), (10), (14) to (16), (18), and (20), when n represents 2, $L_4$ represents a single bond, oxygen (O), sulfur (S), CO, SO, PO, $SO_2$, N—$R_7$, a substituted or unsubstituted alkylene group having 1 to 20 carbon atoms, a substituted or unsubstituted cycloalkylene group having 3 to 20 carbon atoms forming the ring, a substituted or unsubstituted divalent organosilyl group having 2 to 20 carbon atoms, a substituted or unsubstituted divalent aromatic hydrocarbon group having 6 to 24 carbon atoms forming the aromatic ring, or a substituted or unsubstituted divalent aromatic heterocyclic group having 3 to 24 atoms forming the aromatic ring, $R_7$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms, or a substituted or unsubstituted aromatic heterocyclic group having 3 to 24 atoms forming the aromatic ring, when n represents 3, $L_4$ represents N, a substituted or unsubstituted trivalent alkanetriyl group having 1 to 20 carbon atoms, a substituted or unsubstituted trivalent cycloalkanetriyl group having 3 to 20 carbon atoms forming the ring, a substituted or unsubstituted trivalent organosilyl group having 1 to 20 carbon atoms, a substituted or unsubstituted trivalent aromatic hydrocarbon group having 6 to 24 carbon atoms forming the aromatic ring, or a substituted or unsubstituted trivalent aromatic heterocyclic group having 3 to 24 atoms forming the aromatic ring, and when n represents 4, $L_4$ represents a substituted or unsubstituted tetravalent alkane tetrayl group having 1 to 20 carbon atoms, a substituted or unsubstituted tetravalent cycloalkane tetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group having 3 to 24 atoms forming the aromatic ring.

In the general formulae (1), (2), and (7) to (18), o, p, and q each represent 0 or 1, provided that o+p is 1 or more.

Examples of the alkyl group having 1 to 20 carbon atoms and represented by $Y_1$ to $Y_3$ and $R_1$ to $R_7$ include a methyl group, an ethyl group, a propyl group, an isopropyl group, an n-butyl group, an s-butyl group, a t-butyl group, an isobutyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 2-methylpentyl group, a 1-pentylhexyl group, a 1-butylpentyl group, a 1-heptyloctyl group, and a 3-methylpentyl group. Preferred are a methyl group, an ethyl group, a propyl group, an isopropyl group, an n-butyl group, an s-butyl group, an isobutyl group, a t-butyl group, n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 1-pentylhexyl group, a 1-butylpentyl group, and a 1-heptyloctyl group.

Examples of the cycloalkyl group having 3 to 20 carbon atoms forming the ring and represented by $Y_1$ to $Y_3$ and $R_1$ to $R_7$ include a cyclopropyl group, a cyclobutyl group, a cyclopentyl group, a cyclohexyl group. Preferred are a cyclobutyl group, a cyclopentyl group, and a cyclohexyl group.

Examples of the alkoxy group having 1 to 20 carbon atoms and represented by $Y_1$ to $Y_3$ include a methoxy group, an ethoxy group, a methoxy group, an i-propoxy group, an n-propoxy group, an n-butoxy group, an s-butoxy group, and a t-butoxy group. Preferred are a methoxy group, an ethoxy group, a methoxy group, an i-propoxy group, and an n-propoxy group.

Examples of the aralkyl group having 7 to 24 carbon atoms and represented by $Y_1$ to $Y_3$ and $R_1$ to $R_7$ include a benzyl group, a phenethyl group, and a phenylpropyl group.

Examples of the organosilyl group having 1 to 20 carbon atoms and represented by $Y_1$ to $Y_3$ and $R_1$ to $R_7$ include a trimethyl silyl group, a triethyl silyl group, a tributyl silyl group, a trioctyl silyl group, a triisobutyl silyl group, a dimethylethyl silyl group, a dimethylisopropyl silyl group, a dimethylpropyl silyl group, a dimethylbutyl silyl group, a dimethyltertiary butyl silyl group, a diethylisopropyl silyl group, a phenyldimethyl silyl group, a diphenylmethyl silyl group, a diphenyl tertiary butyl group, and a triphenyl silyl group. Preferred are a trimethyl silyl group, a triethyl silyl group, and a tributyl silyl group.

Examples of the aromatic hydrocarbon group having 6 to 24 carbon atoms forming the aromatic ring and represented by $Y_1$ to $Y_3$ and $R_1$ to $R_7$ include monovalent residues such as benzene, naphthalene, biphenyl, terphenyl, fluorene, phenanthrene, triphenylene, perylene, chrysene, fluoranthene, benzofluorene, benzotriphenylene, and benzochrysene. Preferred are monovalent residues such as benzene, naphthalene, biphenyl, terphenyl, fluorene, and phenanthrene. Examples of the divalent aromatic hydrocarbon group having 6 to 24 carbon atoms and represented by $Ar_1$ and $Ar_2$ include divalent residues such as benzene, naphthalene, biphenyl, terphenyl, fluorene, phenanthrene, triphenylene, perylene, chrysene, fluoranthene, benzofluorene, bnezotriphenylene, and benzochrysene. Preferred are divalent residues such as benzene, biphenyl, terphenyl, fluorene, and phenanthrene.

Examples of the aromatic heterocyclic group having 3 to 24 carbon atoms forming the aromatic ring and represented by $Y_1$ to $Y_3$ and $R_1$ to $R_7$ include monovalent residues such as pyridine, pyridazine, pyrimidine, pyrazine, 1,3,5-triazine, carbazole, dibenzofuran, dibenzothiophene, phenoxazine, phenothiazine, and dihydroacridine. Preferred are monovalent residues such as carbazole, dibenzofuran, dibenzothiophene, phenoxazine, and dihydroacridine. Further, examples of the monovalent fused aromatic heterocyclic group having 8 to 24 carbon atoms forming the aromatic ring and represented by at least one $R_1$ include compounds having fused structures of those examples. Examples of the aromatic heterocyclic group having 3 to 24 carbon atoms forming the aromatic ring and represented by $Ar_1$ and $Ar_2$ include divalent residues such as pyridine, pyridazine, pyrimidine, pyrazine, 1,3,5-triazine, carbazole, dibenzofuran, dibenzothiophene, phenoxazine, and phenothiazine. Preferred are divalent residues such as pyridine, pyridazine, pyrimidine, and pyrazine.

Examples of: when n indicated by $L_4$ represents 2, the alkylene group having 1 to 20 carbon atoms, the cycloalkylene group having 3 to 20 carbon atoms forming the ring, the divalent organosilyl group having 2 to 20 carbon atoms, the divalent aromatic hydrocarbon group having 6 to 24 carbon atoms forming the aromatic ring, or the divalent aromatic heterocyclic group having 3 to 24 atoms forming the aromatic ring; when n represents 3, the alkanetriyl group having 1 to 20 carbon atoms, the cycloalkanetriyl group having 3 to 20 carbon atoms forming the ring, the trivalent organosilyl group having 1 to 20 carbon atoms, the trivalent aromatic hydrocarbon group having 6 to 24 carbon atoms forming the aromatic ring, or the trivalent aromatic heterocyclic group having 3 to 24 atoms forming the aromatic ring; and when n represents 4, the alkane tetrayl group having 1 to 20 carbon atoms, the cycloalkane tetrayl group having 3 to 20 carbon atoms forming the ring, the tetravalent aromatic hydrocarbon group having 6 to 24 carbon atoms forming the aromatic ring, or the tetravalent aromatic heterocyclic group having 3 to 24 atoms forming the aromatic ring include divalent to tetravalent groups of the corresponding groups described in $Y_1$ to $Y_3$ and $R_1$ to $R_7$.

Examples of the substituent that can be substituted for the each group in the general formulae (1), (2), and (7) to (18) include alkyl groups each having 1 to 10 carbon atoms (such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group), cycloalkyl groups each having 3 to 40 carbon atoms forming the ring (such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group), alkoxy groups each having 1 to 6 carbon atoms (such as an ethoxy group, a methoxy group, an i-propoxy group, an n-propoxy group, an s-butoxy group, a t-butoxy group, a pentoxy group, and a hexyloxy group), cycloalkoxy groups each having 3 to 10 carbon atoms forming the ring (such as a cyclopentoxy group and a cyclohexyloxy group), aromatic hydrocarbon groups each having 6 to 40 carbon atoms forming the aromatic ring, aromatic heterocyclic groups having 3 to 40 atoms forming the aromatic ring, amino groups substituted with aromatic hydrocarbon groups having 6 to 40 carbon atoms forming the aromatic ring, ester groups having aromatic hydrocarbon groups having 6 to 40 carbon atoms forming the aromatic ring, an ester group, cyano group, nitro group, and halogen atom, each of which has an alkyl group having 1 to 6 carbon atoms.

Of those, alkyl groups each having 1 to 6 carbon atoms, a phenyl group, a pyridyl group, a carbazolyl group, and a dibenzofuranyl group are preferred and the number of substituents is preferably 1 or 2.

The total number of the substituents represented by $Y_1$, $Y_2$, and $Y_3$ in the general formulae (1), (7), (8), (11), (12), (13), (17), and (19) is preferably 2 or less, or the total number of the substituents represented by $Y_1$, $Y_2$, and $Y_3$ with respect to one structure inside $[\ ]_n$ in the general formulae (2), (9), (10), (14), (15), (16), (18), and (20) is preferably 2 or less, the number of the substituents represented by $Y_1$ and $Y_2$ is more preferably 0, or the number of the substituents represented by $Y_3$ is more preferably 0.

In the general formulae (1), (2), and (7) to (18), o+p+q is preferably 2 or less and o+p is more preferably 1.

In the polycyclic compound of the present invention, both $X_1$ and $X_2$, both $X_3$ and $X_4$, both $X_5$ and $X_6$, both $X_7$ and $X_8$, both $X_9$ and $X_{10}$, both $X_{11}$ and $X_{12}$, and both $X_{13}$ and $X_{14}$ in the general formulae (1), (2), (7) to (18) are preferably compounds represented by N—$R_1$. A polycyclic compound in which $X_1$ to $X_{14}$ represent N—$R_1$ has excellent hole transportability, and therefore, can prompt driving of an organic EL device at a low voltage, and in particular, can be used suitably as a host material or a hole transporting material.

At least one $R_1$ preferably represents a substituted or unsubstituted fused aromatic heterocycle having 8 to 24 atoms forming the aromatic ring and all of $R_1$'s more preferably represent fused aromatic heterocycles each having 8 to 24 atoms forming the aromatic ring. By bonding the fused aromatic heterocycle having electron transportability such as dibenzofuran and carbazole, the stability with respect to the hole (oxidation resistance) is enhanced compared that of a nitrogen-containing heterocycle which is not fused ring such as pyrimidine, resulting in long lifetime of the organic EL device. In addition, by bonding a fused aromatic heterocycle having large energy gap and the electron transportability such as dibenzofuran and carbazole to N, the degradation of the efficiency is prevented and the stability with respect to the hole (oxidation resistance) is enhanced in the case of using the organic EL device as a phosphorescence device.

Further, it is preferred that $X_1$ and $X_2$ in the general formulae (1) and (2) be each represented by N—$R_1$, and N—$R_1$ of $X_1$ and N—$R_1$ of $X_2$ be different from each other.

It is preferred that $X_3$ and $X_4$, $X_5$ and $X_6$ in the general formulae (7) to (10) be each represented by N—$R_1$, and N—$R_1$ of $X_3$ and N—$R_1$ of $X_4$ or N—$R_1$ of $X_5$ and N—$R_1$ of $X_6$ be different from each other.

It is preferred that $X_7$ and $X_8$, $X_9$ and $X_{10}$, $X_{11}$ and $X_{12}$ in the general formulae (11) to (16) be each represented by N—$R_1$, and N—$R_1$ of $X_7$ and N—$R_1$ of $X_8$, N—$R_1$ of $X_9$ and N—$R_1$ of $X_{10}$, or N—$R_1$ of $X_{11}$ and N—$R_1$ of $X_{12}$ be different from each other.

It is preferred that $X_{13}$ and $X_{14}$ in the general formulae (17) and (18) be each represented by N—$R_1$, and N—$R_1$ of $X_{13}$ and N—$R_1$ of $X_{14}$ be different from each other.

Thus, in the case where the structures in the formulae (1), (2), and (7) to (18) are asymmetric, crystallization thereof is suppressed and the stability of the thin film is enhanced, whereby the lifetime of the device is improved compared to the case of symmetric structure.

In the polycyclic compound of the present invention, it is preferred that at least one of $X_1$ and $X_2$ in the general formulae (1) and (2) represent an oxygen atom, and it is more preferred that both $X_1$ and $X_2$ represent oxygen atoms. It is preferred that at least one of $X_3$ and $X_4$ in the general formulae (7) and (9) represent an oxygen atom, and it is more preferred that both $X_3$ and $X_4$ represent oxygen atoms. It is preferred that at least one of $X_5$ and $X_6$ in the general formulae (8) and (10) represent an oxygen atom, and it is more preferred that both $X_5$ and $X_6$ represent oxygen atoms. It is preferred that at least one of $X_7$ and $X_8$ in the general formulae (11) and (14) represent an oxygen atom, and it is more preferred that both $X_7$ and $X_8$ represent oxygen atoms. It is preferred that at least one of $X_9$ and $X_{10}$ in the general formulae (12) and (15) represent an oxygen atom, and it is more preferred that both $X_9$ and $X_{10}$ represent oxygen atoms. It is preferred that at least one of $X_{11}$ and $X_{12}$ in the general formulae (13) and (16) represent an oxygen atom, and it is more preferred that both $X_{11}$ and $X_{12}$ represent oxygen atoms. It is preferred that at least one of $X_{13}$ and $X_{14}$ in the general formulae (17) and (18) represent an oxygen atom, and it is more preferred that both $X_{13}$ and $X_{14}$ represent oxygen atoms. Because the oxygen atom has high electronegativity and can improve the electron transportability, the polycyclic compound of the present invention in which $X_1$ to $X_{14}$ represent oxygen atoms can prompt the driving of the organic EL device at a low voltage and can be suitably used as a host material or an electron transporting material. When both $X_1$ and $X_2$, both $X_3$ and $X_4$, both $X_5$ and $X_6$, both $X_7$ and $X_8$, both $X_9$ and $X_{10}$, both $X_{11}$ and $X_{12}$, and both $X_{13}$ and $X_{14}$ represent oxygen atoms, the triplet energy gap can be enlarged, and hence, the luminous efficiency can be improved compared to the case where both of them represent N—$R_1$ or both of them represent $CR_2R_3$.

In addition, as the polycyclic compound of the present invention, a polycyclic compound represented by the general formula (7) or (9) in which both $X_3$ and $X_4$ represent $CR_2R_3$, a polycyclic compound represented by the general formula (13) or (16) in which both $X_{11}$ and $X_{12}$ represent $CR_2R_3$, and a polycyclic compound represented by the general formula (17) and (18) in which both $X_{13}$ and $X_{14}$ represent $CR_2R_3$ are preferred. In those polycyclic compounds, the directions of two C (carbon atoms) are the same with respect to the ring A in the center of the molecule, the triplet energy gap can be enlarged slightly compared to the case where the directions of C (carbon atoms) are inverse, whereby the luminous efficiency can be improved.

Of those polycyclic compounds of the present invention, in the case of a compound represented by the general formula (7), (9), (13), or (16) in which $X_3$ and $X_4$ or $X_{11}$ and $X_{12}$ are positioned at the same side with respect to the central benzene ring (ring A in the general formula (1)), the triplet energy gap can be enlarged slightly compared to the case where those are positioned at the inverse side, whereby the luminous efficiency can be improved. The same holds true in the case where $X_3$ and $X_4$ or $X_{11}$ and $X_{12}$ represent $CR_2R_3$.

Of the polycyclic compounds of the present invention, the compounds represented by the general formulae (11) to (16) have both terminal benzene rings linked at the meta position with respect to the central ring A, and therefore, can enlarge the triplet energy gap and have excellent luminous efficiency.

Of the polycyclic compounds of the present invention, the compounds represented by the general formulae (7) to (10) have both terminal benzene rings linked at the para position with respect to the central ring A, and therefore, have excellent electron transportability and can prompt driving of the organic EL device at a low voltage. Further, because the directions of $X_3$ and $X_4$ are the same with respect to the central ring A, the triplet energy gap can be enlarged, whereby the polycyclic compounds are excellent in the luminous efficiency.

The structure represented by the general formula (4) preferably has a structure selected from the structures represented by the following general formulae (21) to (39). The following structures may have substituents. Me represents a methyl group.

[Chem 16]

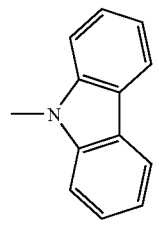

(21)


(22)

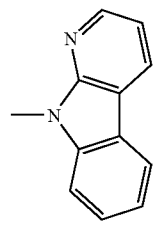

(23)

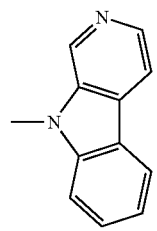

(24)

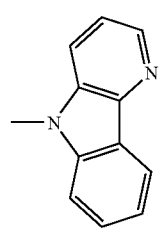

(25)

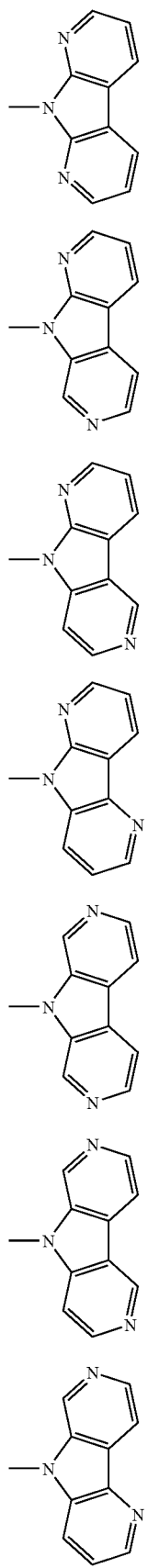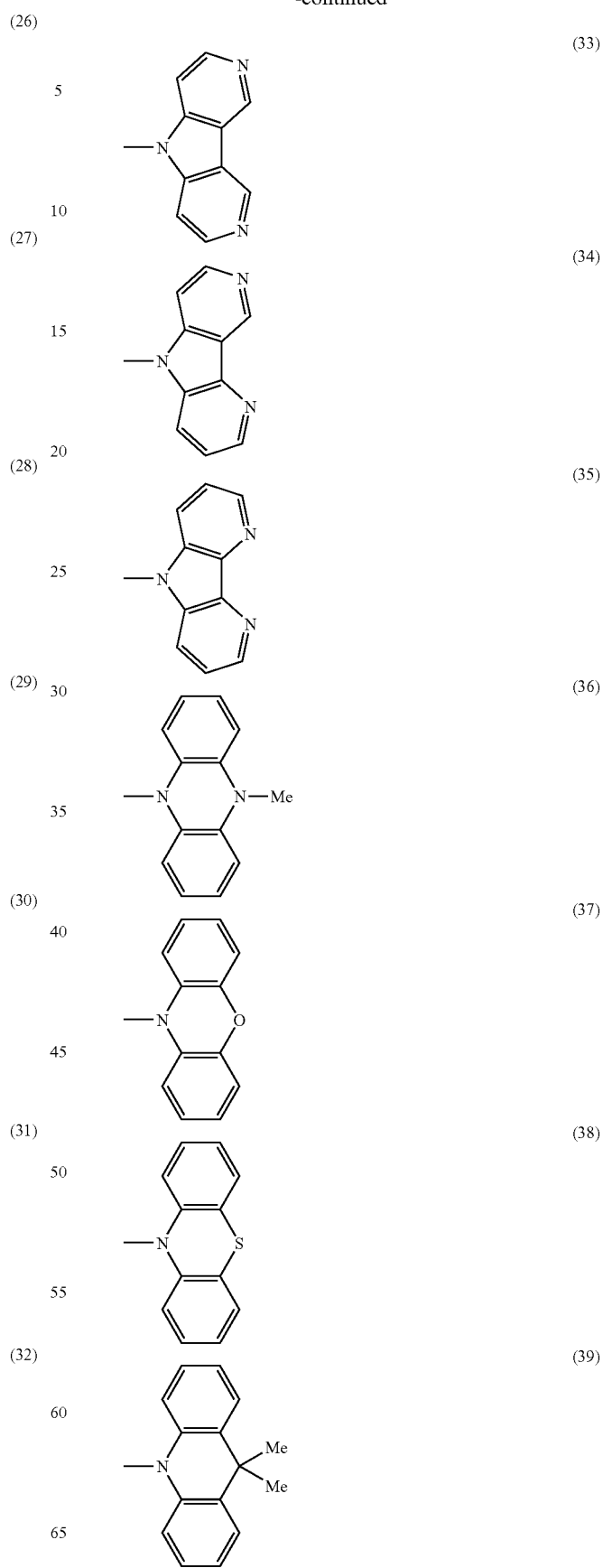

Specific examples of polycyclic compound represented by any one of the general formulae (1), (2), (7) to (20) of the present invention are shown below. However, the present invention is not limited to these exemplified compounds.
[Chem 17]
(1-1)
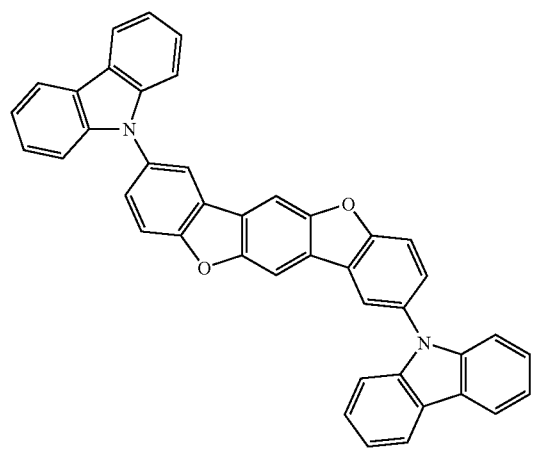
(1-2)
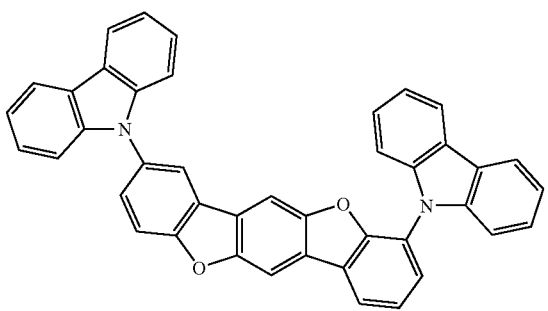
(1-3)
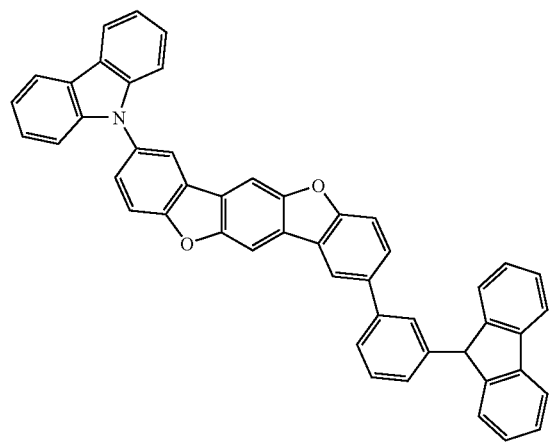
(1-4)
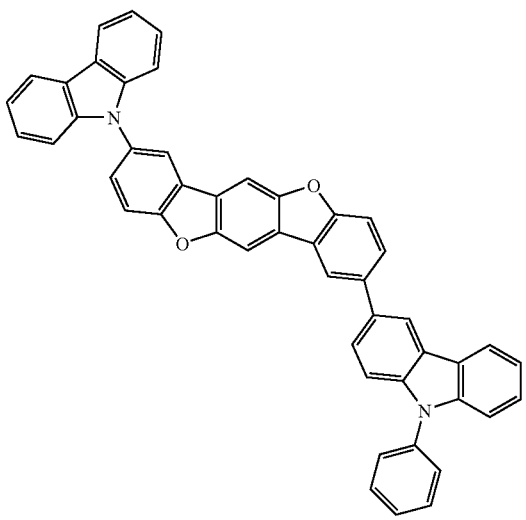
(1-5)
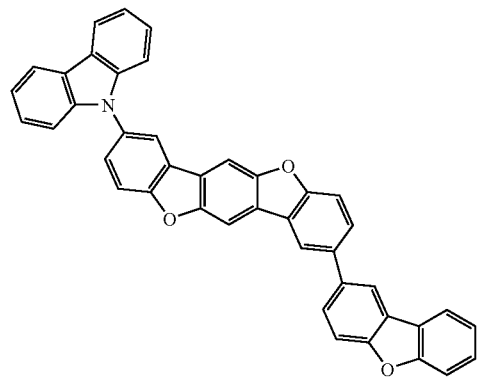
(1-6)
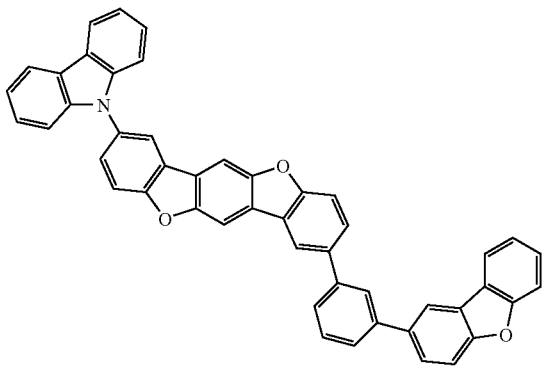

-continued
(1-7)
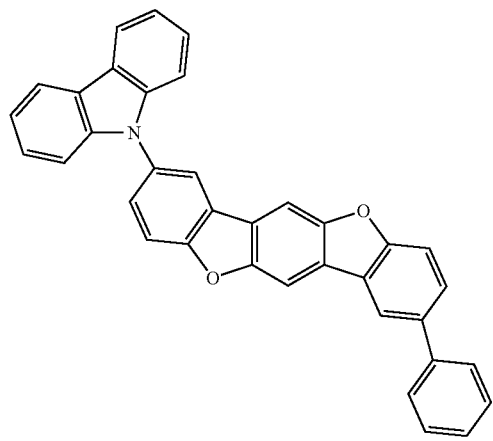
(1-8)
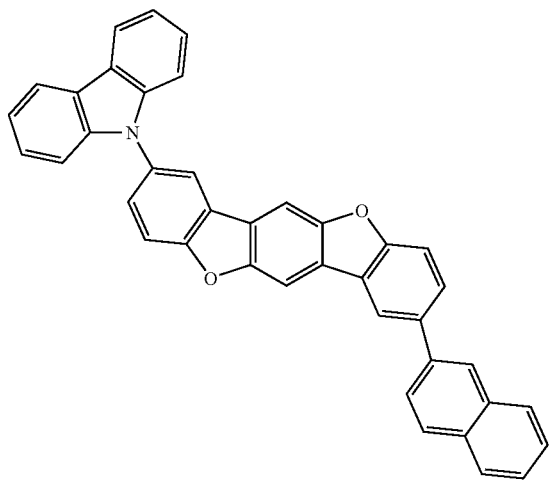
(1-9)
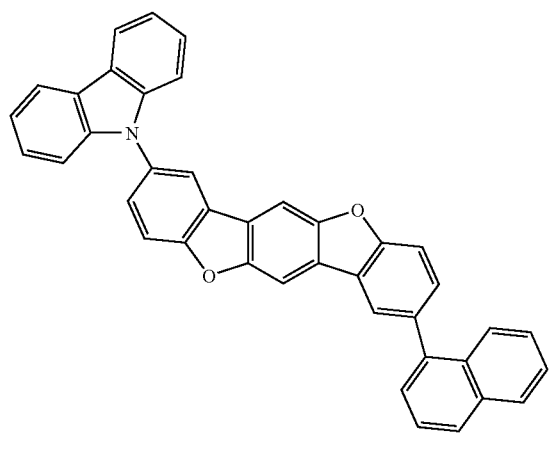
(1-10)
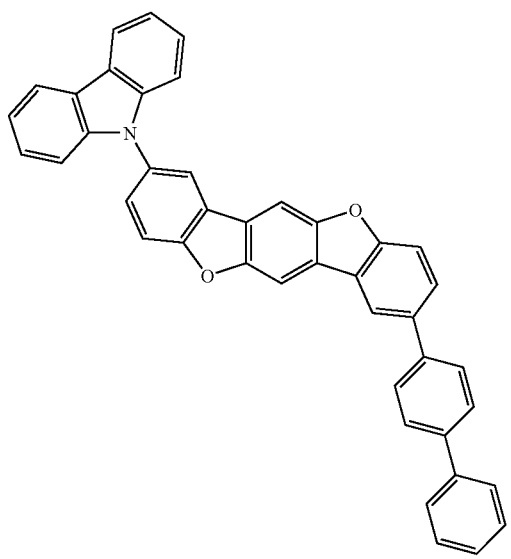
(1-11)
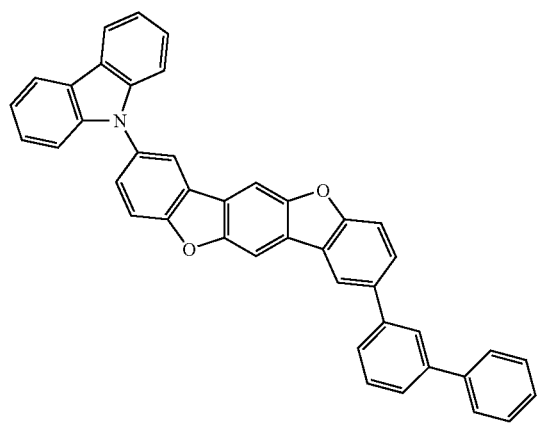
(1-12)
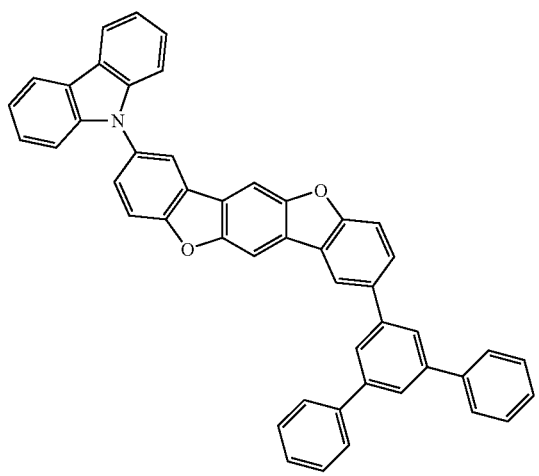

(1-13)
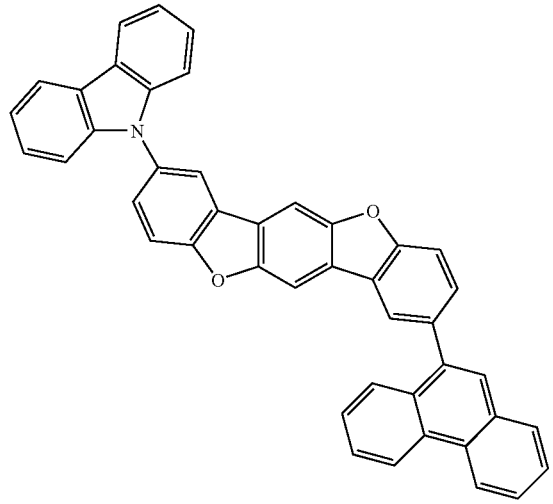
(1-14)
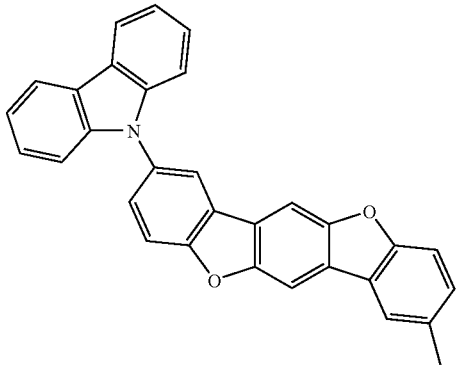
(1-15)
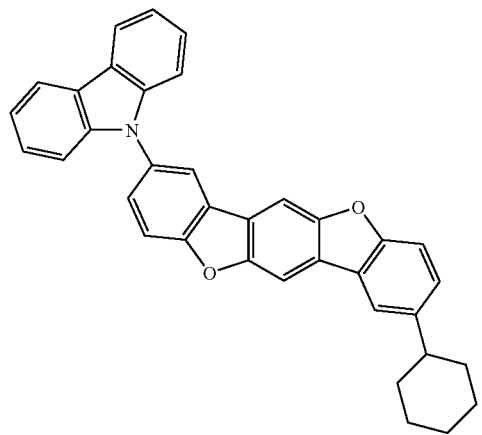
(1-16)
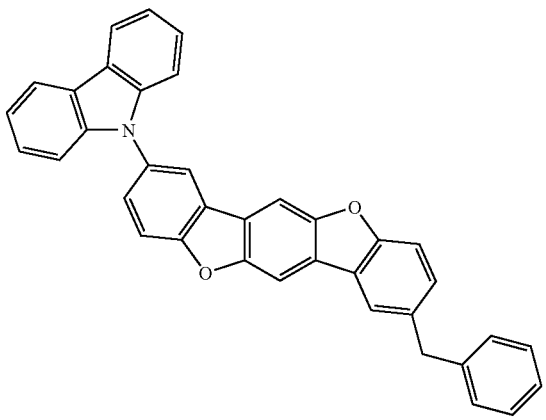
(1-17)
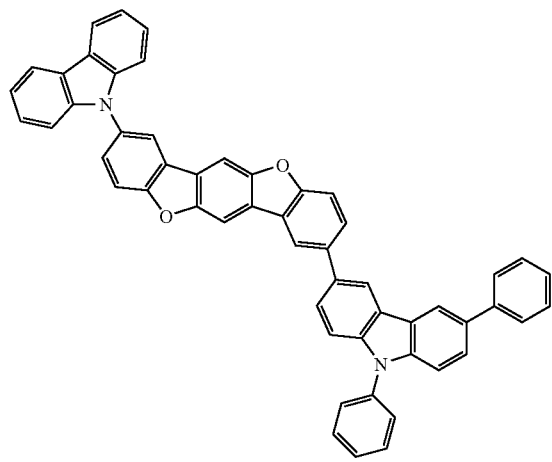
(1-18)
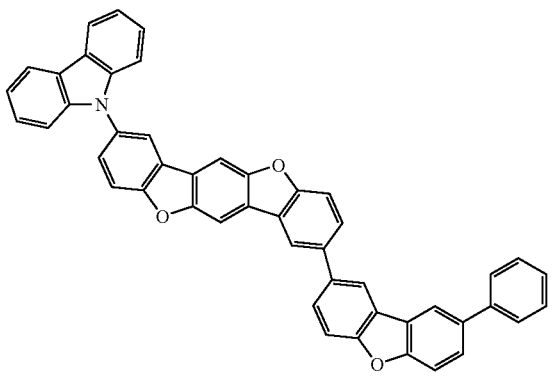

-continued
(1-19)
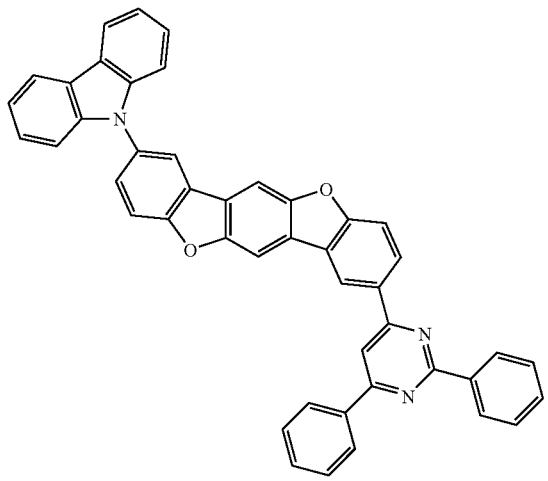
(1-20)
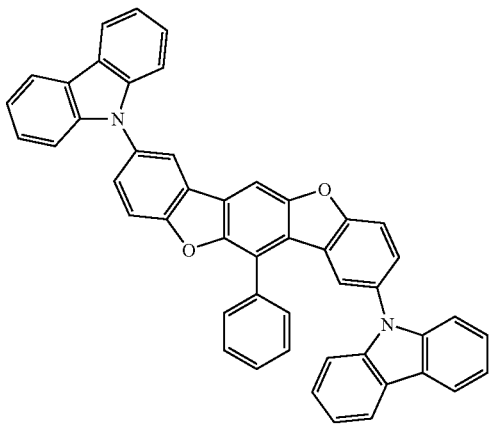
(1-21)
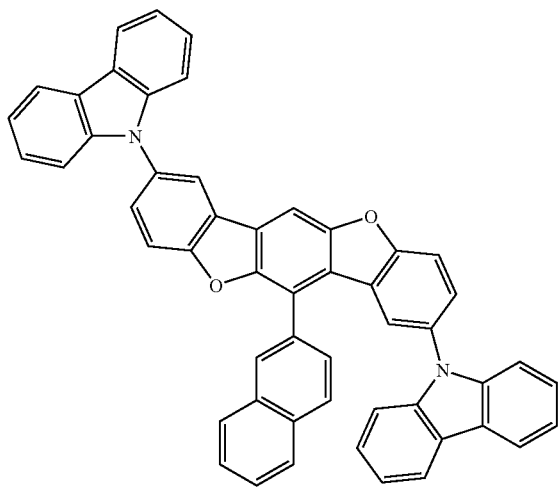
(1-22)
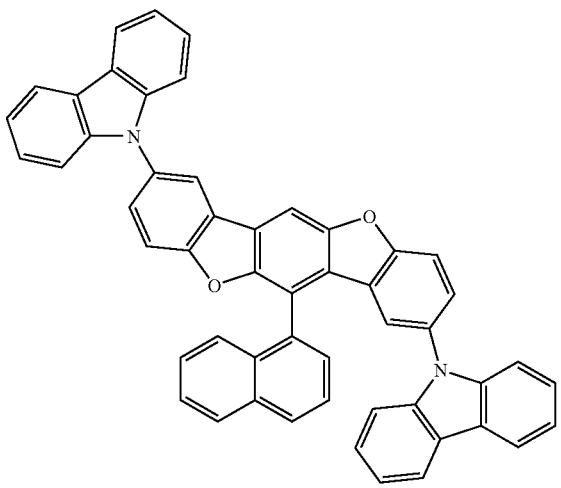
(1-23)
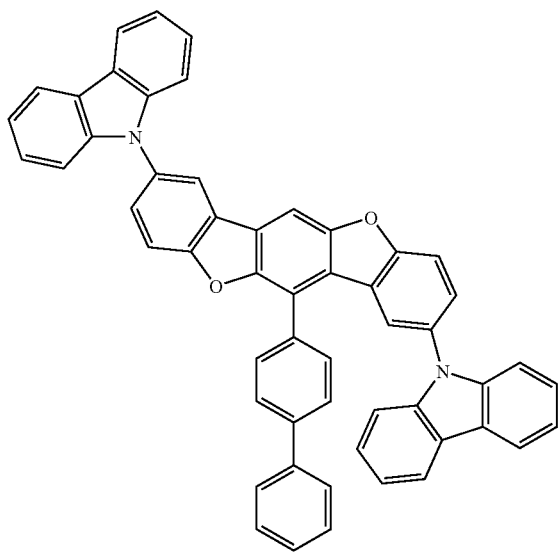
(1-24)
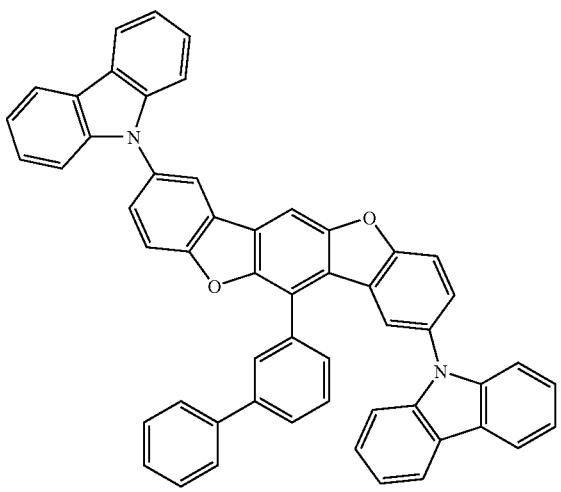

(1-25)
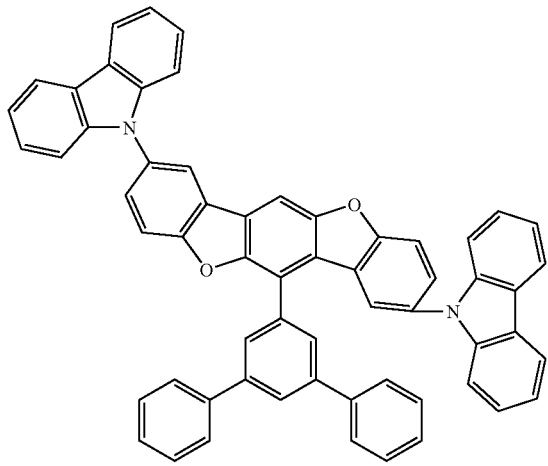
(1-26)
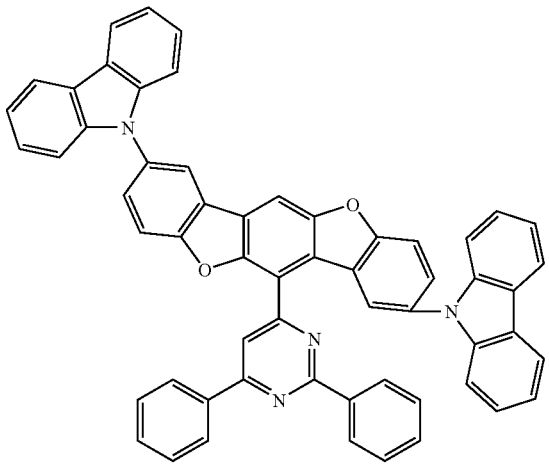
(1-27)
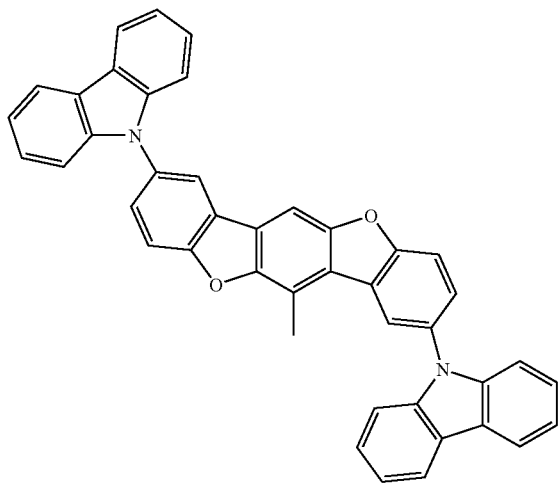
(1-28)
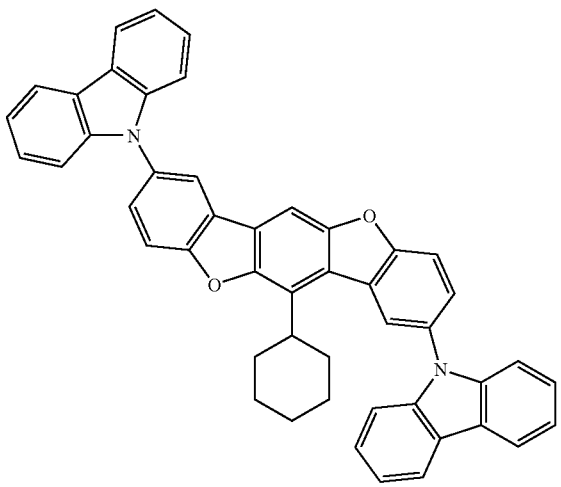
(1-29)
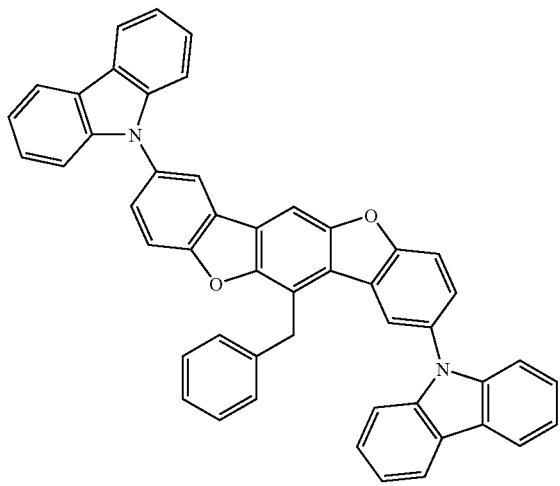
(1-30)
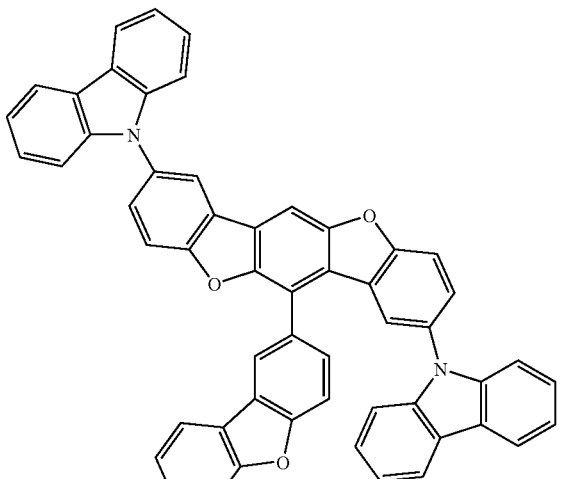

-continued
(1-31)
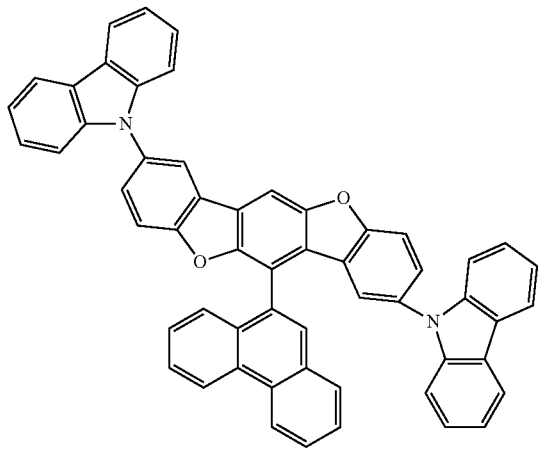
(1-32)
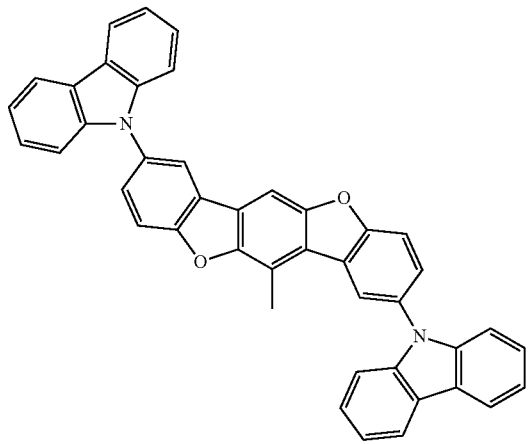
(1-33)
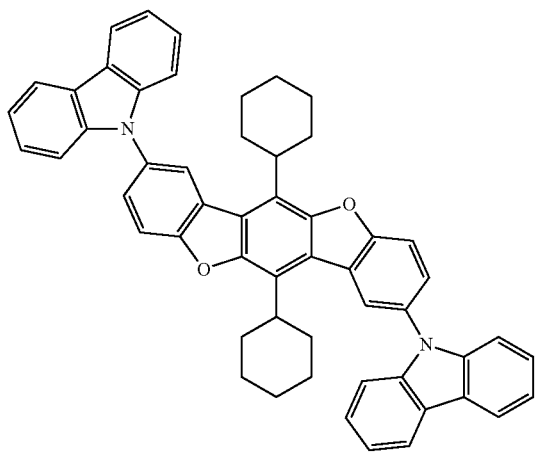
(1-34)
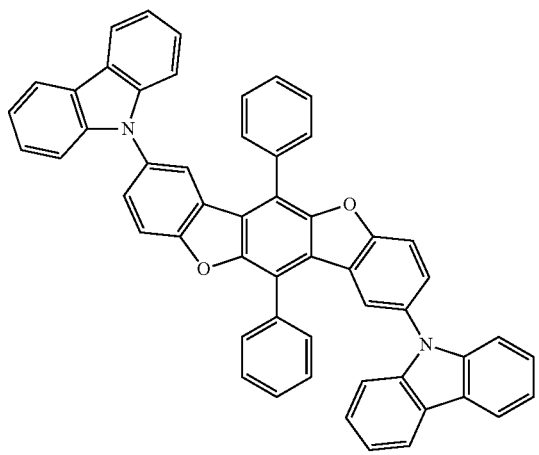
[Chem 19]
(1-35)
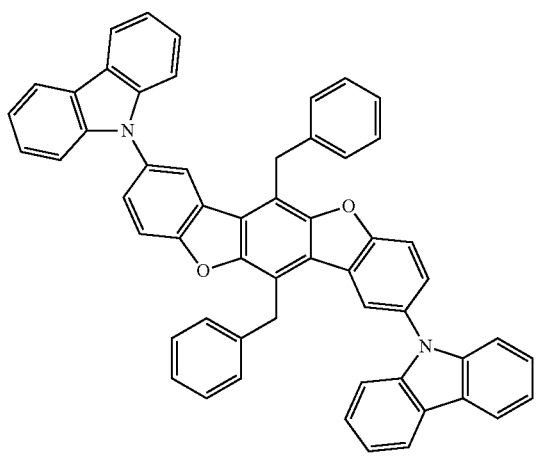
(1-36)
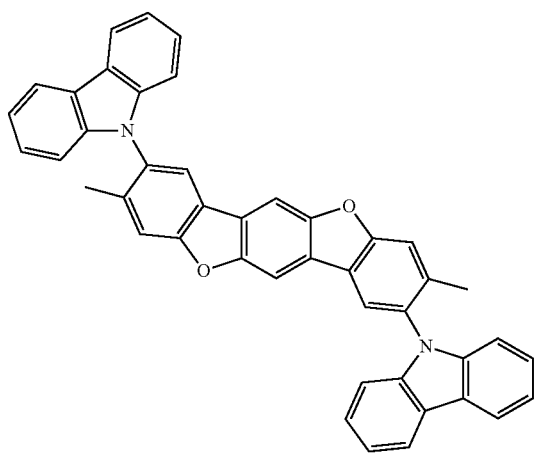

-continued
(1-37)
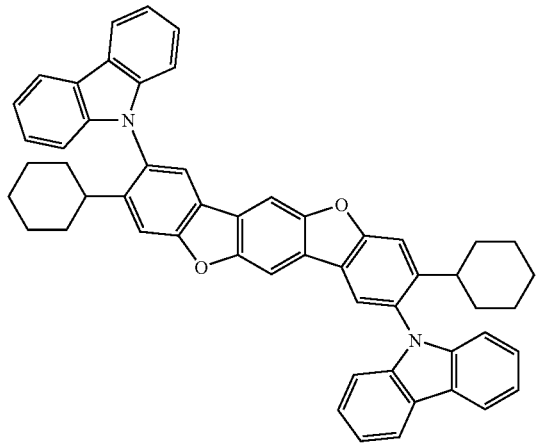
(1-38)
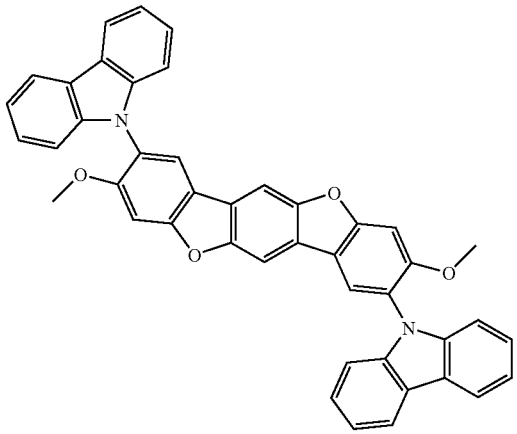
(1-39)
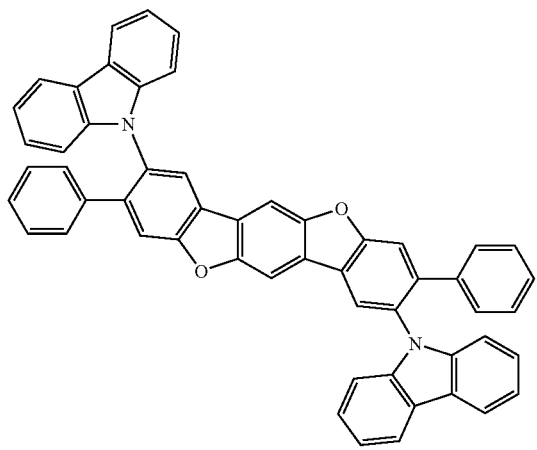
(1-40)
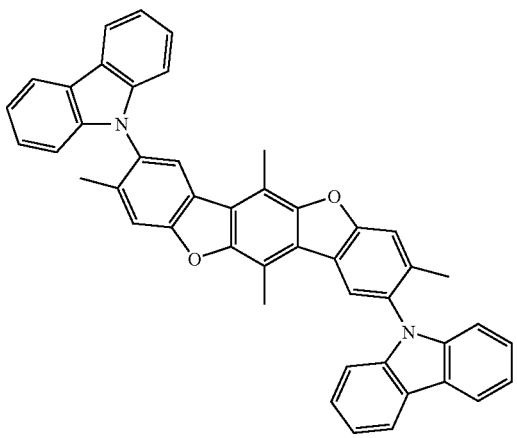
(1-41)
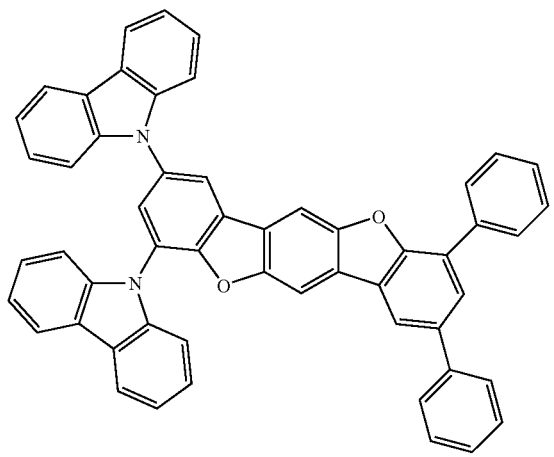
(1-42)
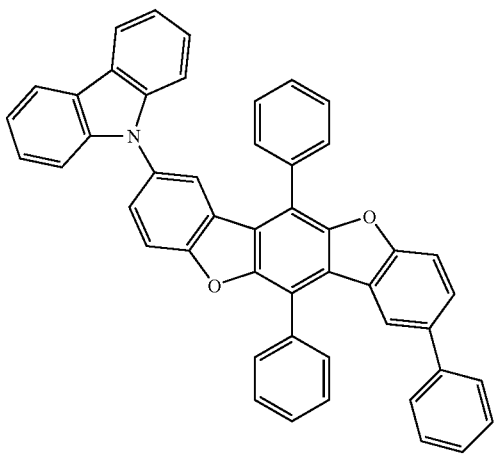

-continued
(1-43)
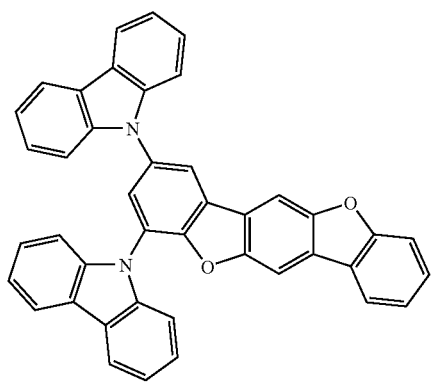
(1-44)
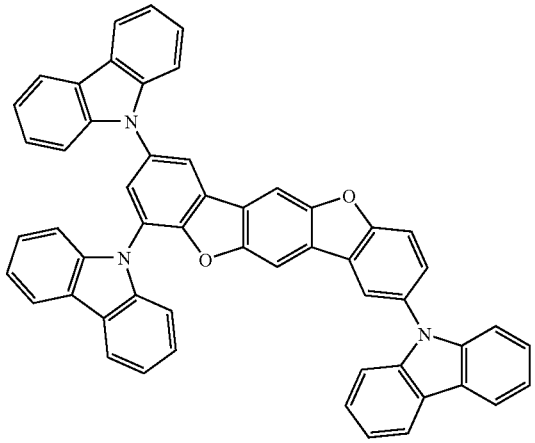
(1-45)
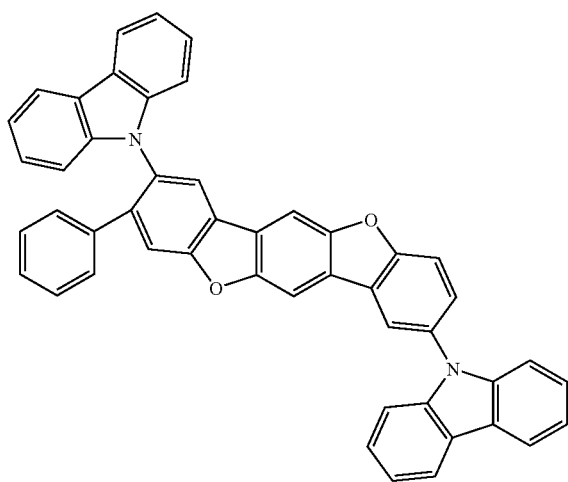
(1-46)
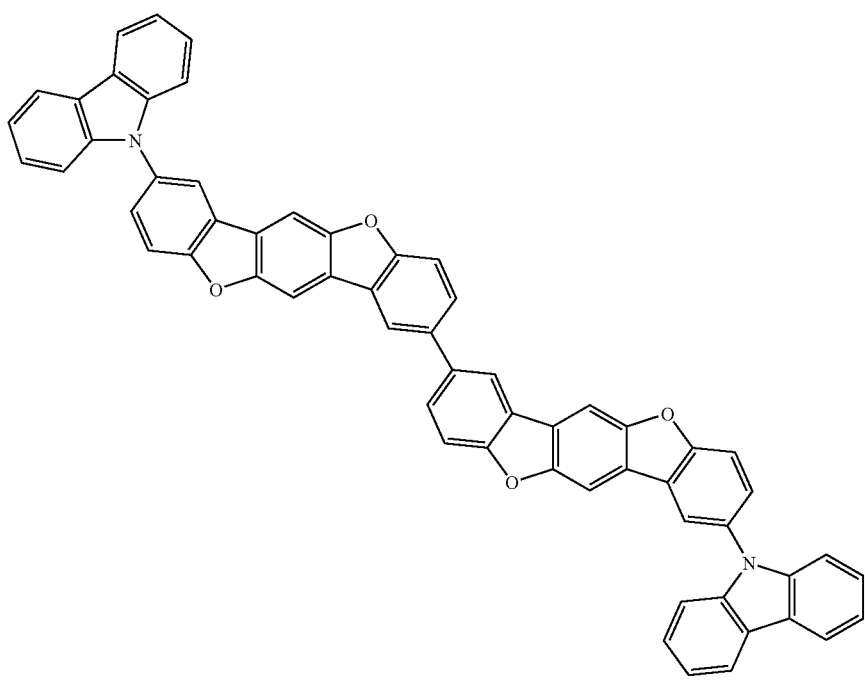

(1-47)
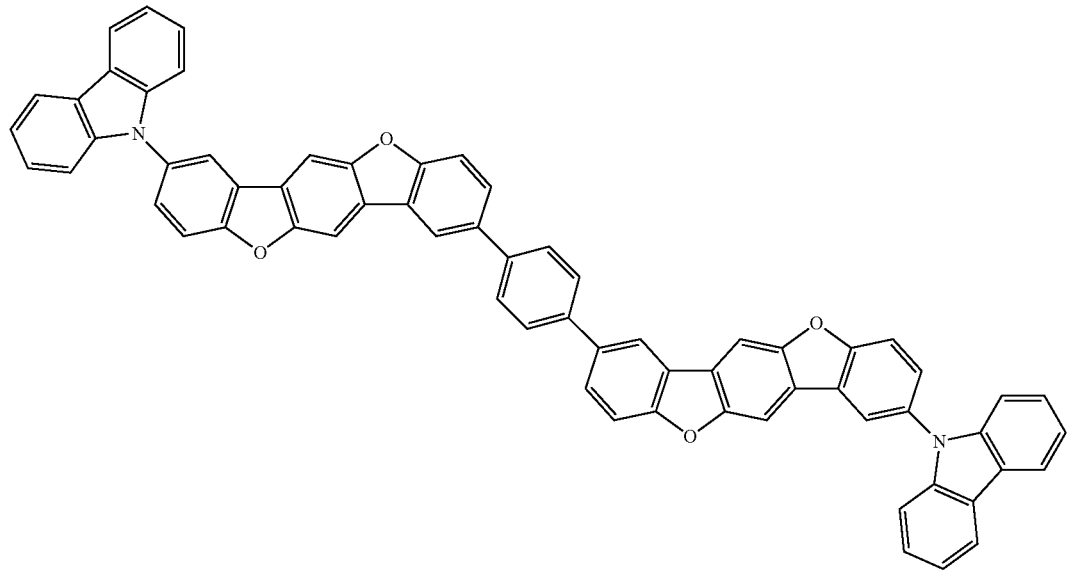
[Chem 20]
(1-48)
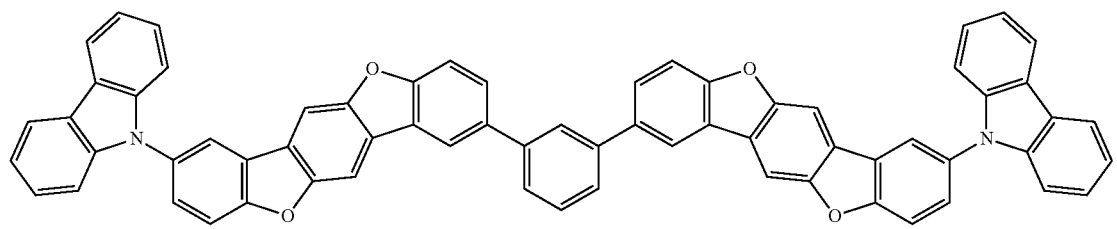
(1-49)
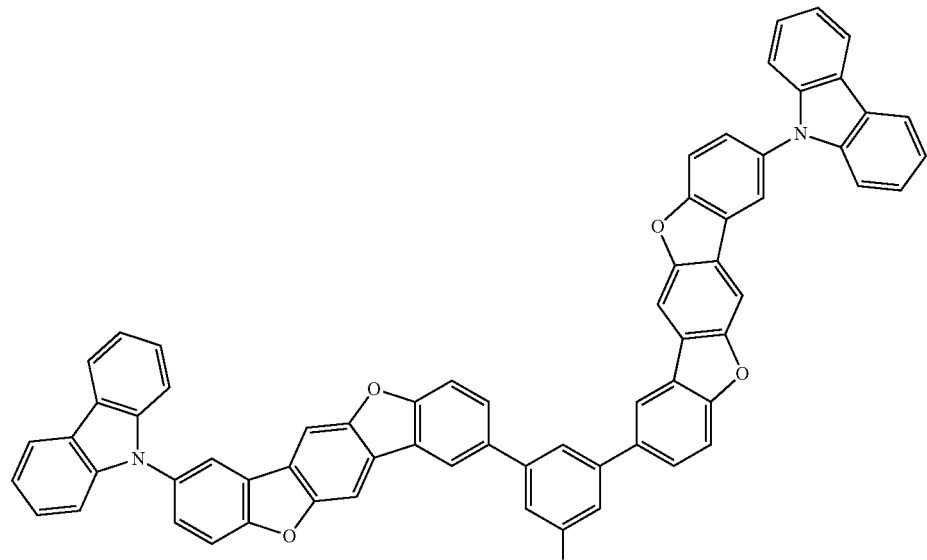

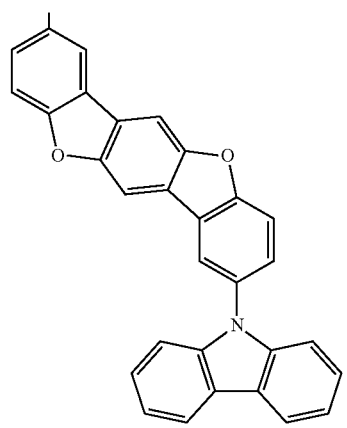
(1-50)
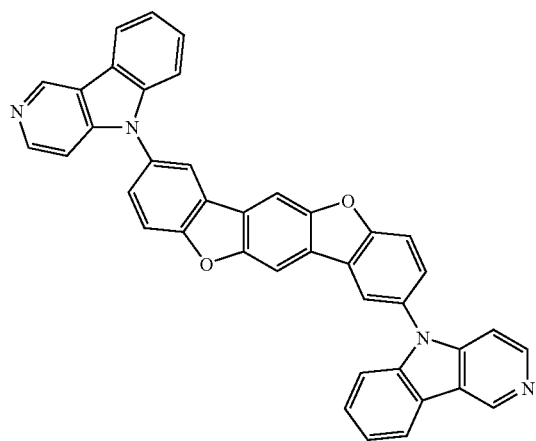
(1-51)
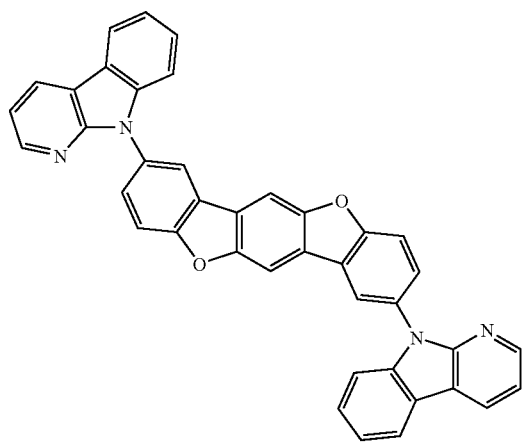
(1-52)
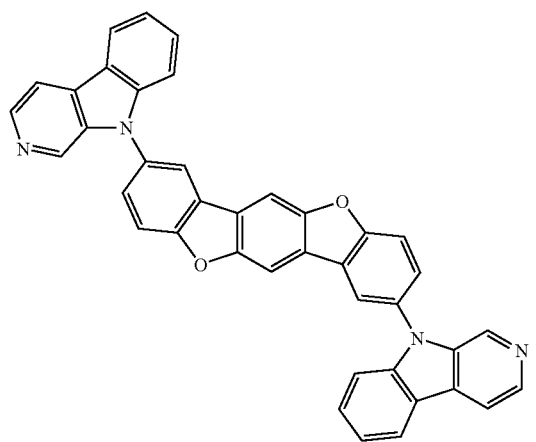
(1-53)
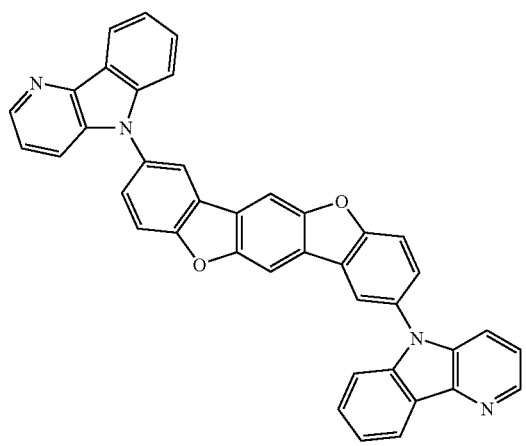

-continued
(1-54)
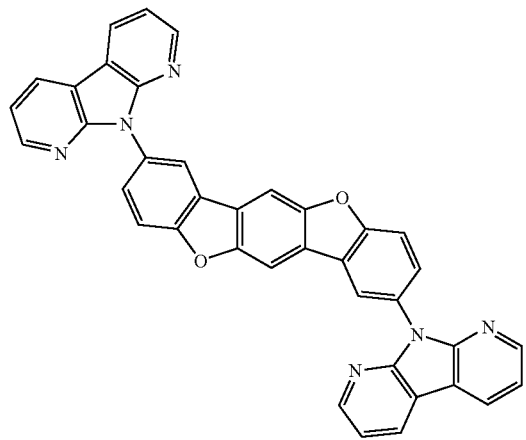
(1-55)
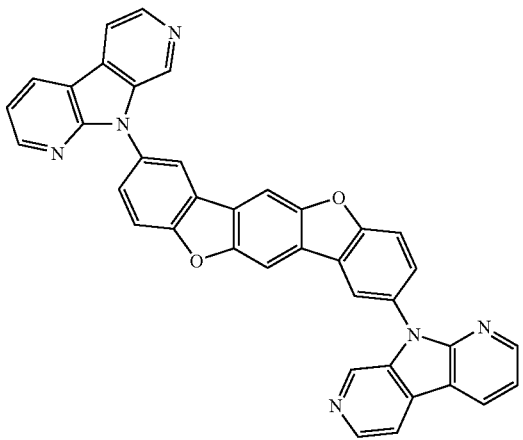
(1-56)
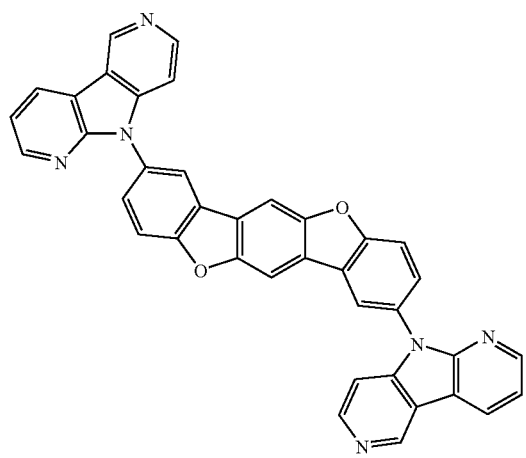
(1-57)
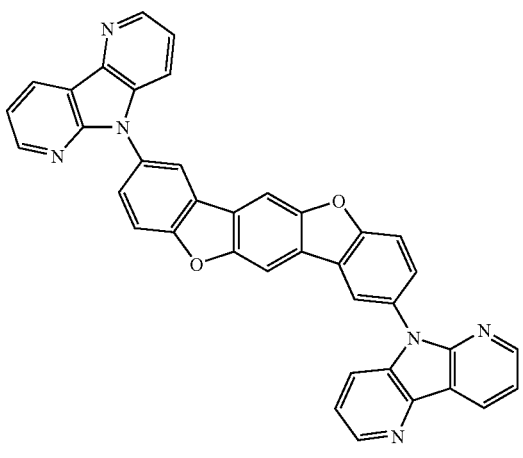
(1-58)
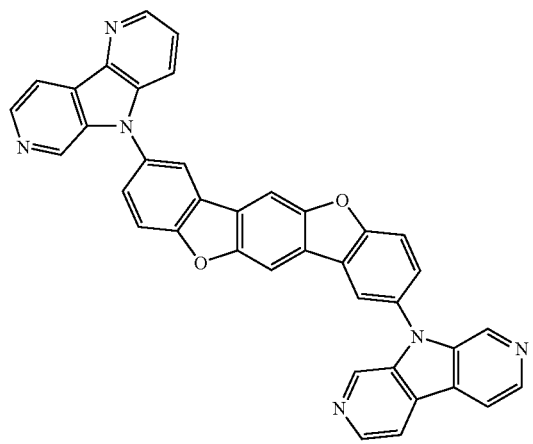
(1-59)
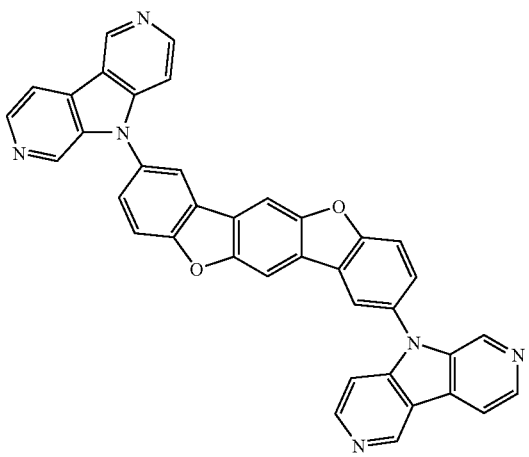

(1-60)
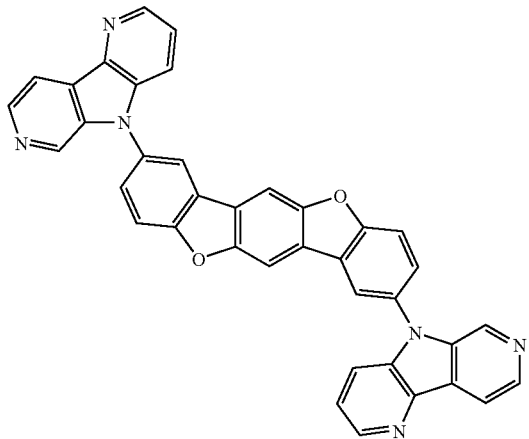
(1-61)
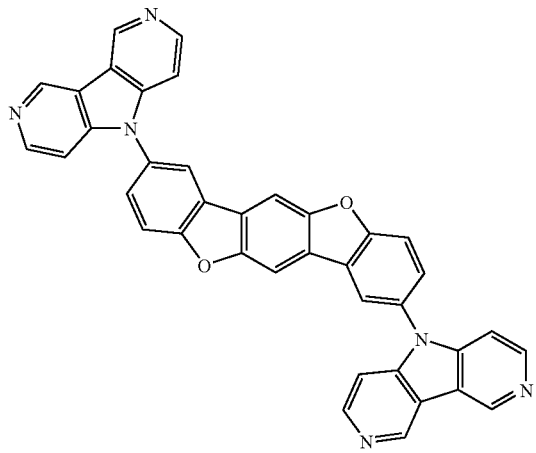
[Chem 21]
(1-62)
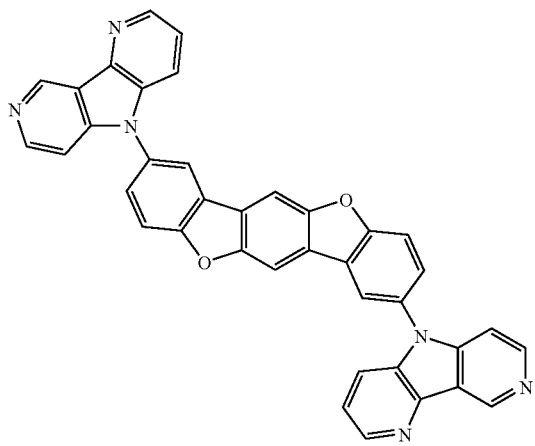
(1-63)
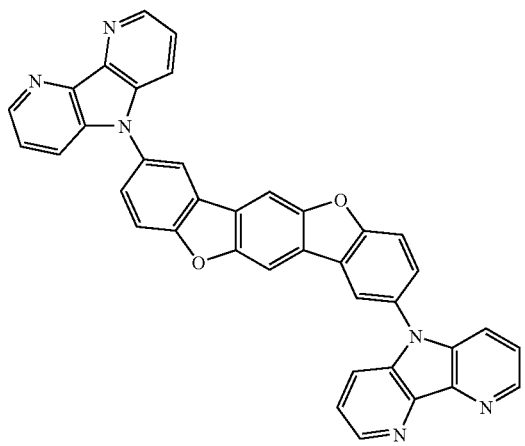
(1-64)
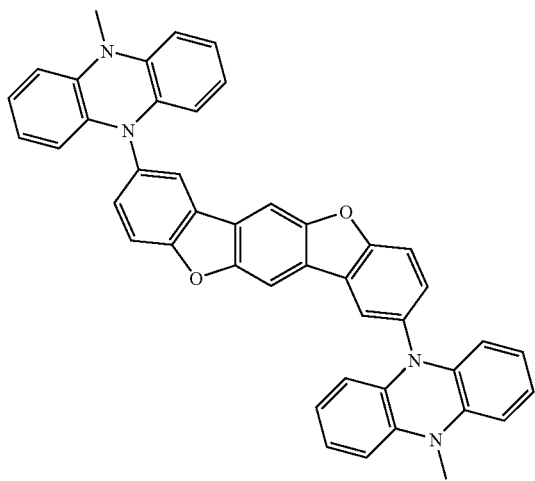
(1-65)
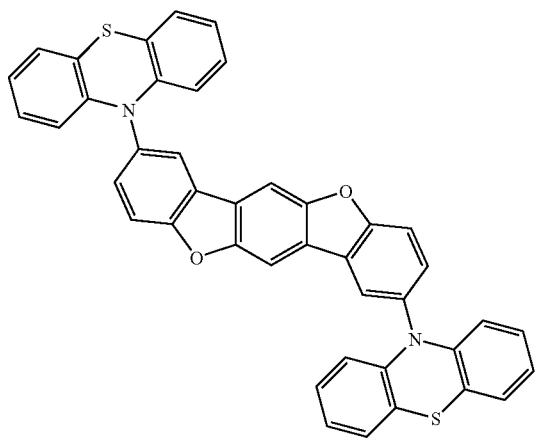

(1-66)
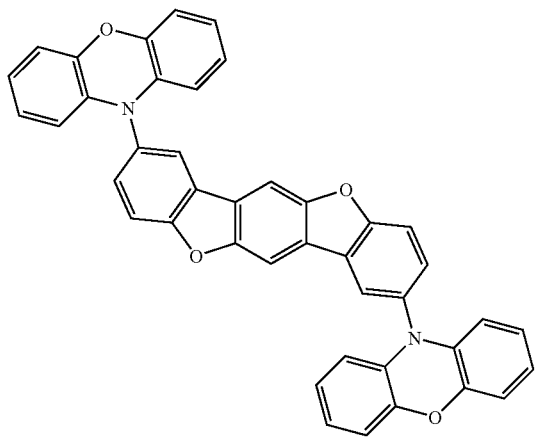
(1-67)
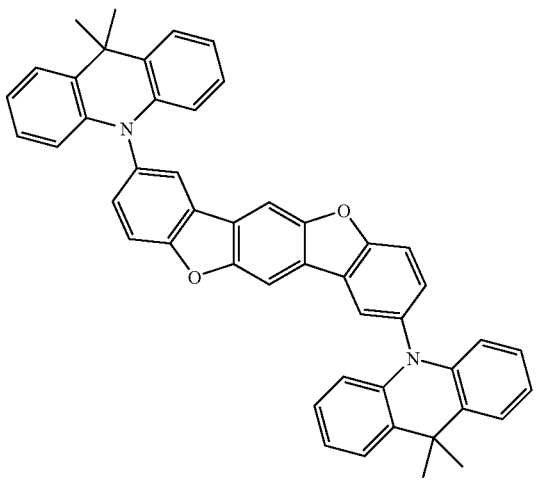
(1-68)
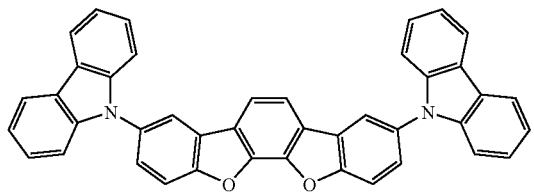
(1-69)
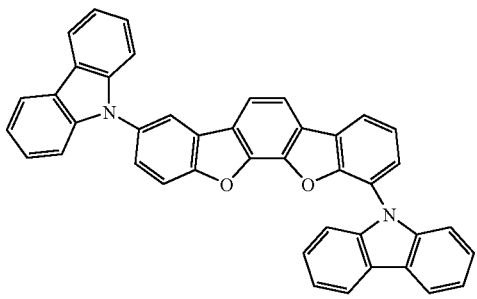
(1-70)
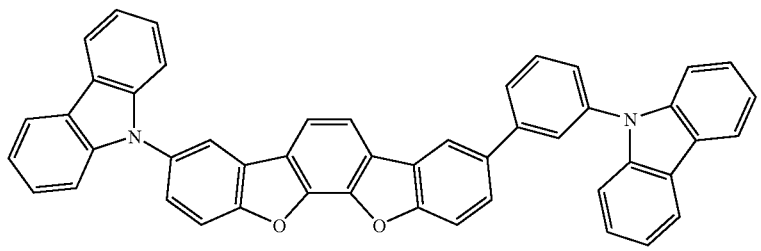
(1-71)
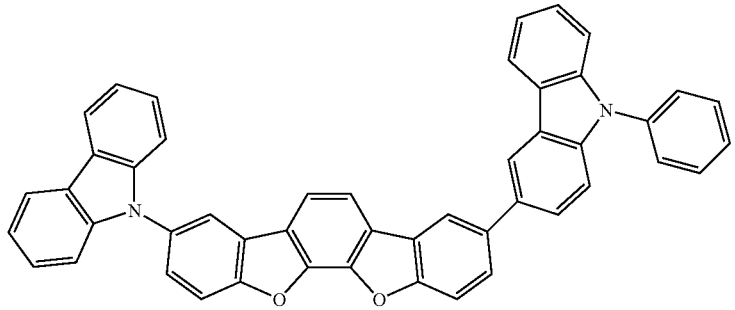
(1-72)
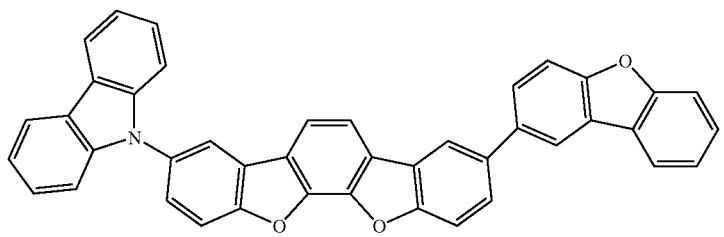

(1-73)
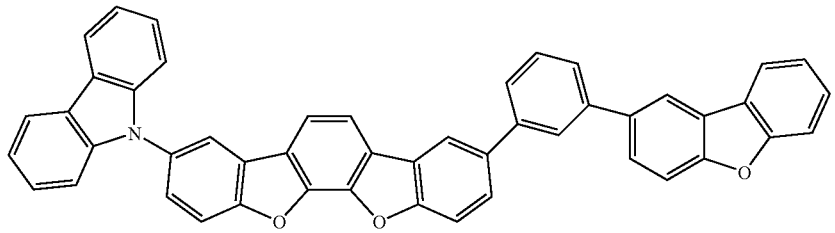
(1-74)
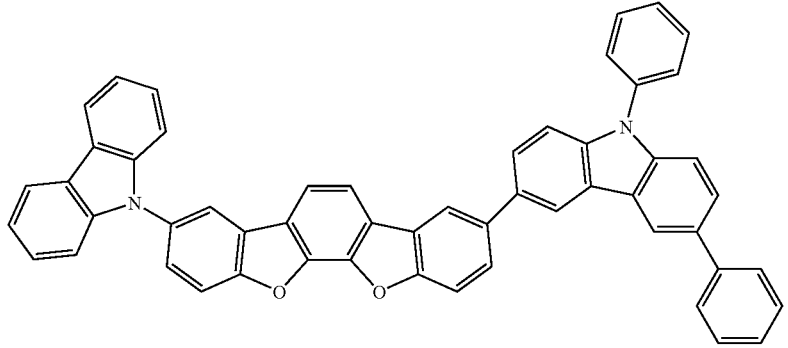
(1-75)
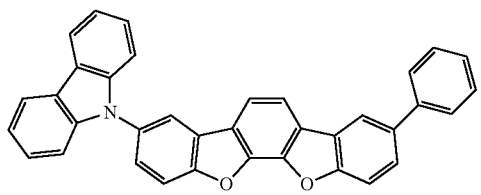
(1-76)
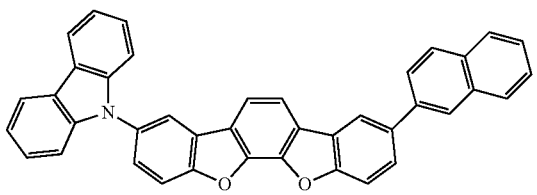
[Chem 22]
(1-77)
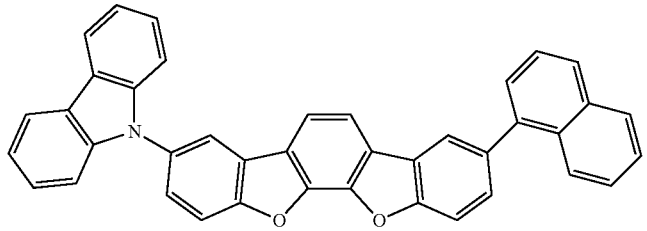
(1-78)
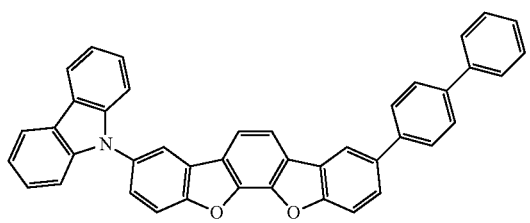
(1-79)
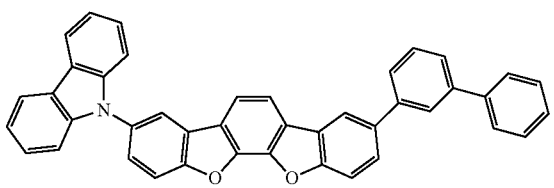
(1-80)
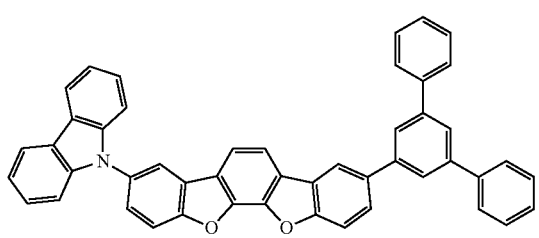
(1-81)
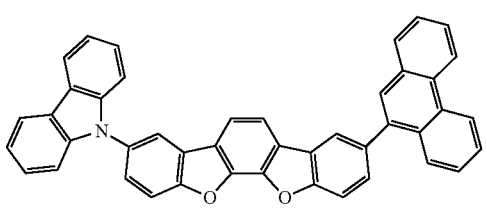

-continued
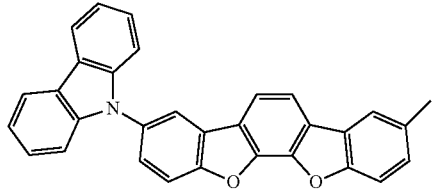
(1-82)
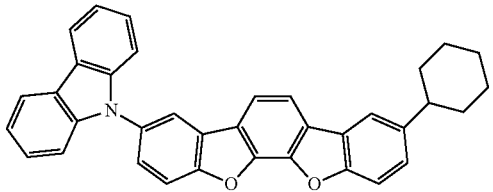
(1-83)
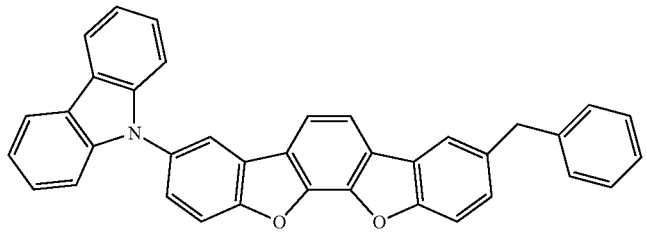
(1-84)
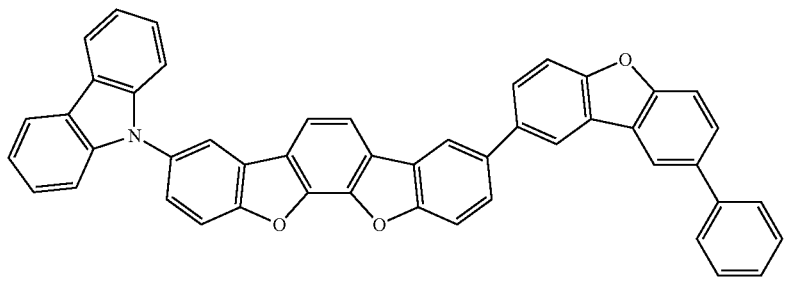
(1-85)
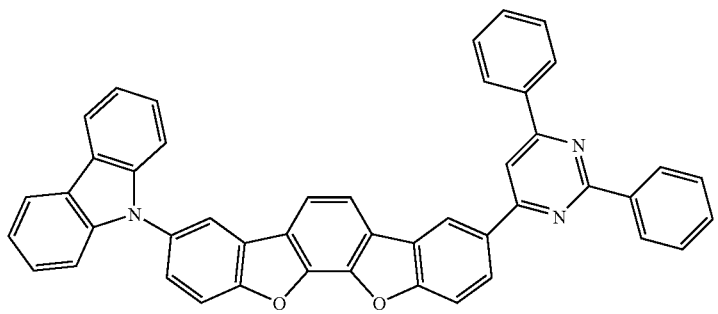
(1-86)
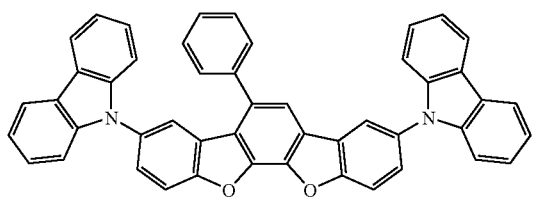
(1-87)
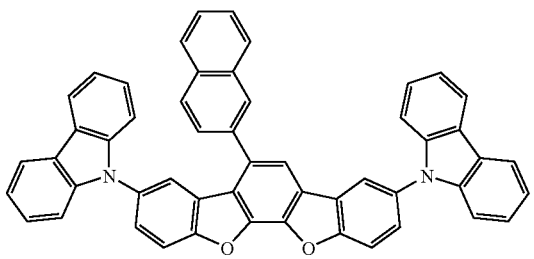
(1-88)
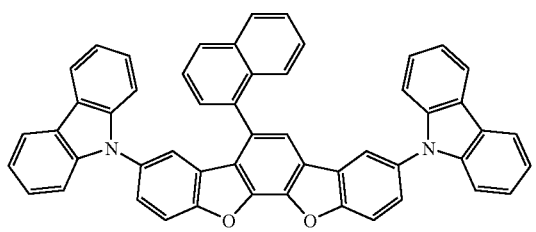
(1-89)
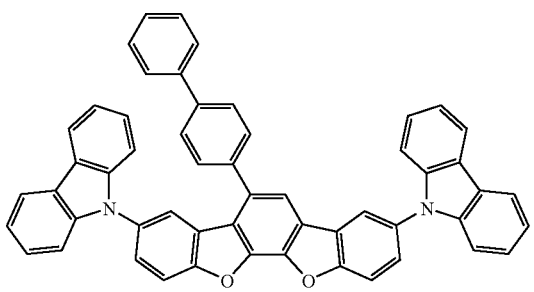
(1-90)

-continued
(1-91)
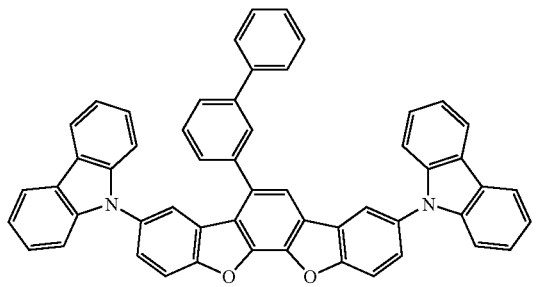
(1-92)
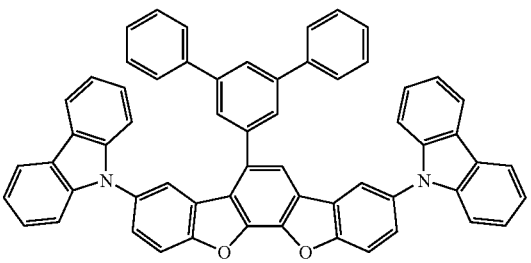
(1-93)
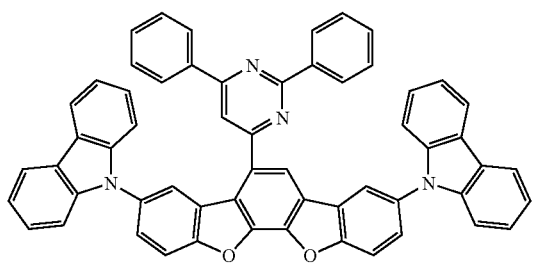
(1-94)
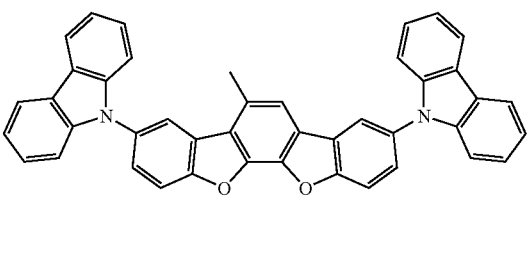
(1-95)
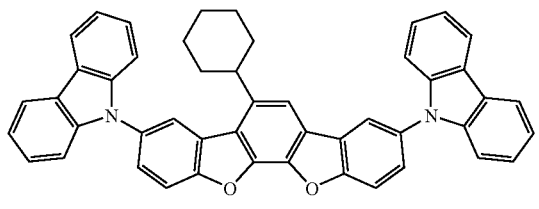
(1-96)
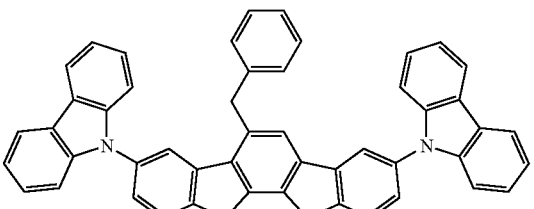
(1-97)
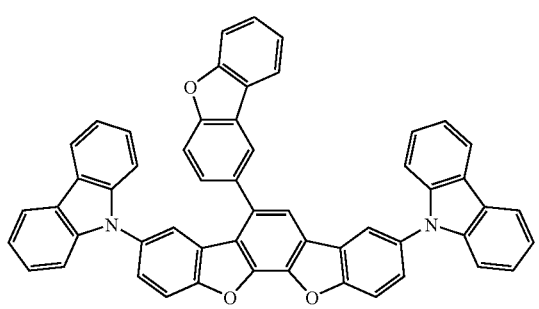
(1-98)
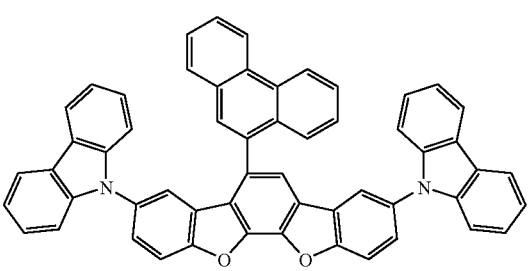
[Chem 23]
(1-99)
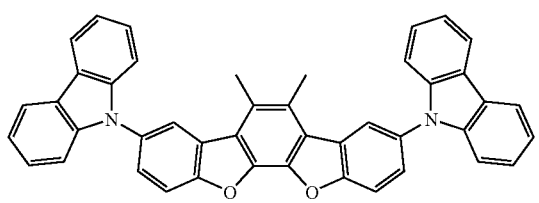
(1-100)
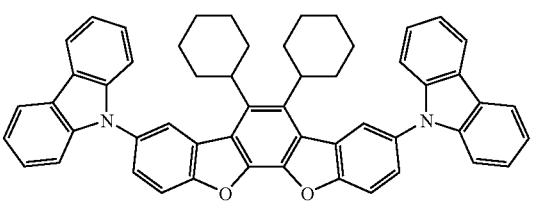

-continued
(1-101)
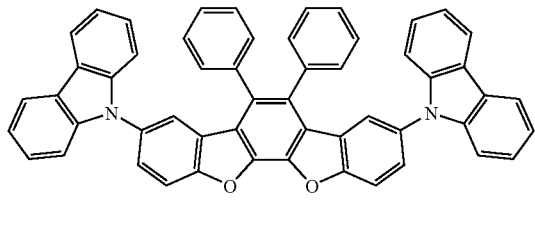
(1-102)
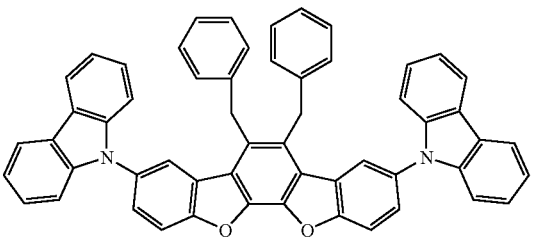
(1-103)
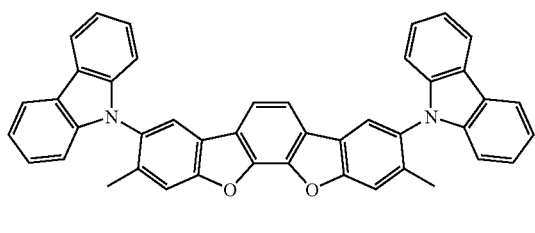
(1-104)
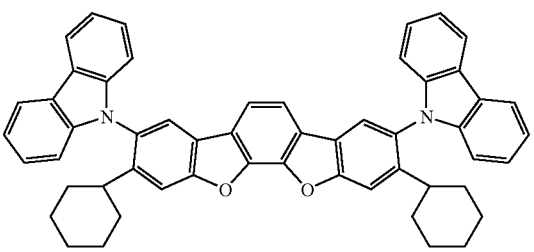
(1-105)
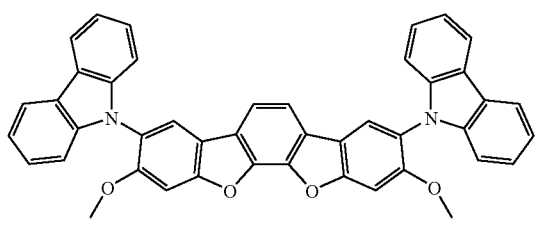
(1-106)
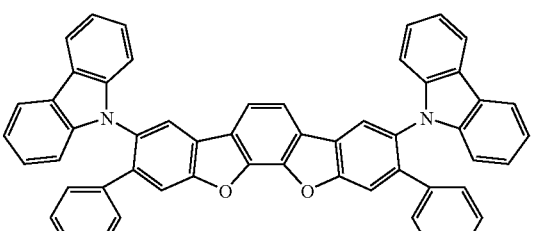
(1-107)
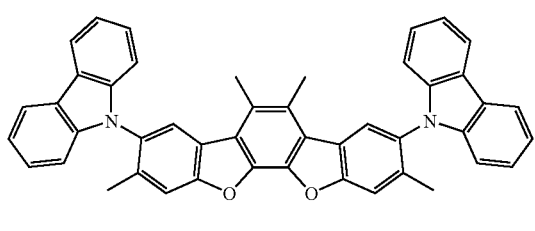
(1-108)
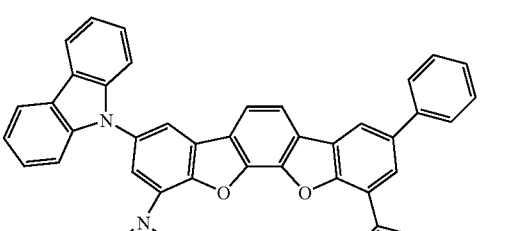
(1-109)
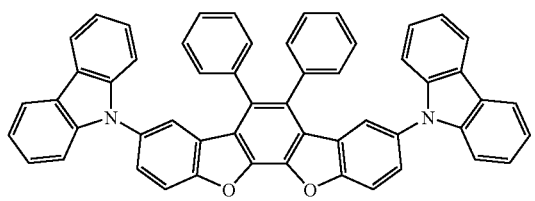
(1-110)
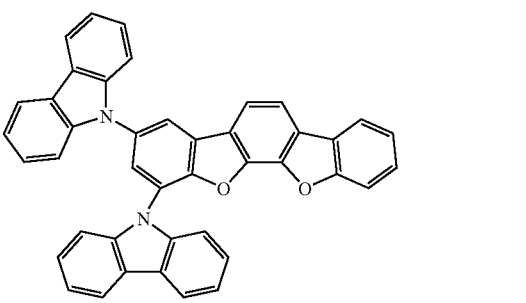

(1-111)
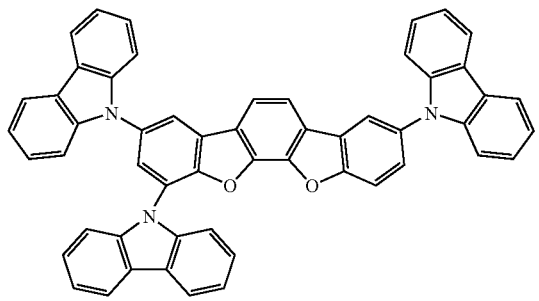
(1-112)
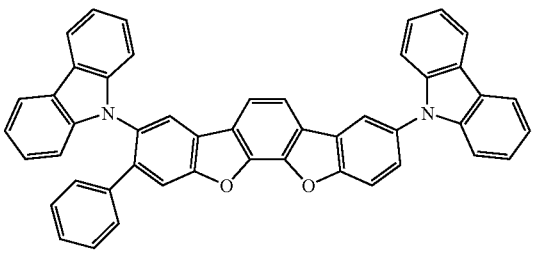
(1-113)
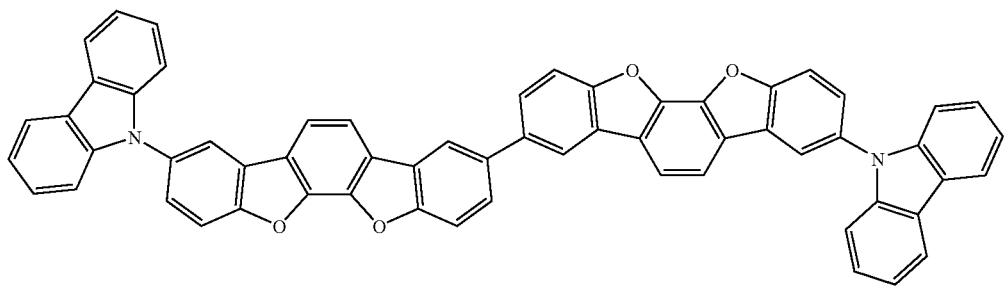
(1-114)
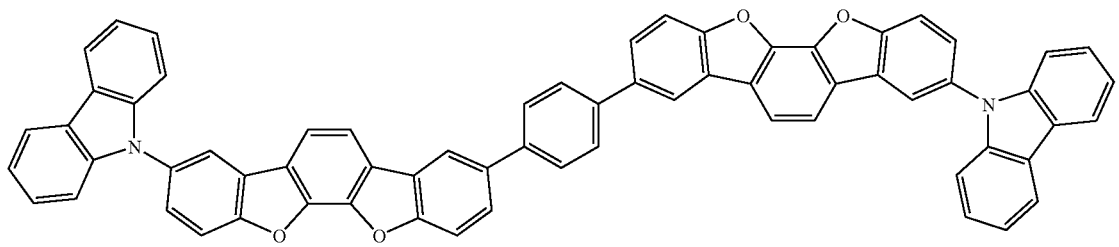
[Chem 24]
(1-115)
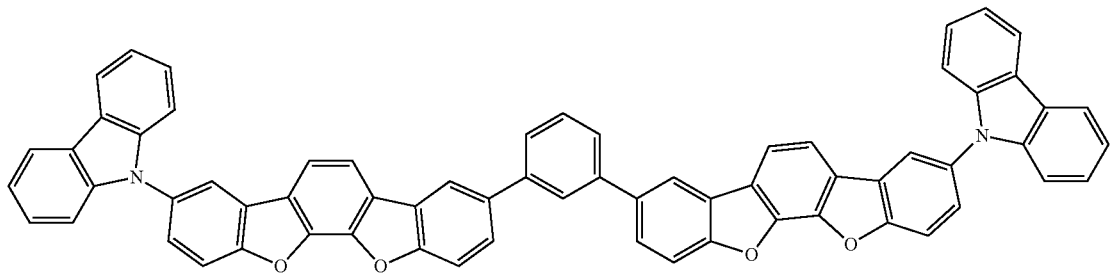

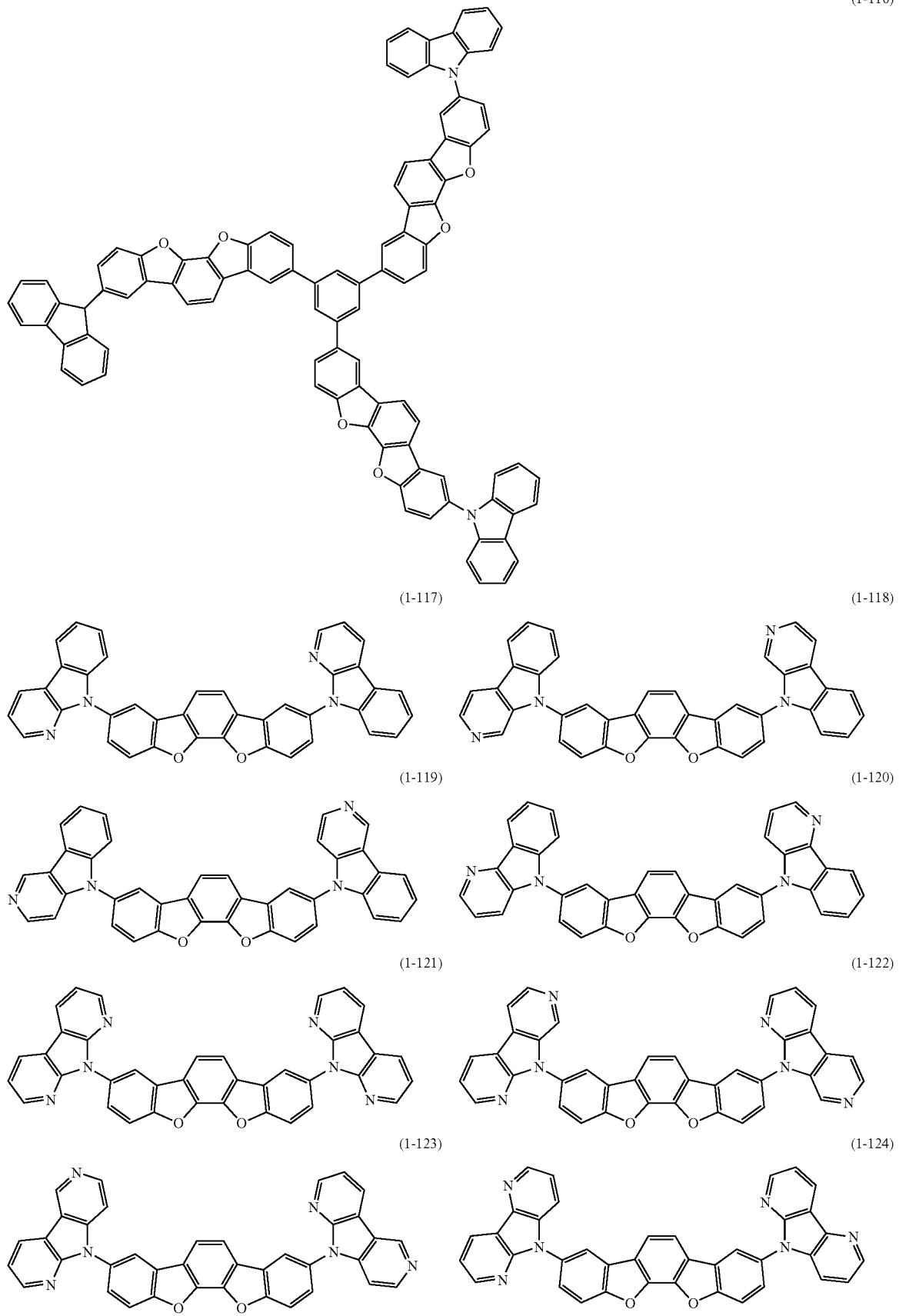

-continued
(1-125)
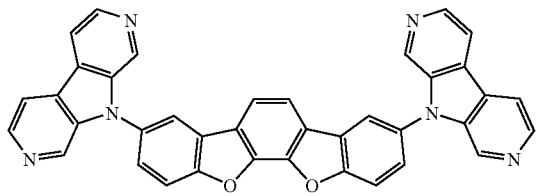
(1-126)
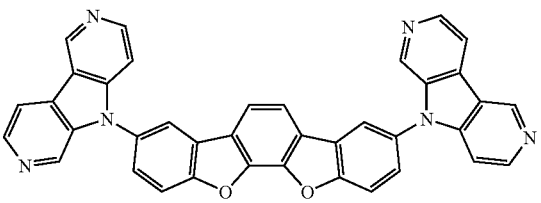
(1-127)
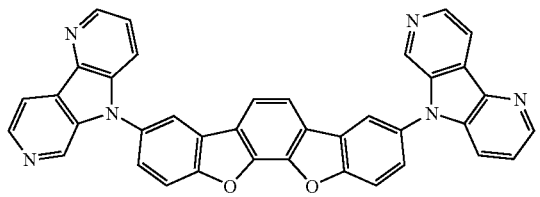
(1-128)
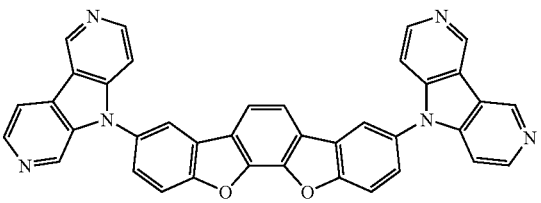
(1-129)
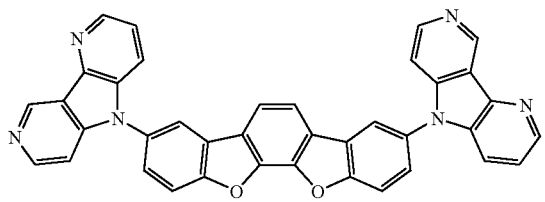
(1-130)
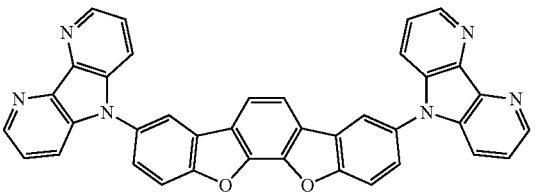
(1-131)
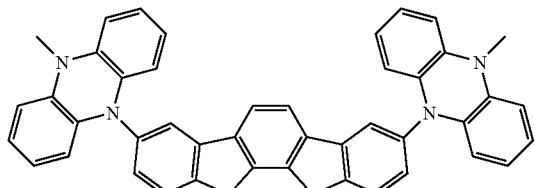
(1-132)
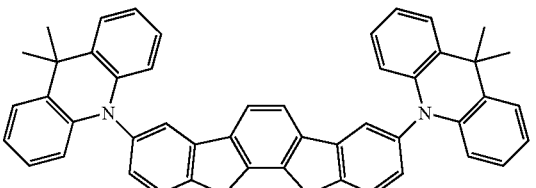
(1-133)
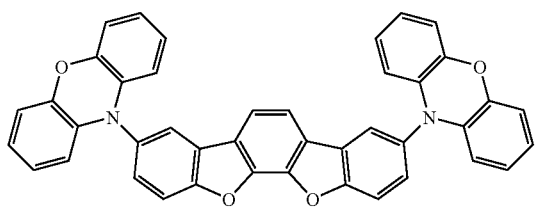
(1-134)
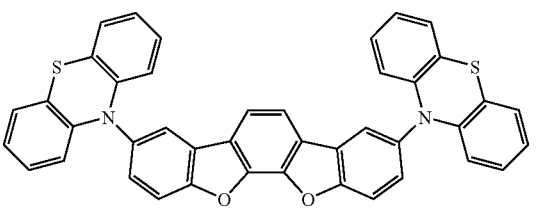
[Chem 25]
(1-135)
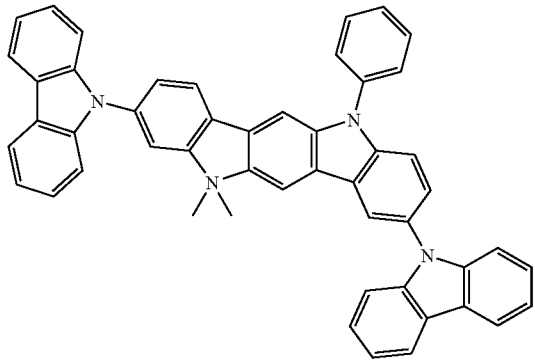
(1-136)
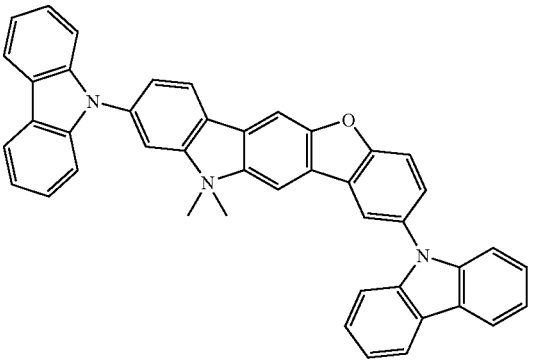

-continued
(1-137)
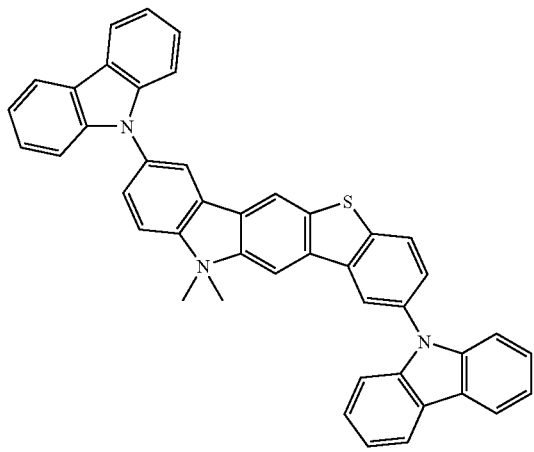
(1-138)
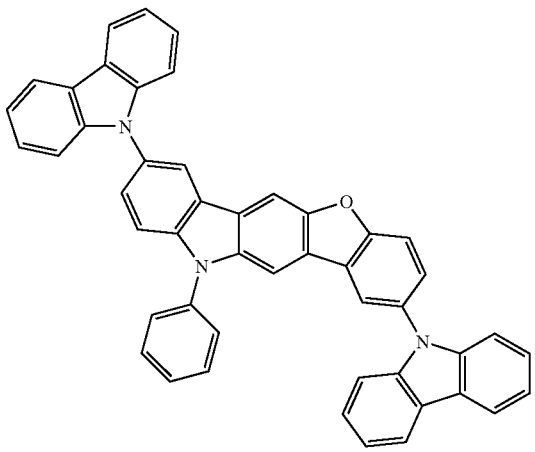
(1-139)
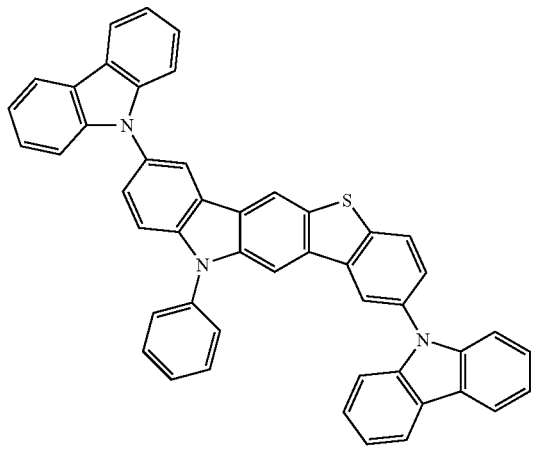
(1-140)
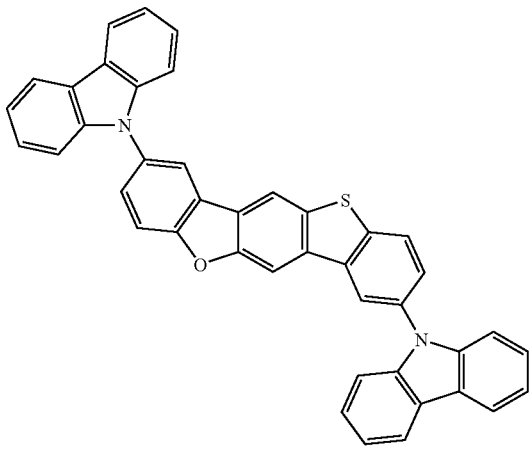
(1-141)
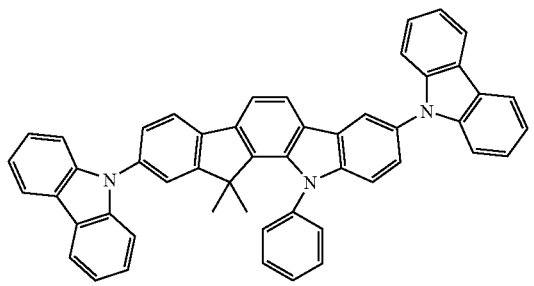
(1-142)
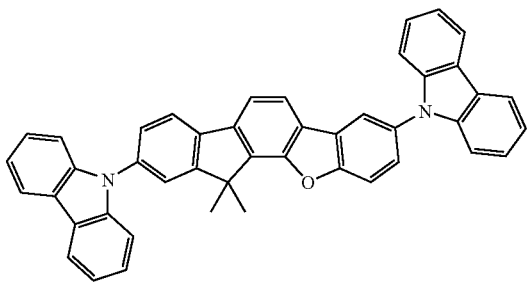
(1-143)
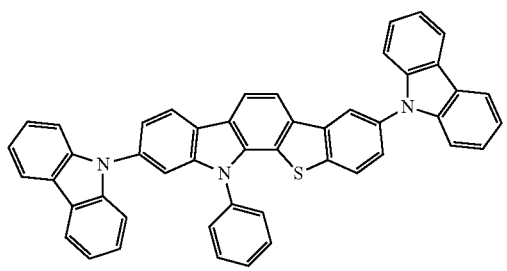
(1-144)
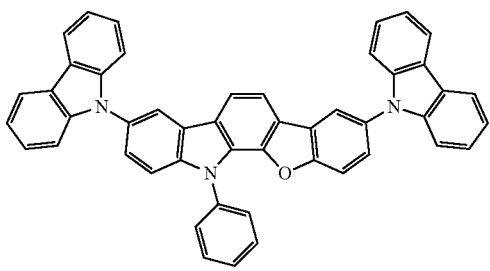

-continued
(1-145)
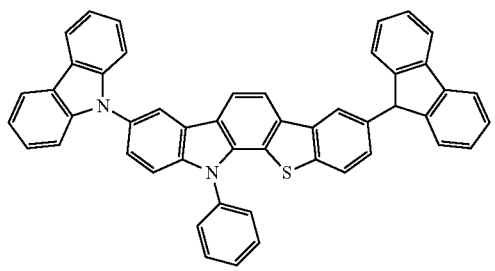
(1-146)
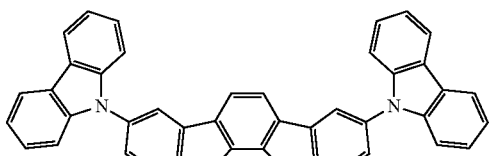
[Chem 26]
(1-147)
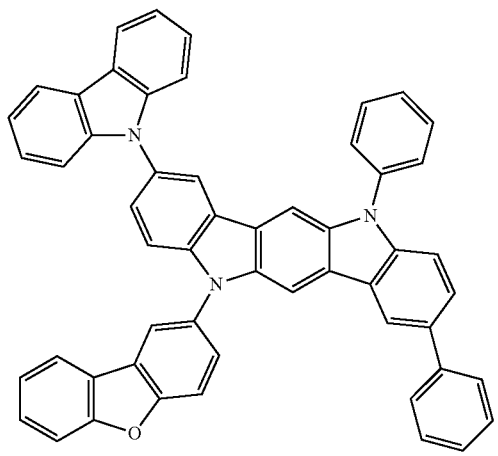
(1-148)
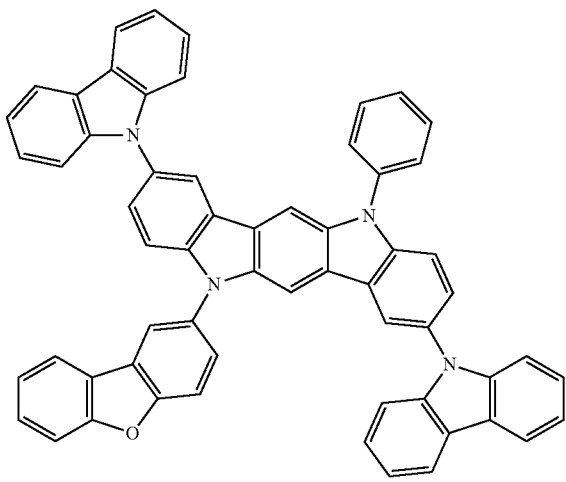
(1-149)
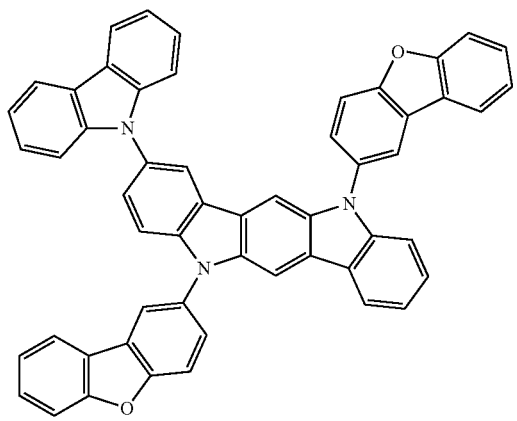
(1-150)
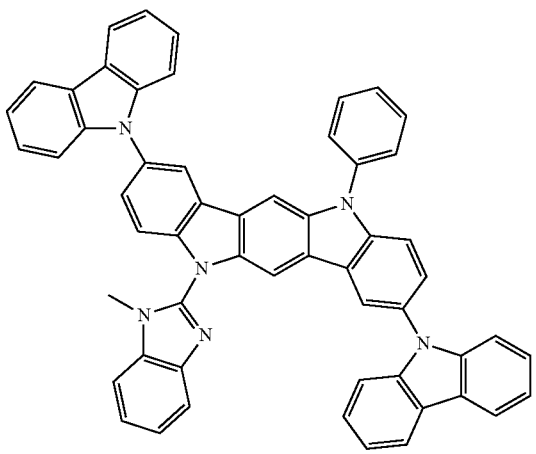
(1-151)
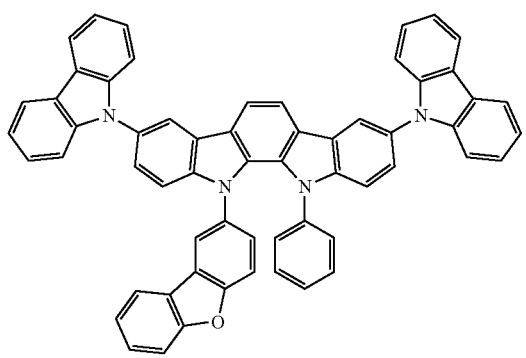
(1-152)
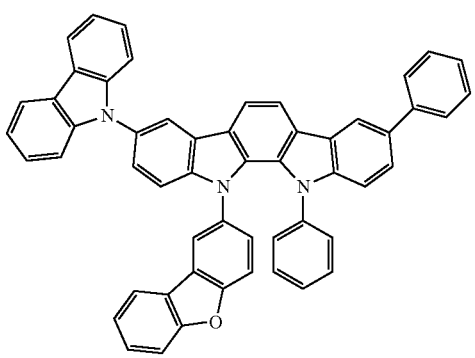

-continued
(1-153)
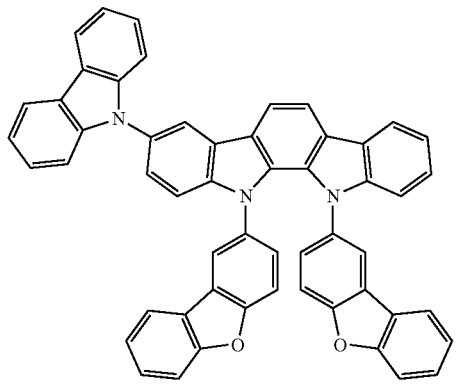
(1-154)
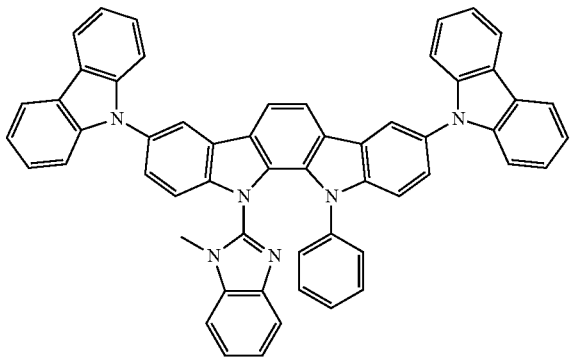
[Chem 27]
(1-155)
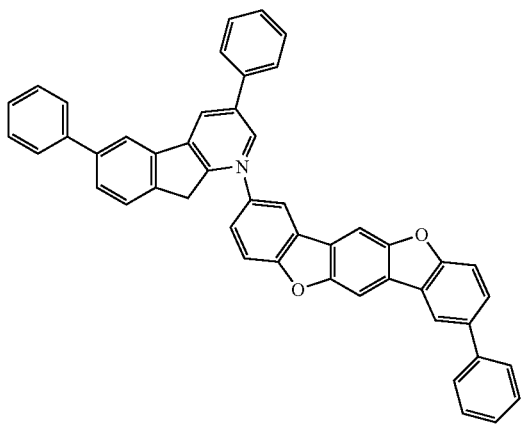
(1-156)
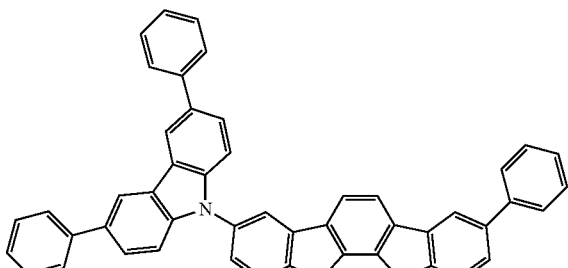
(1-157)
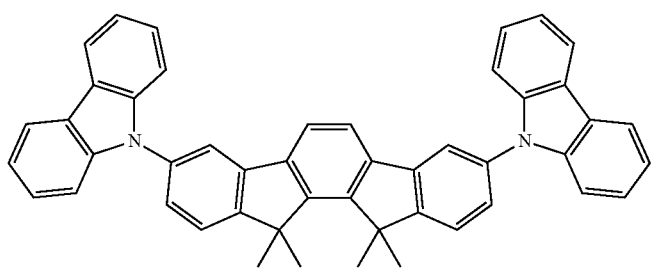
(1-158)
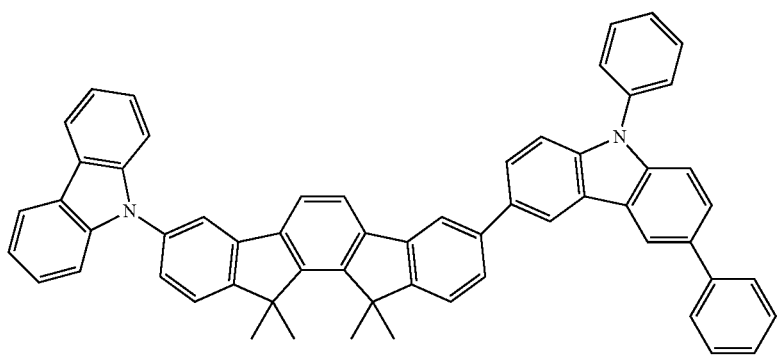

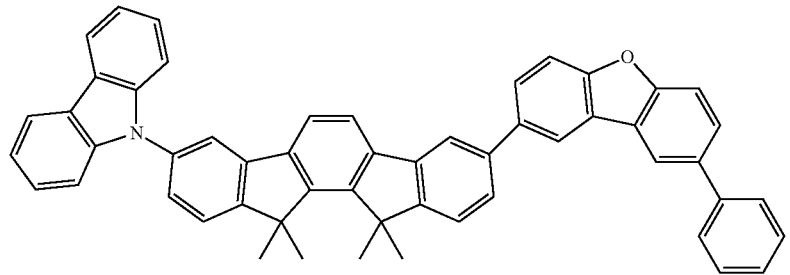
(1-159)
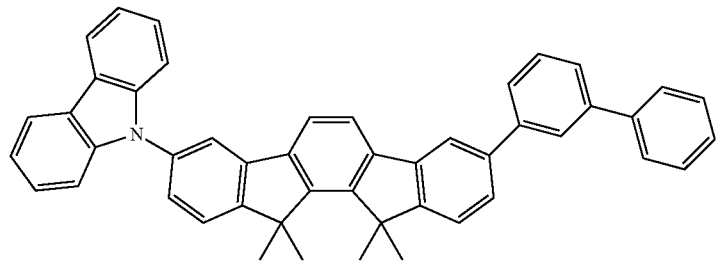
(1-160)
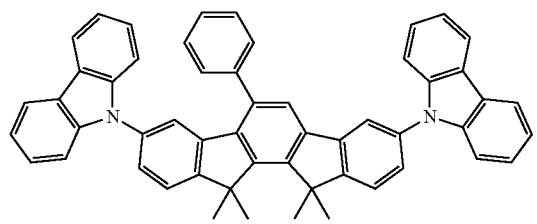
(1-161)
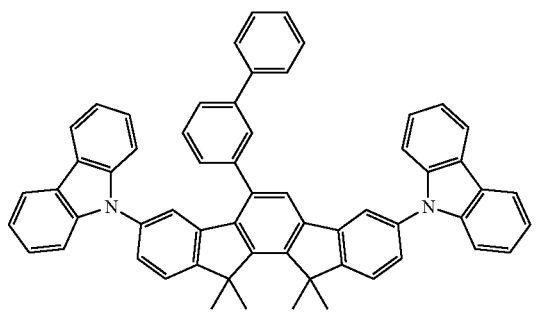
(1-162)
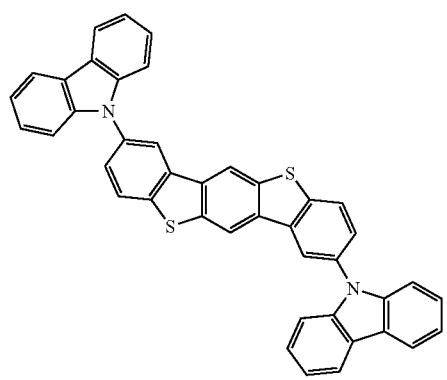
(1-163)
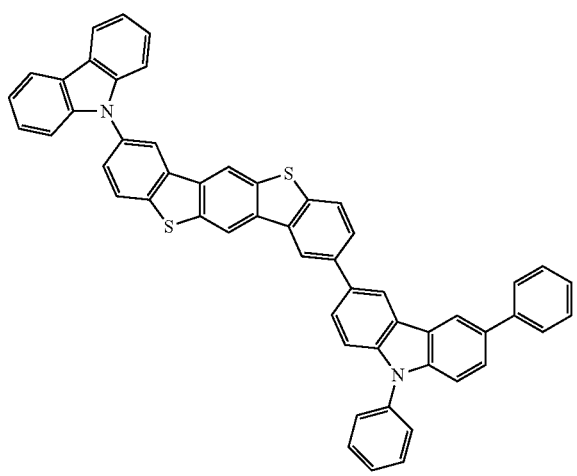
(1-164)

-continued
(1-165)
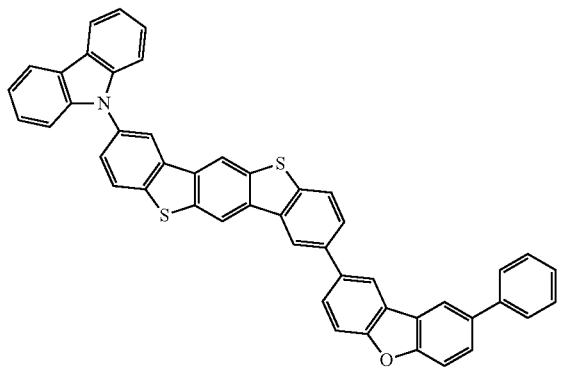
(1-166)
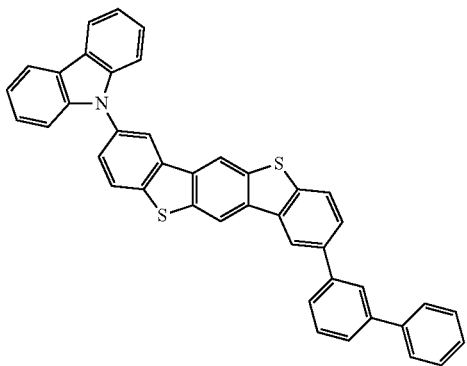
(1-167)
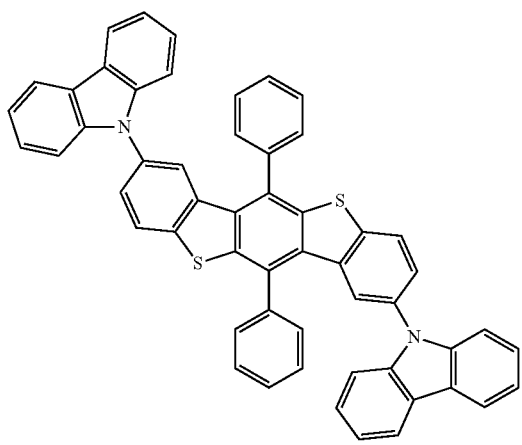
(1-168)
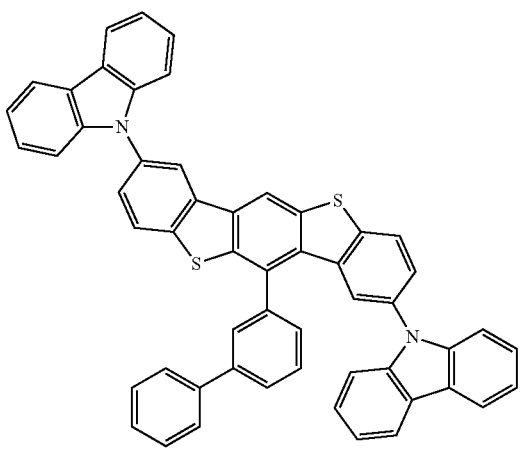
[Chem 28]
(1-169)
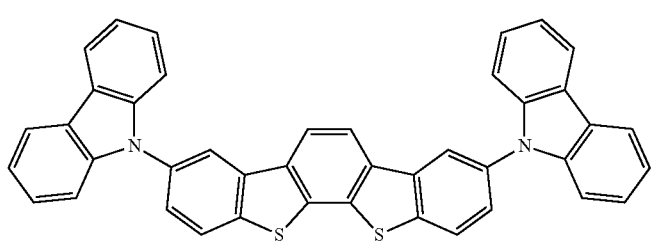
(1-170)
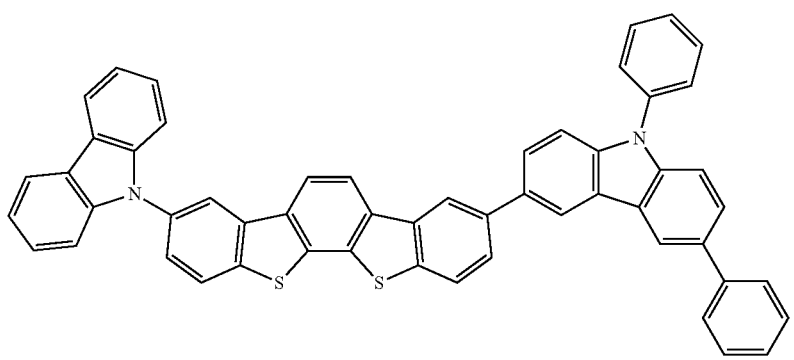

-continued
(1-171)
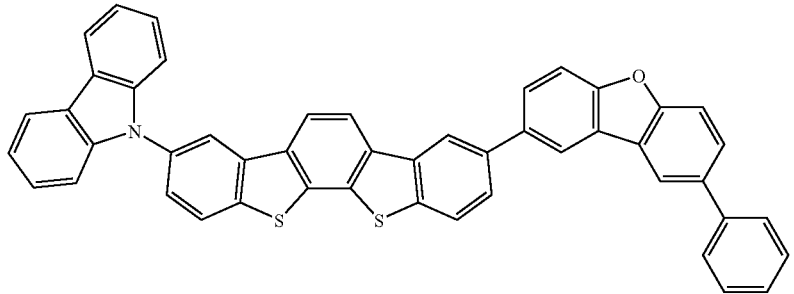
(1-172)
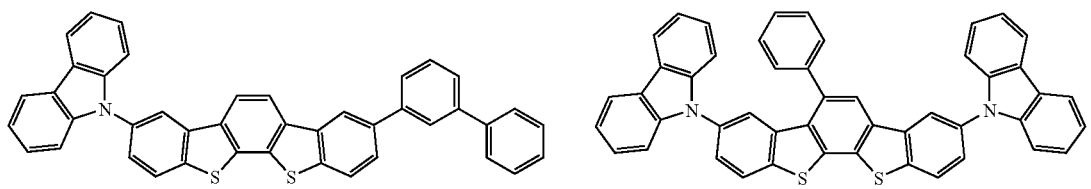
(1-173)
(1-174)
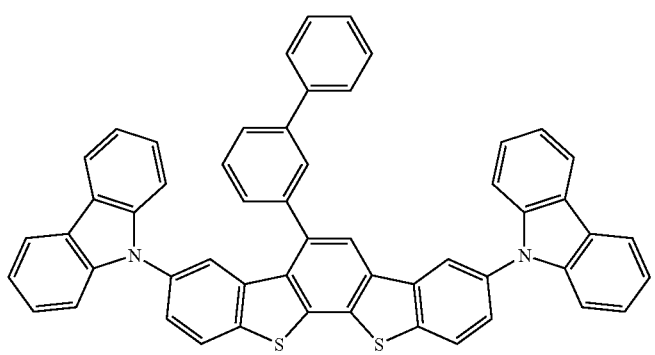
(1-175)
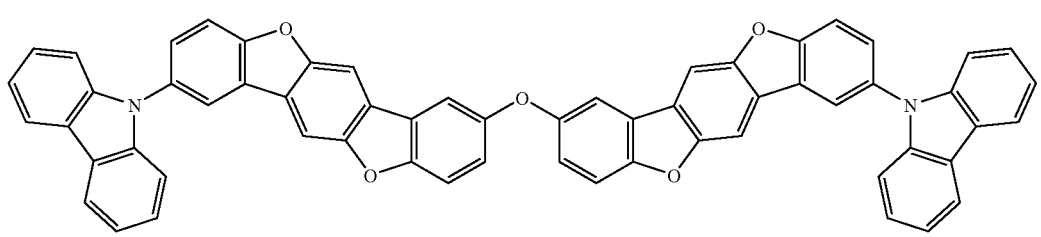
(1-176)
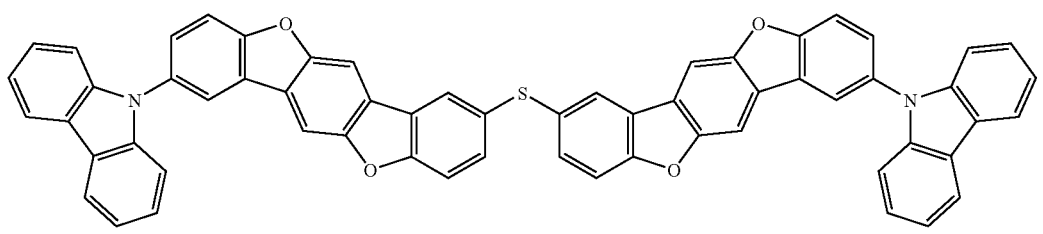
(1-177)
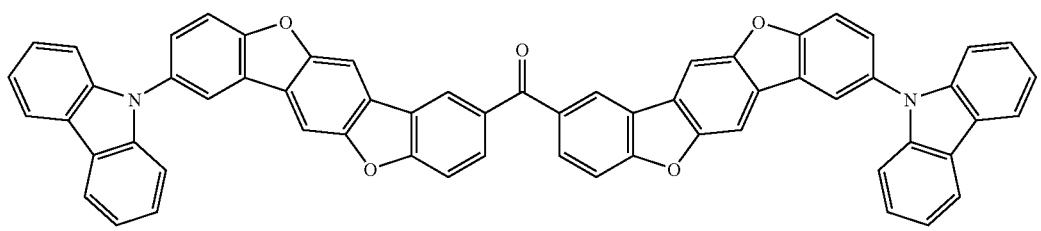

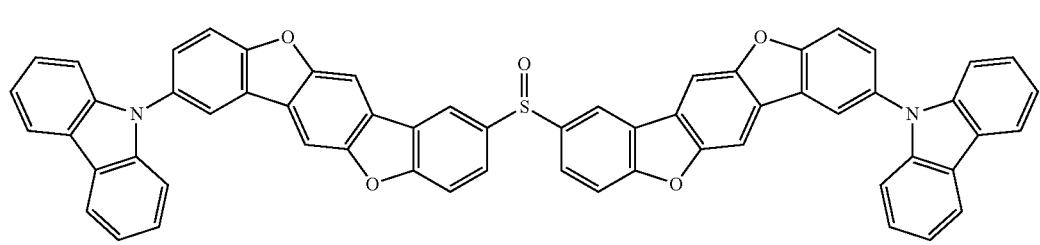
(1-178)
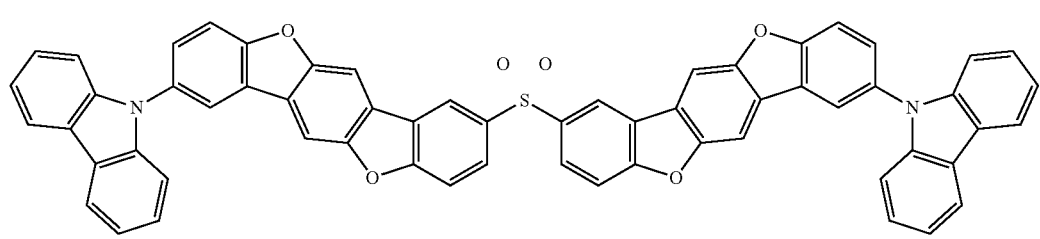
(1-179)
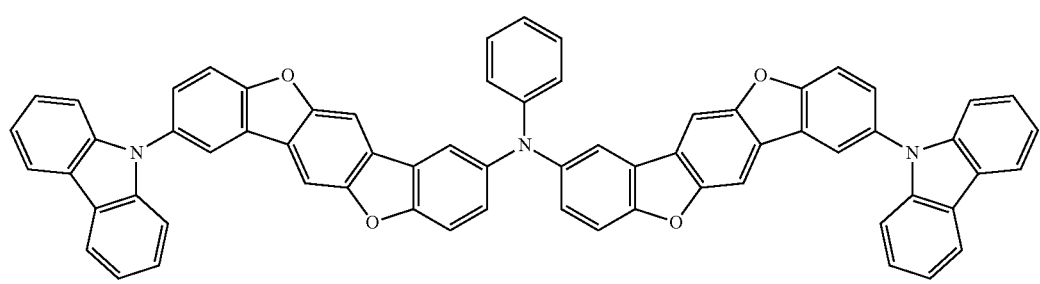
(1-180)
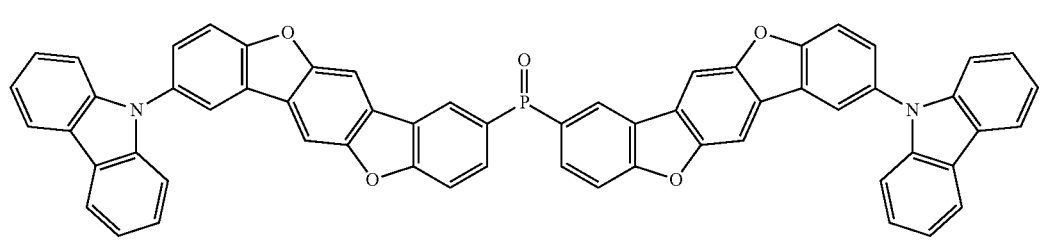
(1-181)
[Chem 29]
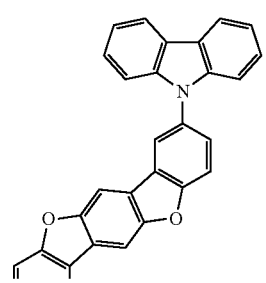
(1-182)

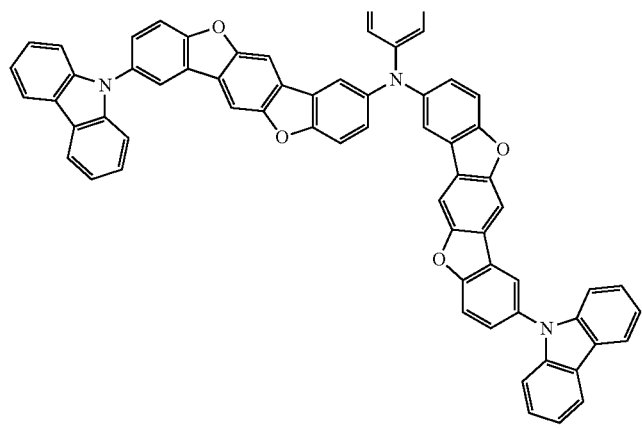
(1-183)
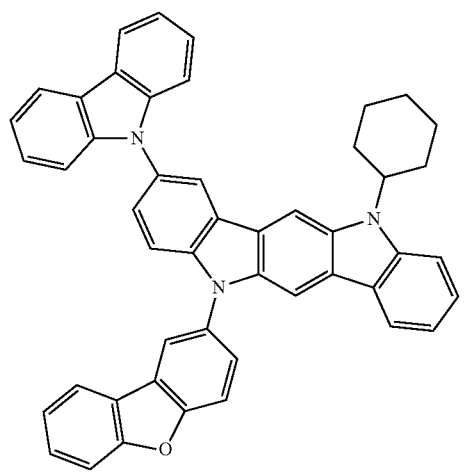
(1-184)
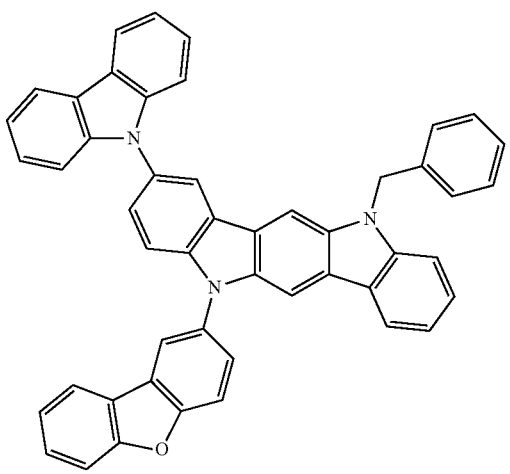
(1-185)
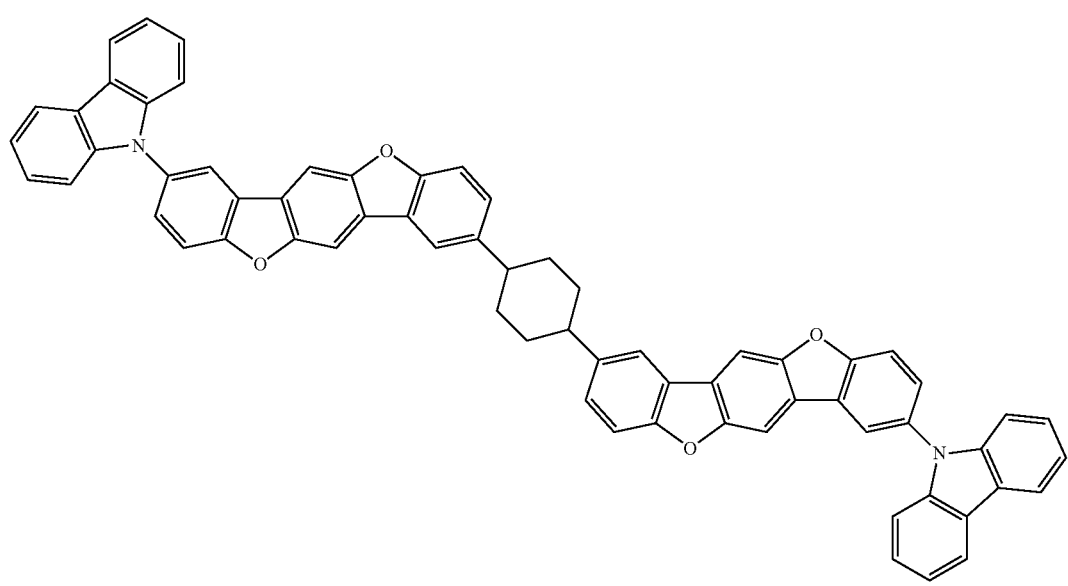

(1-186)
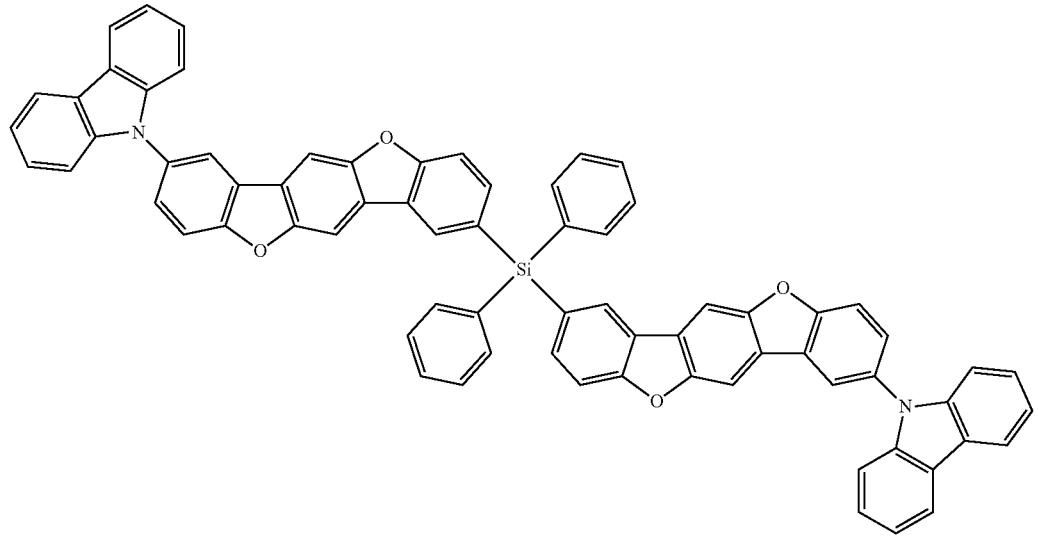
(1-187)
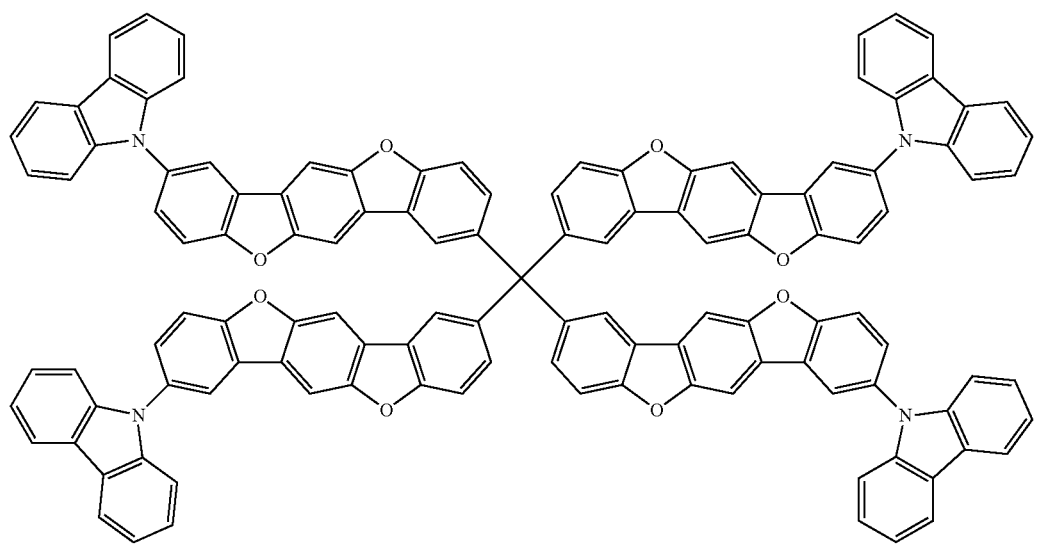
(1-188)
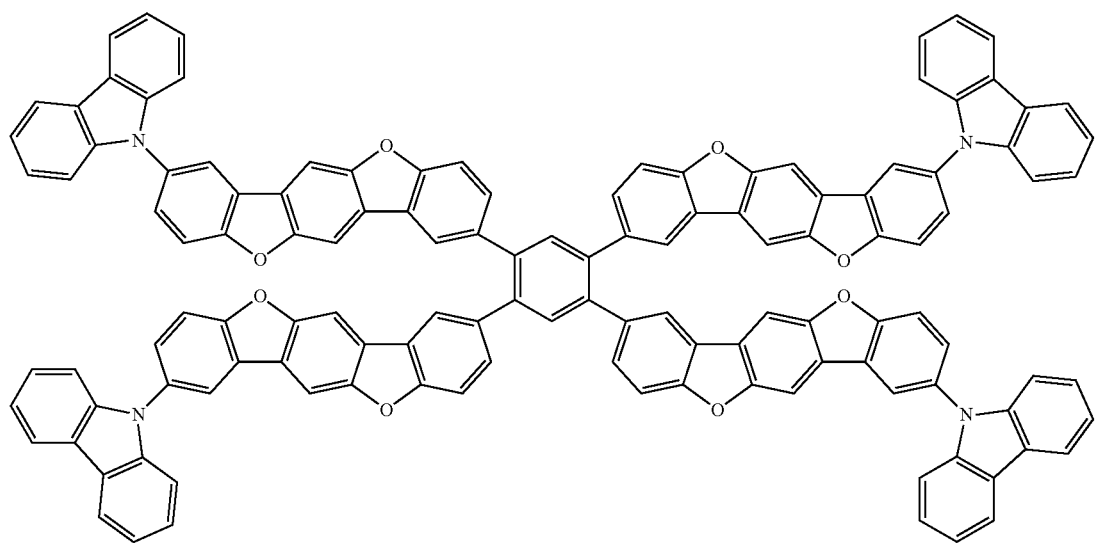

(1-189)
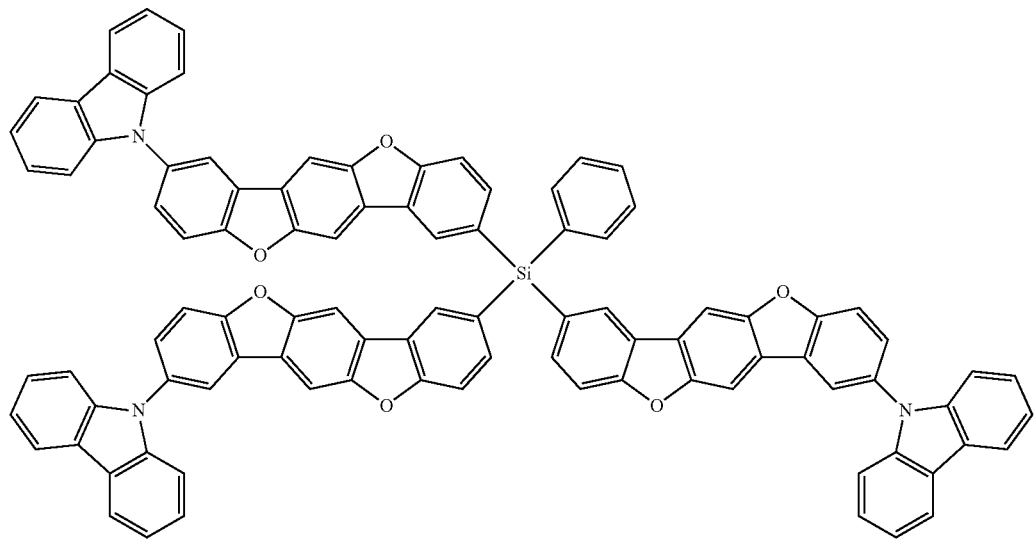
(1-190)
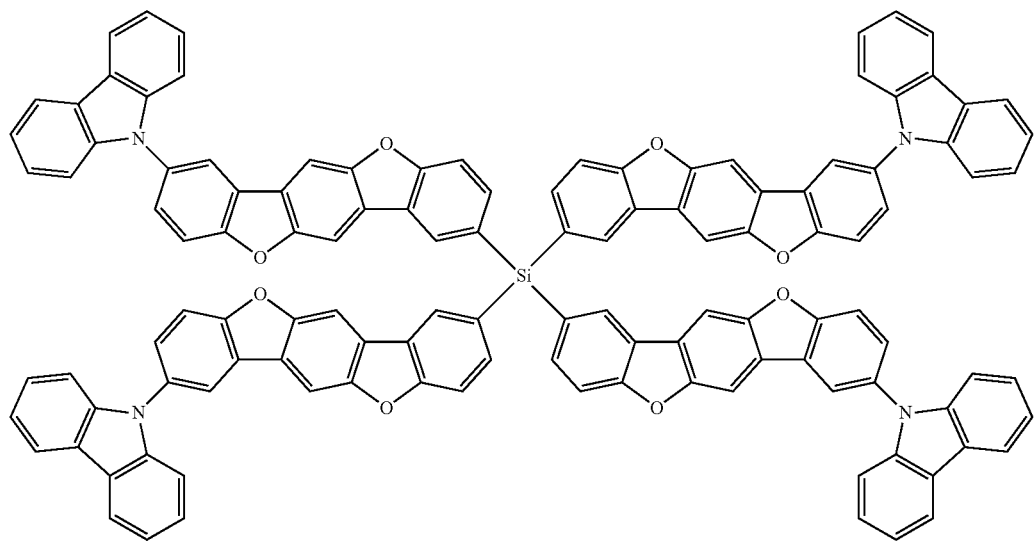
[Chem 30]
(1-191)
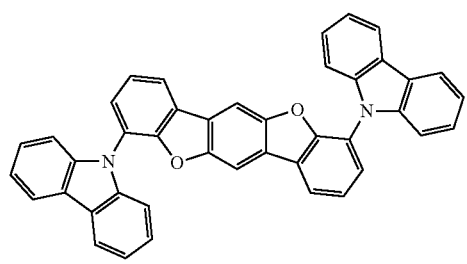
(1-192)
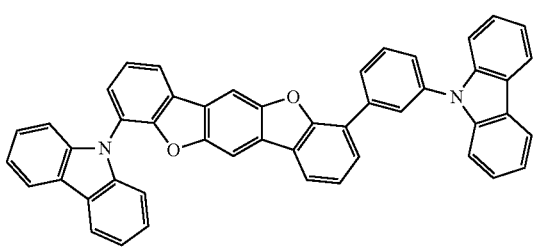

-continued
(1-193)
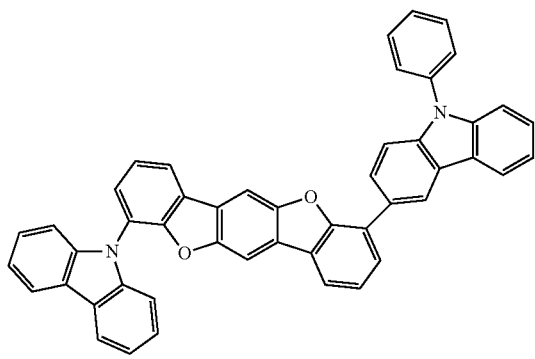
(1-194)
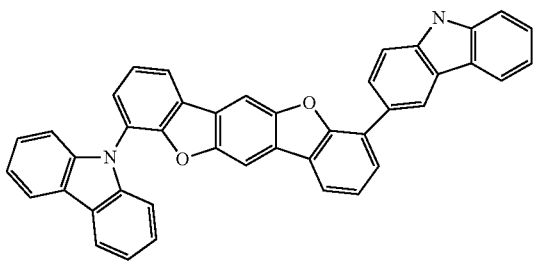
(1-195)
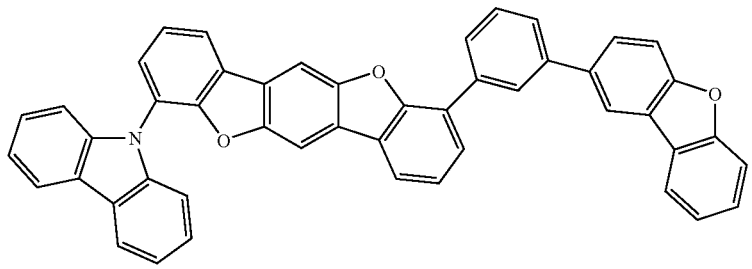
(1-196)
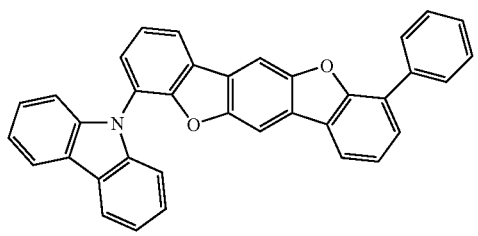
(1-197)
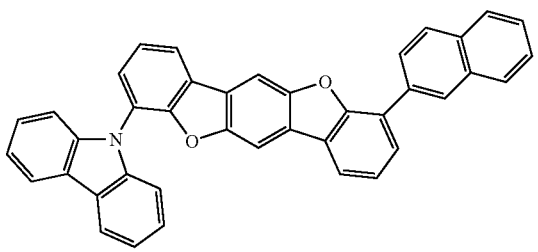
(1-198)
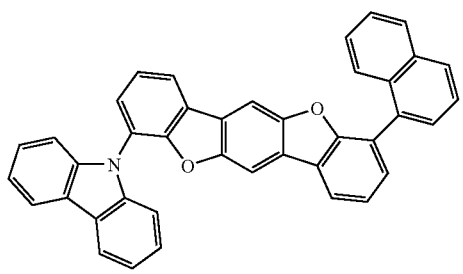
(1-199)
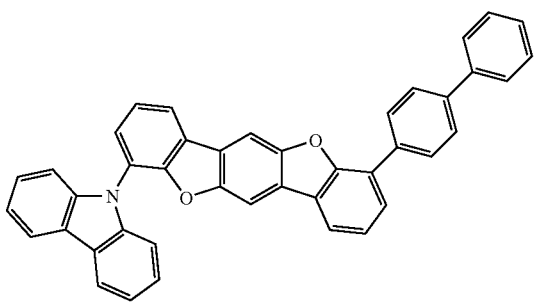
(1-200)
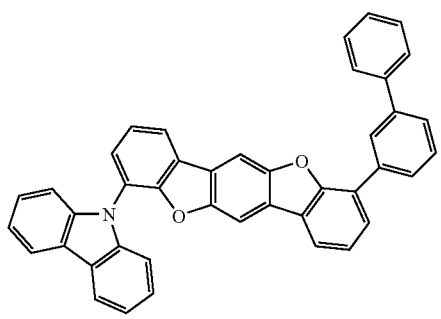
(1-201)
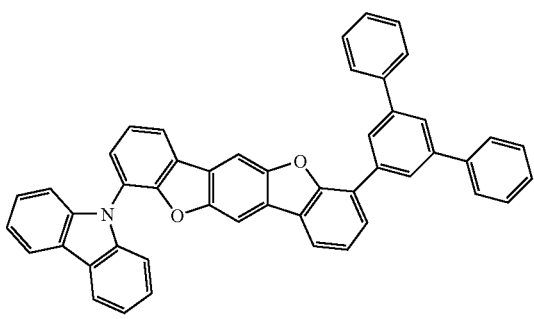

-continued
(1-202)
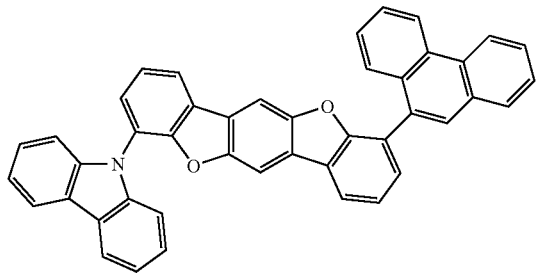
(1-203)
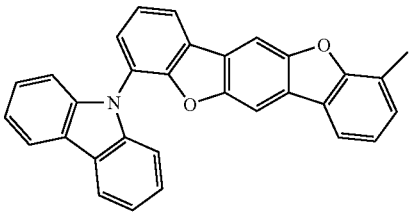
(1-204)
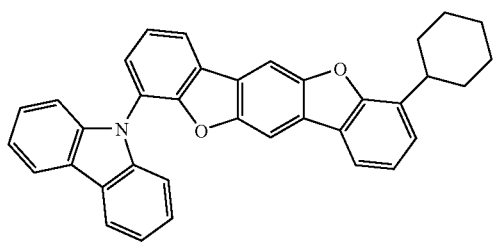
(1-205)
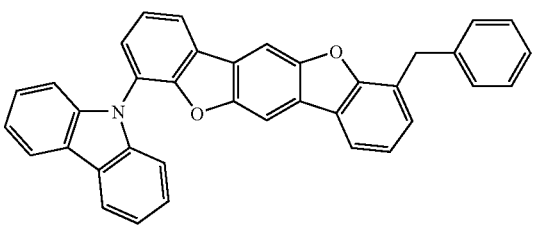
(1-206)
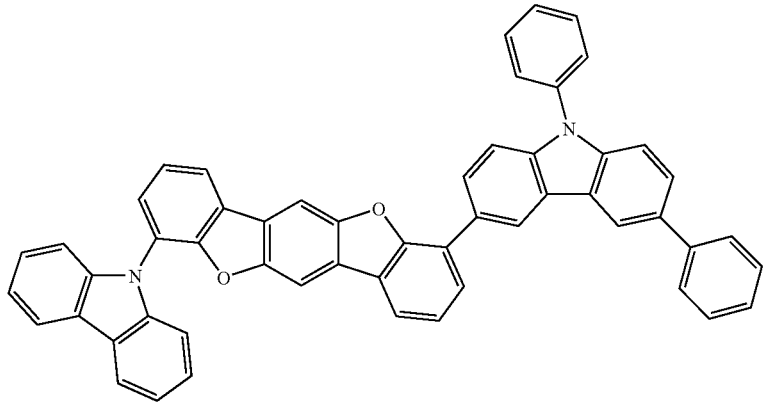
(1-207)
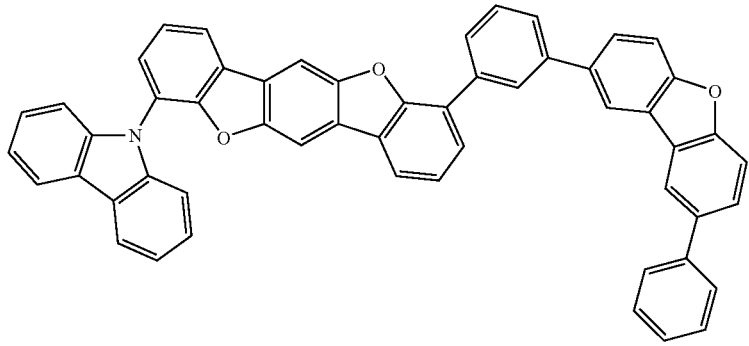
(1-208)
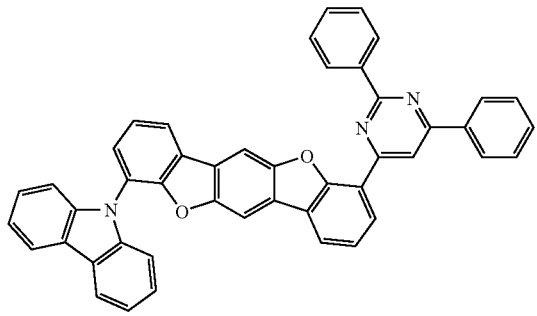

[Chem 31]
(1-209)
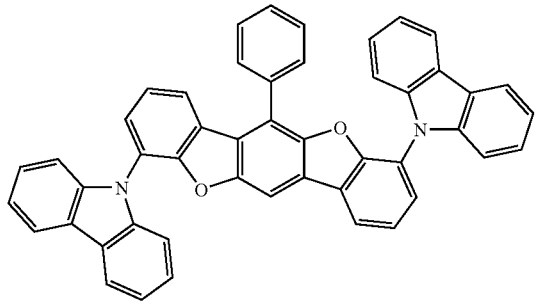
(1-210)
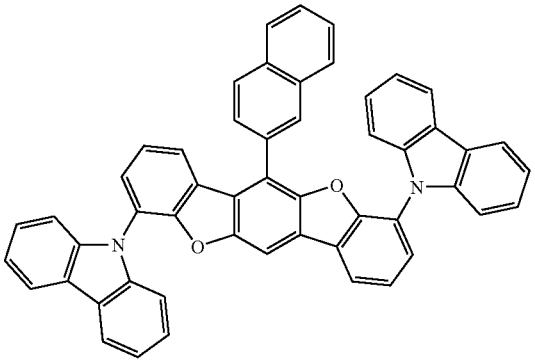
(1-211)
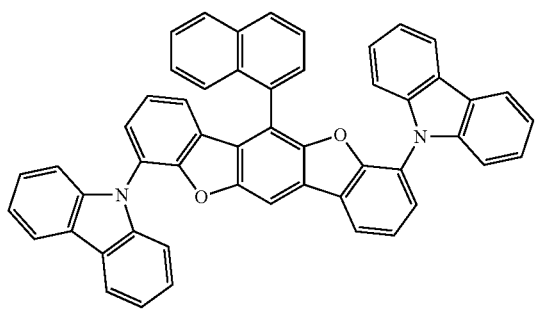
(1-212)
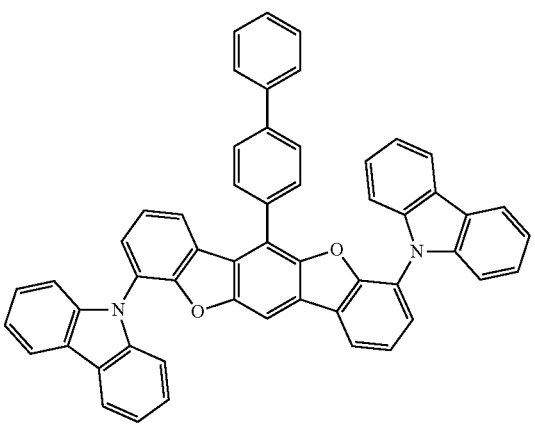
(1-213)
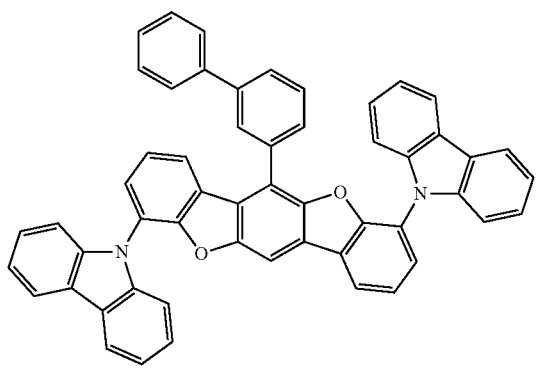
(1-214)
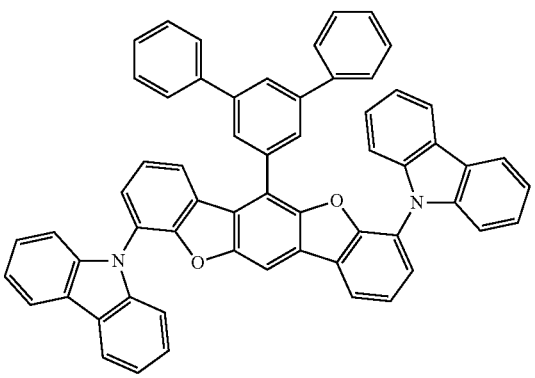
(1-215)
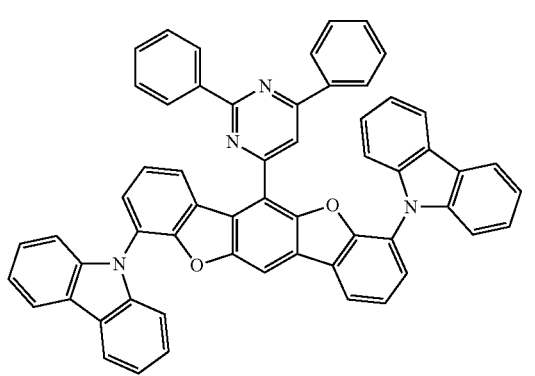
(1-216)
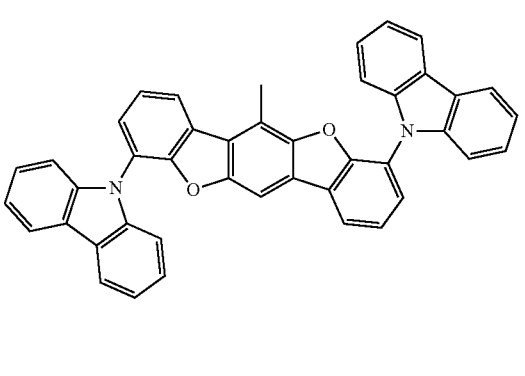

-continued
(1-217)
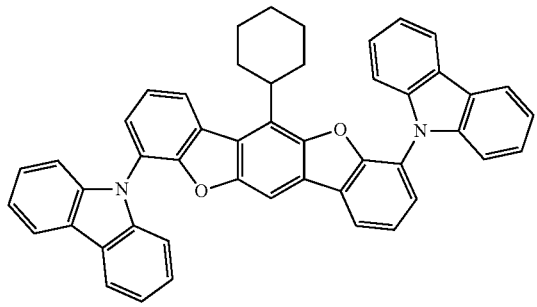
(1-218)
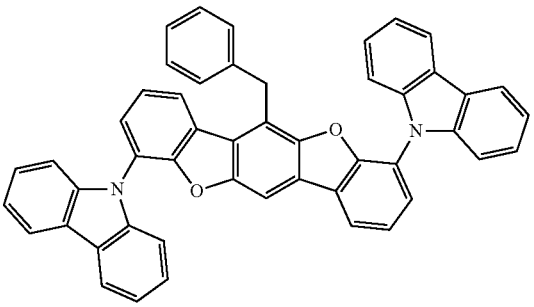
(1-219)
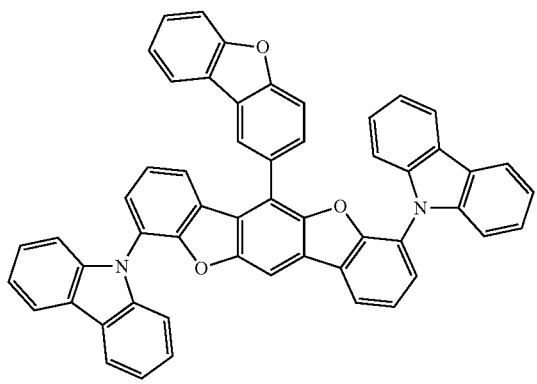
(1-220)
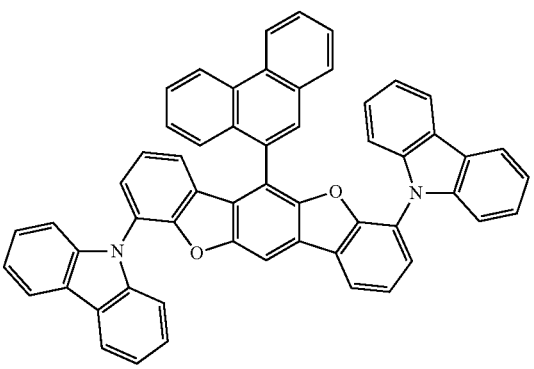
(1-221)
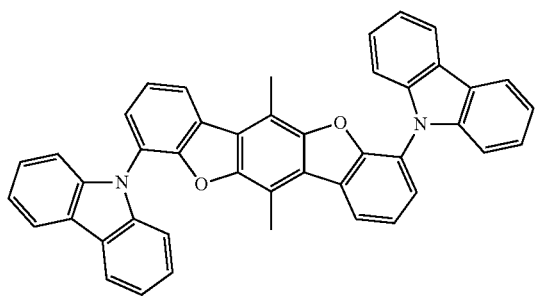
(1-222)
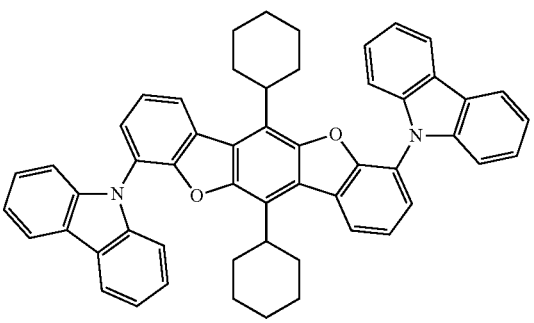
(1-223)
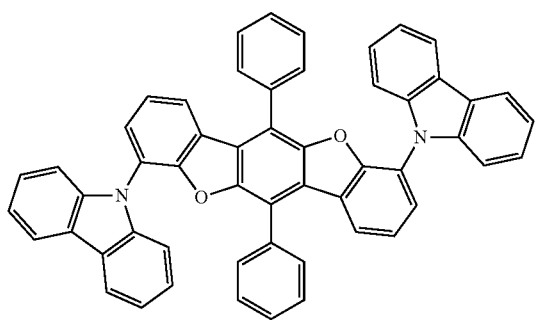

[Chem 32]
(1-224)
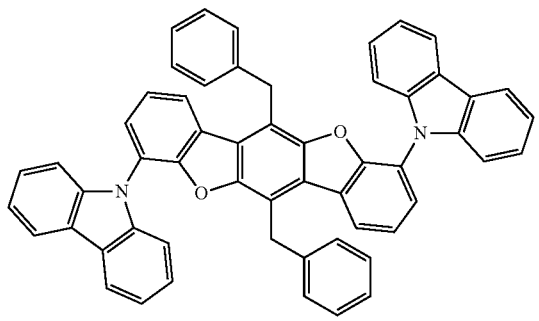
(1-225)
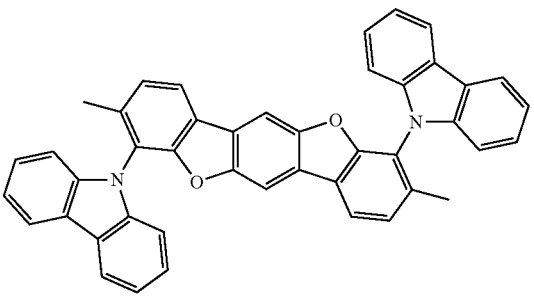
(1-226)
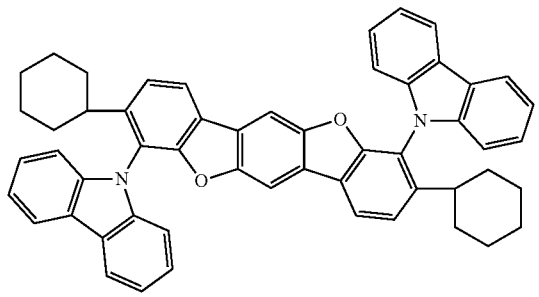
(1-227)
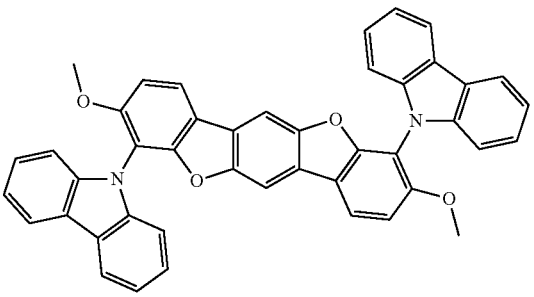
(1-228)
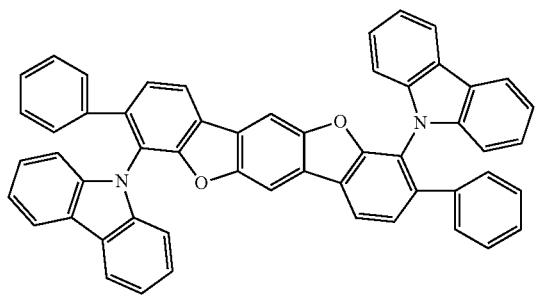
(1-229)
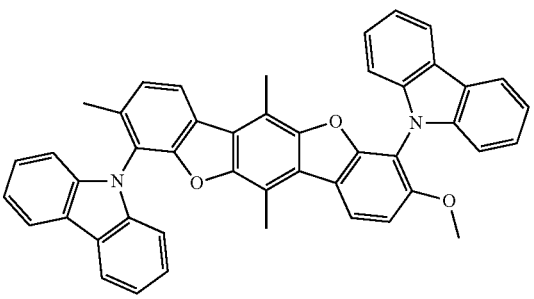
(1-230)
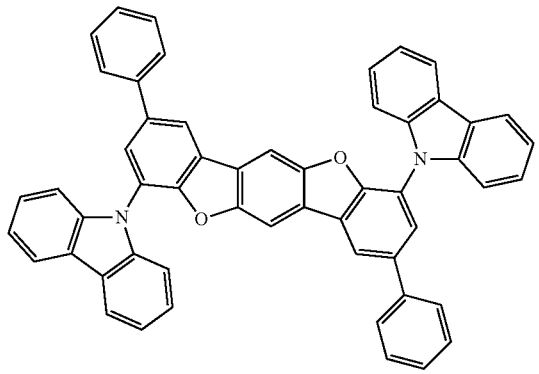
(1-231)
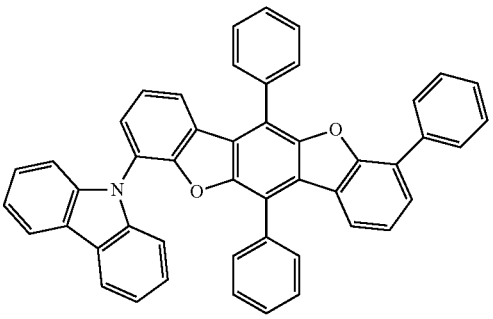

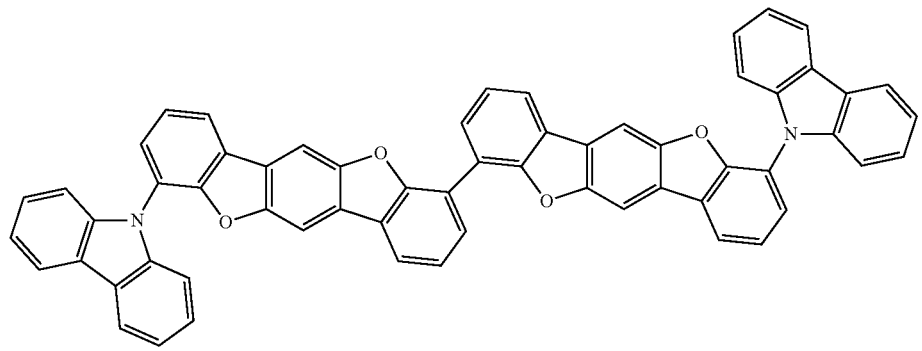
(1-232)
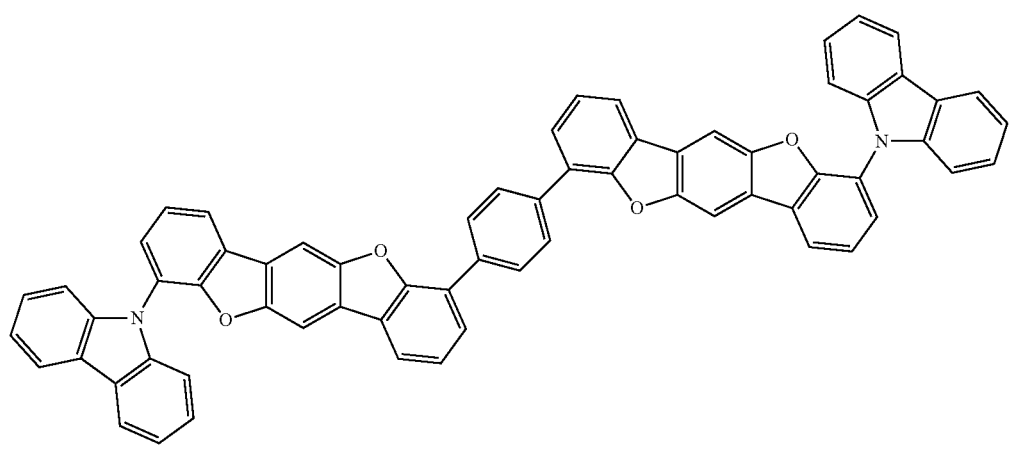
(1-233)
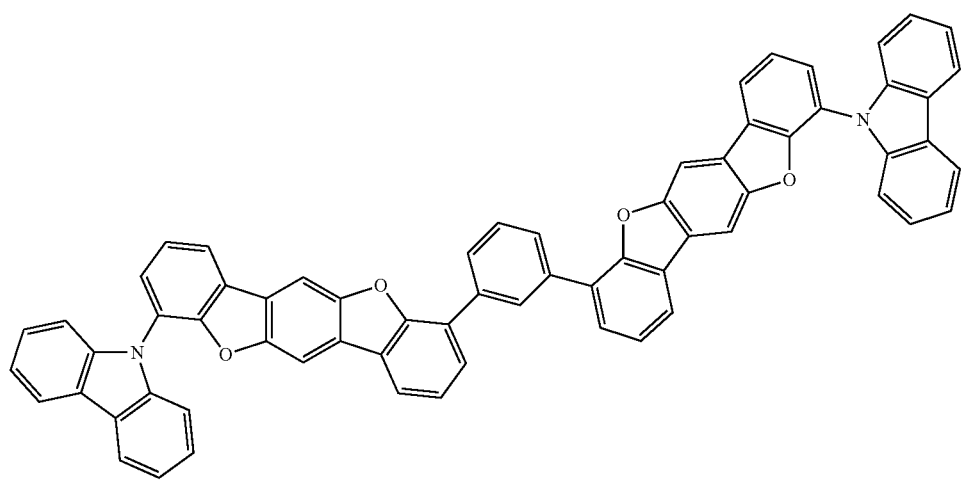
(1-234)

(1-235)
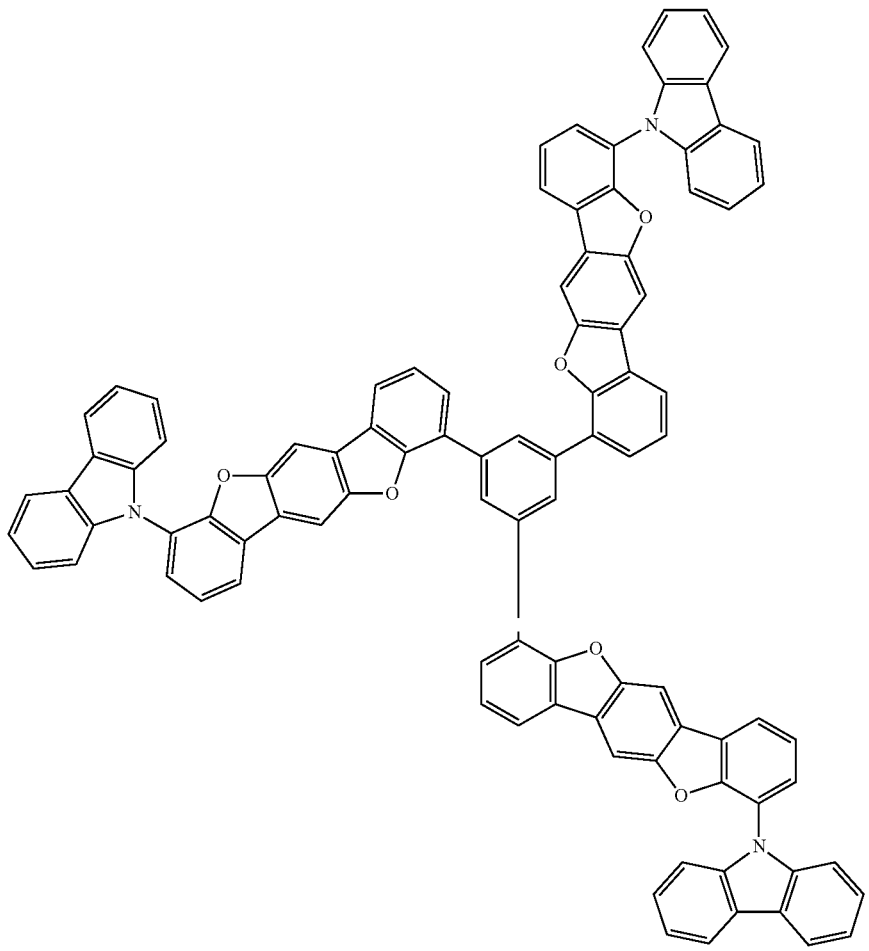
[Chem 33]
(1-236) (1-237)
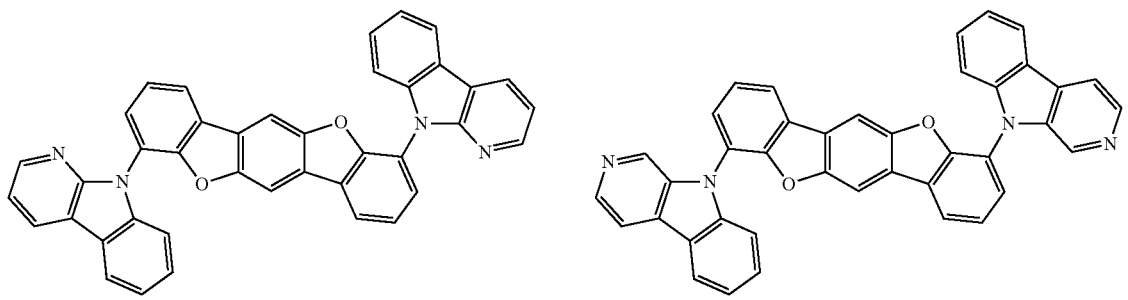
(1-238) (1-239)
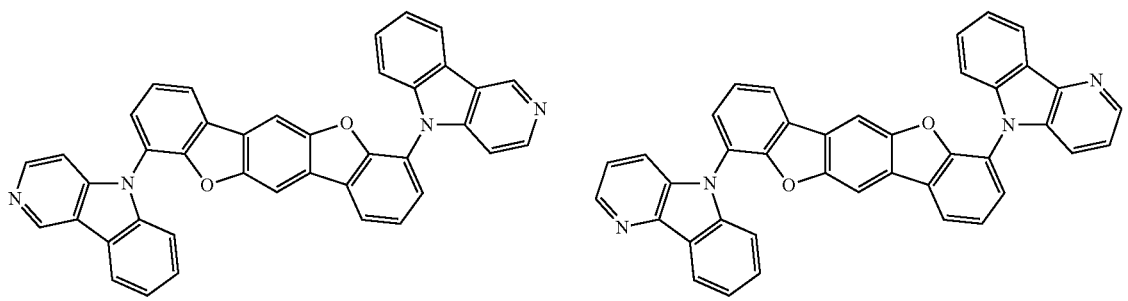

-continued
(1-240)
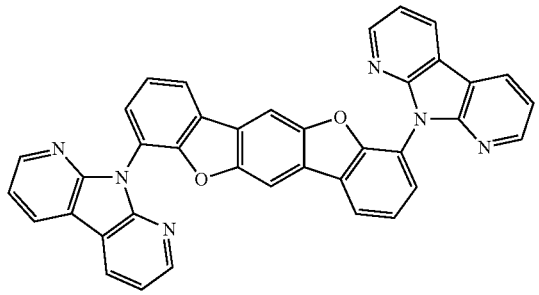
(1-241)
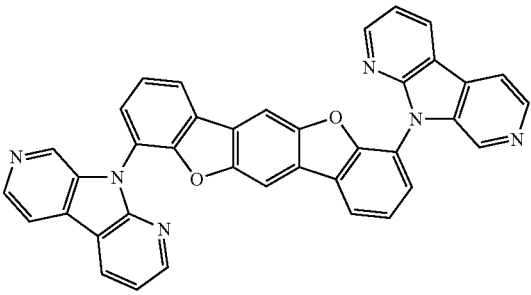
(1-242)
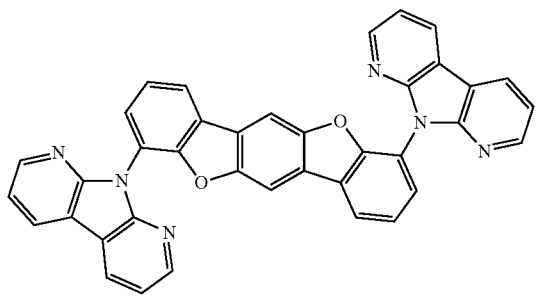
(1-243)
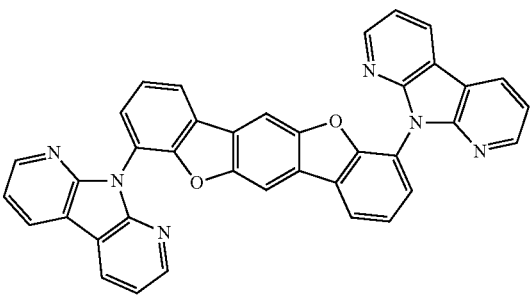
(1-244)
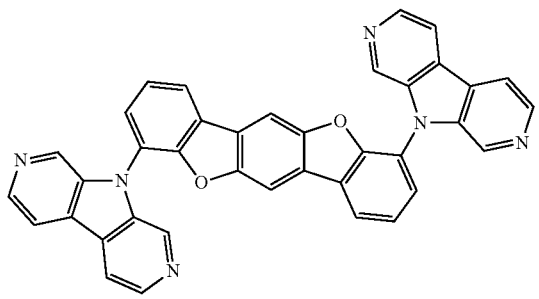
(1-245)
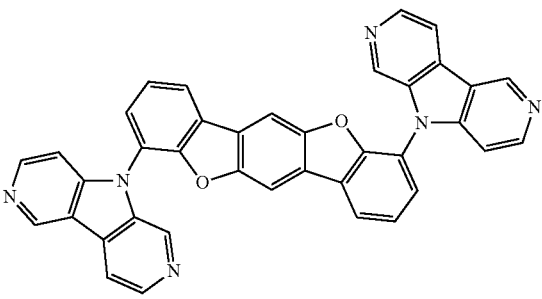
(1-246)
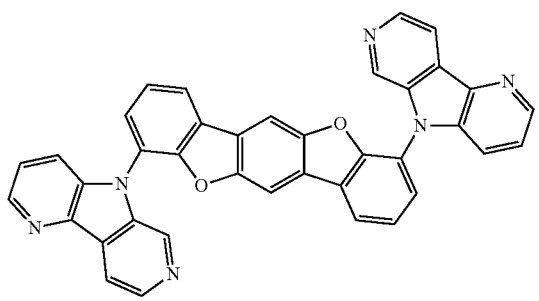
(1-247)
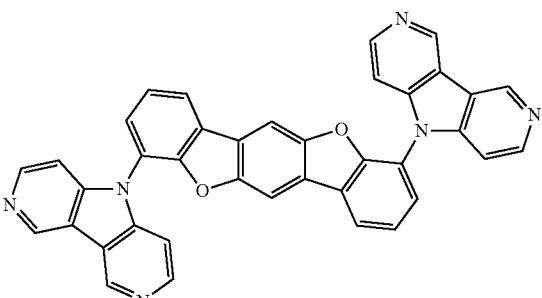
(1-248)
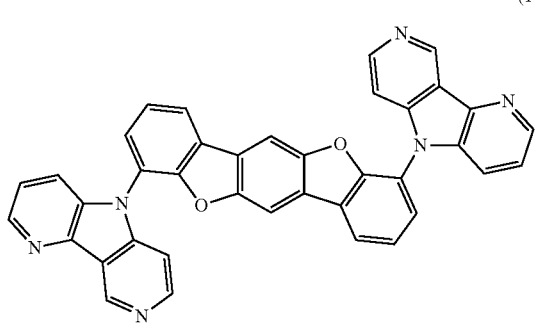
(1-249)
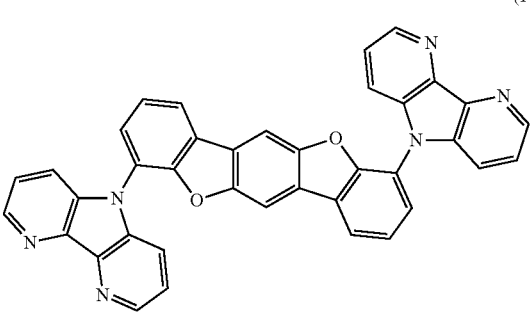

-continued
(1-250)
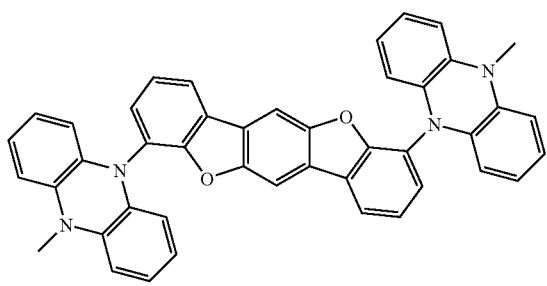
(1-251)
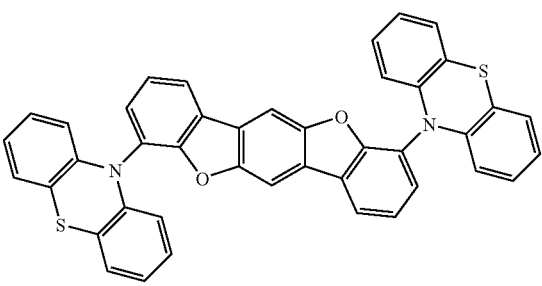
(1-252)
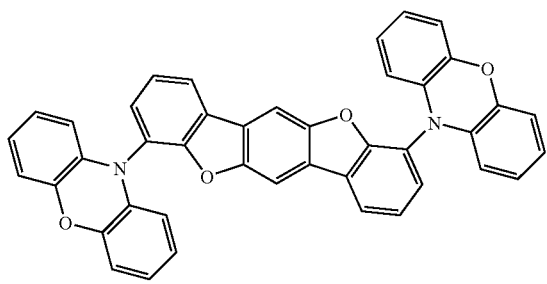
(1-253)
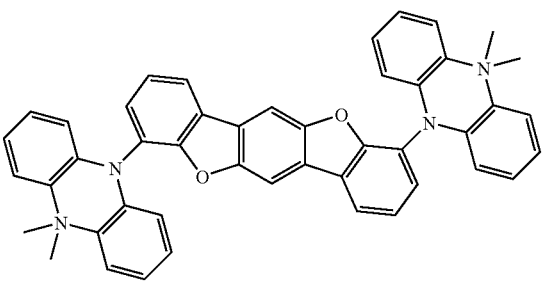
(1-254)
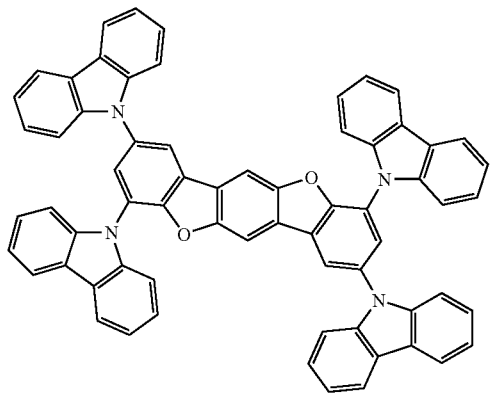
(1-255)
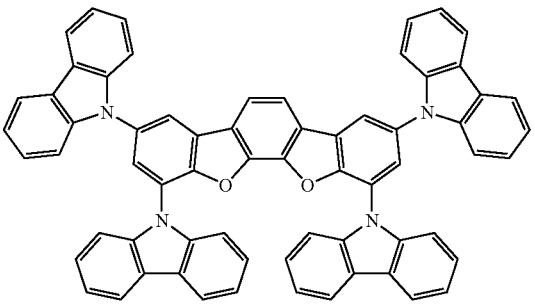
[Chem 34]
(2-1)
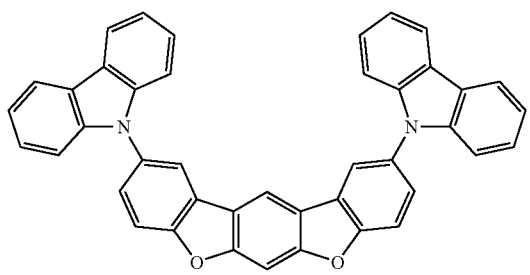
(2-2)
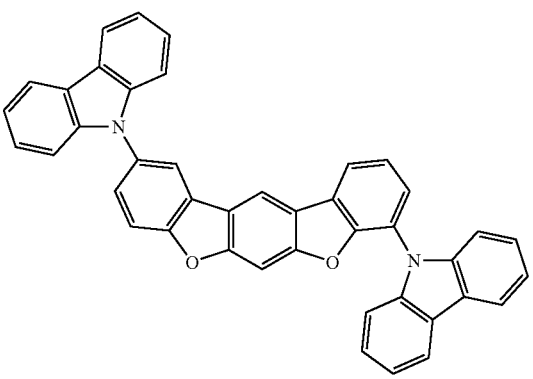

-continued
(2-3)
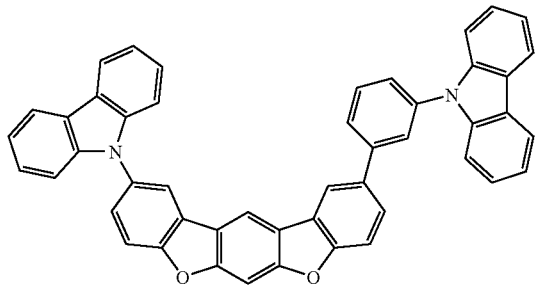
(2-4)
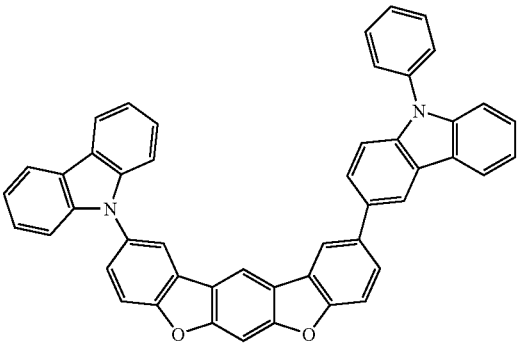
(2-5)
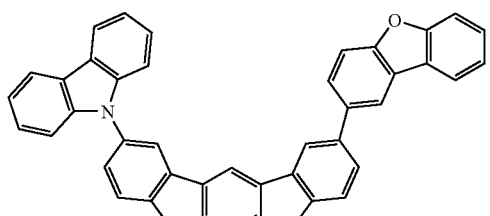
(2-6)
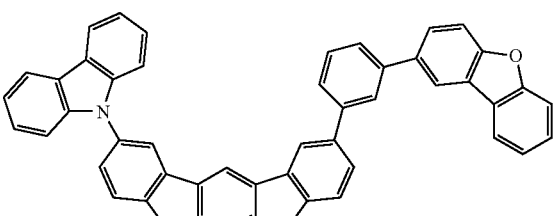
(2-7)
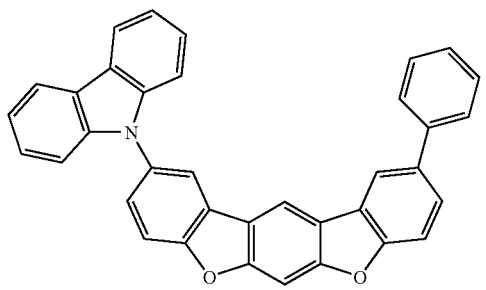
(2-8)
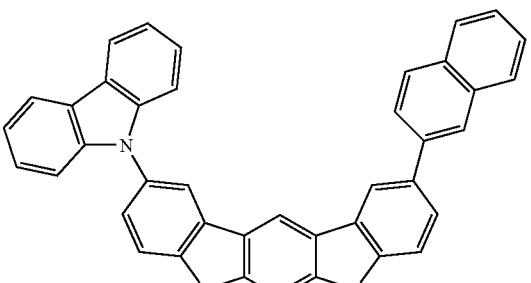
(2-9)
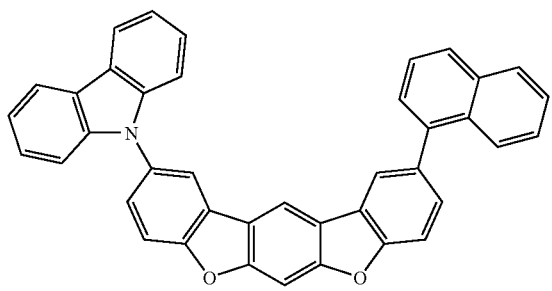
(2-10)
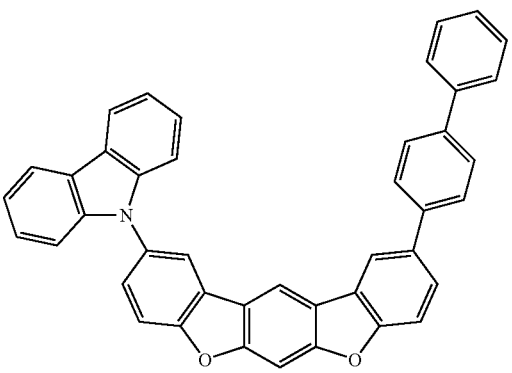
(2-11)
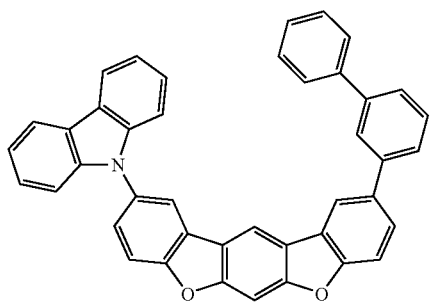
(2-12)
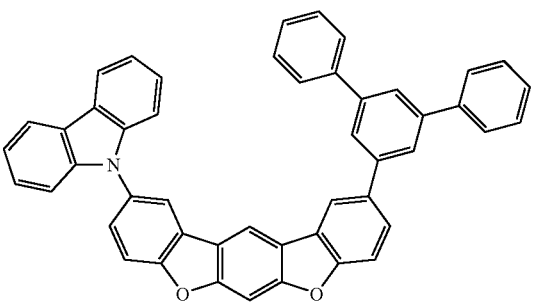

-continued
(2-13)
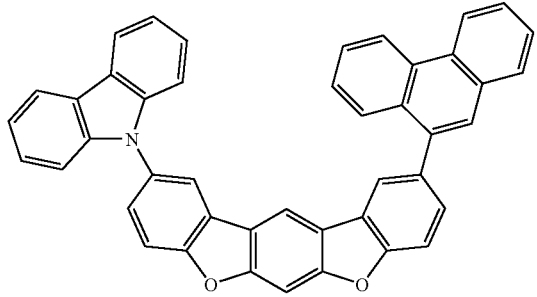
(2-14)
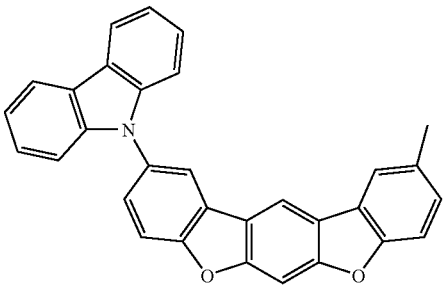
(2-15)
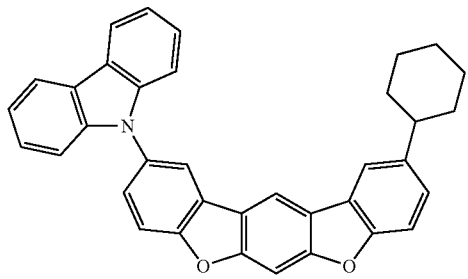
(2-16)
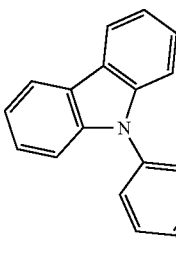
(2-17)
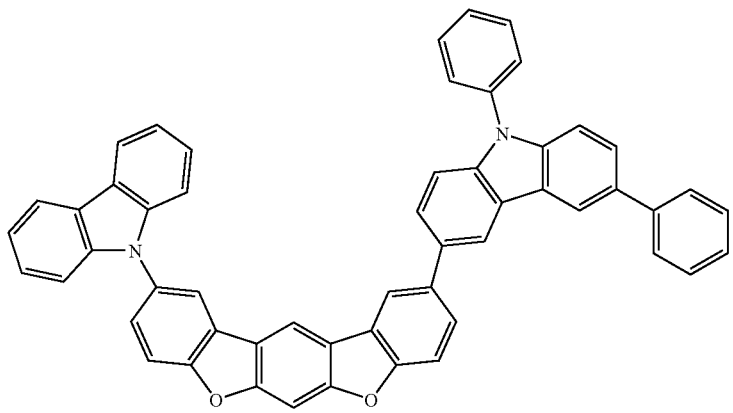
(2-18)
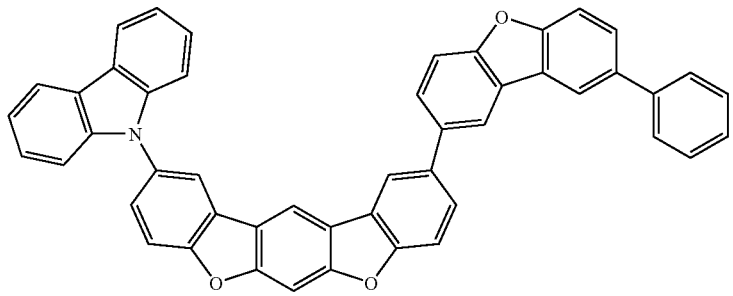
(2-19)
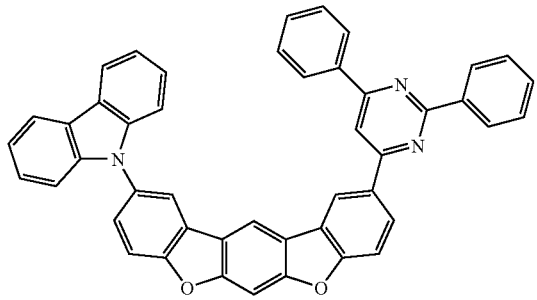

[Chem 35]
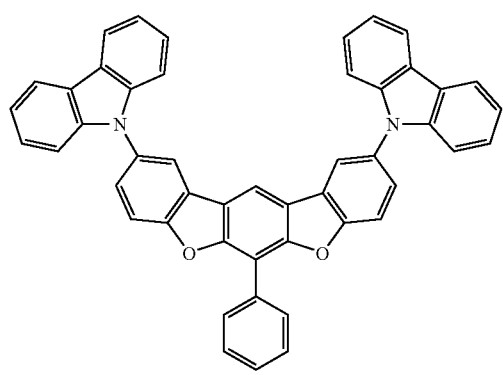
(2-20)
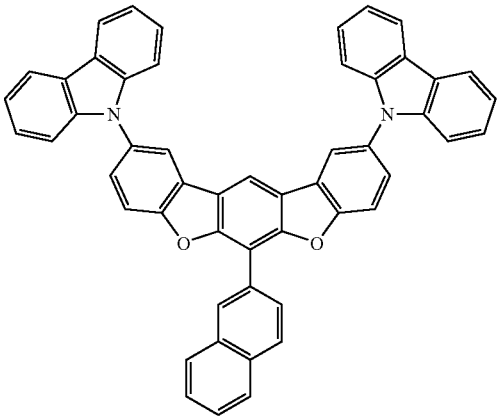
(2-21)
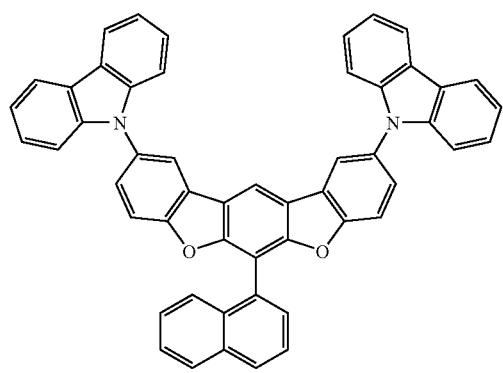
(2-22)
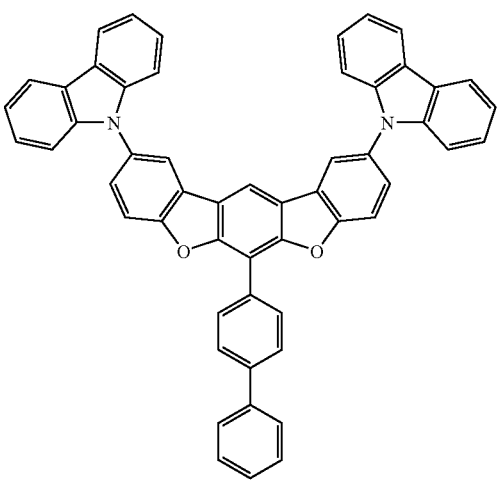
(2-23)
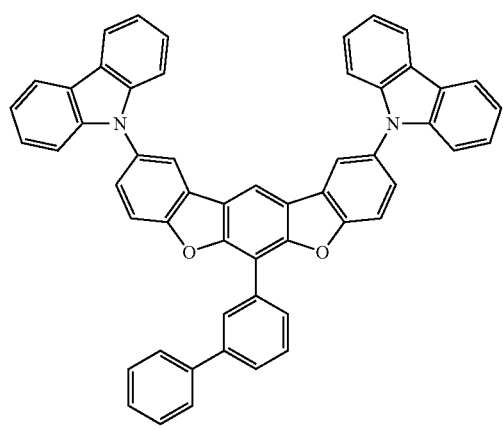
(2-24)
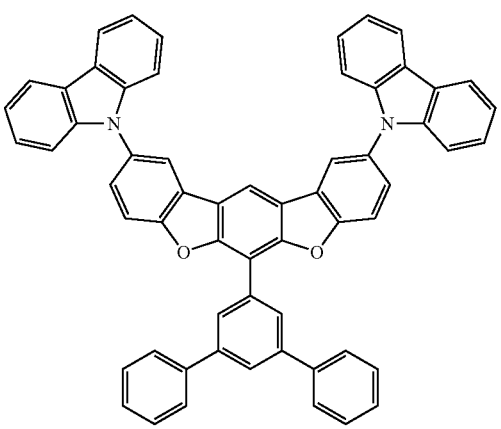
(2-25)

-continued
(2-26)
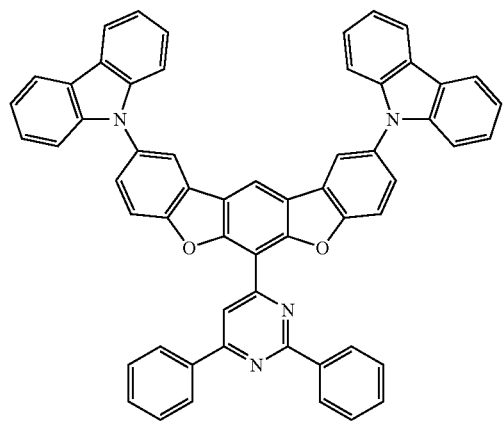
(2-27)
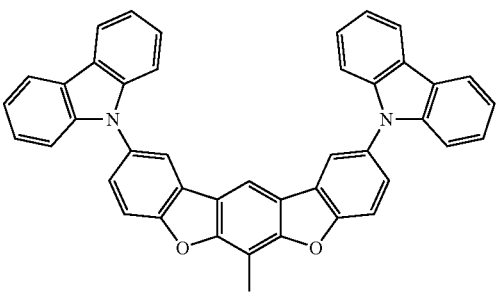
(2-28)
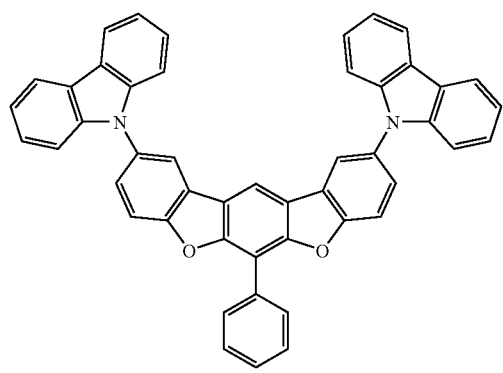
(2-29)
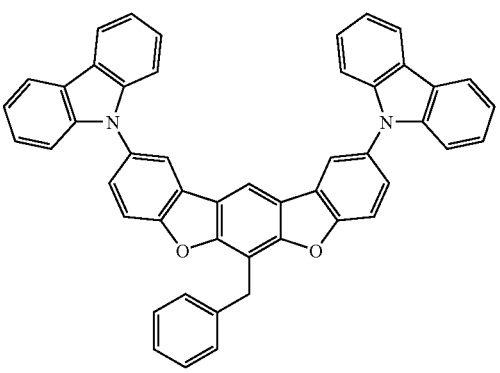
(2-30)
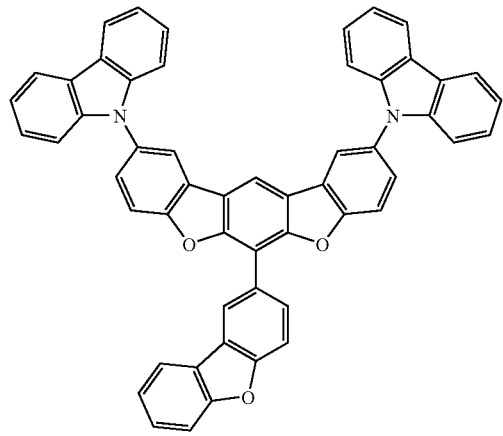
(2-31)
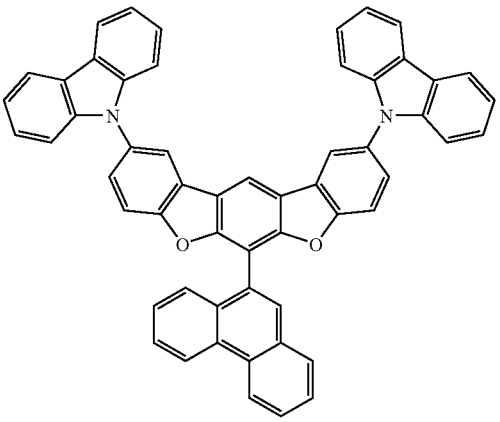
(2-32)
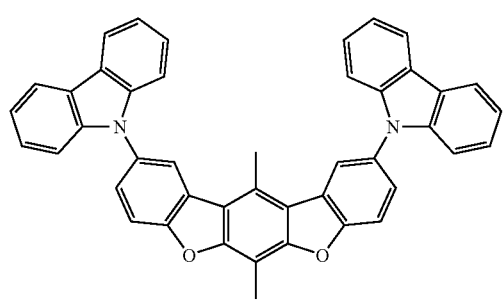
(2-33)
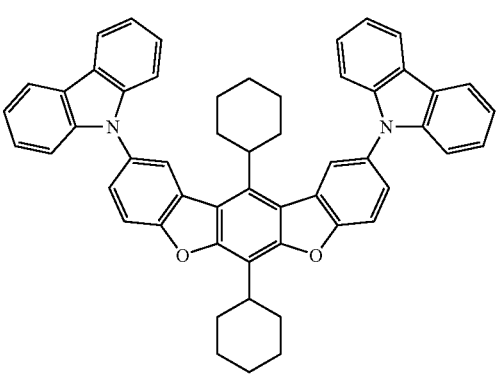

(2-34)
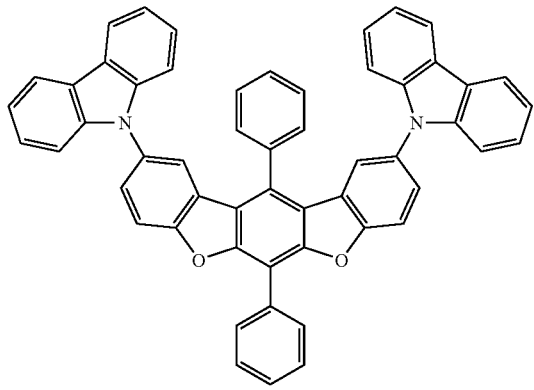
[Chem 36]
(2-35)
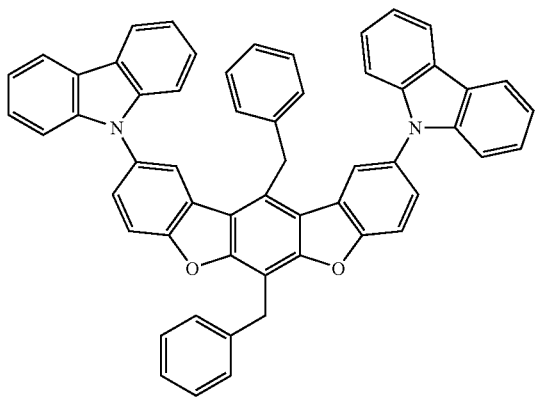
(2-36)
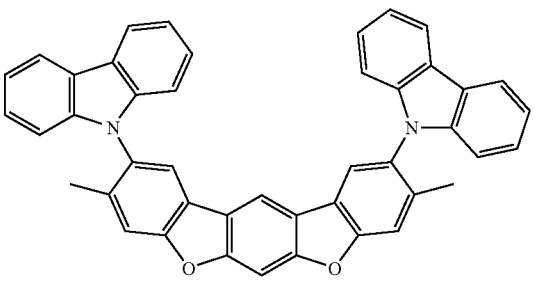
(2-37)
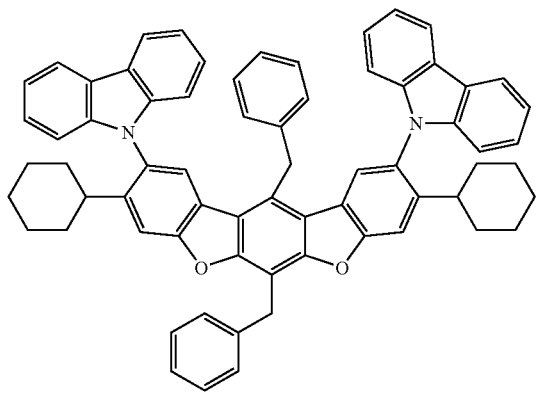
(2-38)
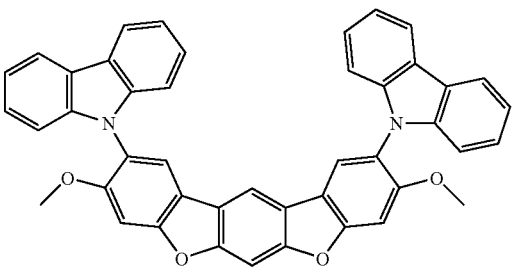
(2-39)
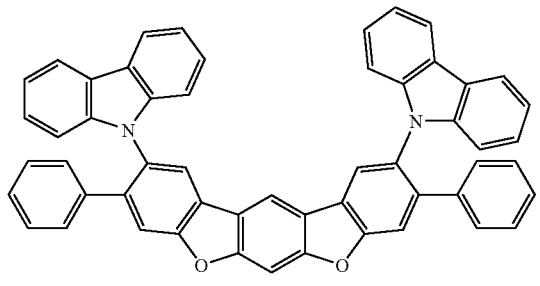
(2-40)
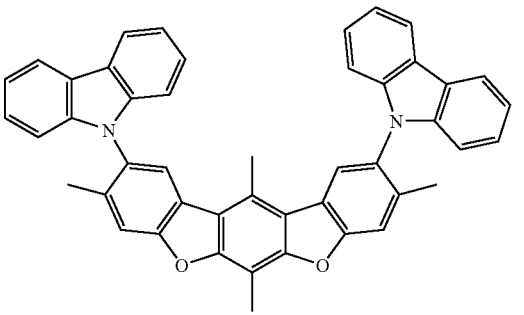

-continued
(2-41)
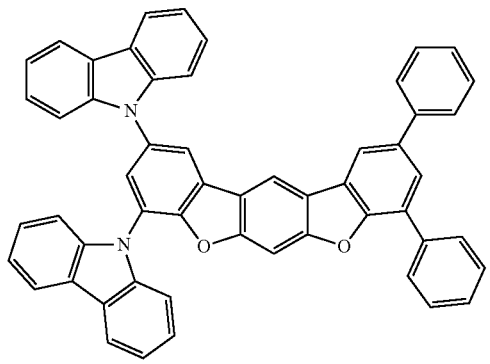
(2-42)
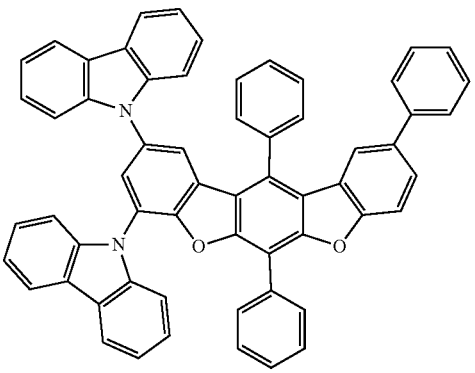
(2-43)
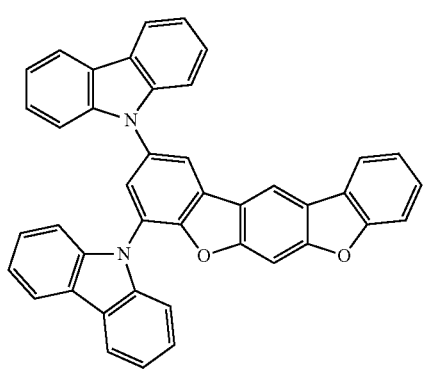
(2-44)
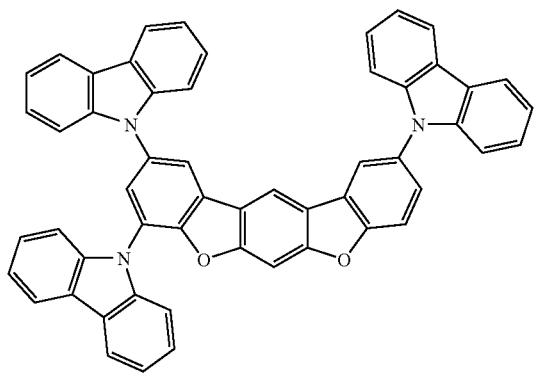
(2-45)
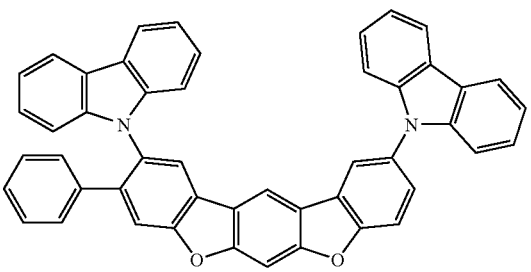
(2-46)
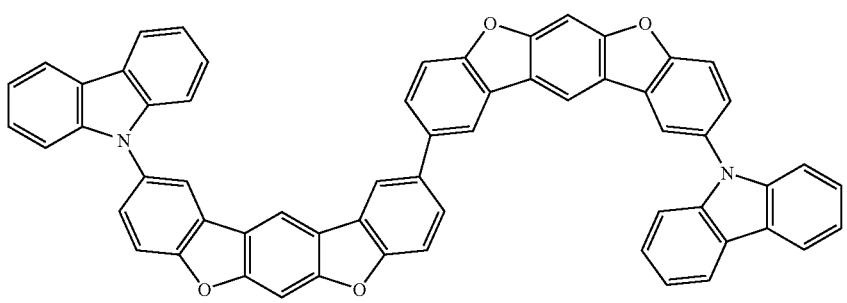

-continued
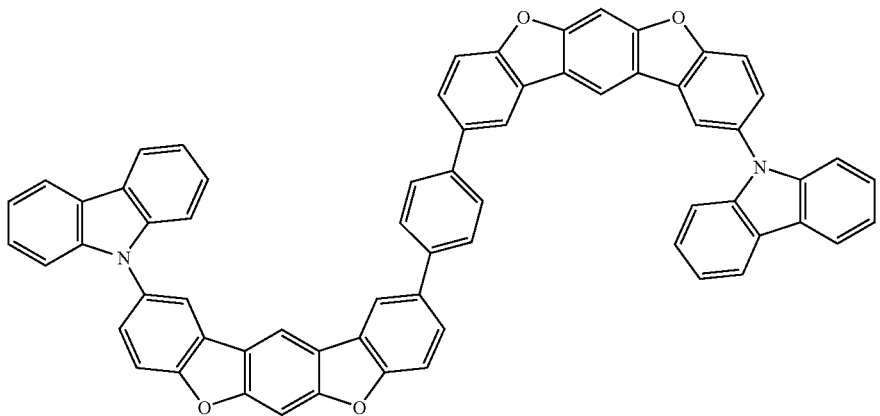
(2-47)
[Chem 37]
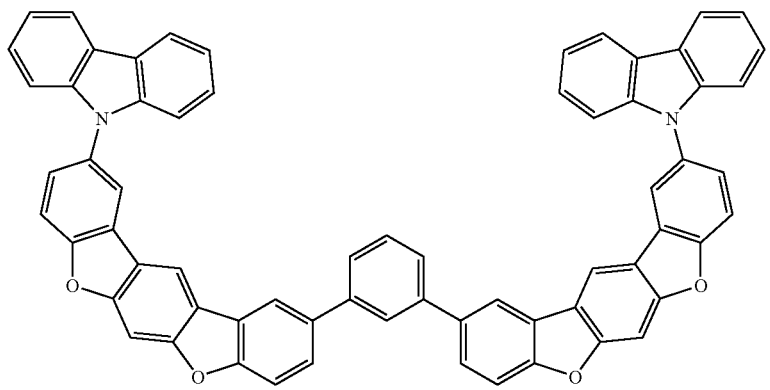
(2-48)
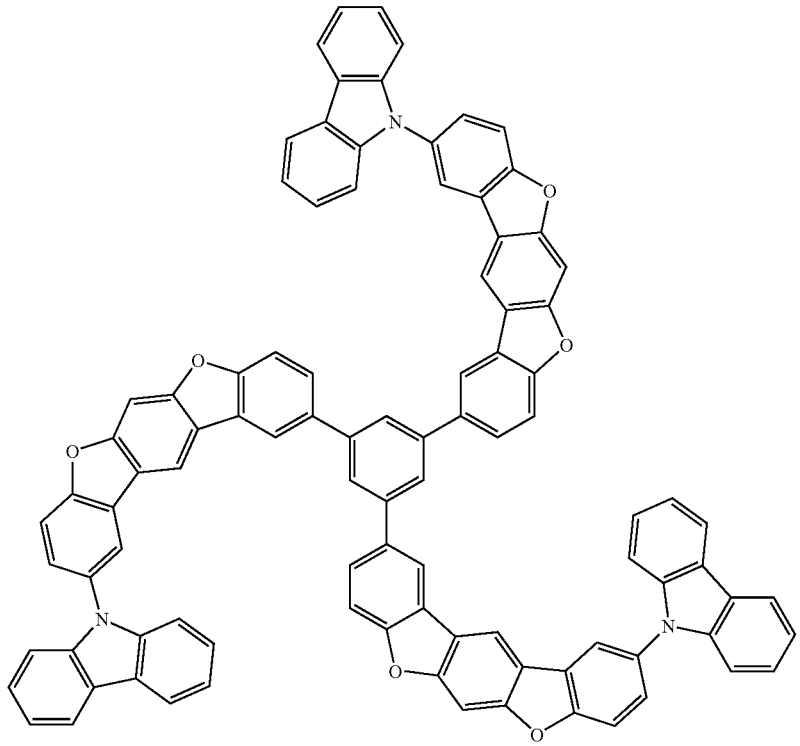
(2-49)

-continued
(2-50)
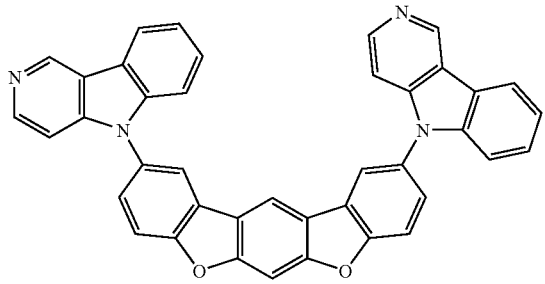
(2-51)
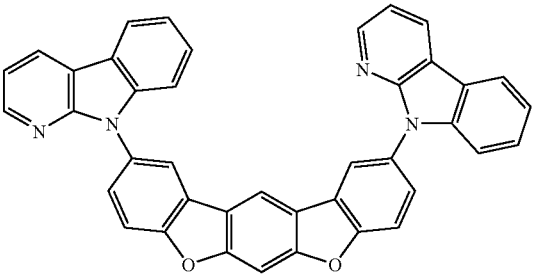
(2-52)
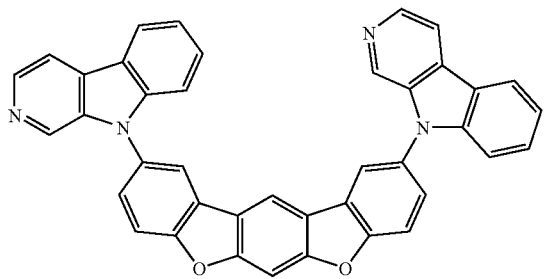
(2-53)
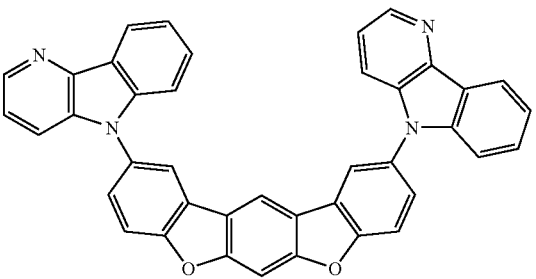
(2-54)
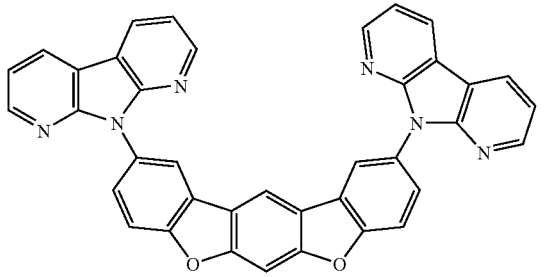
(2-55)
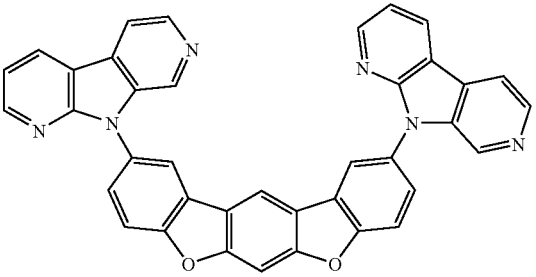
(2-56)
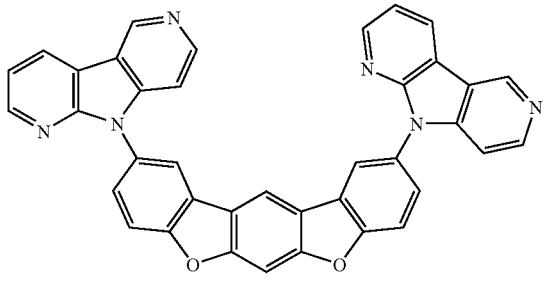
(2-57)
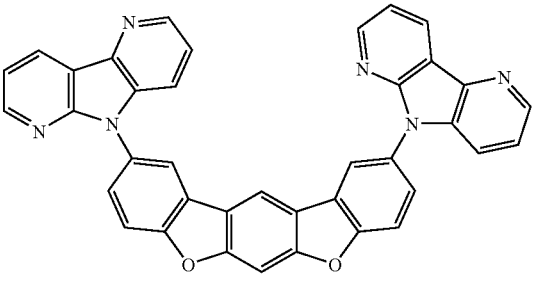
(2-58)
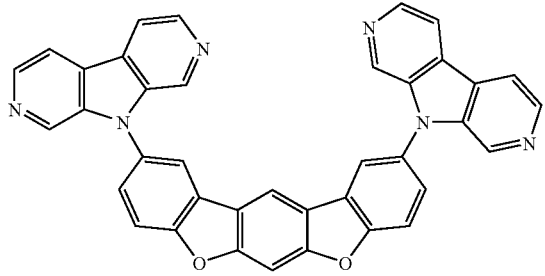
(2-59)
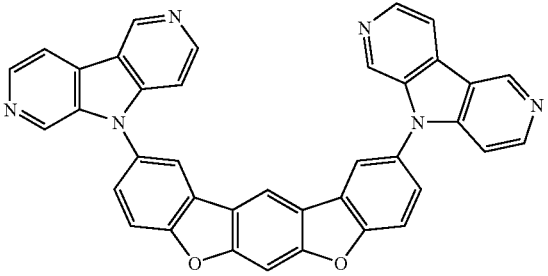

-continued
(2-60)
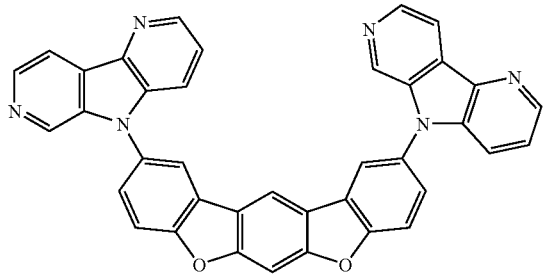
(2-61)
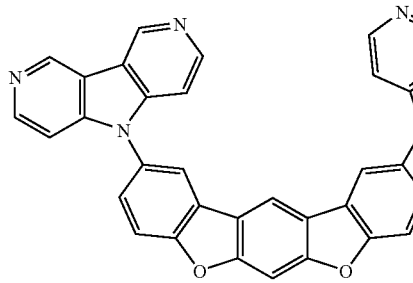
[Chem 38]
(2-62)
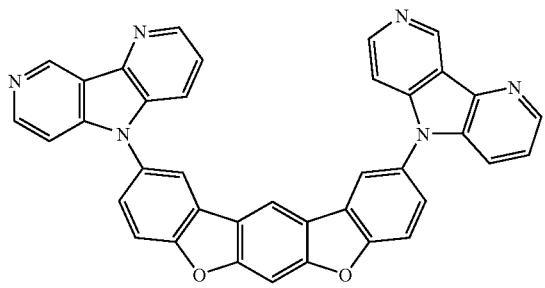
(2-63)
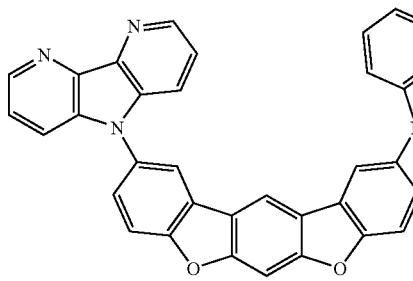
(2-64)
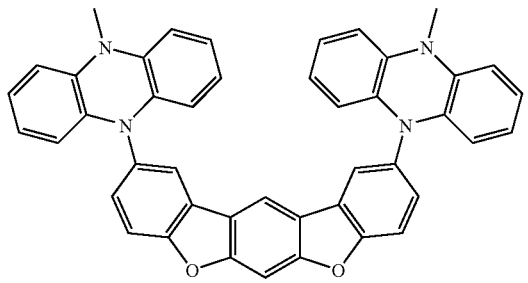
(2-65)
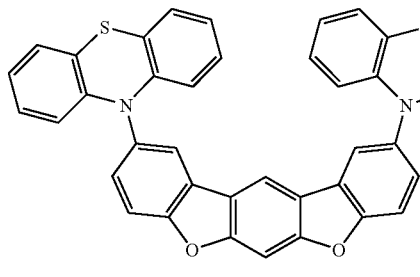
(2-66)
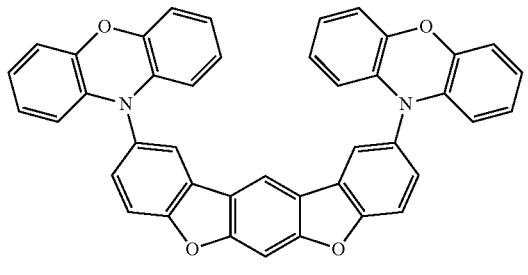
(2-67)
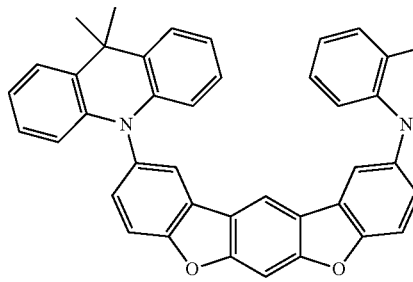
(2-68)
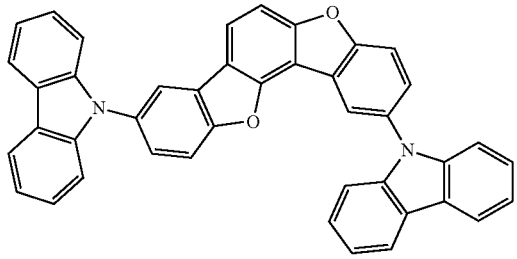
(2-69)
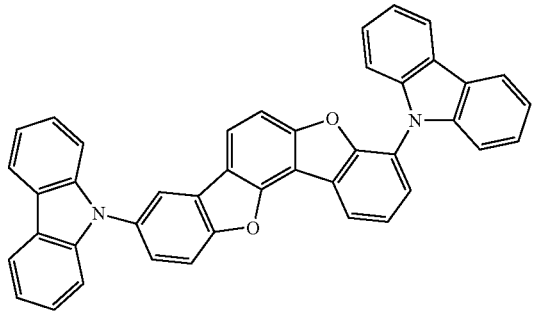

-continued
(2-70)
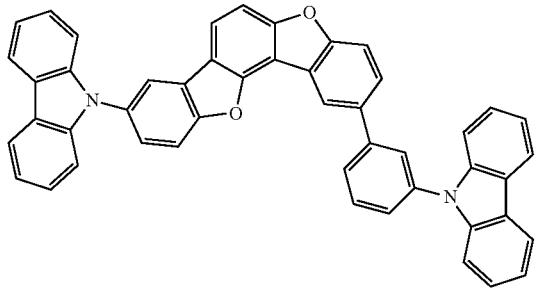
(2-71)
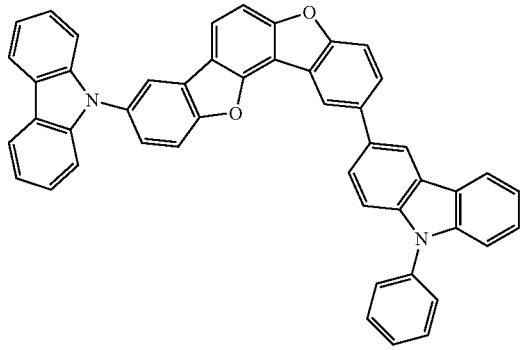
(2-72)
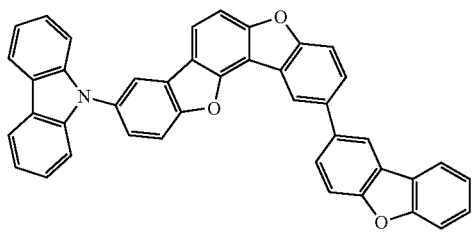
(2-73)
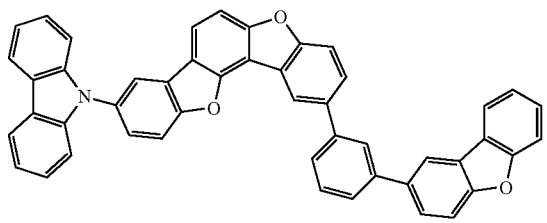
(2-74)
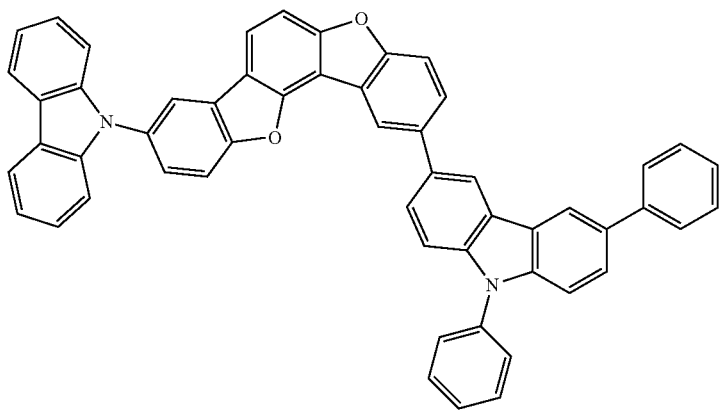
(2-75)
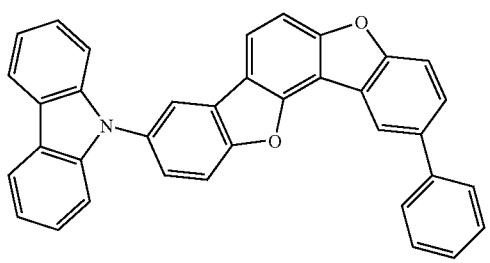
(2-76)
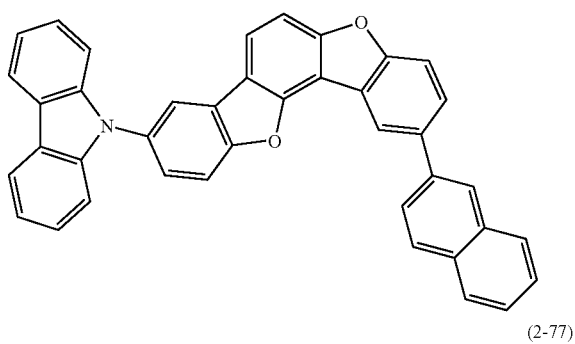
(2-77)
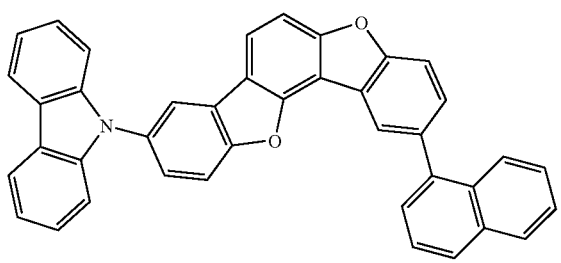

-continued
[Chem 39]
(2-78)
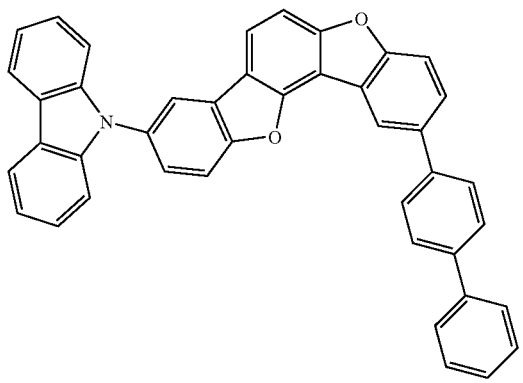
(2-79)
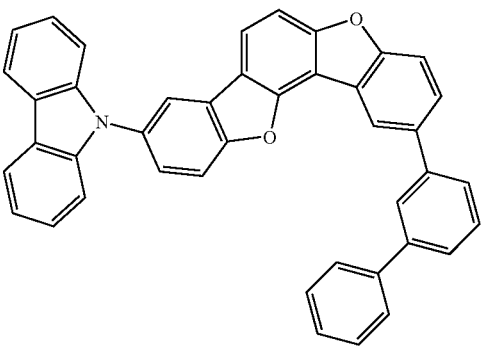
(2-80)
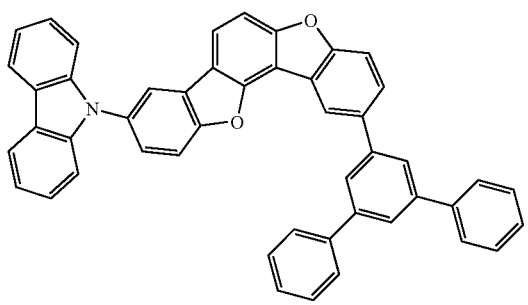
(2-81)
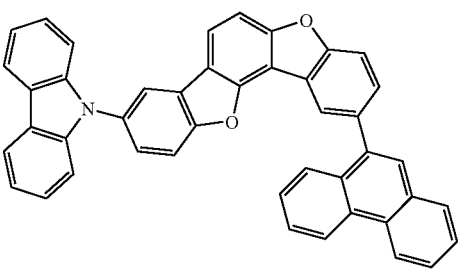
(2-82)
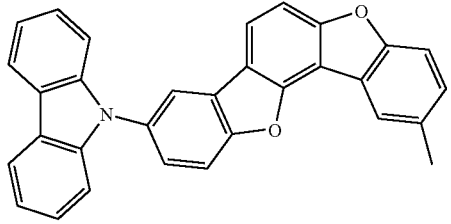
(2-83)
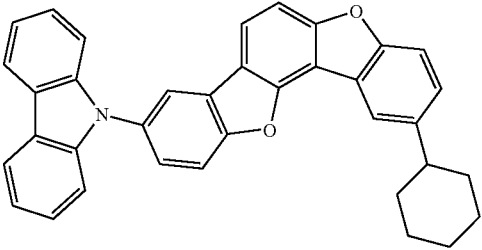
(2-84)
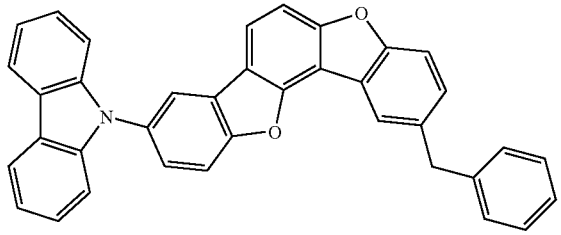
(2-85)
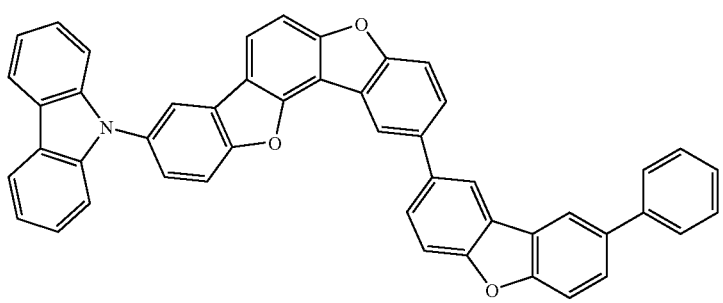

-continued
(2-86)
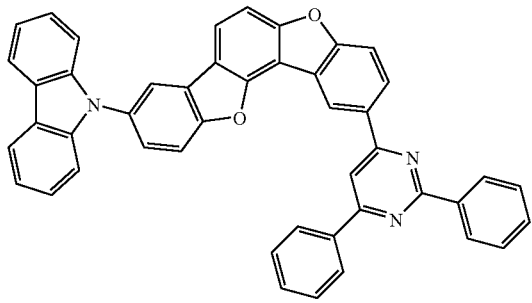
(2-87)
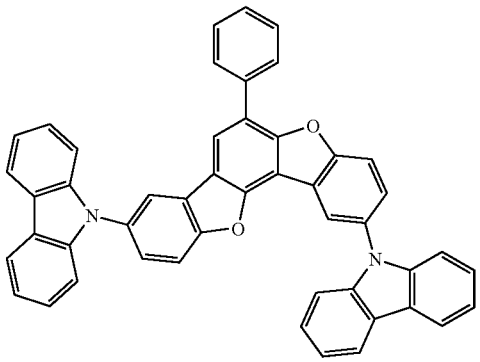
(2-88)
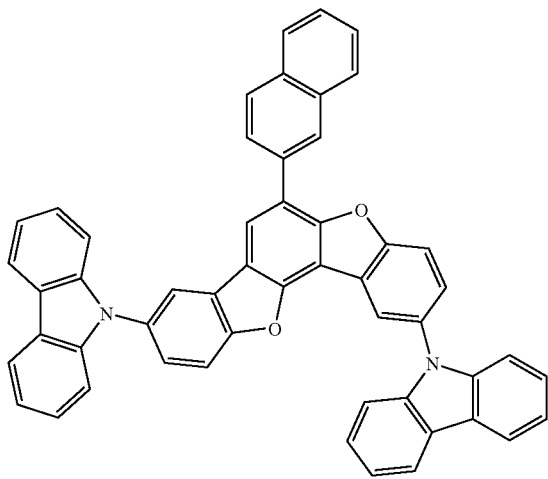
(2-89)
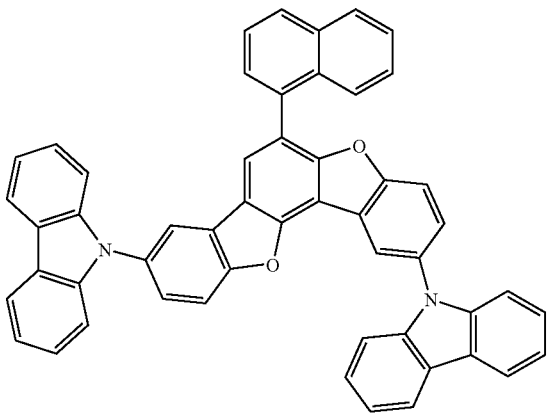
(2-90)
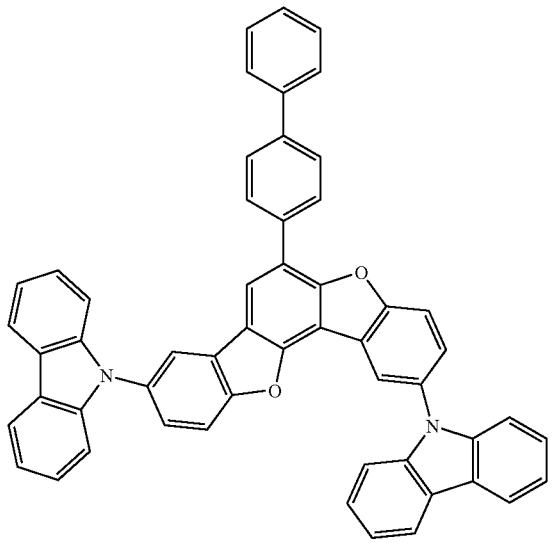
(2-91)
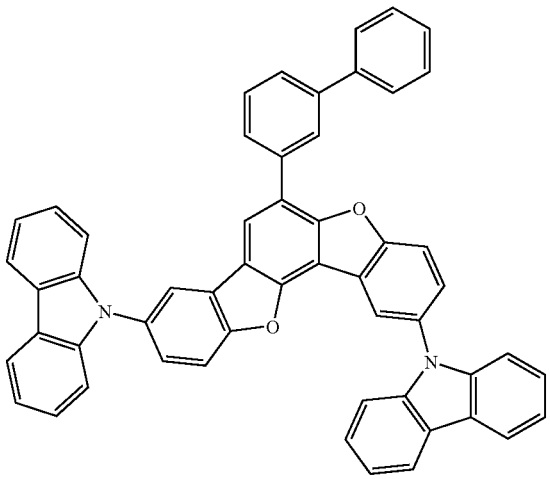

-continued
(2-92)
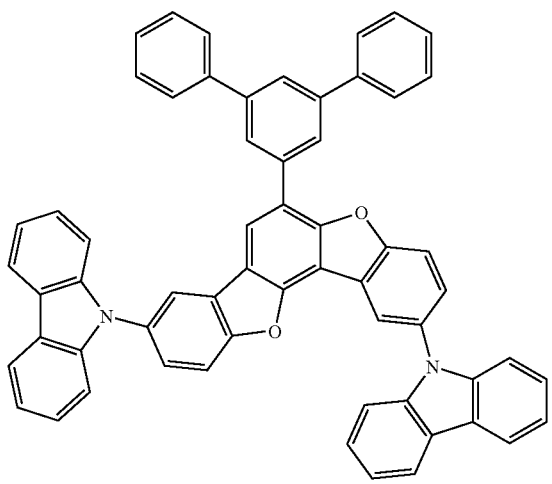
(2-93)
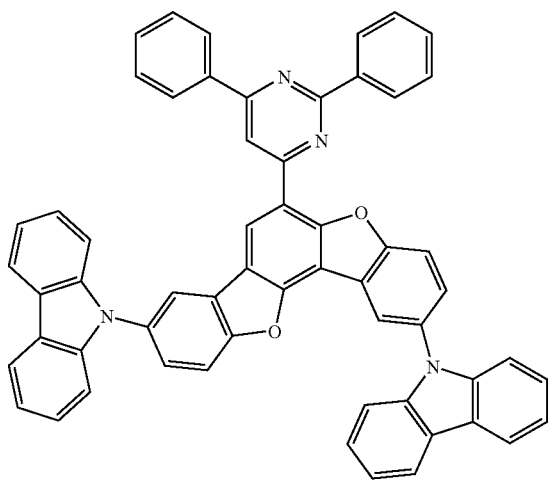
(2-94)
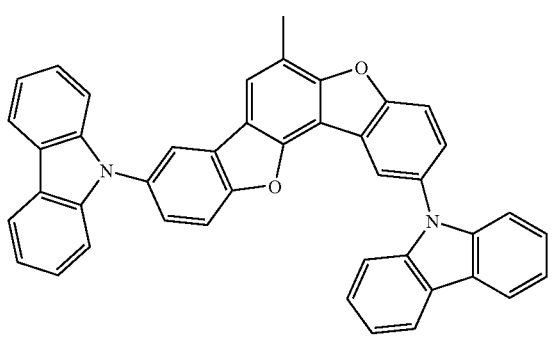
(2-95)
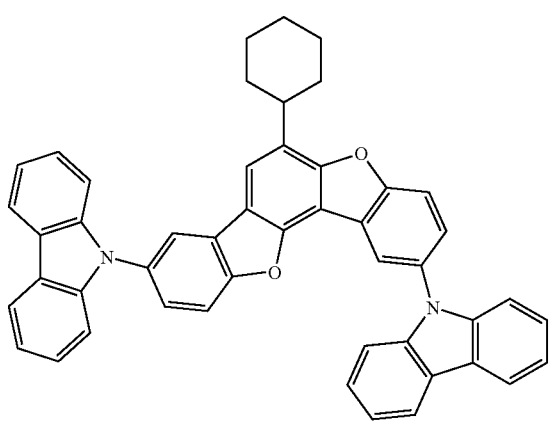
(2-96)
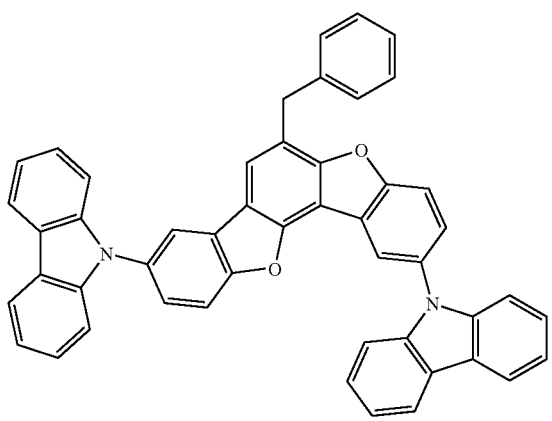
(2-97)
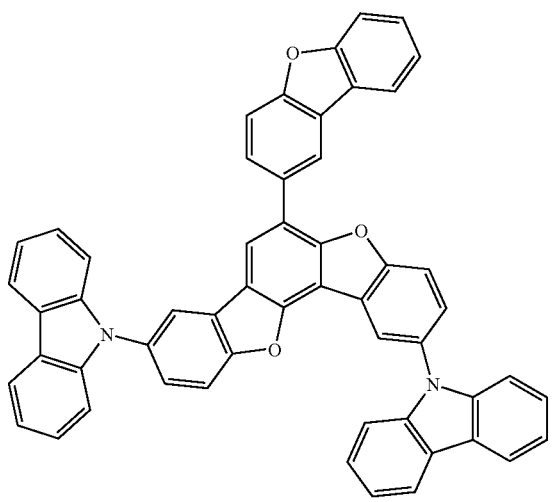

(2-98)
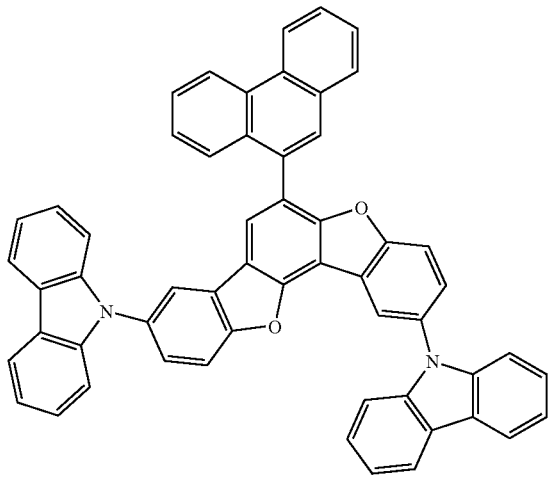
[Chem 40]
(2-99) (2-100)
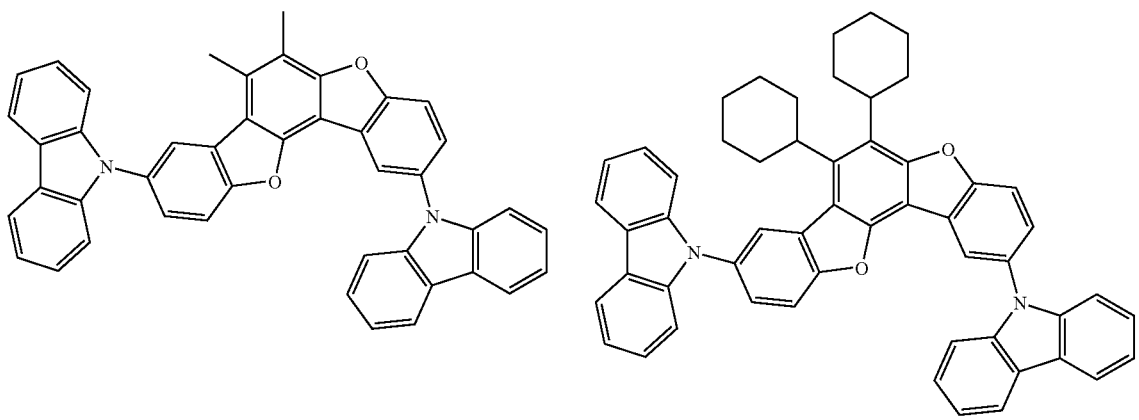
(2-101) (2-102)
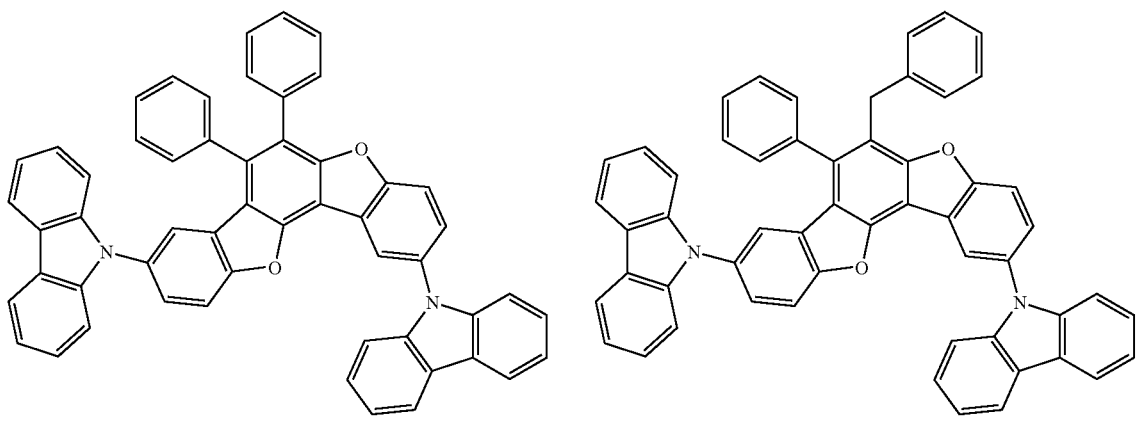

-continued
(2-103)
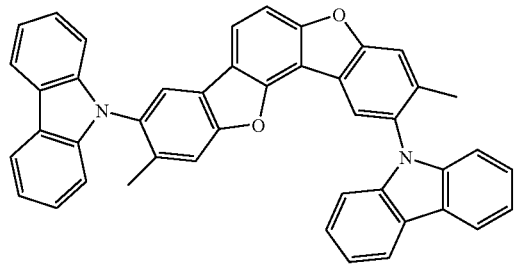
(2-104)
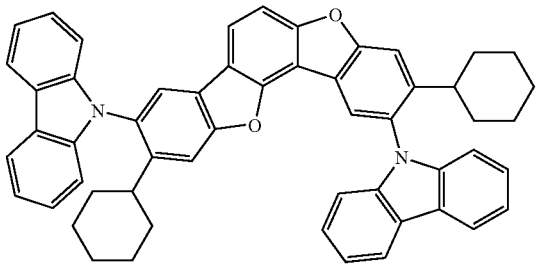
(2-105)
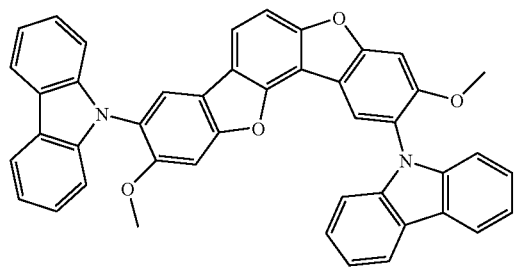
(2-106)
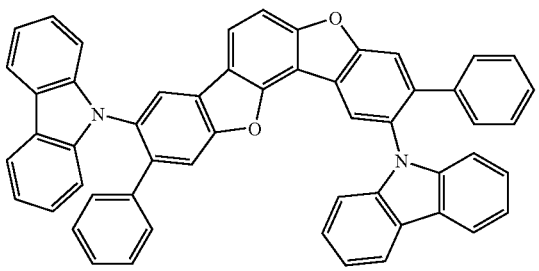
(2-107)
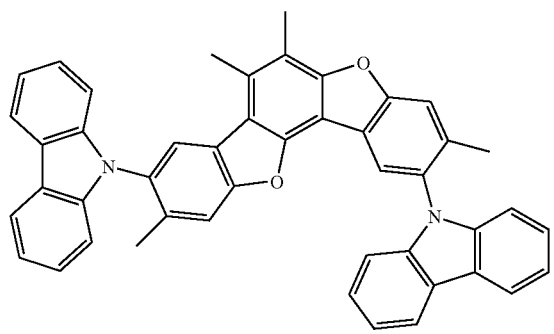
(2-108)
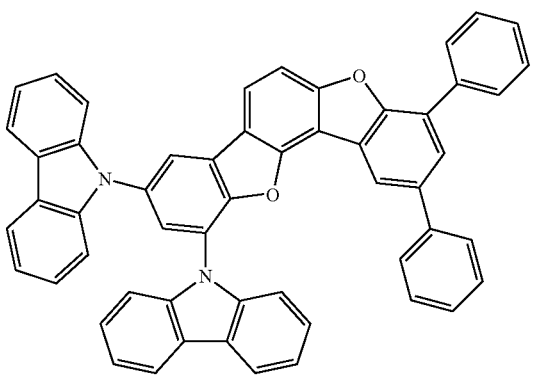
(2-109)
(2-110)

(2-111)
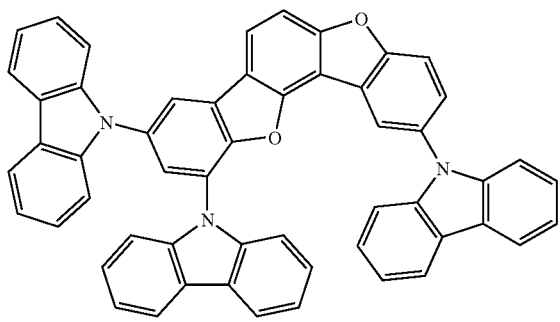
(2-112)
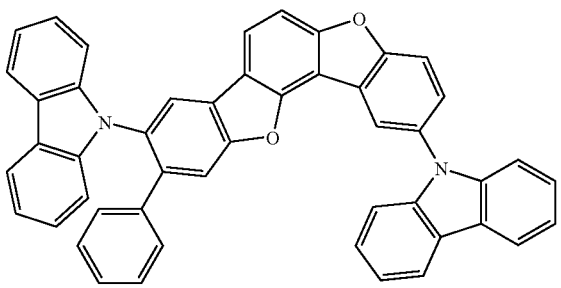
(2-113)
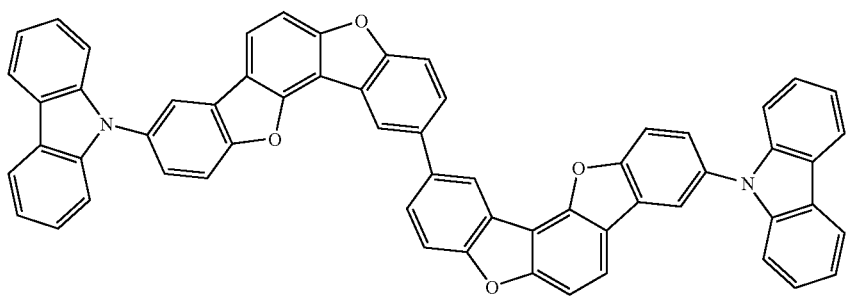
(2-114)
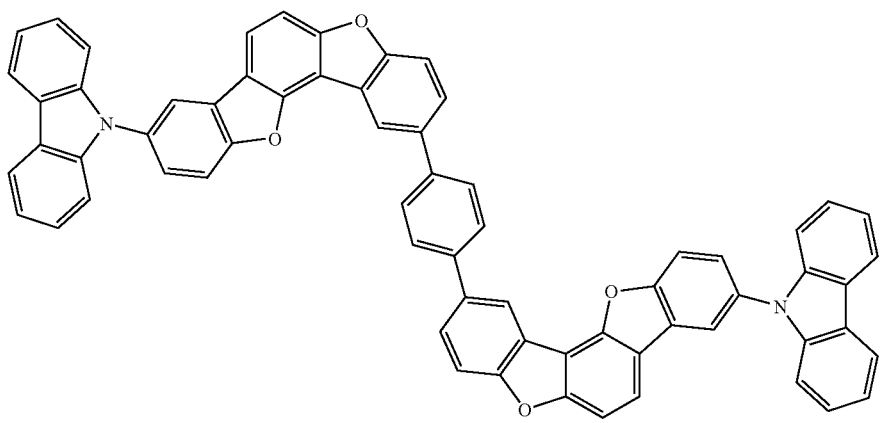
(2-115)
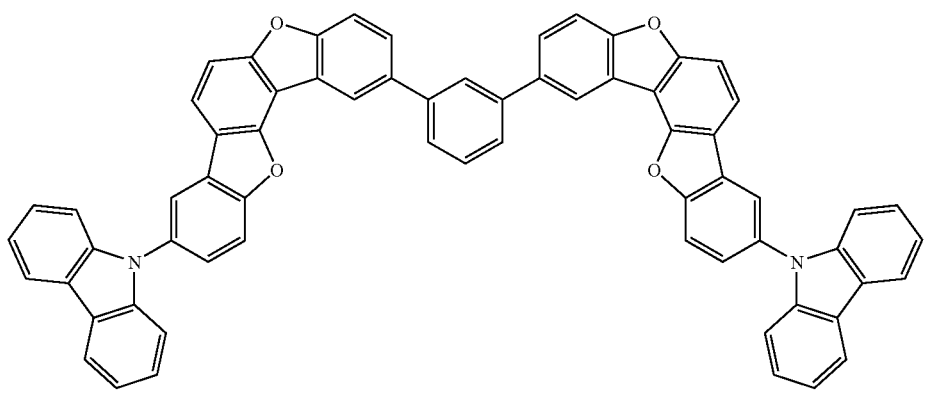

(2-116)
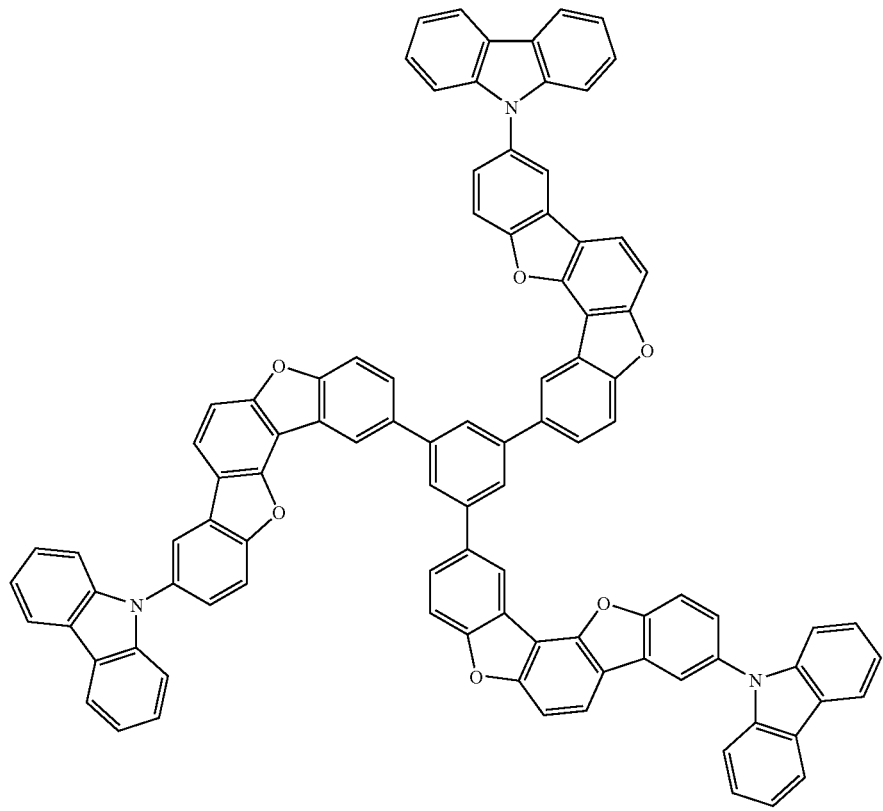
(2-117)
(2-118)
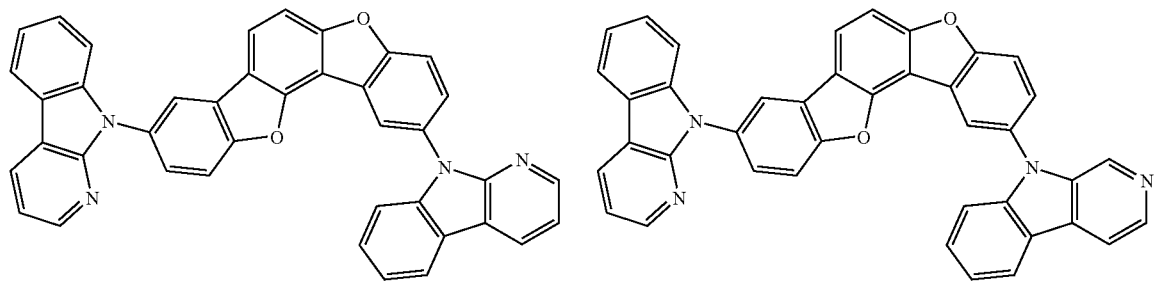
(2-119)
(2-120)
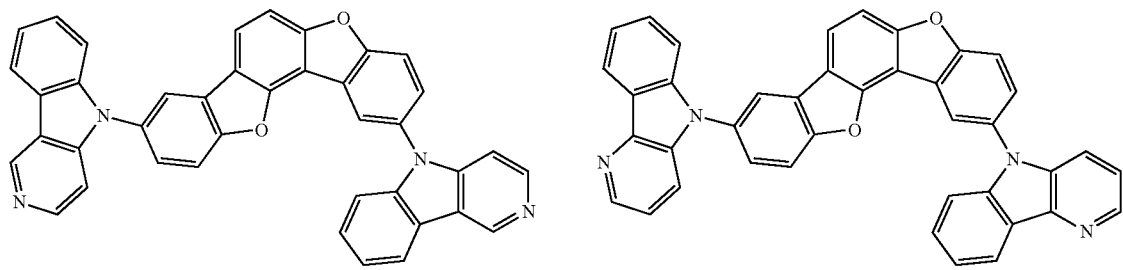

-continued
(2-121)
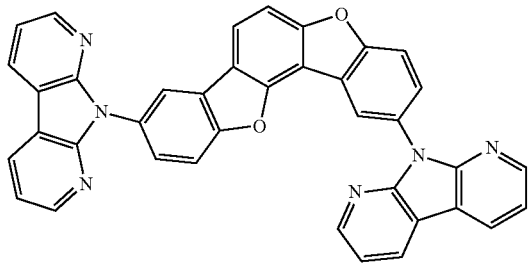
(2-122)
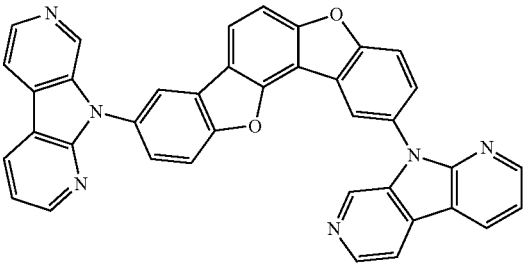
(2-123)
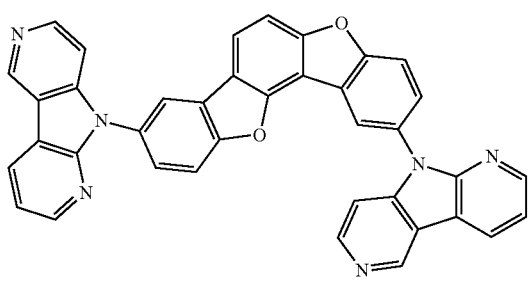
(2-124)
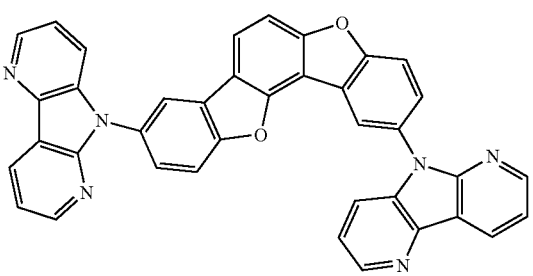
(2-125)
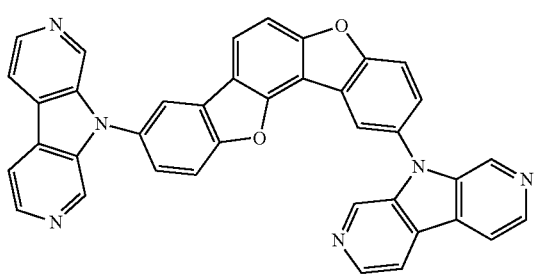
(2-126)
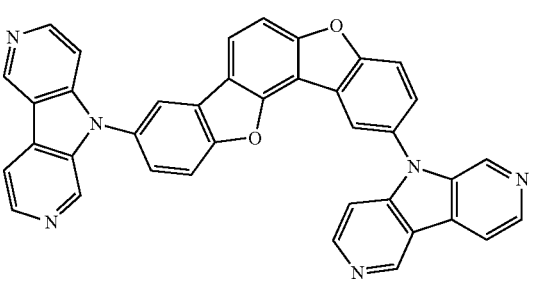
(2-127)
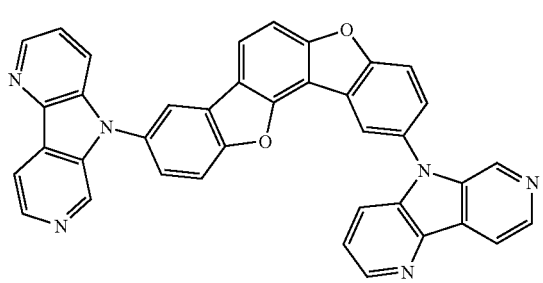
(2-128)
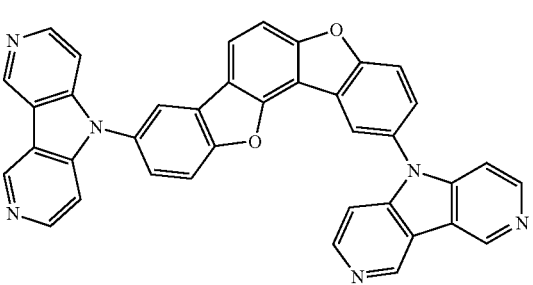
(2-129)
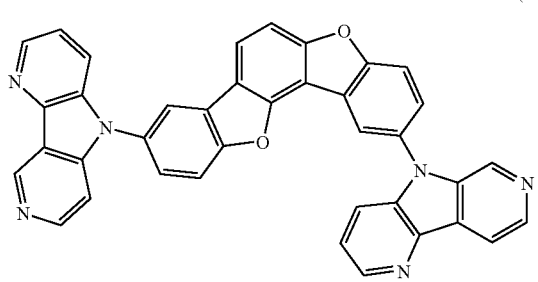
(2-130)
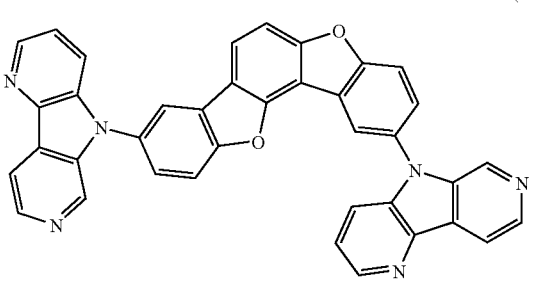

-continued
(2-131)
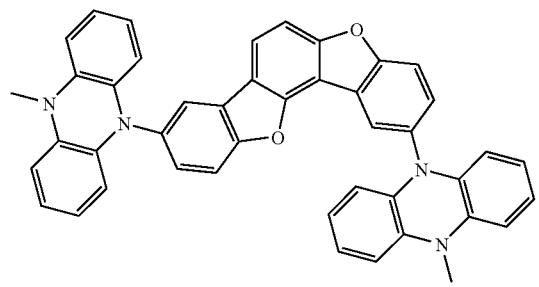
(2-132)
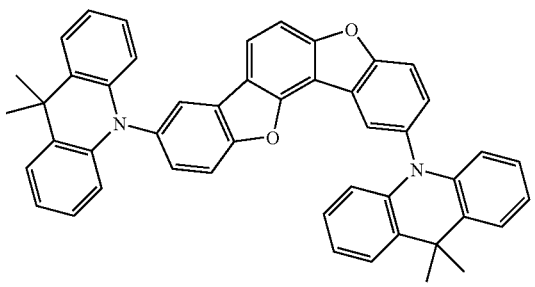
(2-133)
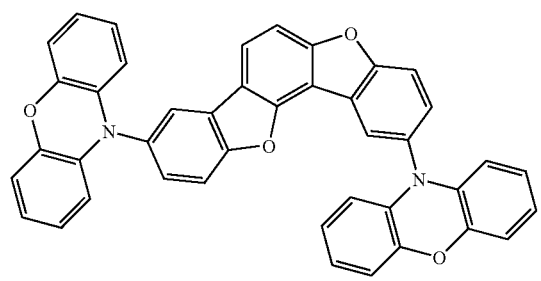
(2-134)
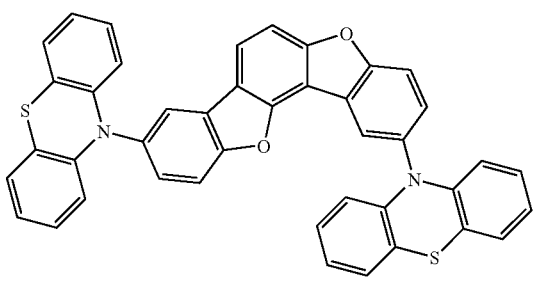
[Chem 42]
(2-135)
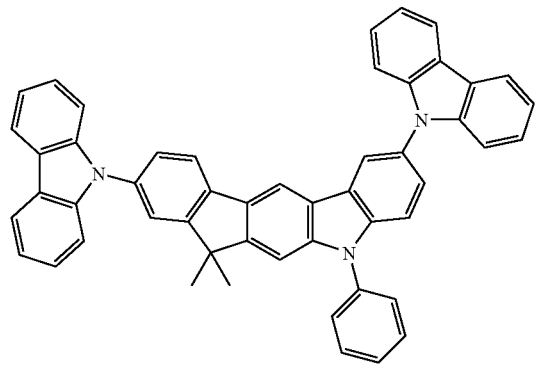
(2-136)
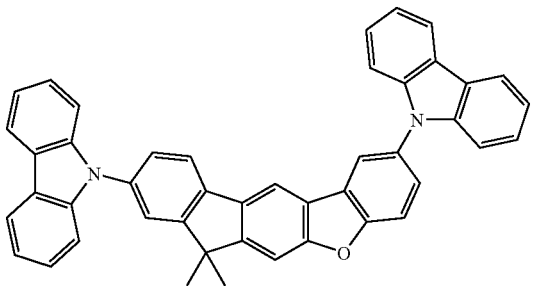
(2-137)
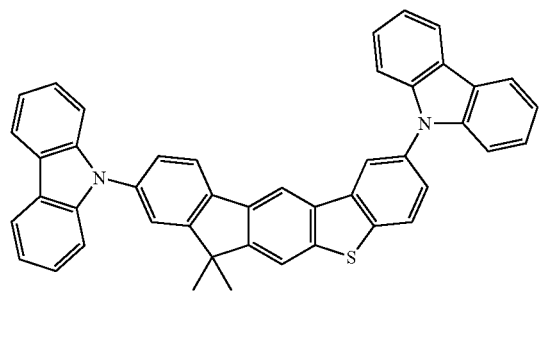
(2-138)
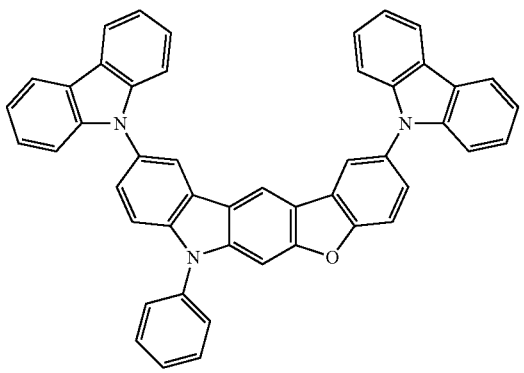

-continued
(2-139)
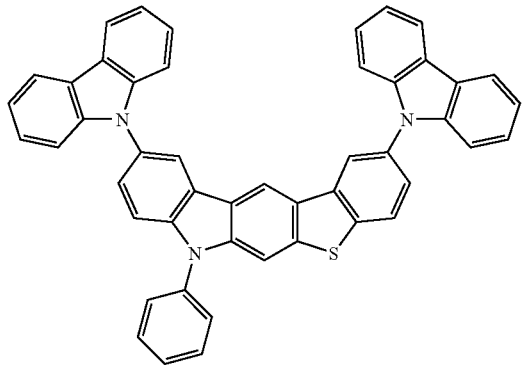
(2-140)
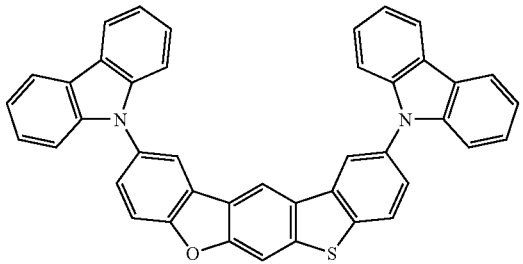
(2-141)
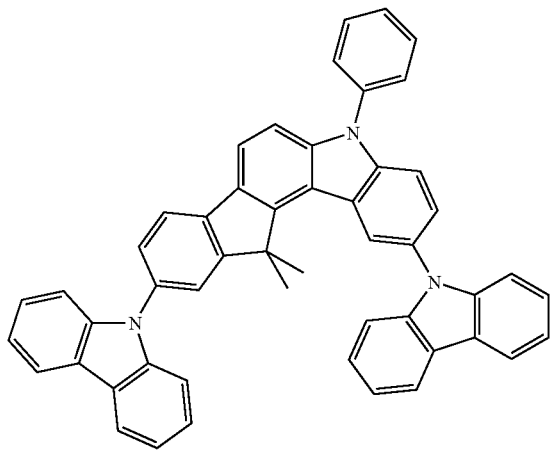
(2-142)
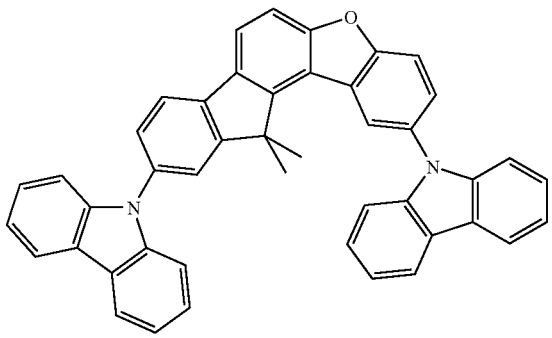
(2-143)
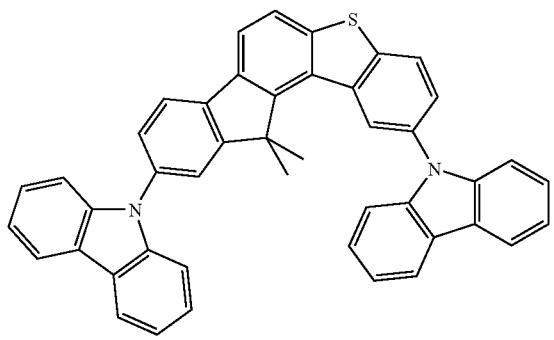
(2-144)
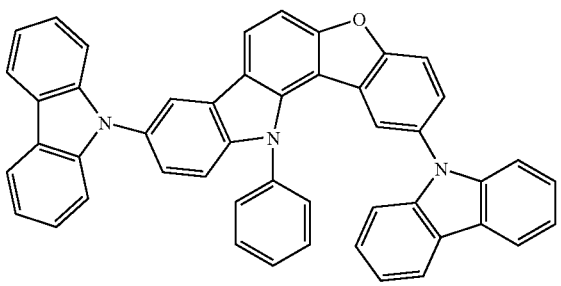
(2-145)
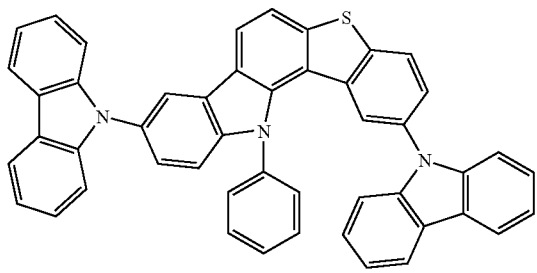
(2-146)
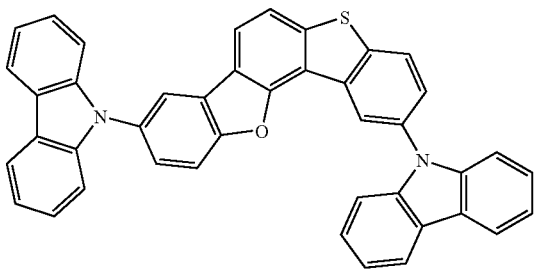

-continued
[Chem 43]
(2-147)
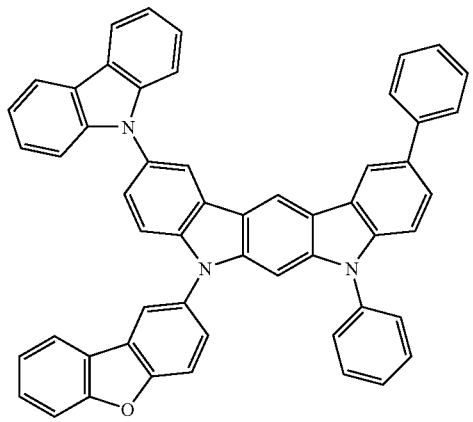
(2-148)
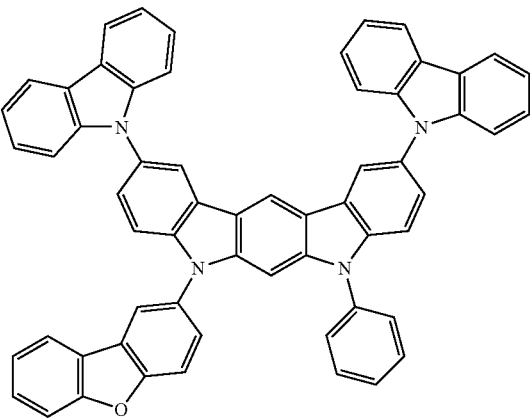
(2-149)
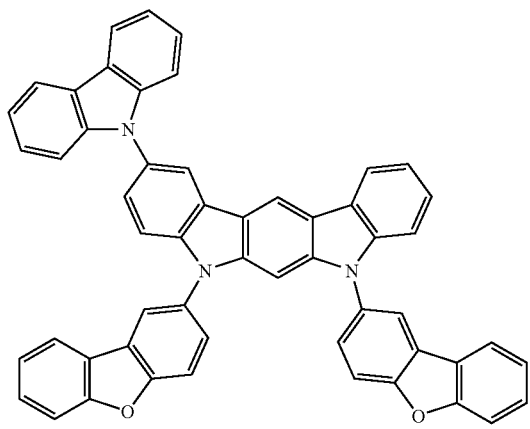
(2-150)
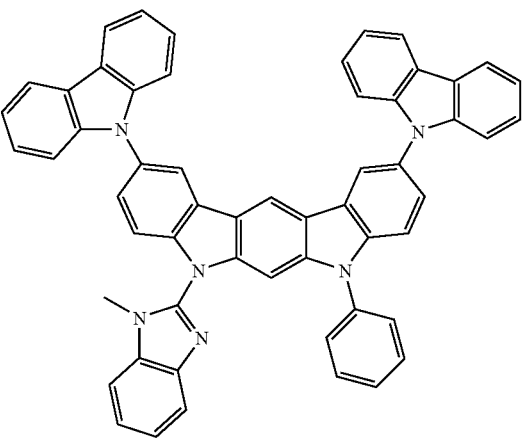
(2-151)
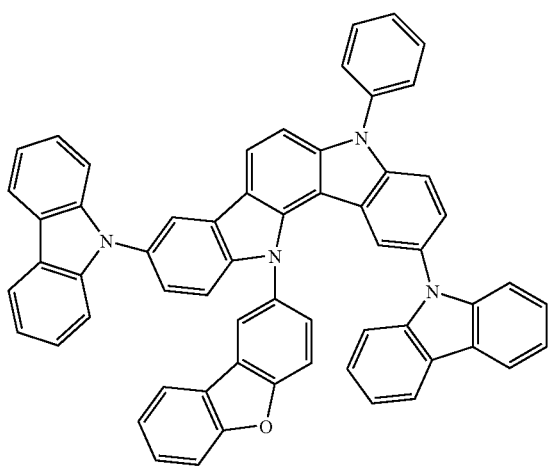
(2-152)
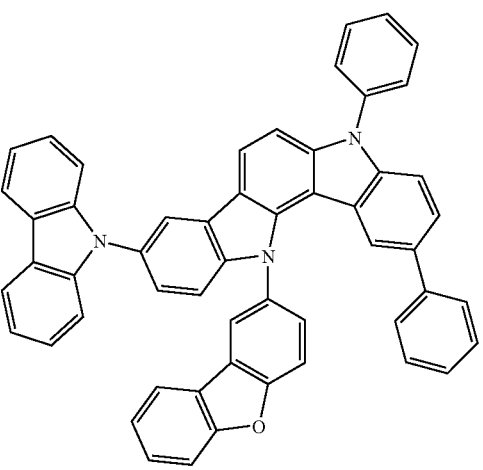

-continued
(2-153)
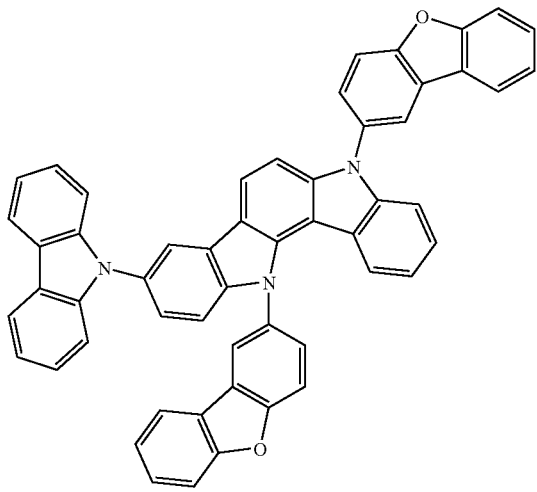
(2-154)
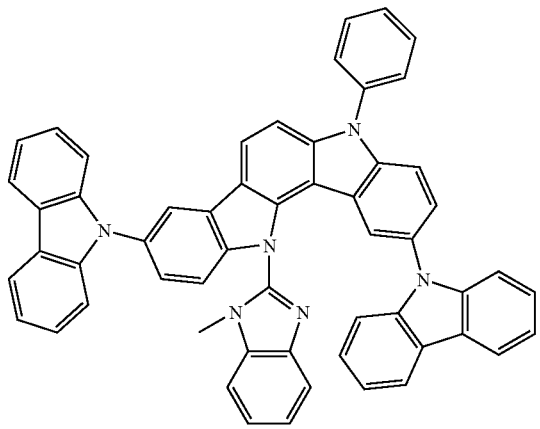
[Chem 44]
(2-155)
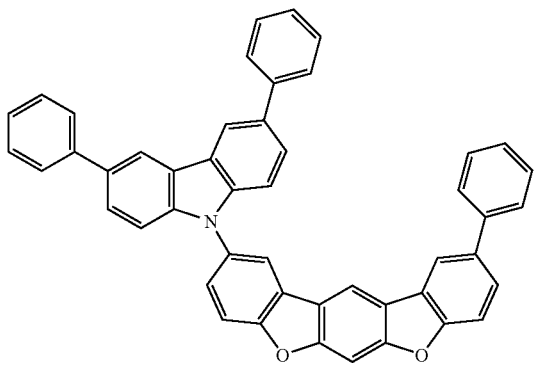
(2-156)
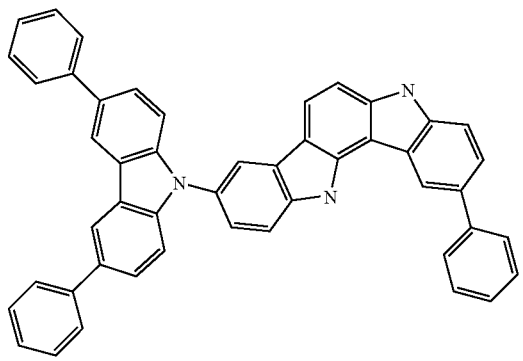
(2-157)
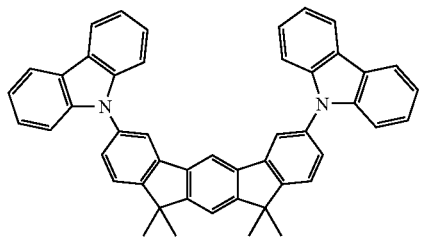
(2-158)
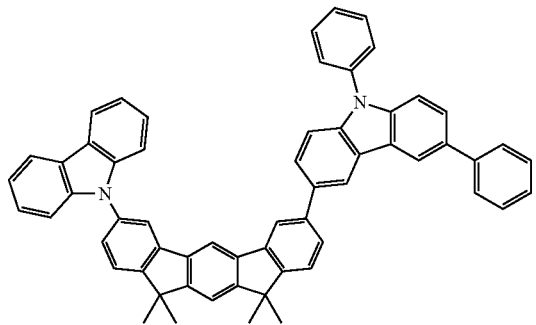
(2-159)
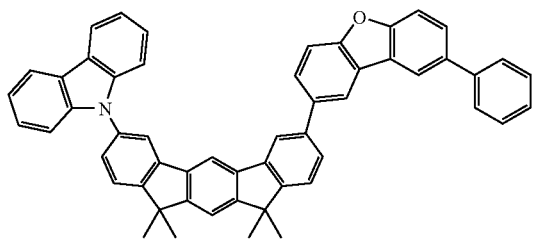
(2-160)
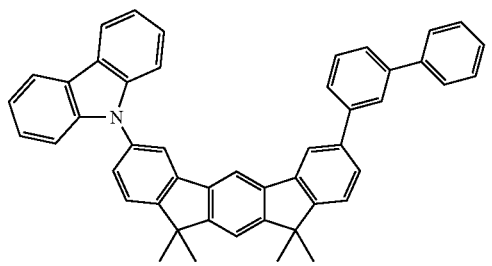

-continued
(2-161)
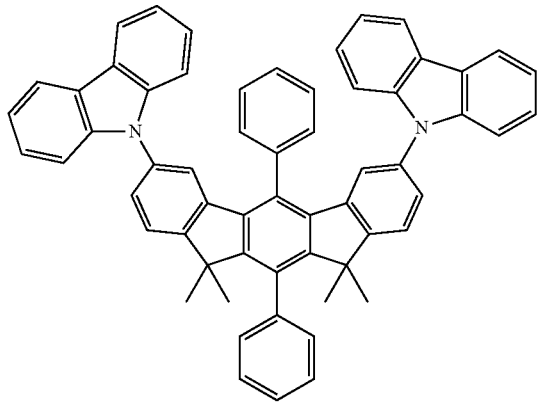
(2-162)
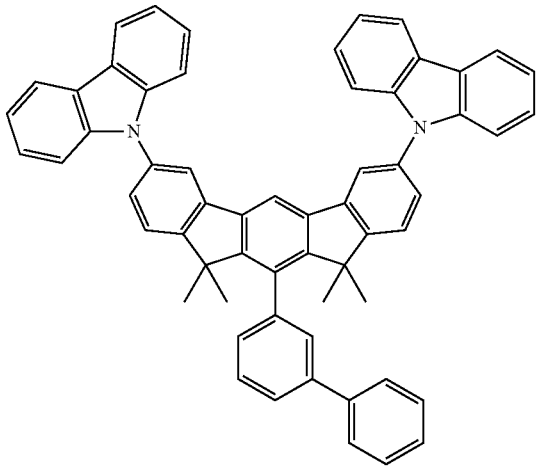
(2-163)
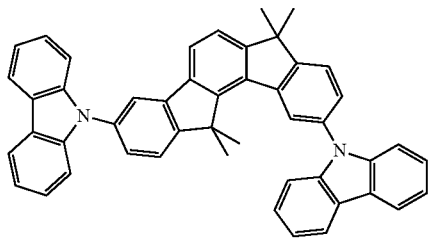
(2-164)
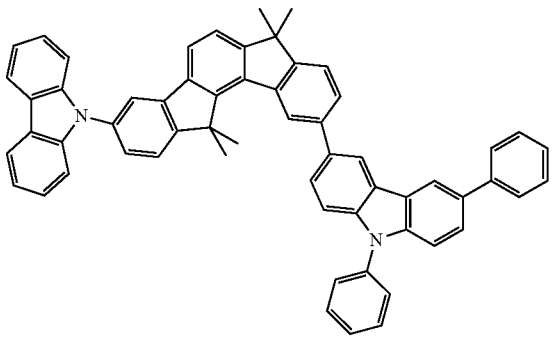
(2-165)
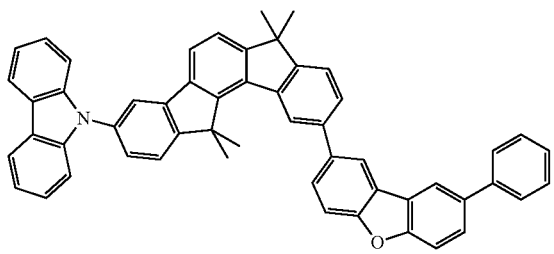
(2-166)
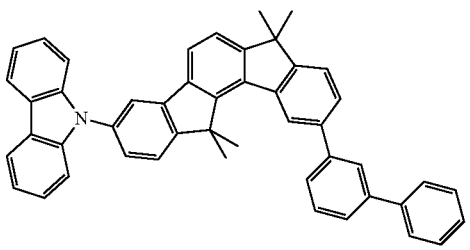
(2-167)
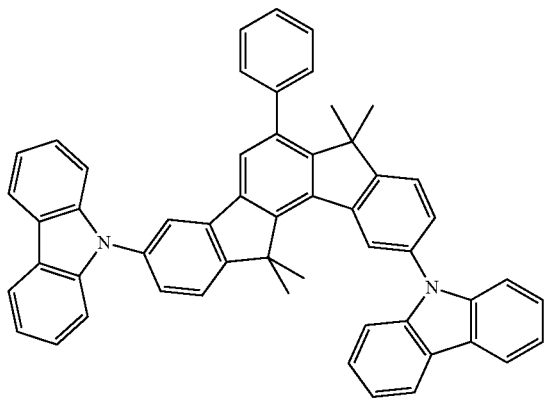
(2-168)
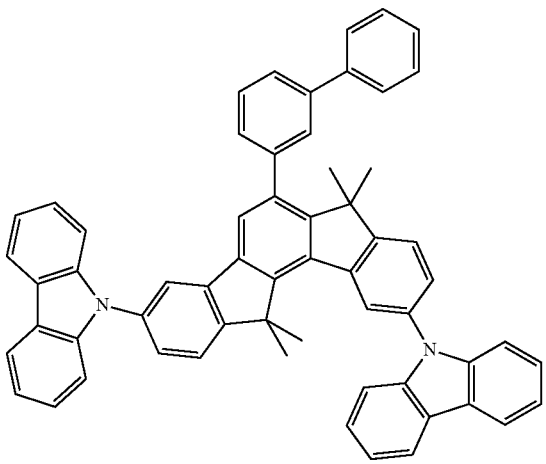

-continued
[Chem 45]
(2-169)
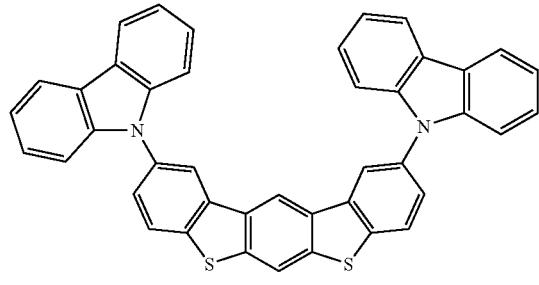
(2-170)
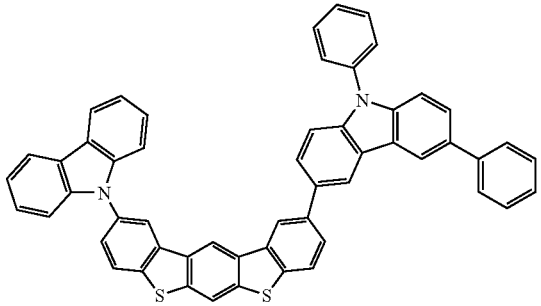
(2-171)
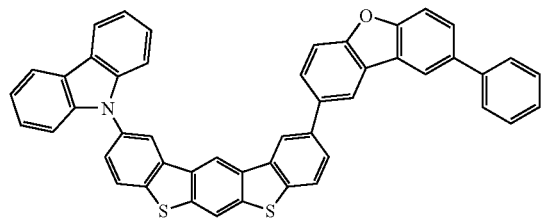
(2-172)
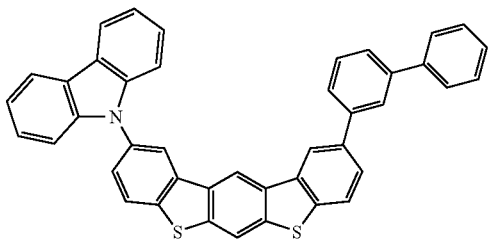
(2-173)
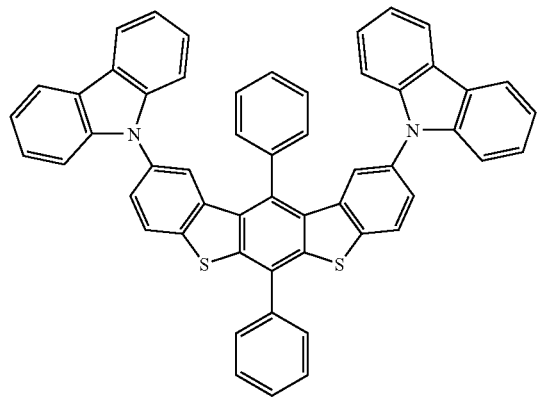
(2-174)
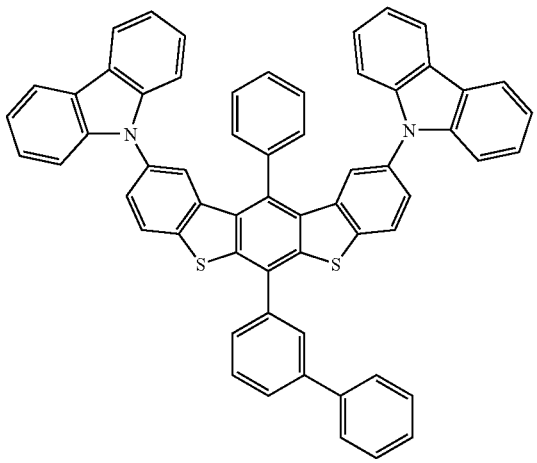
(2-175)
(2-176)
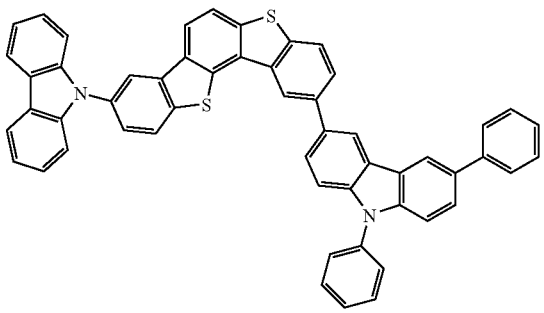

-continued
(2-177)
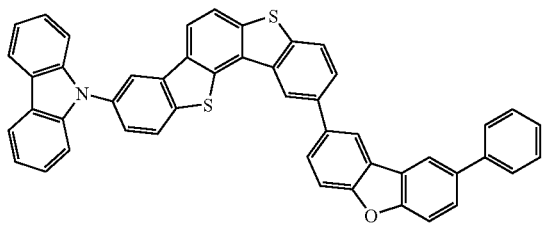
(2-178)
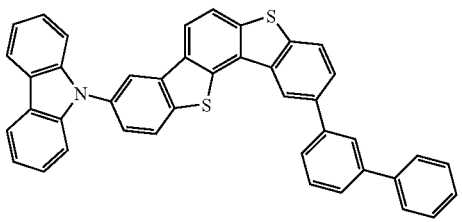
(2-179)
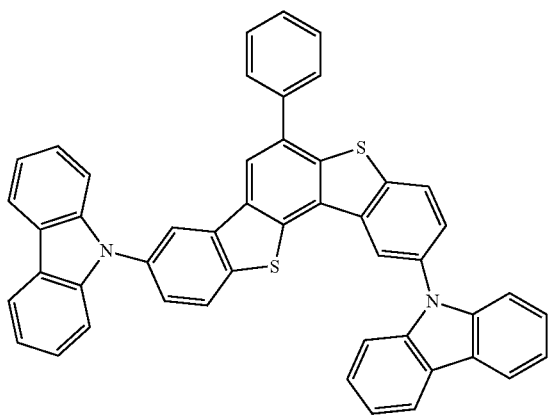
(2-180)
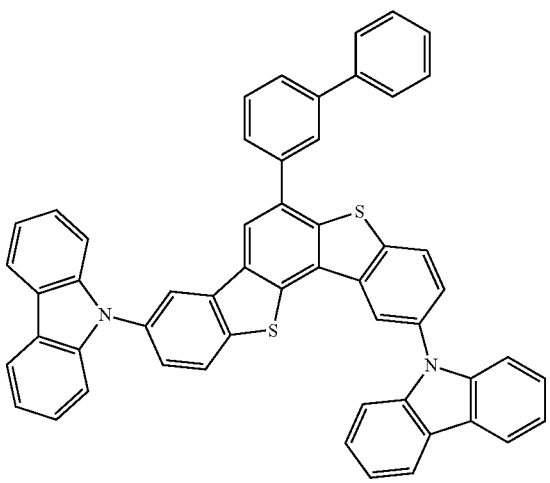
[Chem 46]
(2-181)
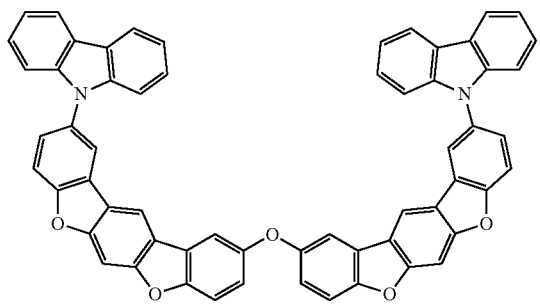
(2-182)
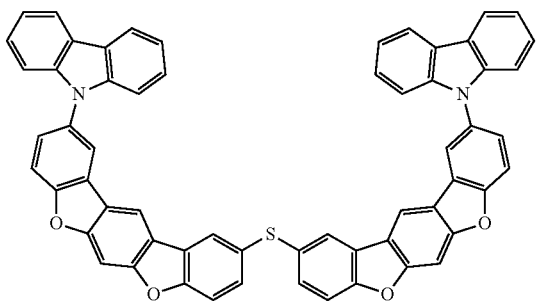
(2-183)
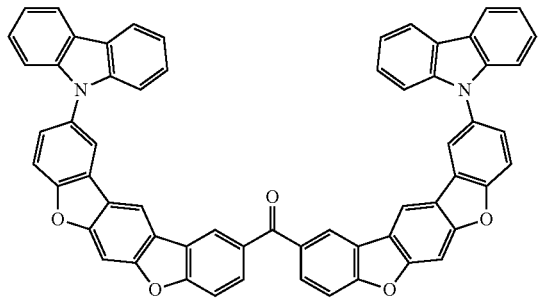
(2-184)
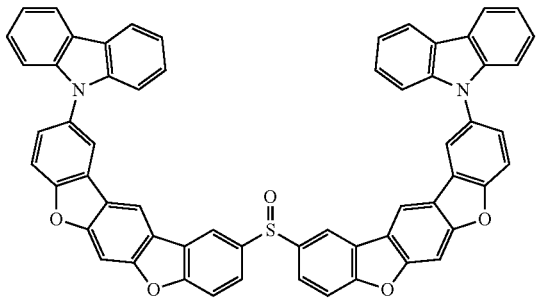

-continued
(2-185)
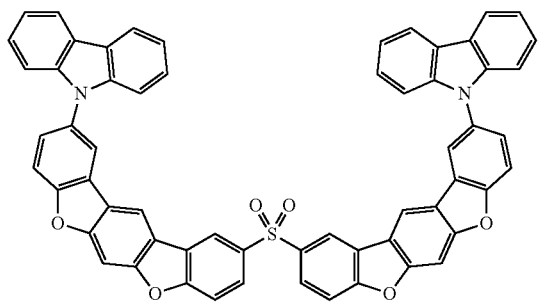
(2-186)
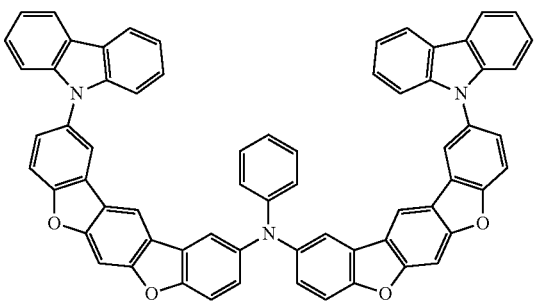
(2-187)
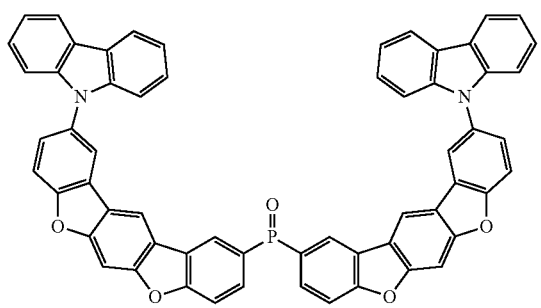
(2-188)
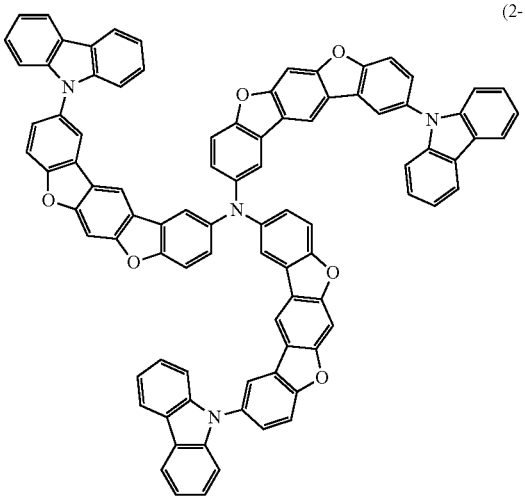
[Chem 47]
(2-189)
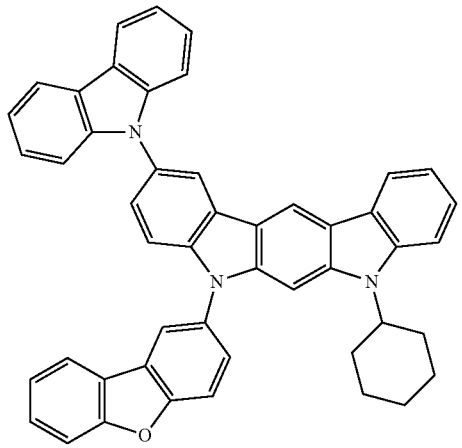
(2-190)
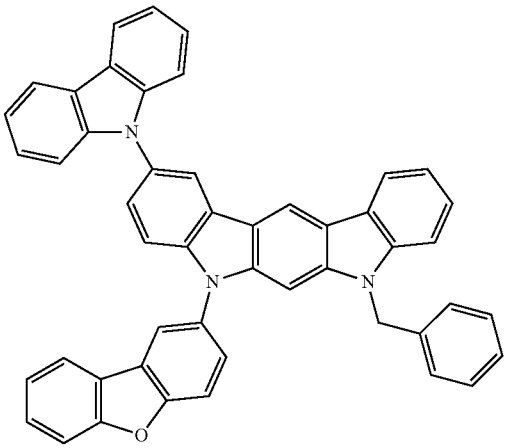
(2-191)
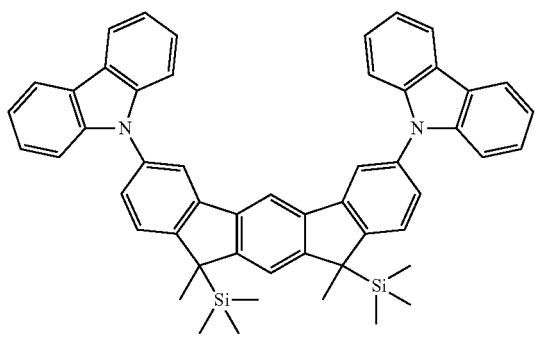

-continued
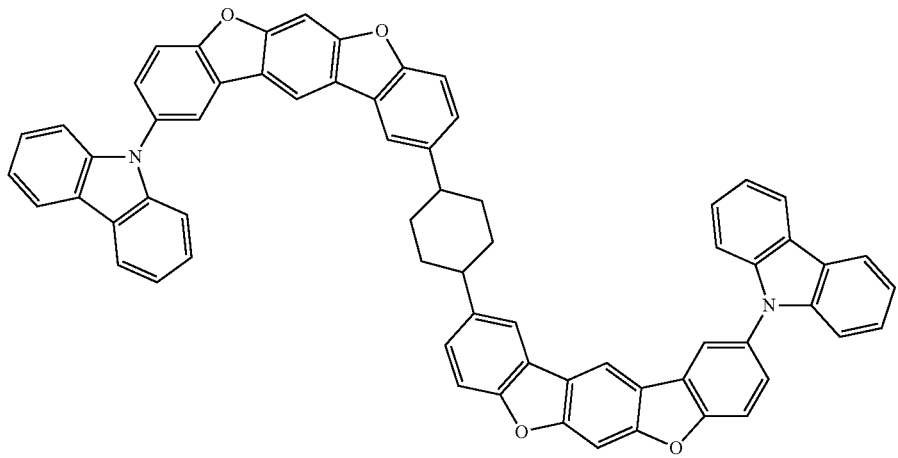
(2-192)
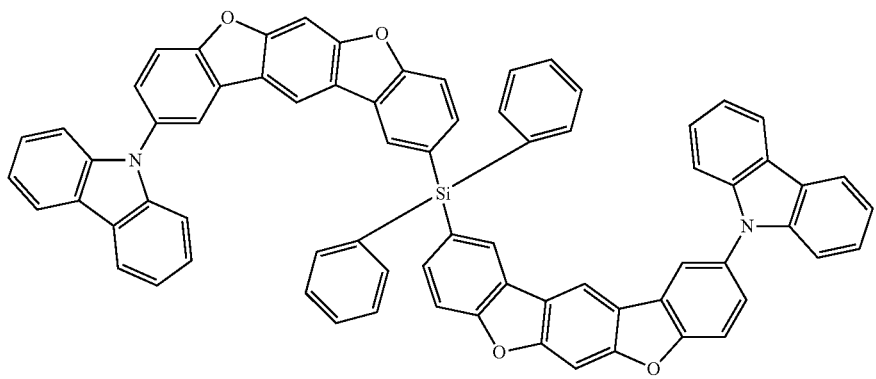
(2-193)
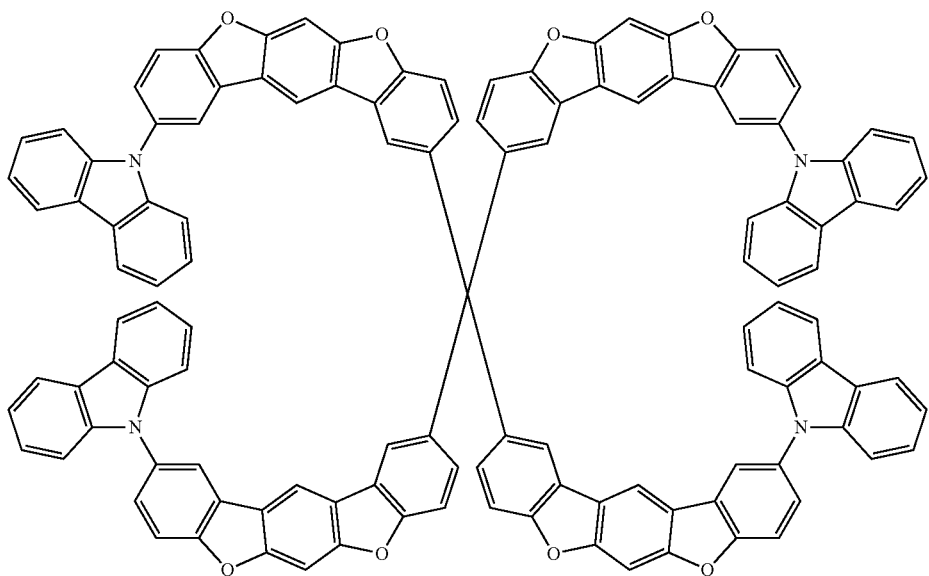
(2-194)

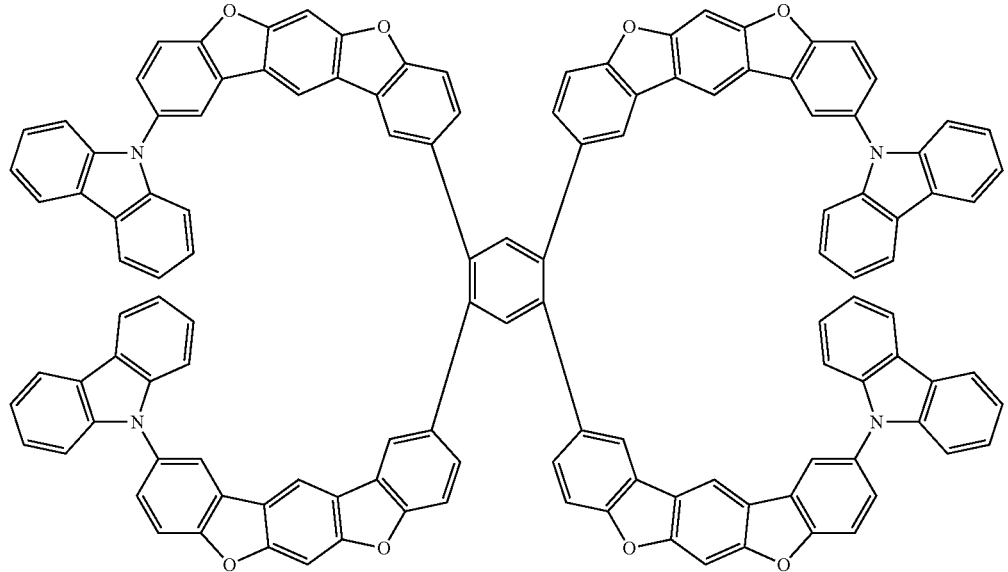
(2-195)
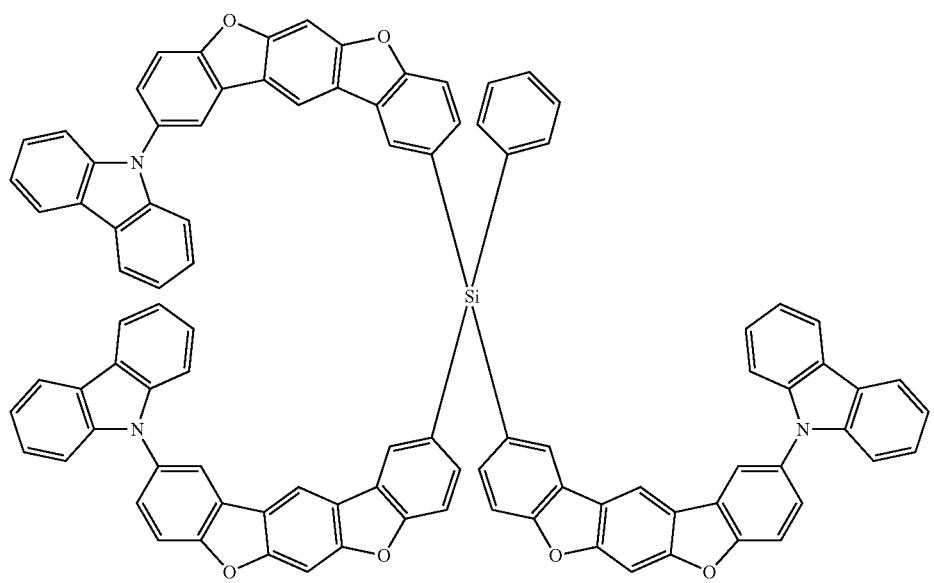
(2-196)

-continued
(2-197)
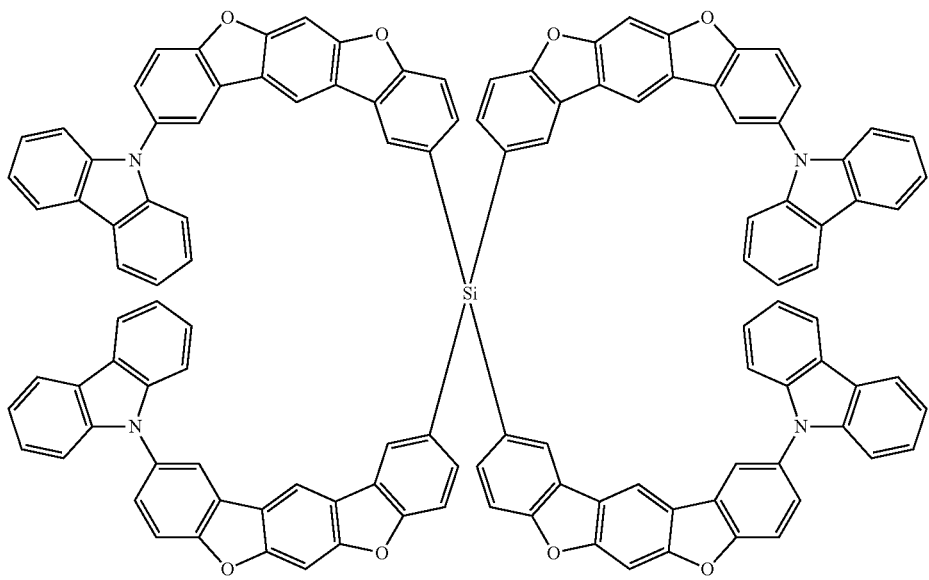
(2-198) (2-199)
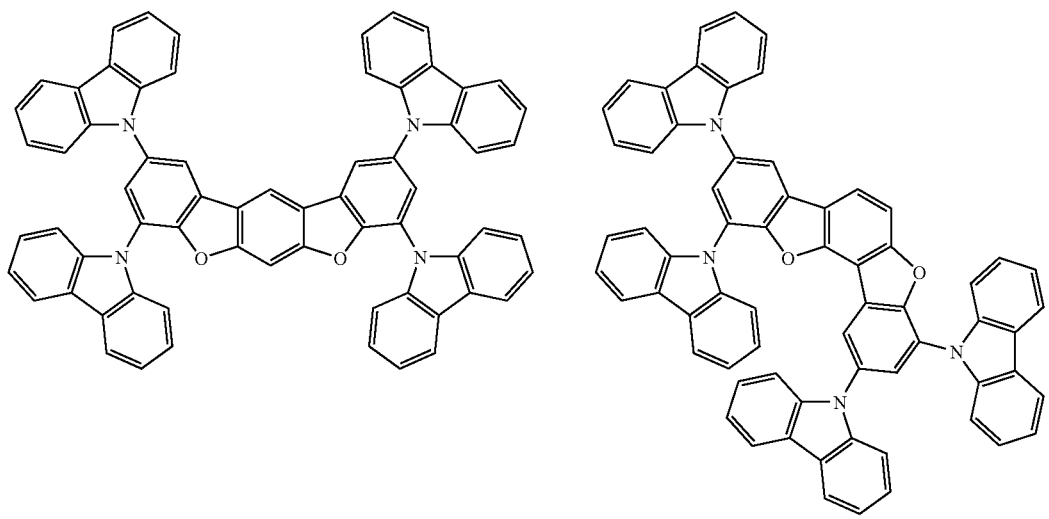
[Chem 48]
(3-1) (3-2)
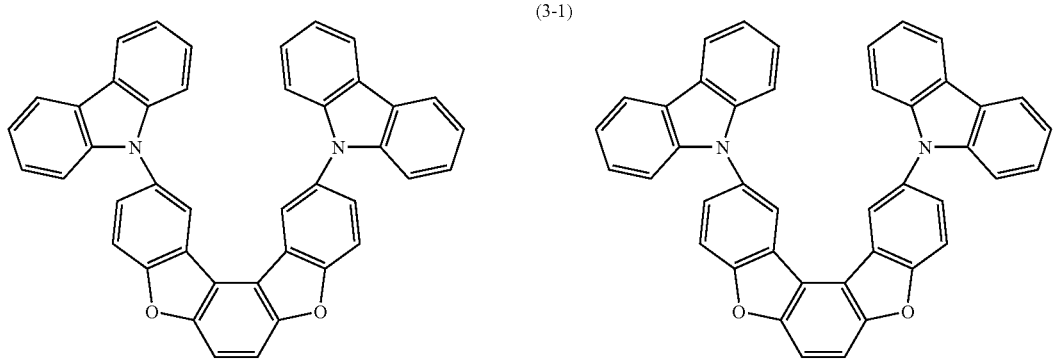

-continued
(3-3)
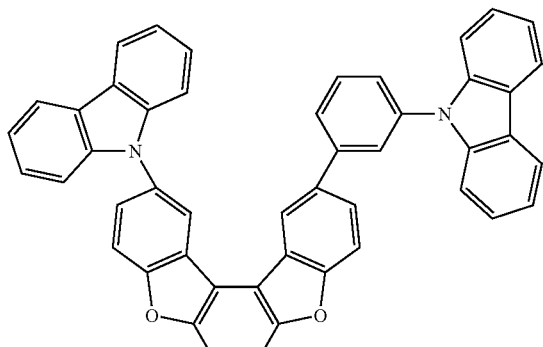
(3-4)
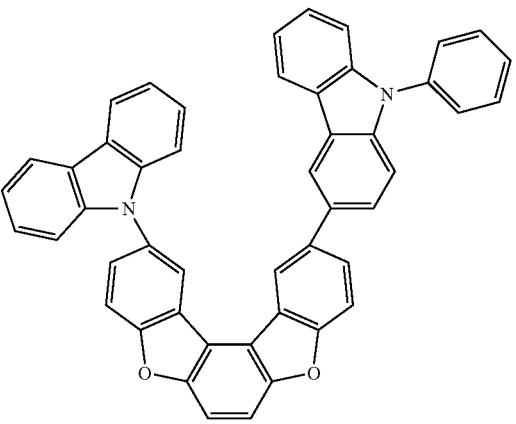
(3-5)
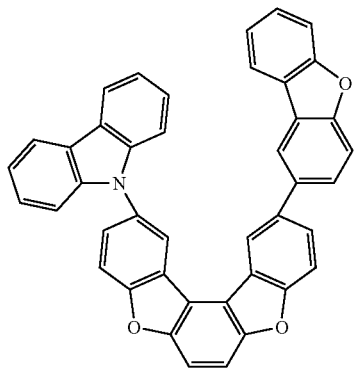
(3-6)
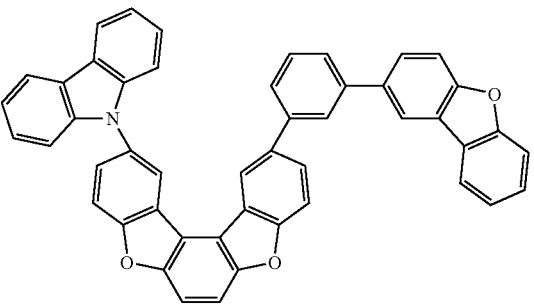
(3-7)
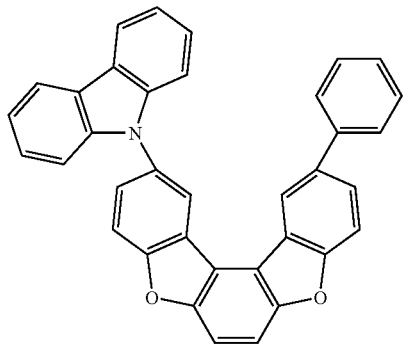
(3-8)
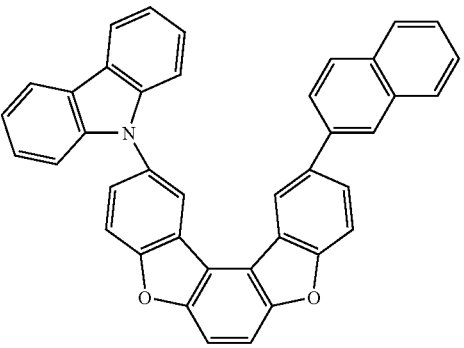
(3-9)
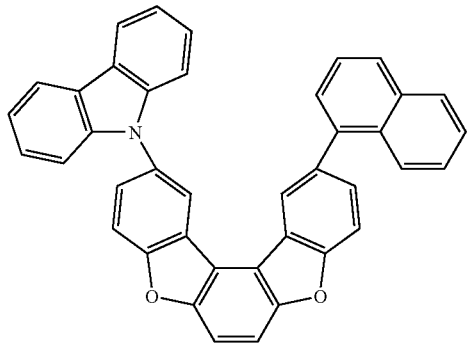
(3-10)
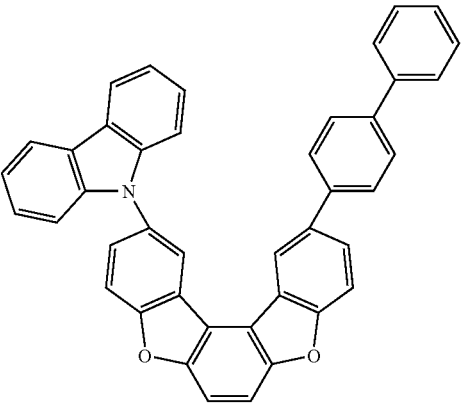

-continued
(3-11)
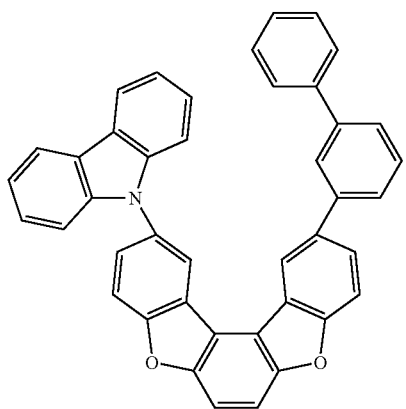
(3-12)
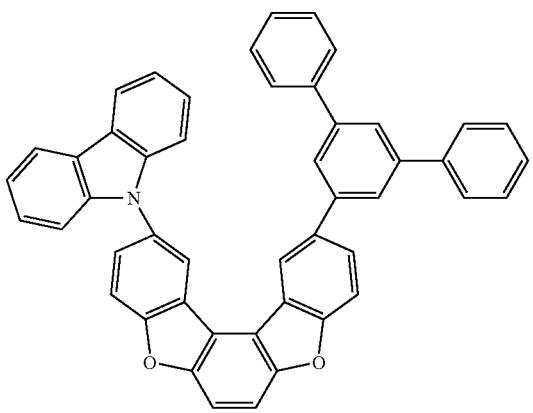
(3-13)
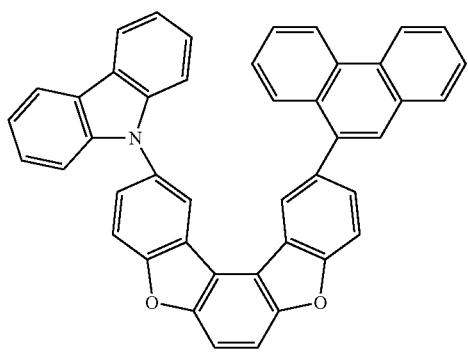
(3-14)
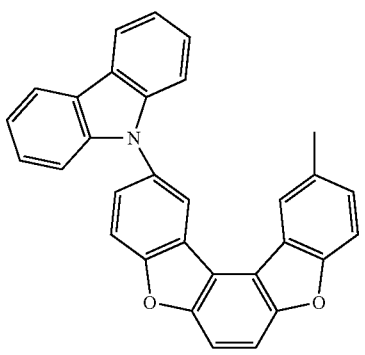
(3-15)
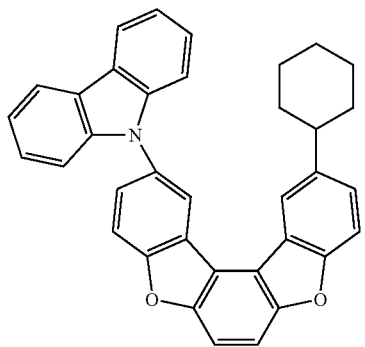
(3-16)
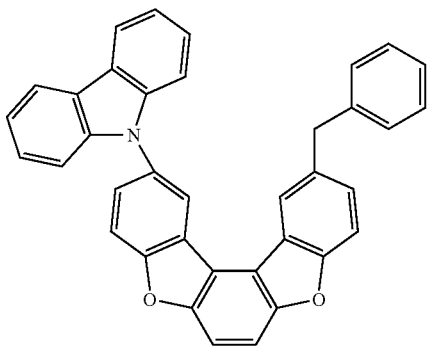
(3-17)
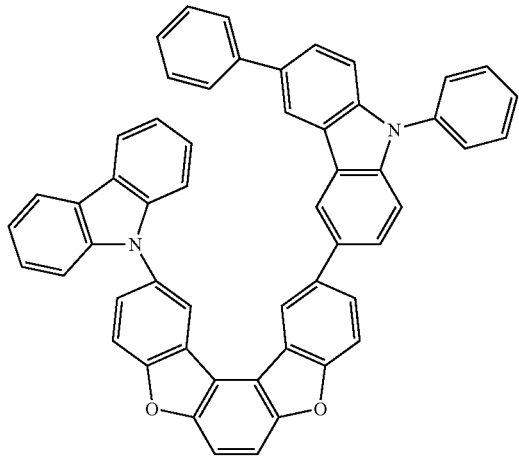
(3-18)
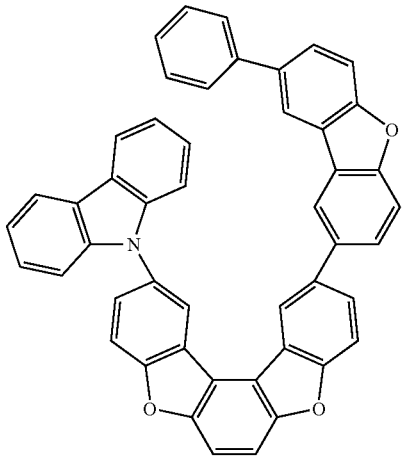

(3-19)
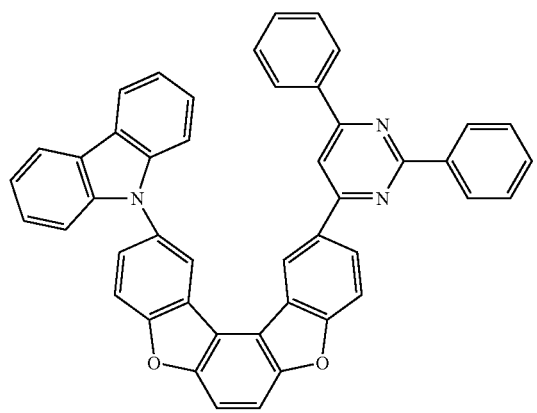
[Chem 49]
(3-20)
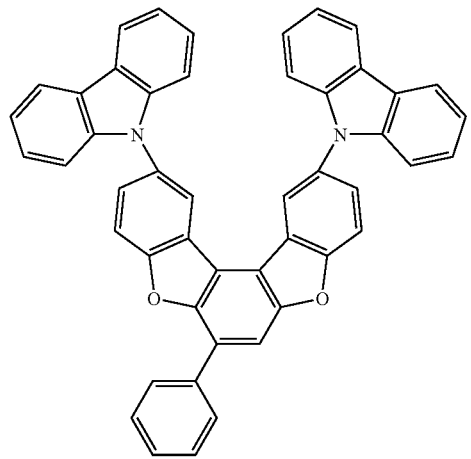
(3-21)
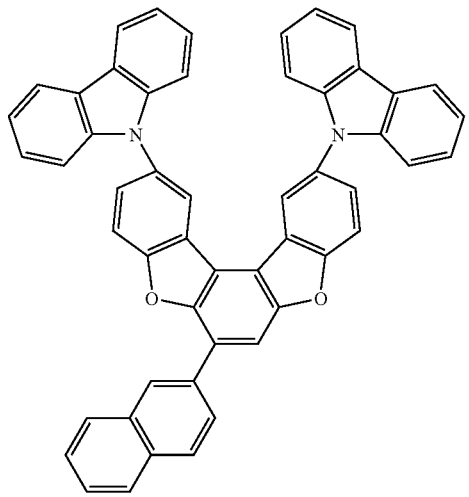
(3-22)
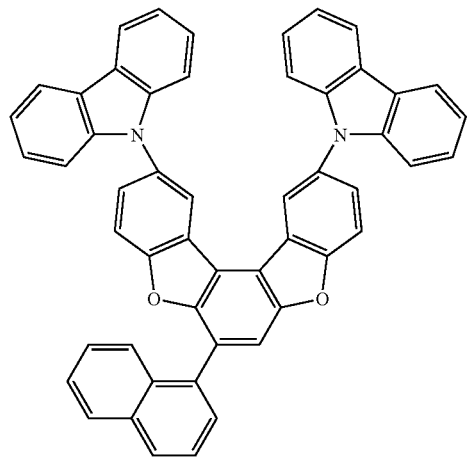
(3-23)
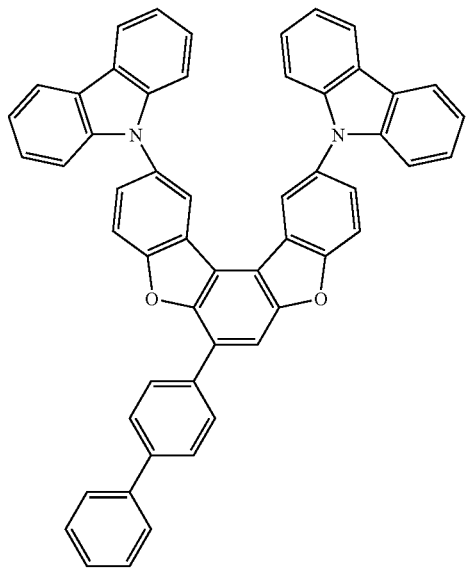

-continued
(3-24)
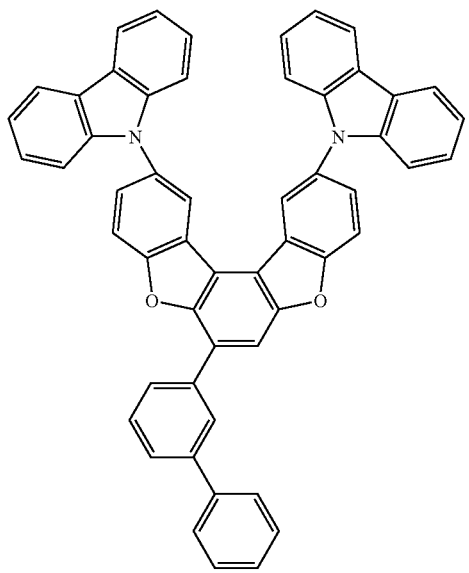
(3-25)
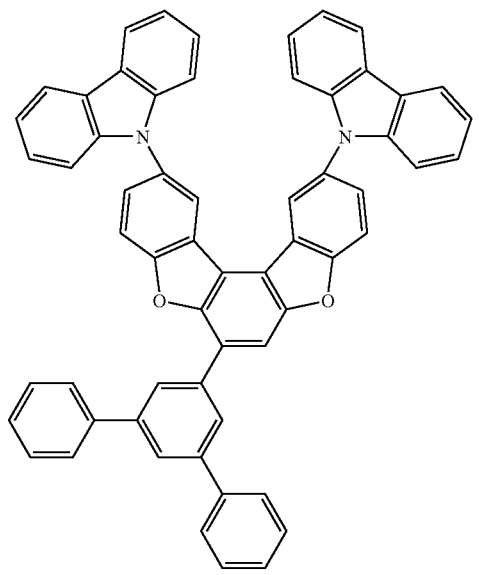
(3-26)
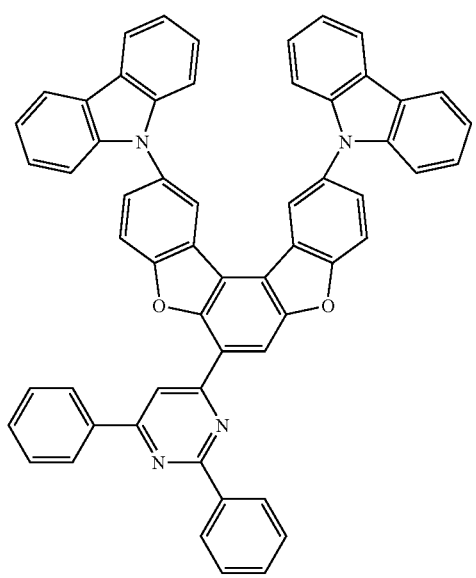
(3-27)
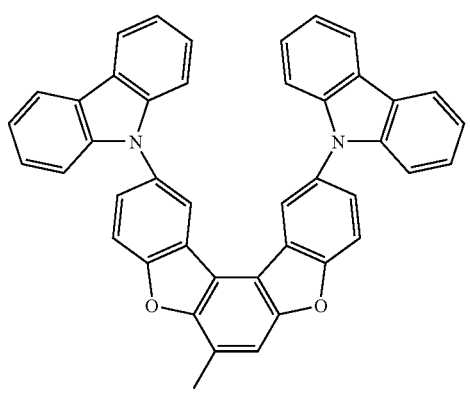
(3-28)
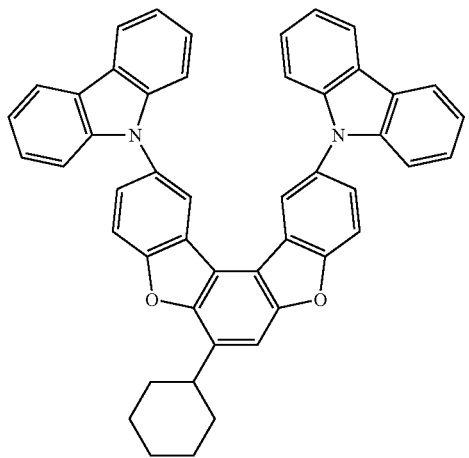
(3-29)
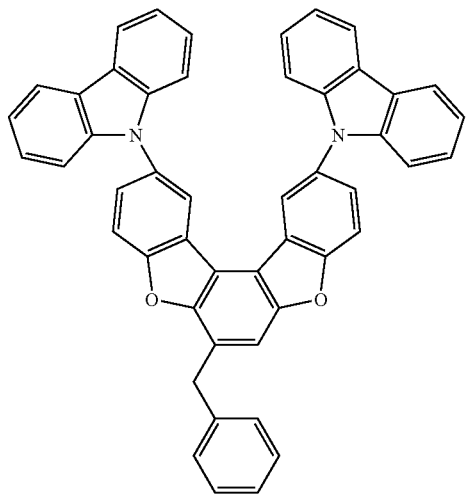

-continued
(3-30)
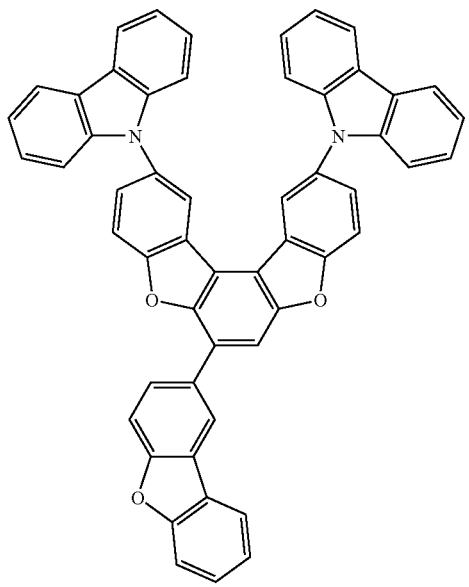
(3-31)
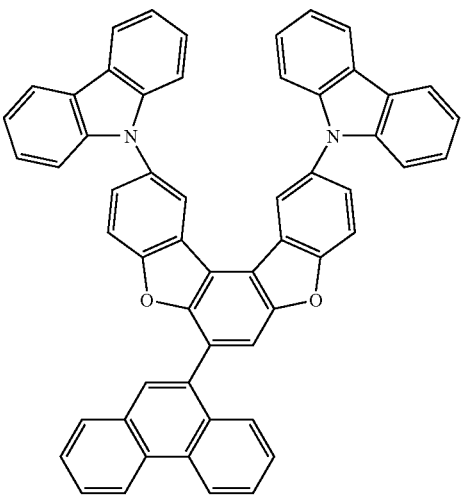
(3-32)
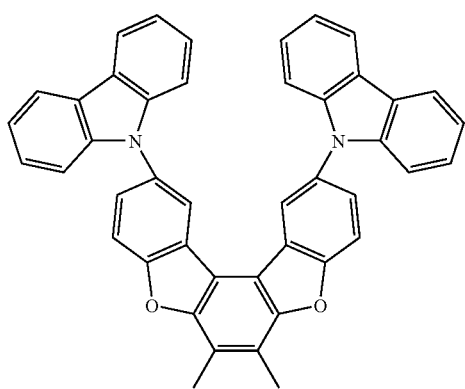
(3-33)
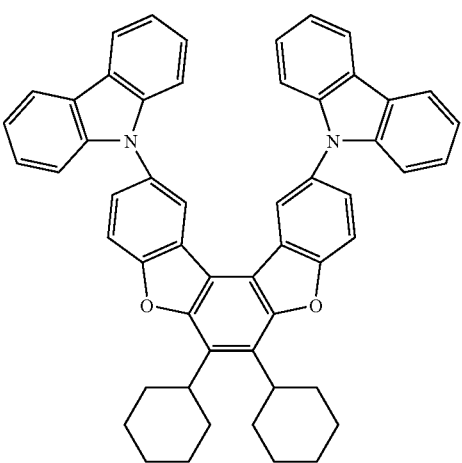
(3-34)
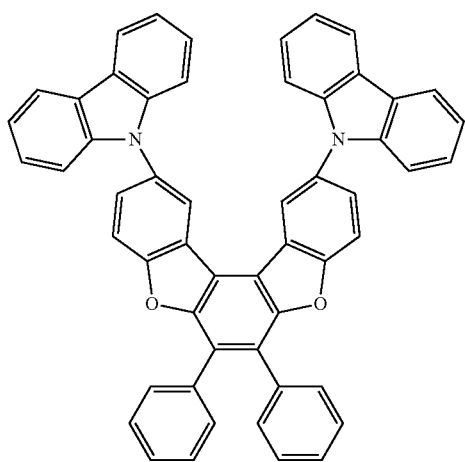

[Chem 51]
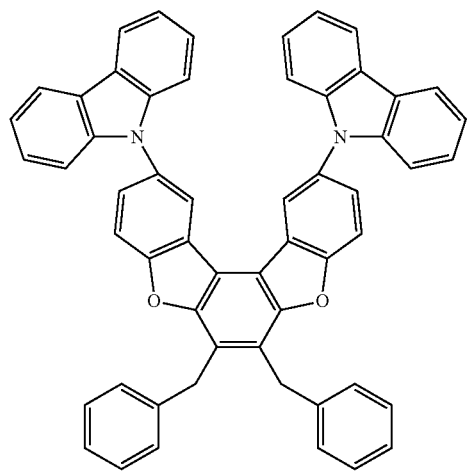 (3-35)
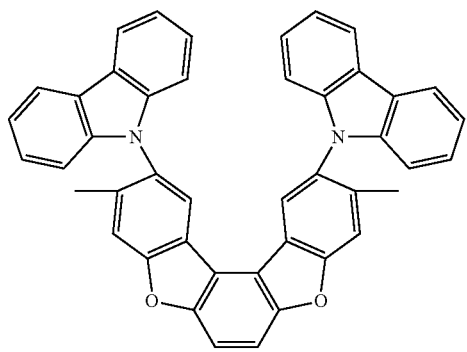 (3-36)
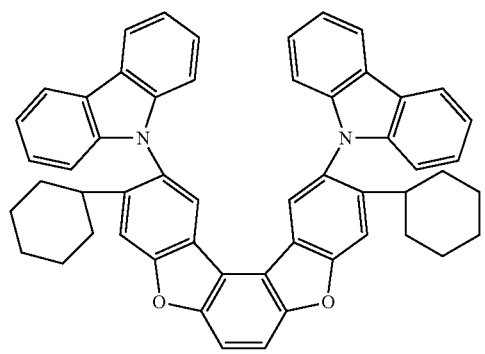 (3-37)
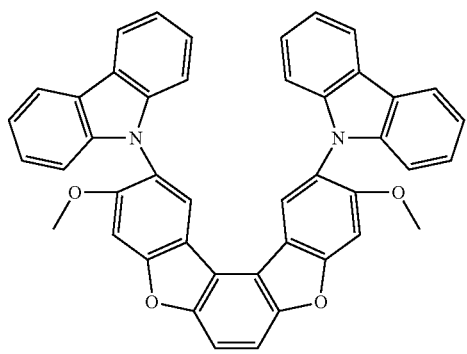 (3-38)
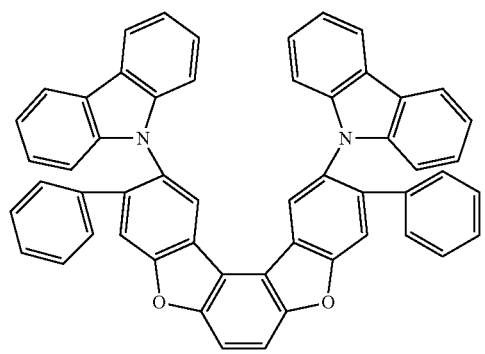 (3-39)
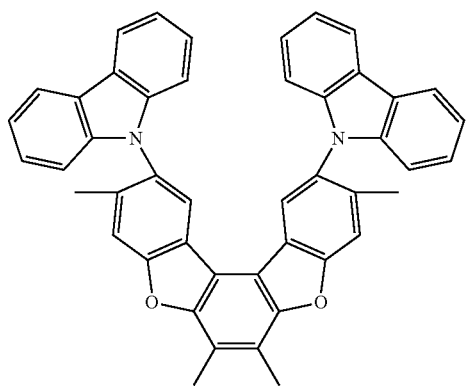 (3-40)

-continued
(3-41)
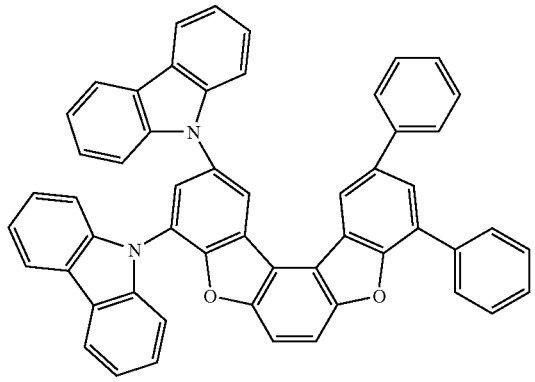
(3-42)
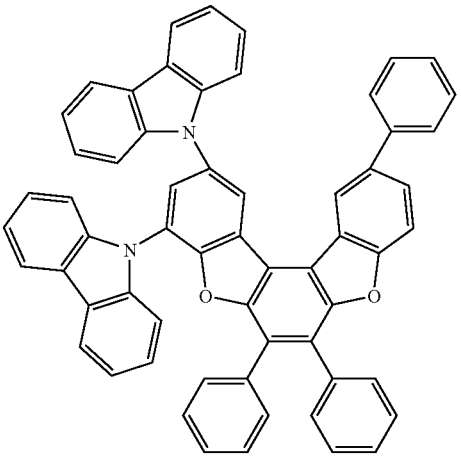
(3-43)
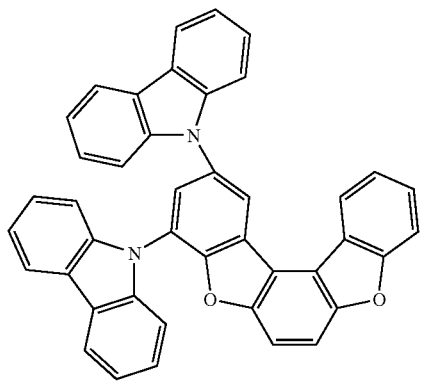
(3-44)
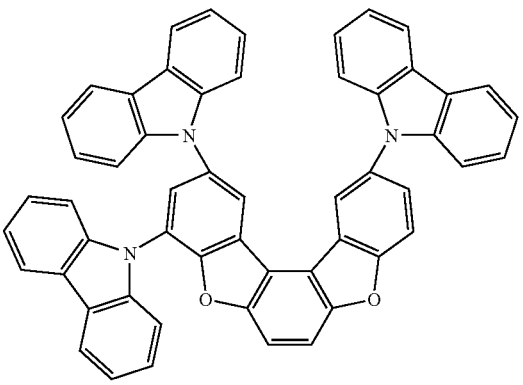
(3-45)
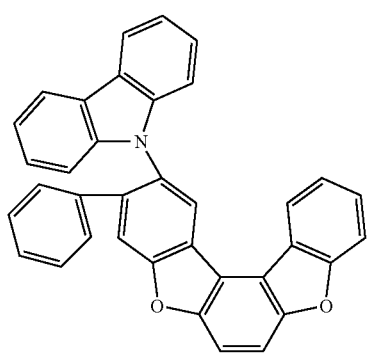
(3-46)
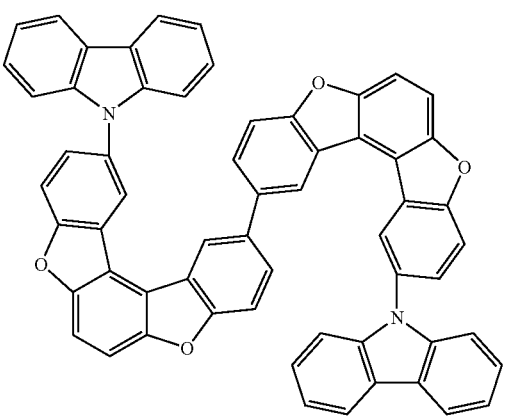

-continued
(3-47)
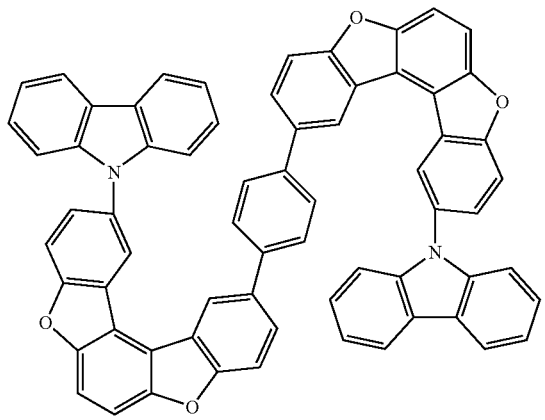
[Chem 51]
(3-48)
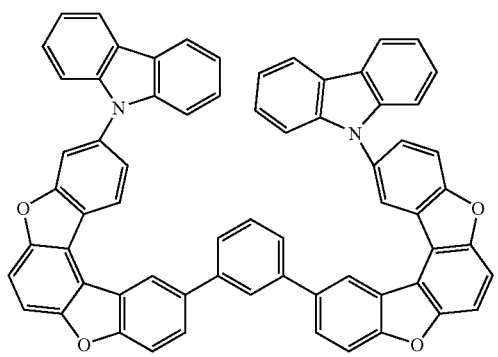
(3-49)
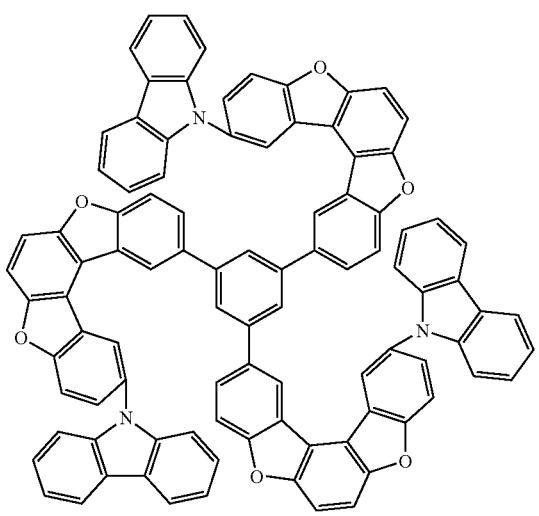
(3-50)
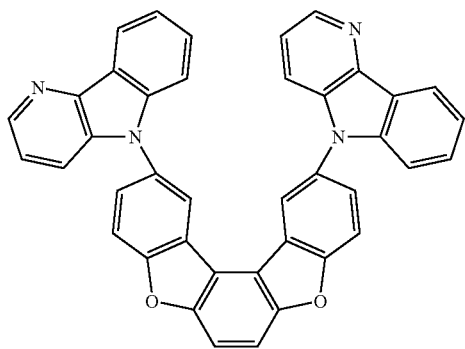
(3-51)
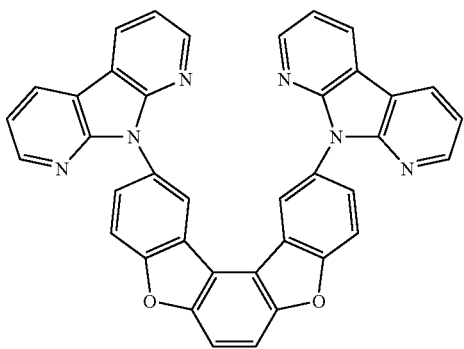

-continued
(3-52) 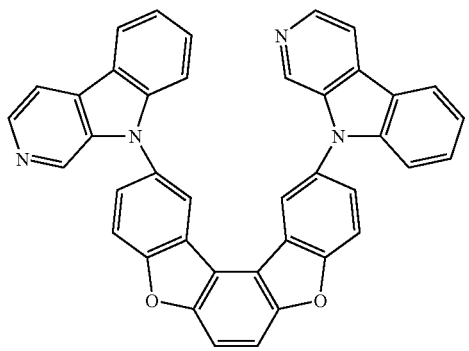
(3-53) 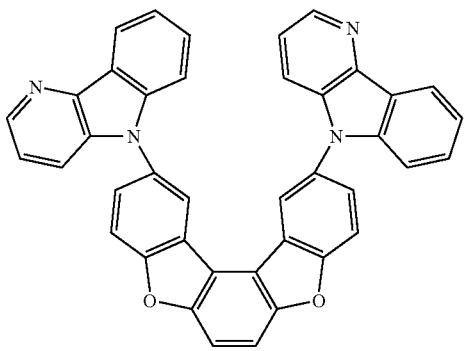
(3-54) 
(3-55) 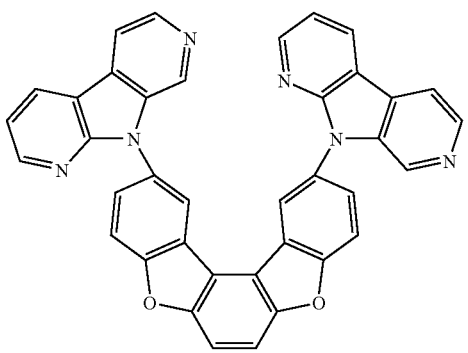
(3-56) 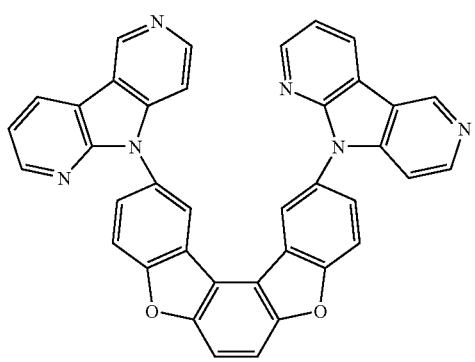
(3-57) 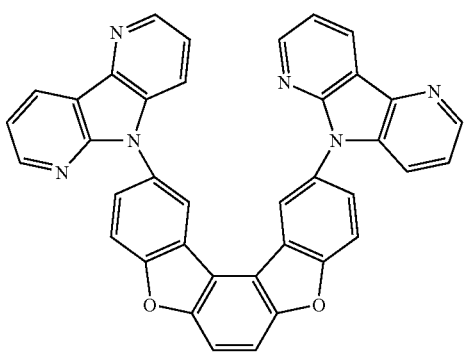
(3-58) 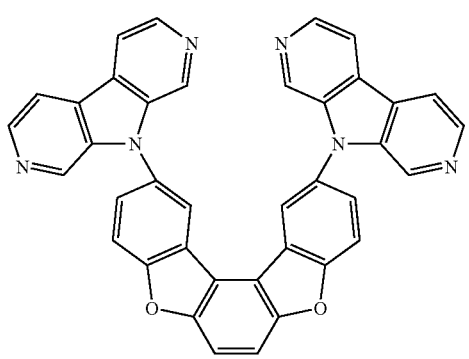
(3-59) 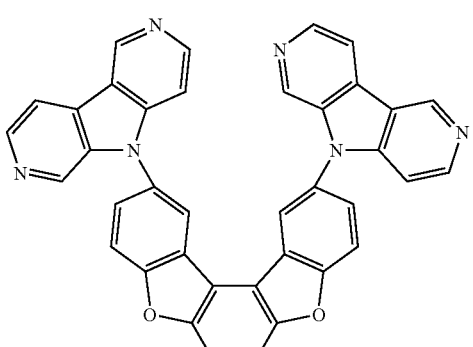

-continued
(3-60)
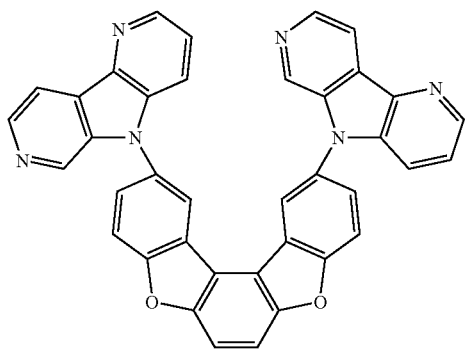
(3-61)
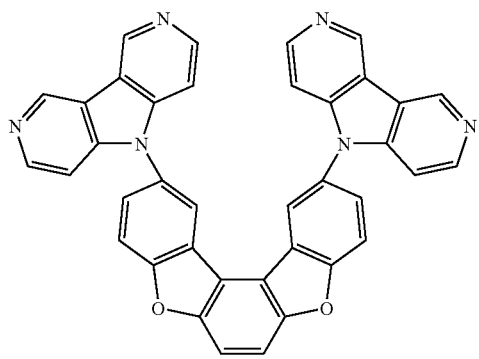
[Chem 52]
(3-62)
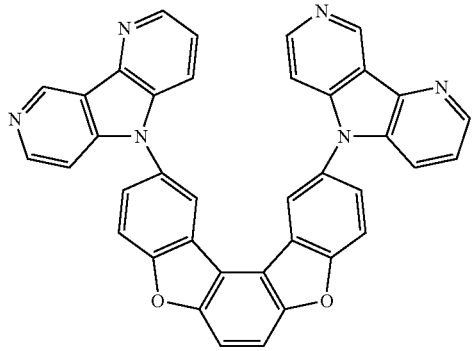
(3-63)
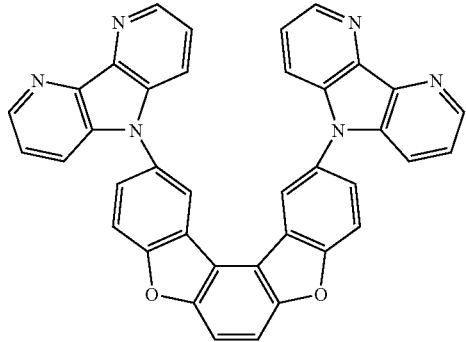
(3-64)
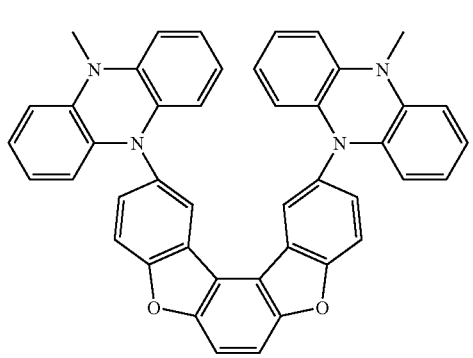
(3-65)
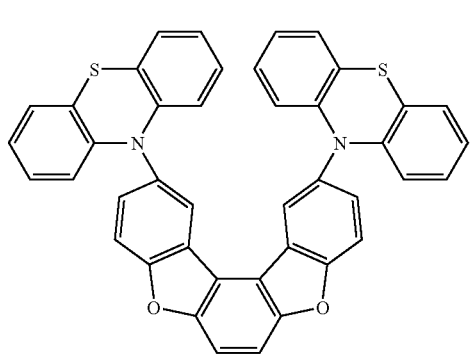
(3-66)
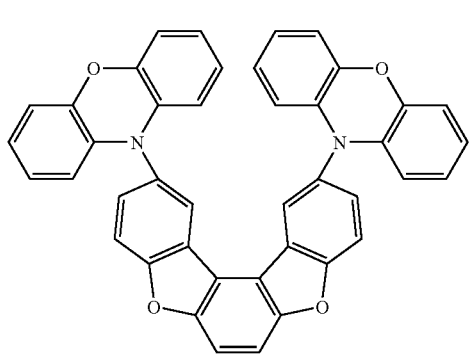
(3-67)
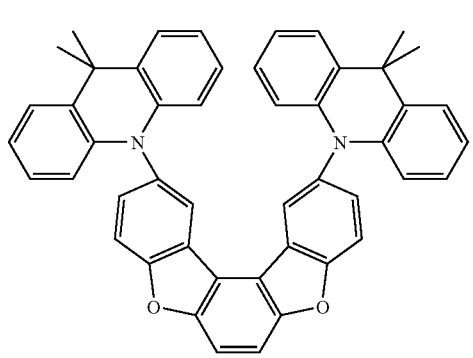

-continued
(3-68)
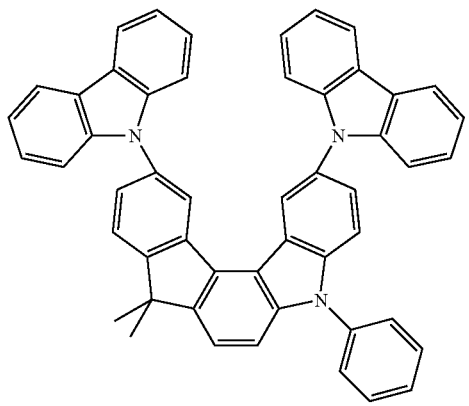
(3-69)
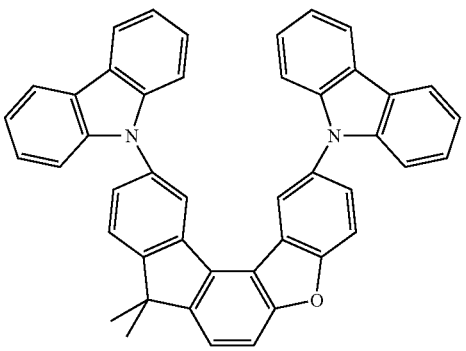
(3-70)
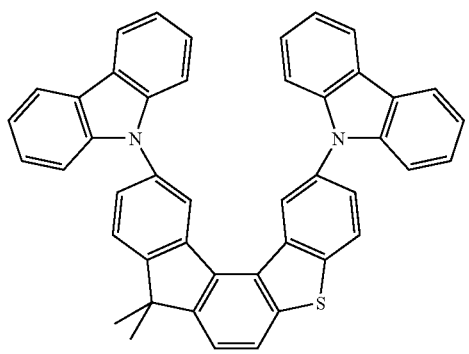
(3-71)
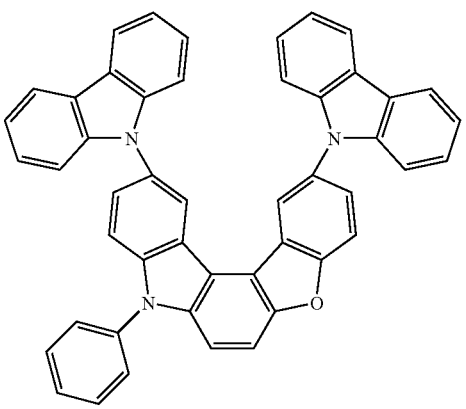
(3-72)
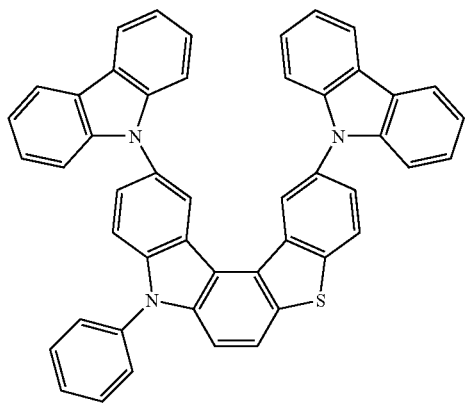
(3-73)
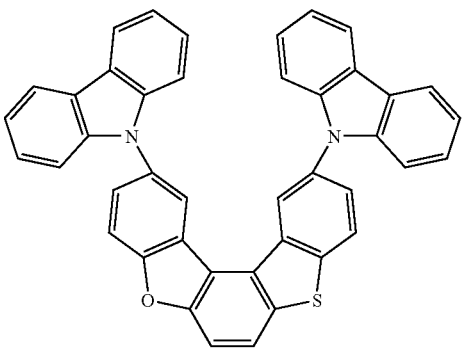
(3-74)
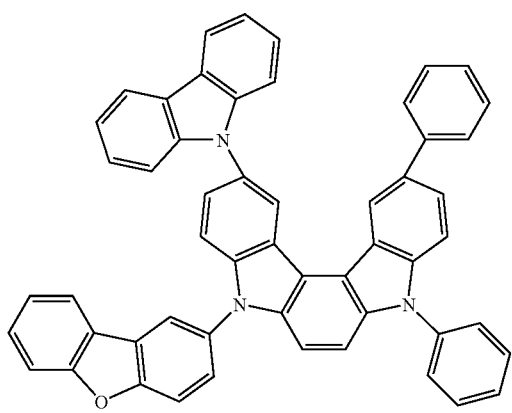
(3-75)
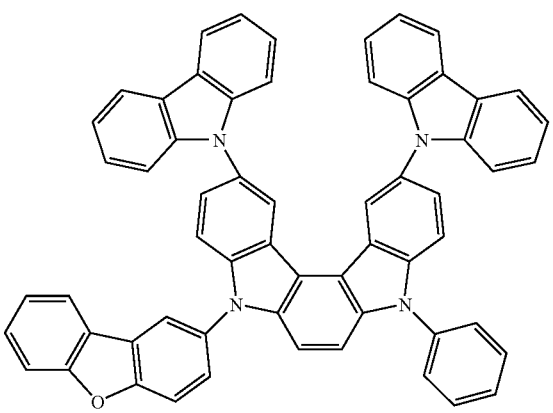

(3-76)
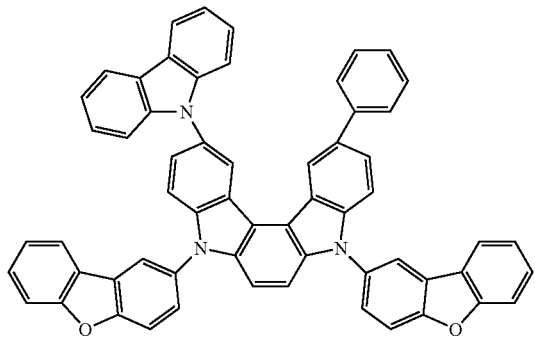
[Chem 53]
(3-77)
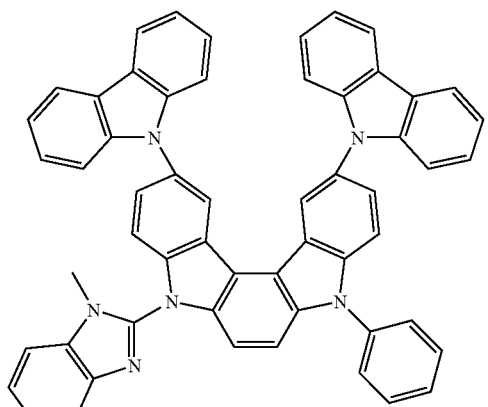
(3-78)
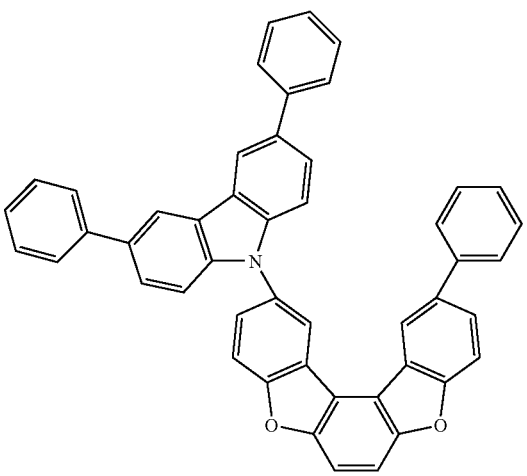
(3-79)
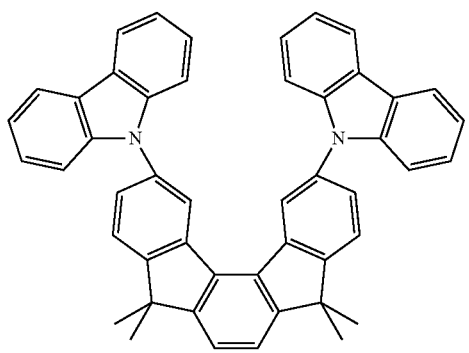
(3-80)
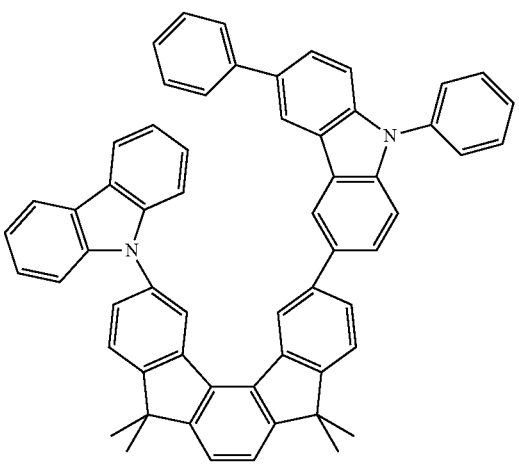

-continued
(3-81)
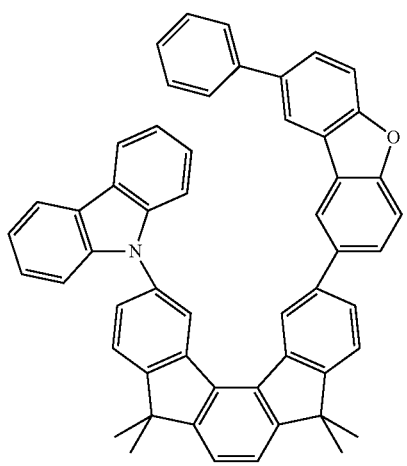
(3-82)
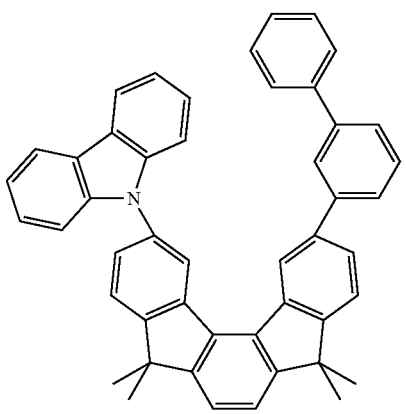
(3-83)
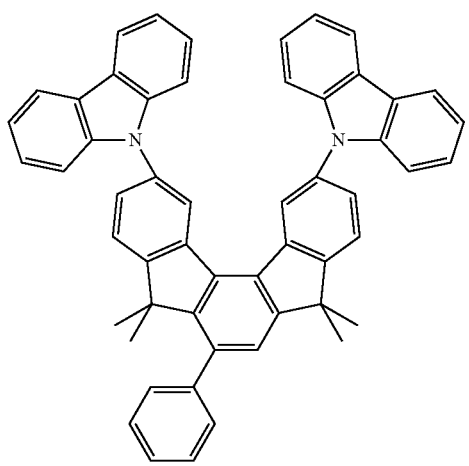
(3-84)
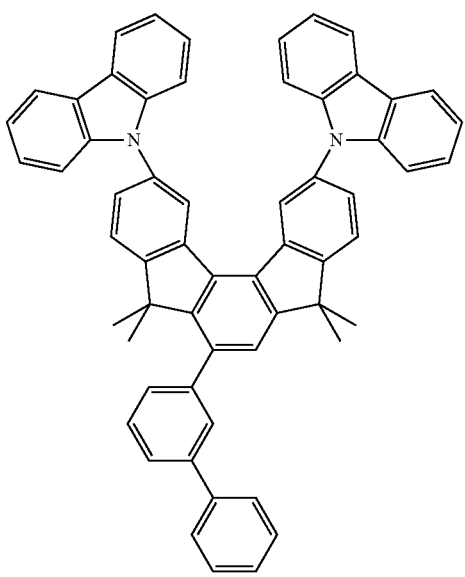
(3-85)
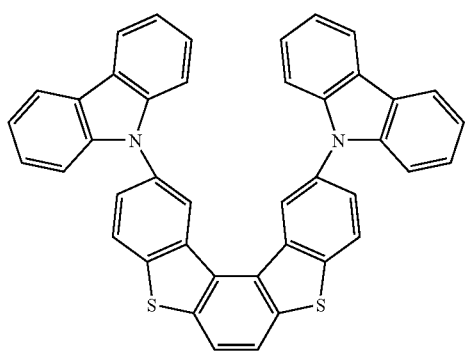
(3-86)
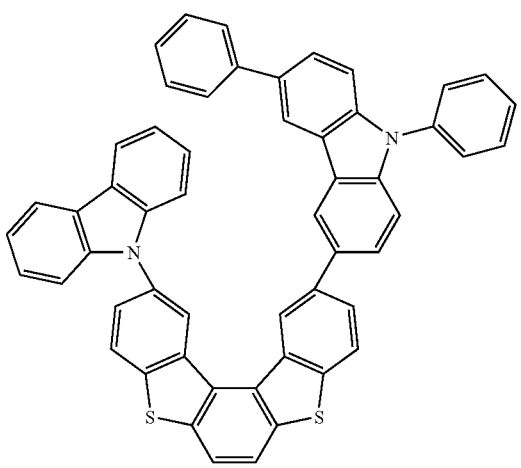

(3-87)
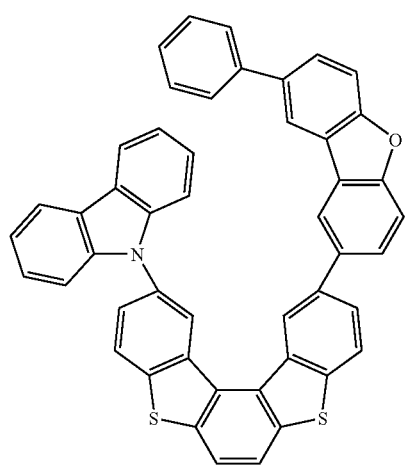
(3-88)
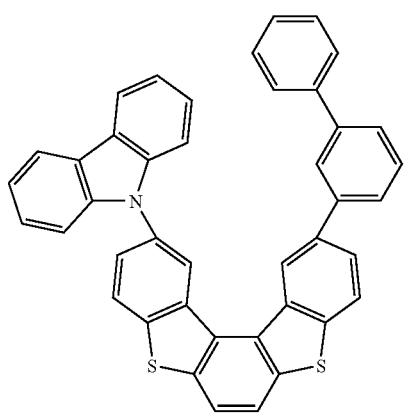
(3-89)
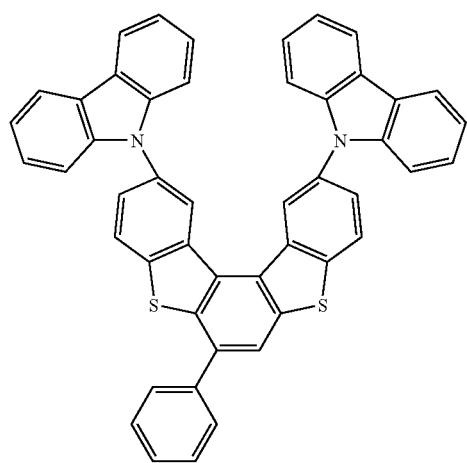
(3-90)
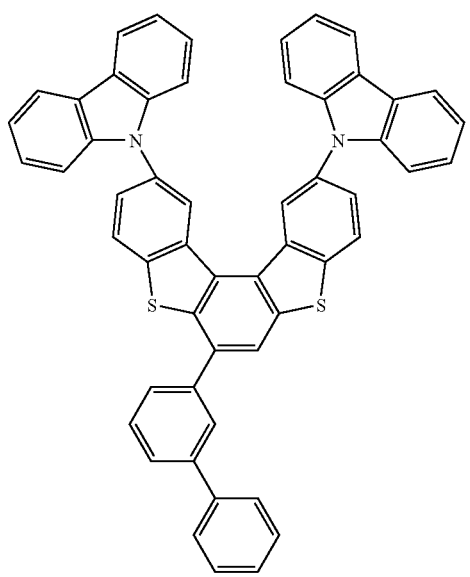
[Chem 54]
(3-91)
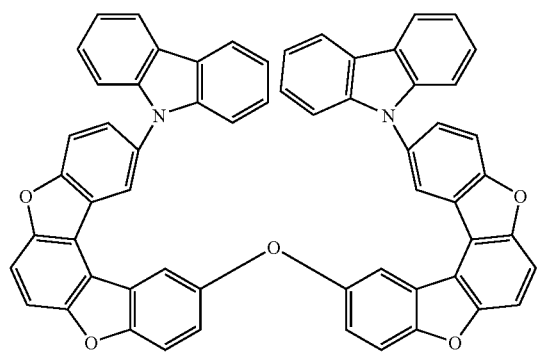
(3-92)
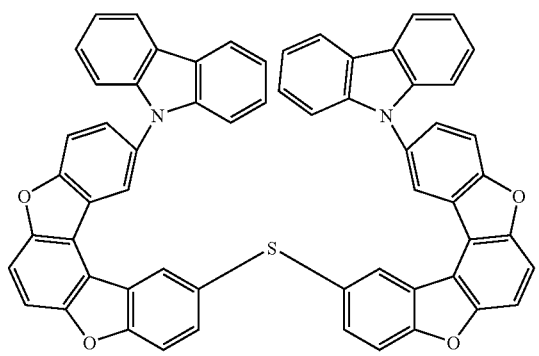

(3-93)
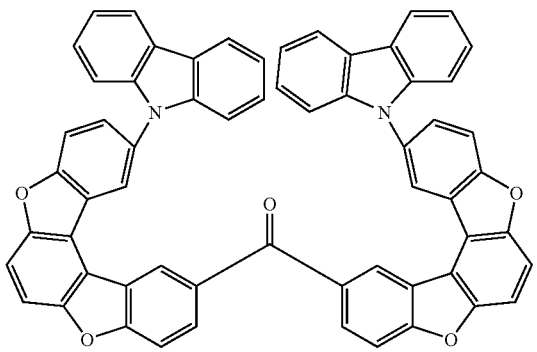
(3-94)
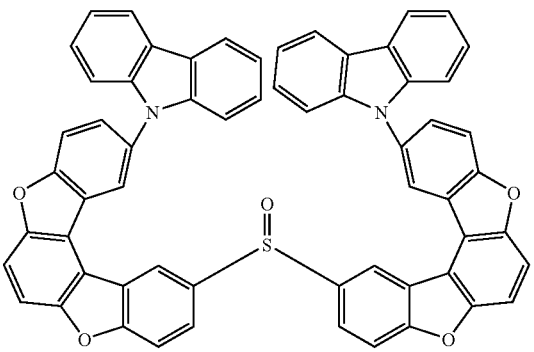
(3-95)
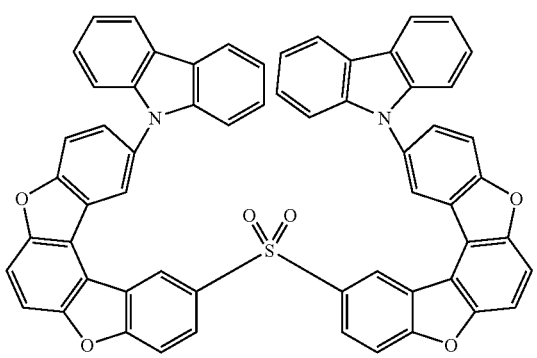
(3-96)
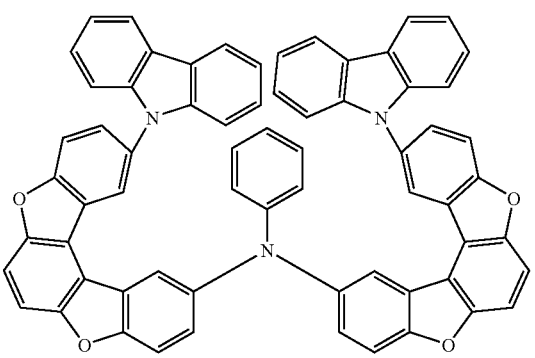
(3-97)
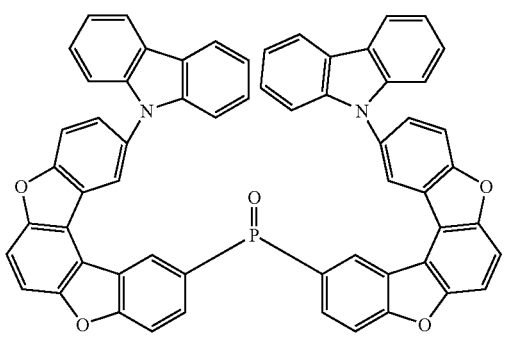
(3-98)
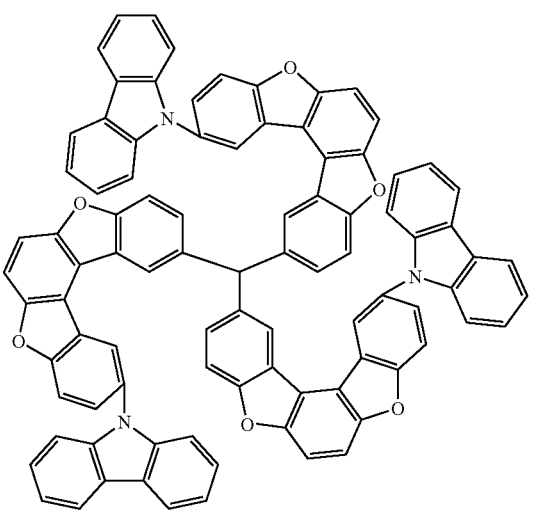

-continued
(3-99)
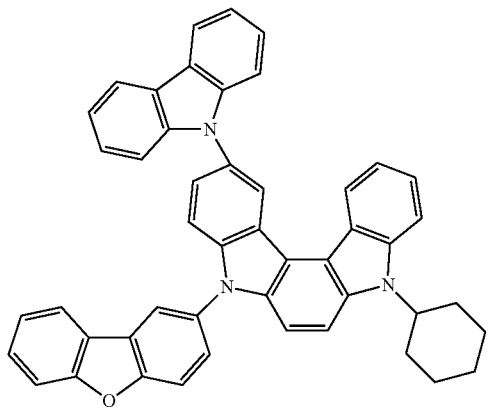
(3-100)
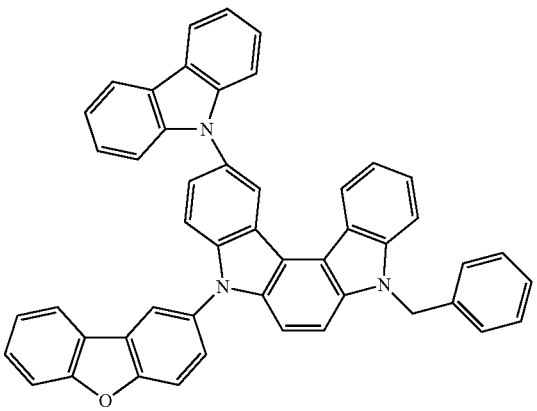
(3-101)
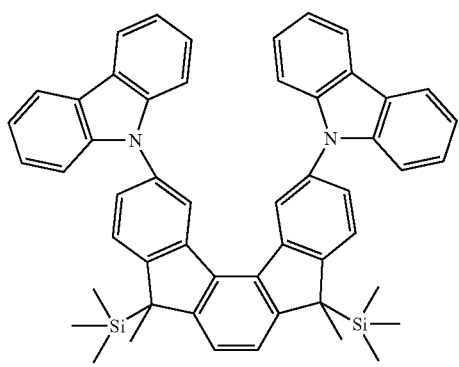
[Chem 55]
(3-102)
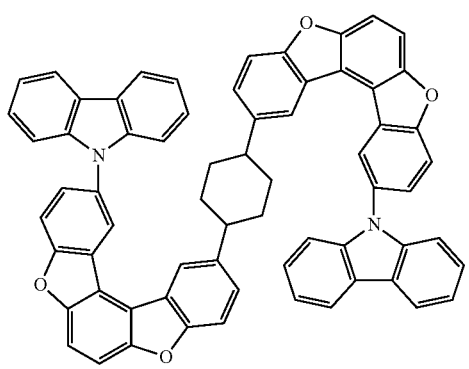
(3-103)
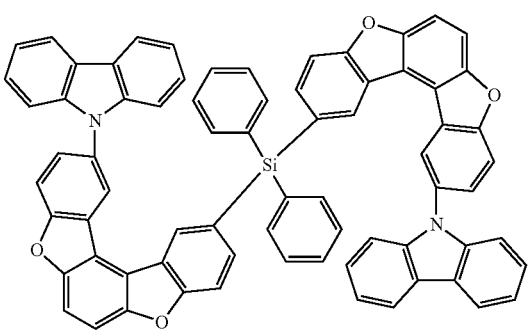

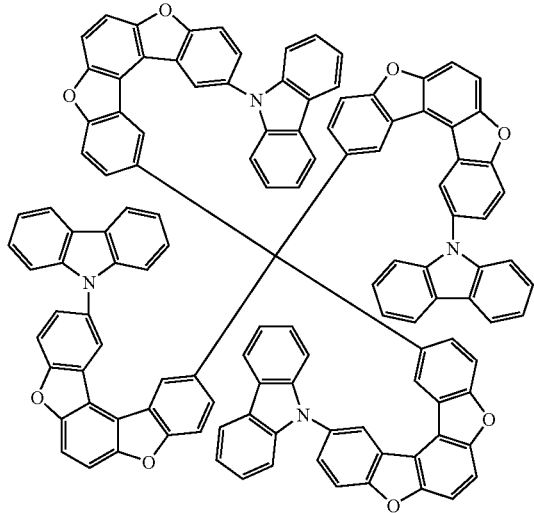
(3-104)
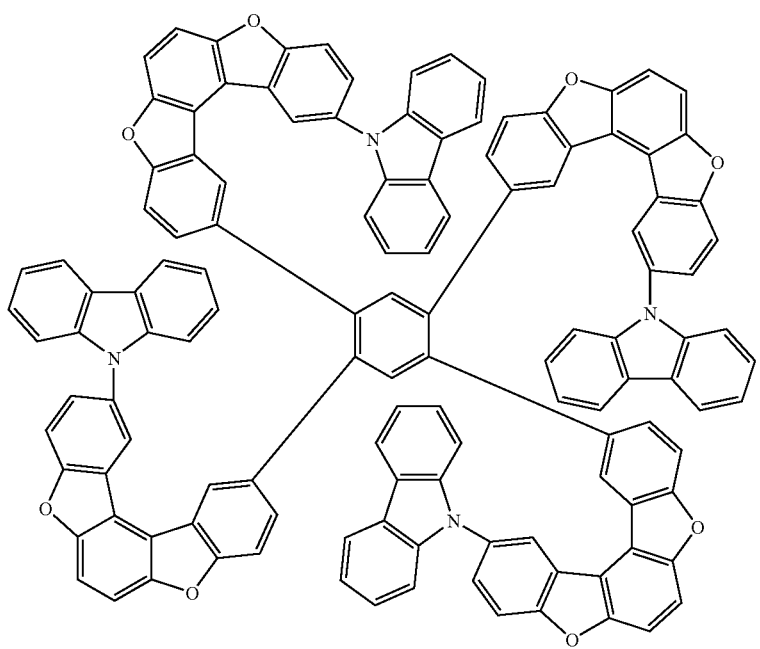
(3-105)

(3-106)
(3-107)

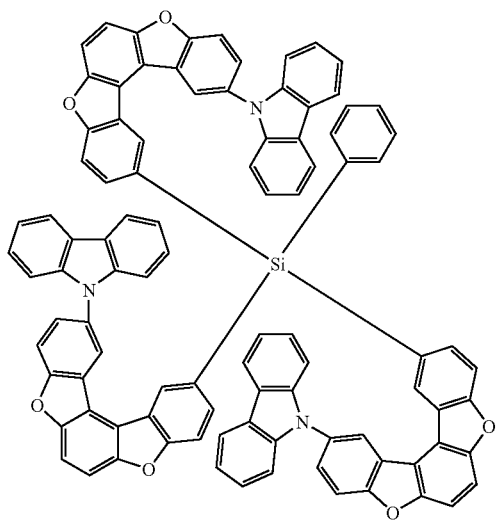
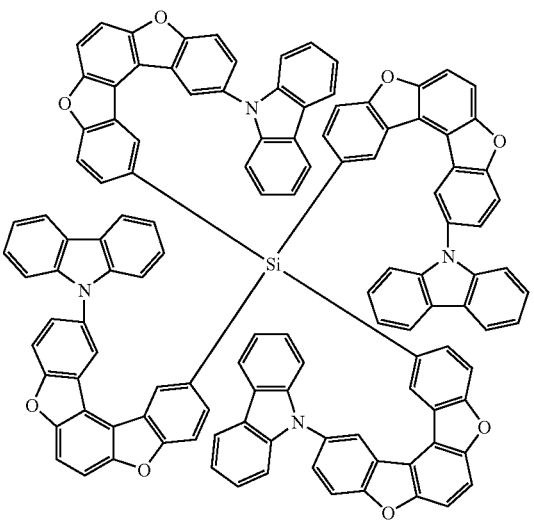

(3-108)

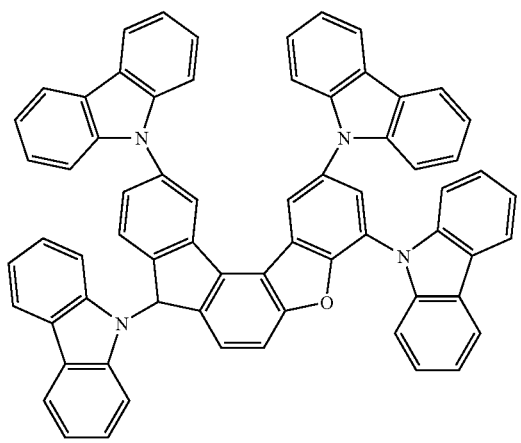

Next, an organic EL device of the present invention is described.

The organic EL device of the present invention has one or more organic thin film layers including a light emitting layer between a cathode and an anode, and at least one layer of the organic thin film layers contains the polycyclic compound.

The polycyclic compound is contained in at least one layer of the organic thin film layers of the organic EL device of the present invention. In particular, in the case where the polycyclic compound is used as a material involved in the host material or the electron transporting layer in the light emitting layer, higher luminous efficiency and longer lifetime of the device can be expected. In addition, in the case where the polycyclic compound is used as a material involved in the electron transport, the organic thin film layer preferably further includes, as a host material, a polycyclic compound having a π-conjugated heteroacene skeleton crosslinked with a carbon atom, a nitrogen atom, an oxygen atom, or a sulfur atom (hereinafter, may be abbreviated as π-conjugated heteroacene compound).

Specific examples of the π-conjugated heteroacene skeleton are described below, but are not limited thereto.

Indenofluorene (crosslinked with a carbon atom)

[Chem 56]

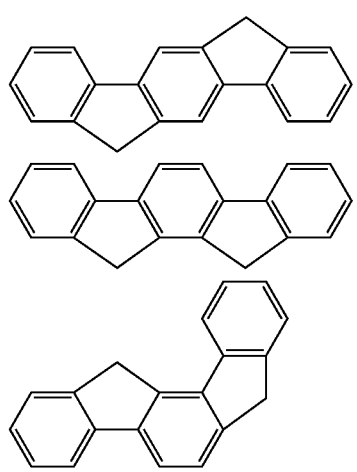

-continued
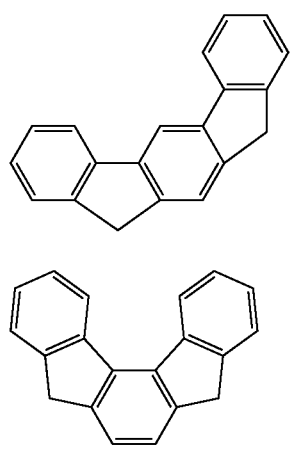
Indolocarbazole (crosslinked with a nitrogen atom)
[Chem 57]
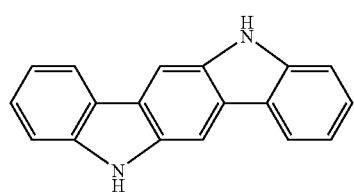
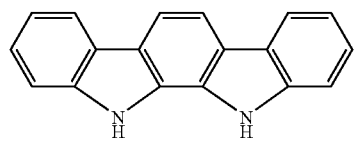
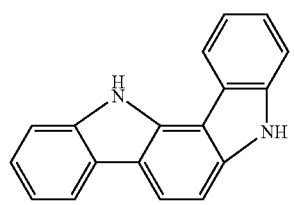
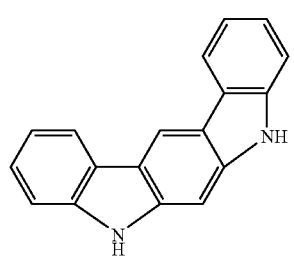
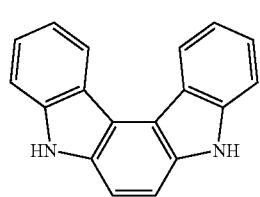
Benzofuranodibenzofuran (crosslinked with an oxygen atom)
[Chem 58]
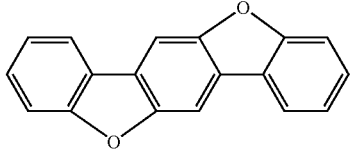
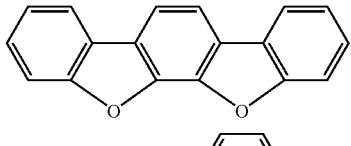
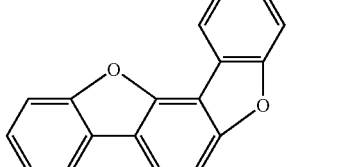
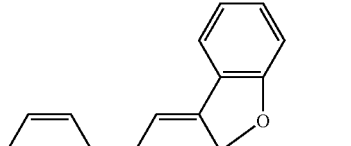
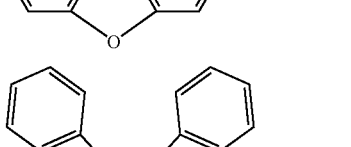
Benzothiophenodibenzothiophene (crosslinked with a sulfur atom)
[Chem 59]
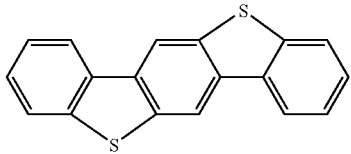
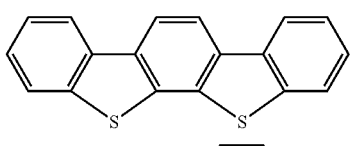
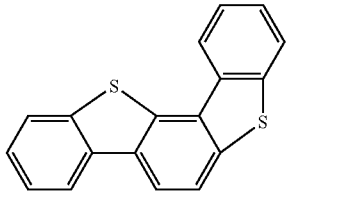

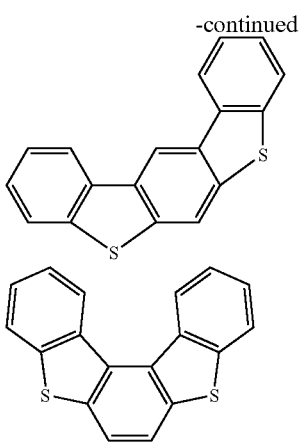

In addition to the foregoing, a π-conjugated heteroacene skeleton crosslinked with a combination of a carbon atom, a nitrogen atom, an oxygen atom, and a sulfur atom is also permitted. Specific examples of the π-conjugated heteroacene skeleton are shown below.

[Chem 60]

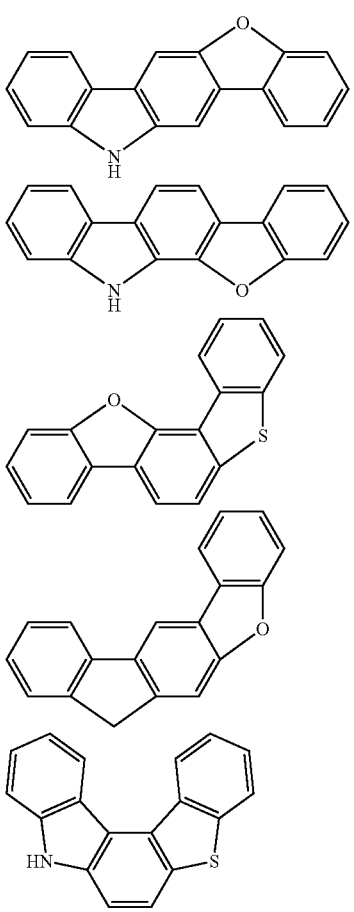

The polycyclic compound of the present invention may have an electron transporting layer between the light emitting layer and the cathode, and the electron transporting layer may contain the polycyclic compound of the present invention. Further, the light emitting layer preferably contains the π-conjugated heteroacene compound.

Alternatively, the polycyclic compound may have a hole transporting layer between the light emitting layer and the anode, and the hole transporting layer may contain the polycyclic compound of the present invention.

Further, in the case where the polycyclic compound of the present invention is used in the electron transporting layer or an electron injecting layer, the organic light emitting device can be driven under a low voltage. In addition, the π-conjugated heteroacene compound is preferably included in the light emitting layer and in the case where the π-conjugated heteroacene compound is used as a light emitting layer, the long lifetime of the organic EL device can be obtained. The case where the polycyclic compound is included in the electron transporting layer or the electron injecting layer and the π-conjugated heteroacene compound is included in the light emitting layer simultaneously is preferred because the organic EL device can be driven at a low voltage and the long lifetime thereof can be obtained.

In particular, the light emitting layer preferably includes a π-conjugated heteroacene compound as a host material, more preferably a π-conjugated heteroacene compound represented by any one of the following general formulae (40) to (43), still more preferably a π-conjugated heteroacene compound represented by any one of the following general formulae (44) to (47), and particularly preferably a π-conjugated heteroacene compound represented by the following general formula (44) or (45). The case where the π-conjugated heteroacene compound represented by any one of the general formulae (40) to (47) is included as a host material is preferred, because the crosslinking part of the heteroacene skeleton is directed in the same direction with respect to the central benzene ring, and hence the triplet energy gap can be enlarged and the luminous efficiency can be improved compared to the case where the direction is inverse. In particular, in the general formulae (40) to (43), it is preferred that at least one of $X_{15}$ and $X_{16}$ represent an oxygen atom and it is more preferred that both of them represent oxygen atoms. This is because the oxygen atom has high electronegativity, and hence can improve electron transportability and prompt the driving of the device at a low voltage, and can be suitably used as an electron transporting material.

[Chem 61]

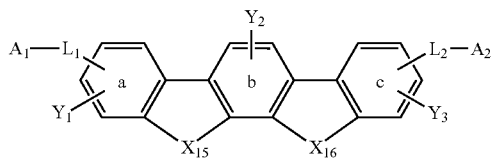

(40)

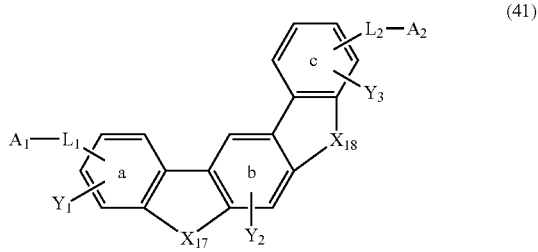

(41)

[In the formulae (40) to (43), $X_{15}$, $X_{16}$, $X_{17}$ and $X_{18}$ each independently represent oxygen (C), sulfur (S), N—$R_1$, or $CR_2R_3$. $R_1$, $R_2$, and $R_3$ each independently represent an alkyl group having 1 to 20 carbon atoms, a substituted or unsubstituted cycloalkyl group having 3 to 20 carbon atoms forming the ring, an aralkyl group having 7 to 24 carbon atoms, an organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_{15}$ and $X_{16}$, or both $X_{17}$ and $X_{18}$ represent N—$R_1$, at least one $R_1$ represents a substituted or unsubstituted monovalent fused aromatic heterocyclic group having 8 to 24 atoms forming the aromatic ring.

In the formulae (42) and (43), n represents 2, 3, or 4, and the material represented by the formulae (42) and (43) includes a dimer using $L_3$ as a linking group for n=2, a trimer using $L_3$ as a linking group for n=3, or a tetramer using $L_3$ as a linking group for n=4.

In the formulae (40) to (43), $L_1$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring a through a carbon-carbon bond.

In the formulae (40) and (41), $L_2$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with the benzene ring c through a carbon-carbon bond, provided that when both $X_{15}$ and $X_{16}$, or both $X_{17}$ and $X_{18}$ represent $CR_2R_3$ and both $L_1$ and $L_2$ represent substituted or unsubstituted divalent aromatic hydrocarbon groups each having 6 to 24 carbon atoms forming the aromatic ring, a case where $L_1$ and $L_2$ are simultaneously linked at para position with respect to a benzene ring b is excluded.

In the formulae (42) and (43), when n represents 2, $L_3$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring c through a carbon-carbon bond, when n represents 3, $L_3$ represents an alkanetriyl group having 1 to 20 carbon atoms, a substituted or unsubstituted cycloalkanetriyl group having 3 to 20 carbon atoms forming the aromatic ring, a trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group which has 3 to 24 atoms and which is linked with a benzene ring c through a carbon-carbon bond, or when n represents 4, $L_3$ represents an alkanetetrayl having 1 to 20 carbon atoms, a substituted or unsubstituted cycloalkanetetrayl having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group which has 3 to 24 atoms forming the aromatic ring and which is linked with the benzene ring c through a carbon-carbon bond, provided that when both $X_{15}$ and $X_{16}$ or both $X_{17}$ and $X_{18}$ represent $CR_2R_3$ and both $L_1$ and $L_3$ represent substituted or unsubstituted divalent, trivalent, or tetravalent aromatic hydrocarbon groups each having 6 to 24 carbon atoms forming the aromatic ring, a case where $L_1$ and $L_3$ are simultaneously linked at para position with respect to the benzene ring b is excluded.

In the formulae (40) to (43), $A_1$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_1$ through a carbon-carbon bond, provided that when $L_1$ represents an alkyl or alkylene group having 1 to 20 carbon atoms, a case where $A_1$ represents a hydrogen atom is excluded.

In the formulae (40) and (41), $A_2$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_2$ through a carbon-carbon bond, provided that when $L_2$ represents an alkyl or alkylene group having 1 to 20 carbon atoms, a case where $A_2$ represents a hydrogen atom is excluded.

In the formulae (40) to (43), $Y_1$, $Y_2$, and $Y_3$ each represent an alkyl group having 1 to 20 carbon atoms, a substituted or unsubstituted cycloalkyl group having 3 to 20 carbon atoms forming the ring, an alkoxy group having 1 to 20 carbon atoms, an aralkyl group having 7 to 24 carbon atoms, a organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group which has 3 to 24 atoms forming the aromatic ring and which is linked with the benzene ring a, b, or c through a carbon-carbon bond, the number of each of $Y_1$ and $Y_3$ is 0, 1, 2, or 3, and the number of $Y_2$ is 0, 1, or 2, provided that when both $X_{15}$ and $X_{16}$ or both $X_{17}$ and $X_{18}$ represent oxygen (C), sulfur (S), or $CR_2R_3$, $L_1$ and $L_2$ represent single bonds, and both $A_1$ and $A_2$ represent hydrogen atoms, a case where a benzene ring b has one or two $Y_2$'s, which represent a methyl group or an unsubstituted phenyl group is excluded.

In the formulae (40) to (43), $A_1$, $A_2$, $L_1$, $L_2$, and $L_3$ are each free of any carbonyl group.]

[Chem 62]

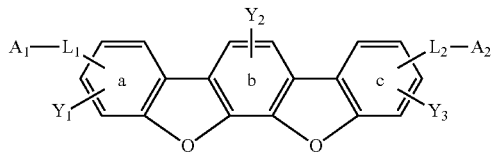

(42)

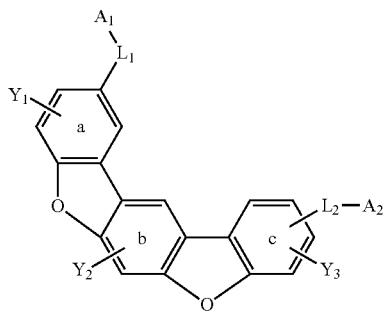
(45)

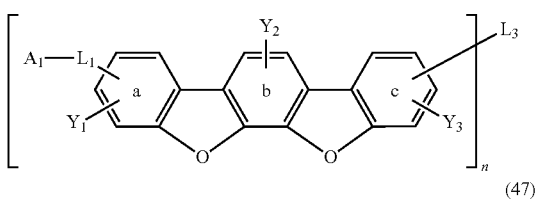
(46)

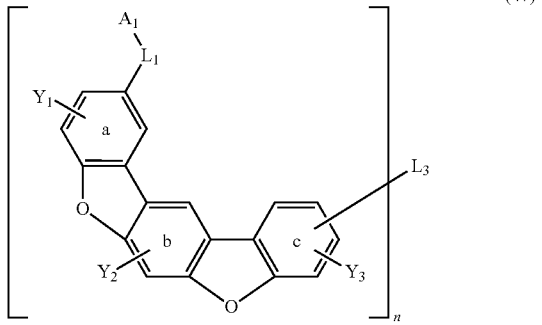
(47)

[In the formulae (45) and (47), n represents 2, 3, or 4, and the material represented by any one of the formulae (45) to (47) includes a dimer using $L_3$ as a linking group for n=2, a trimer using $L_3$ as a linking group for n=3, or a tetramer using $L_3$ as a linking group for n=4.

In the formulae (44) to (47), $L_1$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring a through a carbon-carbon bond.

In the formulae (44) and (45), $L_2$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring c through a carbon-carbon bond.

In the formulae (46) and (47), when n represents 2, $L_3$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with the benzene ring c through a carbon-carbon bond, when n represents 3, $L_3$ represents an alkanetriyl group having 1 to 20 carbon atoms, a substituted or unsubstituted cycloalkanetriyl group having 3 to 20 carbon atoms forming the ring, a trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group which has 3 to 24 atoms and which is linked with the benzene ring c through a carbon-carbon bond, or when n represents 4, $L_3$ represents an alkanetetrayl group having 1 to 20 carbon atoms, a substituted or unsubstituted cycloalkanetetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group which has 3 to 24 atoms forming the aromatic ring and which is linked with the benzene ring c through a carbon-carbon bond.

In the formulae (44) to (47), $A_1$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_1$ through a carbon-carbon bond, provided that when $L_1$ represents an alkyl or alkylene group having 1 to 20 carbon atoms, a case where $A_1$ represents a hydrogen atom is excluded.

In the formulae (44) and (45), $A_2$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_2$ through a carbon-carbon bond, provided that when $L_2$ represents an alkyl or alkylene group having 1 to 20 carbon atoms, a case where $A_2$ represents a hydrogen atom is excluded.

In the formulae (44) to (47), $Y_1$, $Y_2$, and $Y_3$ each represent an alkyl group having 1 to 20 carbon atoms, a substituted or unsubstituted cycloalkyl group having 3 to 20 carbon atoms forming the ring, an alkoxy group having 1 to 20 carbon atoms, an aralkyl group having 7 to 24 carbon atoms, an organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group which has 3 to 24 atoms forming the aromatic ring and which is linked with the benzene ring a, b, or c through a carbon-carbon bond, the number of each of $Y_1$ and $Y_3$ is 0, 1, 2, or 3, and the number of $Y_2$ is 0, 1, or 2, provided that when both $L_1$ and $L_2$ represent single bonds, and both $A_1$ and $A_2$ represent hydrogen atoms, a benzene ring b has one or two $Y_2$'s, which represent a methyl group or an unsubstituted phenyl group is excluded.

In the formulae (44) to (47), A, $A_2$, $L_1$, $L_2$, and $L_3$ are each free of any carbonyl group.]

In the formulae (40) to (47), examples of each group represented by $Y_1$ to $Y_3$, $R_1$ to $R_3$, $L_1$ to $L_3$, and $A_1$ to $A_2$ and the substituent thereof include the same examples exemplified for the formulae (1) to (20).

Specific examples of the π-conjugated heteroacene compound represented by the formulae (40) to (47) of the present invention are described below, but are not limited to those exemplified compounds.

[Chem 63]

(4-1)

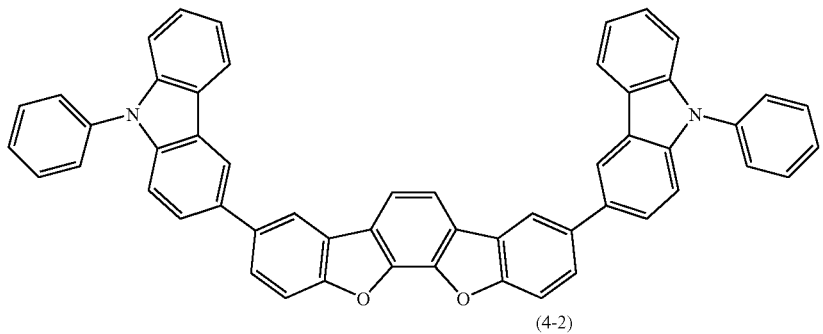

(4-2)

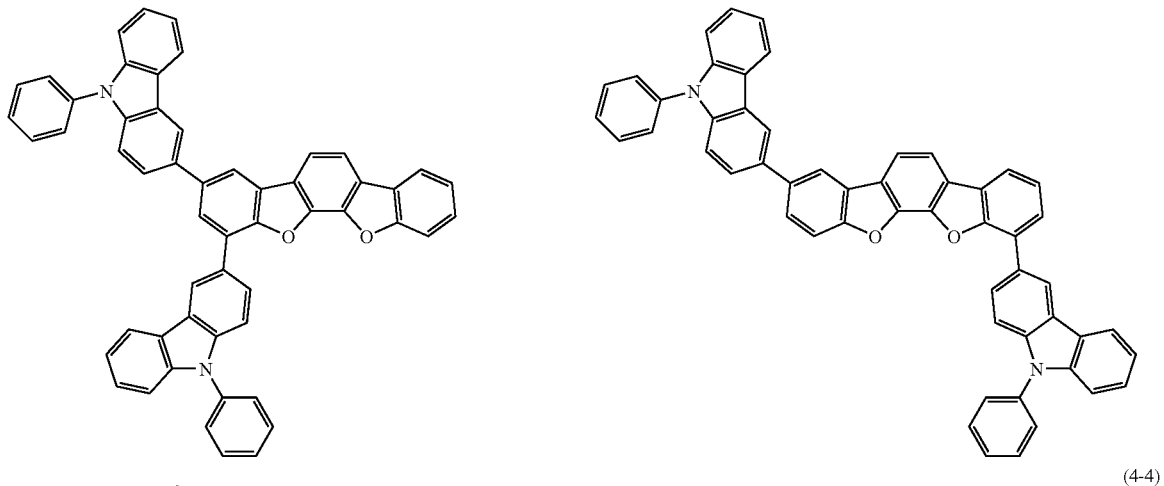

(4-3)

(4-4)

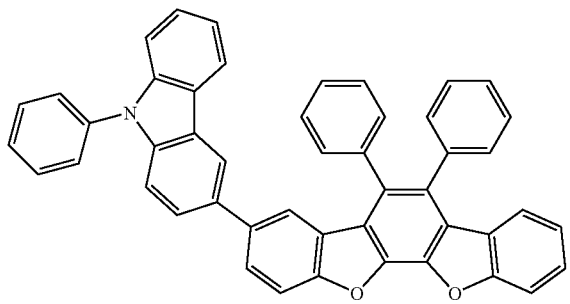

(4-5)

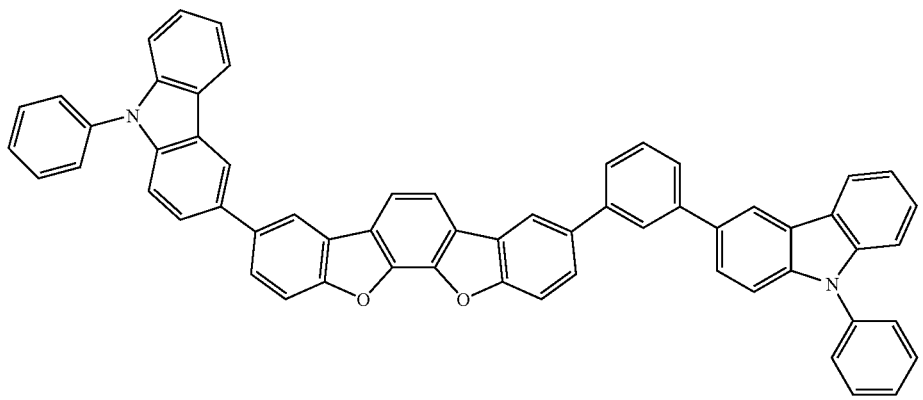

(4-6)
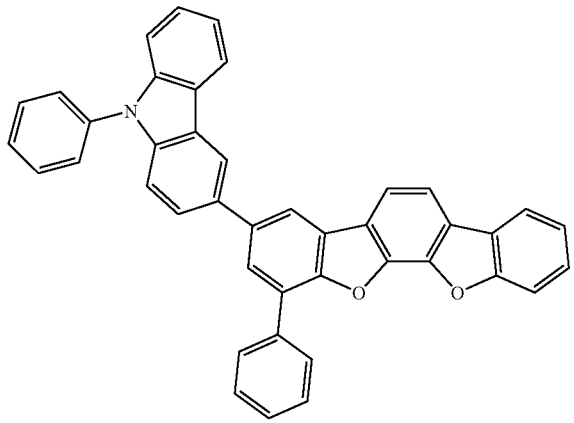
(4-7)
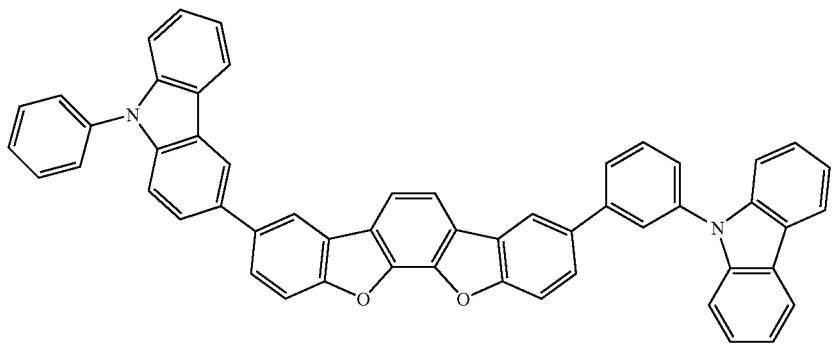
(4-8)            (4-9)
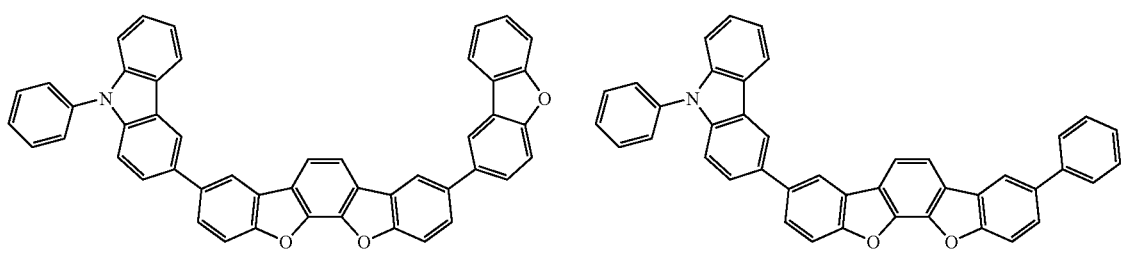
(4-10)
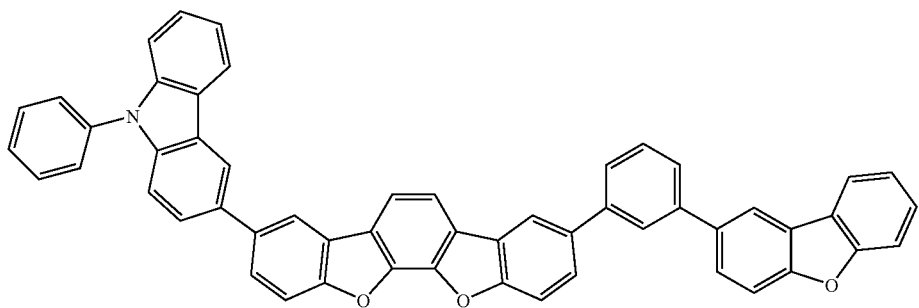

[Chem 64]
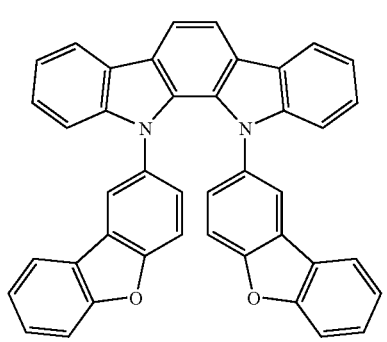
(4-11)
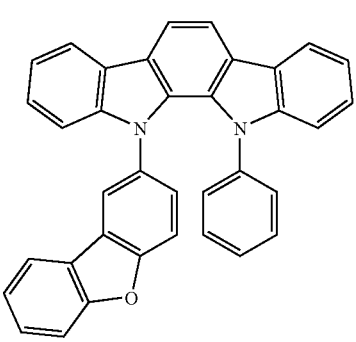
(4-12)
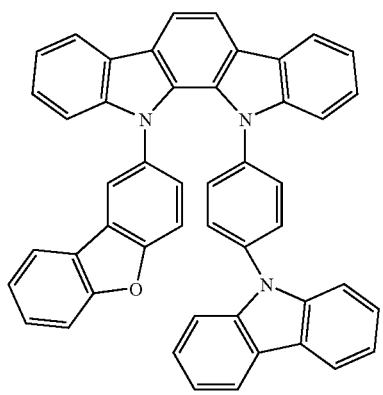
(4-13)
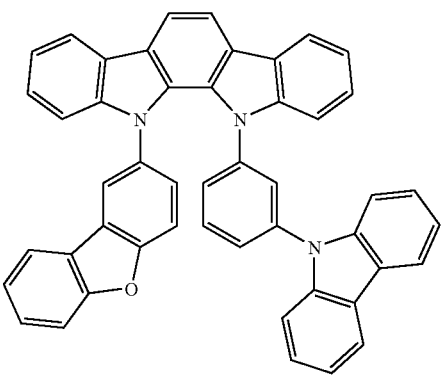
(4-14)
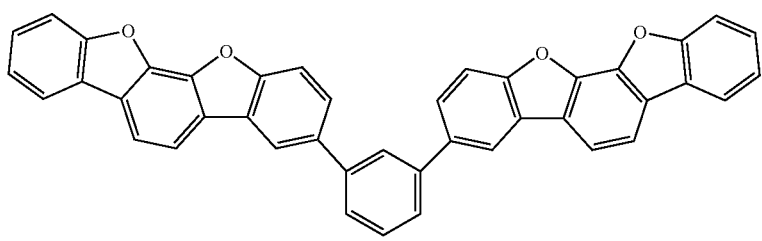
(4-15)
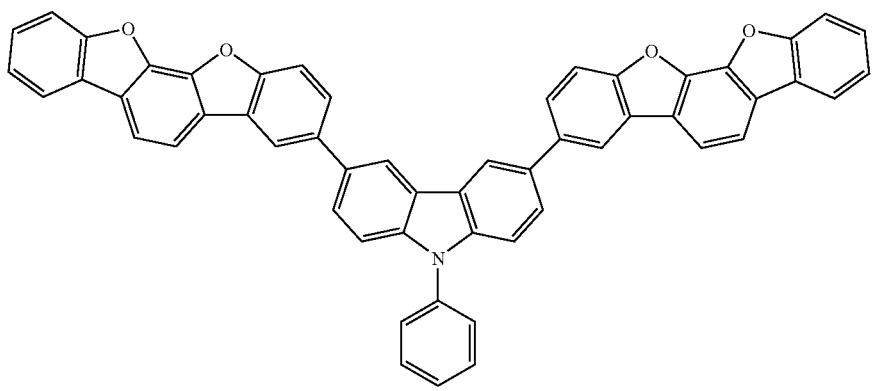
(4-16)

-continued
(4-17)
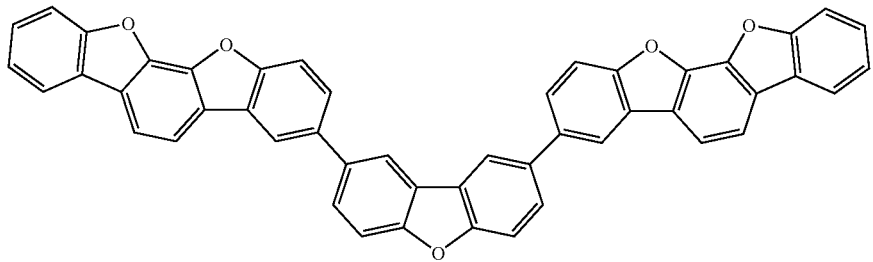
(4-18)
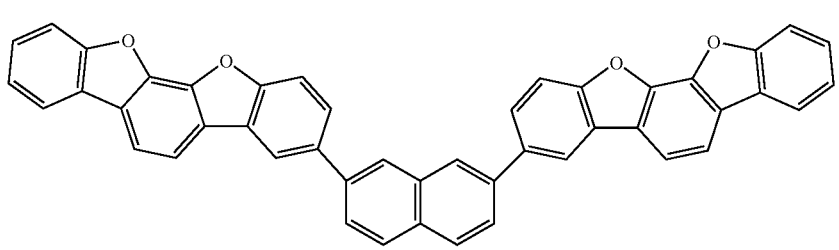
(4-19)
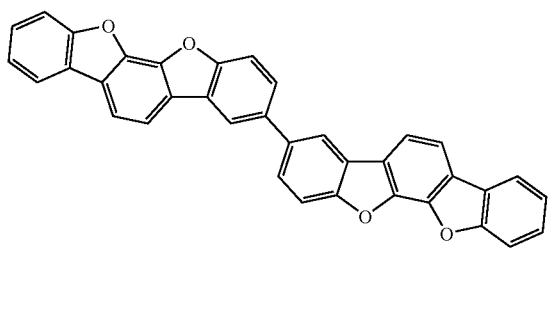
(4-20)
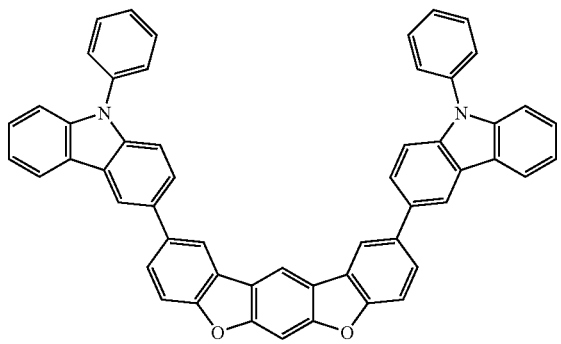
[Chem 65]
(4-21)
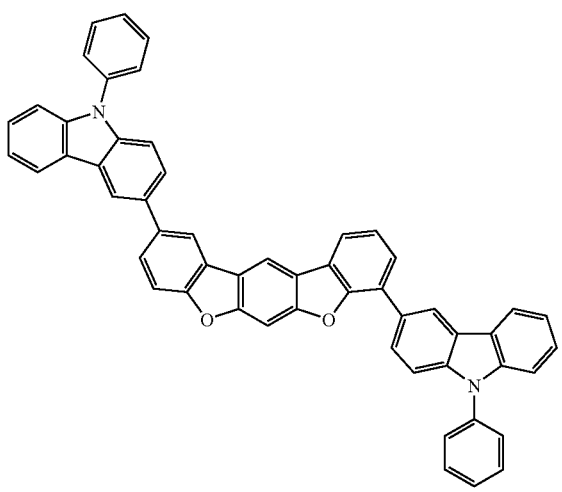
(4-22)
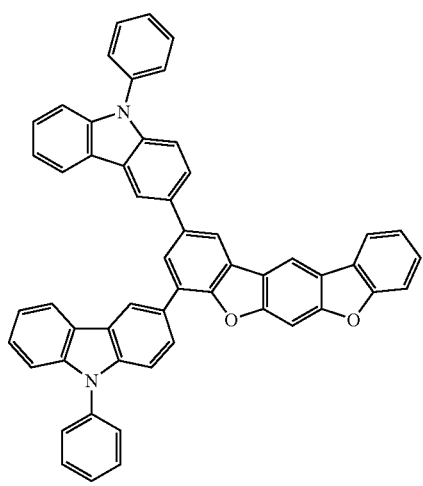

-continued
(4-23)
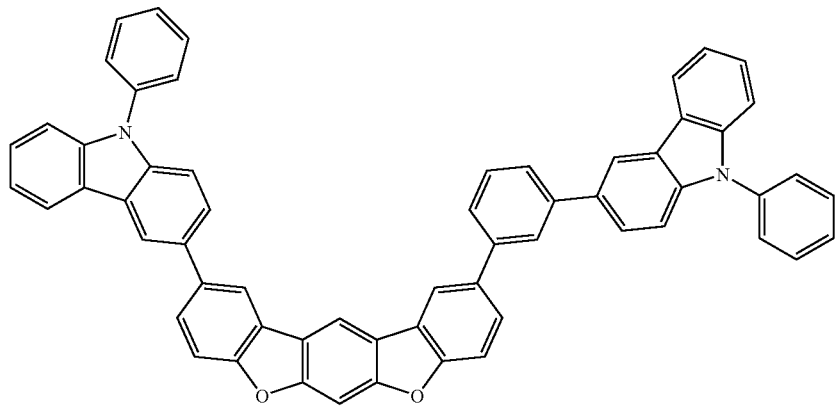
(4-24)
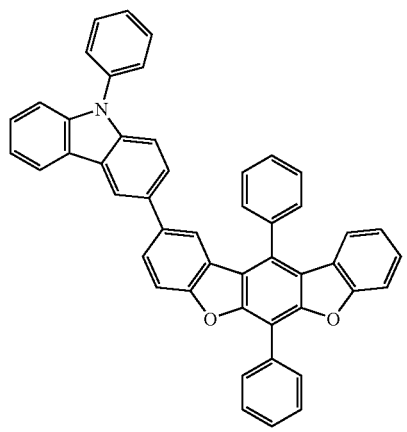
(4-25)
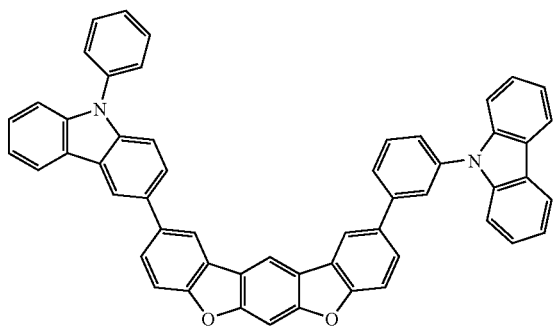
(4-26)
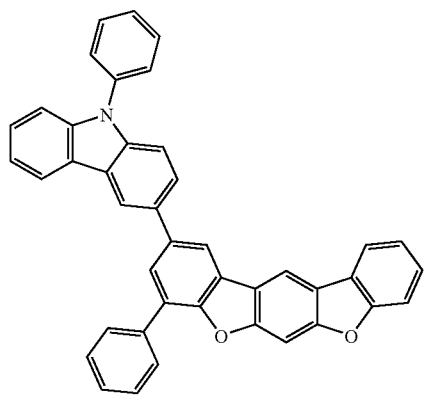
(4-27)
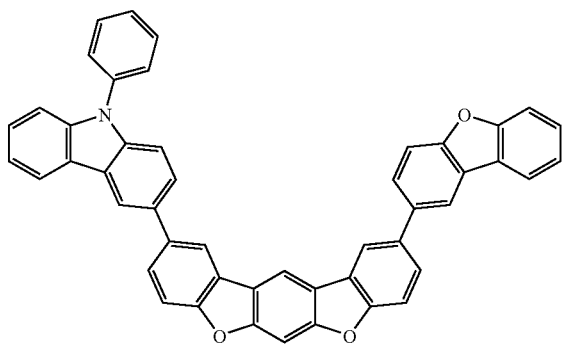
(4-28)
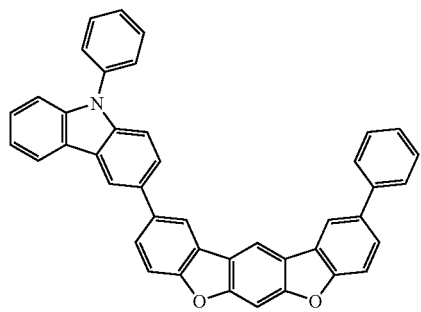
(4-29)
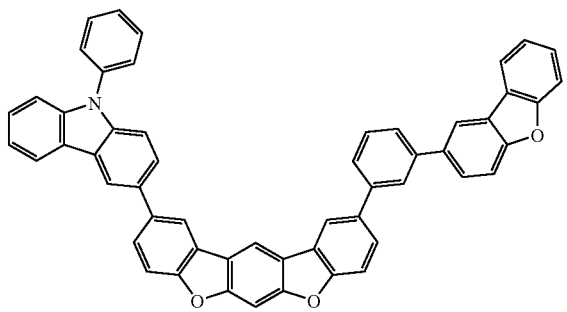

-continued
(4-30)
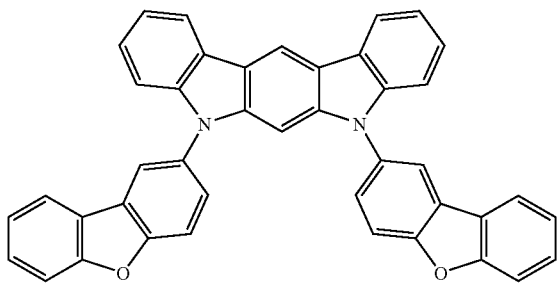
[Chem 66]
(4-31)
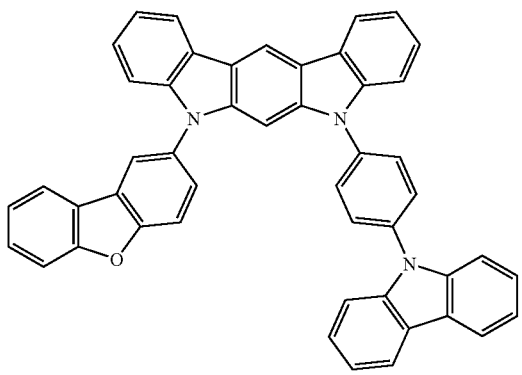
(4-32)
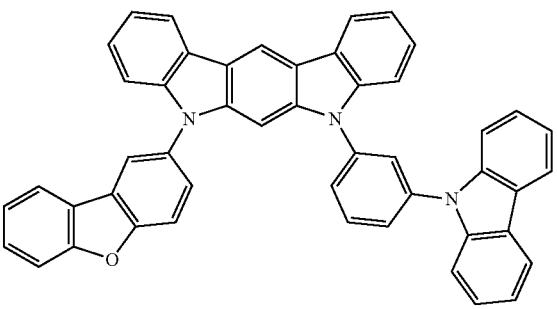
(4-33)
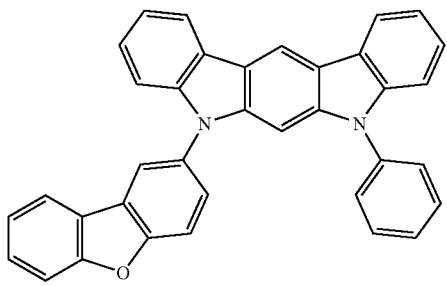
(4-34)
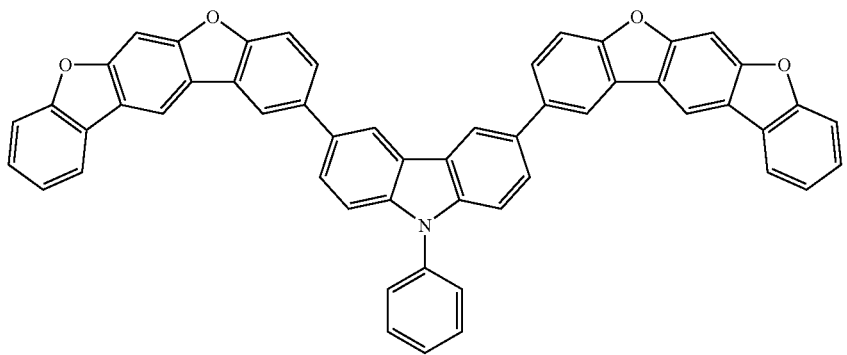
(4-35)
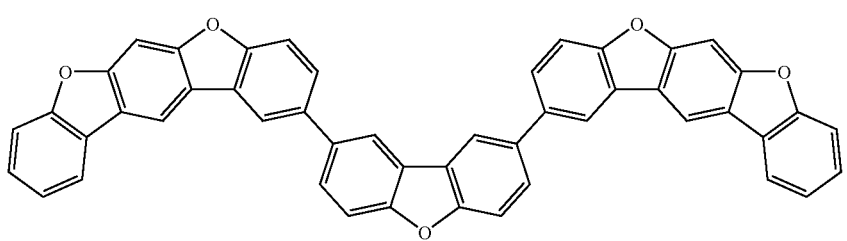

(4-36)
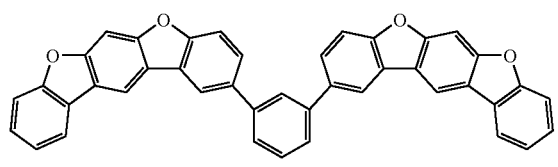
(4-37)
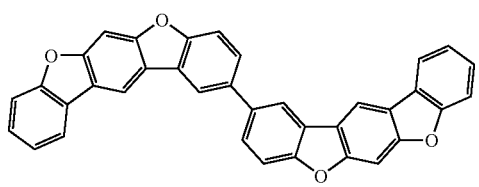
(4-38)
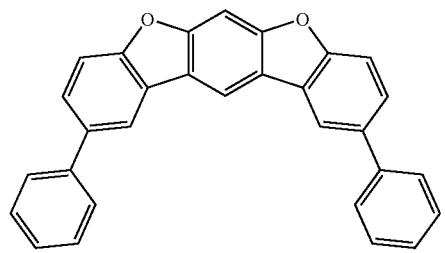
(4-39)
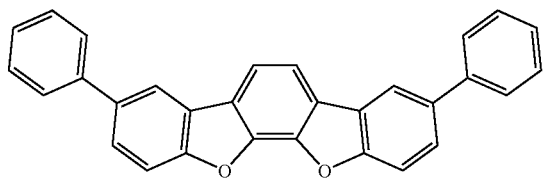
(4-40)
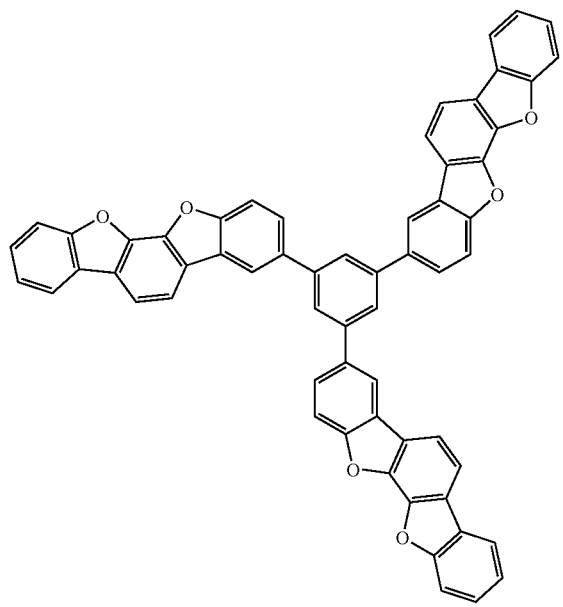
(4-41)
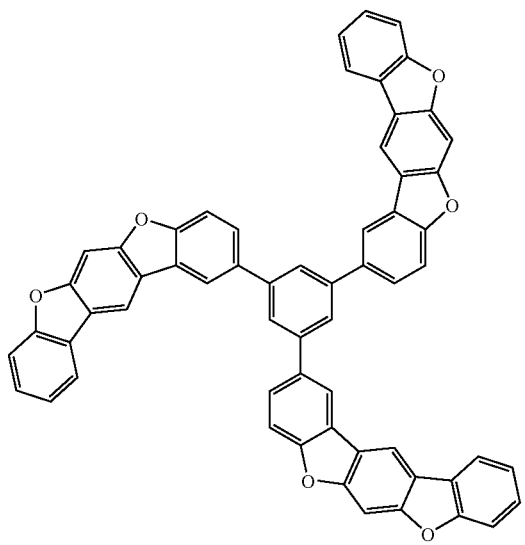
[Chem 67]
(4-42)
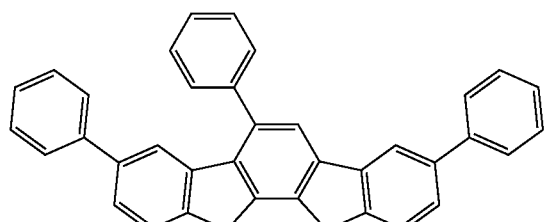
(4-43)
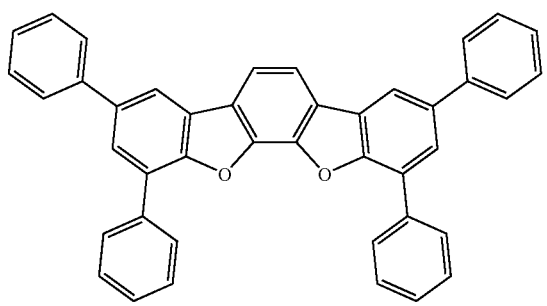

-continued
(4-44)
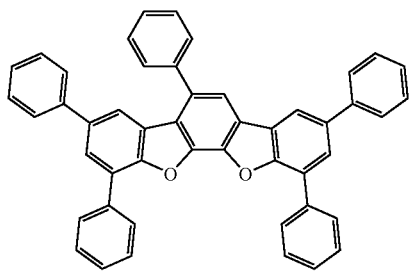
(4-45)
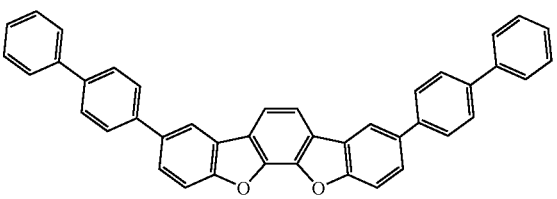
(4-46)
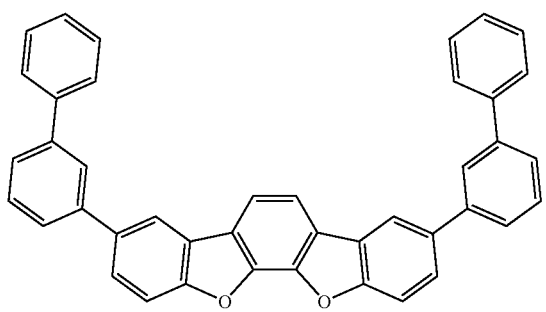
(4-47)
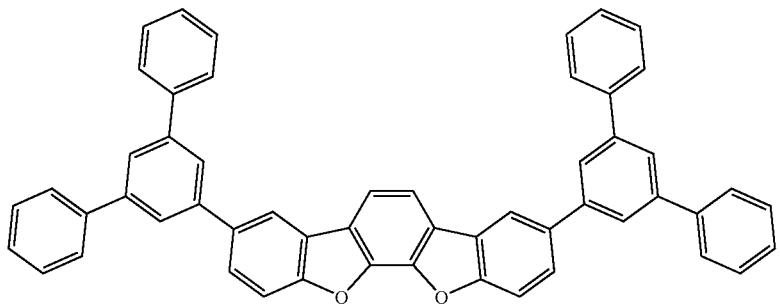
(4-48)
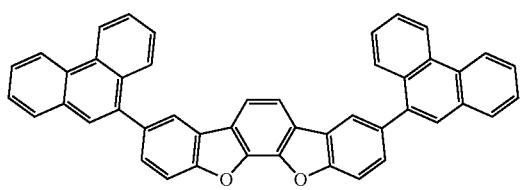
(4-49)
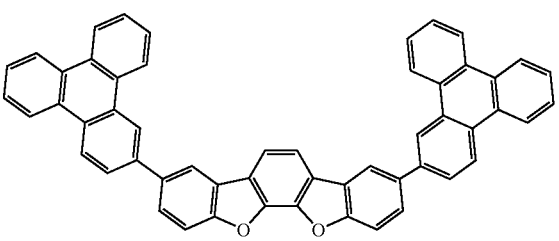
(4-50)
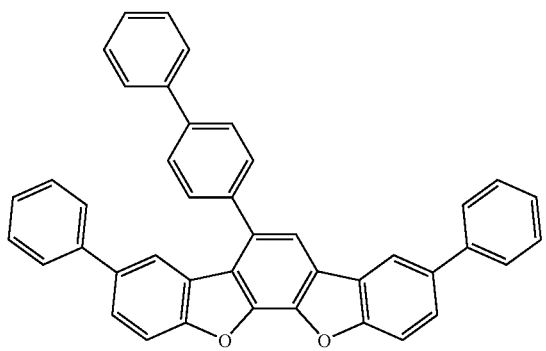
(4-51)
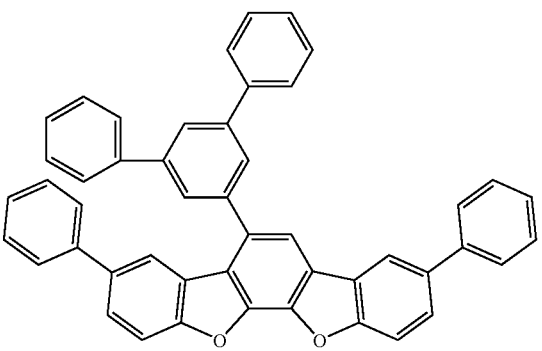

(4-52)
(4-53)
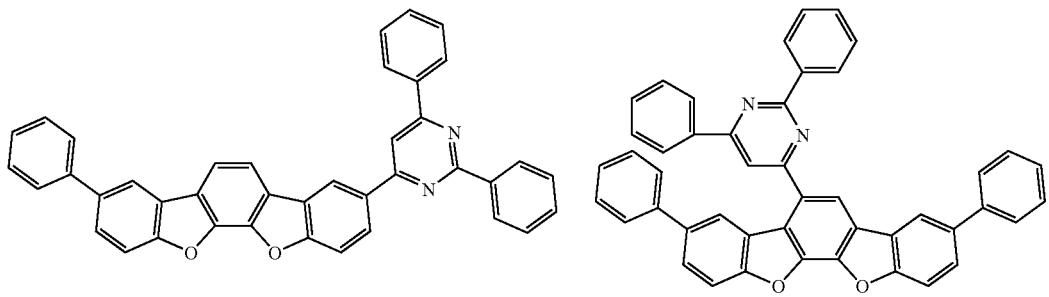
(4-54)
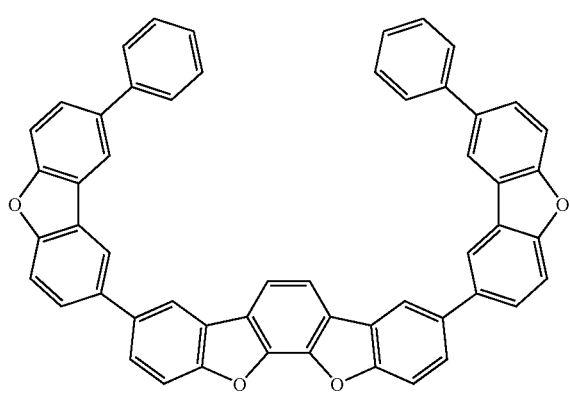
(4-55)
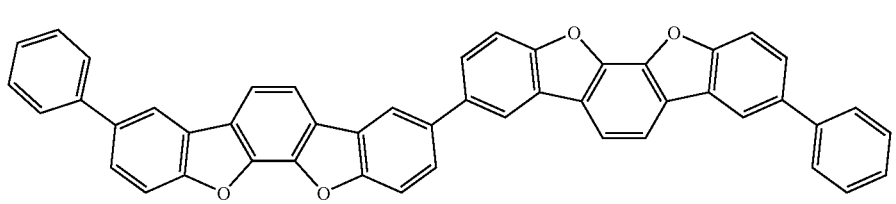
(4-56)
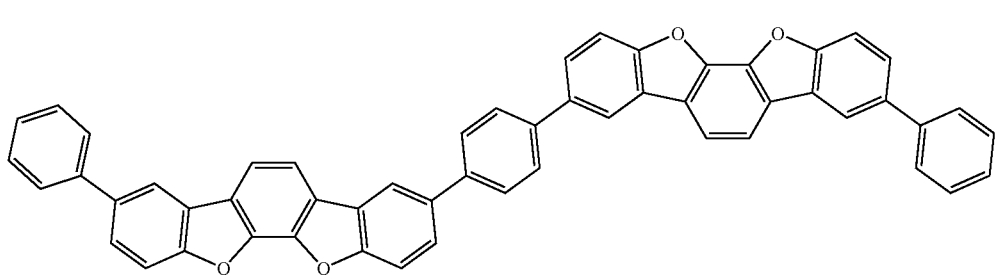
(4-57)
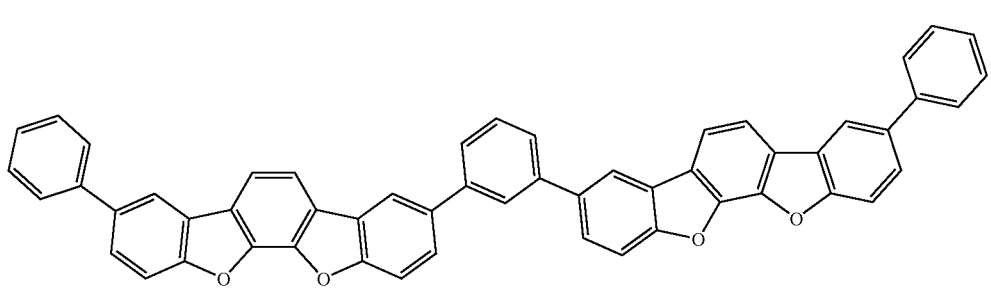

[Chem 68]
(4-58)
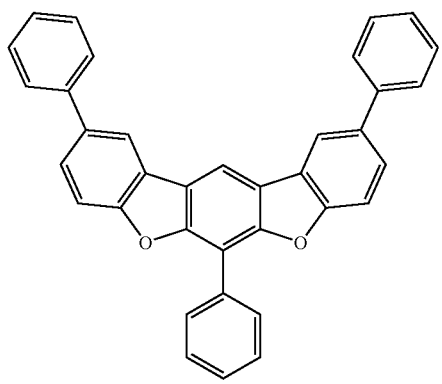
(4-59)
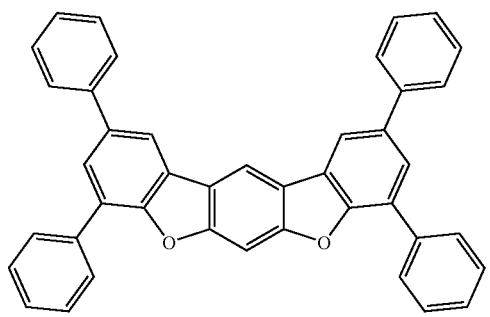
(4-60)
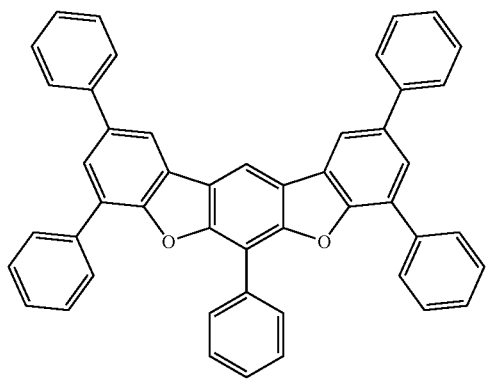
(4-61)
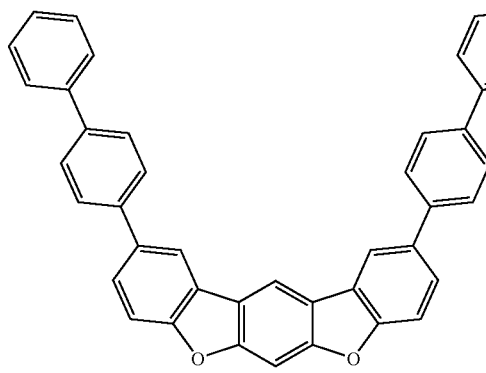
(4-62)
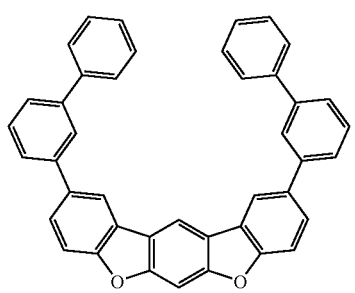
(4-63)
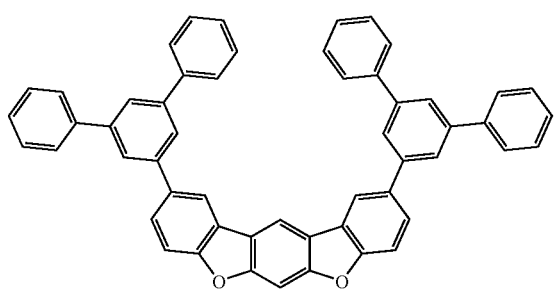
(4-64)
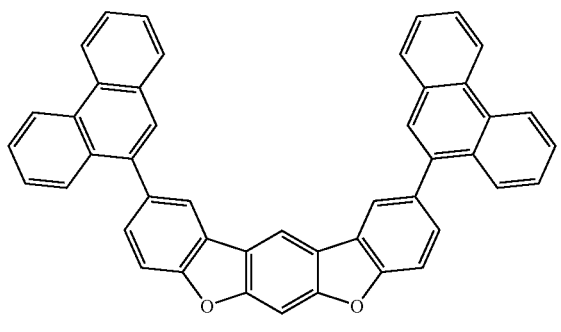
(4-65)
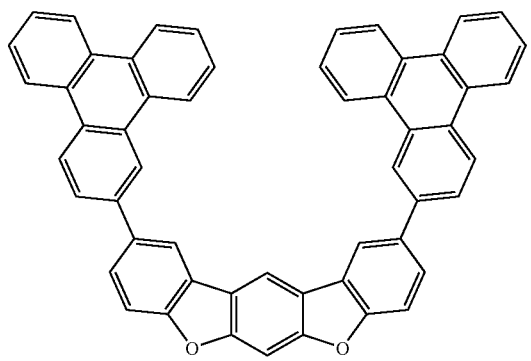

(4-66)
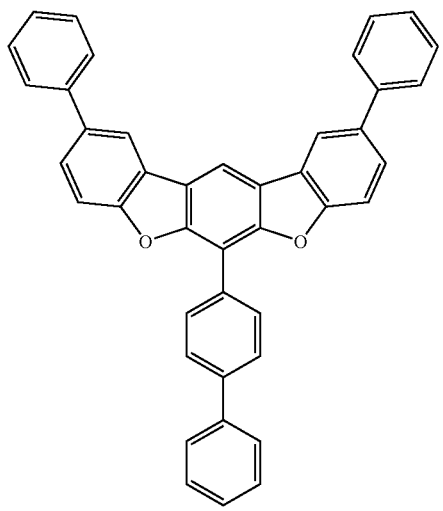
(4-67)
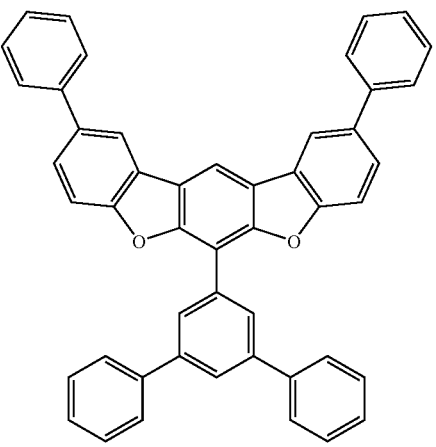
(4-68)
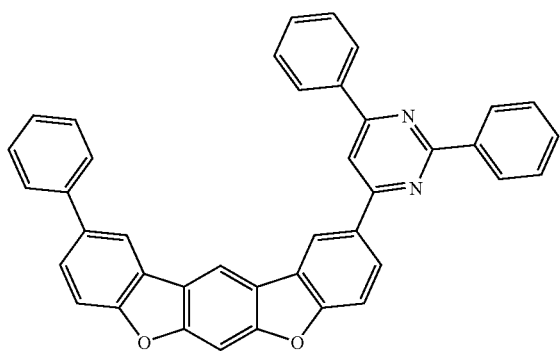
(4-69)
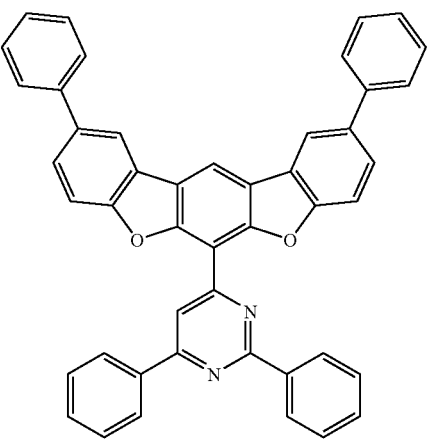
(4-70)
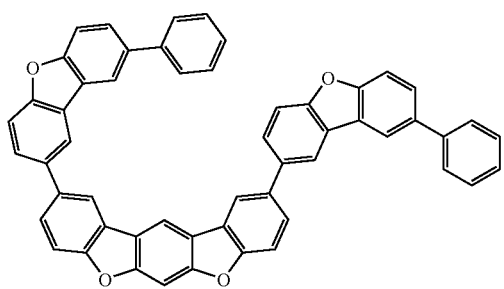
(4-71)
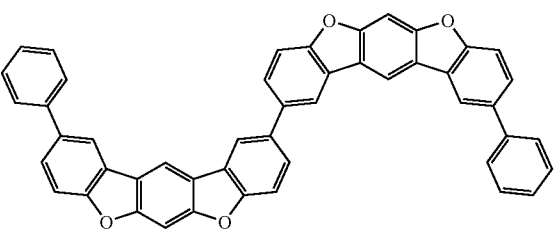

-continued
(4-72)
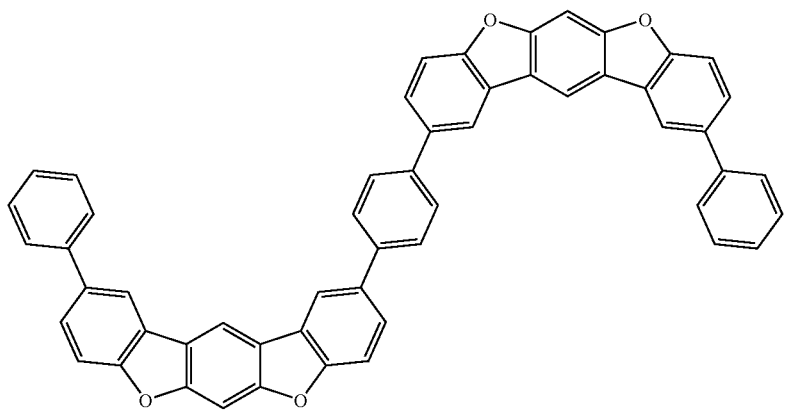
(4-73)
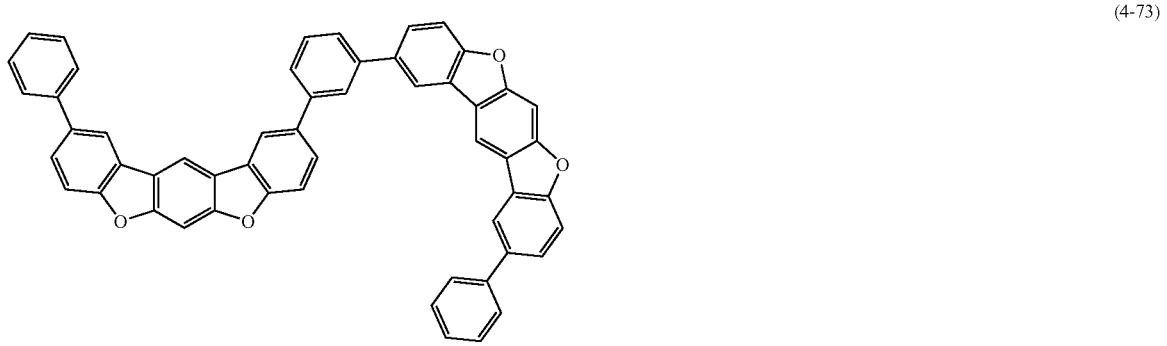
[Chem 69]
(4-74) (4-75)
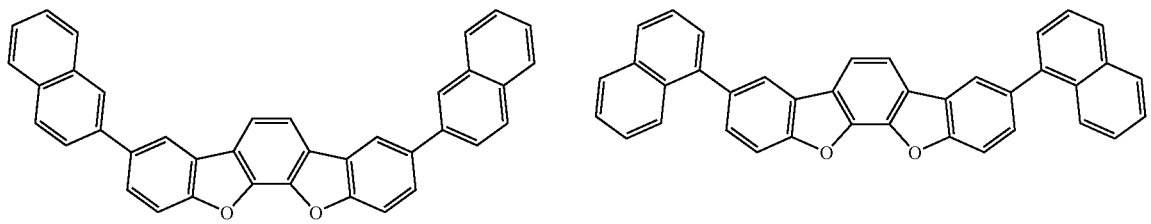
(4-76) (4-77)
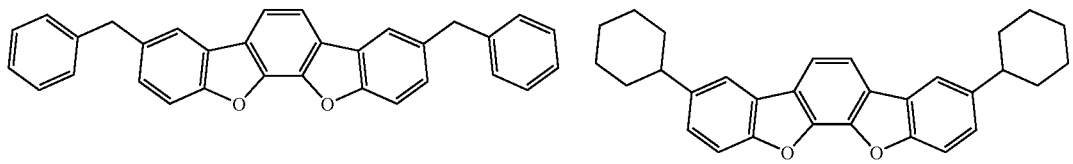
(4-78)
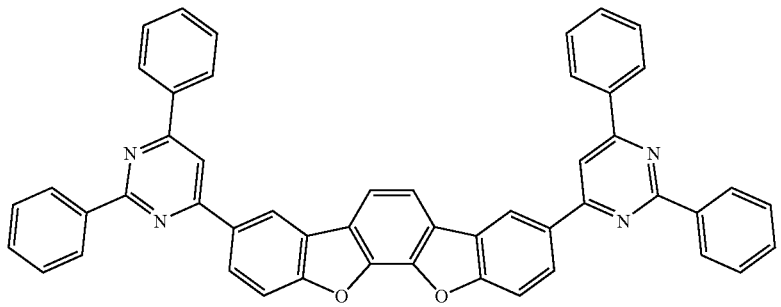

-continued
(4-79)
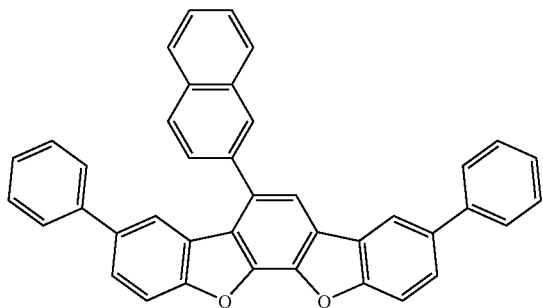
(4-80)
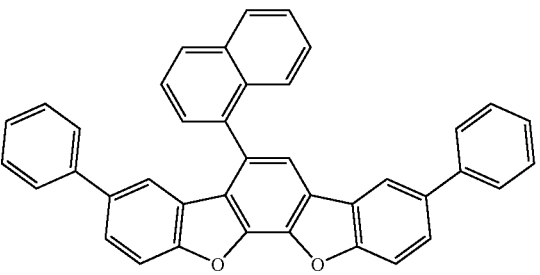
(4-81)
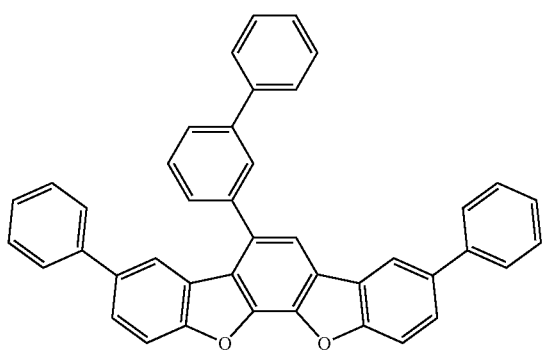
(4-82)
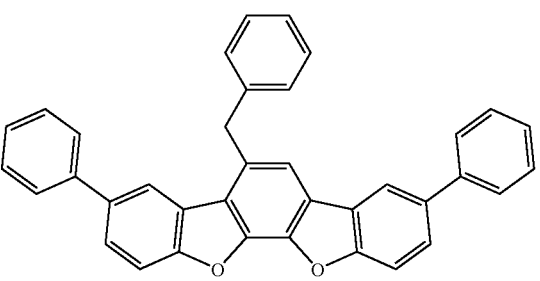
(4-83)
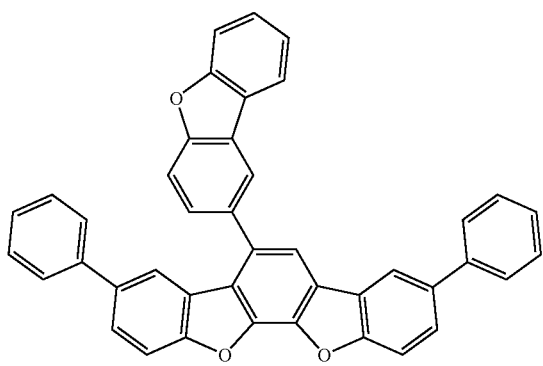
(4-84)
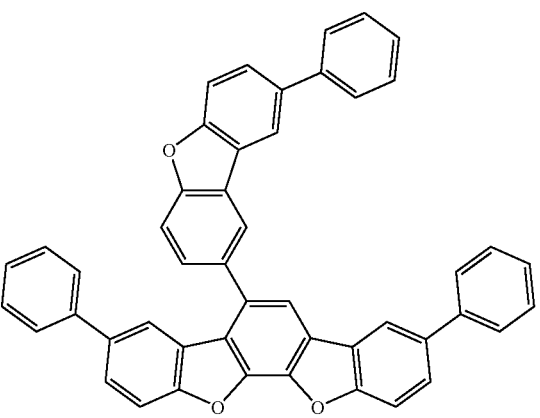
(4-85)
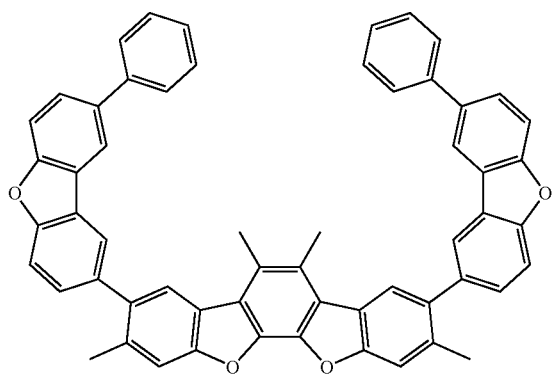
(4-86)
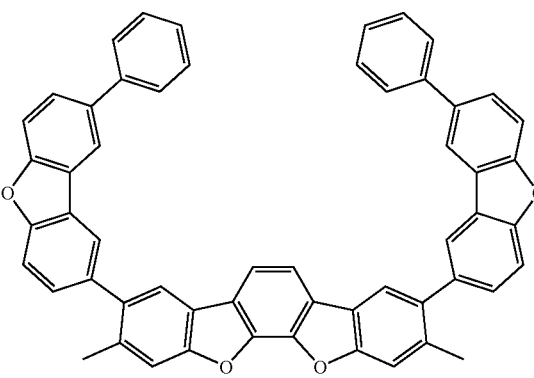

-continued
(4-87)
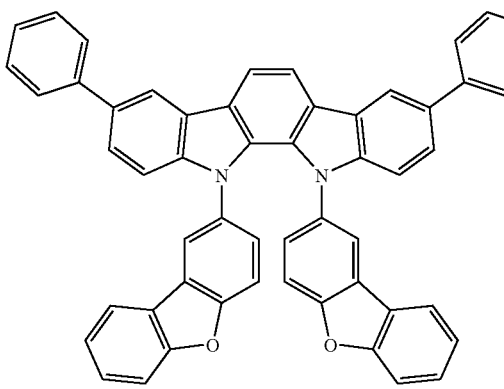
(4-88)
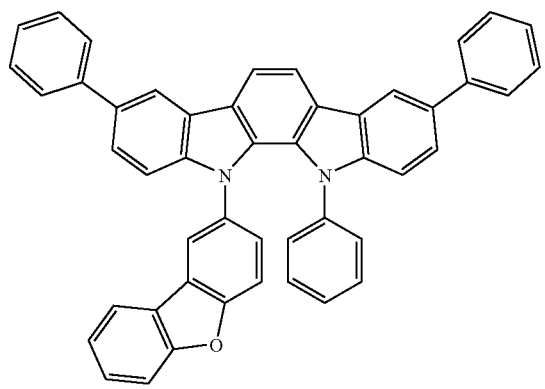
(4-89)
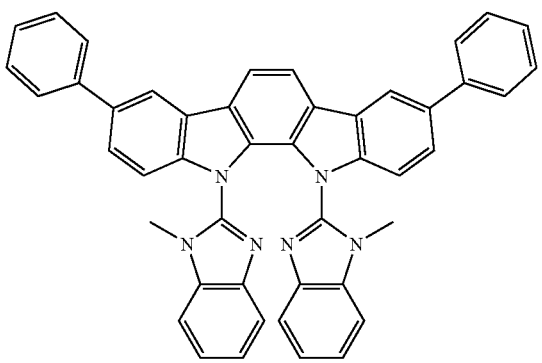
(4-90)
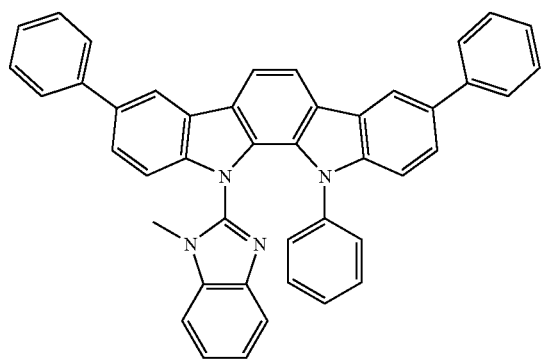
[Chem 70]
(4-91)
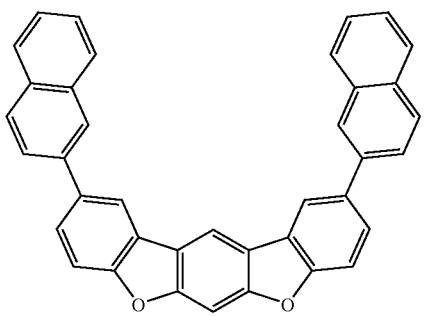
(4-92)
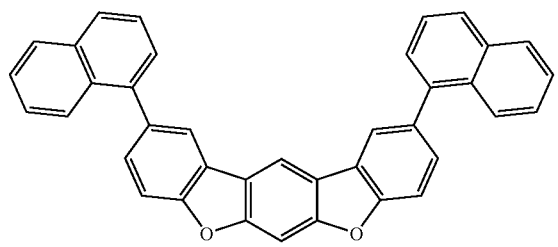
(4-93)
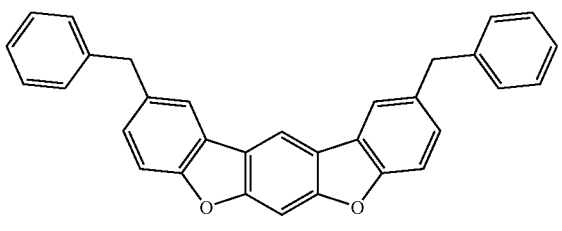
(4-94)
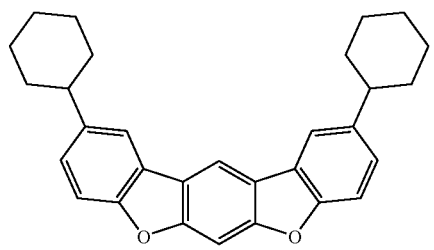

(4-95)
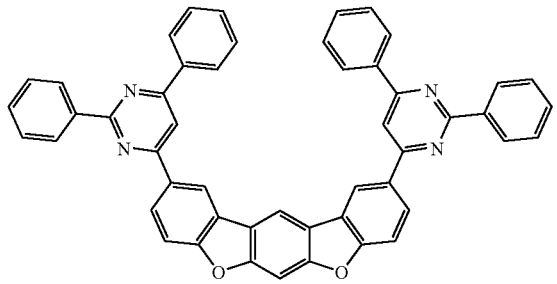
(4-96)
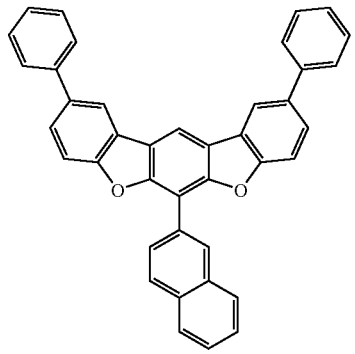
(4-97)
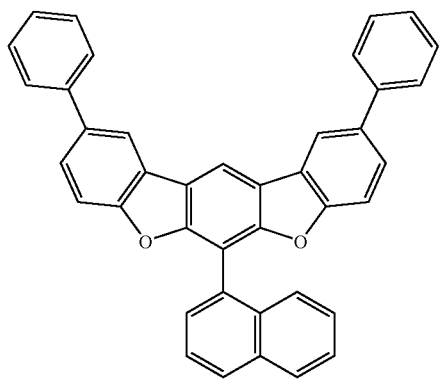
(4-98)
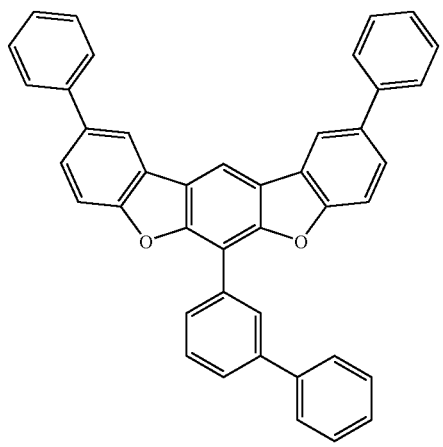
(4-99)
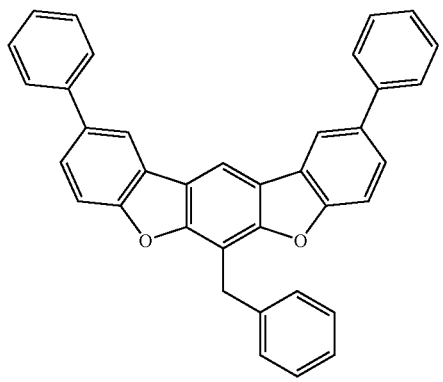
(4-100)
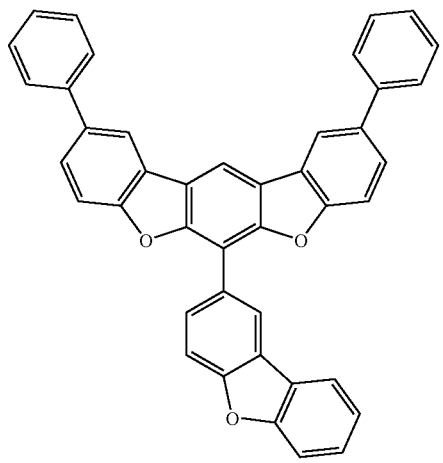

-continued
(4-101)
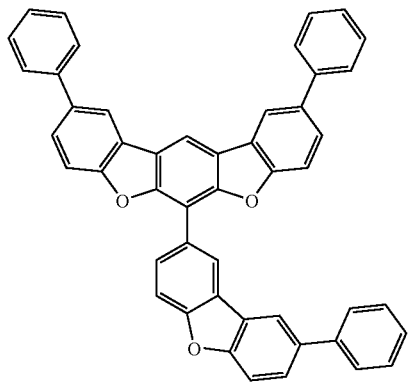
(4-102)
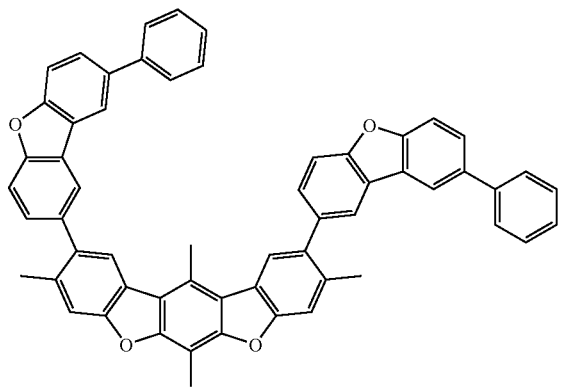
(4-103)
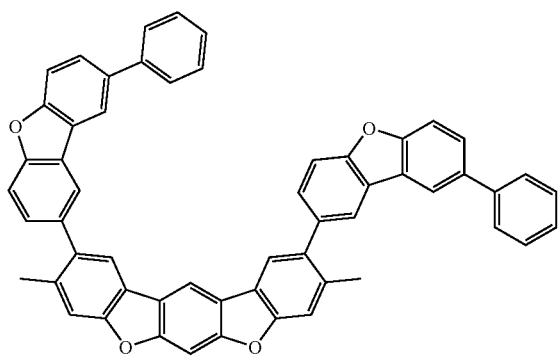
(4-104)
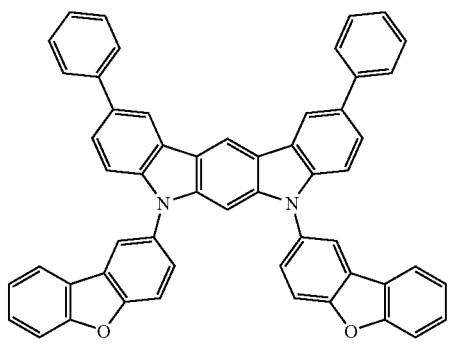
(4-105)
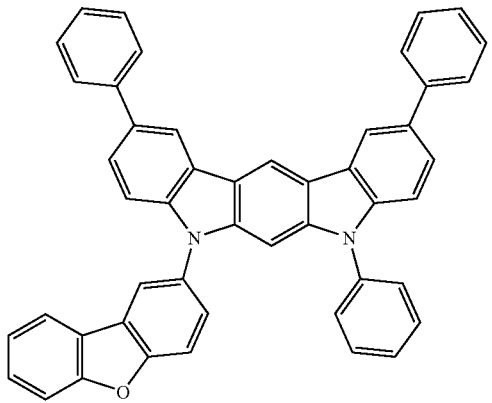
(4-106)
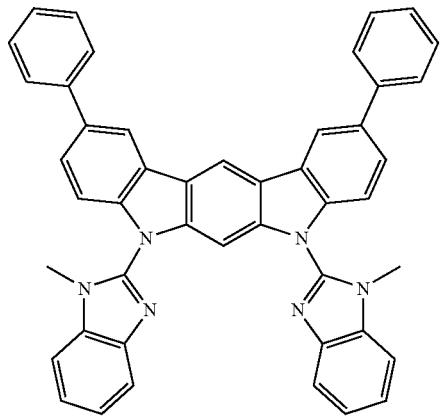
(4-107)
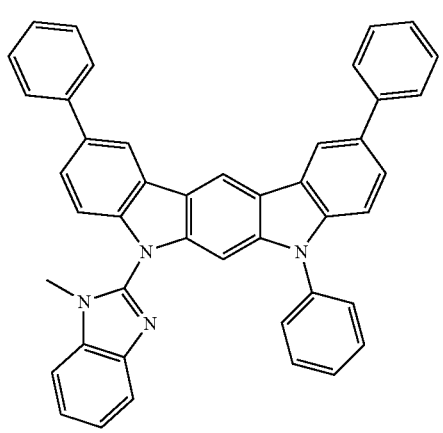

[Chem 71]
(4-108)
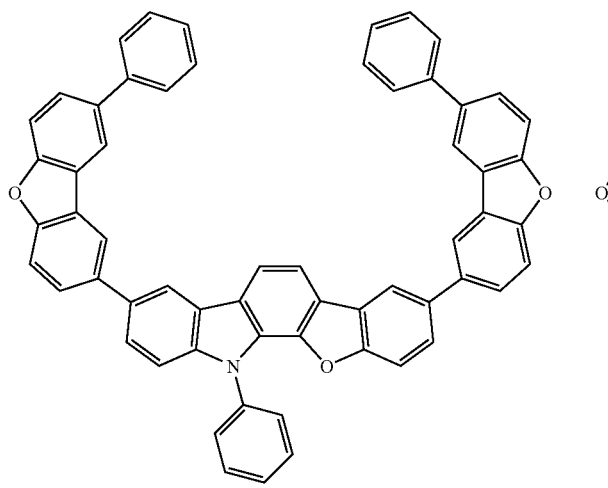
(4-109)
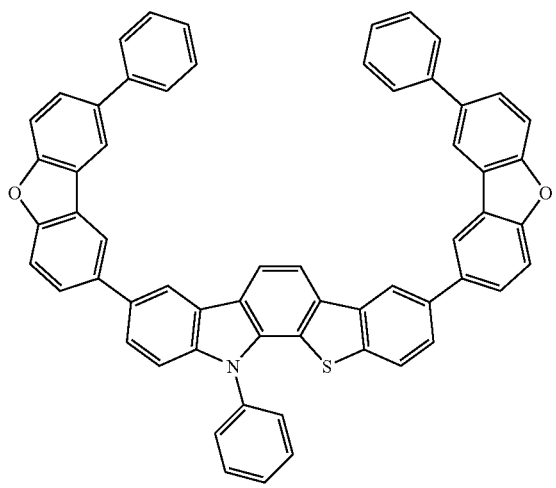
(4-110)
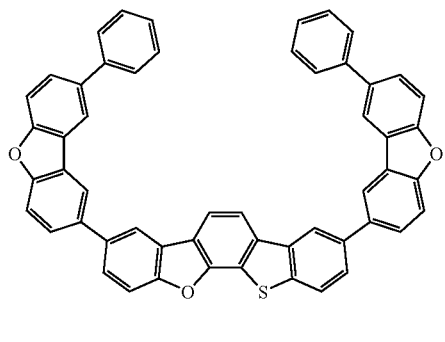
(4-111)
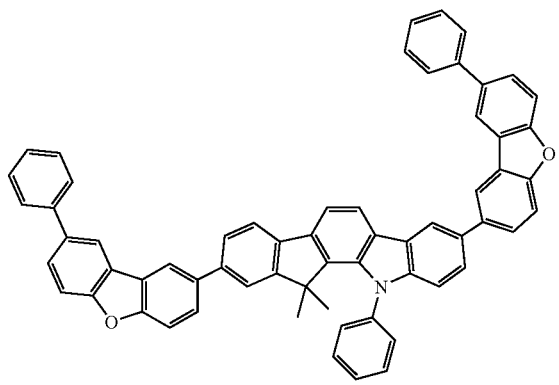
(4-112)
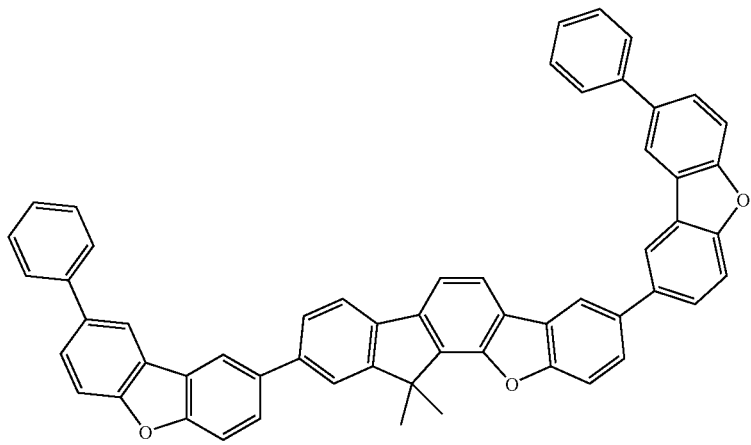

-continued
(4-113)
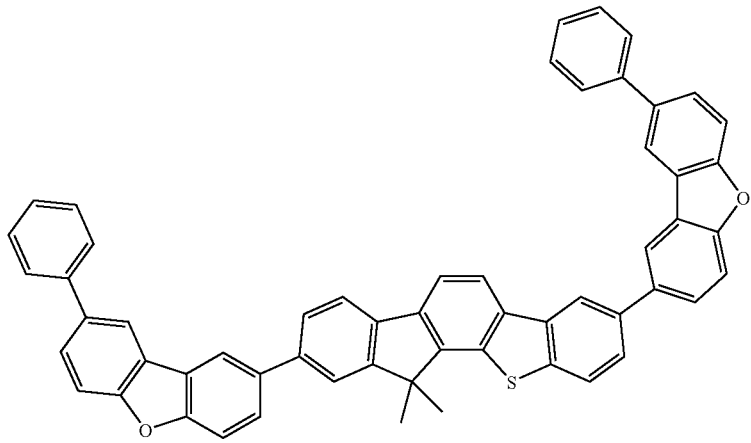
(4-114)
(4-115)
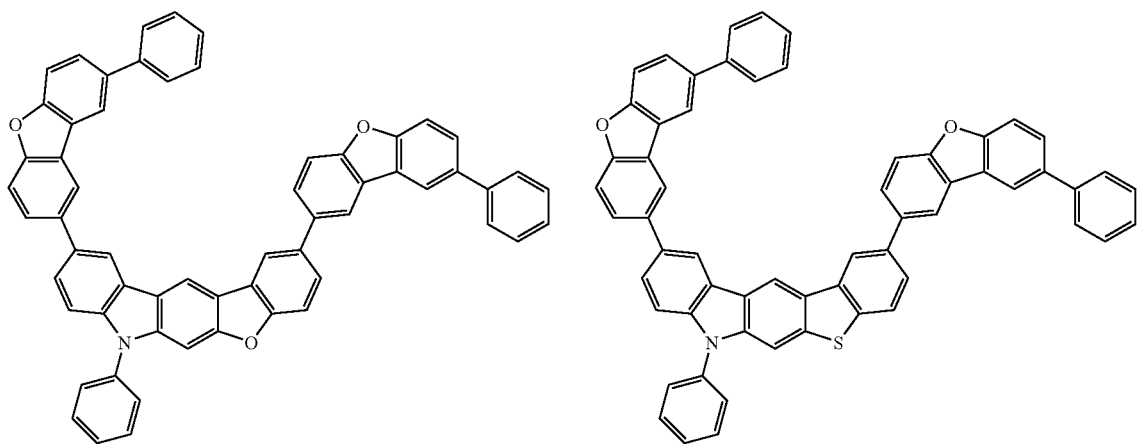
(4-116)
(4-117)
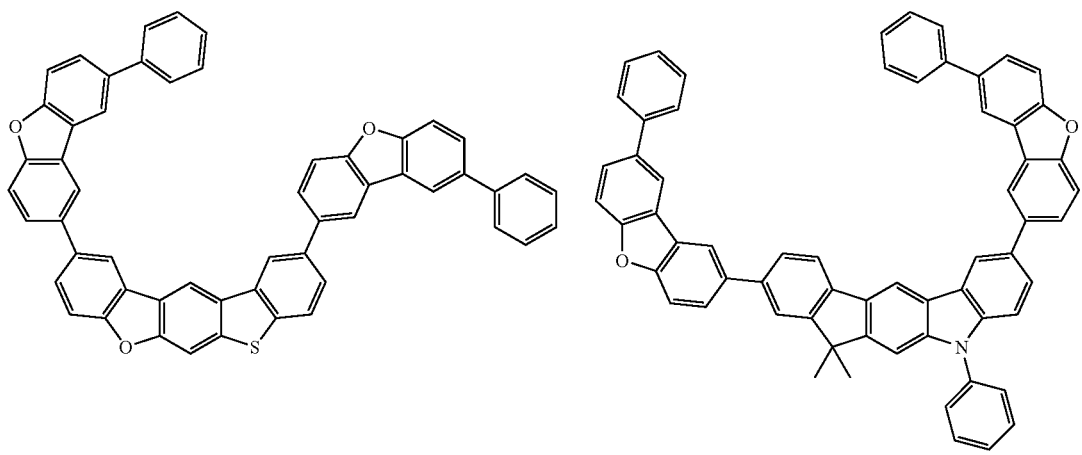

-continued
(4-118) (4-119)
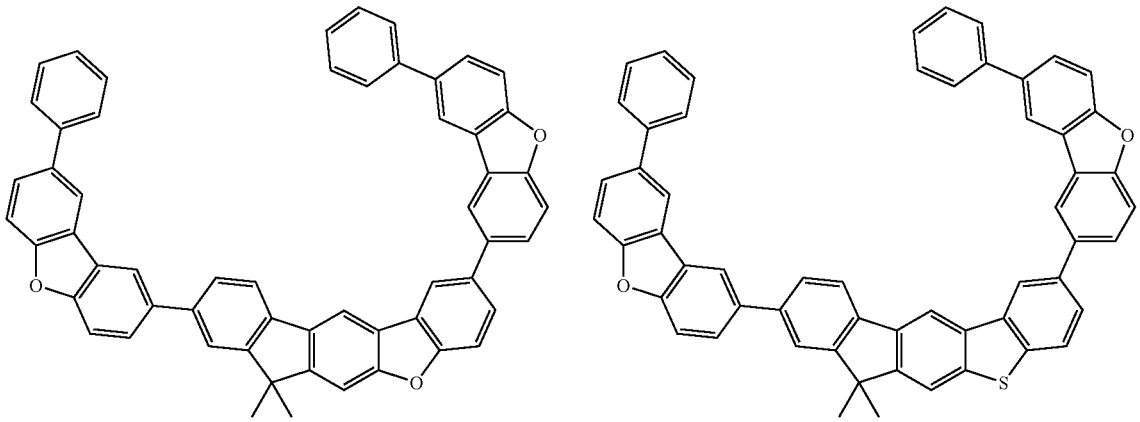
[Chem 72]
(4-120)
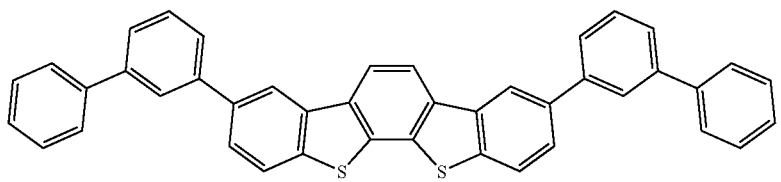
(4-121)
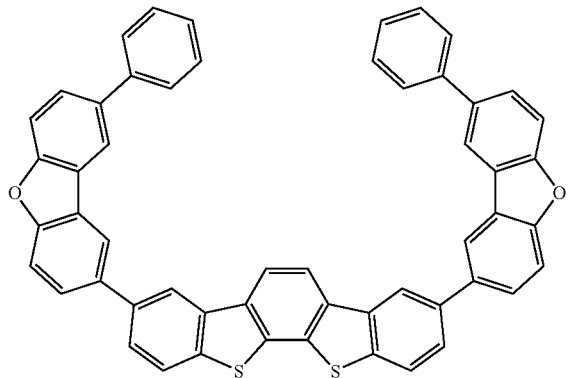
(4-122)
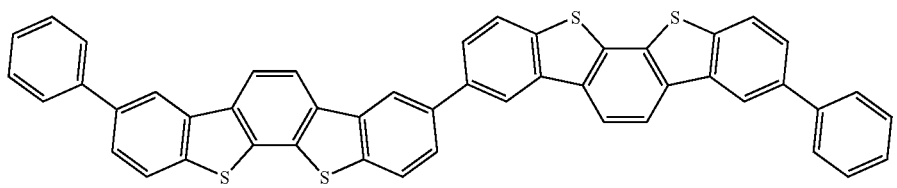
(4-123)
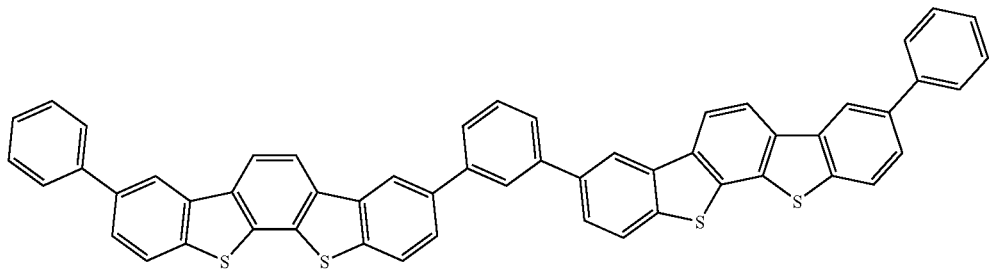

(4-124)
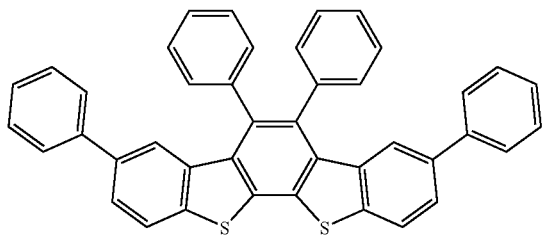
(4-125)
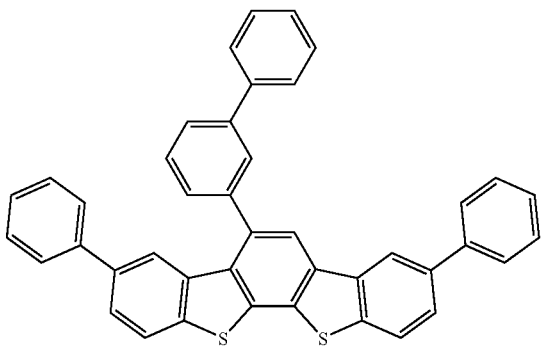
(4-126)
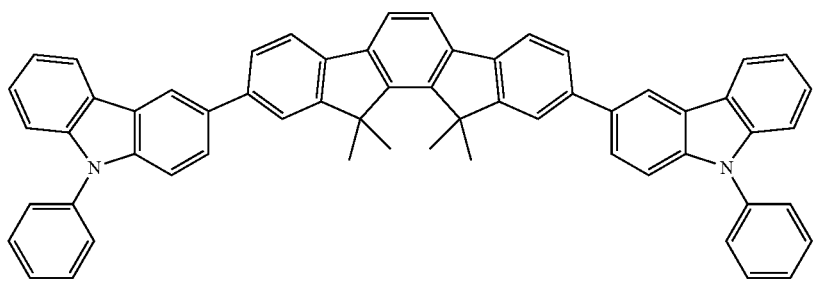
(4-127)
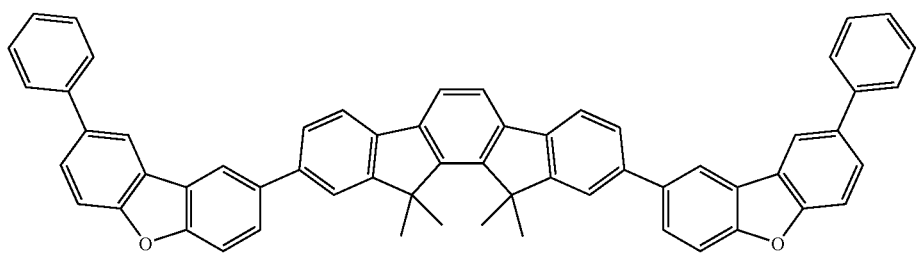
(4-128)
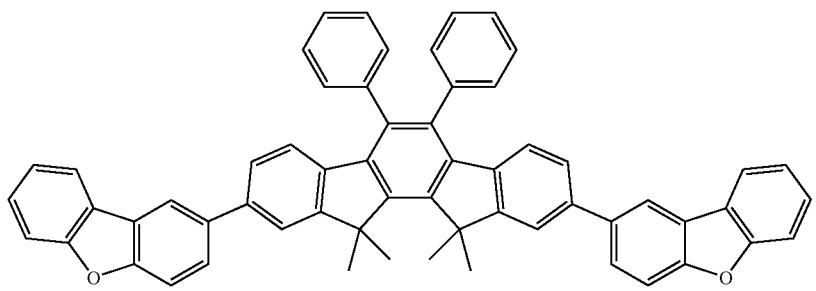
(4-129)
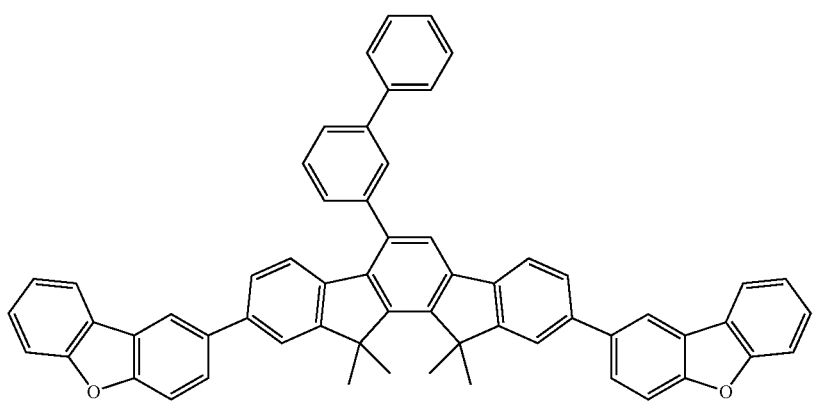

-continued
[Chem 73]
(4-130)
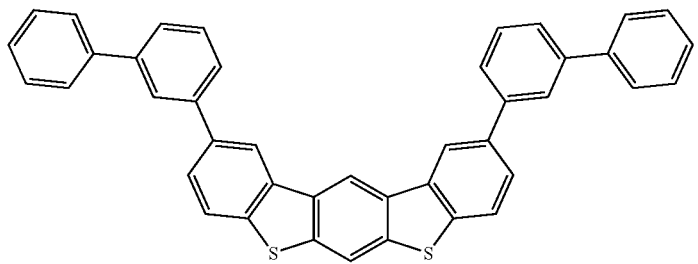
(4-131)
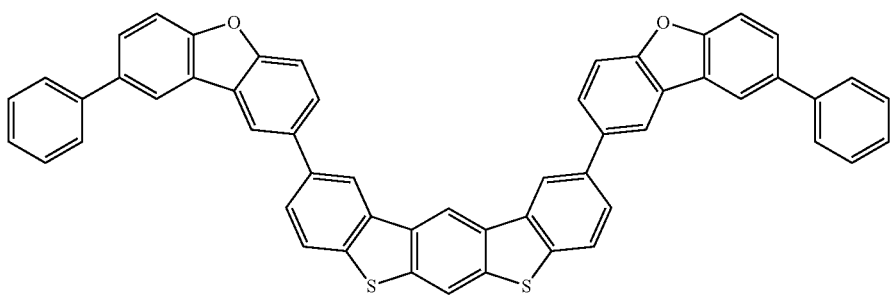
(4-132)
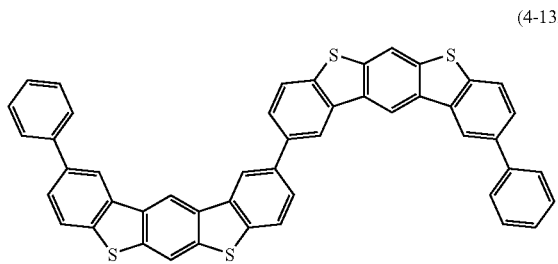
(4-133)
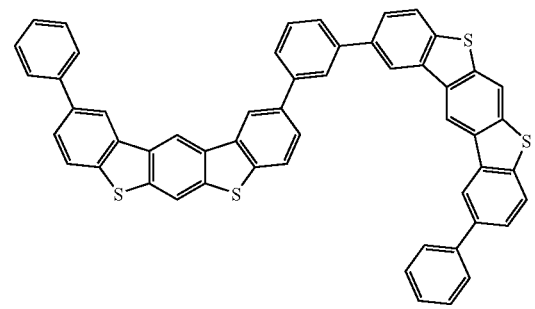
(4-134)
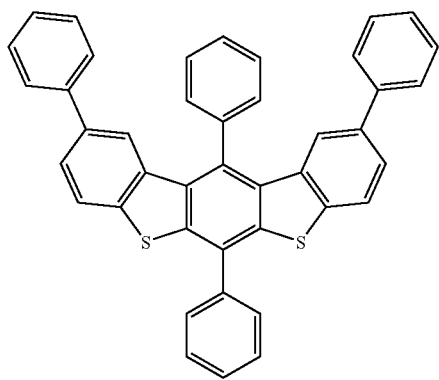
(4-135)
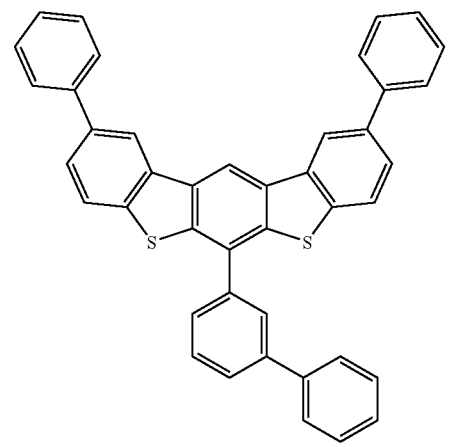

(4-136)
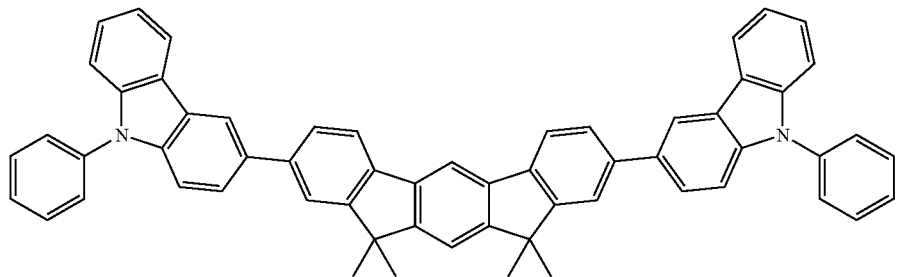
(4-137)
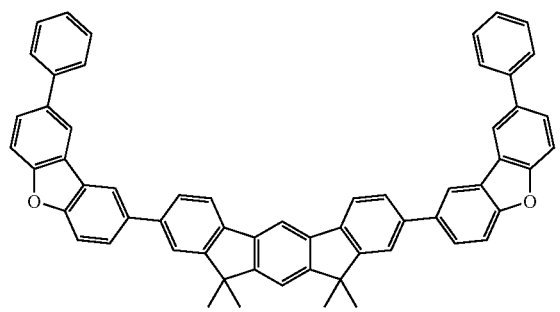
(4-138)
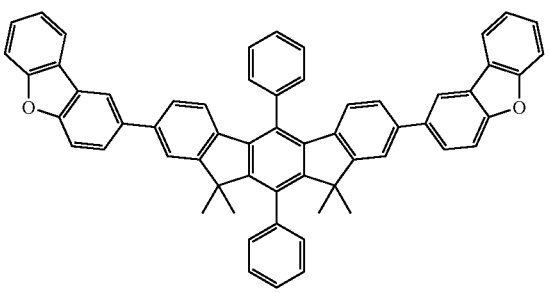
[Chem 74]
(4-139)
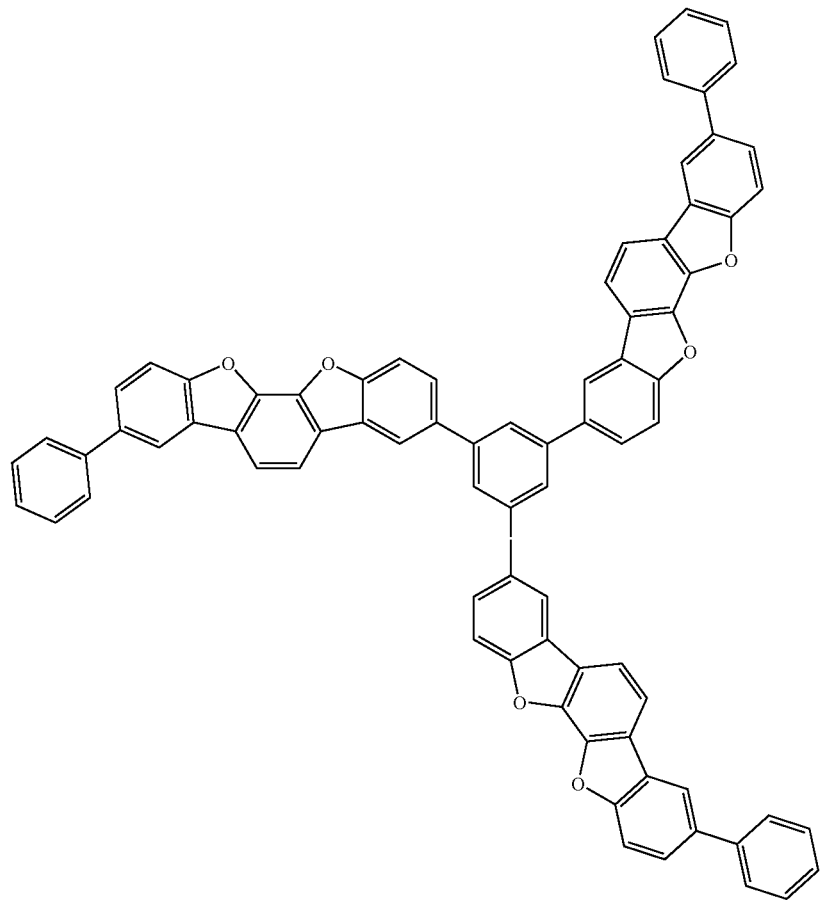

(4-140)
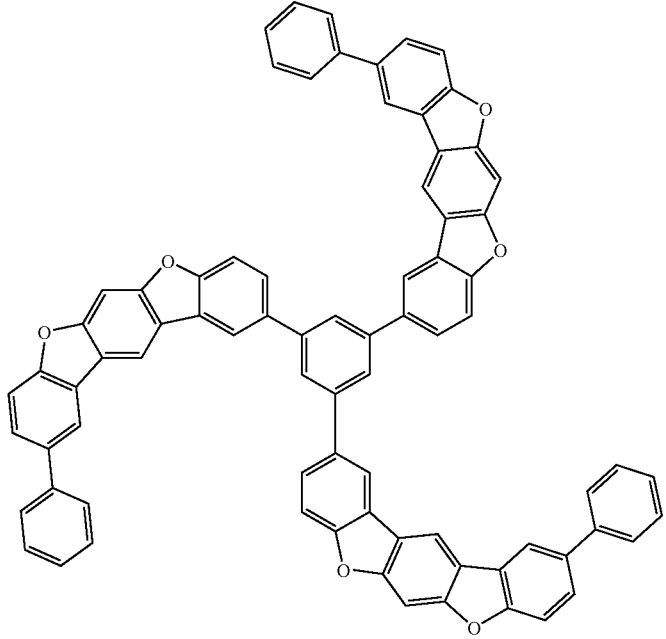
[Chem 75]
(4-141)
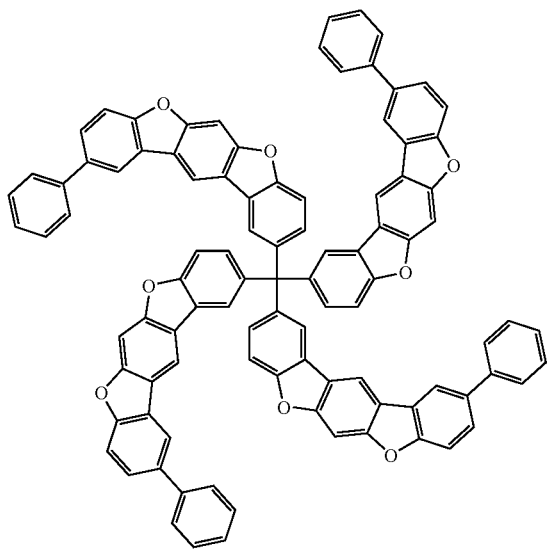
(4-142)
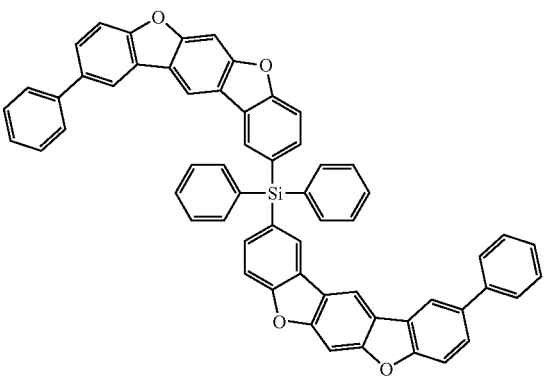

-continued
(4-143)
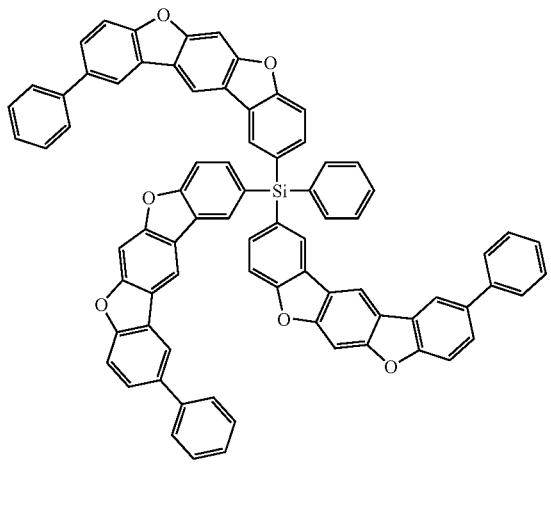
(4-144)
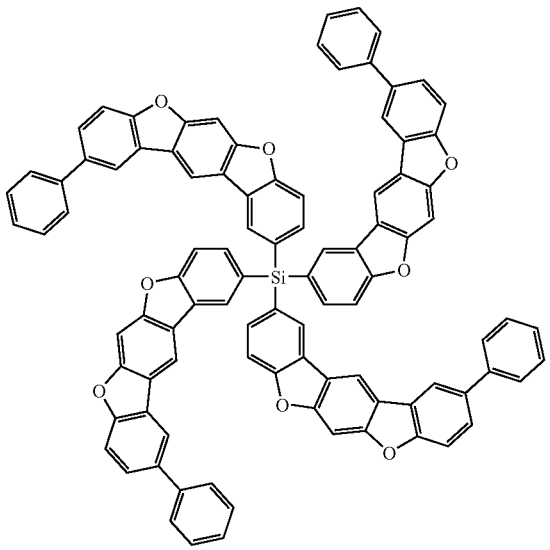
(4-145)
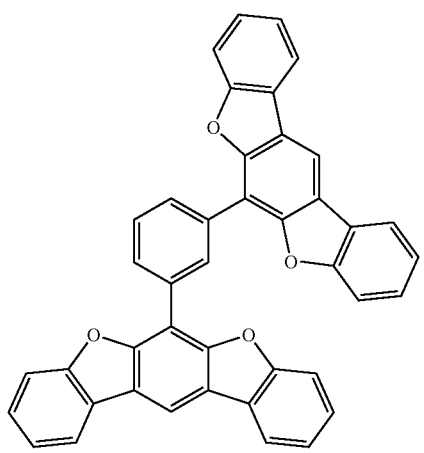
(4-146)
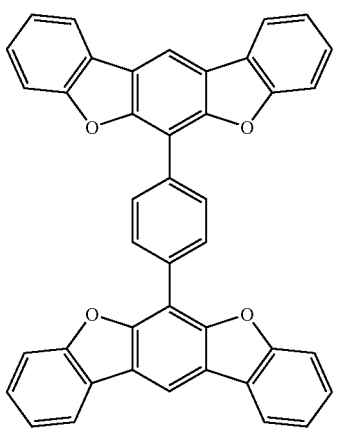
(4-147)
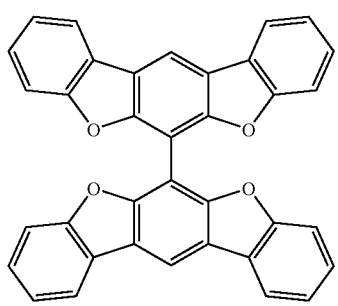
(4-148)
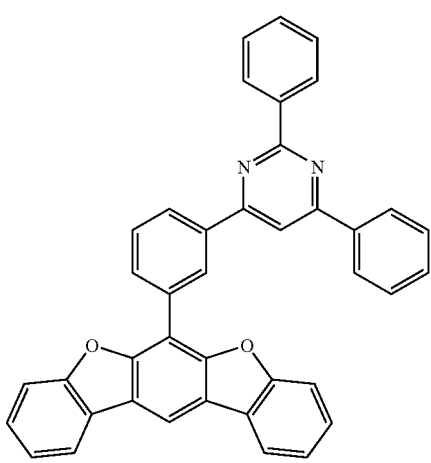

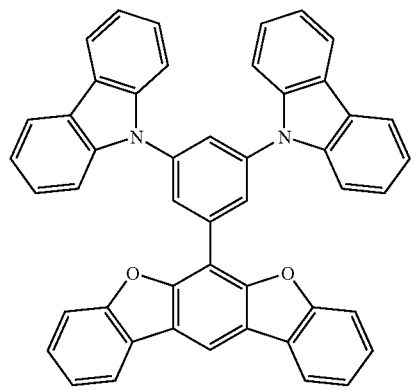
(4-149)
[Chem 76]
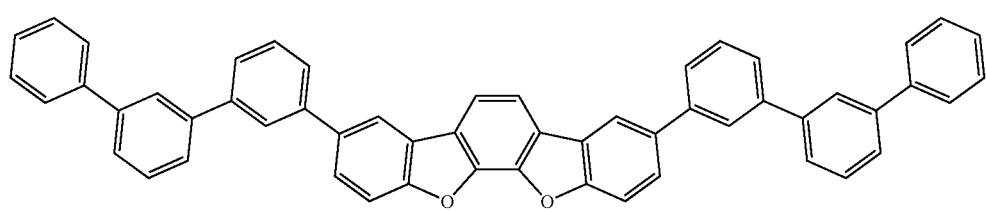
(4-150)
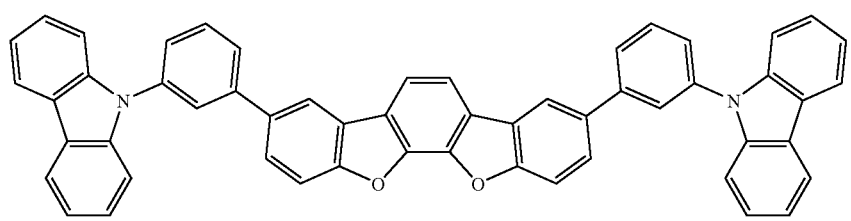
(4-151)
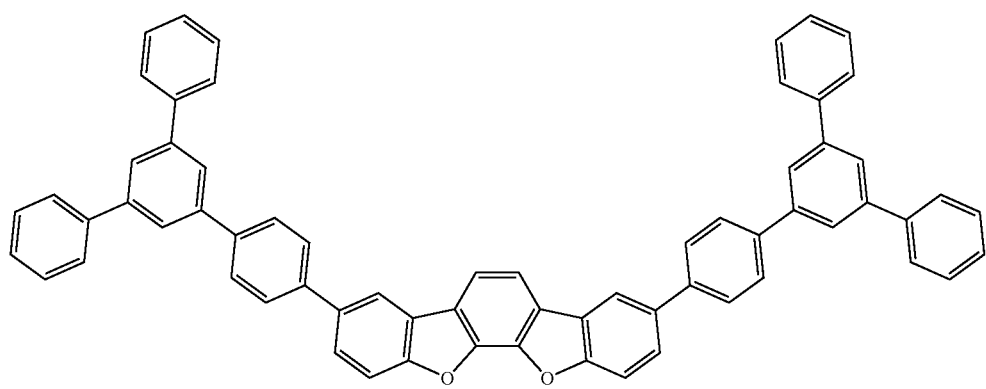
(4-152)
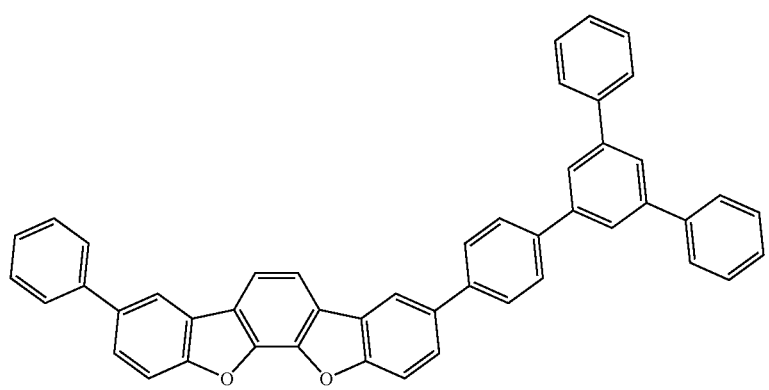
(4-153)

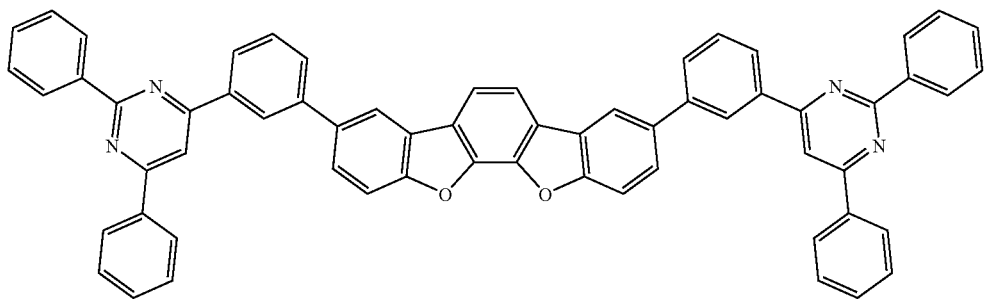
(4-154)
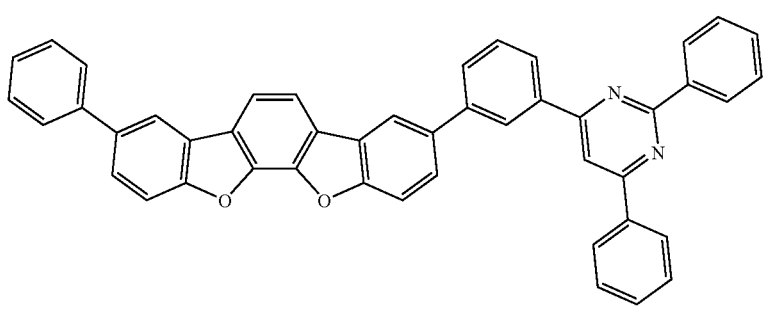
(4-155)
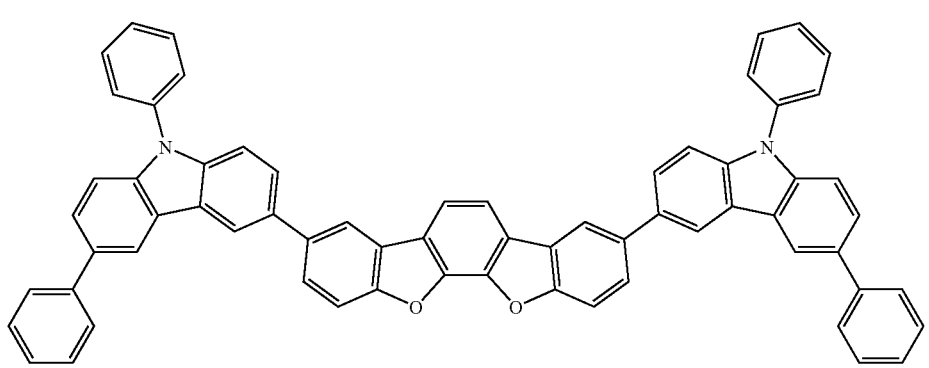
(4-156)
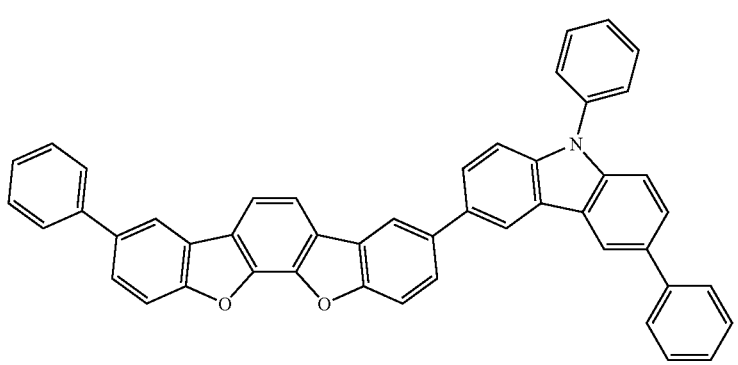
(4-157)
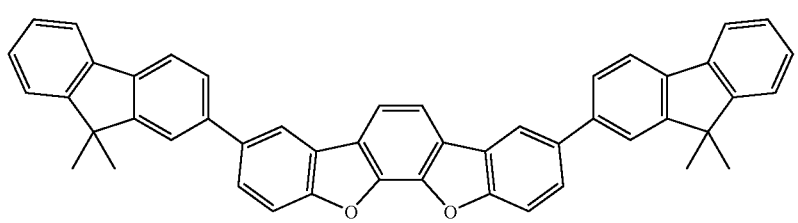
(4-158)

(4-159)
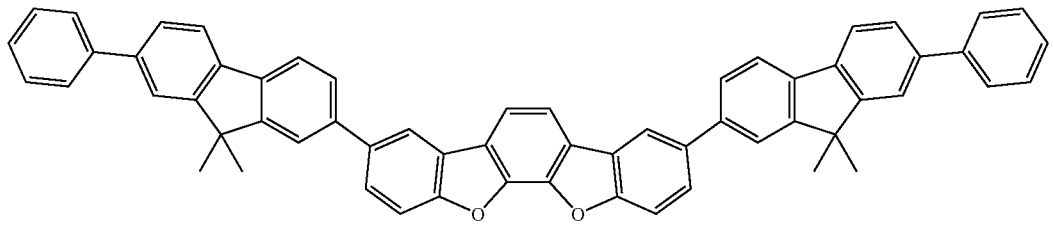
[Chem 77]
(4-160)
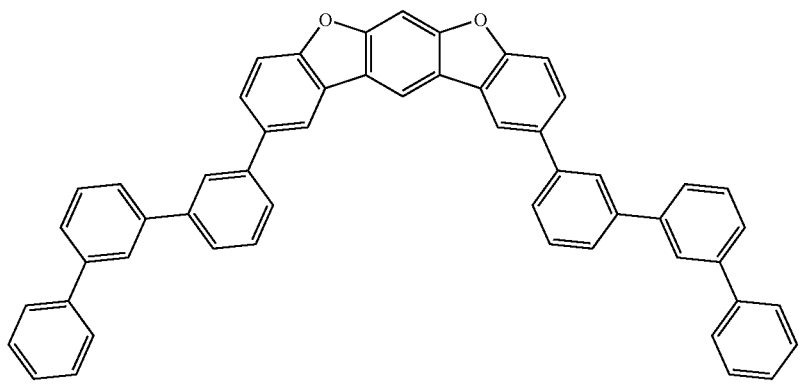
(4-161)
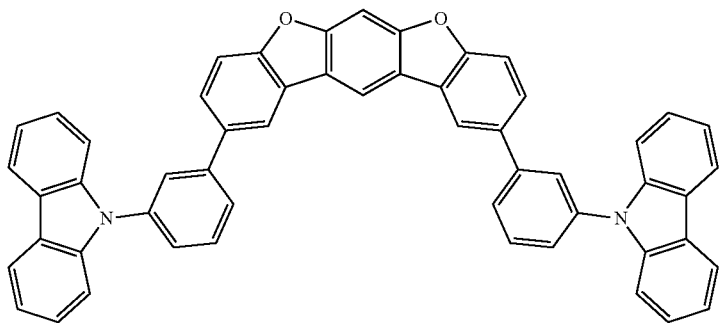
(4-162)
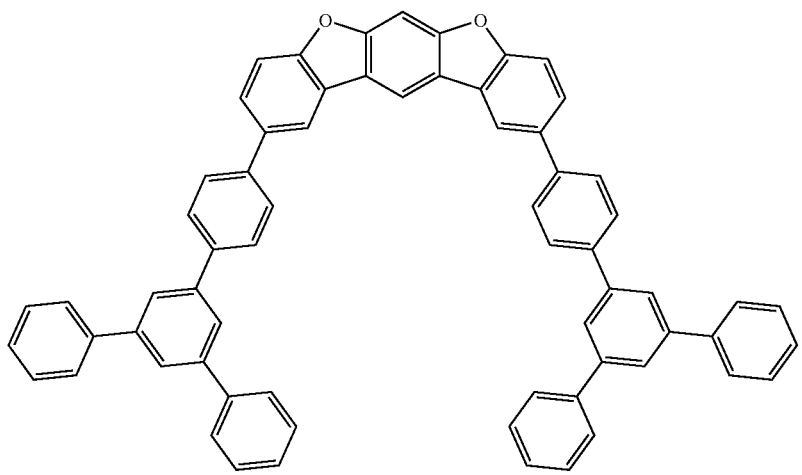

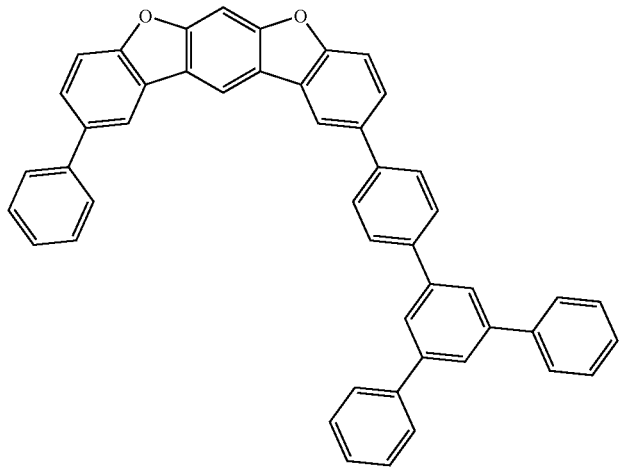
(4-163)
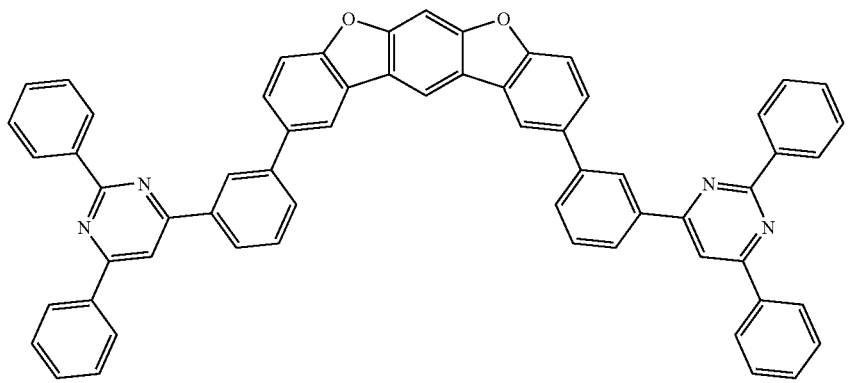
(4-164)
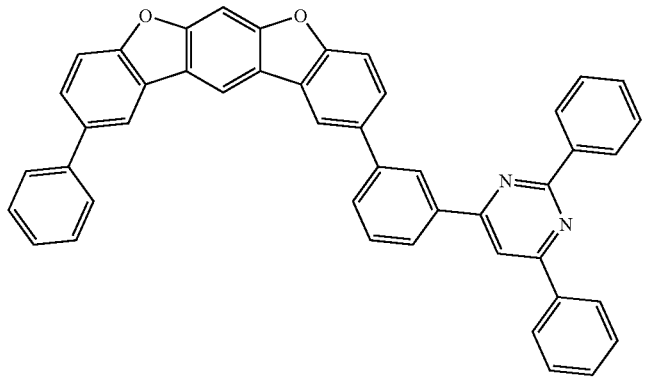
(4-165)
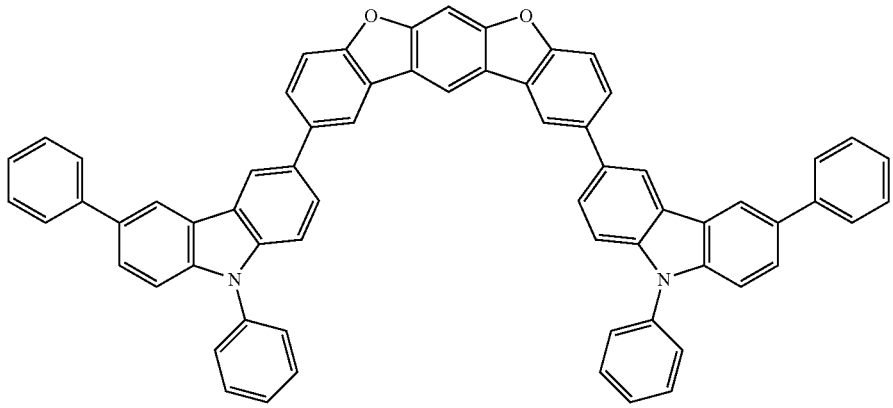
(4-166)

(4-167)
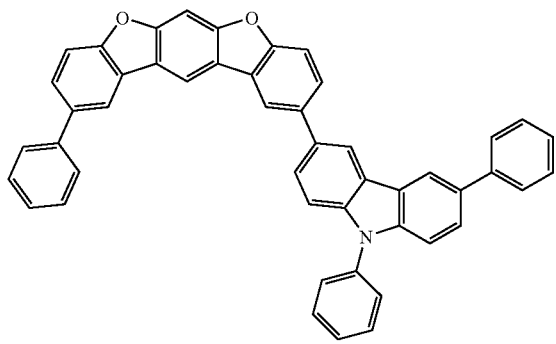
(4-168)
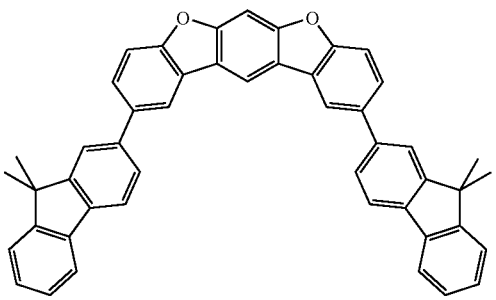
(4-169)
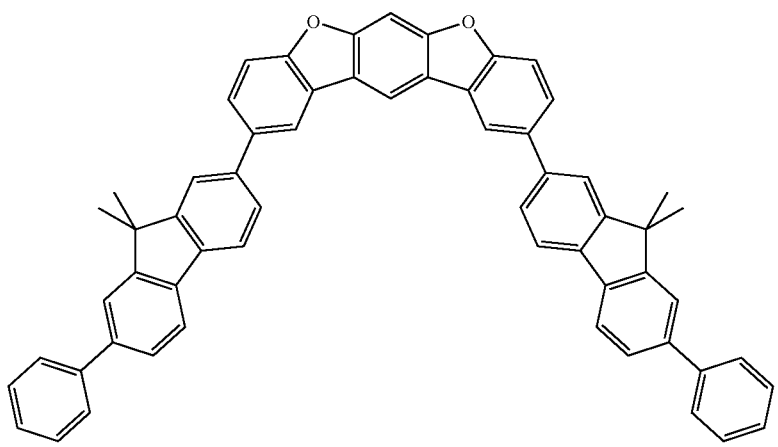
[Chem 78]
(4-170)
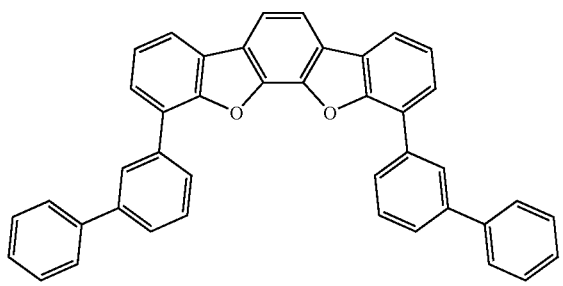
(4-171)
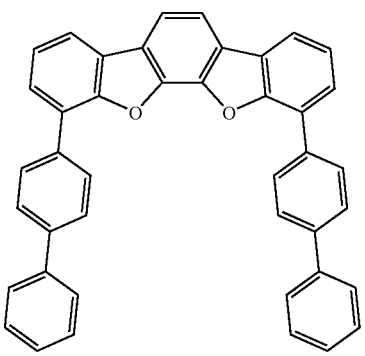
(4-172)
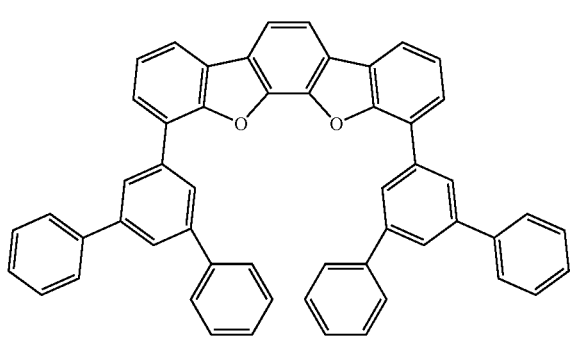

(4-173)
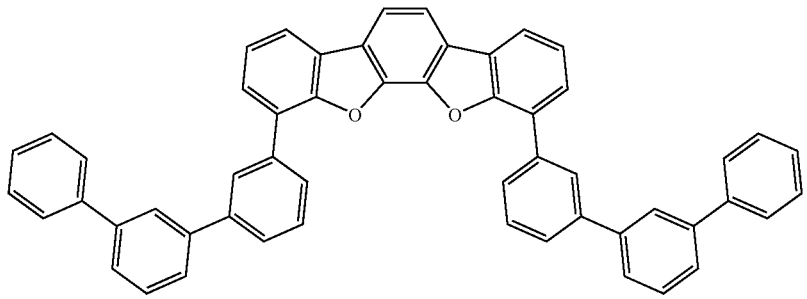
(4-174) (4-175)
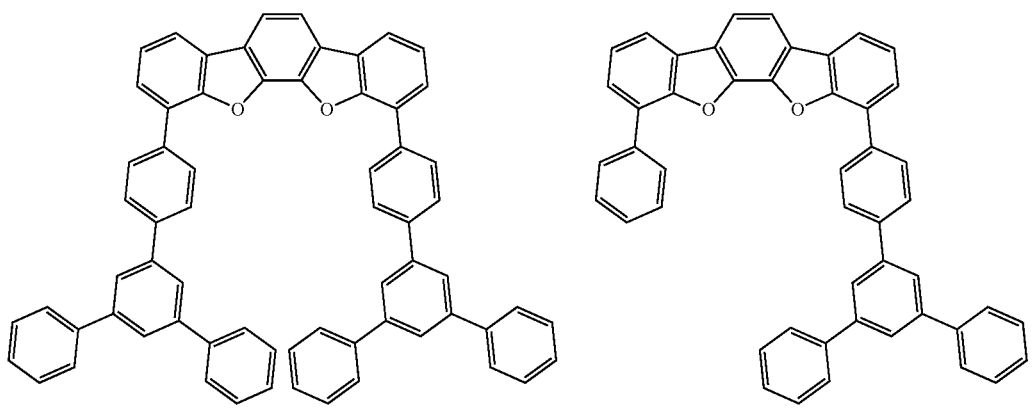
(4-176) (4-177)
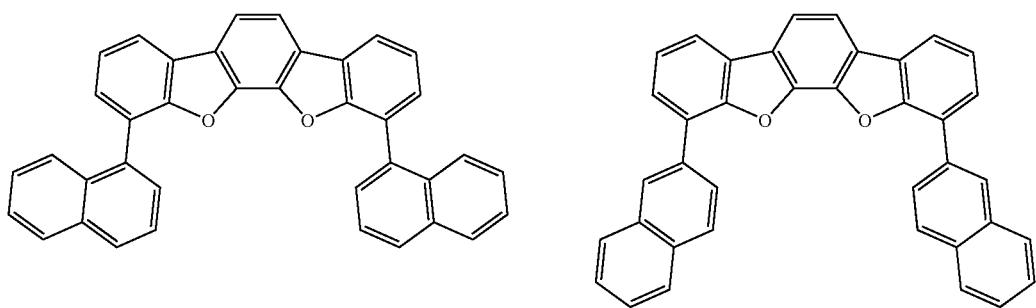
(4-178) (4-179)
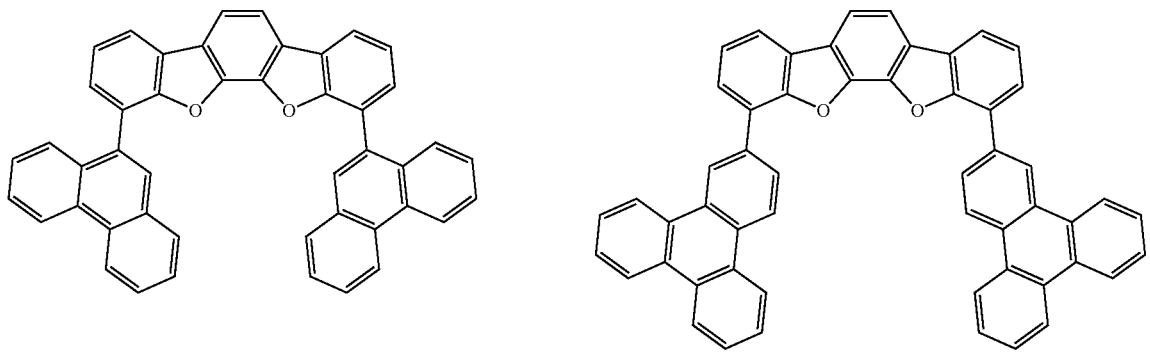

-continued
(4-180)
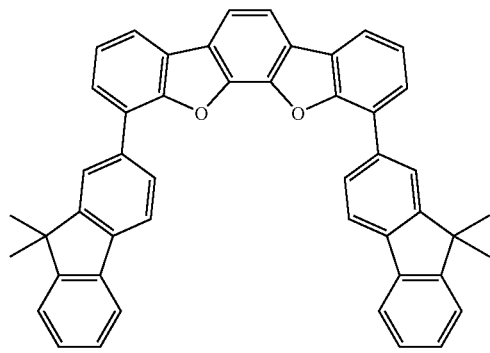
(4-181)
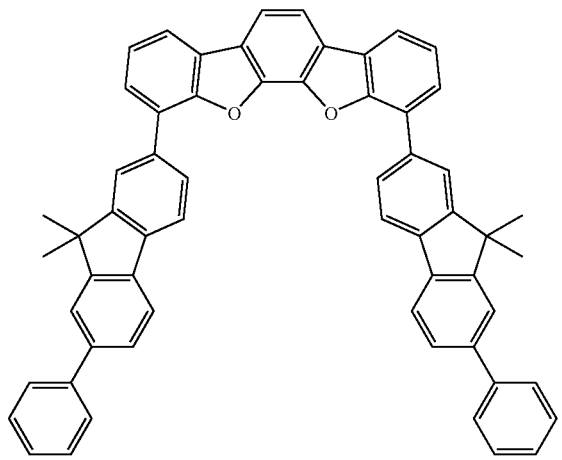
(4-182)
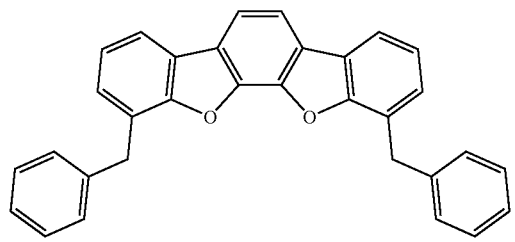
(4-183)
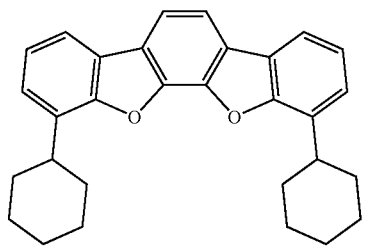
[Chem 79]
(4-184)
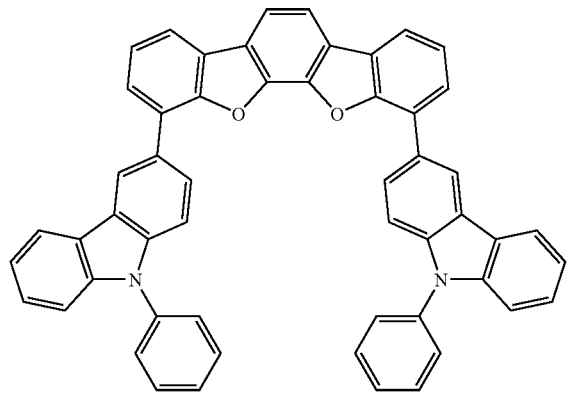
(4-185)
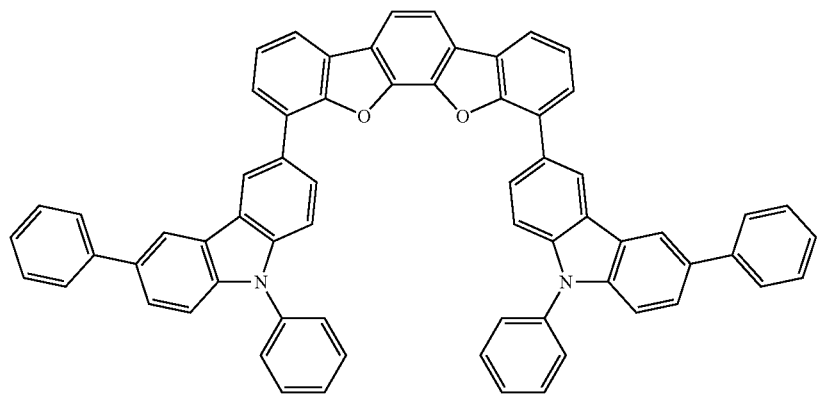

-continued
(4-186)
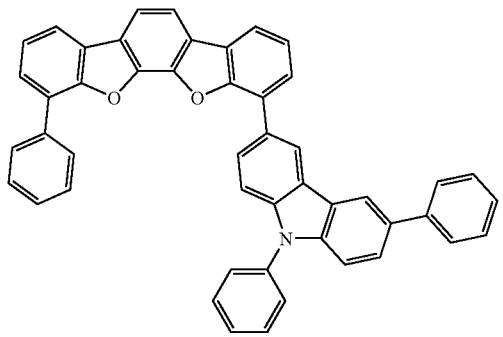
(4-187)
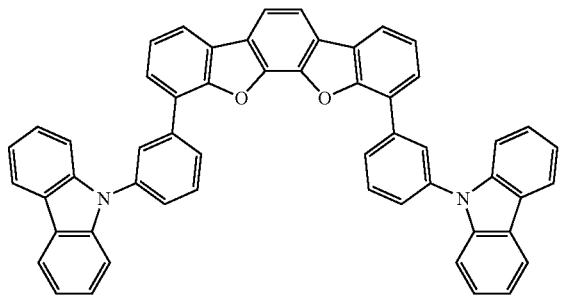
(4-188)
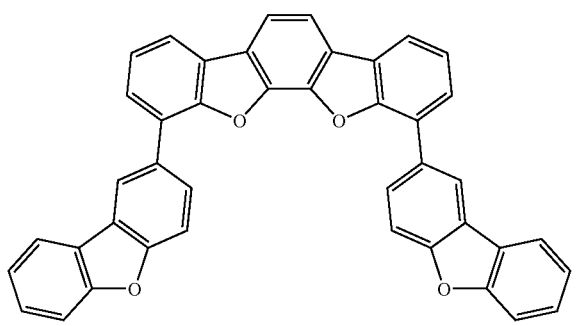
(4-189)
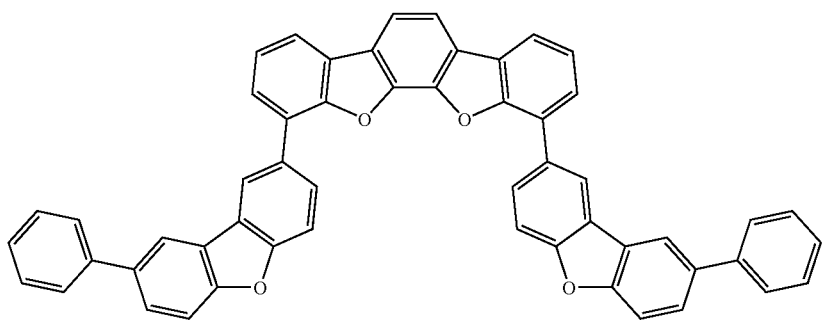
(4-190)
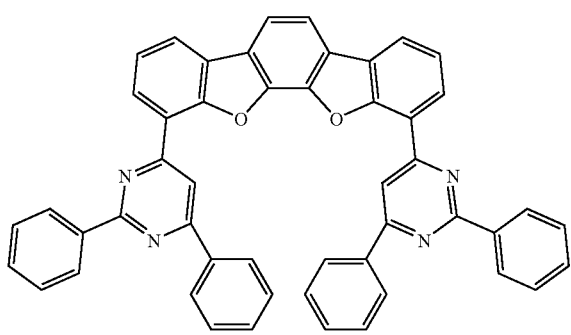

-continued
(4-191)
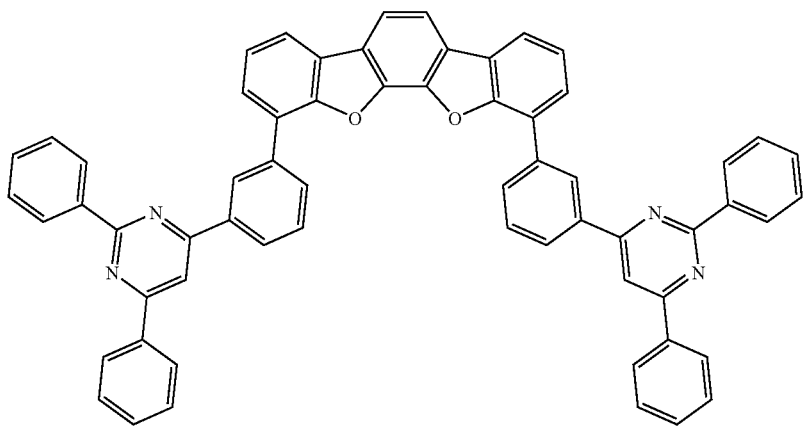
(4-192)
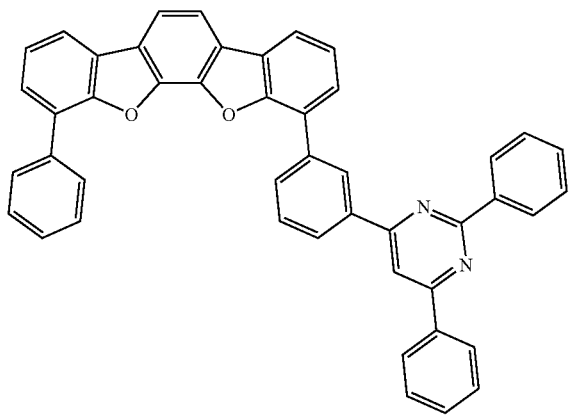
[Chem 80]
(4-193)
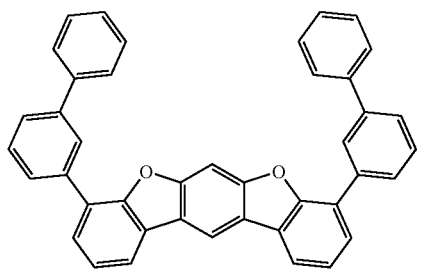
(4-194)
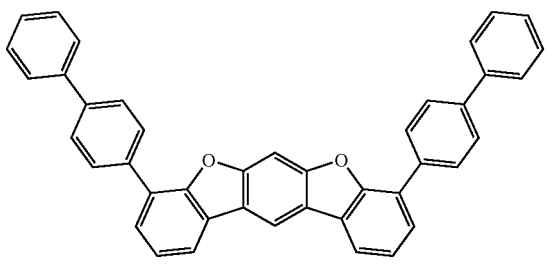
(4-195)
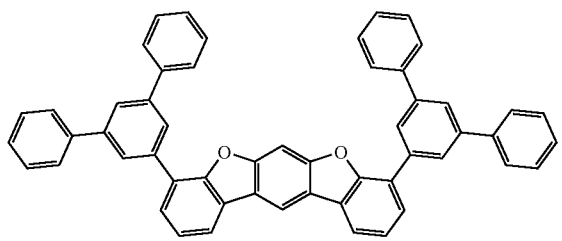
(4-196)
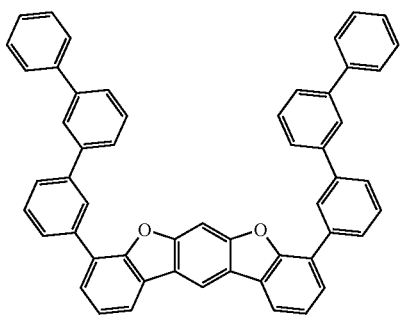

(4-197)
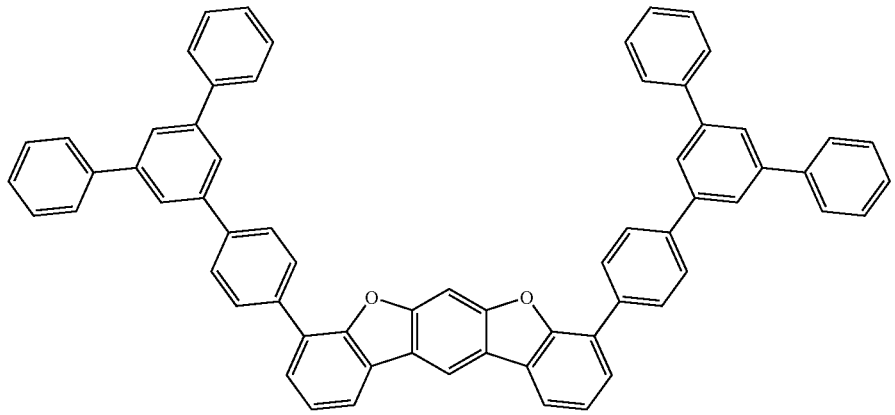
(4-198)
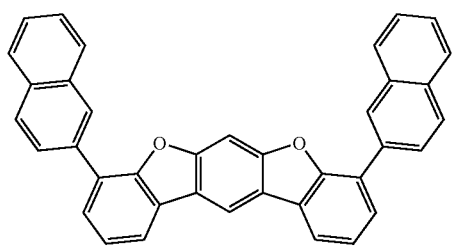
(4-199)
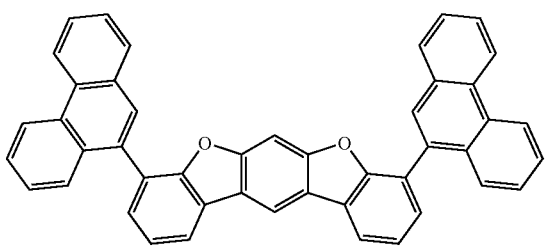
(4-200)
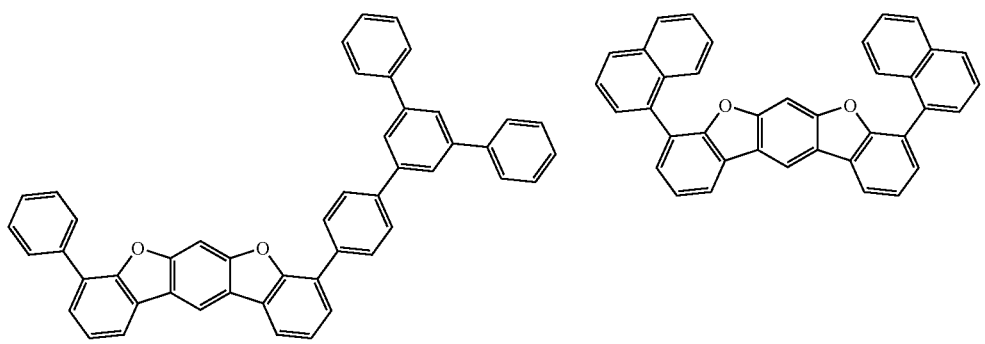
(4-201)
(4-202)
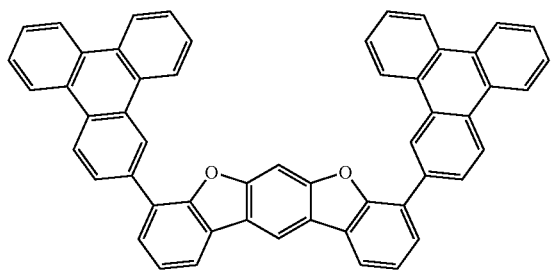
(4-203)
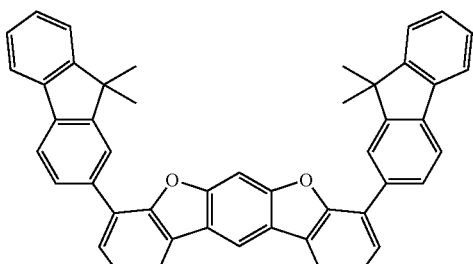

-continued
(4-204)
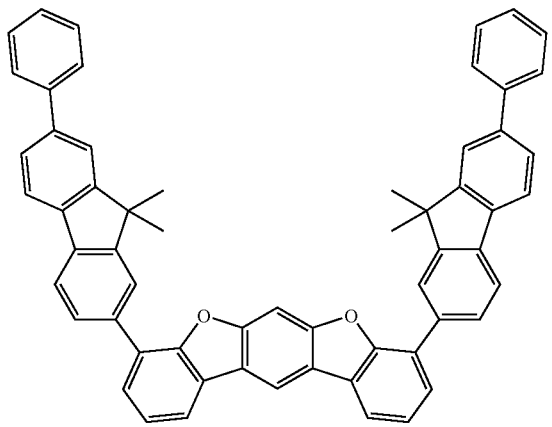
(4-205)
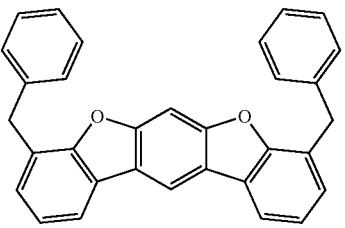
(4-206)
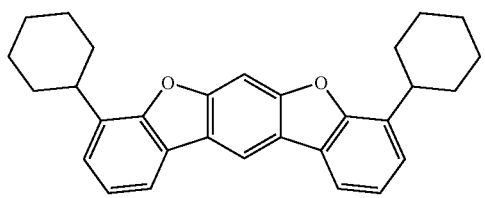
[Chem 81]
(4-207)
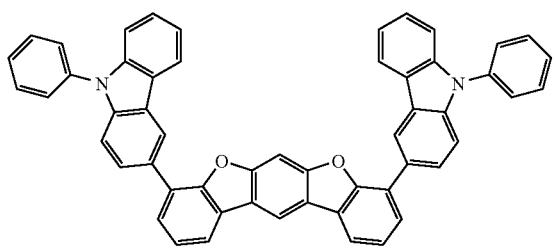
(4-208)
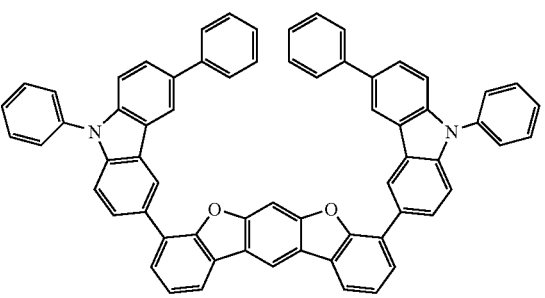
(4-209)
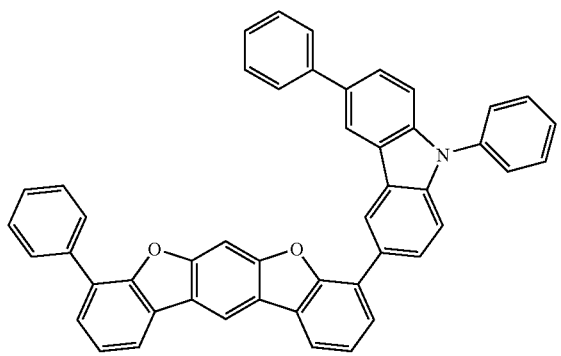
(4-210)
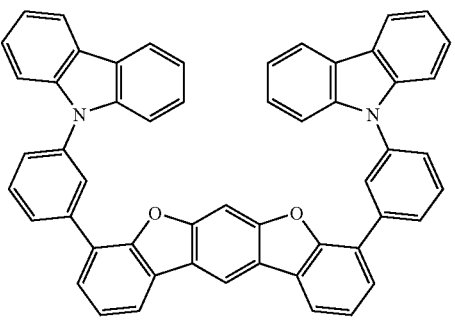

-continued
(4-211)
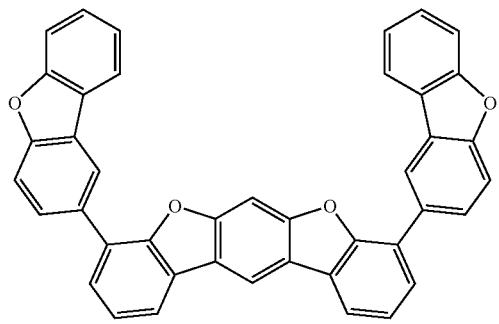
(4-212)
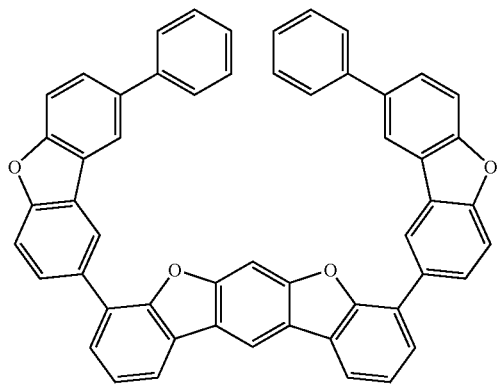
(4-213)
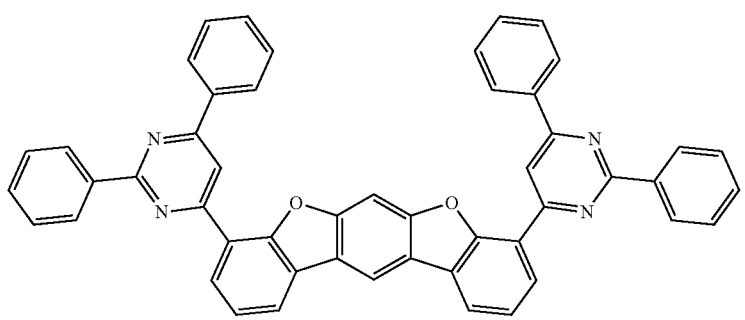
(4-214)
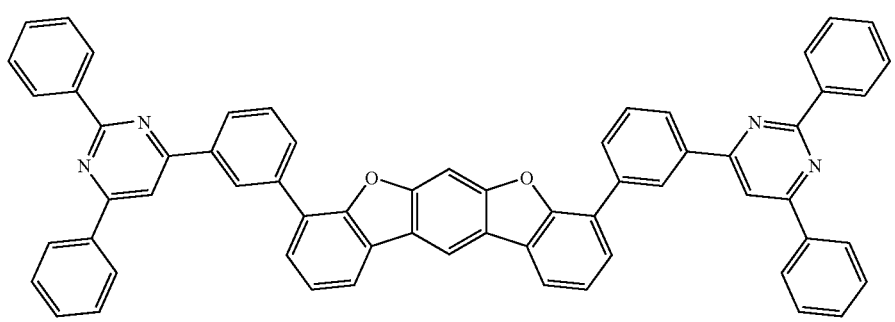
(4-215)
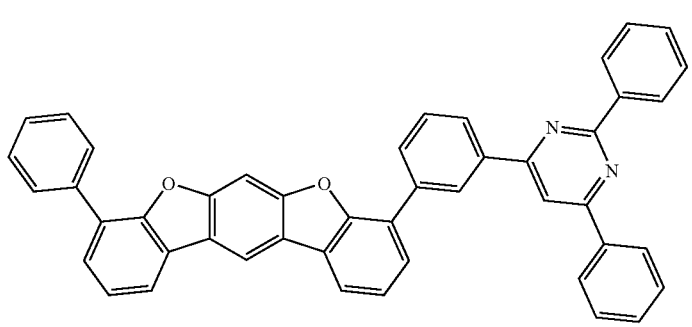

[Chem 82]
(4-216)
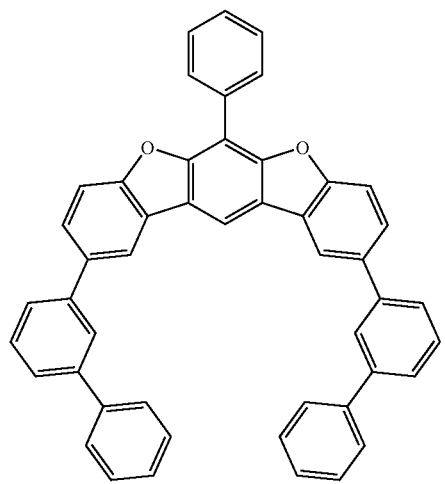
(4-217)
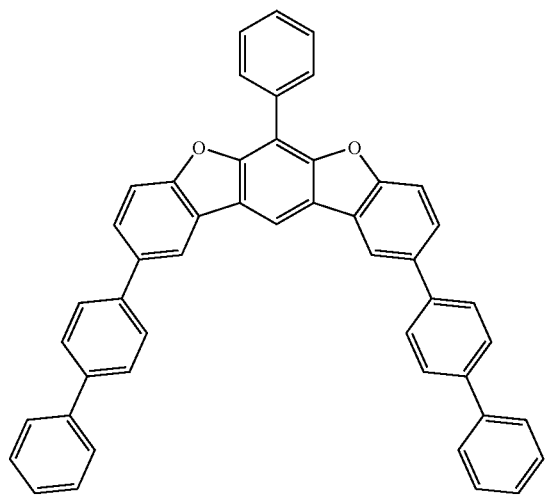
(4-218)
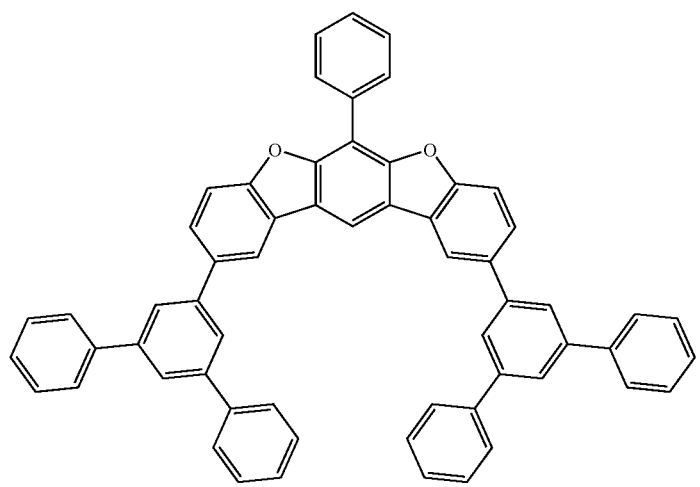
(4-219)
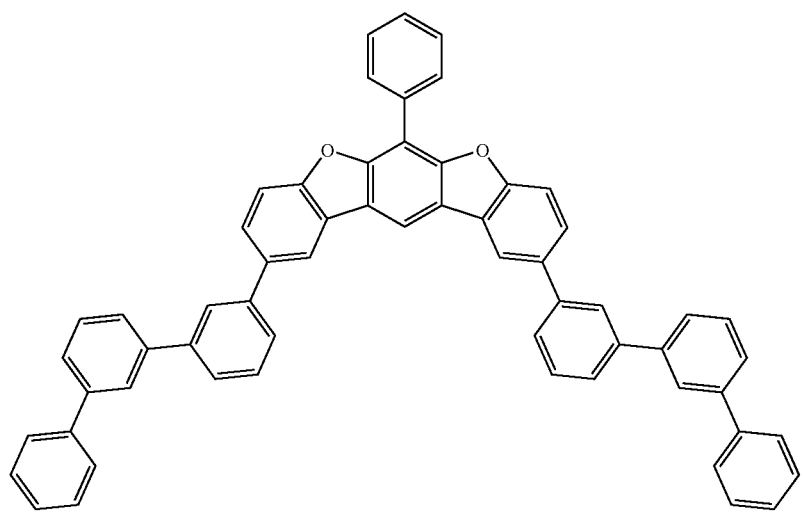

-continued
(4-220)
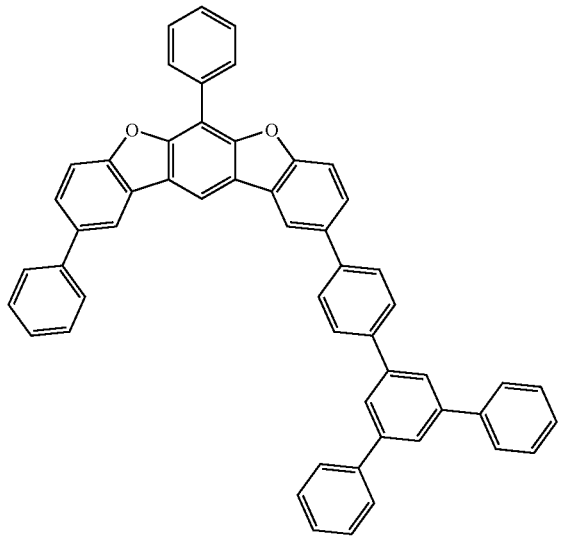
(4-221)
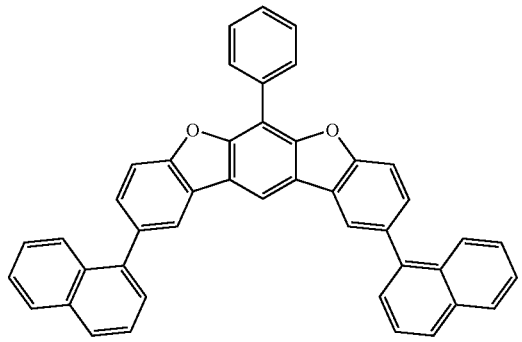
(4-222)
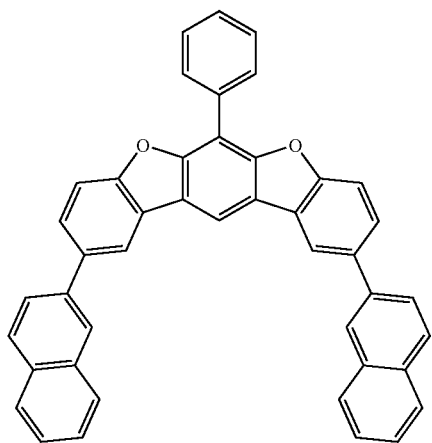
(4-223)
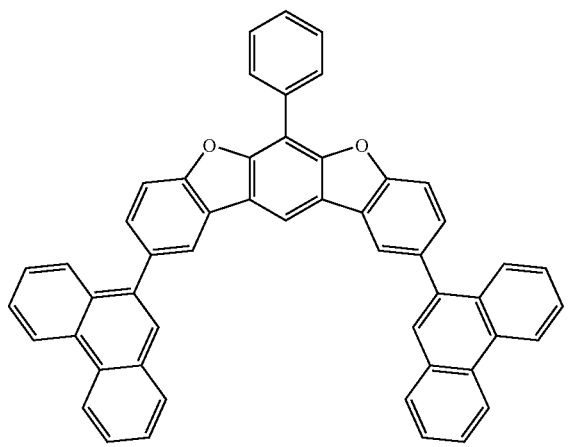
(4-224)
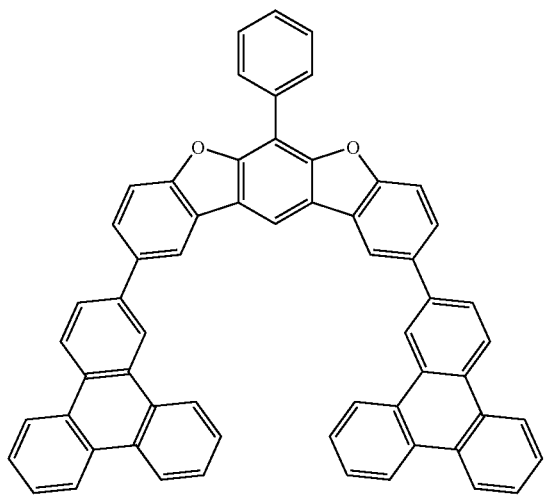
(4-225)
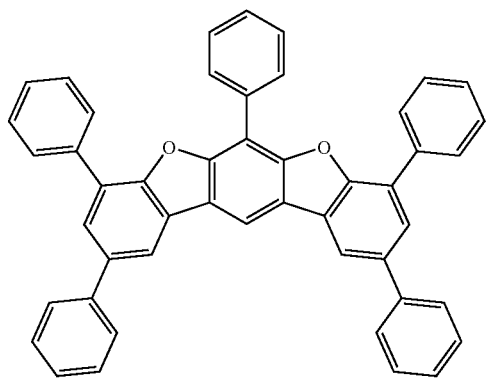

(4-226)
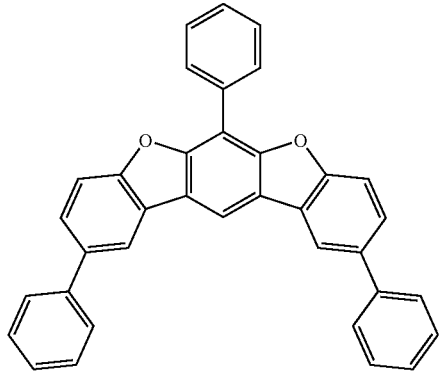
[Chem 83]
(4-227) (4-228)
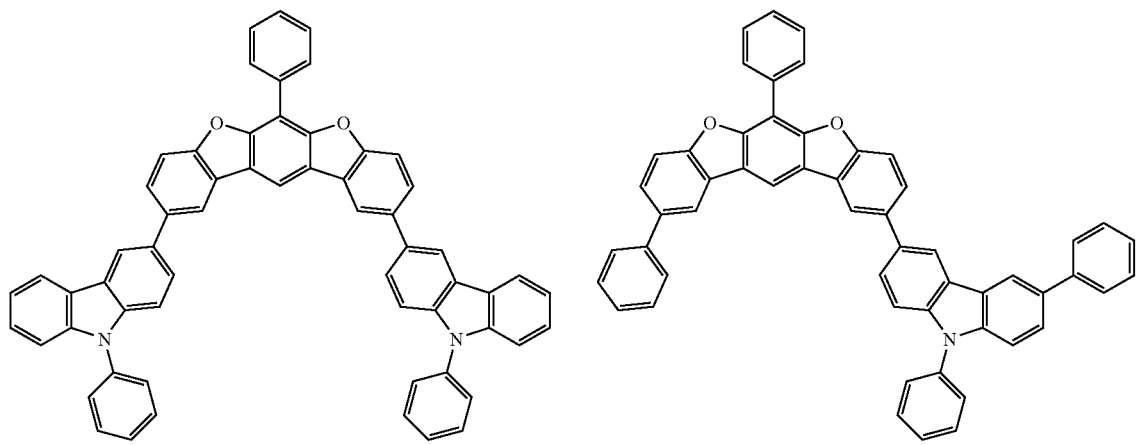
(4-229)
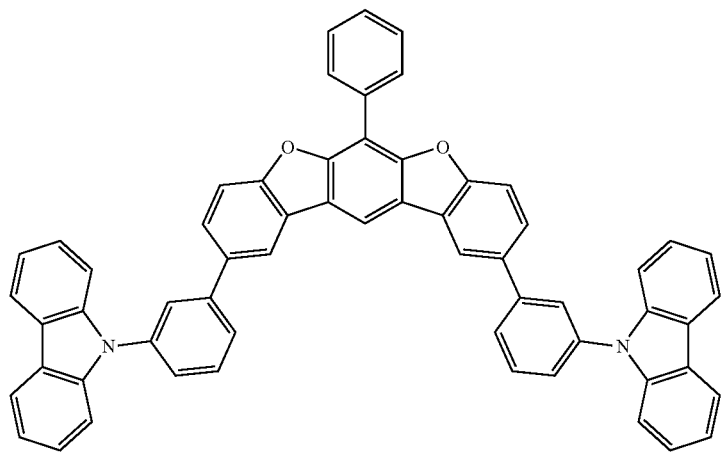

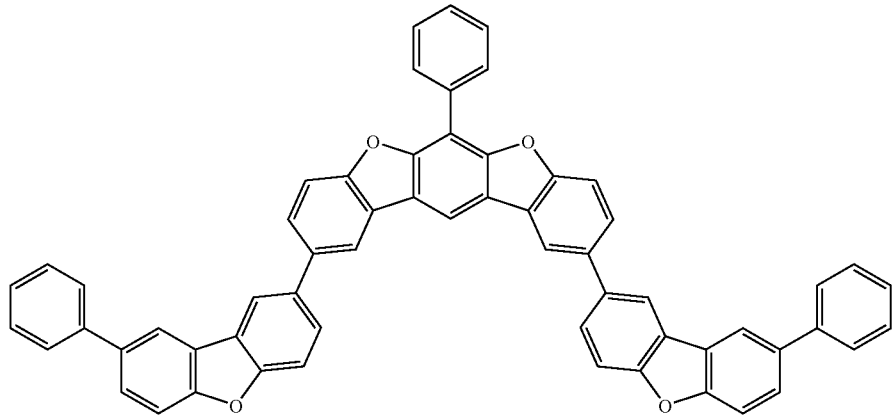
(4-230)
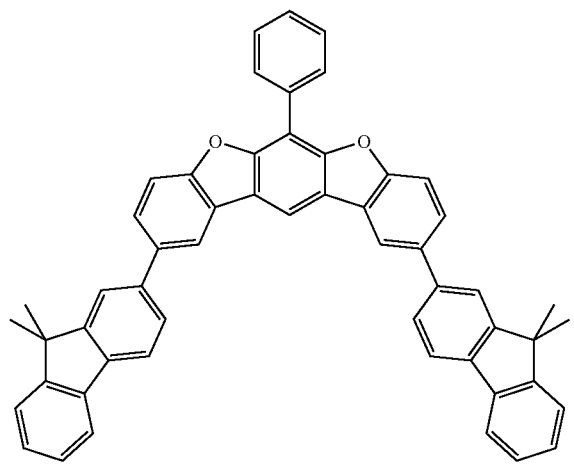
(4-231)
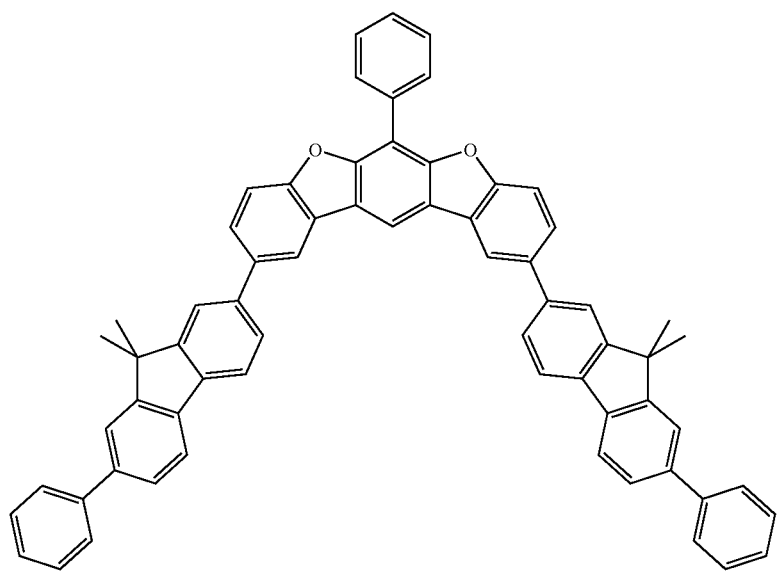
(4-232)

(4-233)
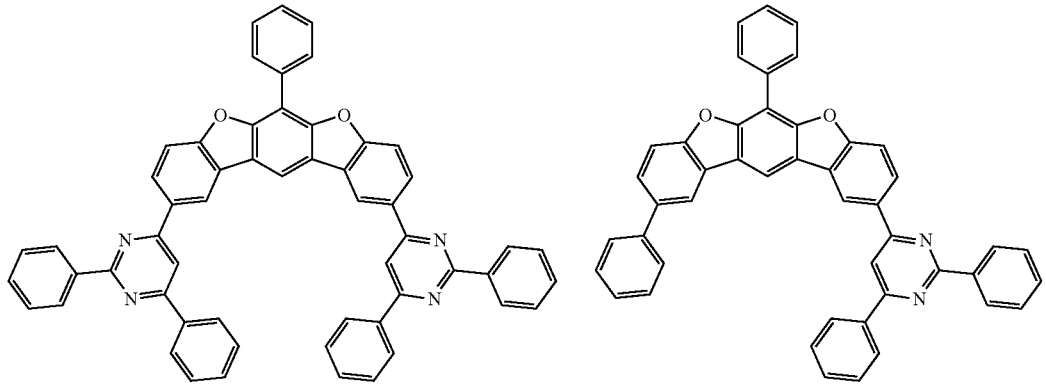
(4-234)
(4-235)
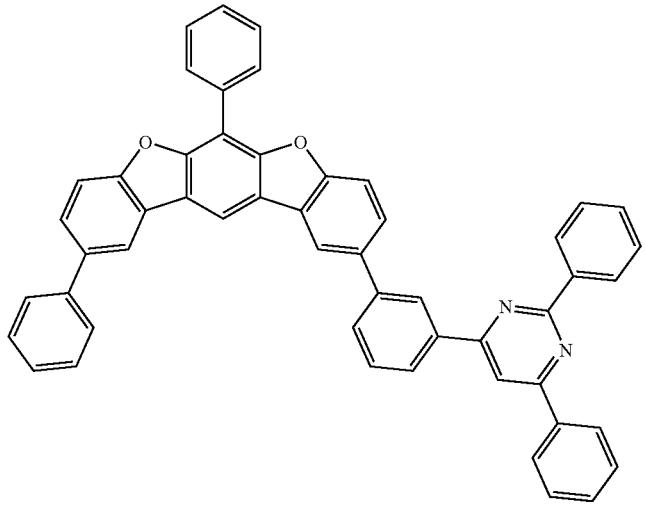
[Chem 84]
(4-236)
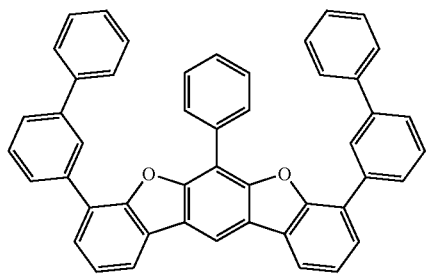
(4-237)
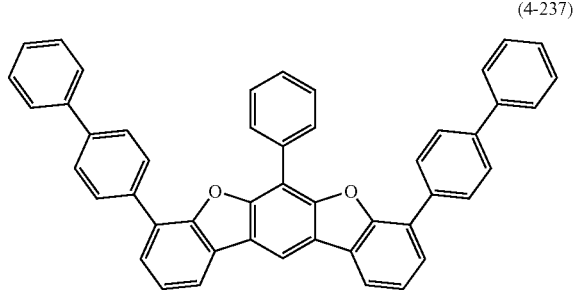
(4-238)
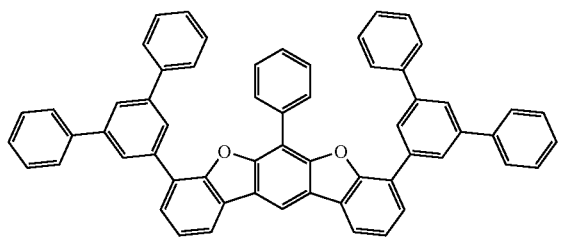
(4-239)
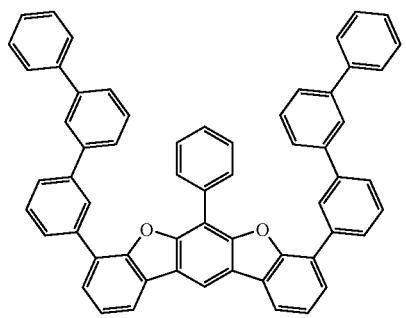

-continued
(4-240)
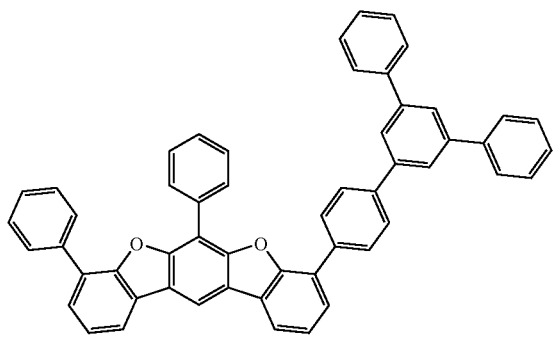
(4-241)
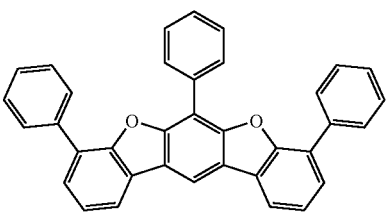
(4-242)
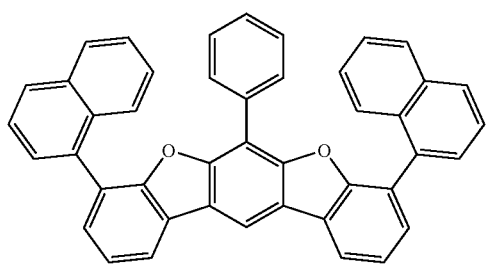
(4-243)
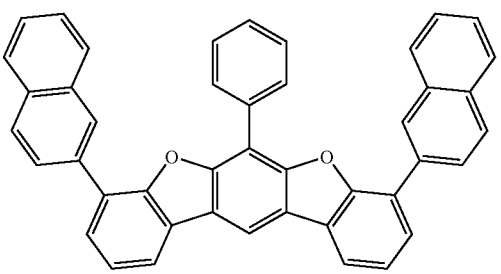
(4-244)
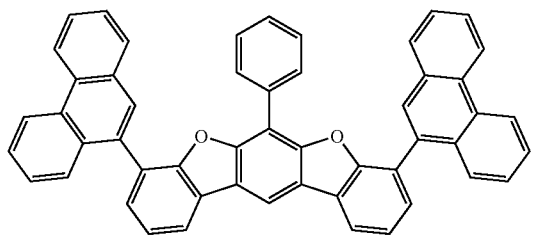
(4-245)
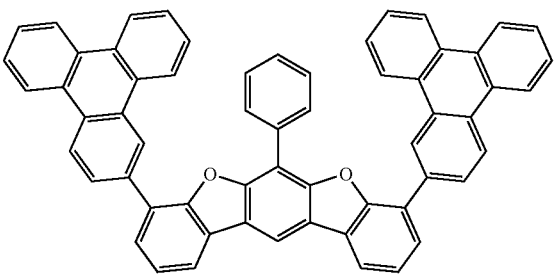
(4-246)
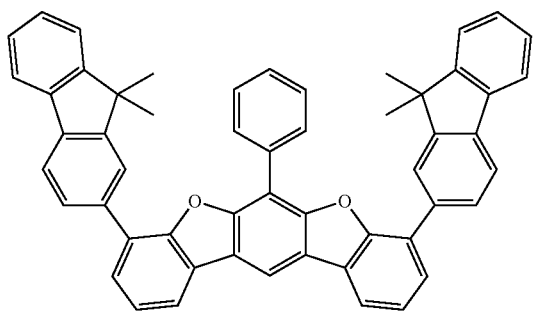
(4-247)
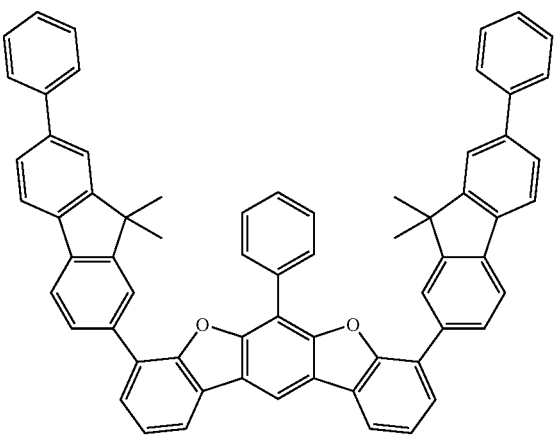

[Chem 85]
(4-248)
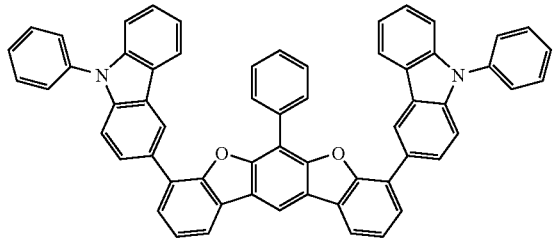
(4-249)
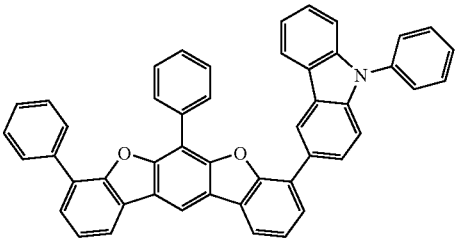
(4-250)
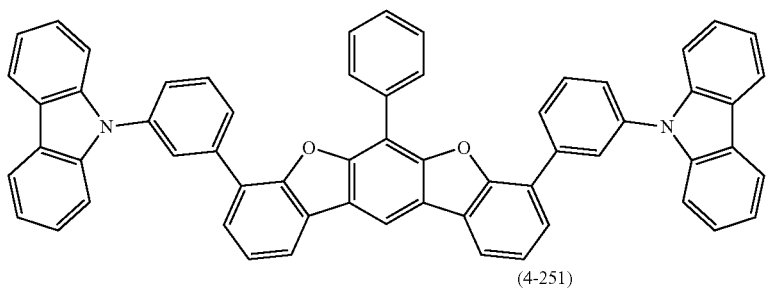
(4-251)
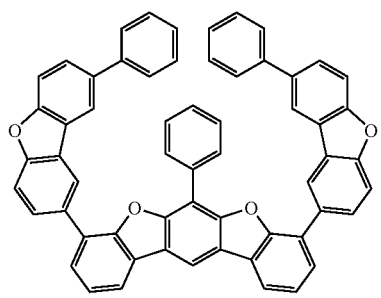
(4-252)
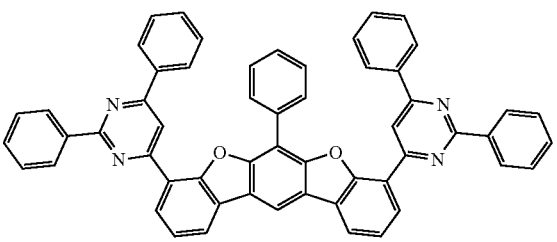
(4-253)
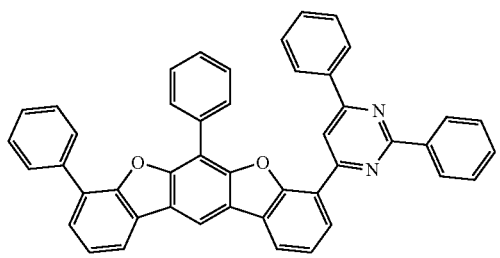
(4-254)
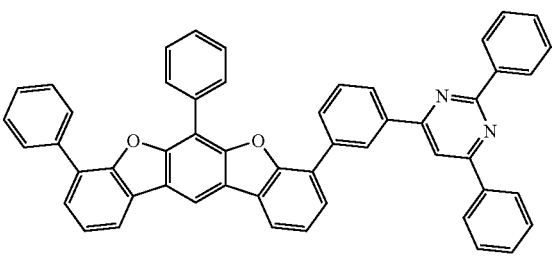
[Chem 86]
(4-255)
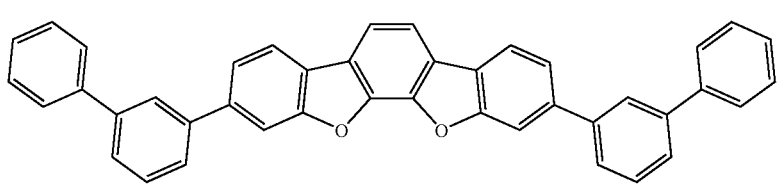
(4-256)
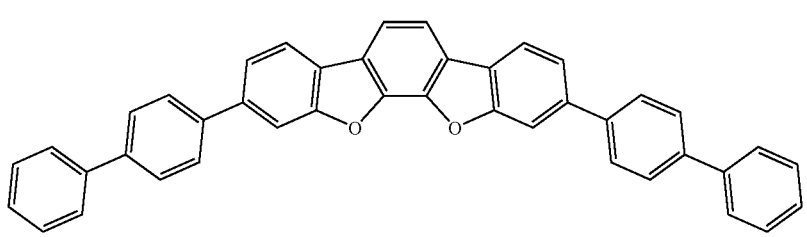

(4-257)
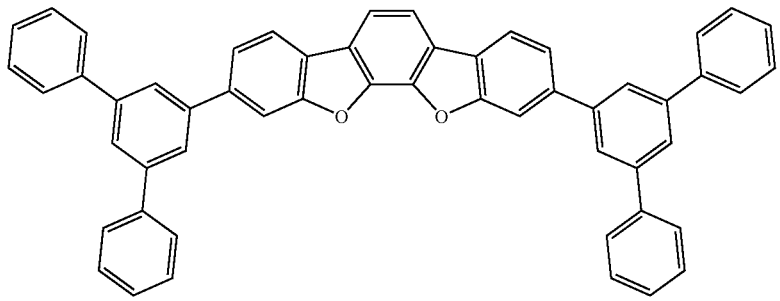
(4-258)
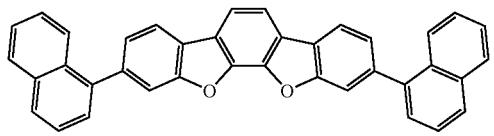
(4-259)
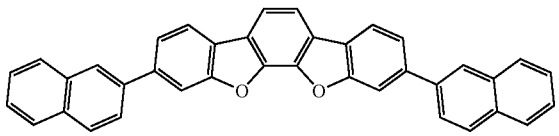
(4-260)
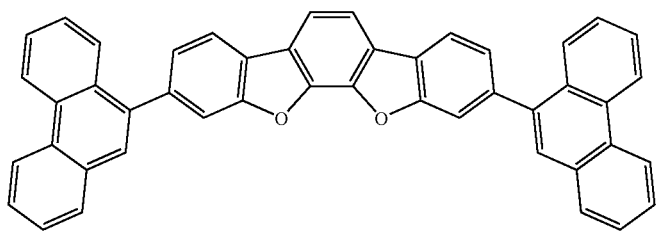
(4-261)
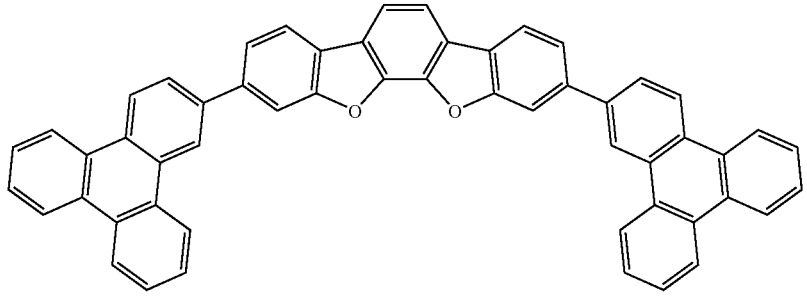
(4-262)
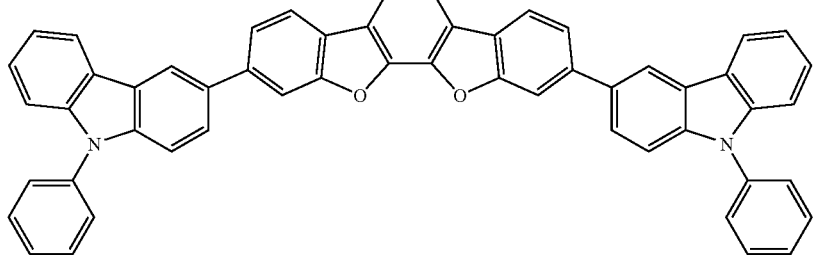
(4-263)
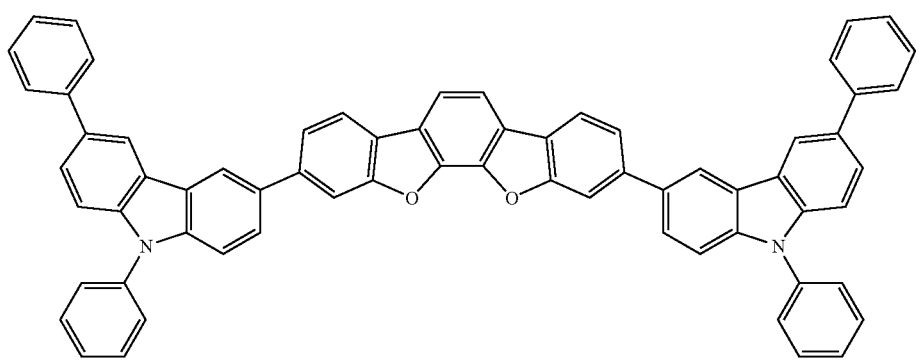

-continued
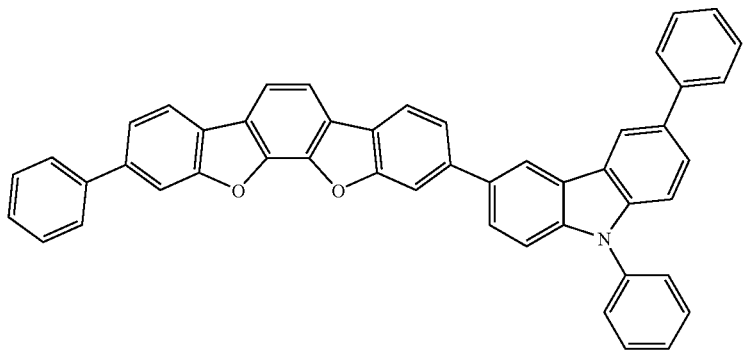
(4-264)
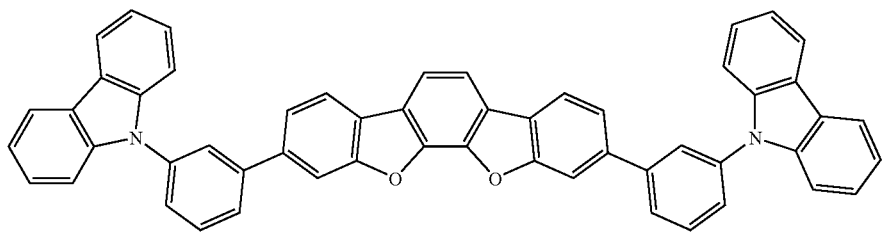
(4-265)
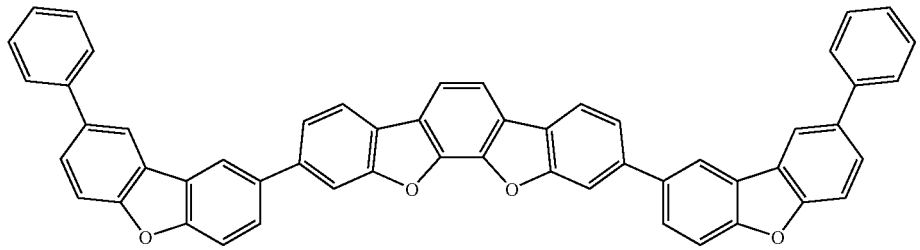
(4-266)
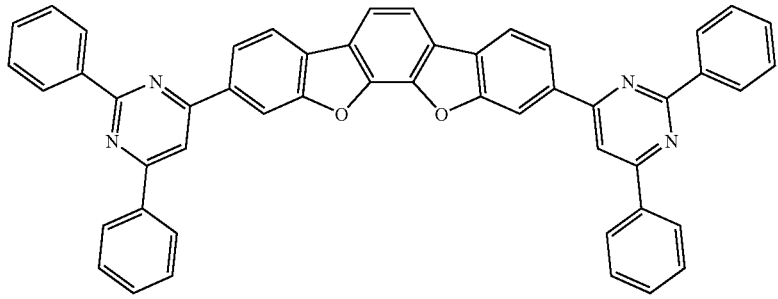
(4-267)
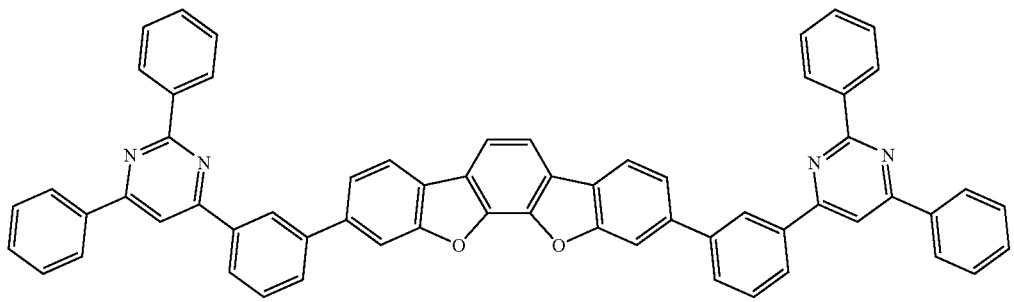
(4-268)

(4-269)
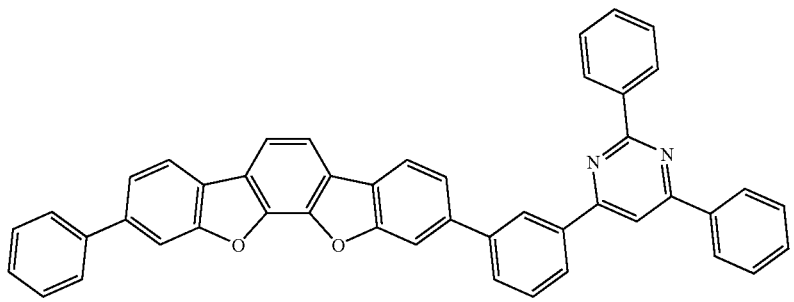
(4-270)
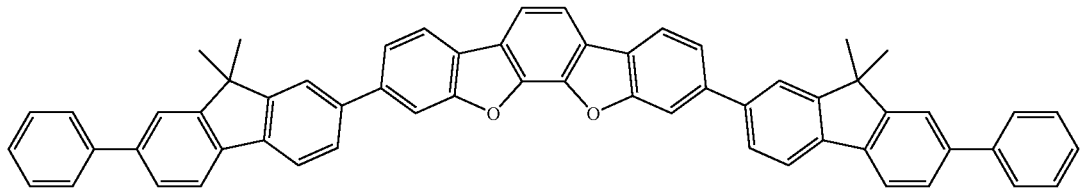
[Chem 87]
(4-271)
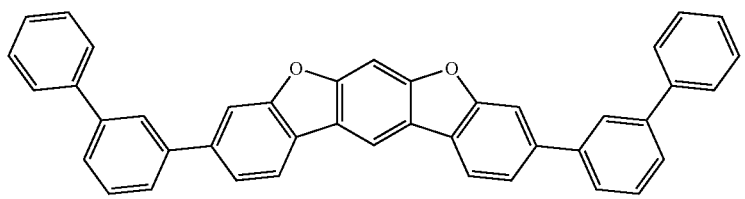
(4-272)
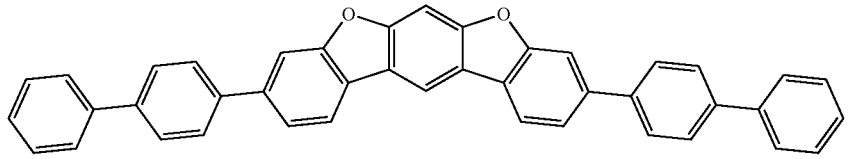
(4-273) (4-274)
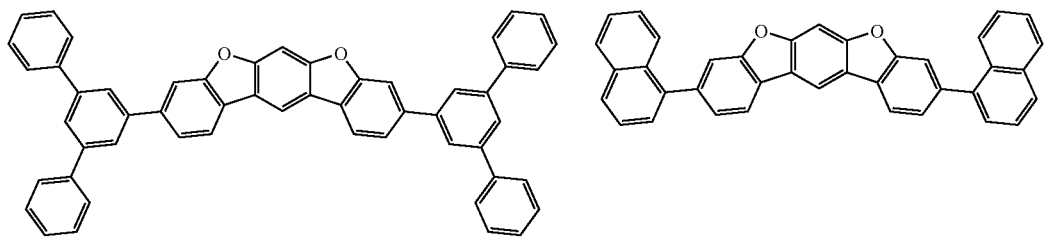
(4-275) (4-276)
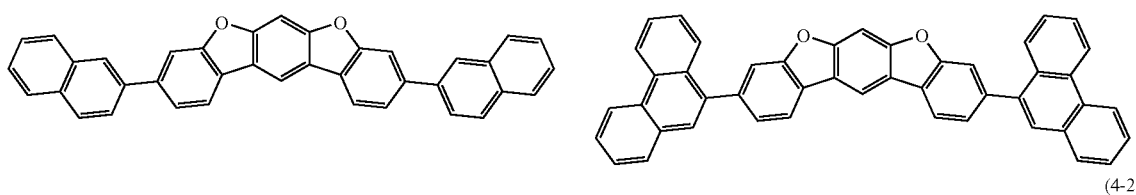
(4-277)
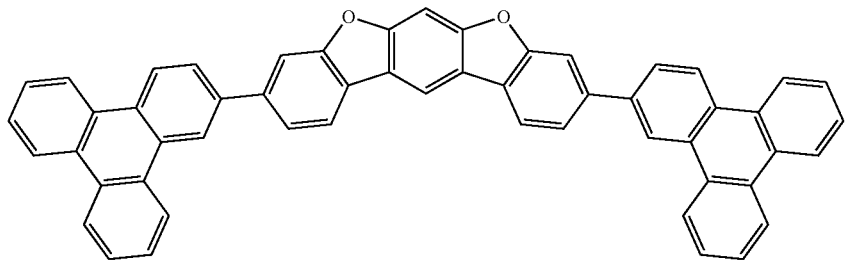

-continued
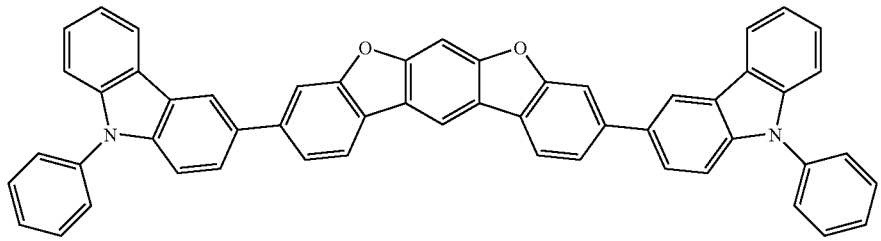
(4-278)
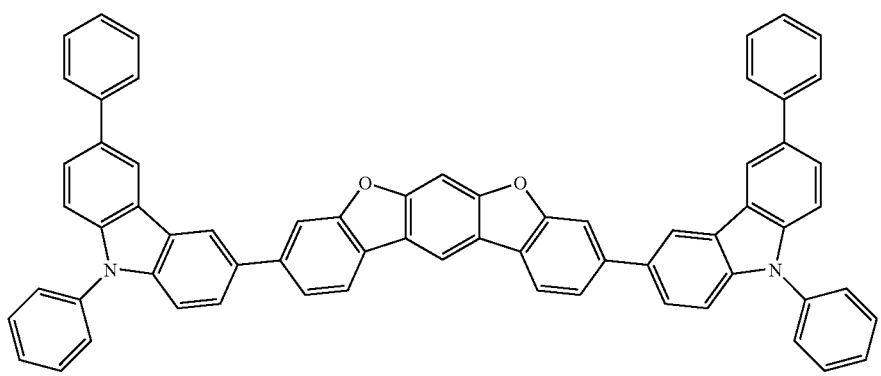
(4-279)
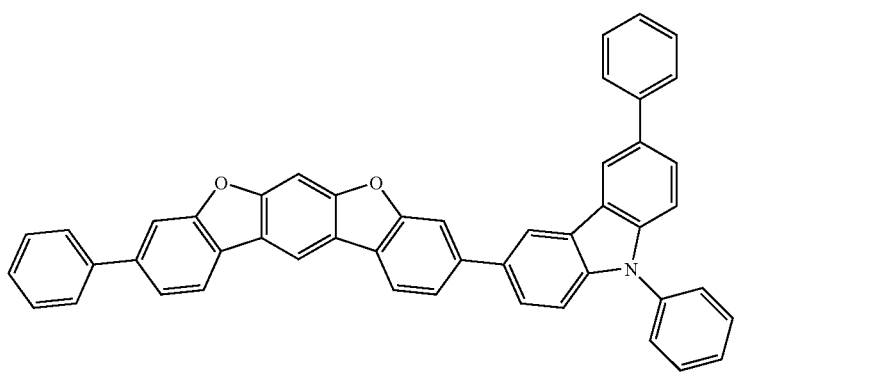
(4-280)
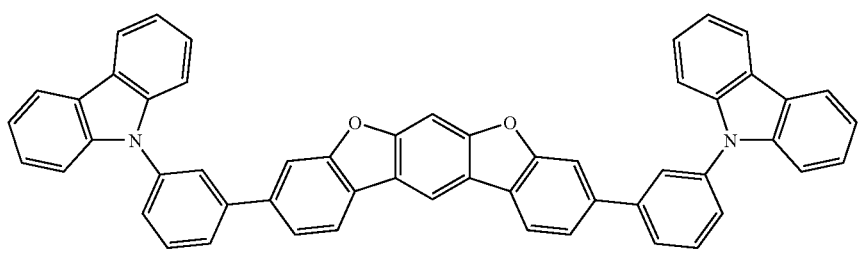
(4-281)
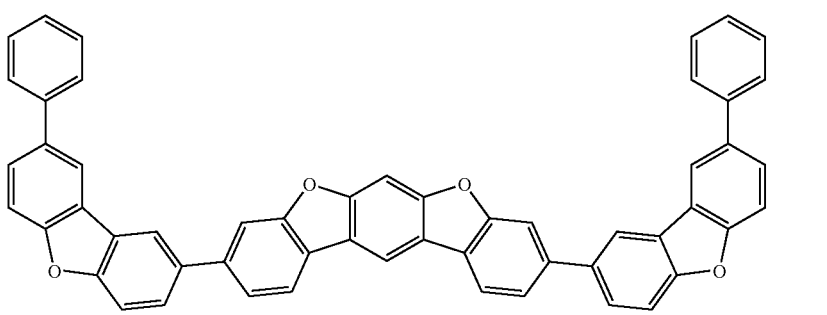
(4-282)

(4-283)
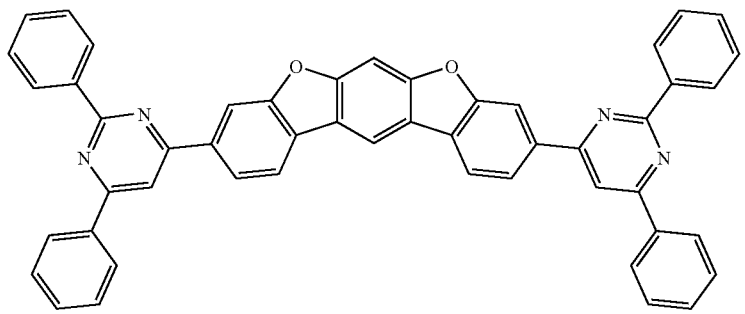
(4-284)
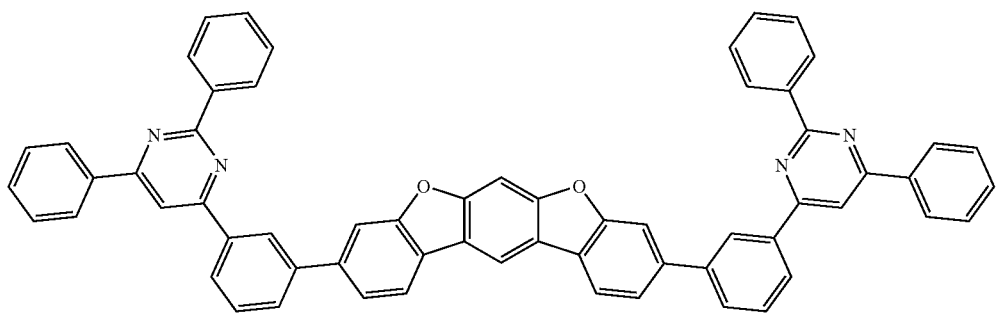
(4-285)
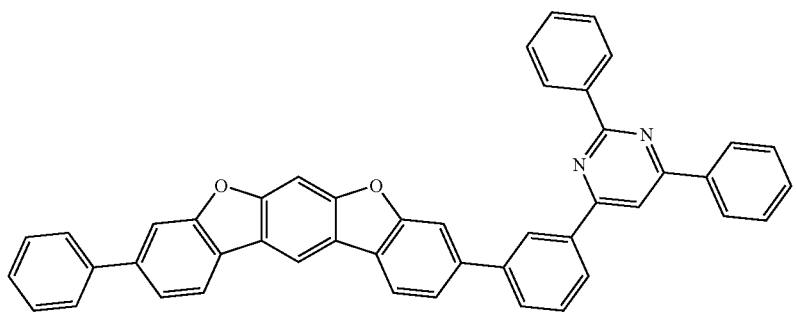
(4-286)
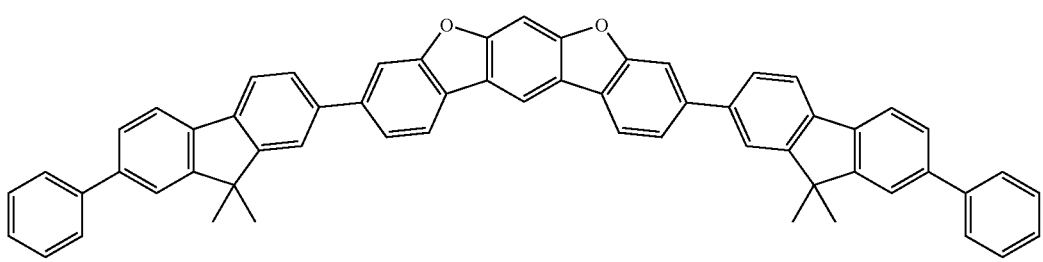
[Chem 88]
(4-287)
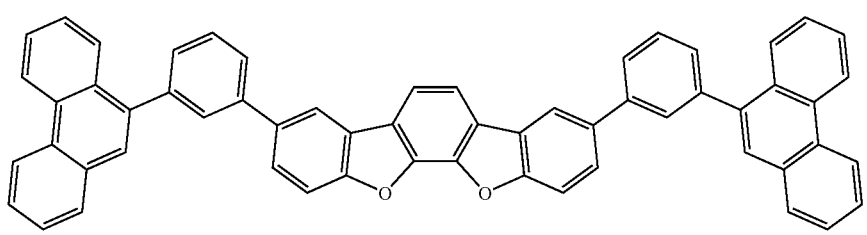

(4-288)
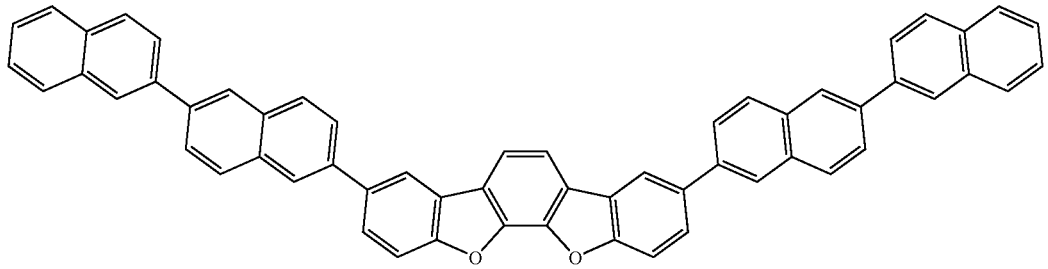
(4-289)
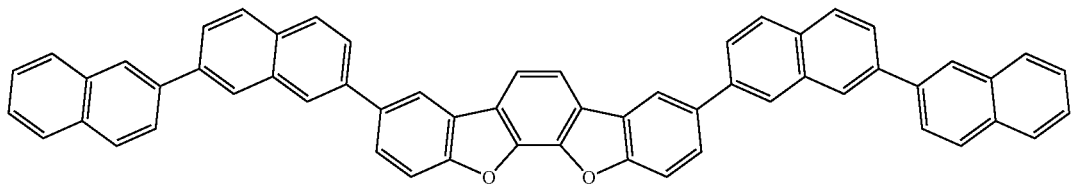
(4-290)
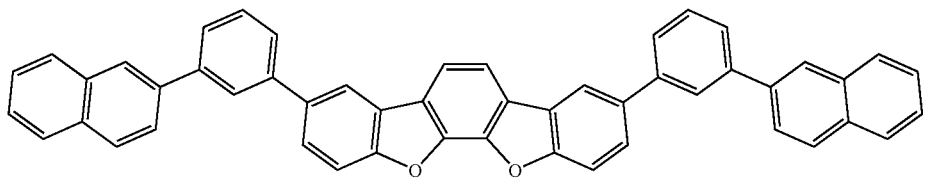
(4-291)
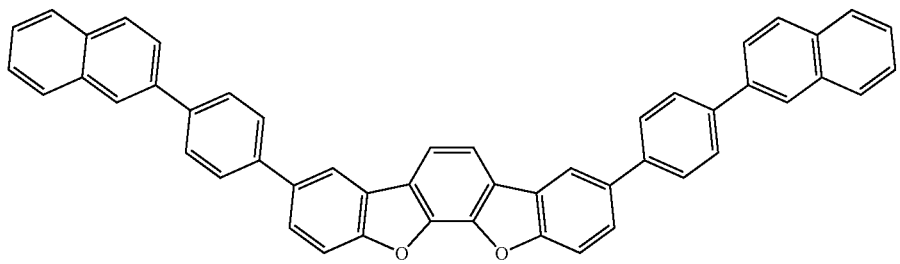
(4-292)
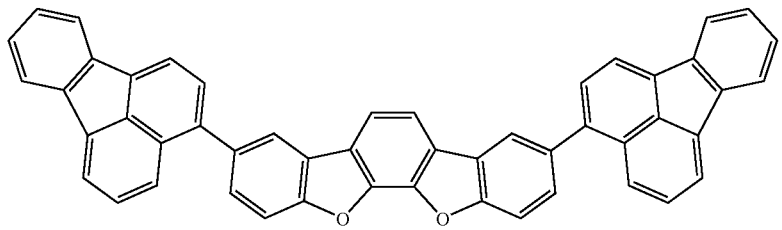
(4-293)
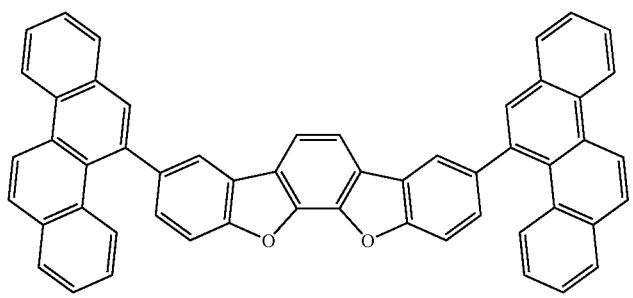

-continued
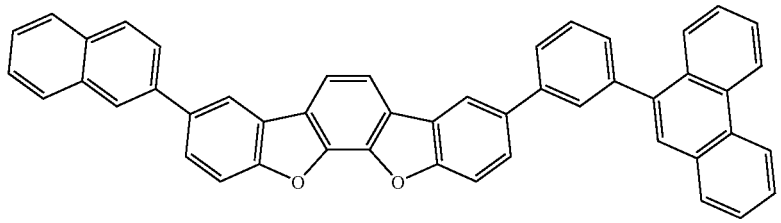
(4-294)
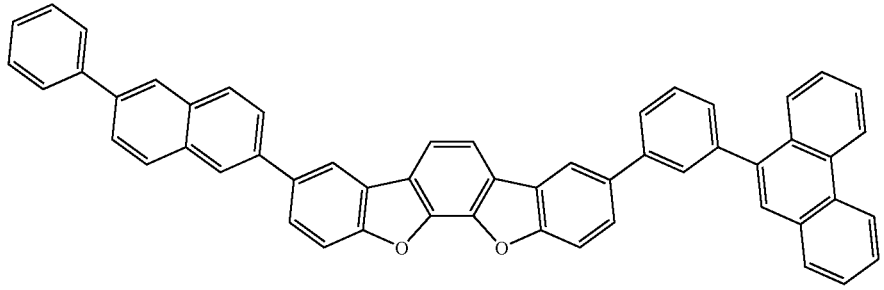
(4-295)
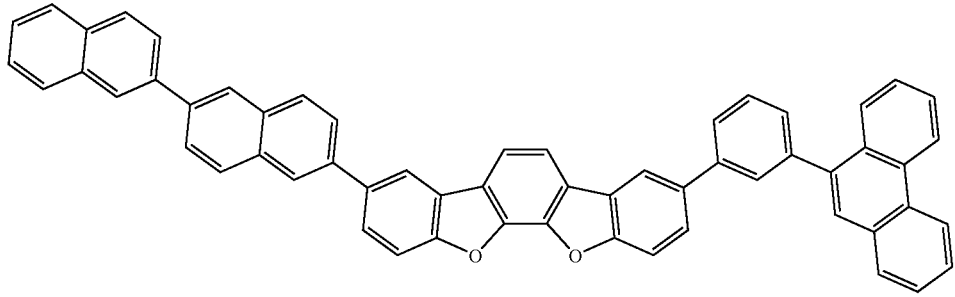
(4-296)
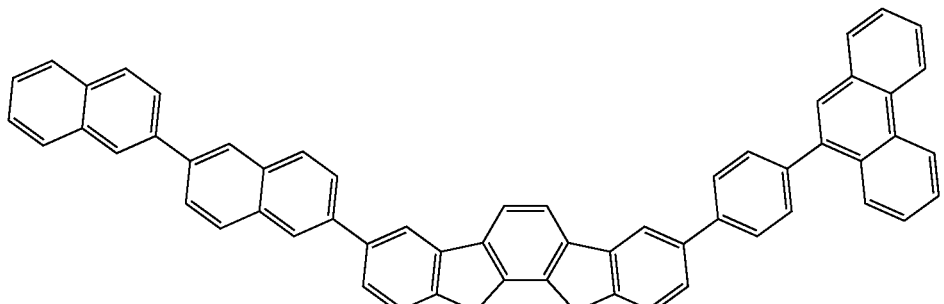
(4-297)
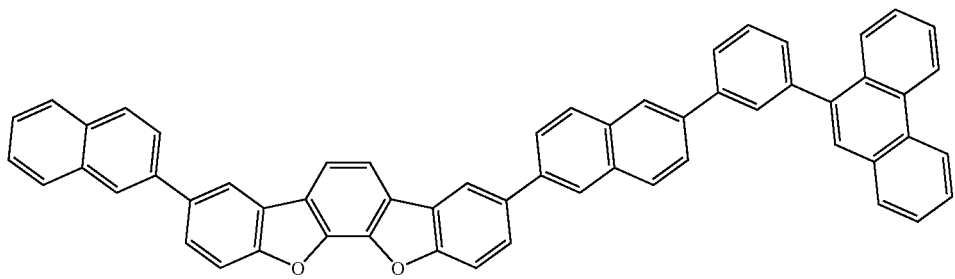
(4-298)

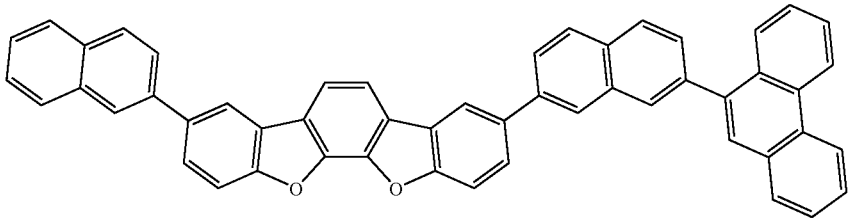
(4-299)
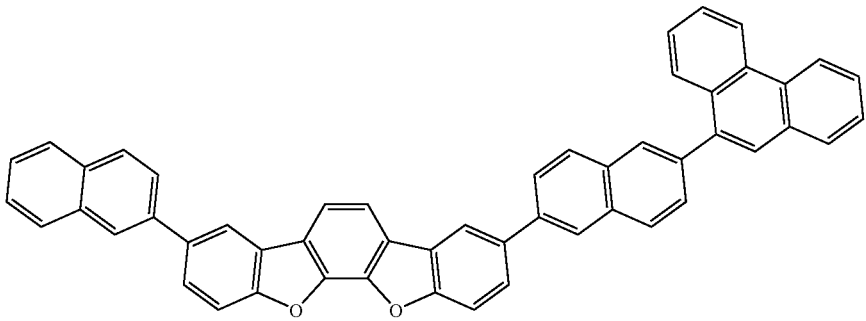
(4-300)
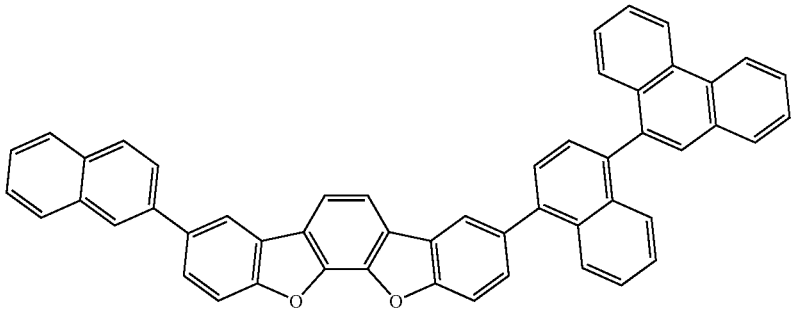
(4-301)
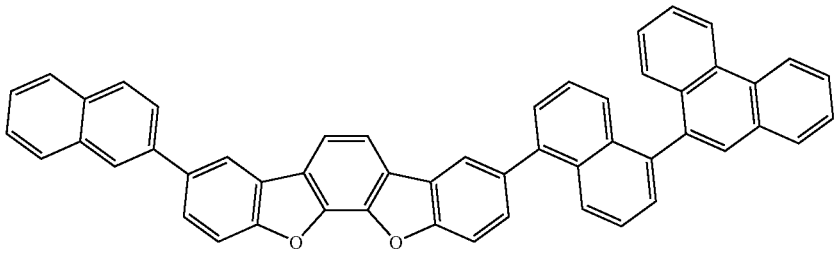
(4-302)
[Chem 89]
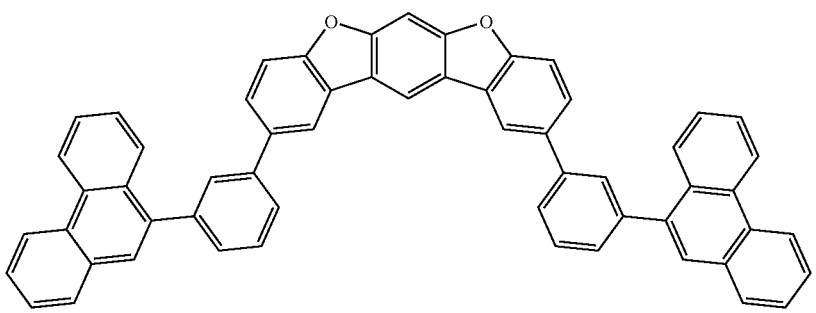
(4-303)

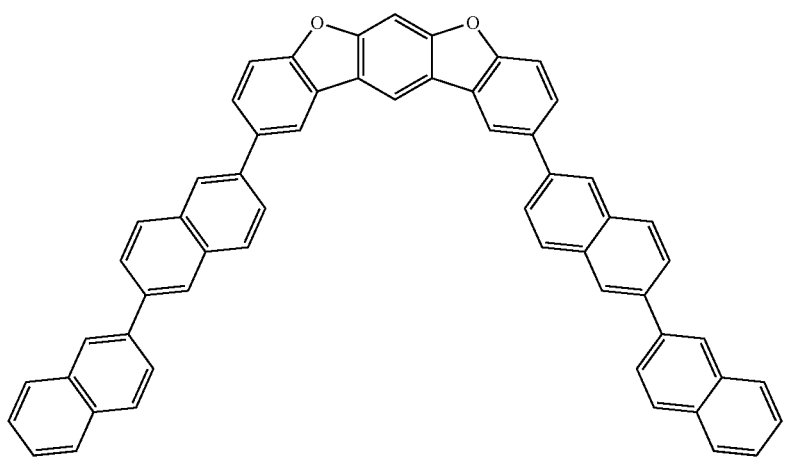

-continued
(4-309)
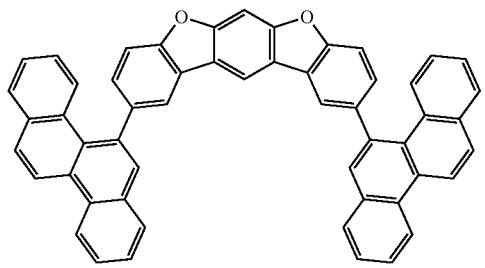
(4-310)
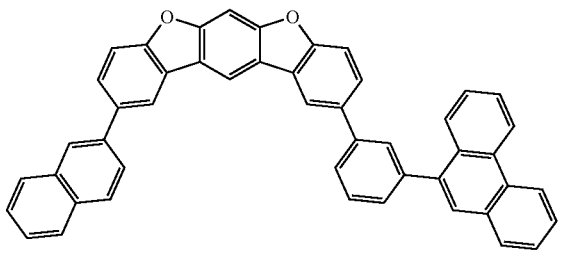
(4-311)
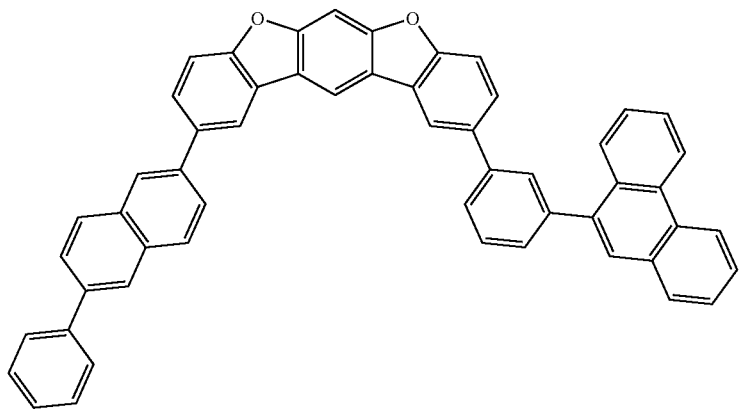
(4-312)
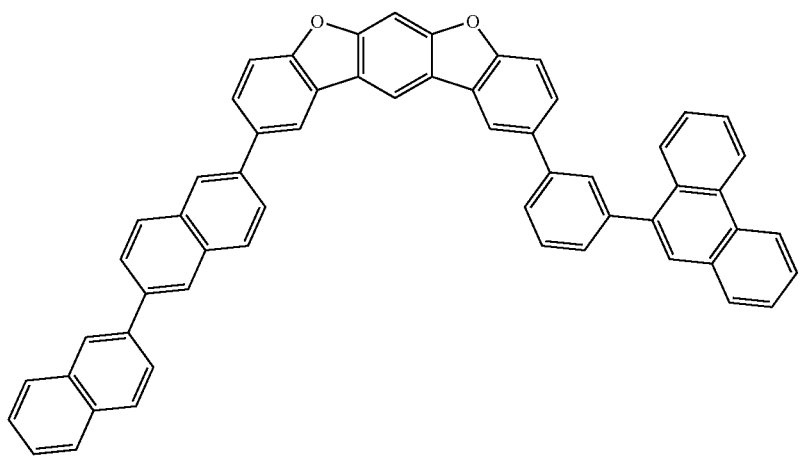
(4-313)
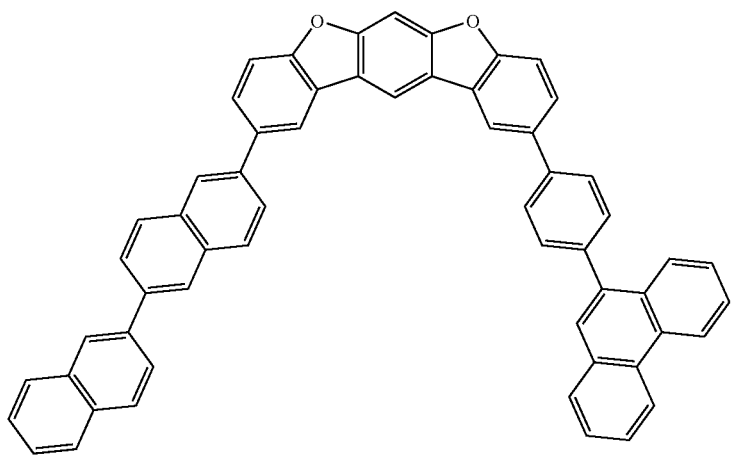

(4-314)
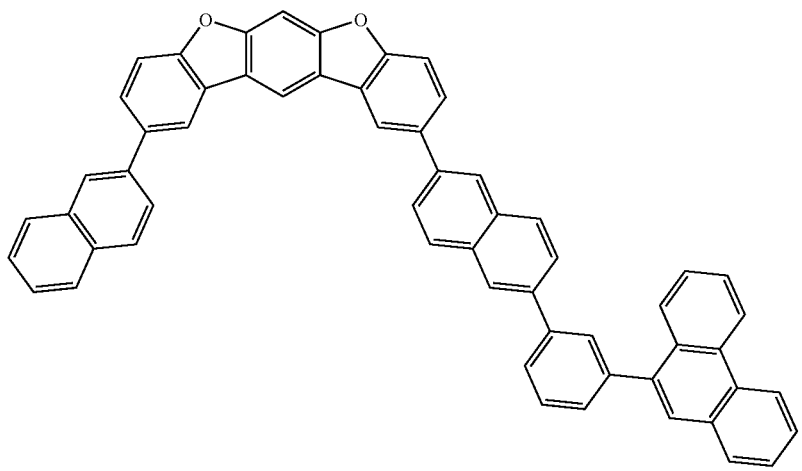
[Chem 90]
(4-315) (4-316)
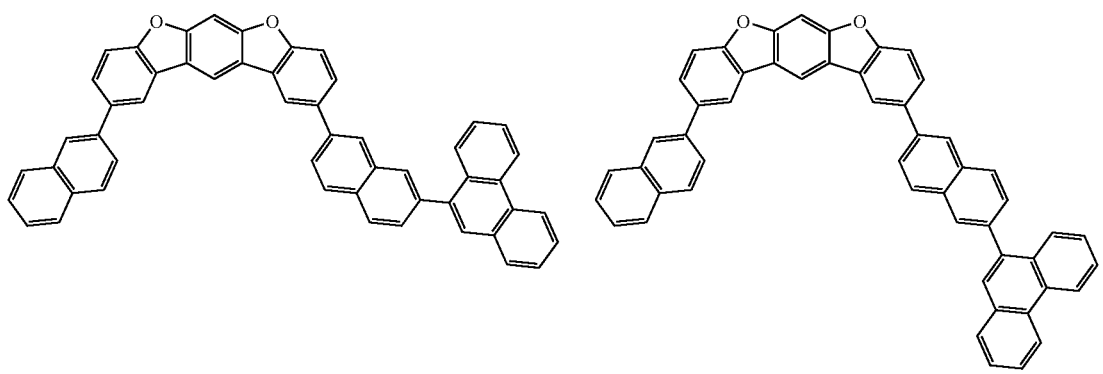
(4-317) (4-318)
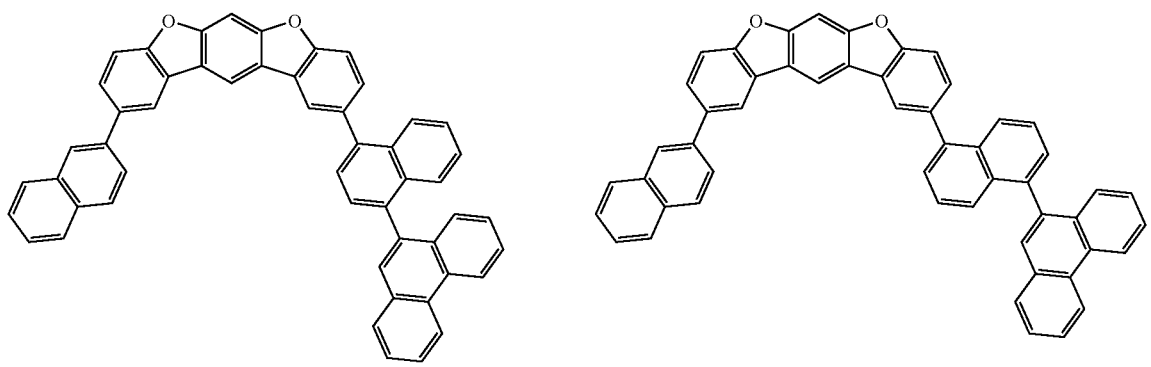
(4-319) (4-320)
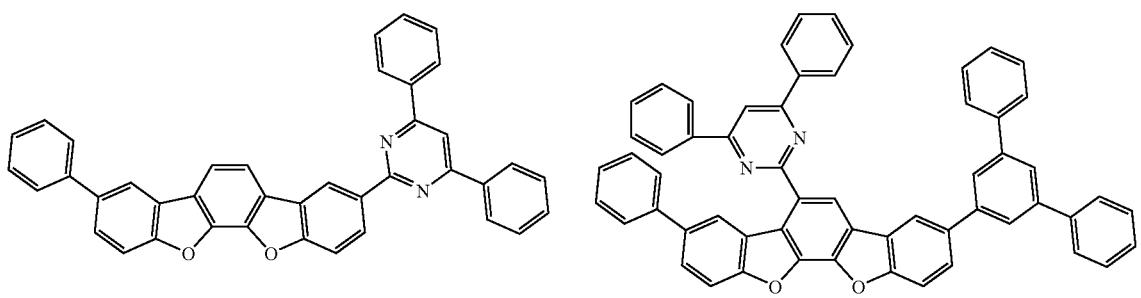

-continued
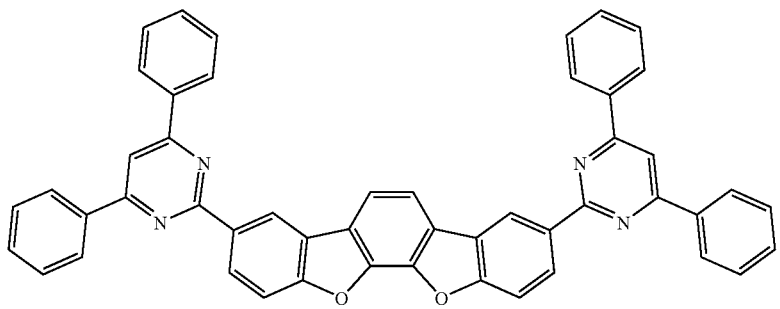
(4-321)
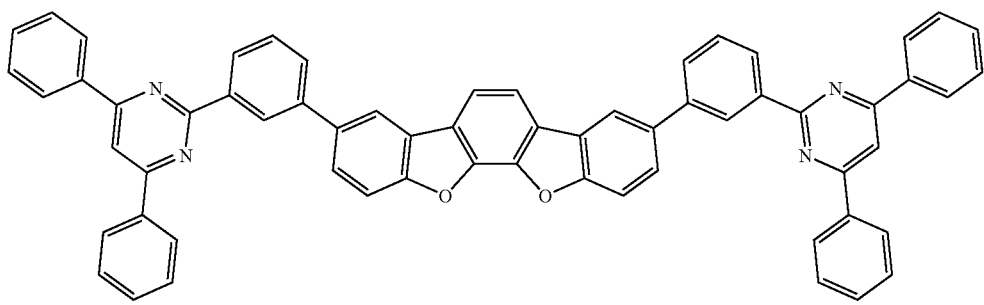
(4-322)
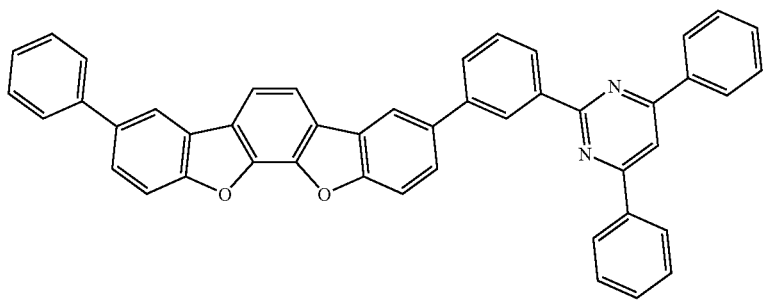
(4-323)
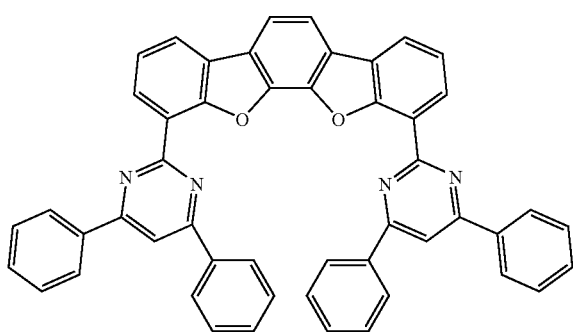
(4-324)

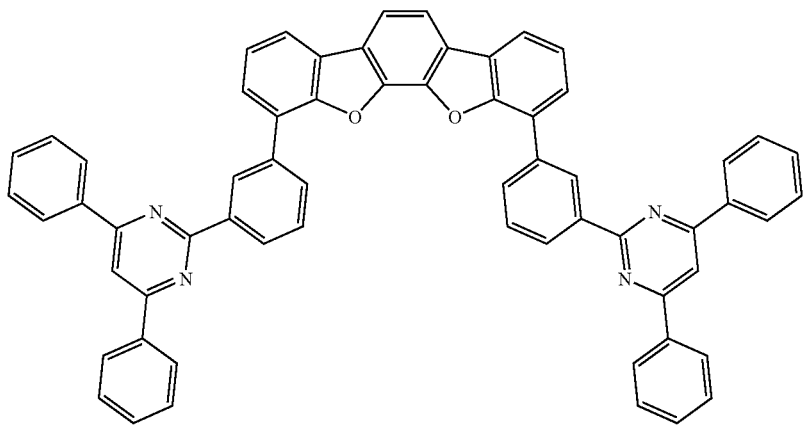
(4-325)
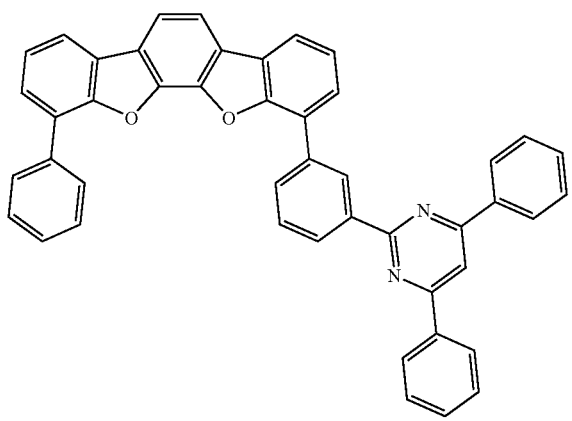
(4-326)
[Chem 91]
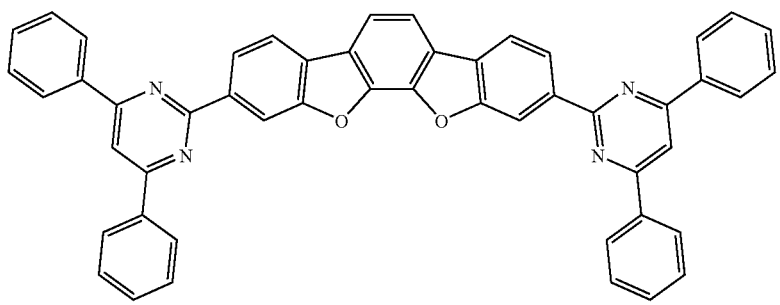
(4-327)
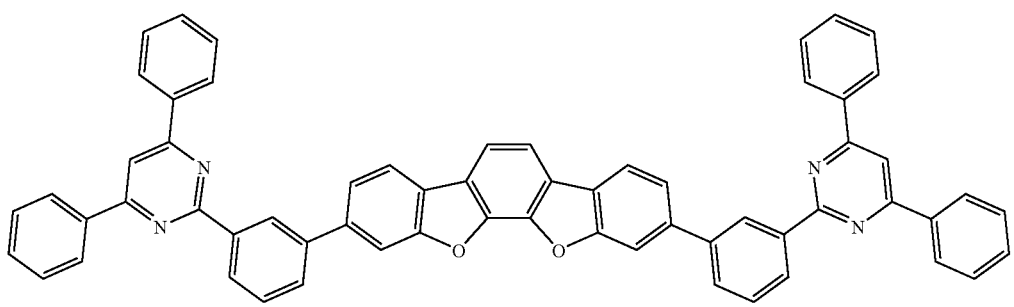
(4-328)

(4-329)
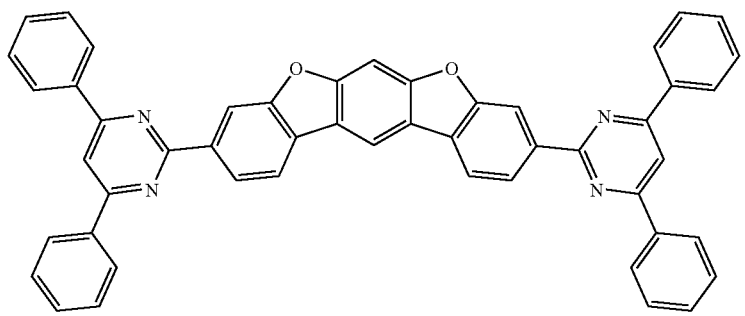
(4-330)
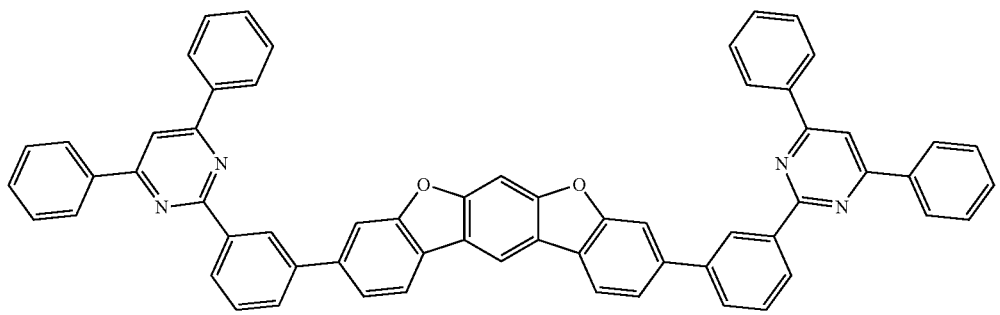
(4-331)
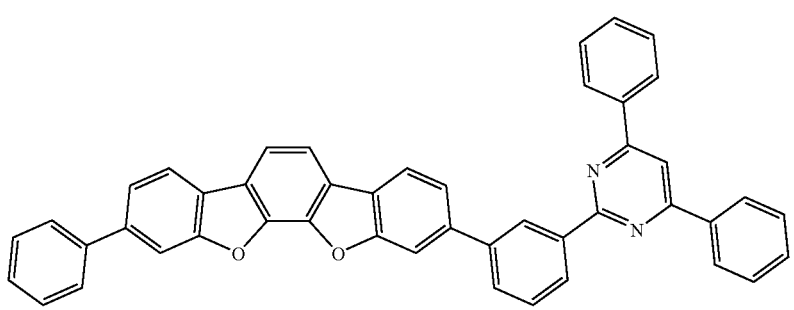
(4-332)
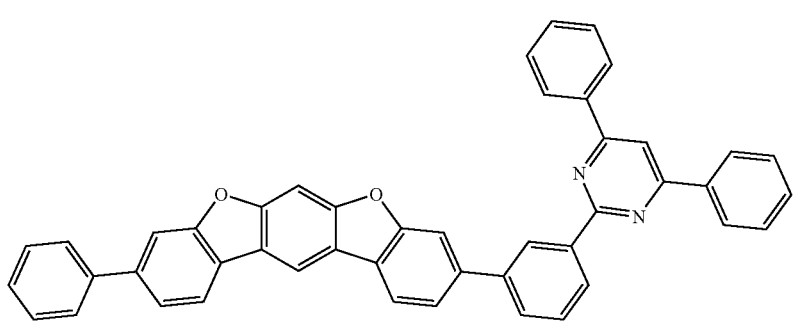
(4-333)
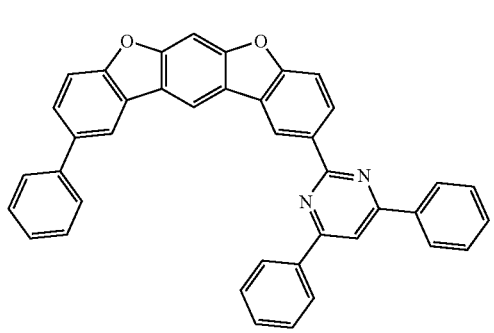
(4-334)
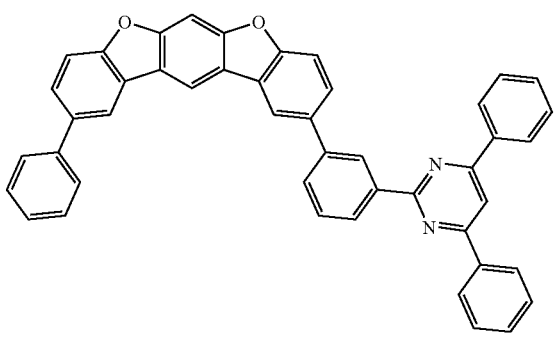

-continued
(4-335)
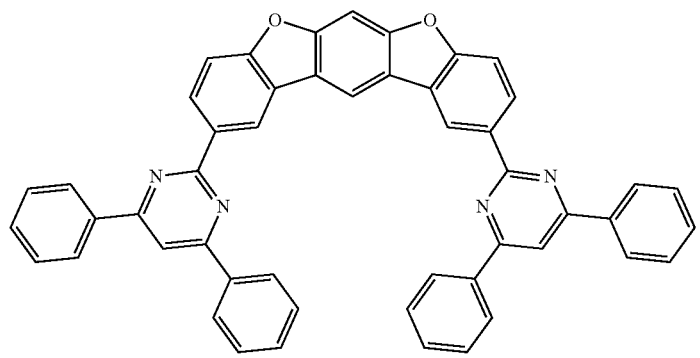
(4-336)
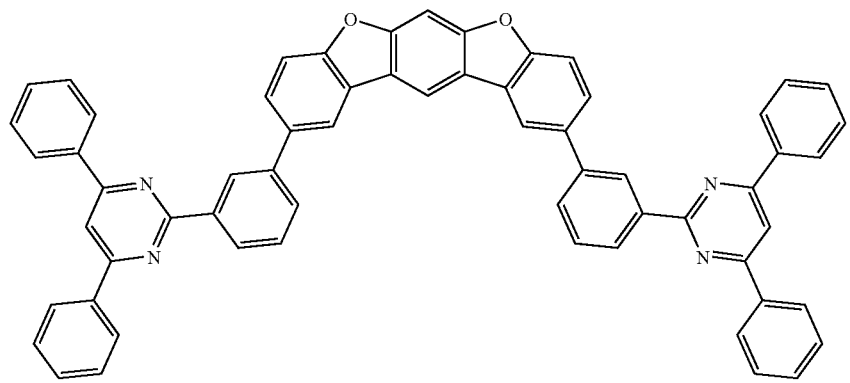
(4-337)
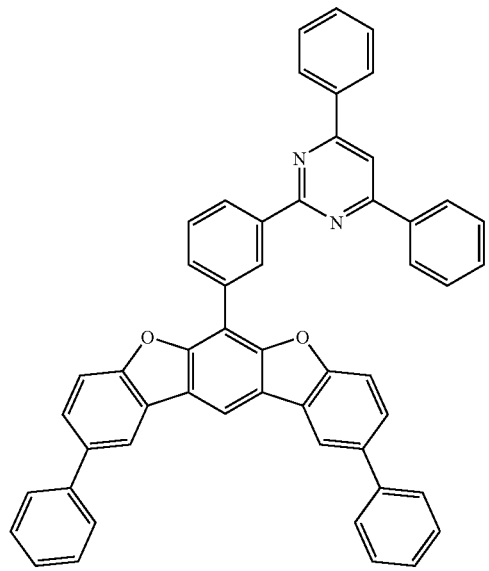
(4-338)
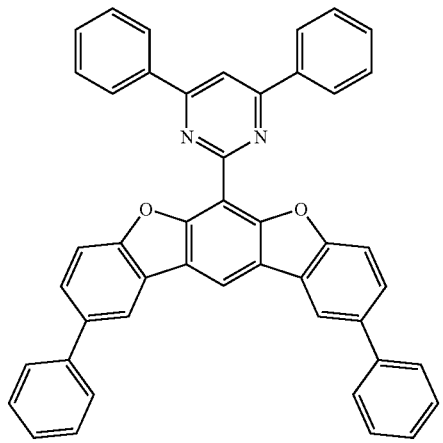
(4-339)
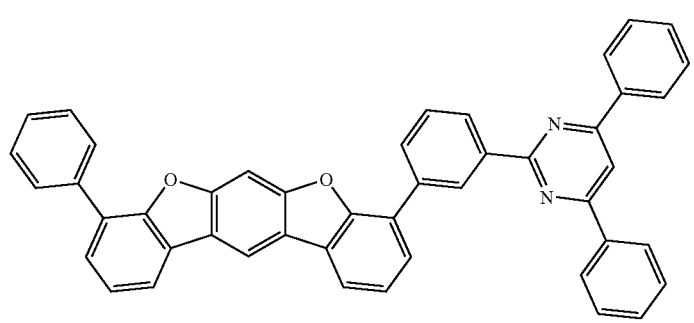

(4-340)
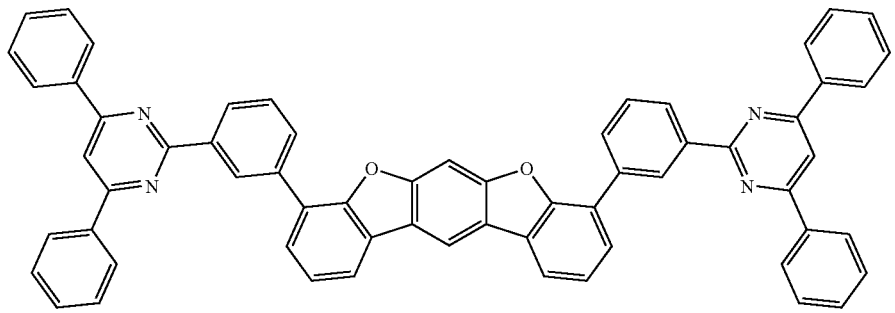
(4-341)
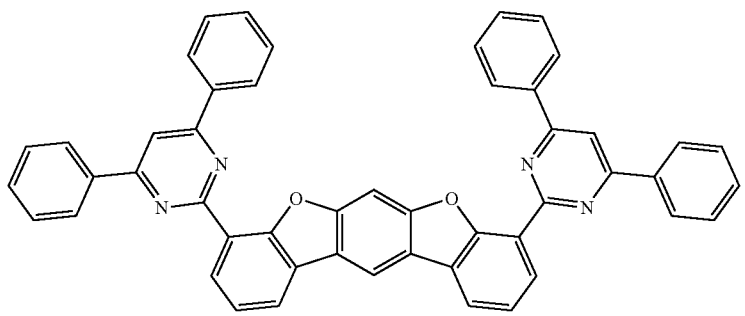
[Chem 92]
(4-342) (4-343)
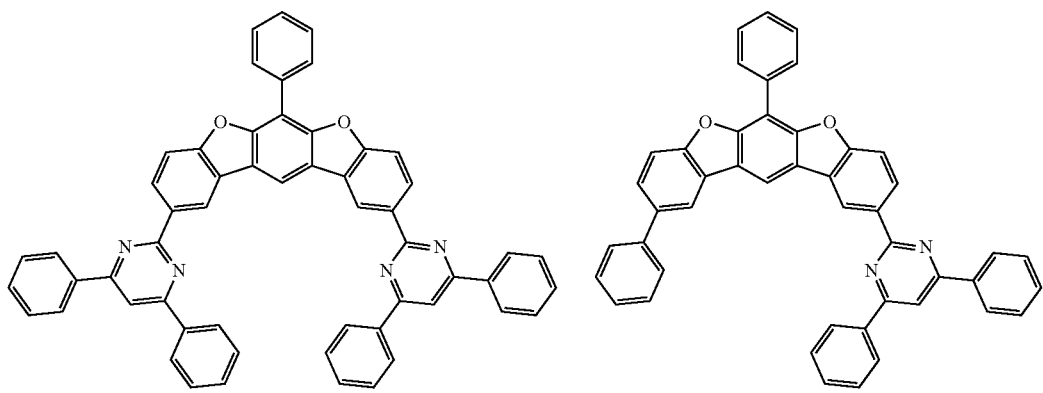
(4-344)
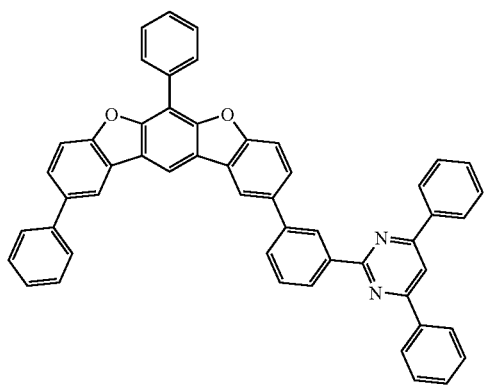
(4-345)
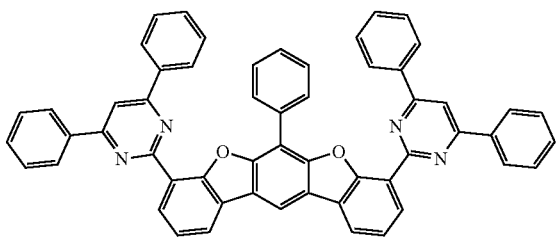

-continued
(4-346)
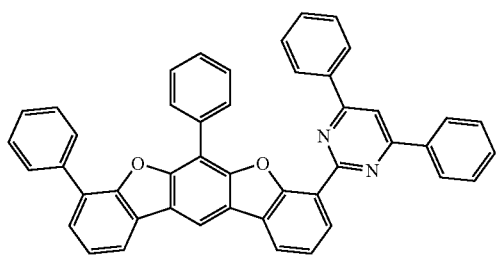
(4-347)
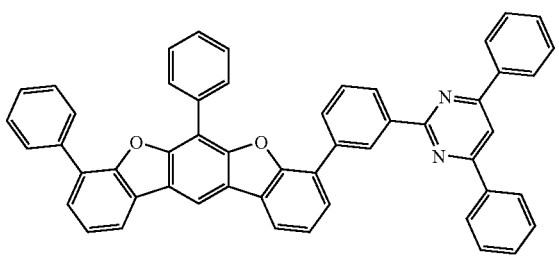
(4-348)
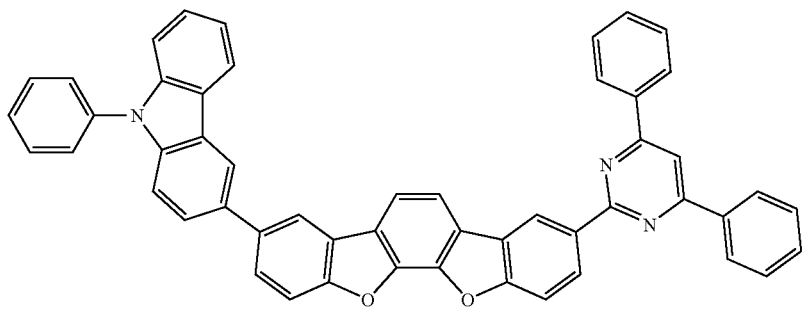
(4-349)
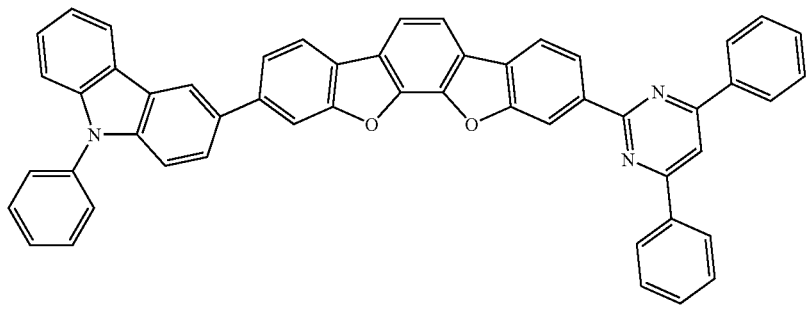
(4-350)
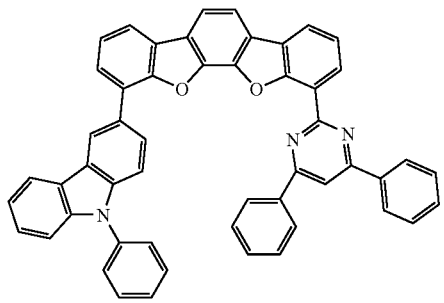
(4-351)
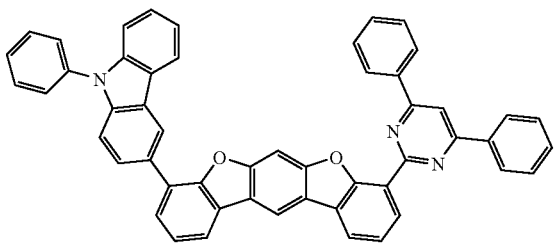
(4-352)
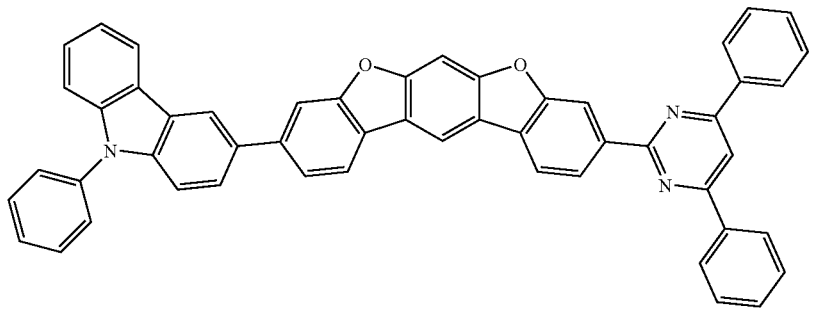

-continued
(4-353)
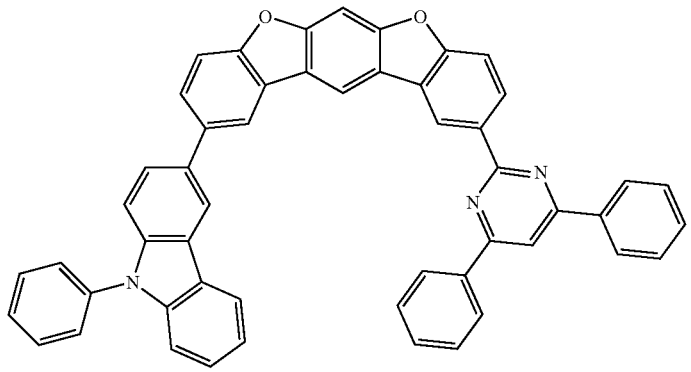
(4-354)
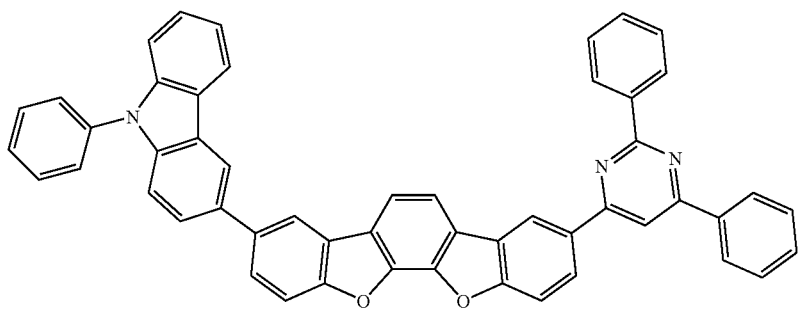
(4-355)
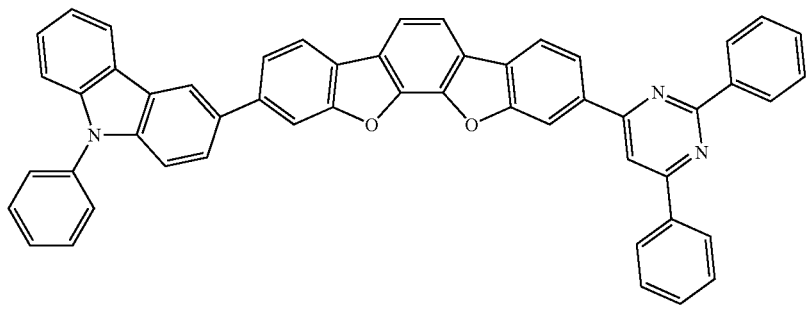
(4-356)
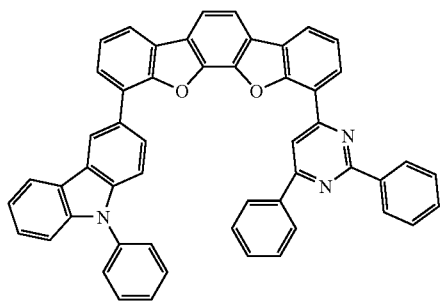
(4-357)
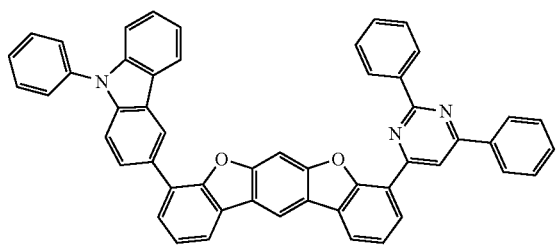
(4-358)
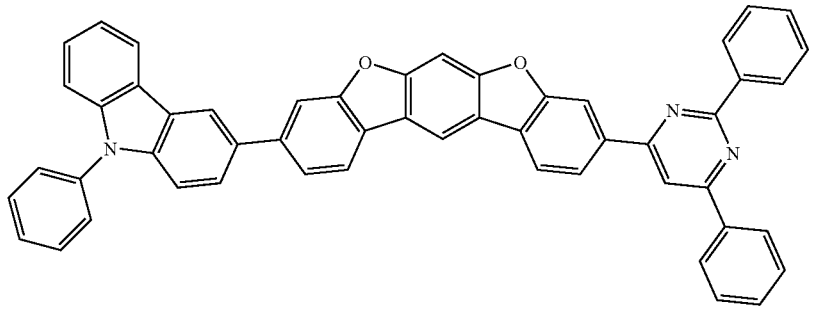

(4-359)

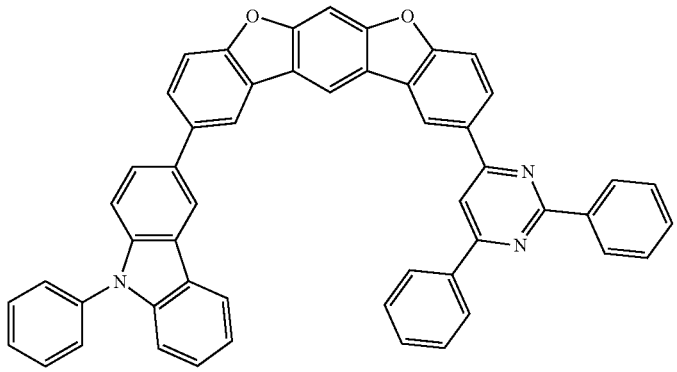

Examples of the structure of the multi-layered organic EL device include layered multi-layer constitutions such as anode/hole transporting layer (hole injecting layer)/light emitting layer/cathode, anode/light emitting layer/electron transporting layer (electron injecting layer)/cathode, anode/hole transporting layer (hole injecting layer)/light emitting layer/electron transporting layer (electron injecting layer)/cathode, and anode/hole transporting layer (hole injecting layer)/light emitting layer/hole barrier layer/electron transporting layer (electron injecting layer)/cathode.

In the organic EL device of the present invention, the light emitting layer preferably includes the polycyclic compound of the present invention as a host material. In addition, the light emitting layer preferably formed of a host material and a phosphorescent material, and the host material is preferably the polycyclic compound.

In addition, the polycyclic compound of the present invention may be a host material used together with the phosphorescent material or an electron transporting material used together with the phosphorescent material. The triplet energy gap is preferably 2.2 to 3.2 eV and more preferably 2.5 to 3.2 eV.

As the phosphorescent material, a compound including iridium (Ir), osmium (Os), ruthenium (Ru), or platinum (Pt) is preferred from the viewpoints that the phosphorescent quantum efficiency is high and the external quantum efficiency of the device can be additionally improved. Metal complexes such as an iridium complex, an osmium complex, a ruthenium complex, and a platinum complex are more preferred. Of those, the iridium complex and the platinum complex are more preferred and an orthometalated iridium complex is most preferred. Specific examples of the metal complexes such as the iridium complex, the osmium complex, the ruthenium complex, and the platinum complex are described below.

[Chem 93]

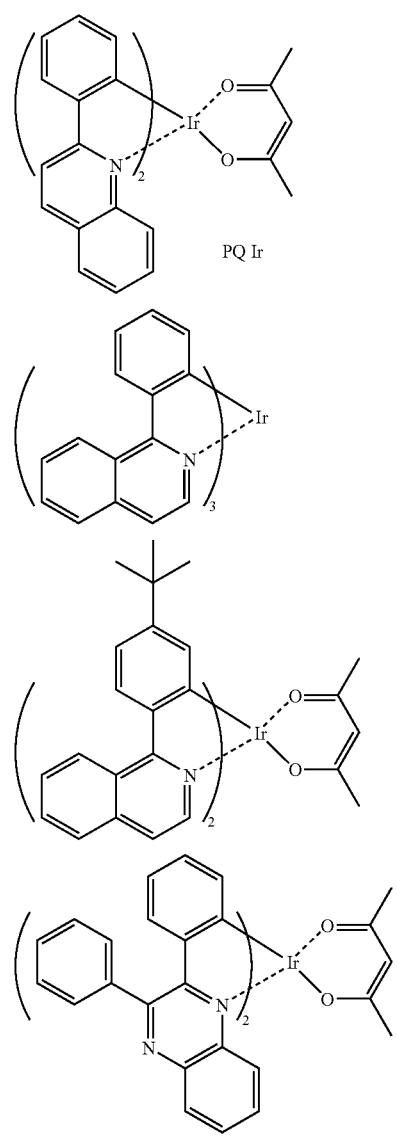

PQ Ir

333
-continued
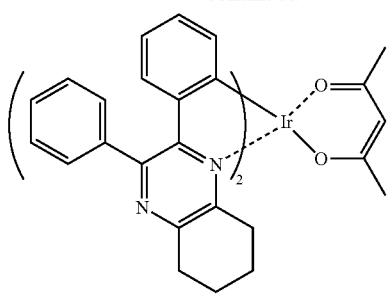
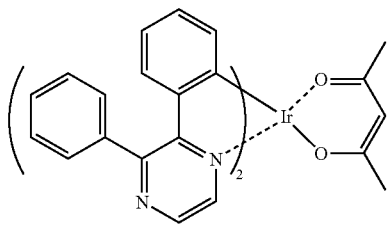
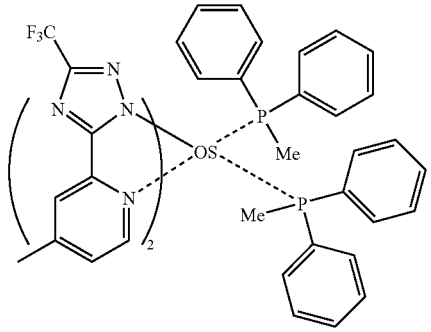
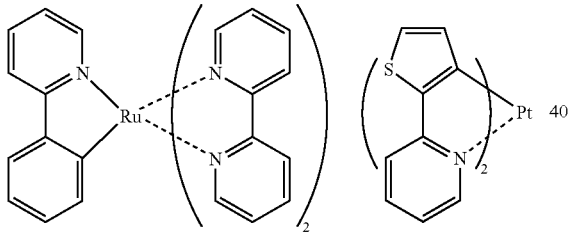
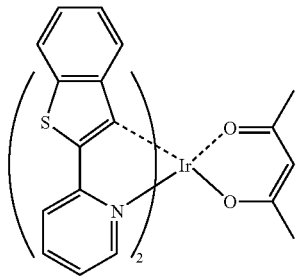
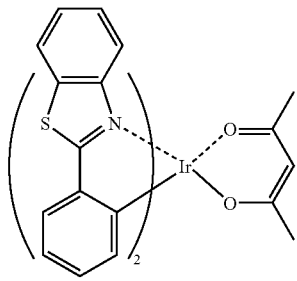
334
-continued
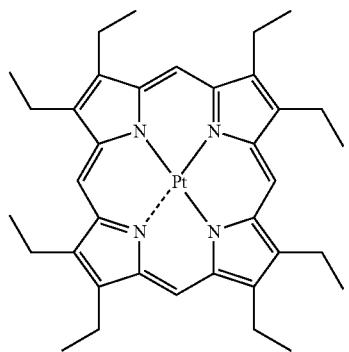
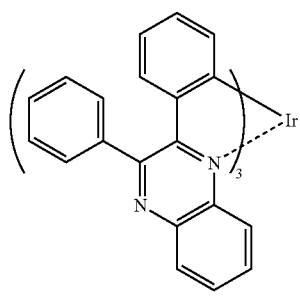
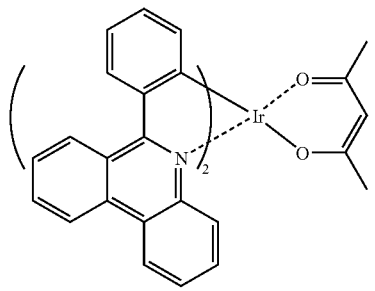
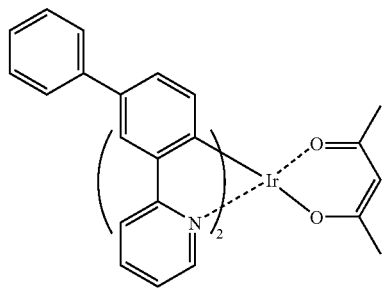
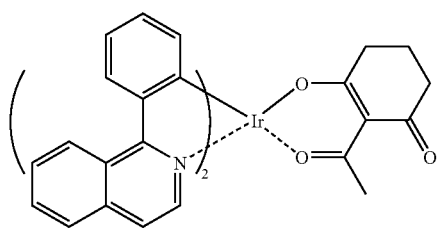

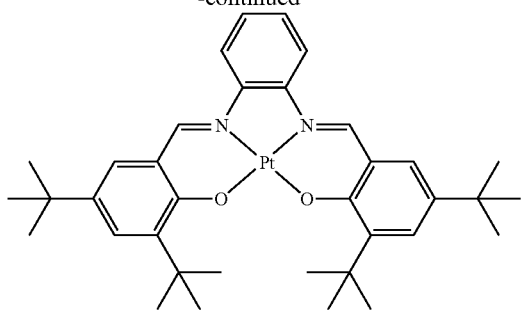
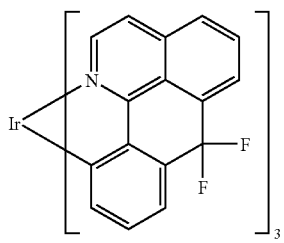
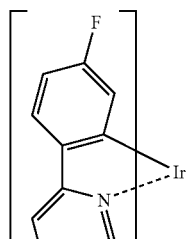
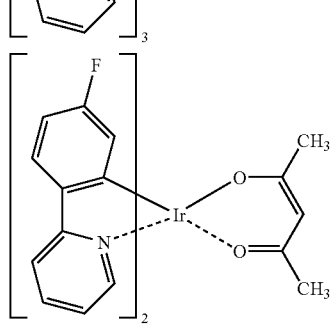
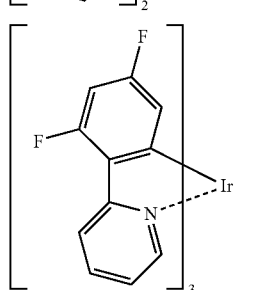
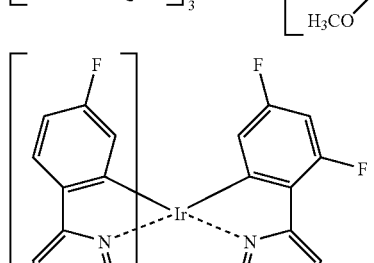
[Chem 94]
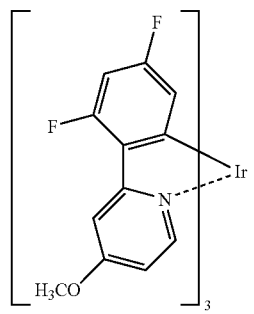
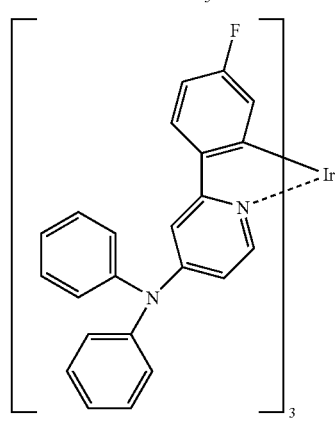
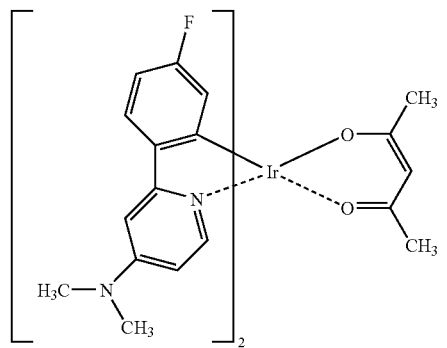
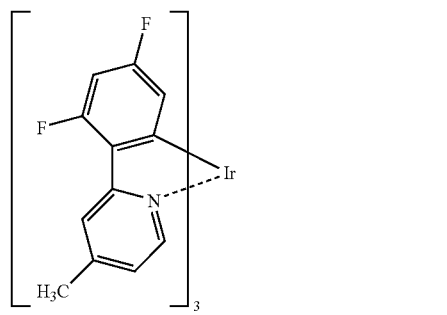
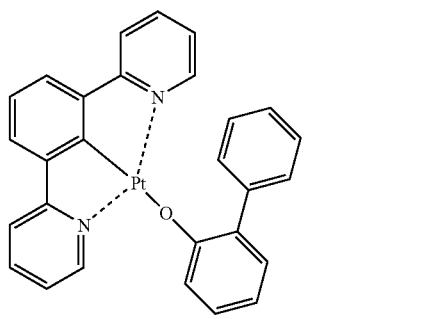

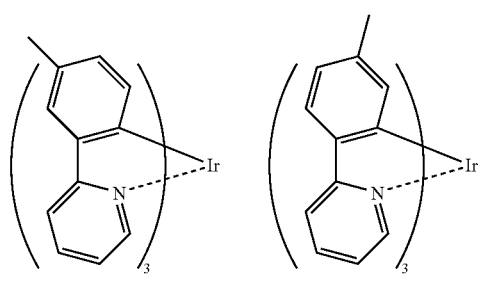
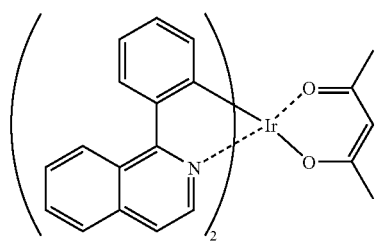
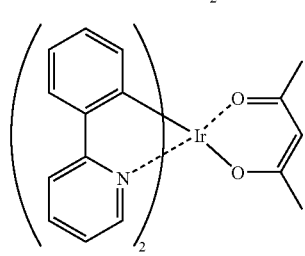
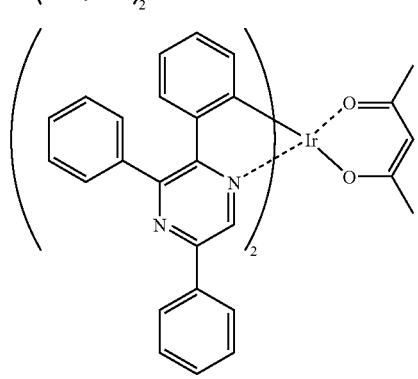
[Chem 95]
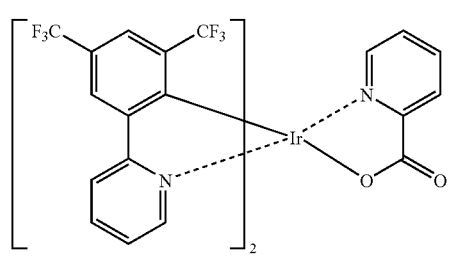
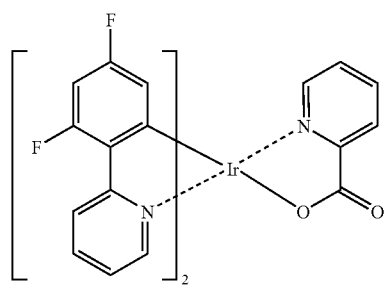
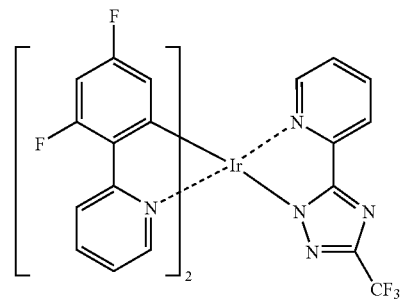
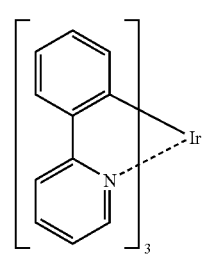
Ir(ppy)₃
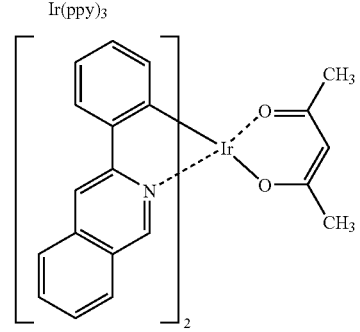
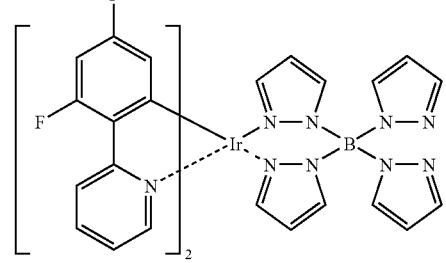
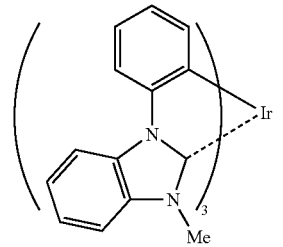
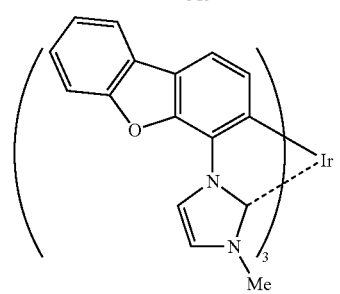

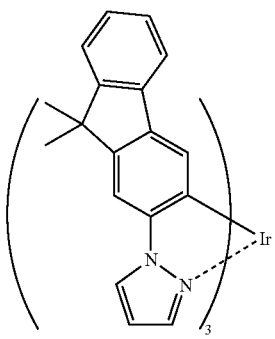
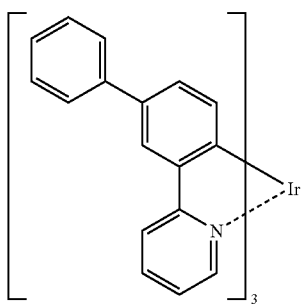
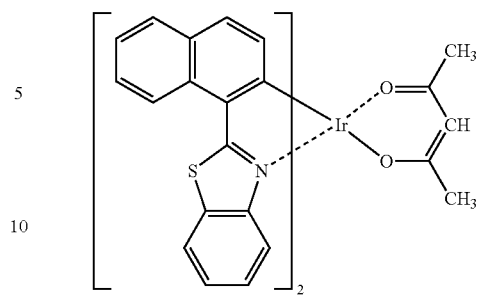
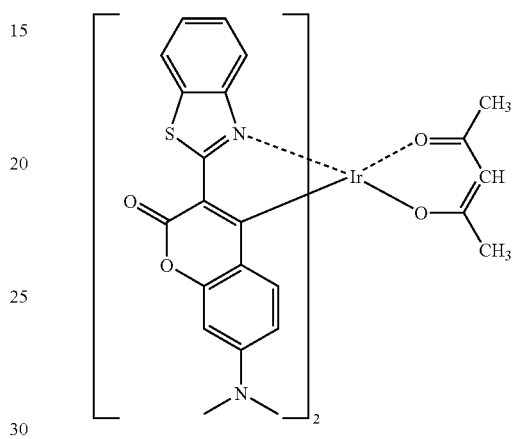
[Chem 96]
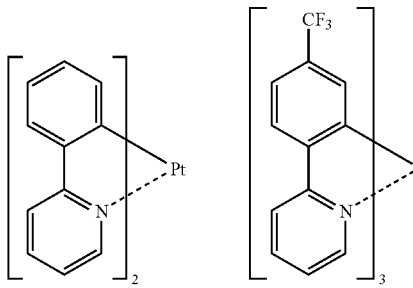
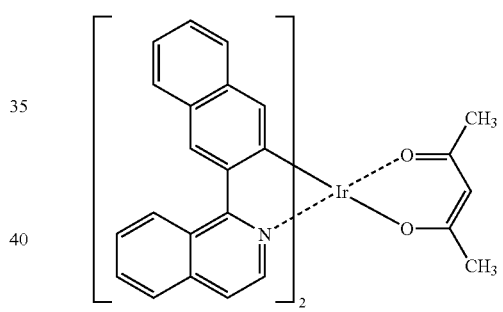
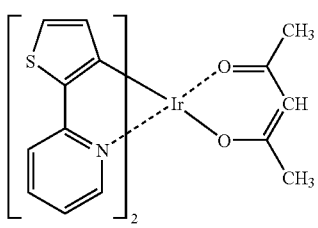
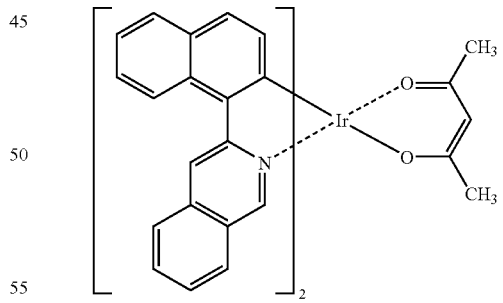
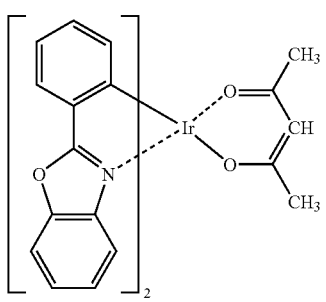
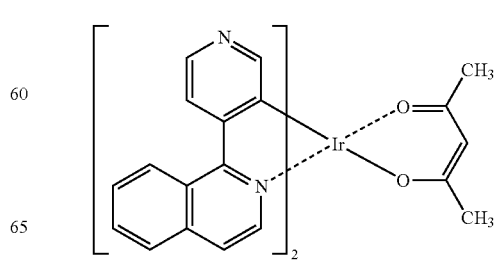

-continued

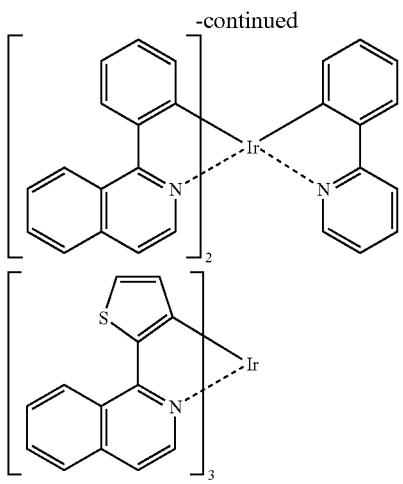

In addition, the organic EL device of the present invention is preferably such that the light emitting layer contains a host material and a phosphorescent material, and contains a metal complex having a local maximum luminous wavelength of 500 nm or less.

The organic EL device of the present invention preferably has a reductive dopant in an interfacial region between the cathode and an organic thin layer (for example, an electron injecting layer or a light emitting layer). Examples of the reductive dopant include at least one kind selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Preferred examples of the alkali metal include an alkali metal having a work function of 2.9 eV or less, such as Na having a work function of 2.36 eV, K having a work function of 2.28 eV, Rb having a work function of 2.16 eV, and Cs having a work function of 1.95 eV. Of those, K, Rb, and Cs are more preferable, Rb or Cs is still more preferable, and Cs is most preferable.

Preferred examples of the alkali earth metal include an alkali earth metal having a work function of 2.9 eV or less, such as Ca having a work function of 2.9 eV, Sr having a work function of 2.0 to 2.5 eV, and Ba having a work function of 2.52 eV.

Preferred examples of the rare earth metal include a rare earth metal having a work function of 2.9 eV or less, such as Sc, Y, Ce, Tb, and Yb.

Of those metals, a preferable metal has a particularly high reductive ability, so improvement of light emission intensity and long life of organic EL device can be attained by adding a relatively small amount of the metal to an electron injecting region.

Examples of the alkali metal compound include an alkali oxide such as $Li_2O$, $Cs_2O$, or $K_2O$, and an alkali halide such as LiF, NaF, CsF, or KF. Of those, LiF, $Li_2O$, or NaF is preferable.

Examples of the alkali earth metal compound include BaO, SrO, CaO, and mixtures thereof such as $Ba_mSr_{1-m}O$ (0<m<1) and $Ba_mCa_{1-m}O$ (0<m<1). Of those, BaO, SrO, and CaO are preferable.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferable.

The alkali metal complex, alkali earth metal complex, and rare earth metal complex are not particularly limited as long as they each include as a metal ion at least one of alkali metal ions, alkali earth metal ions, and rare earth metal ions. Meanwhile, preferable examples of a ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the reductive dopant, it is preferable that the reductive dopant be formed in a shape of a layer or an island in the interfacial region. A preferable example of the forming method includes a method in which an organic substance which is a light emitting material or an electron injecting material for forming the interfacial region is deposited at the same time as the reductive dopant is deposited by a resistant heating deposition method, thereby dispersing the reductive dopant in the organic substance. The disperse concentration by molar ratio of the organic compound to the reductive dopant is 100:1 to 1:100, and is preferably 5:1 to 1:5.

In a case where the reductive dopant is formed into the shape of a layer, the light emitting material or electron injecting material which serves as an organic layer in the interface is formed into the shape of a layer. After that, the reductive dopant is solely deposited by the resistant heating deposition method to form a layer preferably having a thickness of 0.1 to 15 nm.

In a case where the reductive dopant is formed into the shape of an island, the light emitting material or electron injecting material which serves as an organic layer in the interface is formed into the shape of an island. After that, the reductive dopant is solely deposited by the resistant heating deposition method to form an island preferably having a thickness of 0.05 to 1 nm.

When the organic EL device of the present invention has an electron injecting layer between the light emitting layer and the cathode, an electron transporting material to be used in the electron injecting layer is preferably an aromatic heterocyclic compound containing one or more heteroatoms in any one of its molecules, or particularly preferably a nitrogen-containing ring derivative.

The nitrogen-containing ring derivative is preferably, for example, a nitrogen-containing ring metal chelate complex represented by the following general formula (A).

[Chem 97]

(A)

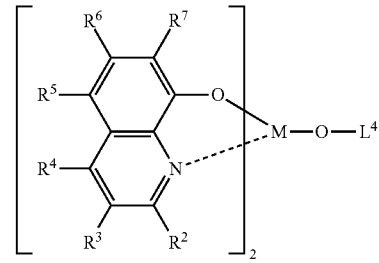

$R^2$ to $R^7$ each independently represent a hydrogen atom, a halogen atom, an amino group, a hydrocarbon group each having 1 to 40 carbon atoms, an alkoxy group, an aryloxy group, an alkoxycarbonyl group, or a heterocyclic group, each of which may be substituted.

Examples of the halogen atom represented by $R^2$ to $R^7$ include a fluorine atom, a chlorine atom, a bromine atom, and an iodine atom.

Examples of the amino group that may be substituted and represented by $R^2$ to $R^7$ include an alkylamino group, an arylamino group, and an aralkylamino group. Examples of the alkyl group in the alkylamino group include alkyl groups each having 1 to 40 carbon atoms such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, and a 1,2,3-trinitropropyl group. Preferred are alkyl groups each having 1 to 20 carbon atoms and more preferred are alkyl groups each having 1 to 10 carbon atoms.

Examples of the aryl group in the arylamino group include aryl groups each having 6 to 40 carbon atoms forming the aromatic ring such as a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group. Preferred are aryl groups each having 6 to 20 carbon atoms forming the aromatic ring and more preferred are aryl groups each having 6 to 10 carbon atoms forming the aromatic ring.

Examples of the aralkyl group in the aralkylamino group include aralkyl groups each having 7 to 40 carbon atoms such as a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Preferred are aralkyl groups each having 7 to 20 carbon atoms and more preferred are aralkyl groups each having 7 to 10 carbon atoms.

Examples of the hydrocarbon groups each having 1 to 40 carbon atoms and represented by $R^2$ to $R^7$ include substituted or unsubstituted alkyl groups, alkenyl groups, cycloalkyl groups, aryl groups, and aralkyl groups.

As the alkyl groups, the same examples of the alkyl groups in the above-mentioned alkylamino group are given, and alkyl groups each having 1 to 20 carbon atoms are preferred and alkyl groups each having 1 to 10 carbon atoms are more preferred.

Examples of the alkenyl group include alkenyl groups each having 2 to 40 carbon atoms such as a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. Preferred are alkenyl groups each having 2 to 20 carbon atoms and more preferred are alkenyl groups each having 2 to 10 carbon atoms.

Examples of the cycloalkyl groups include cycloalkyl groups each having 3 to 40 carbon atoms forming the ring such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. Preferred are cycloalkyl groups each having 3 to 10 carbon atoms forming the ring are preferred.

As the aryl groups, the same examples of the aryl groups in the above-mentioned arylamino groups are given. Preferred are aryl groups each having 6 to 20 carbon atoms forming the aromatic ring and more preferred are aryl groups each having 6 to 10 carbon atoms forming the aromatic ring.

As the aralkyl groups, the same examples of the aralkyl groups in the above-mentioned aralkylamino groups are given. Preferred are aralkyl groups each having 7 to 20 carbon atoms and more preferred are aralkyl groups each having 7 to 10 carbon atoms.

As the alkoxy group that represented by $R^2$ to $R^7$ and may be substituted, the same examples of the alkyl groups in the above-mentioned alkylamino groups are given as alkyl group moieties. Preferred are alkoxy groups each having 1 to 20 carbon atoms and more preferred alkoxy groups each having 1 to 10 carbon atoms.

As the aryloxy group that represented by $R^2$ to $R^7$ and may be substituted, aryloxy groups each having the same aryl group in the above-mentioned arylamino group as an aryl group moiety are given. Preferred are aryl groups each having 6 to 20 carbon atoms forming the aromatic ring and more preferred are aryl groups each having 6 to 10 carbon atoms forming the aromatic ring.

As the alkoxycarbonyl group that represented by $R^2$ to $R^7$ and may be substituted, alkoxycarbonyl groups each having the same alkyl group in the above-mentioned alkylamino group as the alkyl group moiety are given. Preferred are alkoxycarbonyl groups each having 2 to 20 carbon atoms and more preferred are alkoxycarbonyl groups each having 2 to 10 carbon atoms.

The heterocyclic group that represented by $R^2$ to $R^7$ and may be substituted is a monocycle or a fused ring. The heterocyclic group preferably has 1 to 20 carbon atoms forming the aromatic ring, more preferably has 1 to 12 carbon atoms forming the aromatic ring, and still more preferably has 2 to 10 carbon atoms forming the aromatic ring. The heterocyclic group is an aromatic heterocyclic group having at least one hetero atom selected form a nitrogen atom, an oxygen atom, a sulfur atom, and selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, and azepine. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

M represents aluminum (Al), gallium (Ga), or indium (In). Indium is preferred.

$L^4$ in the formula (A) is a group represented by the following formula (A') or (A").

[Chem 98]

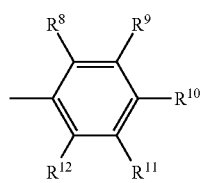

(A')

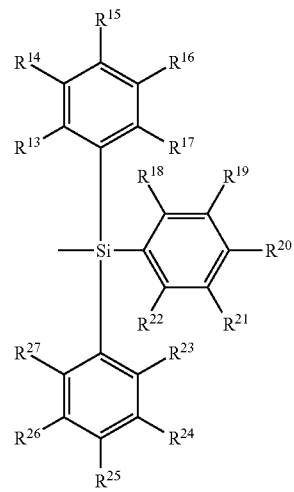

(A")

(In the formula, $R^8$ to $R^{12}$ each independently represent a hydrogen atom, or a substituted or unsubstituted hydrocarbon group having 1 to 40 carbon atoms, and adjacent groups may form a cyclic structure. In addition, $R^{13}$ to $R^{27}$ each independently represent a hydrogen atom, or a substituted or unsubstituted hydrocarbon group having 1 to 40 carbon atoms, and adjacent groups may form a cyclic structure.)

As the hydrocarbon group having 1 to 40 carbon atoms and represented by $R^8$ to $R^{12}$ in the formula (A') and $R^{13}$ to $R^{27}$ in the formula (A"), the same specific examples of $R^2$ to $R^7$ are given.

In addition, examples of the divalent group in $R^8$ to $R^{12}$ and $R^{13}$ to $R^{27}$ in the case where adjacent groups form a cyclic structure include a tetramethylene group, a pentamethylene group, a hexamethylene group, a diphenylmethane-2,2'-diyl group, a diphenylethane-3,3'-diyl group, and diphenylpropane-4,4'-diyl group.

Specific examples of the nitrogen-containing ring metal chelate complex represented by the formula (A) are shown below. However, the present invention is not limited to these exemplified compounds.

[Chem 99]

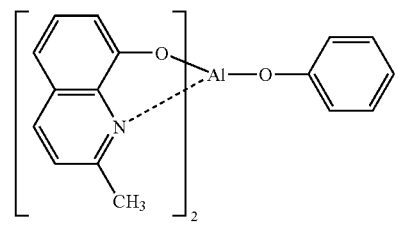

(A-1)

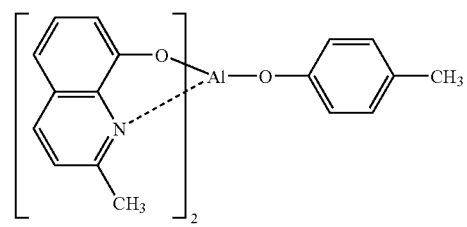

(A-2)

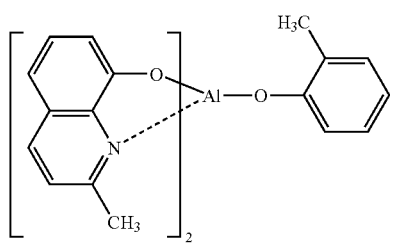
(A-3)
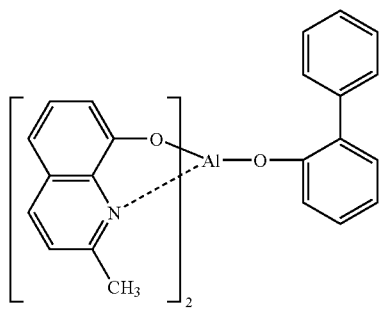
(A-4)
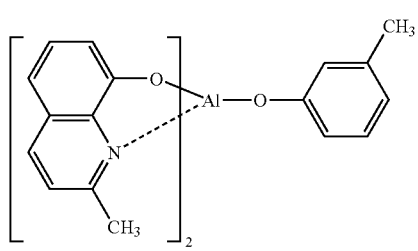
(A-5)
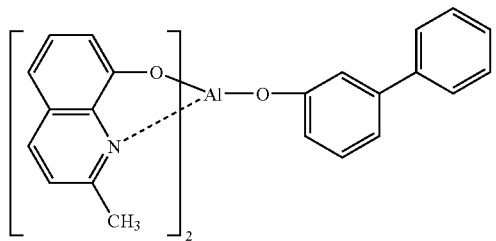
(A-6)
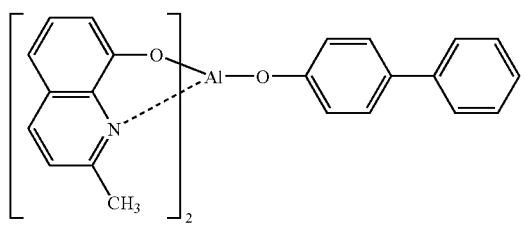
(A-7)
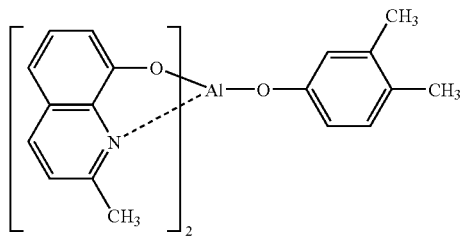
(A-8)
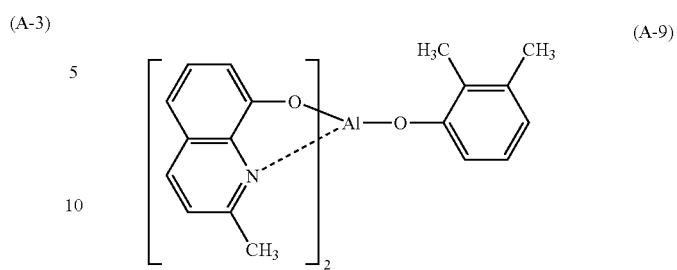
(A-9)
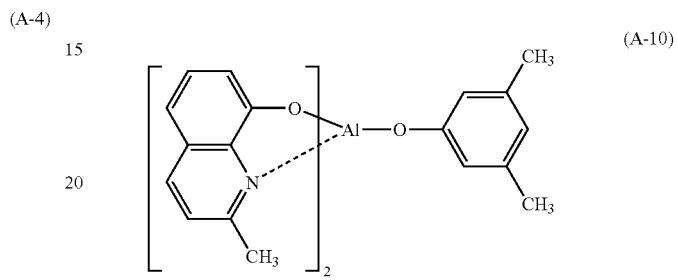
(A-10)
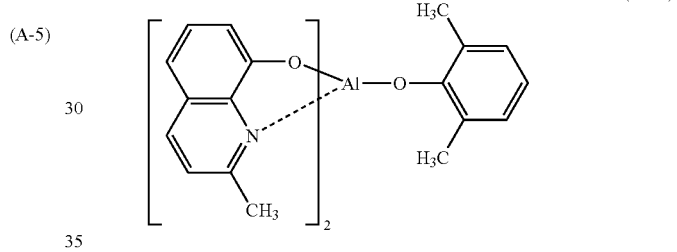
(A-11)
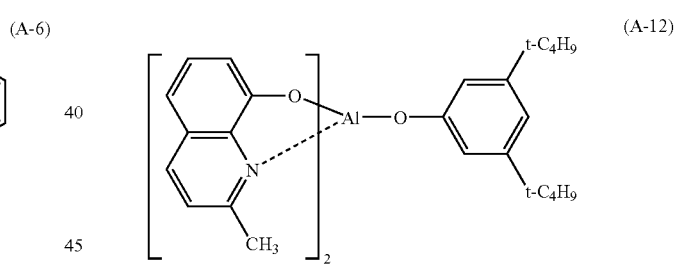
(A-12)
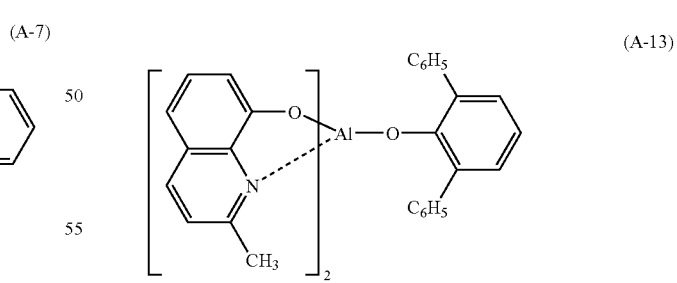
(A-13)
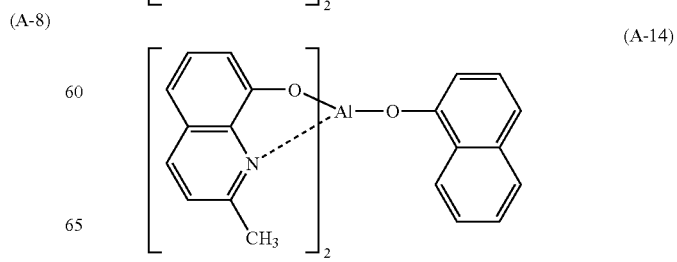
(A-14)

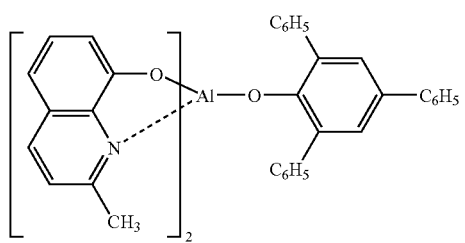
(A-15)
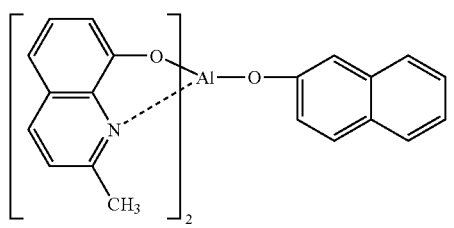
(A-16)
[Chem 100]
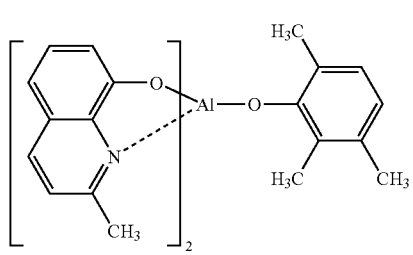
(A-17)
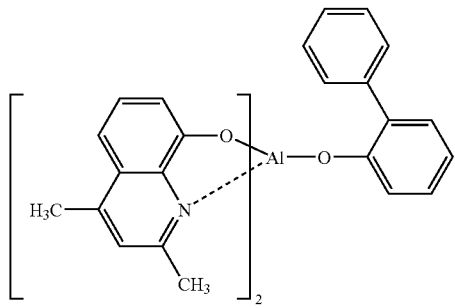
(A-18)
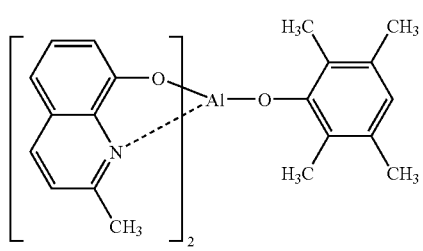
(A-19)
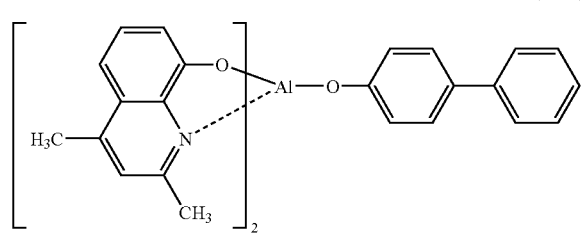
(A-20)
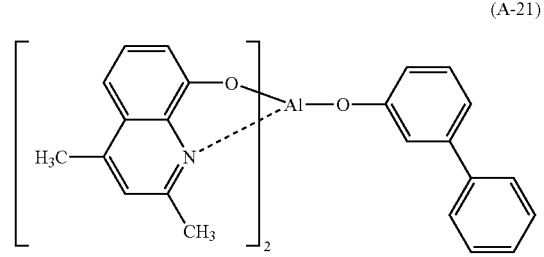
(A-21)
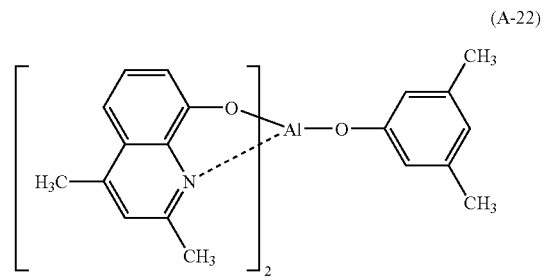
(A-22)
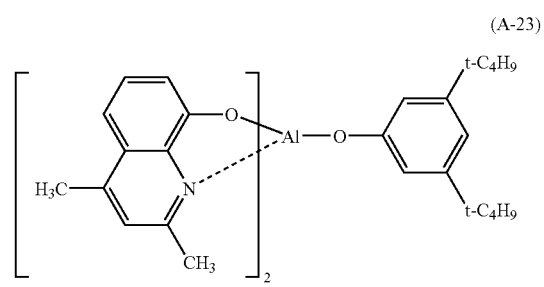
(A-23)
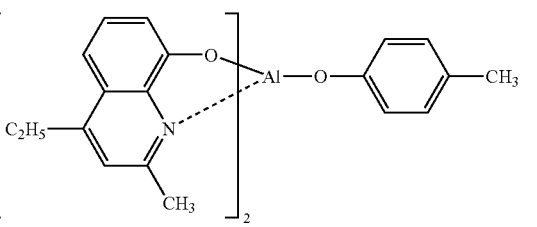
(A-24)
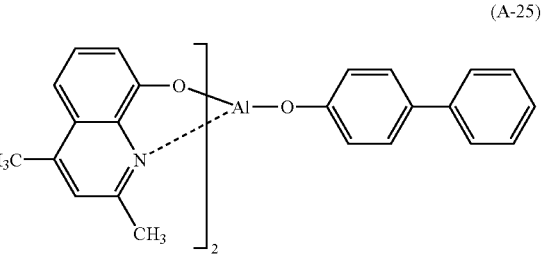
(A-25)
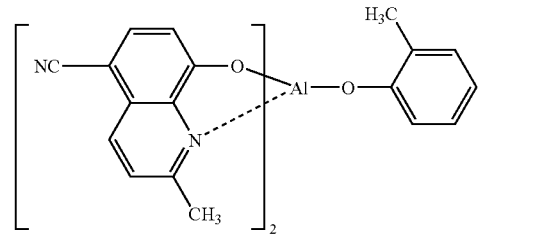
(A-26)

(A-27)
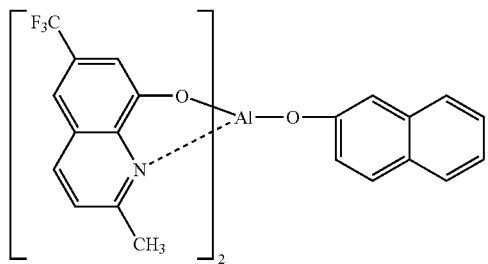

(A-28)
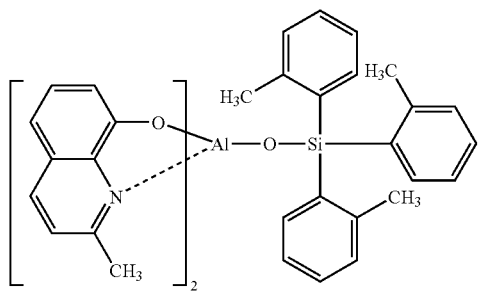

(A-29)
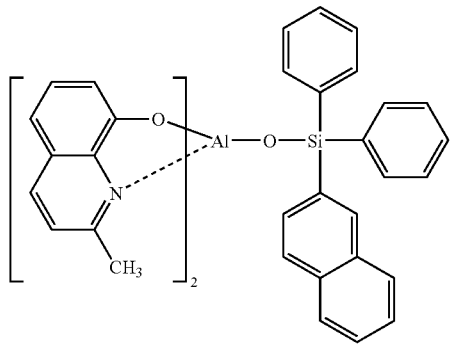

(A-30)
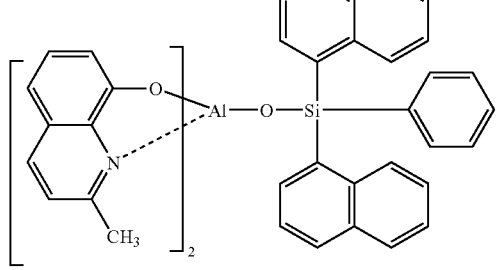

[Chem 101]

(A-31)
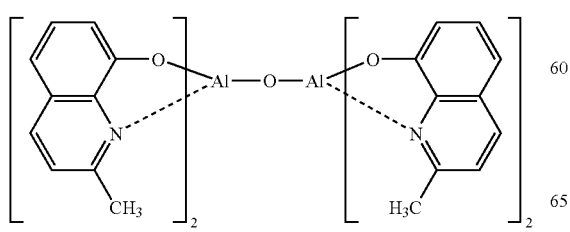

(A-32)
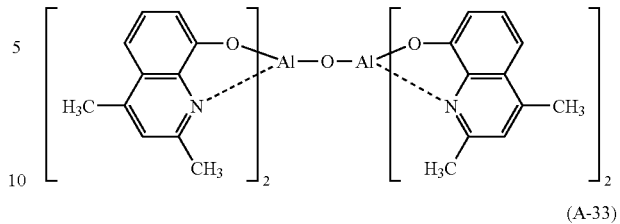

(A-33)
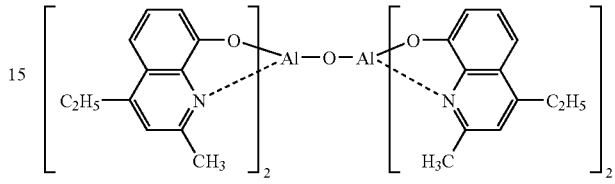

(A-34)
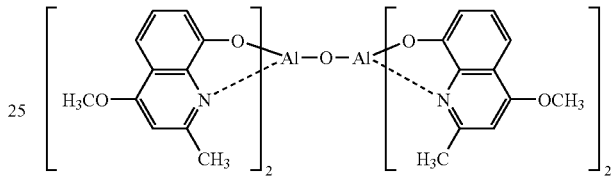

(A-35)
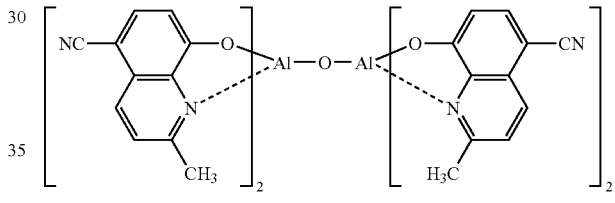

(A-36)
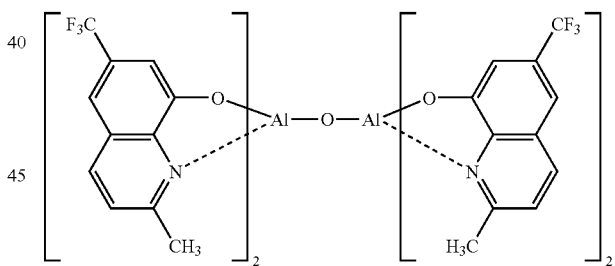

A nitrogen-containing heterocyclic derivative is a nitrogen-containing heterocyclic derivative composed of an organic compound having any one of the following general formulae, and a nitrogen-containing compound which is not a metal complex is also an example of the derivative. Examples of the derivative include a five- or six-membered ring containing a skeleton represented by the following formula (a) and a derivative of a structure represented by the following formula (b).

[Chem 102]

(a)

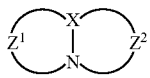
(b)

(In the formula (b), X represents a carbon atom or a nitrogen atom, and $Z^1$ and $Z^2$ each independently represent an atomic group capable of forming a nitrogen-containing heterocycle.)

[Chem 103]

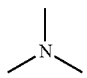
(c)

An organic compound having a nitrogen-containing aromatic polycycle composed of a five- or six-membered ring is preferable. In the case of such nitrogen-containing aromatic polycycle having multiple nitrogen atoms, a nitrogen-containing aromatic polycyclic organic compound having a skeleton obtained by combining the above formulae (a) and (b) or the above formulae (a) and (c) is more preferable.

The nitrogen-containing group of the nitrogen-containing organic compound is selected from, for example, nitrogen-containing heterocyclic groups represented by the following general formulae.

[Chem 104]

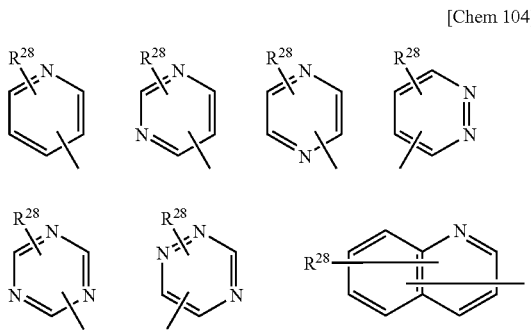

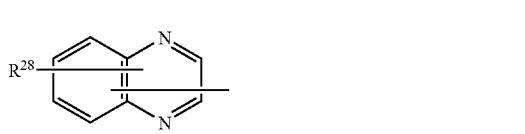

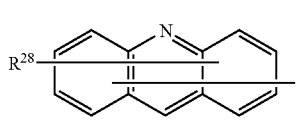

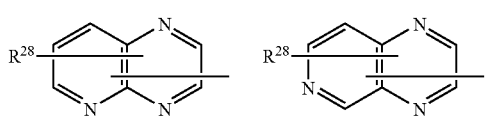

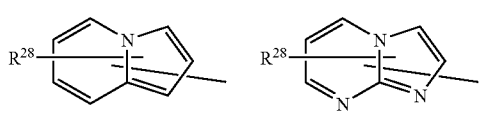

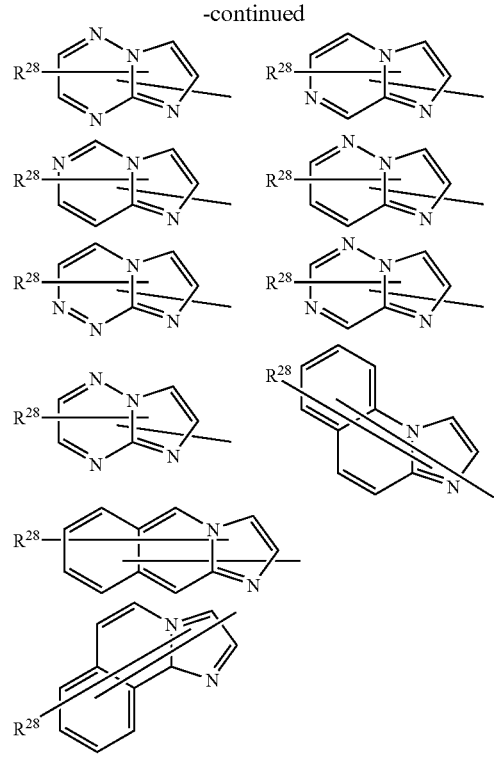

(In each of the formulae, $R^{28}$ represents an aryl group having 6 to 40 carbon atoms, a heteroaryl group having 3 to 40 carbon atoms, an alkyl group having 1 to 20 carbon atoms, or an alkoxy group having 1 to 20 carbon atoms, n represents an integer of 0 to 5, and, when n represents an integer of 2 or more, multiple $R^{28}$s may be identical to or different from each other).

Further, a preferable specific compound is, for example, a nitrogen-containing heterocyclic derivative represented by the following formula.

[Chem 105]

(In the formula, $HAr^a$ represents a nitrogen-containing heterocycle which has 3 to 40 carbon atoms and may have a substituent, $L^b$ represents a single bond, an arylene group which has 6 to 40 carbon atoms and may have a substituent, or a heteroarylene group which has 3 to 40 carbon atoms and may have a substituent, $Ar^b$ represents a divalent aromatic hydrocarbon group which has 6 to 40 carbon atoms and may have a substituent, and $Ar^c$ represents an aryl group which has 6 to 40 carbon atoms and may have a substituent, or a heteroaryl group which has 3 to 40 carbon atoms and may have a substituent.)

$HAr^a$ is selected from, for example, the following group.

[Chem 106]

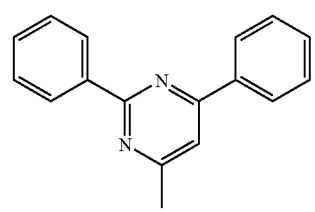

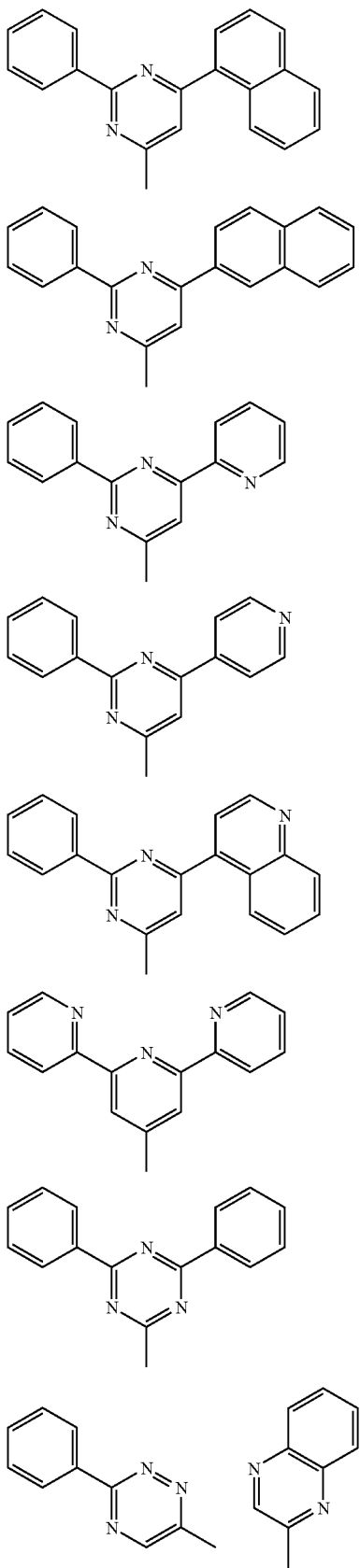
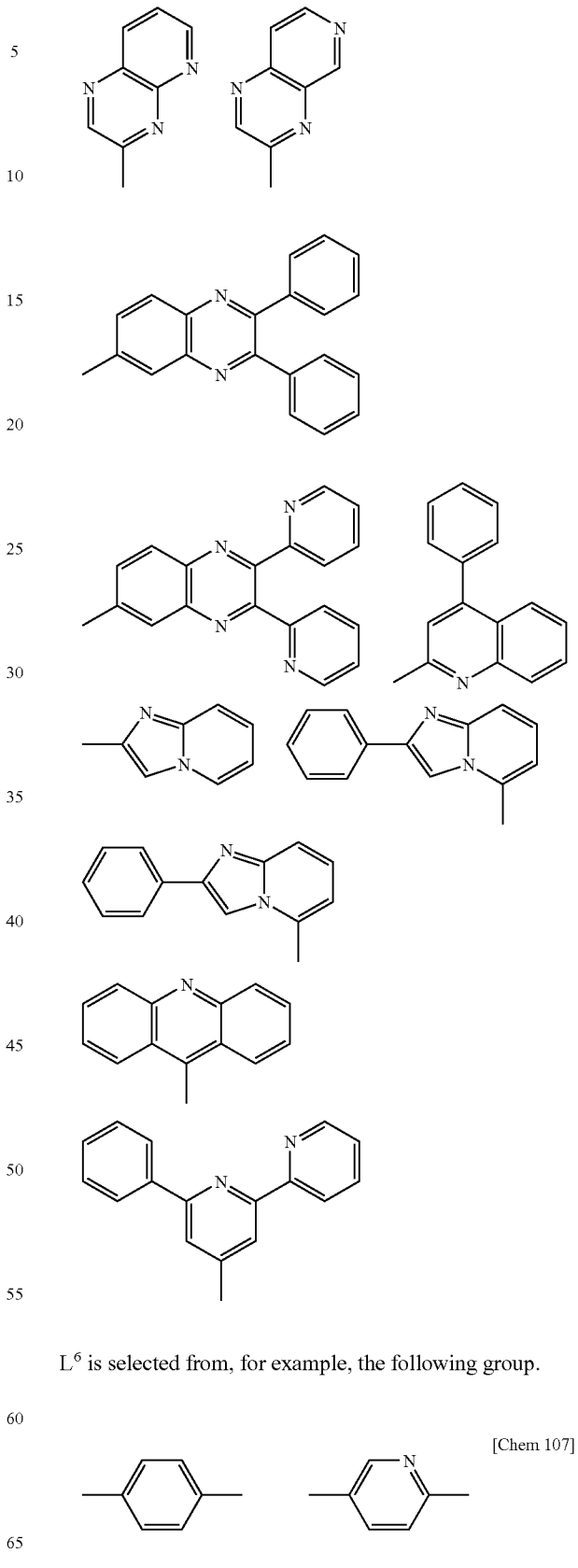
$L^6$ is selected from, for example, the following group.
[Chem 107]
$Ar^c$ is selected from, for example, the following group.

[Chem 108]

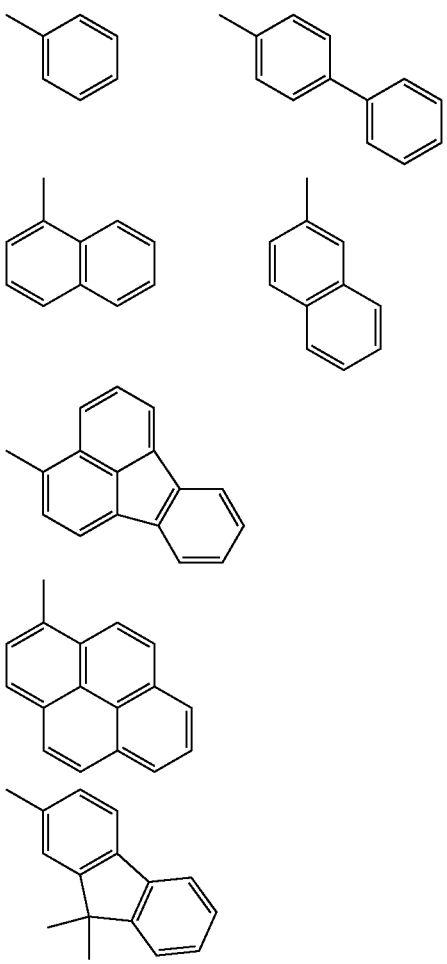

$Ar^b$ is selected from, for example, the following arylanthranil group.

[Chem 109]

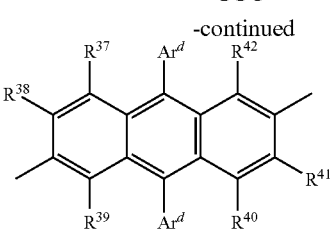

-continued

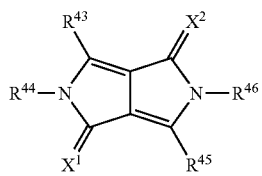

(In the formulae, $R^{29}$ to $R^{42}$ each independently represent a hydrogen atom, a halogen atom, an alkyl group having 1 to 20 carbon atoms, an alkoxy group having 1 to 20 carbon atoms, an aryloxy group having 6 to 40 carbon atoms, an aryl group which has 6 to 40 carbon atoms and may have a substituent, or a heteroaryl group having 3 to 40 carbon atoms, and $Ar^d$ represents an aryl group which has 6 to 40 carbon atoms and may have a substituent, or a heteroaryl group having 3 to 40 carbon atoms.)

In addition, a nitrogen-containing heterocyclic derivative in which $R^{29}$ to $R^{36}$ in $Ar^b$ represented by the above formula each represent a hydrogen atom is preferable.

In addition to the foregoing, the following compound (see JP 09-3448 A) is also suitably used.

[Chem 110]

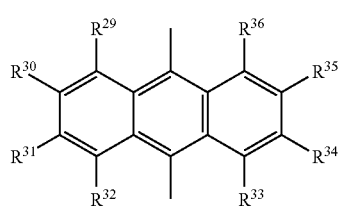

(In the formula, $R^{43}$ to $R^{46}$ each independently represent a hydrogen atom, a substituted or unsubstituted aliphatic group, a substituted or unsubstituted alicyclic group, a substituted or unsubstituted carbocyclic aromatic ring group, or a substituted or unsubstituted heterocyclic group, and $X^1$ and $X^2$ each independently represent an oxygen atom, a sulfur atom, or a dicyanomethylene group.)

In addition to the foregoing, the following compound (see JP 2000-173774 A) is also suitably used.

[Chem 111]

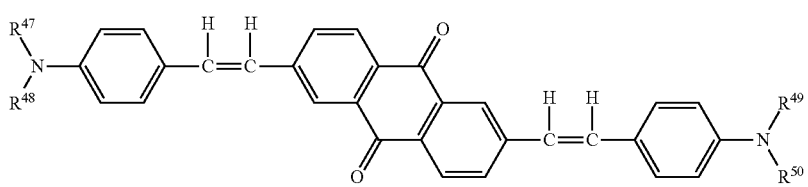

In the formula, $R^{47}$, $R^{48}$, $R^{49}$, and $R^{50}$ represent groups identical to or different from one another, and each represent an aryl group represented by the following formula.

[Chem 112]

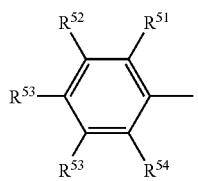

(In the formula, $R^{51}$, $R^{52}$, $R^{53}$, $R^{54}$, and $R^{55}$ represent groups identical to or different from one another, and each may represent a hydrogen atom, or at least one of them may represent a saturated or unsaturated alkoxyl, alkyl, amino, or alkylamino group.)

Further, a polymer compound containing the nitrogen-containing heterocyclic group or nitrogen-containing heterocyclic derivative is also permitted.

In addition, the electron transporting layer preferably contains at least one of the nitrogen-containing heterocyclic derivatives represented by the following general formulae (201) to (203).

[Chem 113]

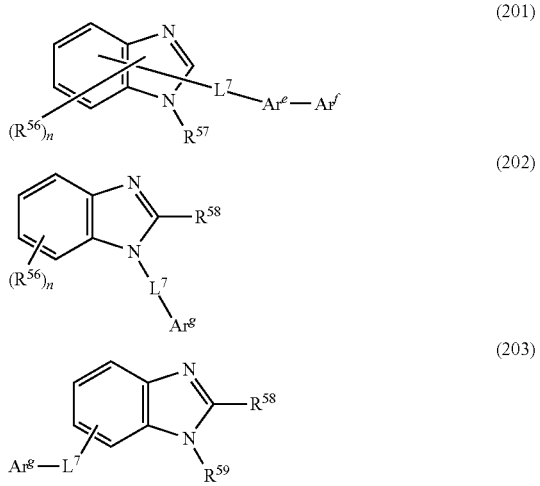

(201)

(202)

(203)

In the formulae (201) to (203), $R^{56}$ represents a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent, n represents an integer of 0 to 4, $R^{57}$ represents an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group having 1 to 20 carbon atoms, $R^{58}$ and $R^{59}$ each independently represent a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent, $L^7$ represents a single bond, an arylene group which has 6 to 60 carbon atoms and may have a substituent, a pyridinylene group which may have a substituent, a quinolinylene group which may have a substituent, or a fluorenylene group which may have a substituent, $Ar^e$ represents an arylene group which has 6 to 60 carbon atoms and may have a substituent, a pyridinylene group which may have a substituent, or a quinolinylene group which may have a substituent, and $Ar^f$ represents a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

In the formulae, $Ar^g$ represents an aryl group which has 6 to 60 carbon atoms and may have a substituent, a pyridyl group which may have a substituent, a quinolyl group which may have a substituent, an alkyl group which has 1 to 20 carbon atoms and may have a substituent, an alkoxy group which has 1 to 20 carbon atoms and may have a substituent, or a group represented by —$Ar^e$—$Ar^f$ ($Ar^e$ and $Ar^f$ each have the same meaning as that described above).

It should be noted that, in the formulae (201) to (203), $R^{56}$ represents a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

The aryl group which has 6 to 60 carbon atoms is preferably an aryl group having 6 to 40 carbon atoms, or more preferably an aryl group having 6 to 20 carbon atoms, and specific examples of such groups include a phenyl group, a naphthyl group, an anthryl group, a phenanthryl group, a naphthacenyl group, a chrysenyl group, a pyrenyl group, a biphenyl group, a terphenyl group, a tolyl group, a t-butylphenyl group, a (2-phenylpropyl)phenyl group, a fluoranthenyl group, a fluorenyl group, a monovalent group composed of spirobifluorene, a perfluorophenyl group, a perfluoronaphthyl group, a perfluoroanthryl group, a perfluorobiphenyl group, a monovalent group composed of 9-phenylanthracene, a monovalent group composed of 9-(1'-naphthyl) anthracene, a monovalent group composed of 9-(2'-naphthyl)anthracene, a monovalent group composed of 6-phenylchrysene, and a monovalent group composed of 9-[4-(diphenylamino) phenyl]anthracene; a phenyl group, a naphthyl group, a biphenyl group, a terphenyl group, a 9-(10-phenyl) anthryl group, a 9-[10-(1'-naphthyl)]anthryl group, a 9-[10-(2'-naphthyl)]anthryl group, or the like is preferable.

The alkyl group which has 1 to 20 carbon atoms is preferably an alkyl group having 1 to 6 carbon atoms, and specific examples of such group include a methyl group, an ethyl group, a propyl group, a butyl group, a pentyl group, a hexyl group, and a haloalkyl group such as a trifluoromethyl group. An alkyl group having 3 or more carbon atoms may be linear, cyclic, or branched.

The alkoxy group which has 1 to 20 carbon atoms is preferably an alkoxy group having 1 to 6 carbon atoms, and specific examples of such group include a methoxy group, an ethoxy group, a propoxy group, a butoxy group, a pentyloxy group, and a hexyloxy group. An alkoxy group having 3 or more carbon atoms may be linear, cyclic, or branched.

Examples of the substituent of each group represented by $R^{56}$ include a halogen atom, an alkyl group which has 1 to 20 carbon atoms and may have a substituent, an alkoxy group which has 1 to 20 carbon atoms and may have a substituent, an aryloxy group which has 6 to 40 carbon atoms and may have a substituent, an aryl group which has 6 to 40 carbon atoms and may have a substituent, or a heteroaryl group which has 3 to 40 carbon atoms and may have a substituent.

Examples of the halogen atom include fluorine, chlorine, bromine, and iodine.

Examples of the alkyl group which has 1 to 20 carbon atoms, the alkoxy group which has 1 to 20 carbon atoms, and the aryl group which has 6 to 40 carbon atoms include the same examples as those described above.

Examples of the aryloxy group which has 6 to 40 carbon atoms include a phenoxy group and a biphenyloxy group.

Examples of the heteroaryl group which has 3 to 40 carbon atoms include a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, and a triazolyl group.

n represents an integer of 0 to 4, or preferably 0 to 2.

In the formula (201), $R^{57}$ represents an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group having 1 to 20 carbon atoms.

Specific examples of the respective groups, and preferable carbon numbers and preferable substituents of those groups are the same as those described for R.

In the formulae (202) and (203), $R^{58}$ and $R^{59}$ each independently represent a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

Specific examples of the respective groups, and preferable carbon numbers and preferable substituents of those groups are the same as those described for $R^{56}$.

In the formulae (201) to (203), $L^7$ represents a single bond, an arylene group which has 6 to 60 carbon atoms and may have a substituent, a pyridinylene group which may have a substituent, a quinolinylene group which may have a substituent, or a fluorenylene group which may have a substituent.

The arylene group which has 6 to 60 carbon atoms is preferably an arylene group having 6 to 40 carbon atoms, or more preferably an arylene group having 6 to 20 carbon atoms, and specific examples of such groups include divalent groups each formed by removing one hydrogen atom from the aryl group described for R. Examples of the substituent of each group represented by $L^7$ include the same examples as those described for $R^{56}$.

In addition, $L^7$ preferably represents a group selected from the group consisting of the following groups.

[Chem 114]

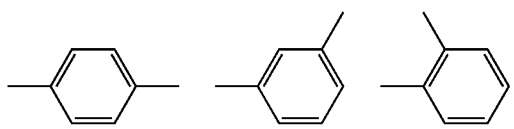

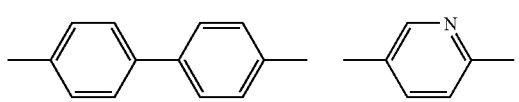

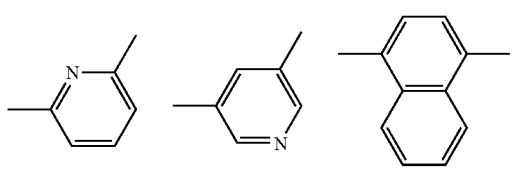

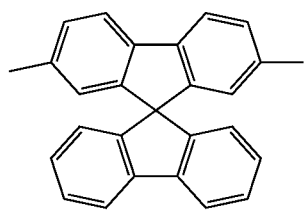

In the formula (201), Ar$^e$ represents an arylene group which has 6 to 60 carbon atoms and may have a substituent, a pyridinylene group which may have a substituent, or a quinolinylene group which may have a substituent. Examples of the substituents of the respective groups represented by Ar$^e$ and Ar$^g$ include the same examples as those described for $R^{56}$.

In addition, Ar$^e$ preferably represents any one of the groups selected from fused ring groups represented by the following formulae (101) to (110).

[Chem 115]

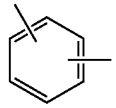 (101)

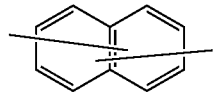 (102)

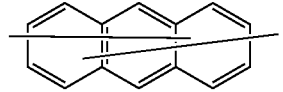 (103)

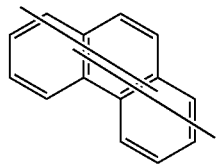 (104)

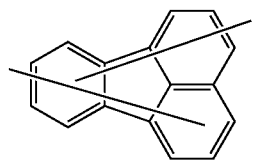 (105)

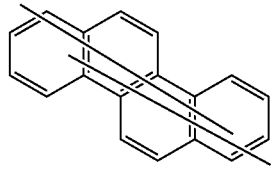 (106)

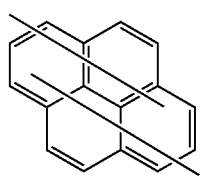 (107)

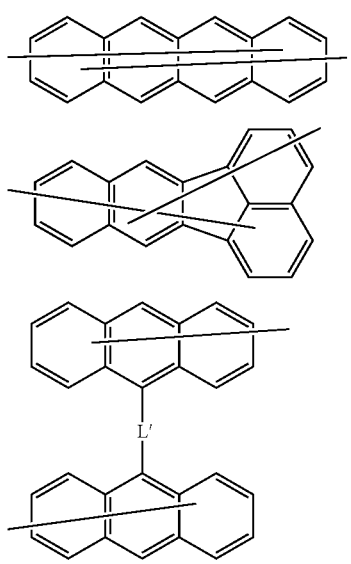

(108)

(109)

(110)

In the formulae (101) to (110), each fused ring may be bonded with a bonding group composed of a halogen atom, an alkyl group which has 1 to 20 carbon atoms and may have a substituent, an alkoxy group which has 1 to 20 carbon atoms and may have a substituent, an aryloxy group which has 6 to 40 carbon atoms and may have a substituent, an aryl group which has 6 to 40 carbon atoms and may have a substituent, or a heteroaryl group which has 3 to 40 carbon atoms and may have a substituent, and, when multiple bonding groups of this kind are present, the bonding groups may be identical to or different from each other. Specific examples of the respective groups include the same examples as those described above.

In the formula (110), L' represents a single bond or a group selected from the group consisting of the following groups.

[Chem 116]

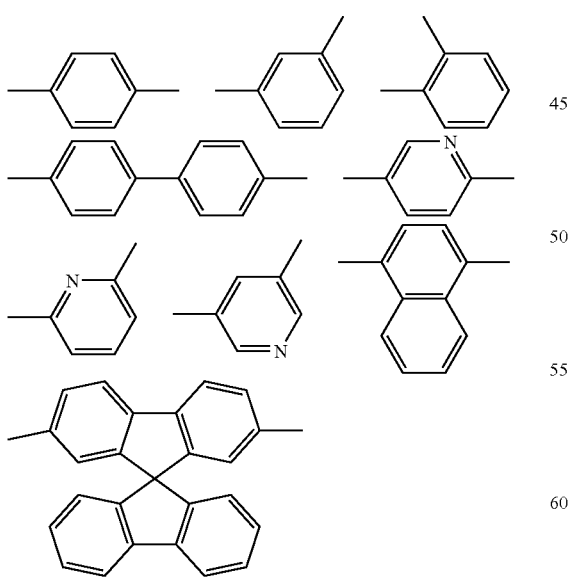

The formula (103) represented by $Ar^e$ is preferably a fused ring group represented by the following formulae (111) to (125).

[Chem 117]

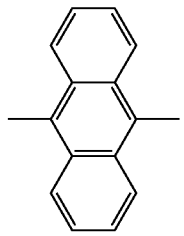

(111)

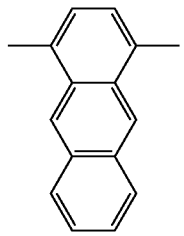

(112)

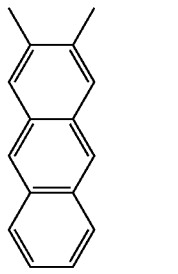

(113)

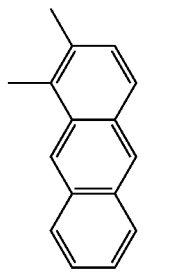

(114)

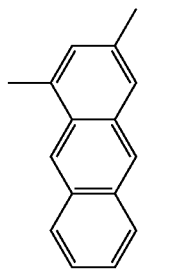

(115)

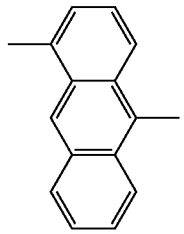

(116)

-continued (117) 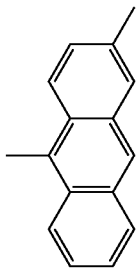

(118) 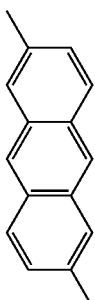

(119) 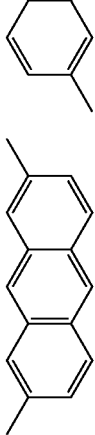

(120)  wait...

-continued

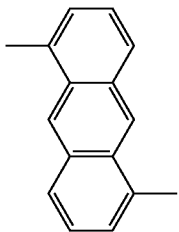
(117)

(118)

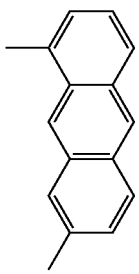
(119)

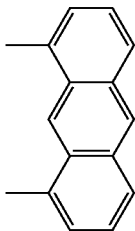
(120)

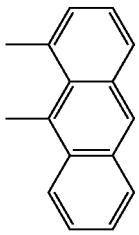
(121)

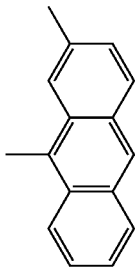
(122)

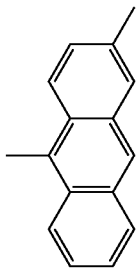
(123)

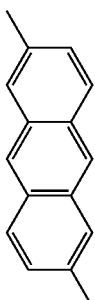
(124)

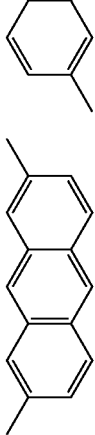
(125)

In the formulae (111) to (125), each fused ring may be bonded with a bonding group composed of a halogen atom, an alkyl group which has 1 to 20 carbon atoms and may have a substituent, an alkoxy group which has 1 to 20 carbon atoms and may have a substituent, an aryloxy group which has 6 to 40 carbon atoms and may have a substituent, an aryl group which has 6 to 40 carbon atoms and may have a substituent, or a heteroaryl group which has 3 to 40 carbon atoms and may have a substituent, and, when multiple bonding groups of this kind are present, the bonding groups may be identical to or different from each other. Specific examples of the respective groups include the same examples as those described above.

In the formula (201), $Ar^f$ represents a hydrogen atom, an aryl group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

Specific examples of the respective groups, and preferable carbon numbers and preferable substituents of those groups are the same as those described for $R^{56}$.

In the formulae (202) and (203), $Ar^g$ represents an aryl group which has 6 to 60 carbon atoms and may have a substituent, a pyridyl group which may have a substituent, a quinolyl group which may have a substituent, an alkyl group which has 1 to 20 carbon atoms and may have a substituent, an alkoxy group which has 1 to 20 carbon atoms and may have a substituent, or a group represented by —$Ar^e$—$Ar^f$ ($Ar^e$ and $Ar^f$ each have the same meaning as that described above).

Specific examples of the respective groups, and preferable carbon numbers and preferable substituents of those groups are the same as those described for $R^{56}$.

In addition, $Ar^g$ preferably represents any one of the groups selected from fused ring groups represented by the following formulae (126) to (135).

[Chem 118]

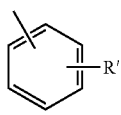
(126)

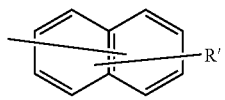
(127)

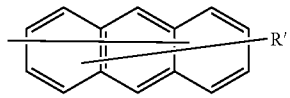
(128)

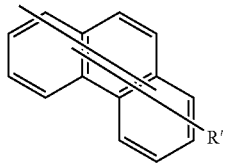
(129)

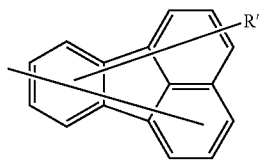
(130)

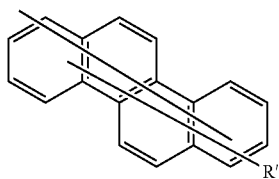
(131)

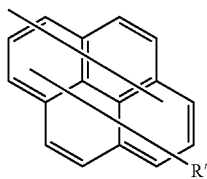
(132)

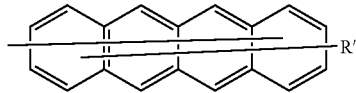
(133)

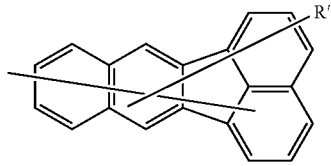
(134)

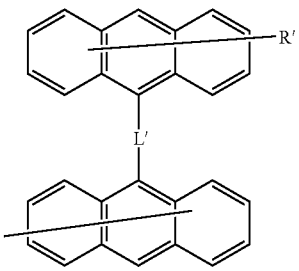
(135)

In the formulae (126) to (135), each fused ring may be bonded with a bonding group composed of a halogen atom, an alkyl group which has 1 to 20 carbon atoms and may have a substituent, an alkoxy group which has 1 to 20 carbon atoms and may have a substituent, an aryloxy group which has 6 to 40 carbon atoms and may have a substituent, an aryl group which has 6 to 40 carbon atoms and may have a substituent, or a heteroaryl group which has 3 to 40 carbon atoms and may have a substituent, and, when multiple bonding groups of this kind are present, the bonding groups may be identical to or different from each other. Specific examples of the respective groups include the same examples as those described above.

In the formula (135), L' is the same as that described above.

In the formulae (126) to (135), R' represents a hydrogen atom, an alkyl group which has 1 to 20 carbon atoms and may have a substituent, an aryl group which has 6 to 40 carbon atoms and may have a substituent, or a heteroaryl group which has 3 to 40 carbon atoms and may have a substituent. Specific examples of the respective groups include the same examples as those described above.

The general formula (128) represented by $Ar^g$ is preferably a fused ring group represented by the following formulae (136) to (158).

[Chem 119]

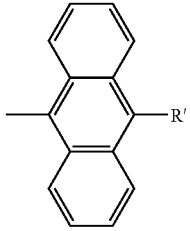
(136)

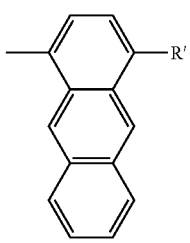
(137)

(138) 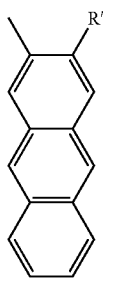
(139) 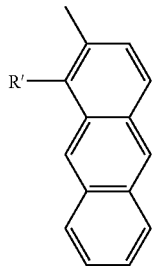
(140) 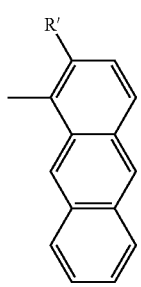
(141) 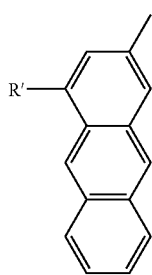
(142) 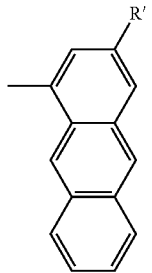
(143) 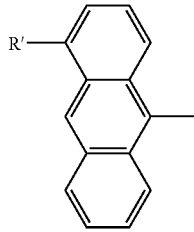
(144) 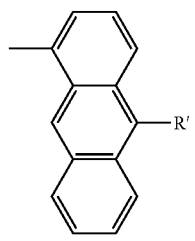
(145) 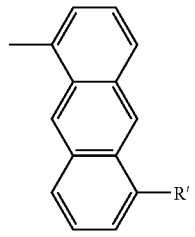
(146) 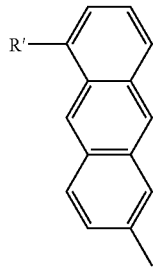
(147) 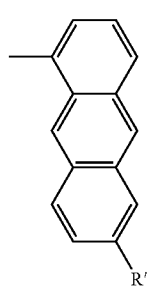
(148) 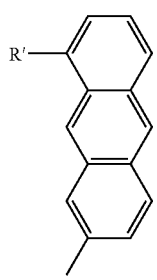
(149) 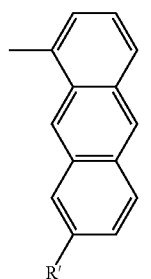

(150) 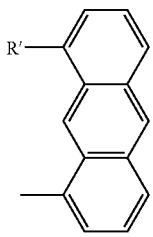

(151) 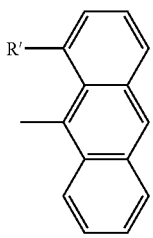

(152) 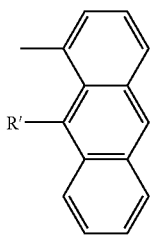

(153) 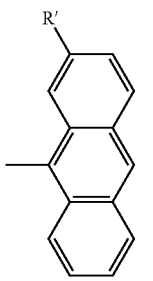

(154) 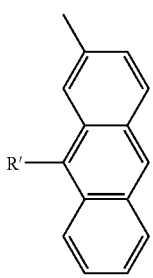

(155) 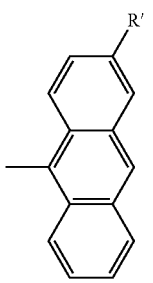

(156) 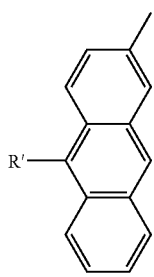

(157) 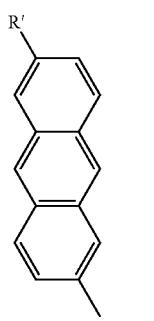

(158) 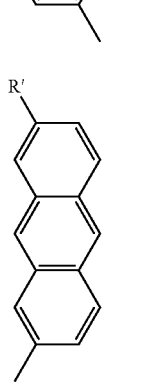

In the formulae (136) to (158), each fused ring may be bonded with a bonding group composed of a halogen atom, an alkyl group which has 1 to 20 carbon atoms and may have a substituent, an alkoxy group which has 1 to 20 carbon atoms and may have a substituent, an aryloxy group which has 6 to 40 carbon atoms and may have a substituent, an aryl group which has 6 to 40 carbon atoms and may have a substituent, or a heteroaryl group which has 3 to 40 carbon atoms and may have a substituent, and, when multiple bonding groups of this kind are present, the bonding groups may be identical to or different from each other. Specific examples of the respective groups include the same examples as those described above. R' is the same as that described above.

In addition, it is preferred that $Ar^f$ and $Ar^g$ each independently represent a group selected from the group consisting of the following groups.

[Chem 120]

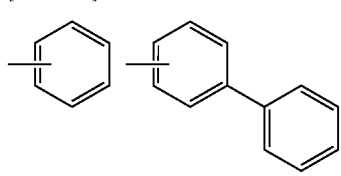

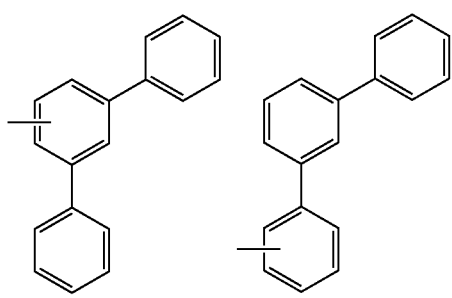
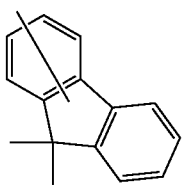
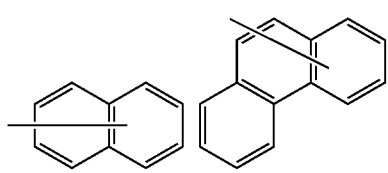
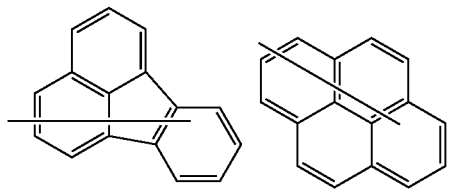

Specific examples of the nitrogen-containing heterocyclic derivatives represented by the formulae (201) to (203) of the present invention are shown below. However, the present invention is not limited to these exemplified compounds.

It should be noted that HAr in the following tables represent any one of the following parts in the formulae (201) to (203).

[Chem 121]

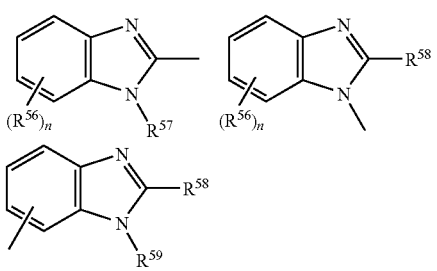

| HAr—L$^7$—Ar$^e$—Ar$^f$ | | | |
|---|---|---|---|
| HAr | L$^7$ | Ar$^e$ | Ar$^f$ |

[Chem 122]

| | | | | |
|---|---|---|---|---|
| 1-1 | 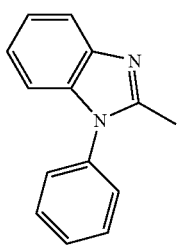 | 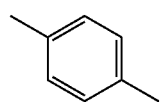 | 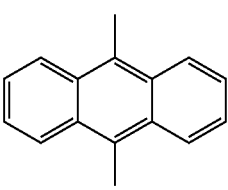 | 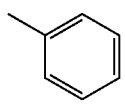 |
| 2 | 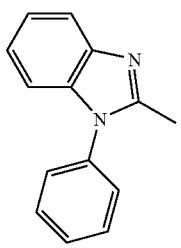 | 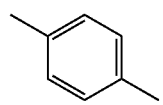 | 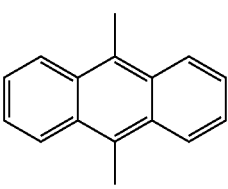 | 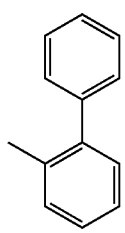 |

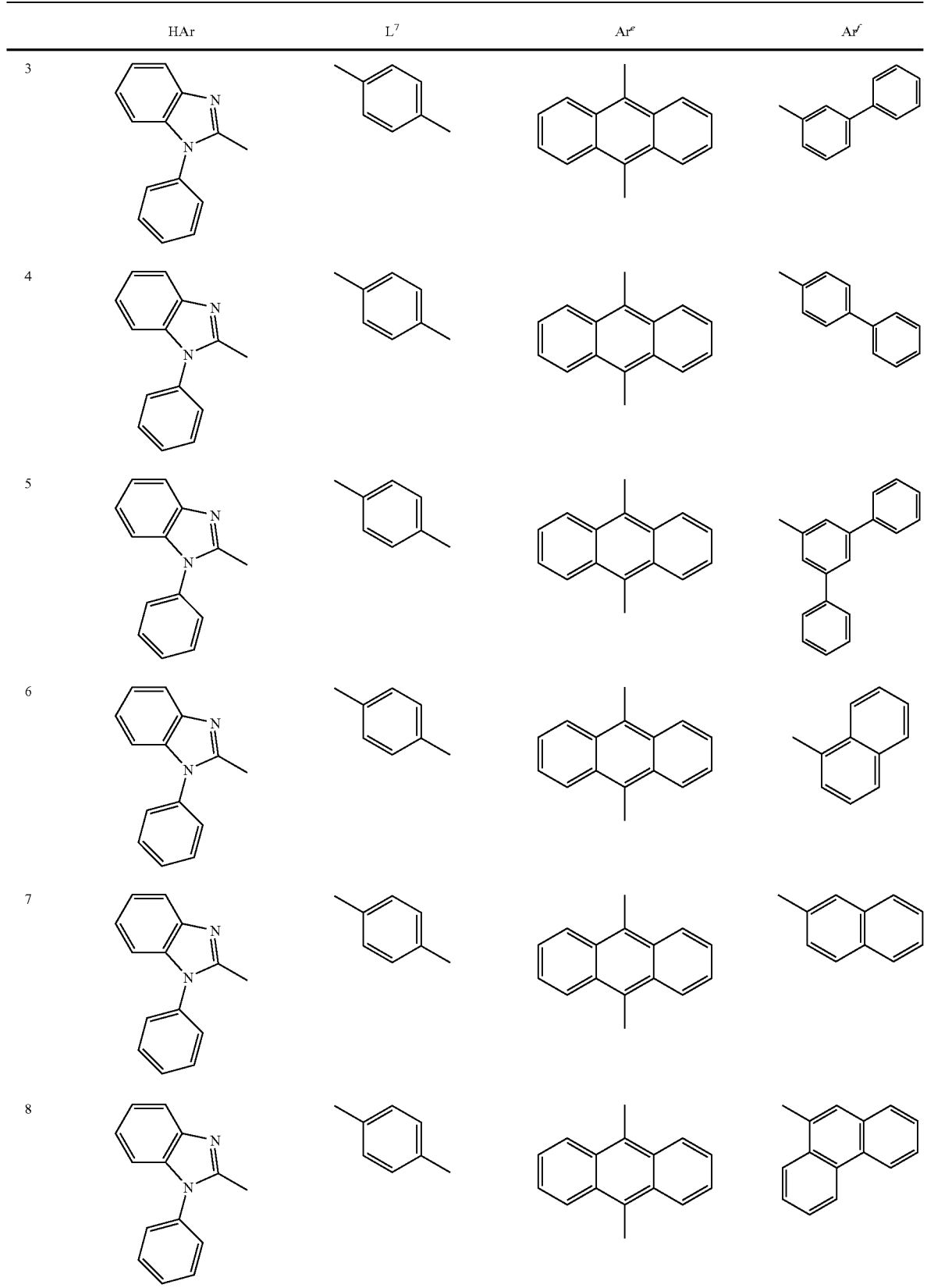

-continued
| | HAr | L⁷ | Arᵉ | Arᶠ |
|---|---|---|---|---|
| 9 | 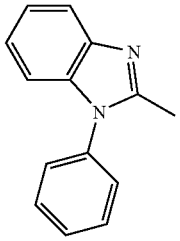 | 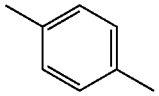 | 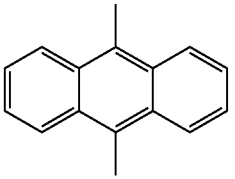 | 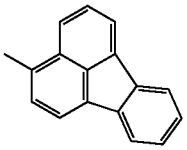 |
| 10 | 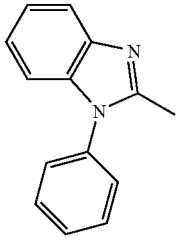 | 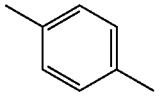 | 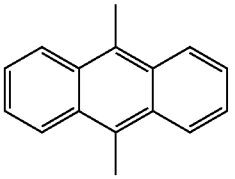 | 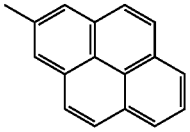 |
| 11 | 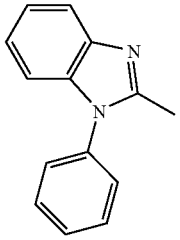 | 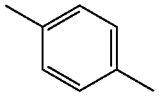 | 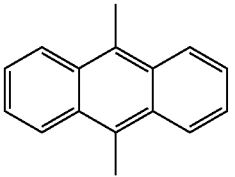 | 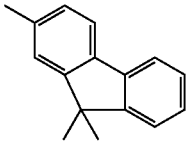 |
| 12 | 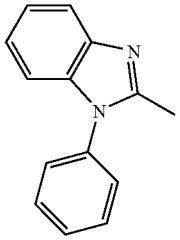 | 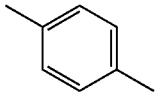 | 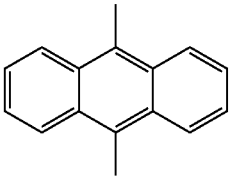 | 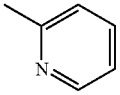 |
| 13 | 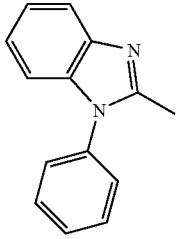 | 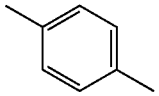 | 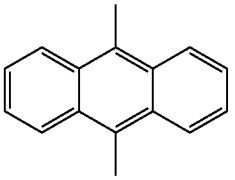 | 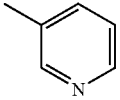 |
| 14 | 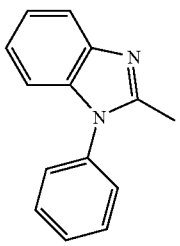 |  | 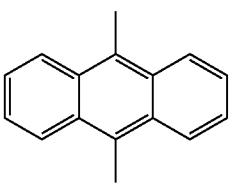 | 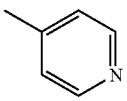 |

-continued
| | HAr | L⁷ | Arᵉ | Ar^f |
|---|---|---|---|---|
[Chem 123]
| | HAr | L⁷ | Arᵉ | Ar^f |
|---|---|---|---|---|
| 2-1 | 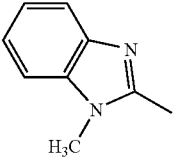 | 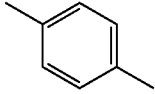 | 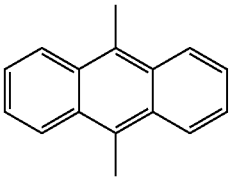 | 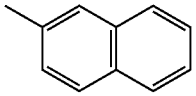 |
| 2 | 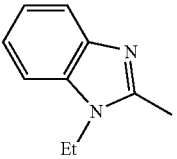 | 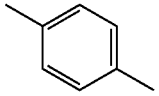 | 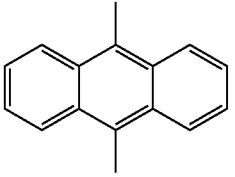 | 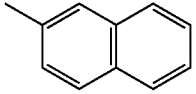 |
| 3 | 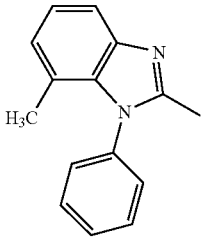 | 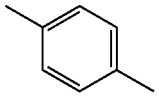 | 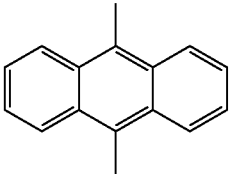 | 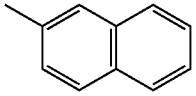 |
| 4 | 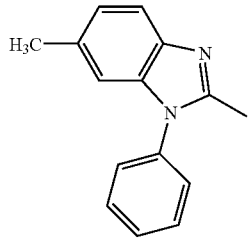 | 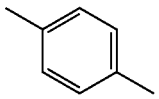 | 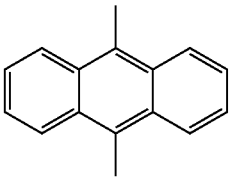 | 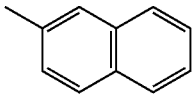 |
| 5 | 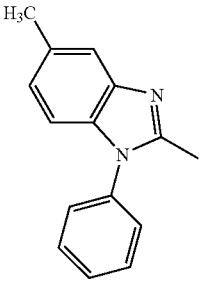 | 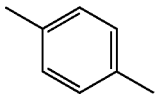 | 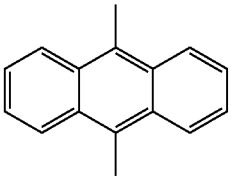 | 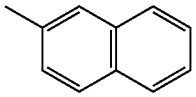 |
| 6 | 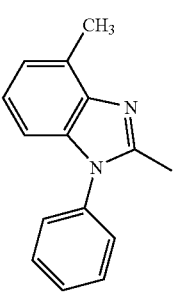 | 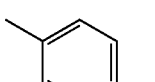 | 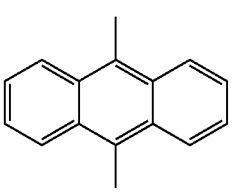 | 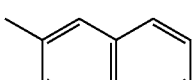 |

-continued
| HAr | L⁷ | Arᵉ | Ar^f |
|---|---|---|---|
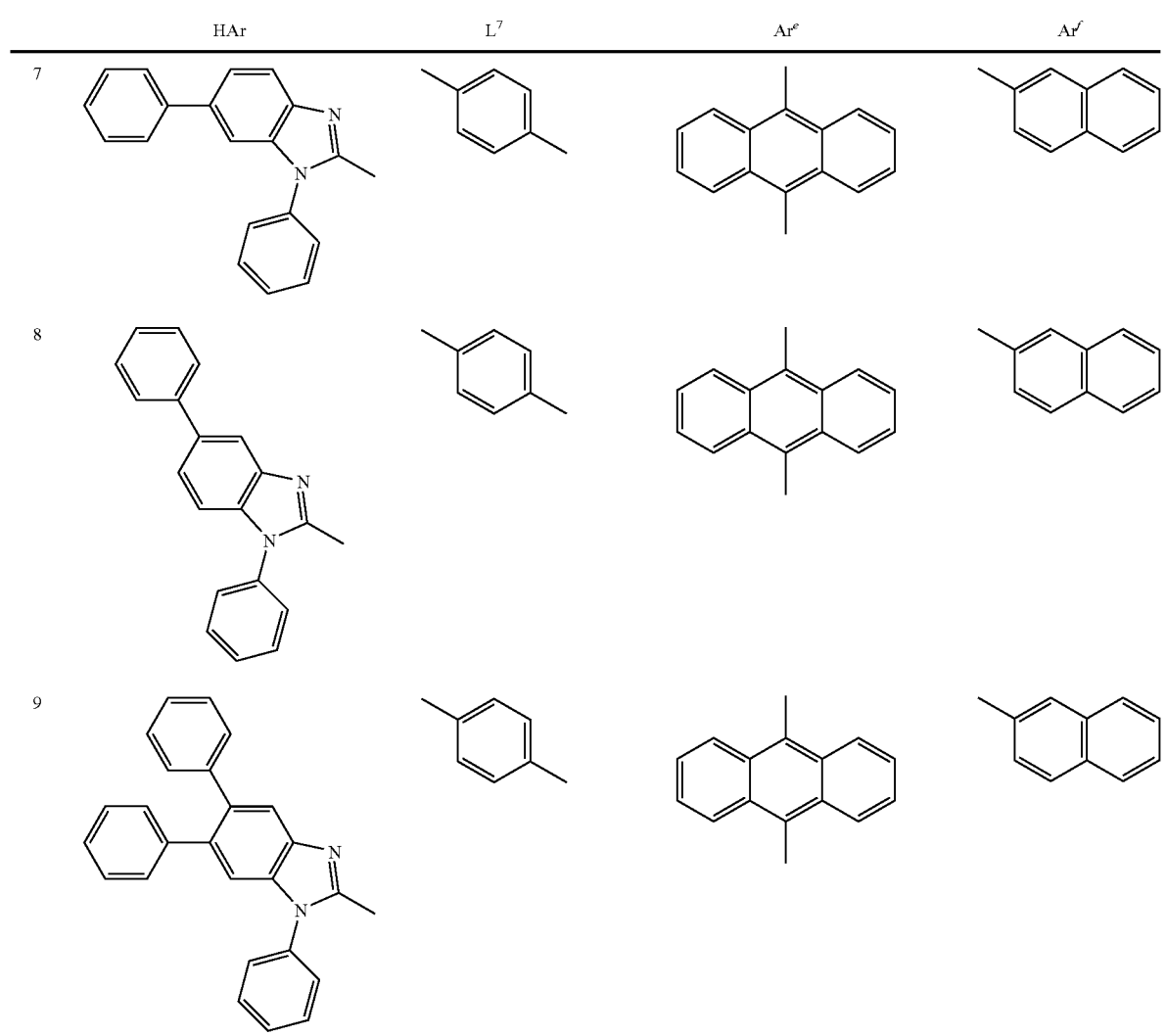
[Chem 124]
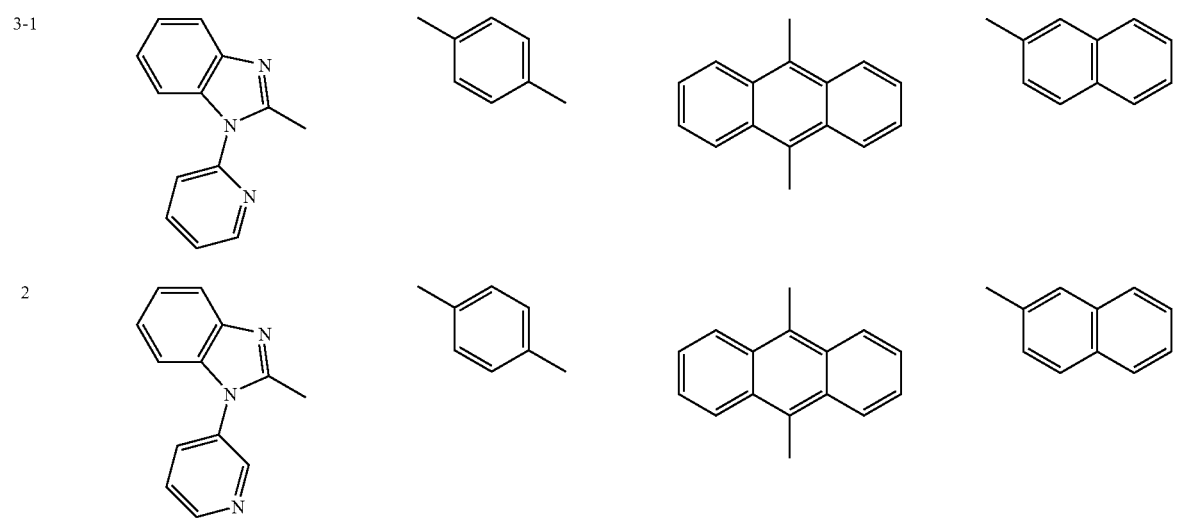

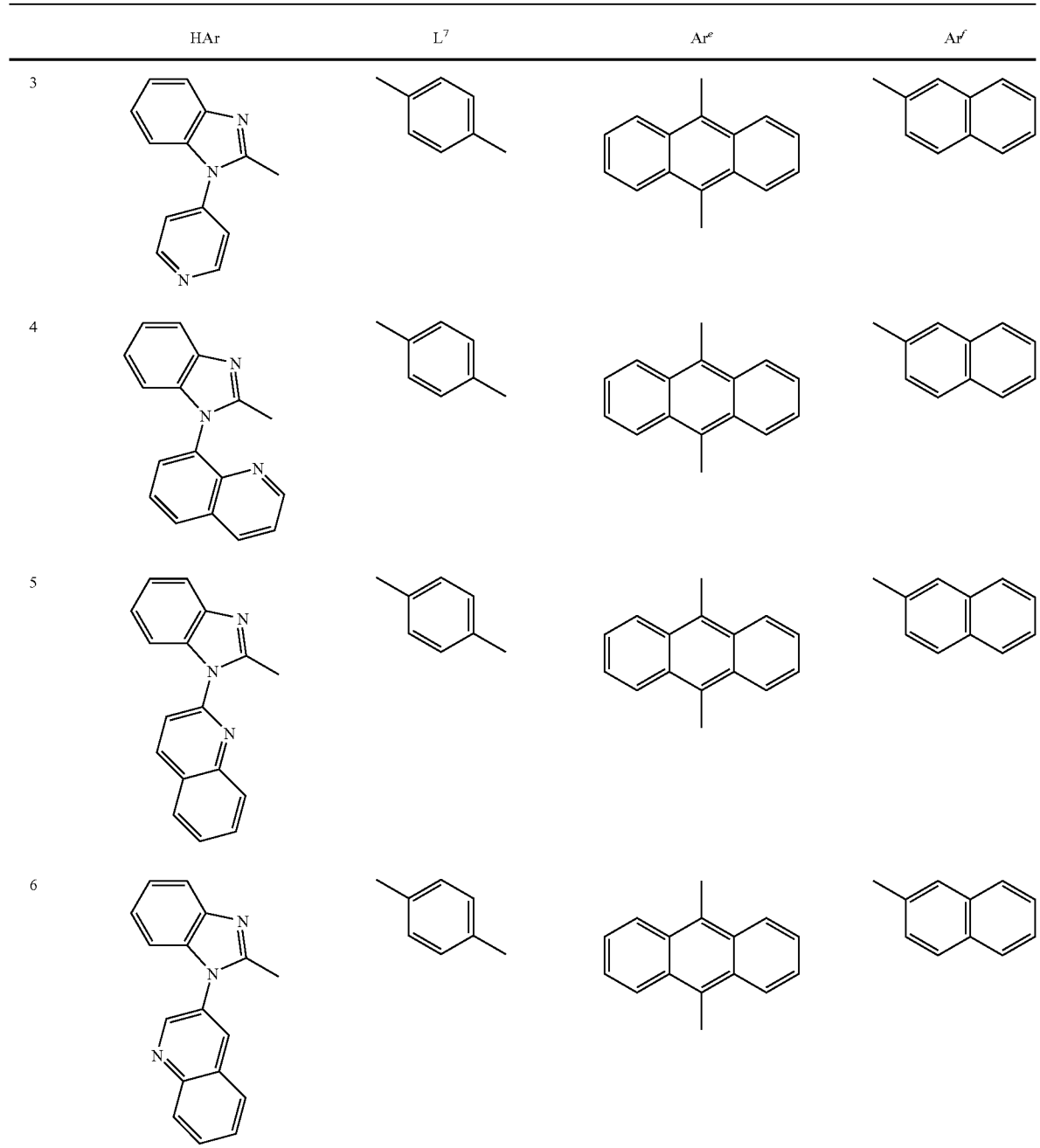
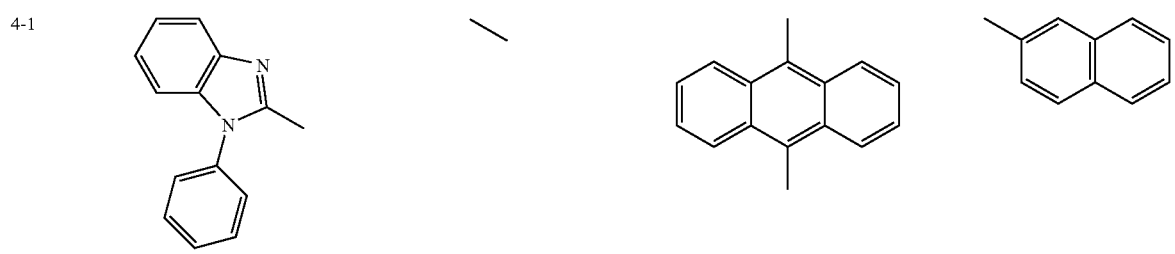

-continued

| | HAr | L⁷ | Arᵉ | Arᶠ |
|---|---|---|---|---|
| 2 | 1-phenyl-2-methyl-benzimidazole | 1,3-dimethylbenzene | 9,10-dimethylanthracene | 2-methylnaphthalene |
| 3 | 1-phenyl-2-methyl-benzimidazole | 1,2-dimethylbenzene | 9,10-dimethylanthracene | 2-methylnaphthalene |
| 4 | 1-phenyl-2-methyl-benzimidazole | 2,5-dimethylpyridine | 9,10-dimethylanthracene | 2-methylnaphthalene |
| 5 | 1-phenyl-2-methyl-benzimidazole | 2,6-dimethylpyridine | 9,10-dimethylanthracene | 2-methylnaphthalene |
| 6 | 1-phenyl-2-methyl-benzimidazole | 3,5-dimethylpyridine | 9,10-dimethylanthracene | 2-methylnaphthalene |
| 7 | 1-phenyl-2-methyl-benzimidazole | 4,4'-dimethylbiphenyl | 9,10-dimethylanthracene | 2-methylnaphthalene |

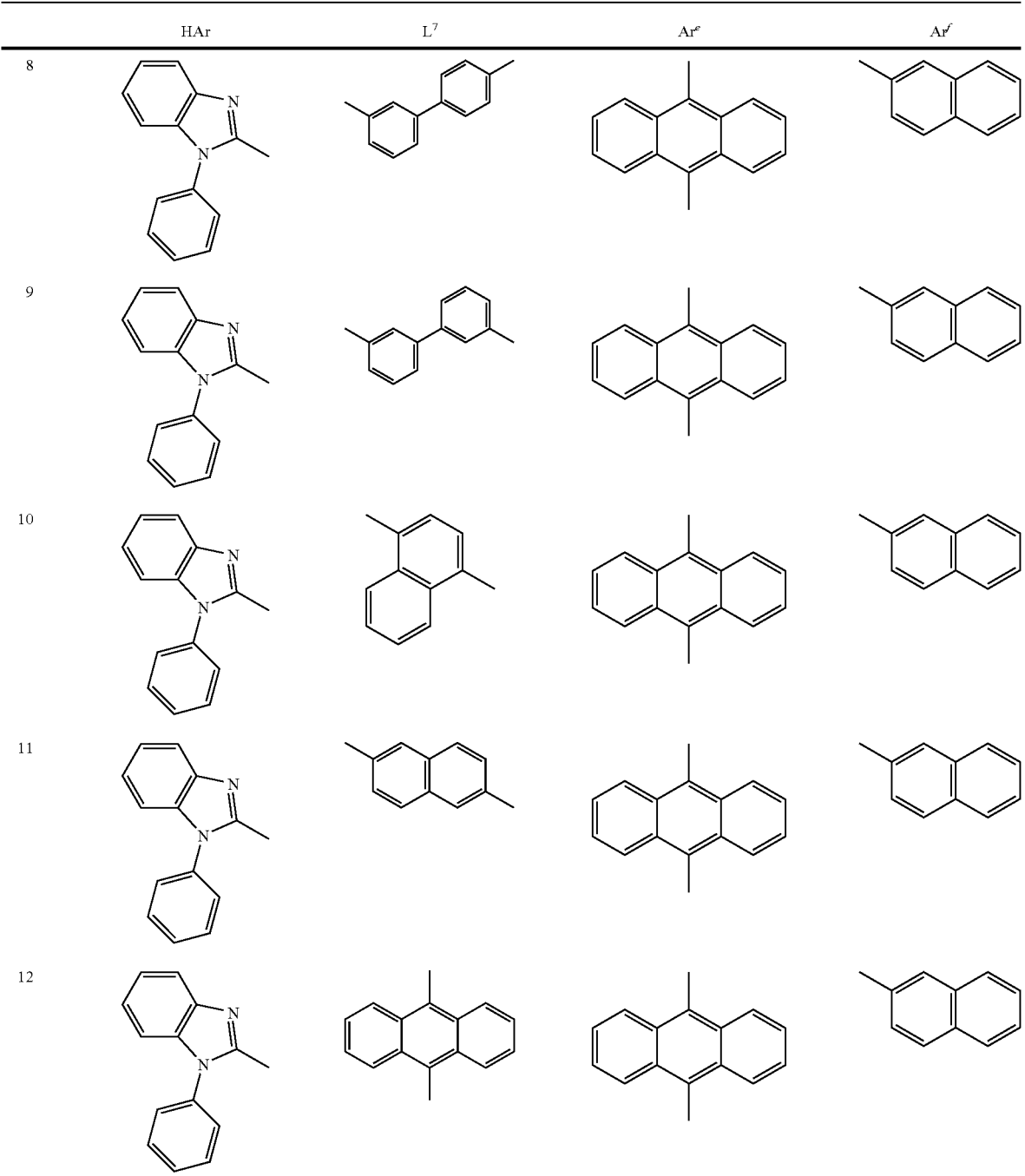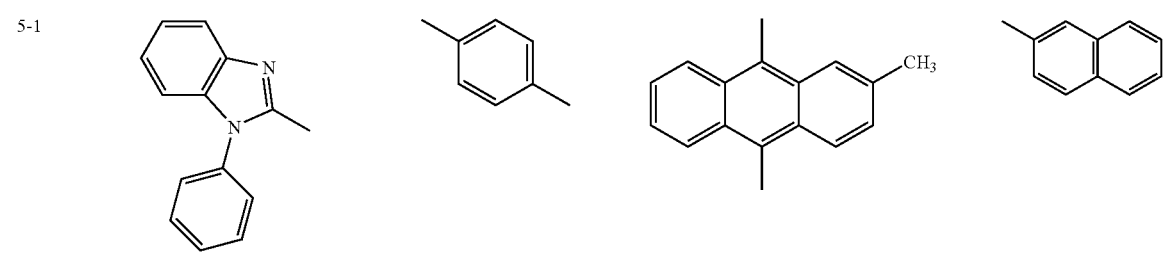

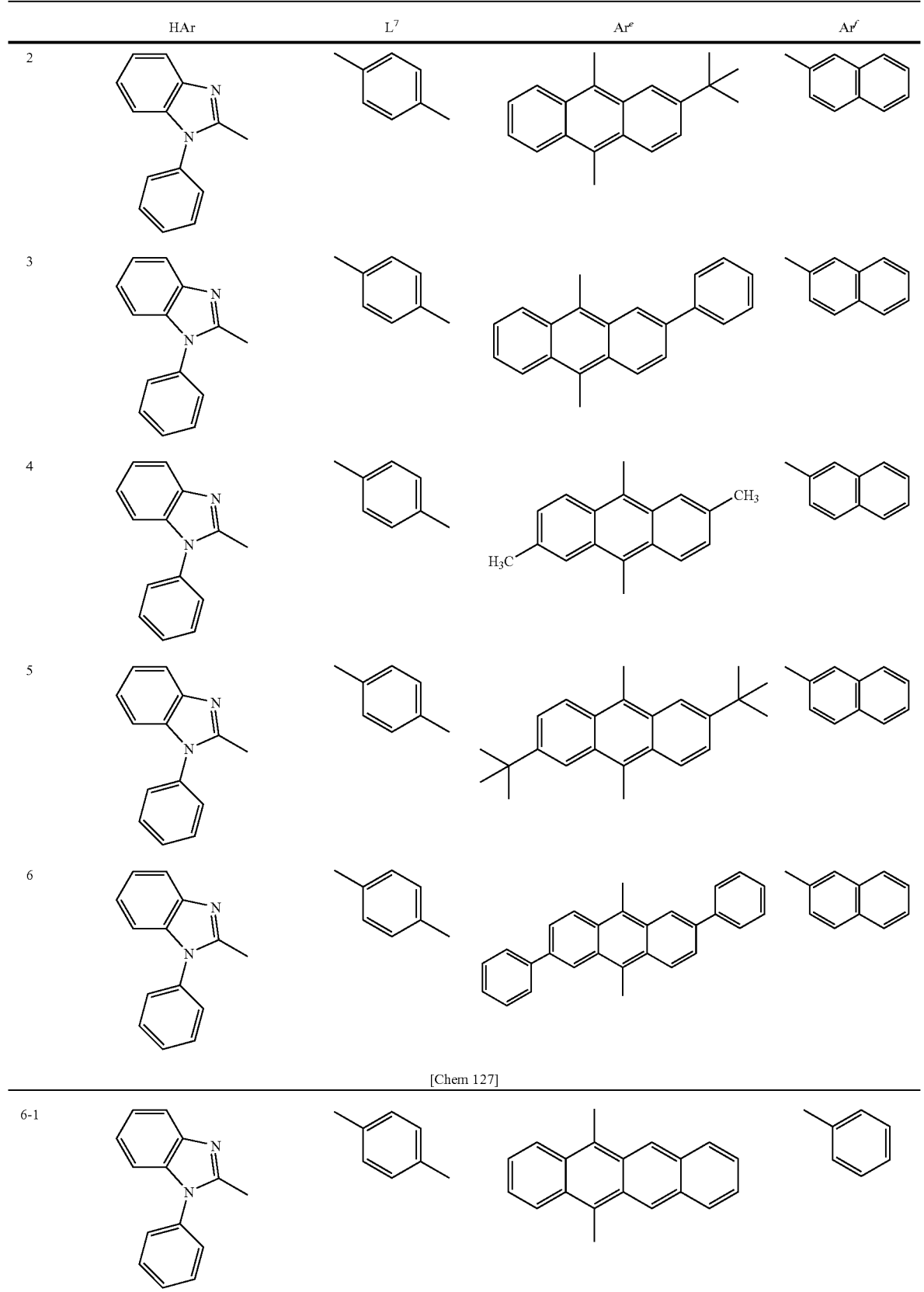

-continued
| HAr—L⁷—Arᵉ—Arᶠ | | | |
|---|---|---|---|
| HAr | L⁷ | Arᵉ | Arᶠ |
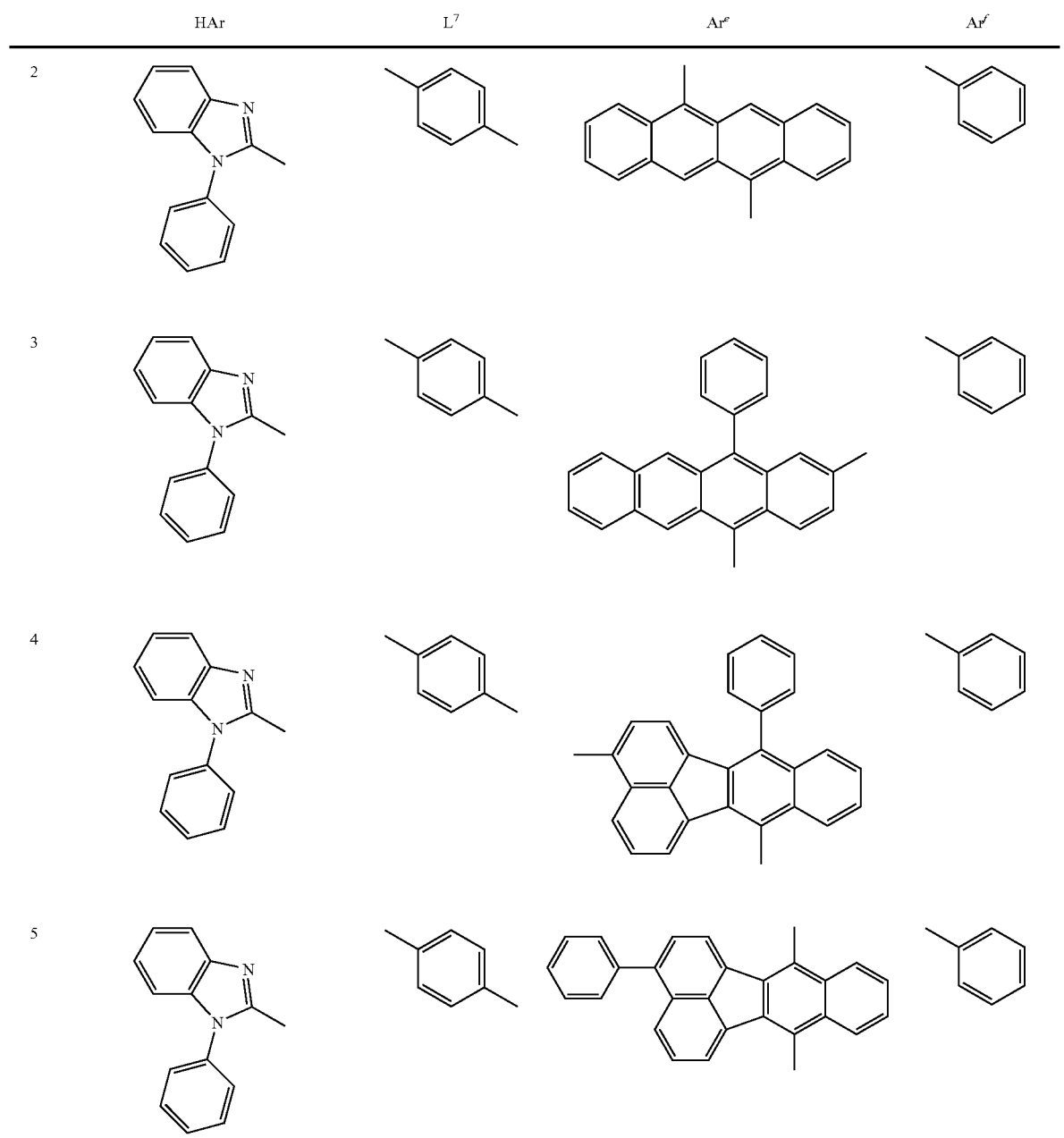
[Chem 128]
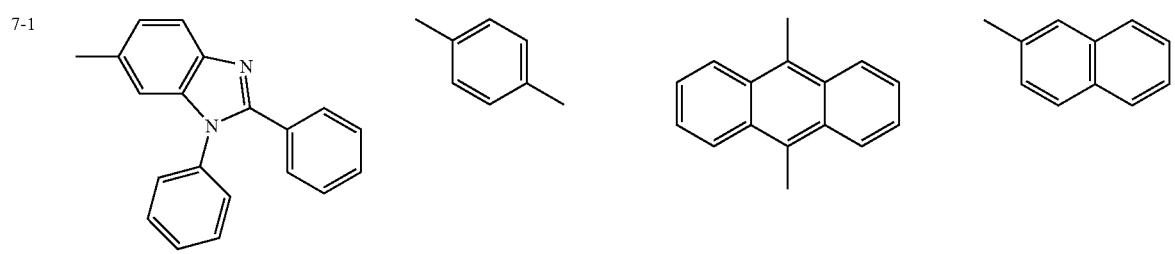

-continued

| | HAr—L⁷—Arᵉ—Ar^f | | | |
|---|---|---|---|---|
| | HAr | L⁷ | Arᵉ | Ar^f |
| 2 | (1,2-diphenyl-5-methylbenzimidazole) | p-phenylene | 9,10-dimethylanthracene | 2-methylnaphthalene |
| 3 | (1,2-diphenyl-4-methylbenzimidazole) | p-phenylene | 9,10-dimethylanthracene | 2-methylnaphthalene |
| 4 | (1,2-diphenyl-7-methylbenzimidazole) | p-phenylene | 9,10-dimethylanthracene | 2-methylnaphthalene |
| 5 | (1-phenyl-2-methyl-5-methylbenzimidazole) | p-phenylene | 9,10-dimethylanthracene | 2-methylnaphthalene |
| 6 | (1-methyl-2-phenyl-5-methylbenzimidazole) | p-phenylene | 9,10-dimethylanthracene | 2-methylnaphthalene |
| 7 | (1-phenyl-2-methyl-6-methylbenzimidazole) | p-phenylene | 9,10-dimethylanthracene | 2-methylnaphthalene |

-continued
| | HAr | L[7] | Ar[e] | Ar[f] |
|---|---|---|---|---|
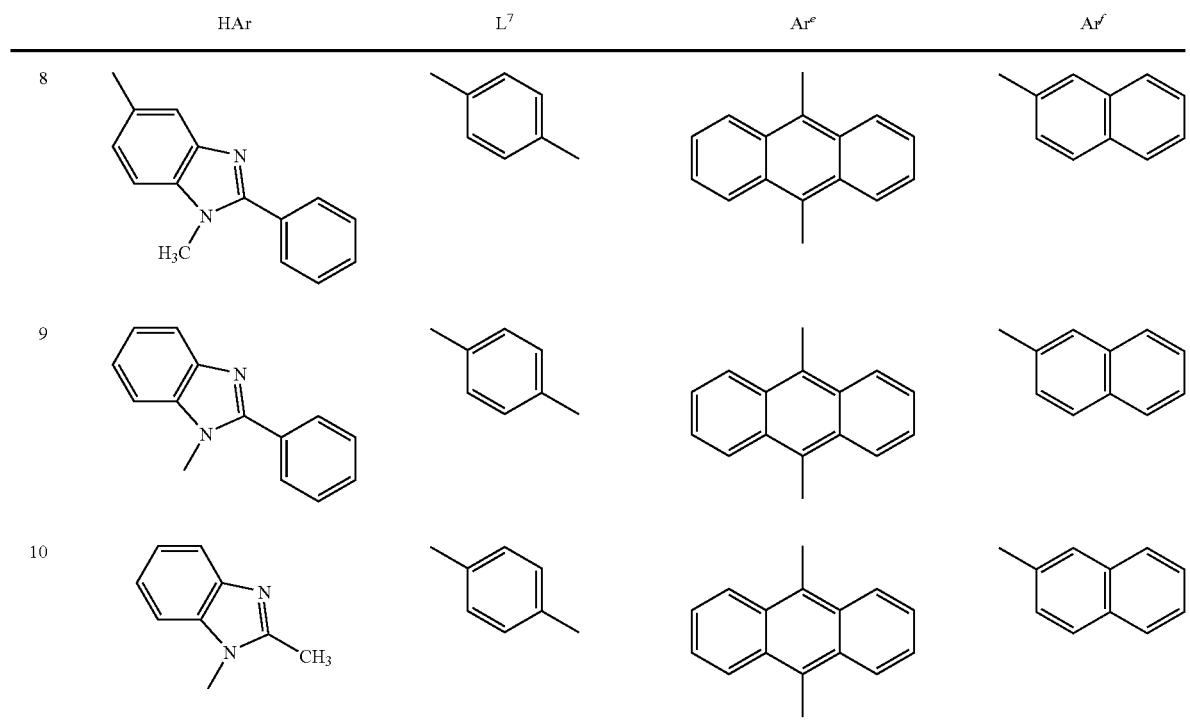
[Chem 129]
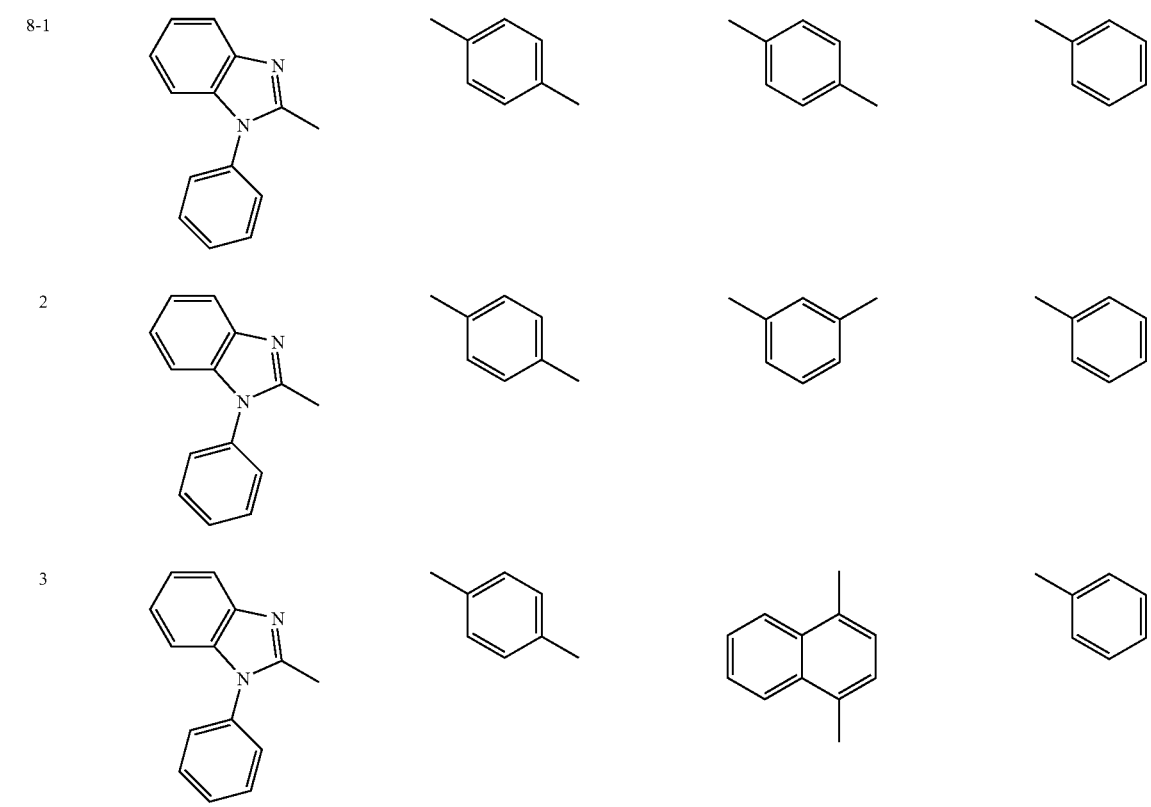

-continued
| | HAr | L[7] | Ar[e] | Ar[f] |
|---|---|---|---|---|
| 4 | 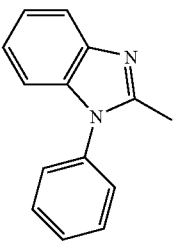 | 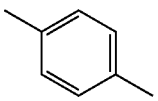 | 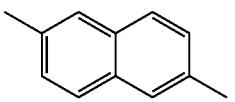 | 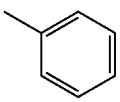 |
| 5 | 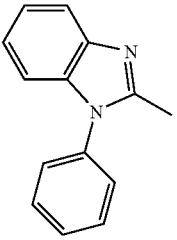 | 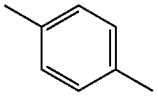 | 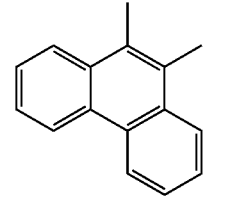 | 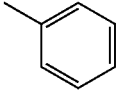 |
| 6 | 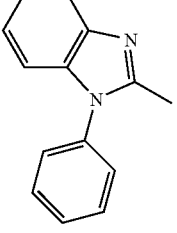 | 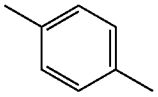 | 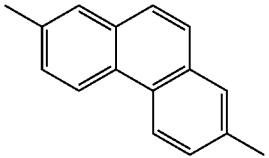 | 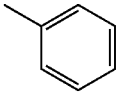 |
| 7 | 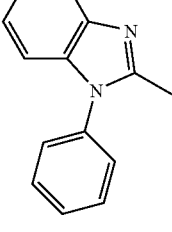 | 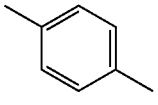 | 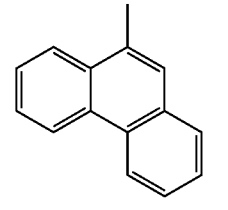 | —H |
| 8 | 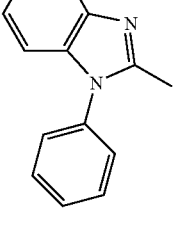 | 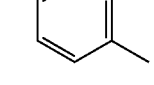 | 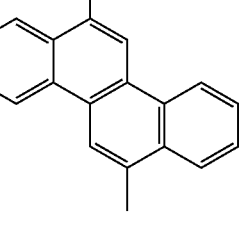 | 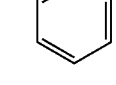 |
| 9 | 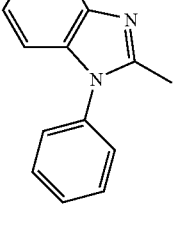 | 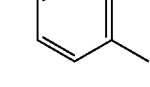 | 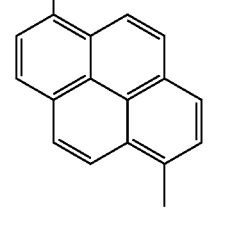 | 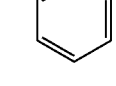 |

-continued
| | HAr | L⁷ | Arᵉ | Arᶠ |
|---|---|---|---|---|
| 10 | 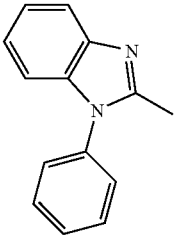 | 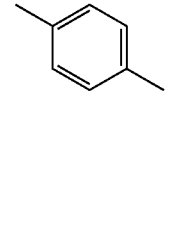 | 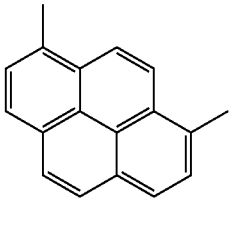 | 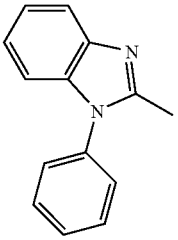 |
| 11 | 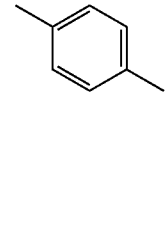 | 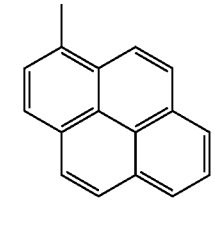 | 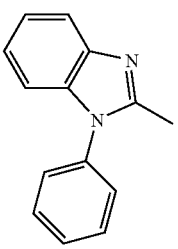 | —H |
| 12 | 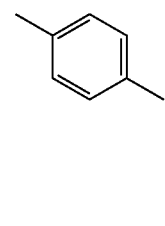 | 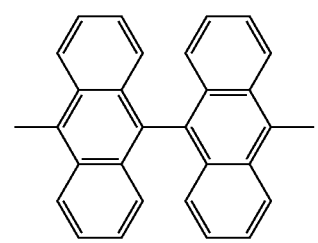 | 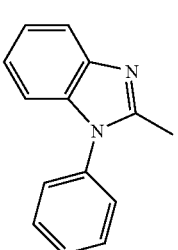 | 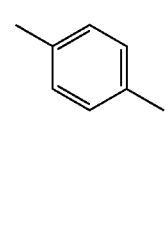 |
| 13 | 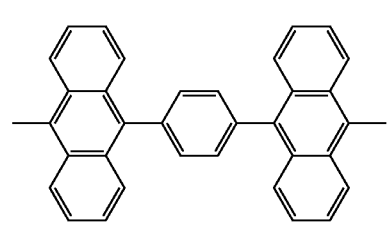 | 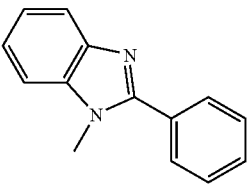 | 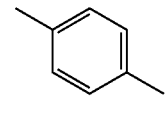 | 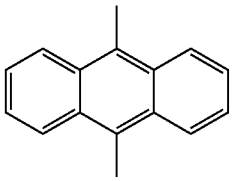 |
[Chem 130]
| | HAr | L⁷ | Arᵉ | Arᶠ |
|---|---|---|---|---|
| 9-1 | 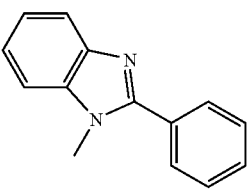 | 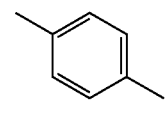 | 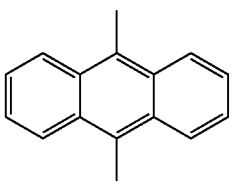 | |
| 2 | | | | |

-continued

| | HAr | L⁷ | Arᵉ | Arᶠ |
|---|---|---|---|---|
| 3 | | | | |
| 4 | | | | |
| 5 | | | | |
| 6 | | | | |
| 7 | | | | |
| 8 | | | | |
| 9 | | | | |

-continued

| | HAr | L⁷ | Arᵉ | Arᶠ |
|---|---|---|---|---|
| 10 | | | | |
| 11 | | | | |
| 12 | | | | |
| 13 | | | | |
| 14 | | | | |

[Chem 131]

| | HAr | L⁷ | Arᵉ | Arᶠ |
|---|---|---|---|---|
| 10-1 | | | | |
| 2 | | | | |

-continued
| | HAr | L[7] | Ar[e] | Ar[f] |
|---|---|---|---|---|
| 3 | 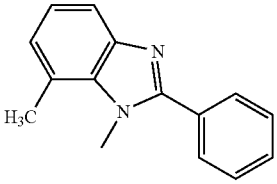 | 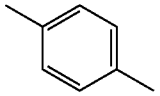 | 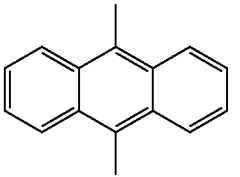 | 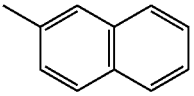 |
| 4 | 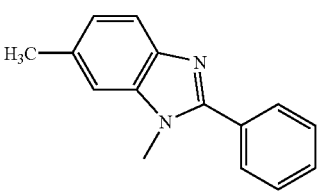 | 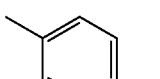 | 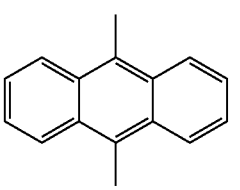 | 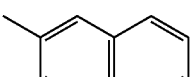 |
| 5 | 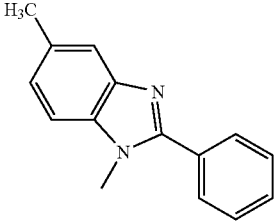 | 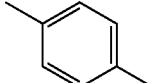 | 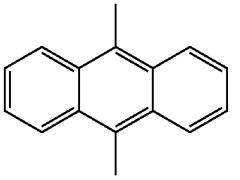 | 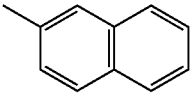 |
| 6 | 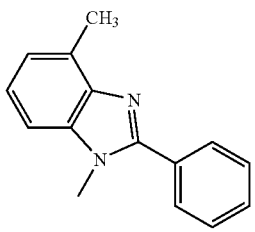 | 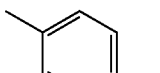 | 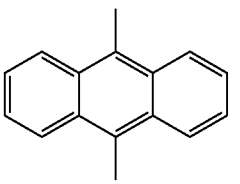 | 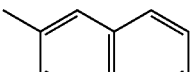 |
| 7 | 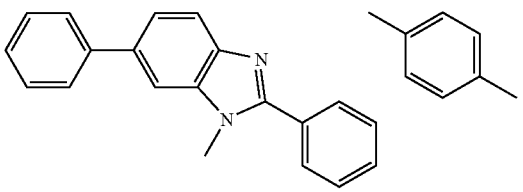 | 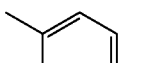 | 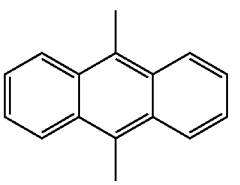 | 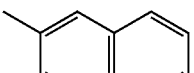 |
| 8 | 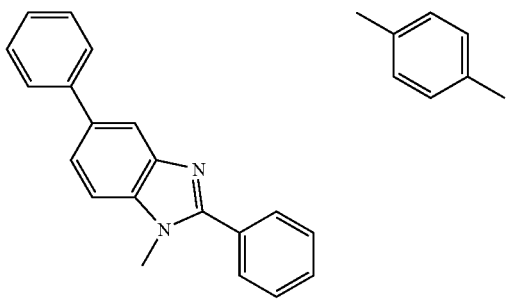 | 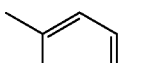 | 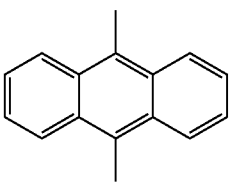 | 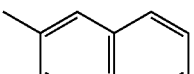 |

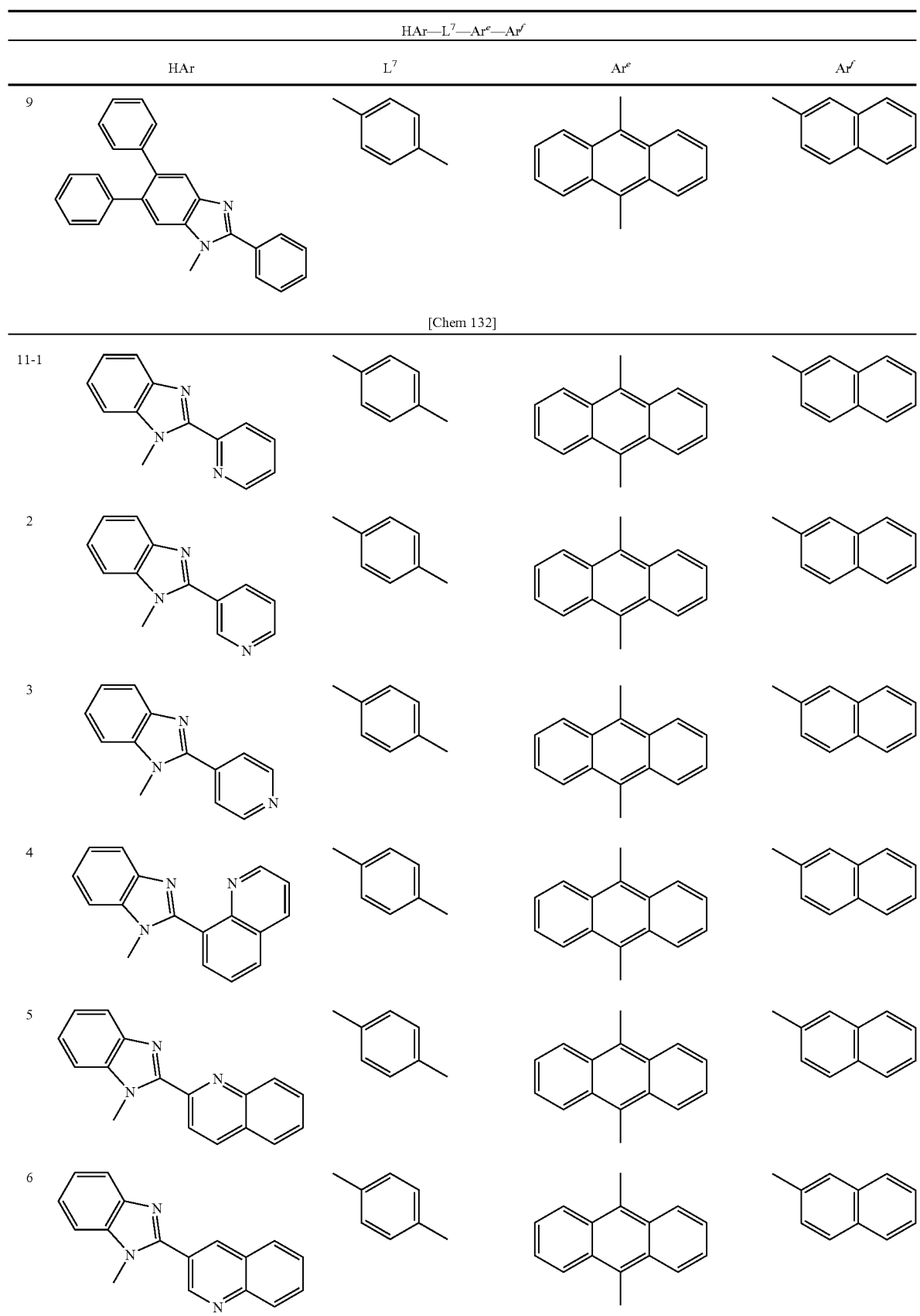

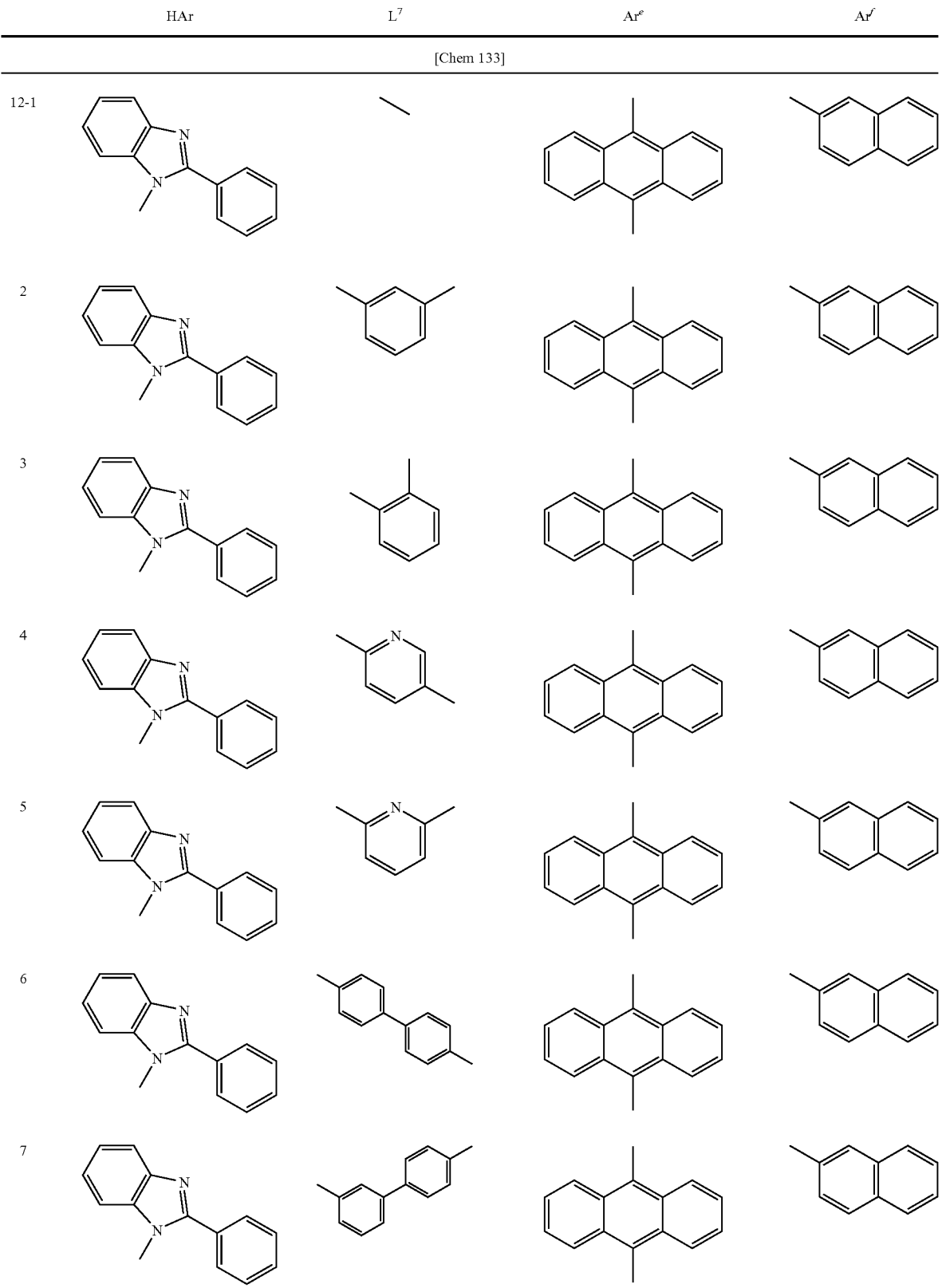

-continued
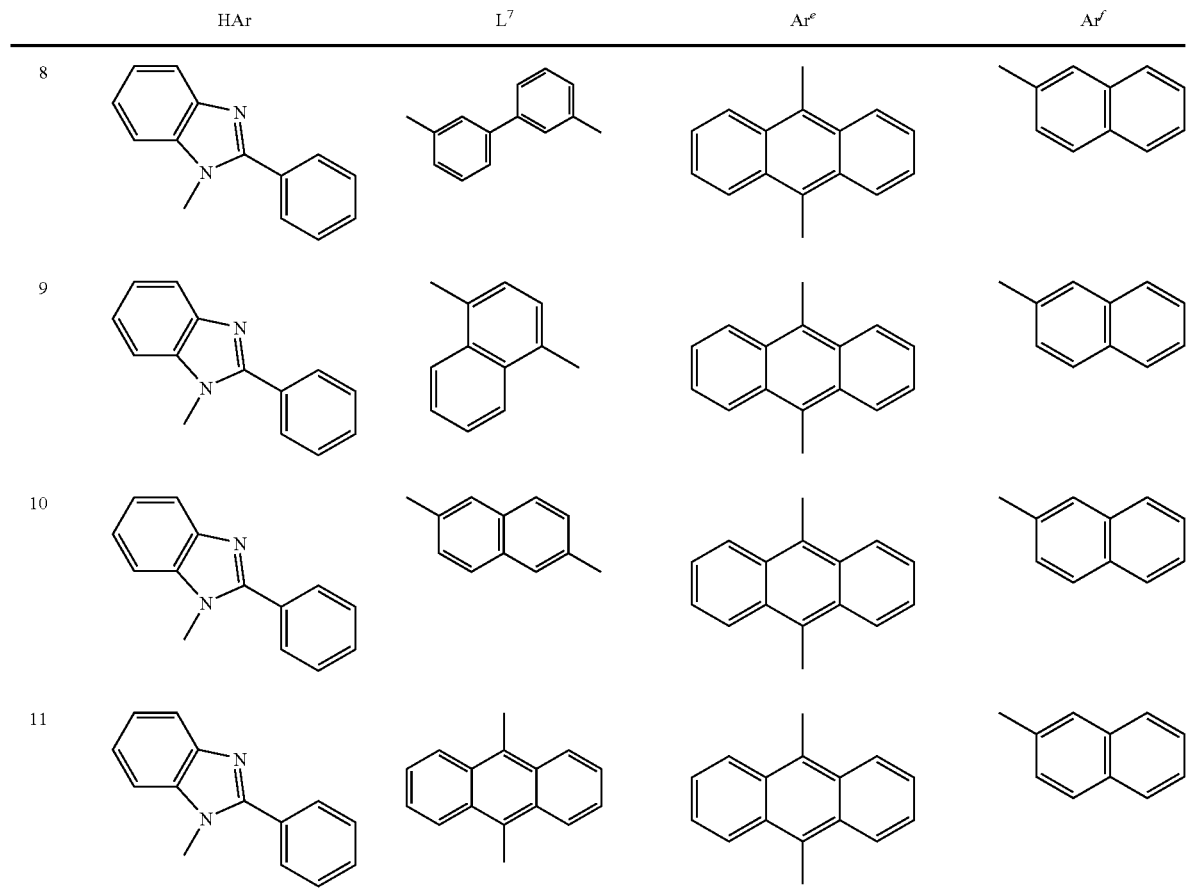
[Chem 134]
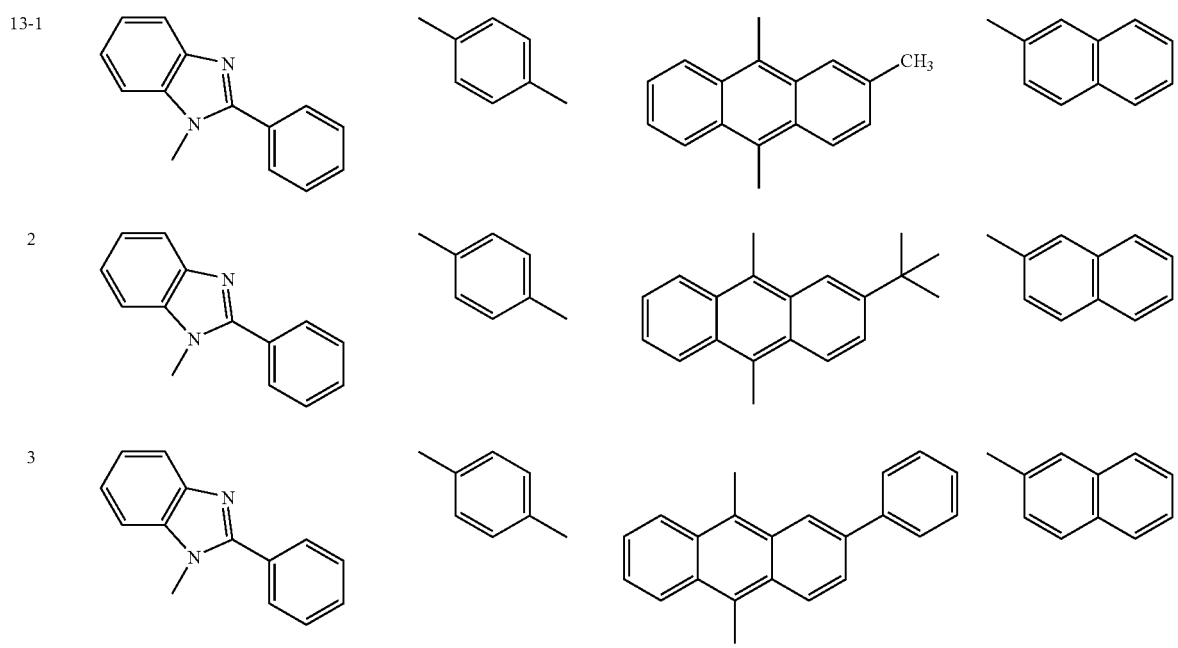

-continued
| | HAr | L[7] | Ar[e] | Ar[f] |
|---|---|---|---|---|
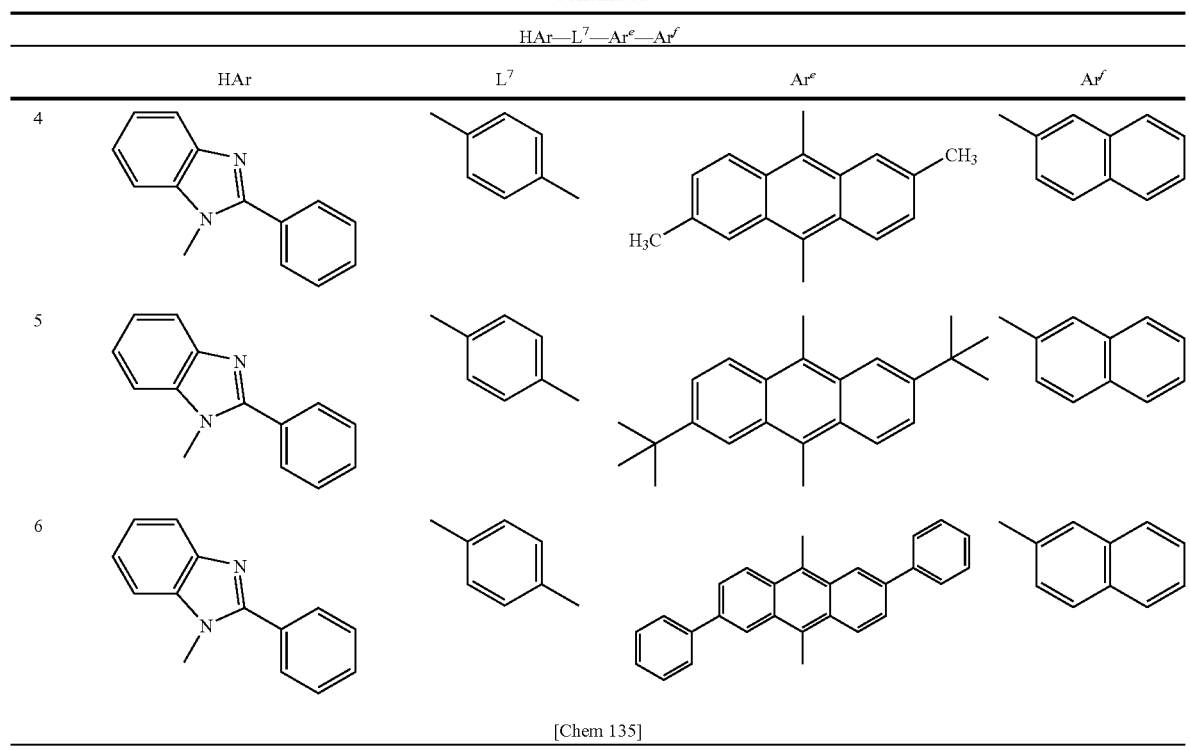
[Chem 135]
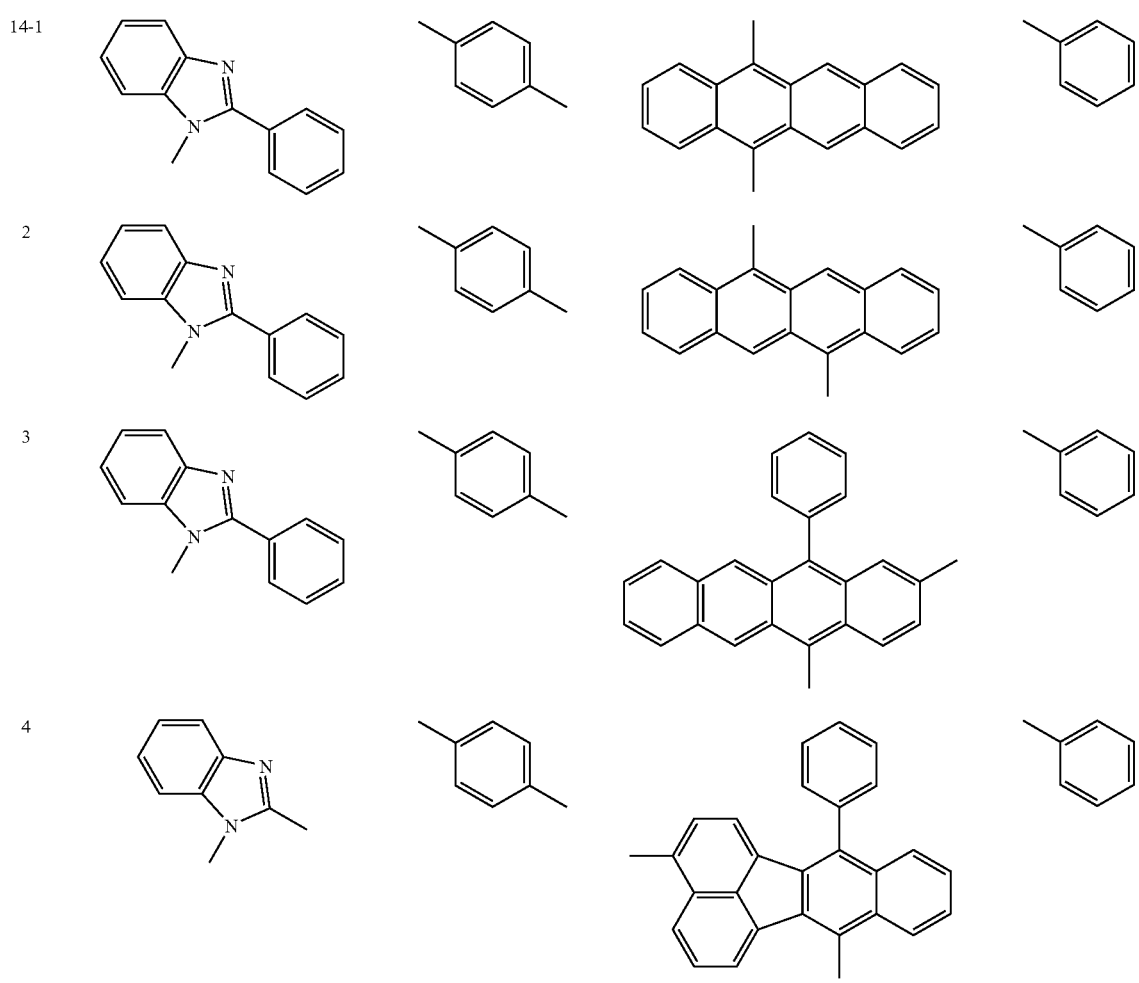

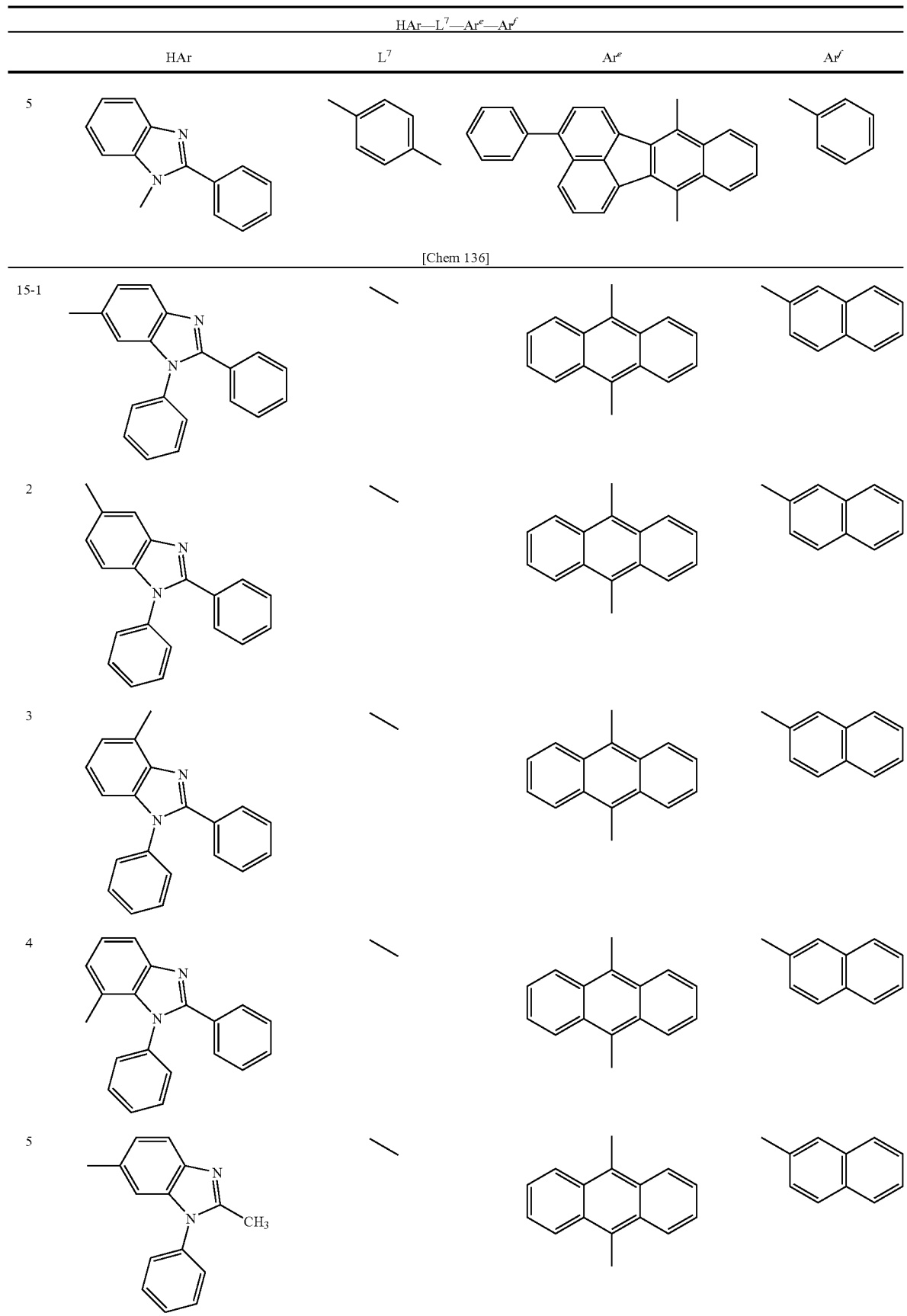

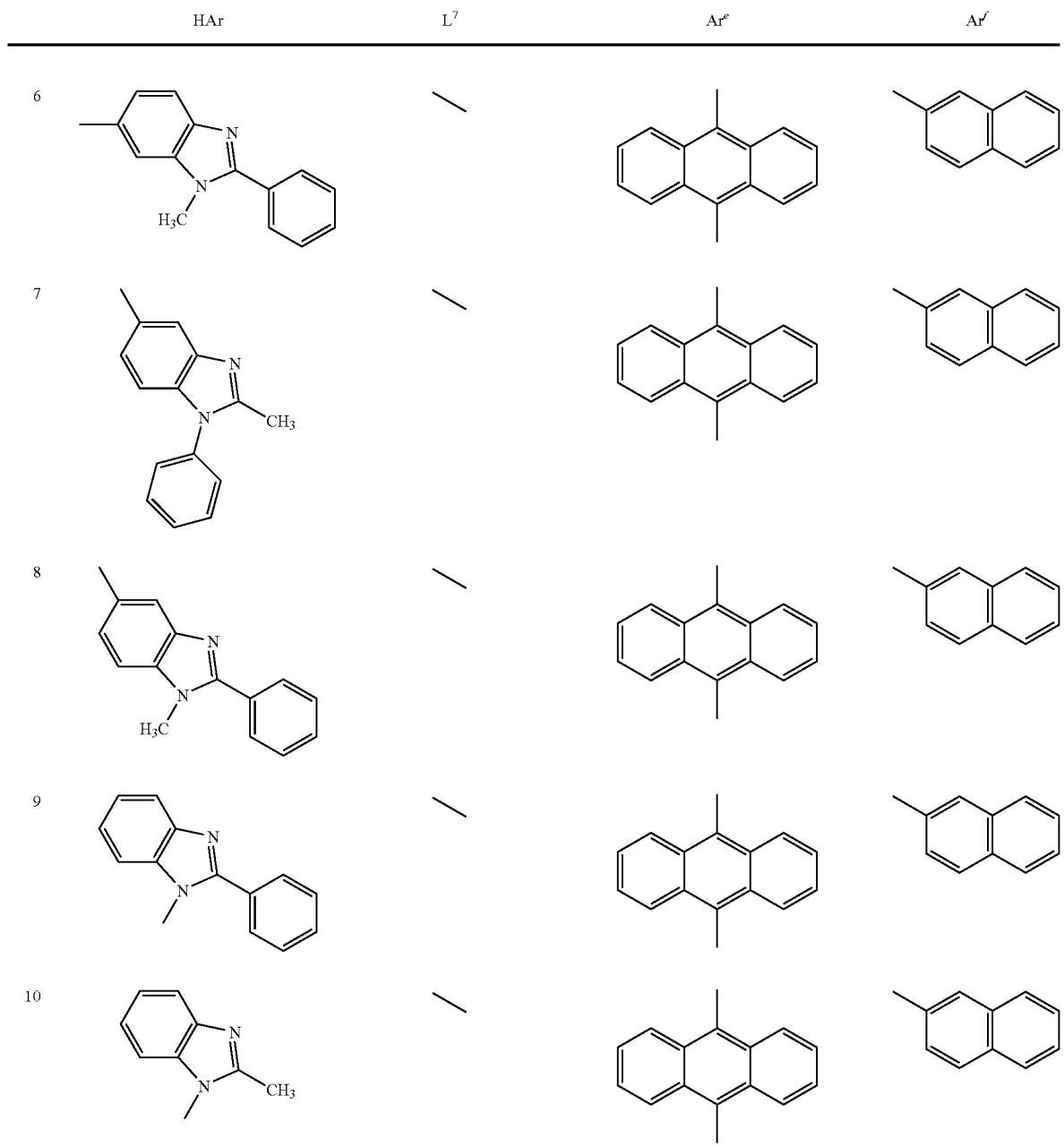
[Chem 137]
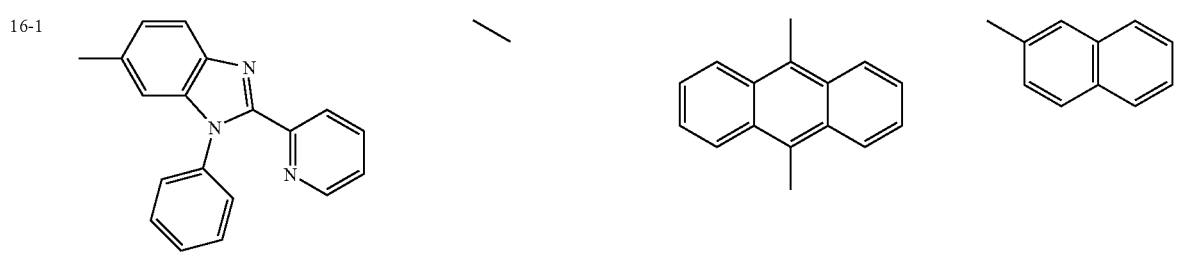

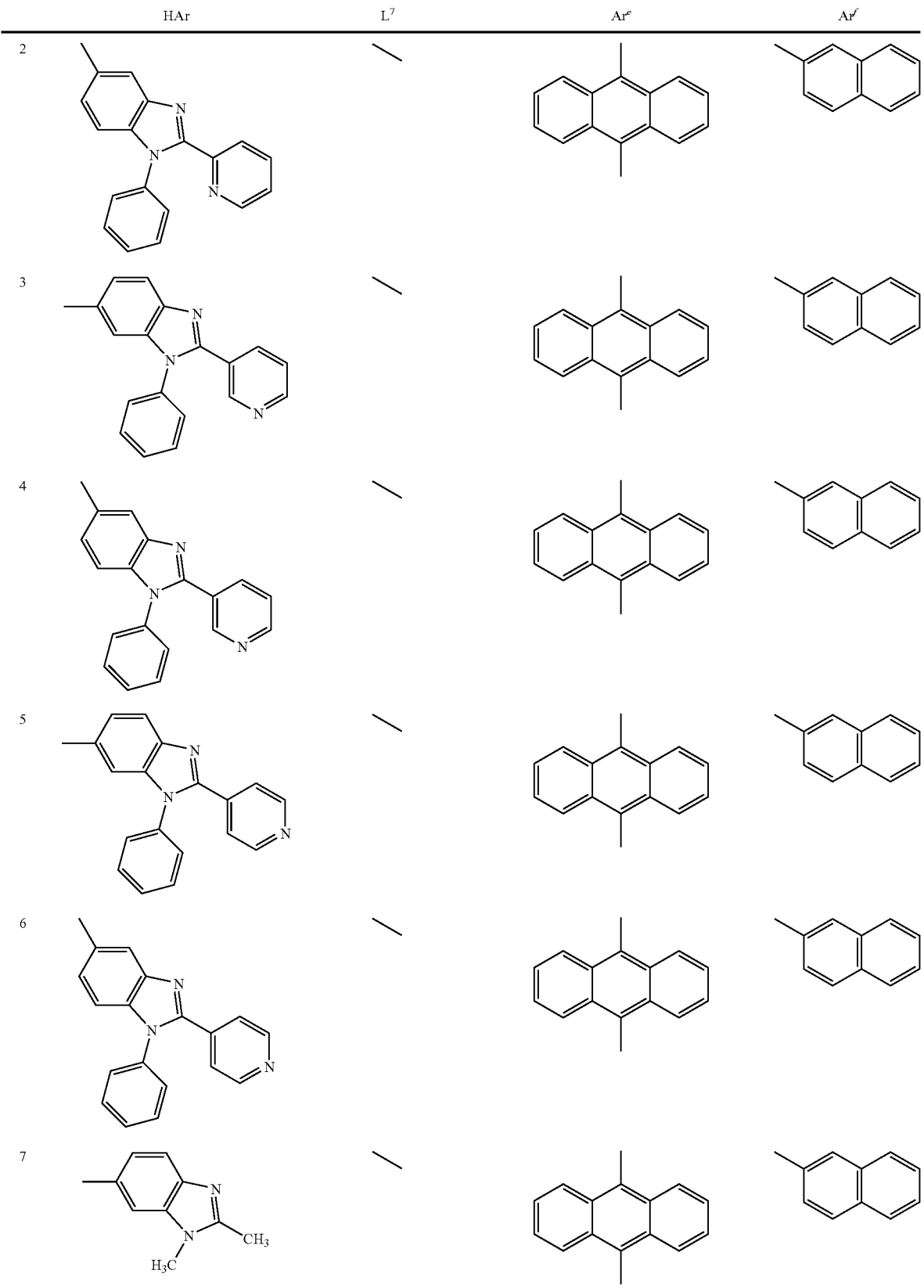

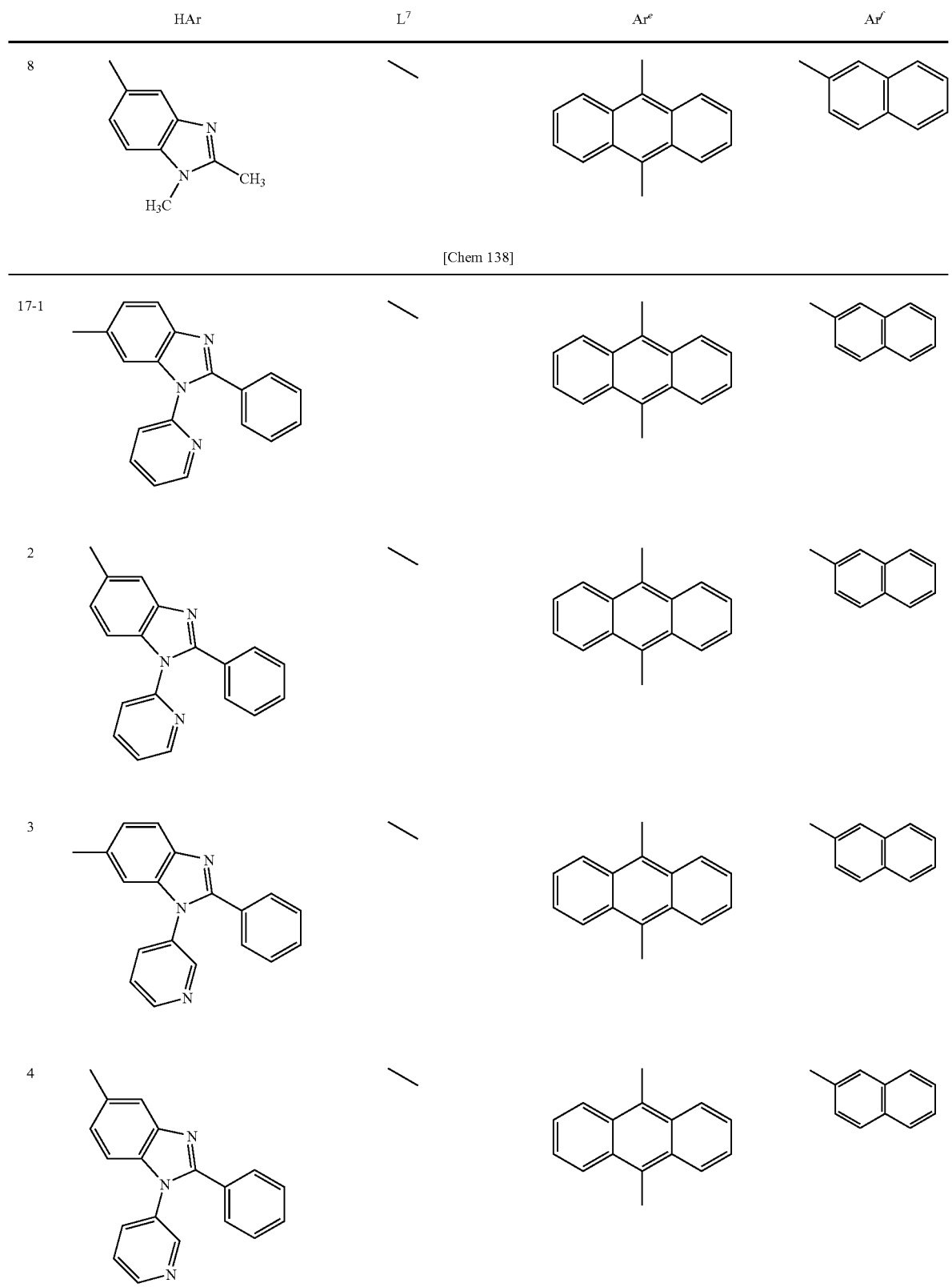

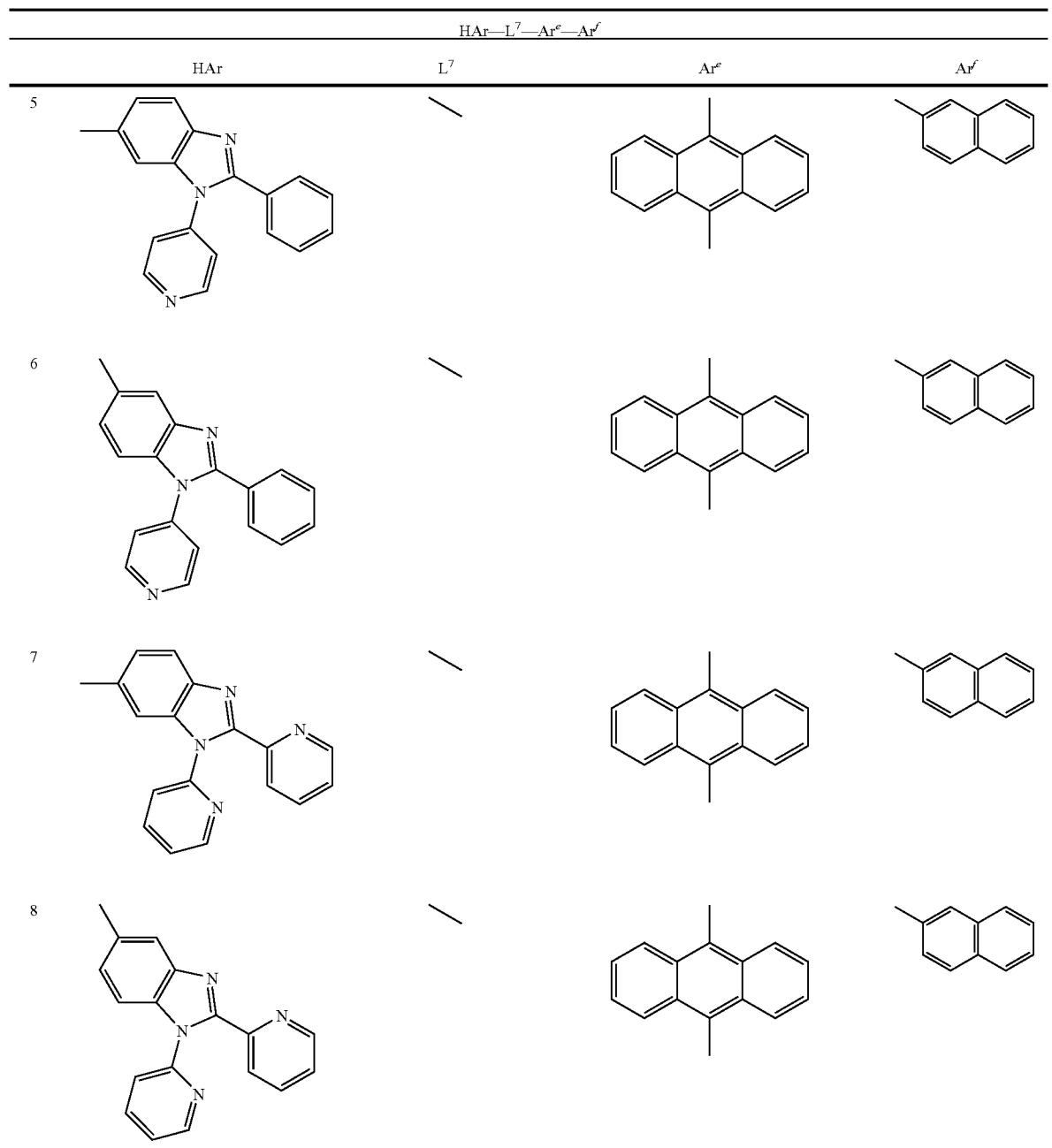

Of those specific examples, (1-1), (1-5), (1-7), (2-1), (3-1), (4-2), (4-6), (7-2), (7-7), (7-8), (7-9), (9-1), and (9-7) are particularly preferred.

In addition, as the nitrogen-containing ring derivative, nitrogen-containing five-membered ring derivative are also preferably exemplified. Examples of the nitrogen-containing five-membered ring include an imidazole ring, a triazole ring, a tetrazole ring, an oxadiazole ring, a thiadiazole ring, an oxatriazole ring, and a thiatriazole ring. Examples of the nitrogen-containing five-membered ring derivative include a benzoimidazole ring, a benzotriazole ring, a pyridinoimidazole ring, a pyrimidinoimidazole ring, and a pyridazinoimidazole ring. Particularly preferred is the compound represented by the following general formula (B).

[Chem 139]

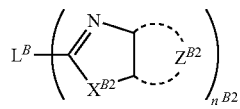

(B)

In the general formula (B), $L^B$ represents a divalent or more bonding group. Examples thereof include a carbon atom, a silicon atom, a nitrogen atom, a boron atom, an oxygen atom, a sulfur atom, metal atoms (for example, a barium atom, a beryllium atom), aromatic hydrocarbon rings, and aromatic heterocycles. Of those, preferred are a carbon atom, a nitrogen atom, a silicon atom, a boron atom, an oxygen atom, a sulfur atom, aromatic hydrocarbon rings, and aromatic heterocyclic groups, and more preferred are a carbon atom, a silicon atom, aromatic hydrocarbon rings, and aromatic heterocyclic groups.

The aromatic hydrocarbon rings and aromatic heterocyclic groups represented by $L^B$ may have a substituent. Examples of the substituent include alkyl groups, alkenyl groups, aryl groups, amino groups, alkoxy groups, aryloxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, sulfonyl groups, halogen atoms, cyano groups, and aromatic heterocyclic groups. Preferred are alkyl groups, aryl groups, alkoxy groups, aryloxy groups, halogen atoms, cyano groups, and aromatic heterocyclic groups, more preferred are alkyl groups, aryl groups, alkoxy groups, aryloxy groups, and aromatic heterocyclic groups, and particularly preferred are alkyl groups, aryl groups, alkoxy groups, and aromatic heterocyclic groups.

Specific examples of $L^B$ include compounds represented below.

[Chem 140]

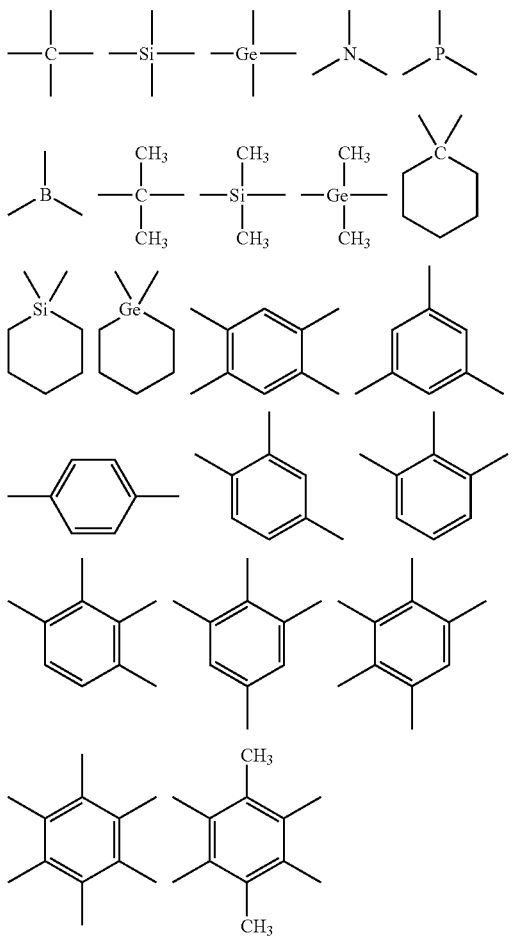

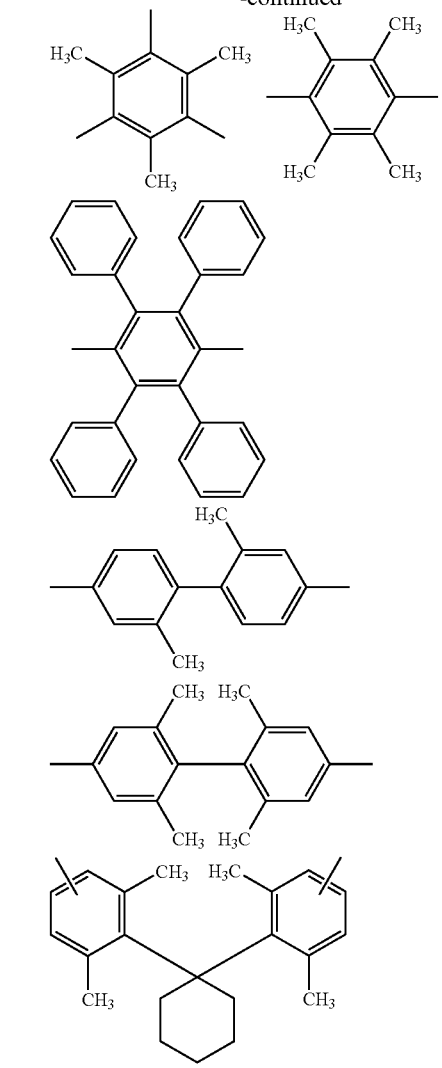

$X^{B2}$ in the general formula (B) represents —O—, —S—, or —N($R^{B2}$)—. $R^{B2}$ represents a hydrogen atom, an aliphatic hydrocarbon group, an aryl group, or a heterocyclic group.

The aliphatic hydrocarbon group represented by $R^{B2}$ is a linear or branched alkyl group (having preferably 1 to 20, more preferably 1 to 12, or particularly preferably 1 to 8 carbon atoms such as a methyl group, an ethyl group, an isopropyl group, a t-butyl group, an n-octyl group, an n-decyl group, or an n-hexadecyl group), a cycloalkyl group (having preferably 3 to 10 carbon atoms forming the ring such as a cyclopropyl group, a cyclopentyl group, or a cyclohexyl group), an alkenyl group (having preferably 2 to 20, more preferably 2 to 12, or particularly preferably 2 to 8 carbon atoms such as a vinyl group, an allyl group, a 2-butenyl group, or a 3-pentenyl group), or an alkynyl group (having preferably 2 to 20, more preferably 2 to 12, or particularly preferably 2 to 8 carbon atoms such as a propargyl group or a 3-pentynyl group), or is preferably an alkyl group.

The aryl group represented by $R^{B2}$ is a monocycle or a fused ring, and is an aryl group having preferably 6 to 30, more preferably 6 to 20, or still more preferably 6 to 12 carbon atoms forming the ring. Examples of such groups include a phenyl group, a 2-methylphenyl group, a 3-methylphenyl group, a 4-methylphenyl group, a 2-methoxyphenyl group, a 3-trifluoromethylphenyl group, a pentafluorophenyl group, a 1-naphthyl group, and a 2-naphthyl group. Of those, a phenyl group or a 2-methylphenyl group is preferable.

The heterocyclic group represented by $R^{B2}$ is a monocycle or a fused ring, and is a heterocyclic group having preferably 1 to 20, more preferably 1 to 12, or still more preferably 2 to 10 carbon atoms forming the aromatic ring. The heterocyclic group is an aromatic heterocyclic group containing at least one heteroatom selected from a nitrogen atom, an oxygen atom, a sulfur atom, and a selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, azepine, and the like. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

The aliphatic hydrocarbon group, the aryl group, and the heterocyclic group each represented by $R^{B2}$ may each have a substituent, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or an aromatic heterocyclic group, more preferably an alkyl group, an aryl group, an alkoxy group, an aryloxy group, a halogen atom, a cyano group, or an aromatic heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$R^{B2}$ preferably represents an aliphatic hydrocarbon group, an aryl group, or a heterocyclic group, more preferably represents an aliphatic hydrocarbon group (having preferably 6 to 30, more preferably 6 to 20, or still more preferably 6 to 12 carbon atoms) or an aryl group, or still more preferably represents an aliphatic hydrocarbon group (having preferably 1 to 20, more preferably 1 to 12, or still more preferably 2 to 10 carbon atoms).

$X^{B2}$ preferably represents —O— or —N($R^{B2}$)—, or more preferably represents —N($R^{B2}$)—.

$Z^{B2}$ represents atoms necessary for forming an aromatic ring. The aromatic ring formed of $Z^{B2}$ is any one of aromatic hydrocarbon rings and aromatic heterocyclic rings. Specific examples thereof include a benzene ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellulazole ring, a thiadiazole ring, an oxadiazole ring, and a pyrazole ring. Preferred are a benzene ring, a pyridine ring, a pyrazine ring, a pyrimidine ring, and a pyridazine ring, more preferred are a benzene ring, a pyridine ring, and a pyrazine ring, still more preferred are a benzene ring and a pyridine ring, and particularly preferred is a pyridine ring.

The aromatic ring formed of $Z^{B2}$ may further form a fused ring with any other rings, or may have a substituent. Examples of the substituent include the same examples as those described for the substituent of the group represented by $L^{B}$, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or a heterocyclic group, more preferably an alkyl group, an aryl group, an alkoxy group, an aryloxy group, a halogen atom, a cyano group, or a heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$n^{B2}$ represents an integer of 1 to 4, or preferably 2 or 3.

Of the nitrogen-containing five-membered ring derivatives each represented by the general formula (B), a derivative represented by the following general formula (B') is more preferable.

[Chem 141]

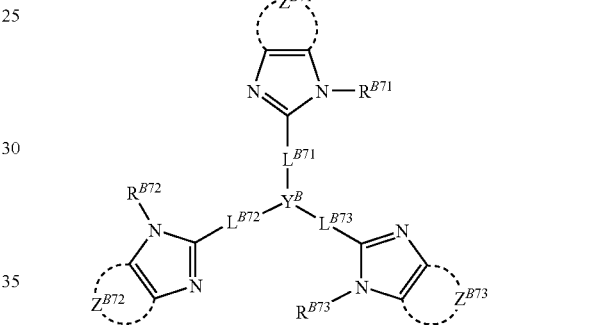

(B')

In the general formula (B'), $R^{B71}$, $R^{B72}$, and $R^{B73}$ each have the same meaning as that of $R^{B2}$ in the general formula (B), and the preferable ranges of $R^{B71}$, $R^{B72}$, and $R^{B73}$ are also the same as those of $R^{B2}$.

In the formula, $Z^{B71}$, $Z^{B72}$ and $Z^{B73}$ each have the same meaning as that of $Z^{B2}$ in the general formula (B), and the preferable ranges of $Z^{B71}$, $Z^{B72}$, and $Z^{B73}$ are also the same as those of $Z^{B2}$.

In the formula, $L^{B71}$, $L^{B72}$, and $L^{B73}$ each represent a linking group, and examples of the linking group include examples obtained by making the examples of $L^{B}$ in the general formula (B) divalent. The linking group is preferably a single bond, a divalent aromatic hydrocarbon ring group, or a linking group composed of a combination of two or more of them, or is more preferably a single bond. $L^{B71}$, $L^{B72}$, and $L^{B73}$ may each have a substituent. Examples of the substituent include the same examples as those described for the substituent of the group represented by $L^{B}$ in the general formula (B), and preferable examples of the substituent also include the same preferable examples as those described for the substituent of the group represented by $L^{B}$ in the general formula (B).

In the formula, $Y^{B}$ represents a nitrogen atom, a 1,3,5-benzenetriyl group, or a 2,4,6-triazinetriyl group. The 1,3,5-benzenetriyl group may have a substituent at any one of its 2-, 4-, and 6-positions, and examples of the substituent include an alkyl group, an aromatic hydrocarbon ring group, and a halogen atom.

Specific examples of the nitrogen-containing five-membered ring derivative represented by the general formula (B)

or (B') are shown below. However, the present invention is not limited to these exemplified compounds.
[Chem 142]
(B-1)
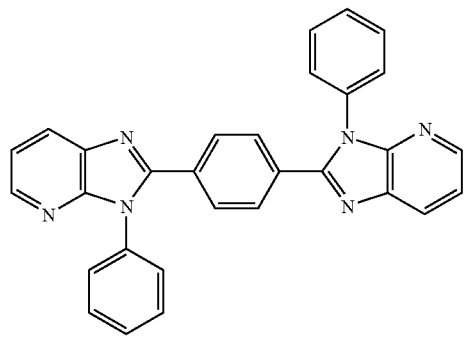
(B-2)
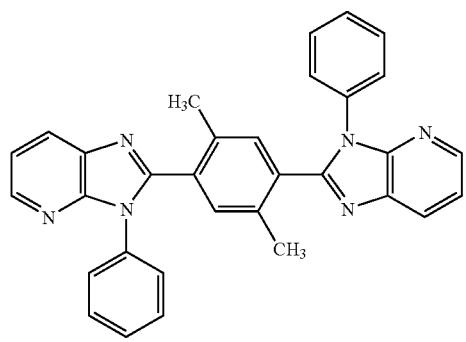
(B-3)
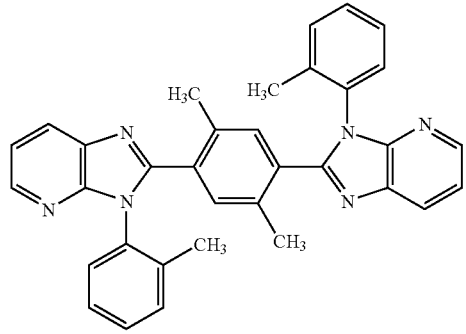
(B-4)
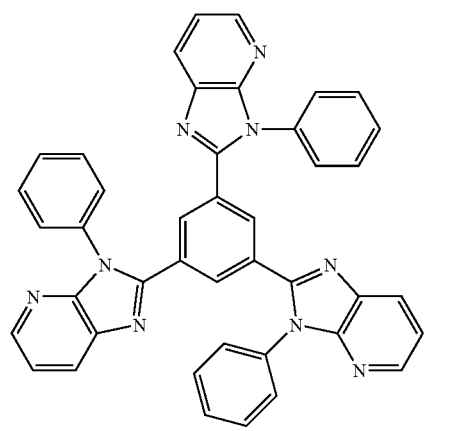
-continued
(B-5)
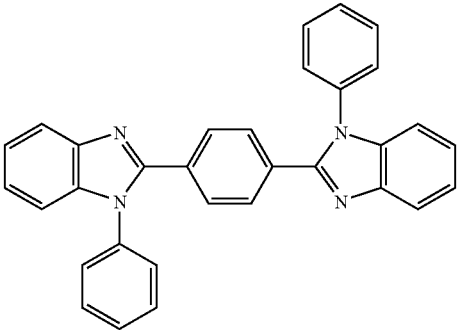
(B-6)
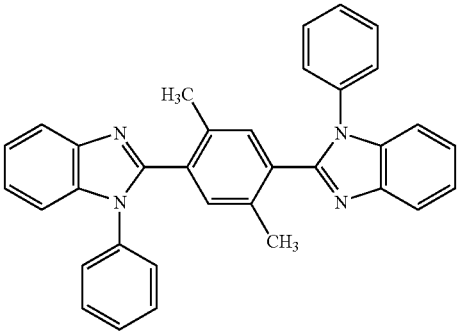
(B-7)
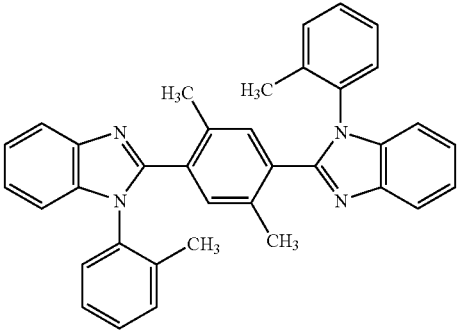
(B-8)
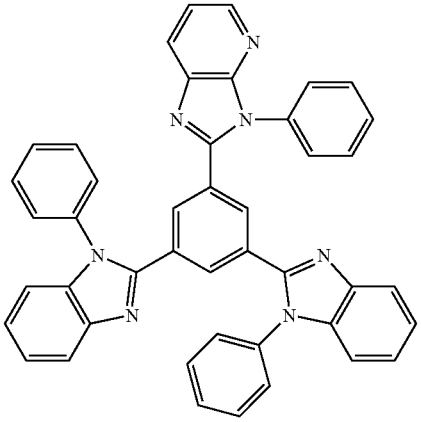

[Chem 143]
(B-9)
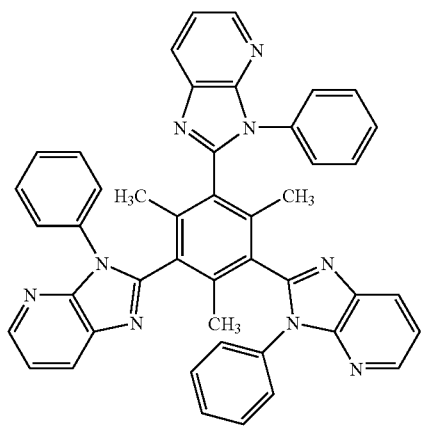
(B-12)
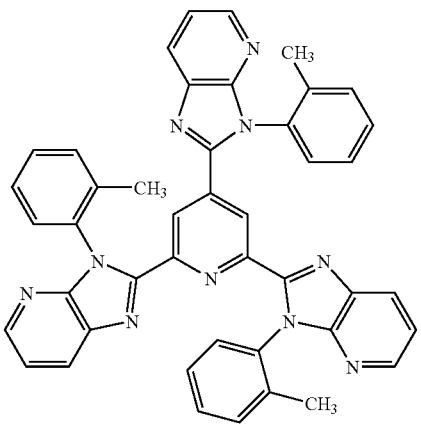
(B-10)
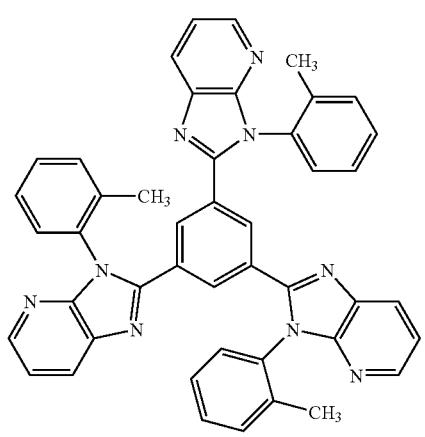
(B-13)
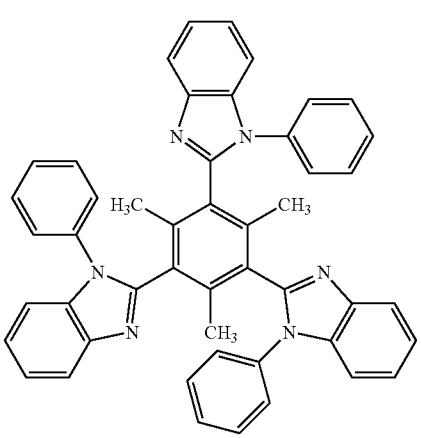
(B-11)
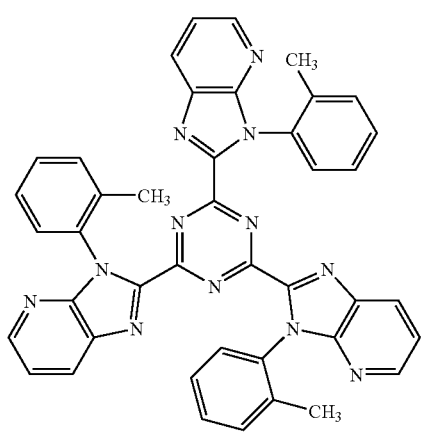
(B-14)

(B-15)

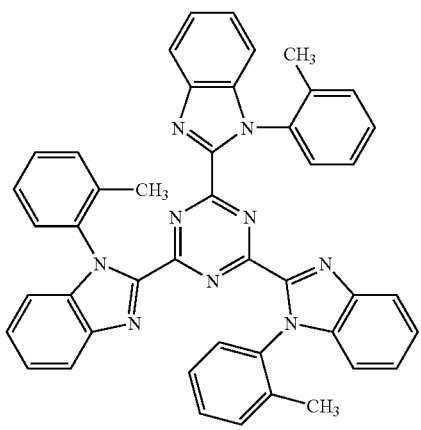

[Chem 144]

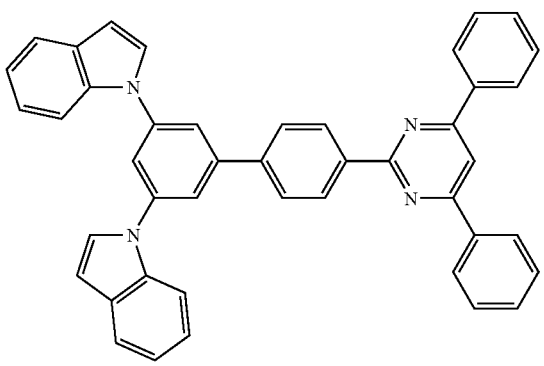

(B-16)

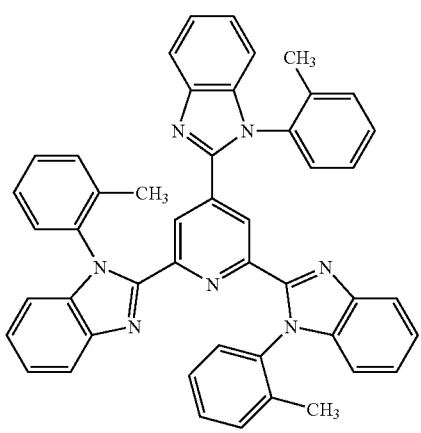

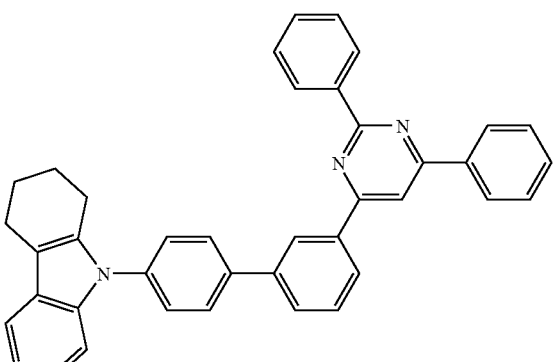

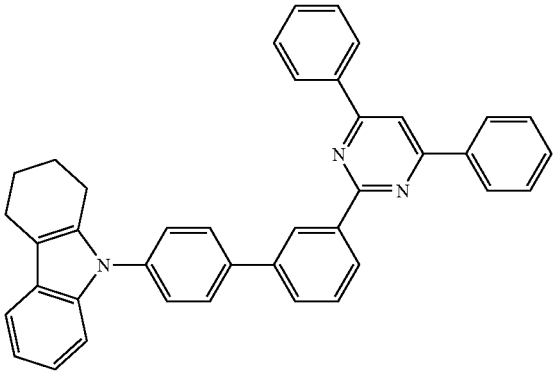

A compound of which each of the electron injecting layer and the electron transporting layer is constituted is, for example, a compound having a structure obtained by combining an electron-deficient, nitrogen-containing five-membered ring skeleton or electron-deficient, nitrogen-containing six-membered ring skeleton and a substituted or unsubstituted indole skeleton, substituted or unsubstituted carbazole skeleton, or substituted or unsubstituted azacarbazole skeleton as well as the polycyclic compound of the present invention. In addition, a suitable electron-deficient, nitrogen-containing five-membered ring skeleton or electron-deficient, nitrogen-containing six-membered ring skeleton is a molecular skeleton such as a pyridine, pyrimidine, pyrazine, triazine, triazole, oxadiazole, pyrazole, imidazole, quinoxaline, or pyrrole skeleton, or benzimidazole or imidazopyridine obtained when two or more of them fuse with each other. Of those combinations, a preferable combination is, for example, a combination of a pyridine, pyrimidine, pyrazine, or triazine skeleton and a carbazole, indole, azacarbazole, or quinoxaline skeleton. The above-mentioned skeleton may be substituted or unsubstituted.

Specific examples of an electron transportable compound are shown below. However, the present invention is not particularly limited to these examples.

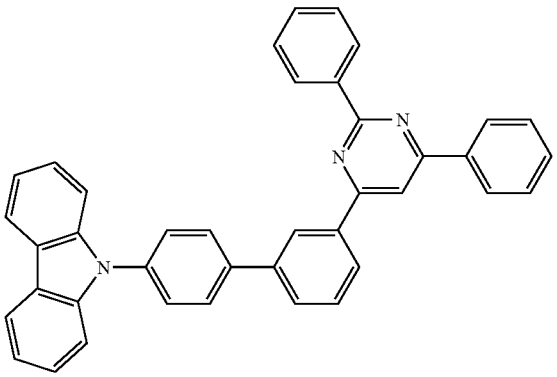

435
-continued
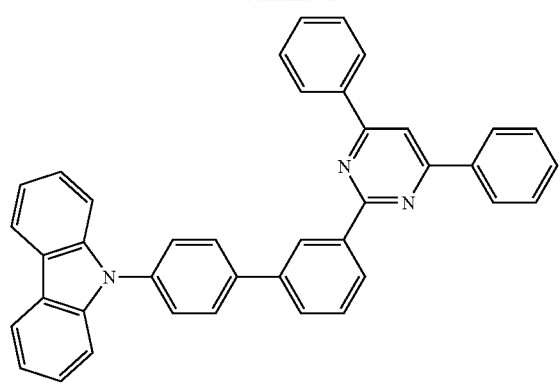
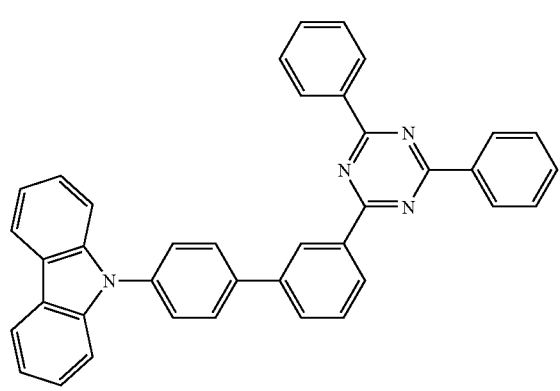
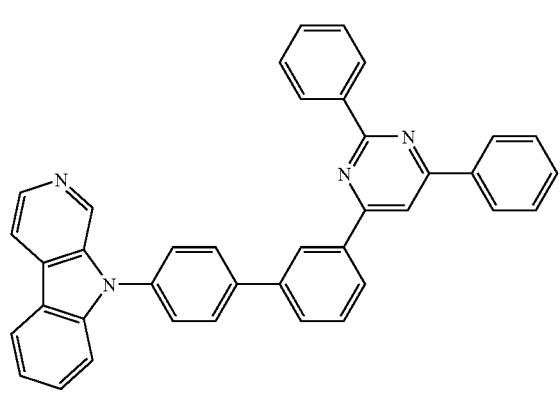
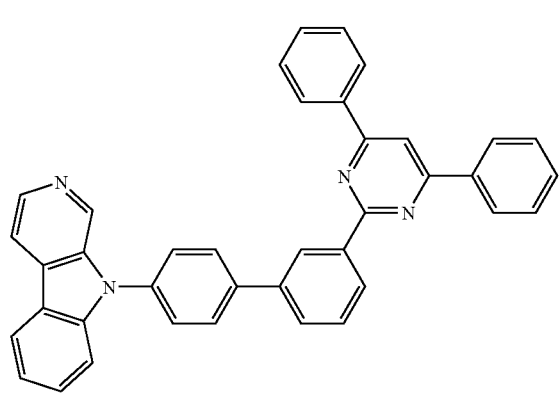
436
-continued
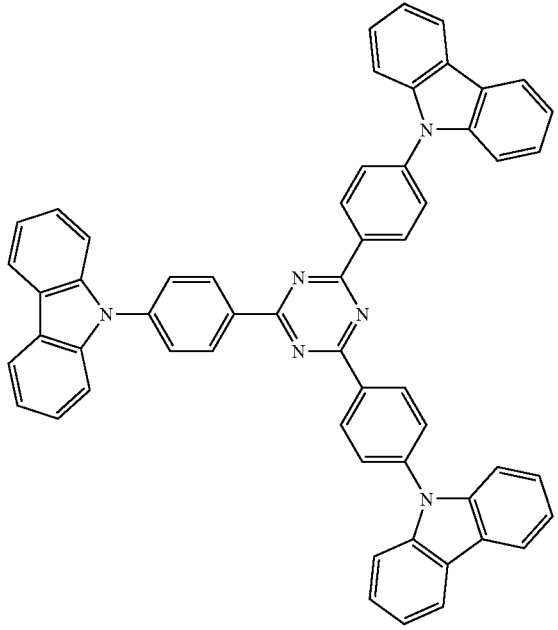
[Chem 145]
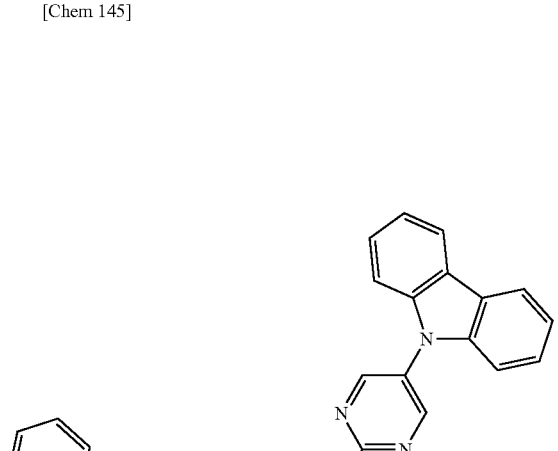
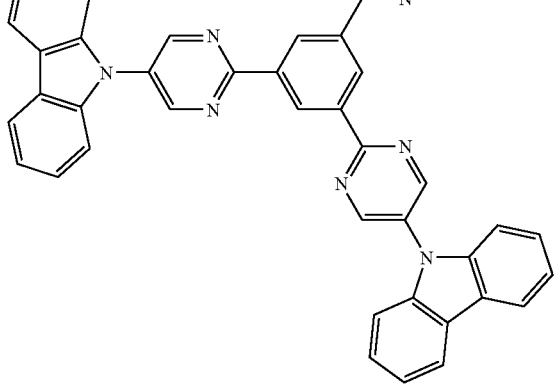

437
-continued
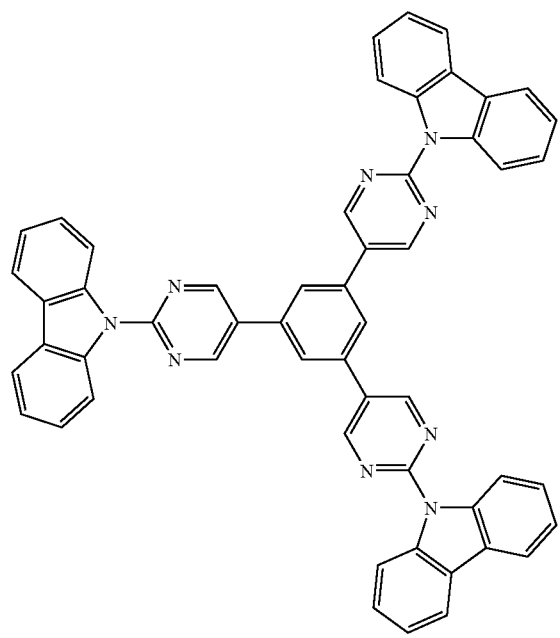
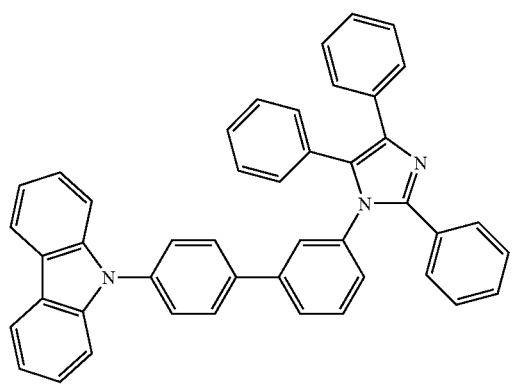
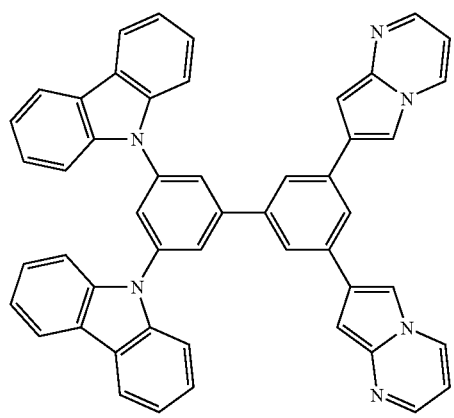
438
-continued
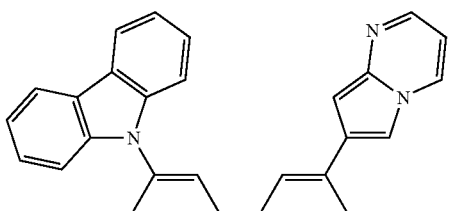
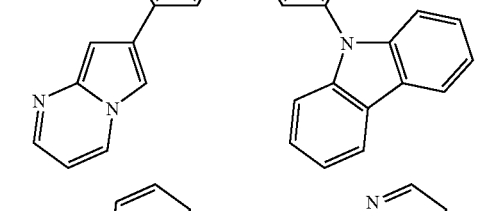
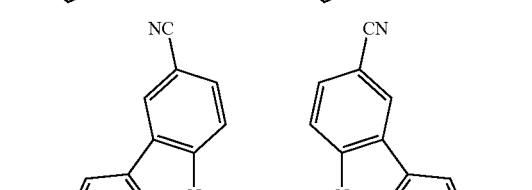
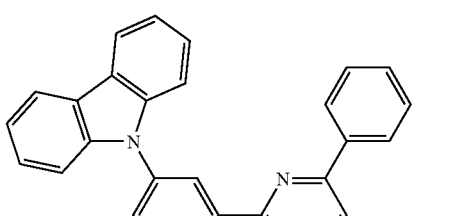

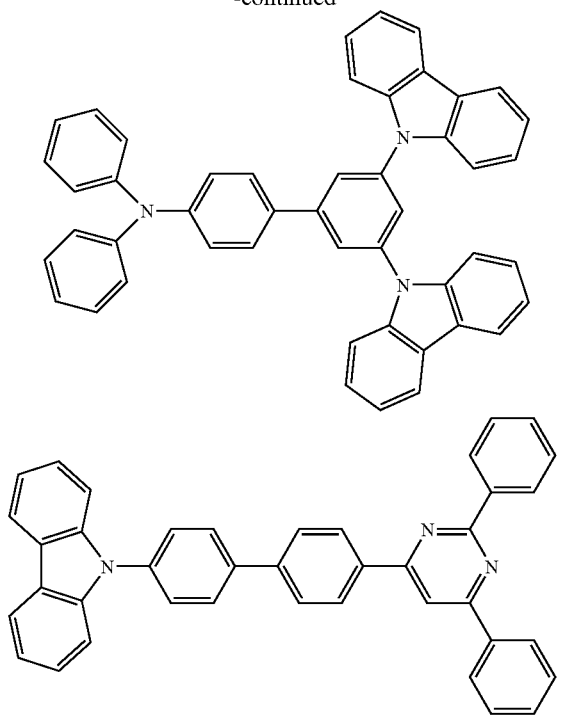

Each of the electron injecting layer and the electron transporting layer may be of a monolayer structure composed of one or two or more kinds of the above materials, or may be of a multi-layered structure composed of multiple layers identical to or different from each other in composition. Materials for those layers each preferably have a π-electron-deficient, nitrogen-containing heterocyclic group.

In addition, an insulator or semiconductor serving as an inorganic compound as well as the nitrogen-containing ring derivative is preferably used as a component of the electron injecting layer. When the electron injecting layer is constituted of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferable that the electron injecting layer be composed of the above-mentioned substance such as the alkali metal chalcogenide since the electron injecting property can be further improved. To be specific, preferable examples of the alkali metal chalcogenide include $Li_2O$, $K_2O$, $Na_2S$, $Na_2Se$, and $Na_2O$, and preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

In addition, examples of the semiconductor include oxides, nitrides, and oxide nitrides containing at least one element selected from the group consisting of Ba, Ca, Sr, Yb, Al, Ga, In, Li, Na, Cd, Mg, Si, Ta, Sb, and Zn, and they may be used alone or in combination of two or more. It is preferable that the inorganic compound composing the electron injecting layer form a crystallite or amorphous insulating thin film. When the electron injecting layer is composed of the insulating thin film described above, a more uniform thin film can be formed, and defects of pixels such as dark spots can be decreased. Examples of the inorganic compound include alkali metal chalcogenides, alkaline earth metal chalcogenides, alkali metal halides, and alkaline earth metal halides.

In addition, the above-mentioned reducing dopant can be preferably incorporated into the electron injecting layer in the present invention.

It should be noted that the thickness of each of the electron injecting layer and the electron transporting layer, which is not particularly limited, is preferably 1 to 100 nm.

An aromatic amine compound such as an aromatic amine derivative represented by a general formula (I) is suitably used in the hole injecting layer or hole transporting layer (a hole injecting/transporting layer is also included in this category).

[Chem 146]

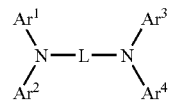

(I)

In the general formula (I), $Ar^1$ to $Ar^4$ each represent a substituted or unsubstituted aryl group having 6 to 50 carbon atoms forming the aromatic ring, or a substituted or unsubstituted heteroaryl group having 5 to 50 atoms forming the aromatic ring.

Examples of the substituted or unsubstituted aryl group having 6 to 50 carbon atoms forming the aromatic ring include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having 5 to 50 atoms forming the aromatic ring include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group. Preferred are a phenyl group, a naphthyl group, a biphenyl group, an anthranyl group, a phenanthryl group, a pyrenyl group, a chrycenyl group, a fluoranthenyl group, and a fluorenyl group.

L represents a linking group, and specifically, a substituted or unsubstituted arylene group having 6 to 50 carbon atoms forming the aromatic ring, a substituted or unsubstituted heteroarylene group having 5 to 50 atoms forming the aromatic ring, or a divalent group in which two or more arylene groups or heteroarylene groups are bonded by a single bond, an ether bond, a thioether bond, with an alkylene group having 1 to 20 carbon atoms, an alkenylene group having 2 to 20 carbon atoms, and an amino group. Examples of the arylene group having 6 to 50 carbon atoms forming the aromatic ring include a 1,4-phenylene group, a 1,2-phenylene group, a 1,3-phenylene group, a 1,4-naphthylene group, a 2,6-naphthylene group, a 1,5-naphthylene group, a 9,10-anthranylene group, a 9,10-phenanthrenylene group, a 3,6-phenanthrenylene group, 1,6-pyrenylene group, a 2,7-pyrenylene group, a 6,12-chrycenylene group, a 4,4'-biphenylene group, a 3,3'-biphenylene group, a 2,2-biphenylene group, and a 2,7-fluorenylene group. Examples of the arylene group having 5 to 50 atoms forming the aromatic ring include a 2,5-thiophenylene group, a 2,5-silolylene group, and a 2,5-oxadiazolylene group. Preferred are a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenlene group, a 2,2'-biphenylene group, and a 2,7-fluorenylene group.

In the case where L represents a linking group formed of two or more arylene groups or heteroarylene groups, adjacent arylene groups or heteroarylene groups may be bonded to each other through a divalent group to form a ring. Examples of the divalent group forming a ring include a tetramethylene group, a pentamethylene group, a hexamethylene group, a diphenylmethane-2,2'-diyl group, a diphenyl ethane-3,3'-diyl group, and a diphenylpropane-4,4'-diyl group.

The substituent of each of $Ar^1$ to $Ar^4$ and L is, for example, a substituted or unsubstituted aryl group having 6 to 50 carbon atoms forming the aromatic ring, a substituted or unsubstituted heteroaryl group having 5 to 50 atoms forming the aromatic ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms forming the aromatic ring, a substituted or unsubstituted heteroaryloxy group having 5 to 50 atoms forming the aromatic ring, a substituted or unsubstituted arylthio group having 6 to 50 carbon atoms forming the aromatic ring, a substituted or unsubstituted heteroarylthio group having 5 to 50 atoms forming the aromatic ring, a substituted or unsubstituted alkoxycarbonyl group having 2 to 50 carbon atoms, an amino group substituted by a substituted or unsubstituted aryl group having 6 to 50 carbon atoms forming the aromatic ring or by a substituted or unsubstituted heteroaryl group having 5 to 50 atoms forming the aromatic ring, a halogen group, a cyano group, a nitro group, or a hydroxyl group.

Examples of the substituted or unsubstituted aryl group having 6 to 50 carbon atoms forming the aromatic ring include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having 5 to 50 atoms forming the aromatic ring include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Examples of the substituted or unsubstituted alkyl group having 1 to 50 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

Examples of the substituted or unsubstituted aralkyl group having 7 to 50 carbon atoms include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Examples of the substituted or unsubstituted aryloxy group having 6 to 50 carbon atoms forming the aromatic ring is represented by —OY'. Examples of Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 41'-t-butyl-p-terphenyl-4-yl group.

Examples of the substituted or unsubstituted heteroaryloxy group having 5 to 50 atoms forming the aromatic ring is represented by —OZ'. Examples of Z' include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxadinyl group, a 2-phenoxadinyl group, a 3-phenoxadinyl group, a 4-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and 4-t-butyl3-indolyl group.

The substituted or unsubstituted arylthio group having 6 to 50 carbon atoms forming the aromatic ring is represented by —SY". Examples of Y" include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

The substituted or unsubstituted heteroarylthio group having 5 to 50 atoms forming the aromatic ring is represented by —SZ". Examples of Z" include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

The substituted or unsubstituted alkoxycarbonyl group having 2 to 50 carbon atoms is represented by —COOZ. Examples of Z include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

The substituted or unsubstituted aryl group having 6 to 50 carbon atoms forming the aromatic ring or an amino group substituted with a substituted or unsubstituted heteroaryl group having 5 to 50 atoms forming the aromatic ring is represented by —NPQ. Examples of P and Q include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t- butyl-p-terphenyl-4-yl group, a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Specific examples of the compound represented by the general formula (I) are shown below. However, the present invention is not limited to these examples.

[Chem 147]

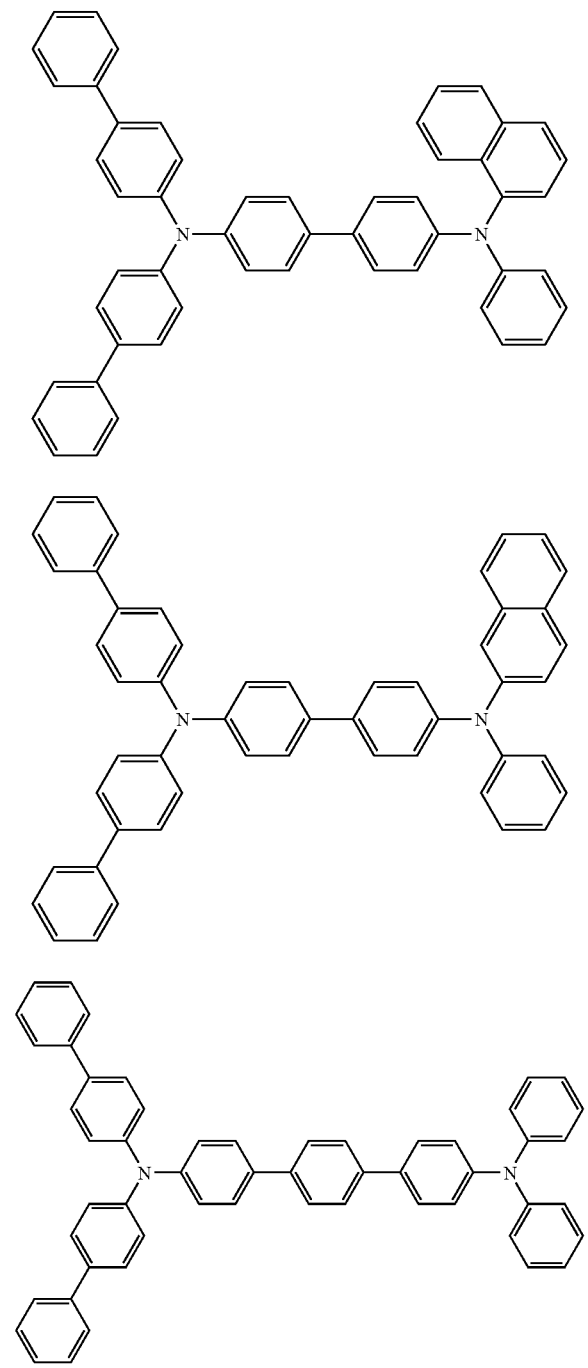

451
-continued
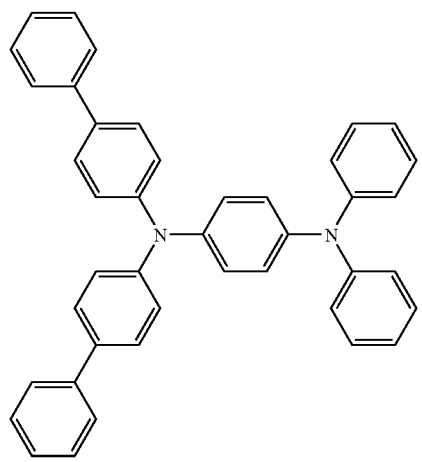
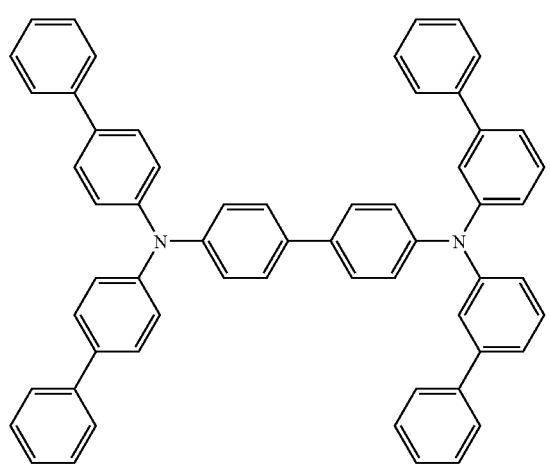
452
-continued
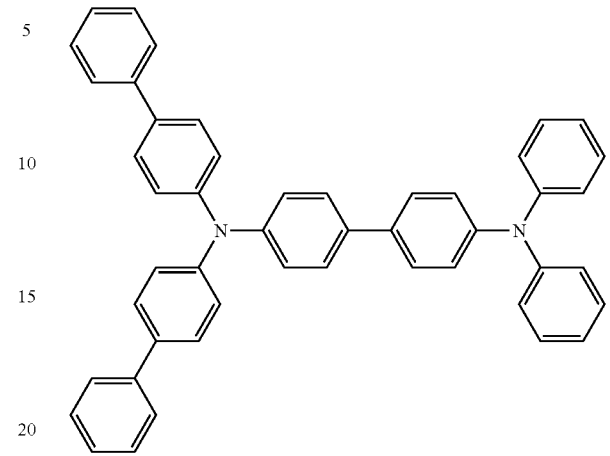
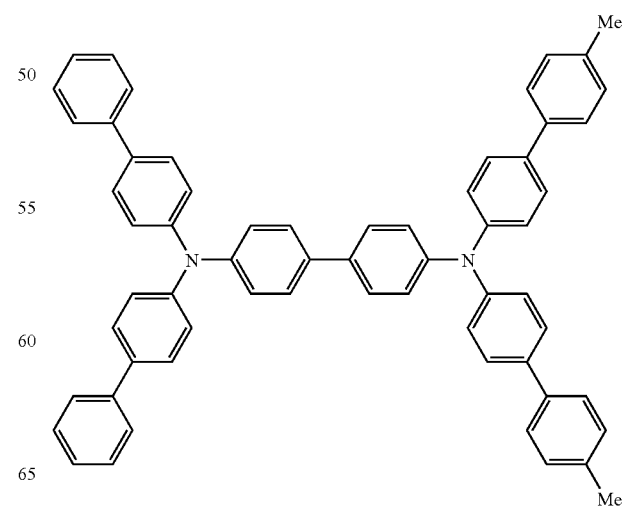

453
-continued
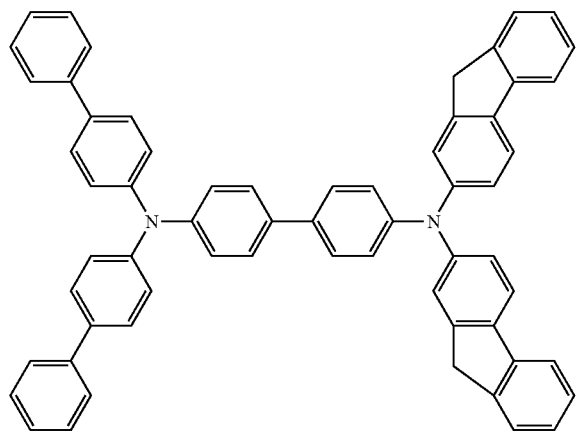
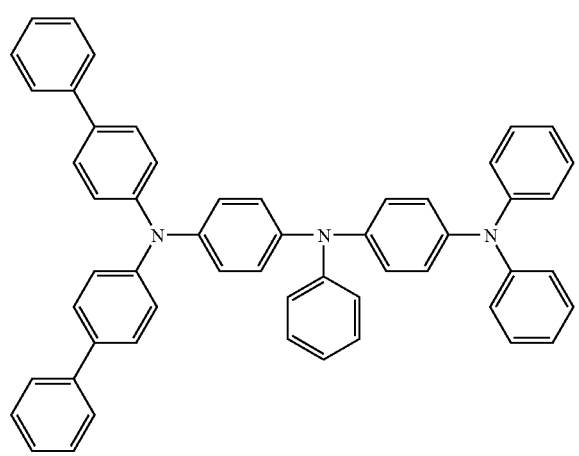
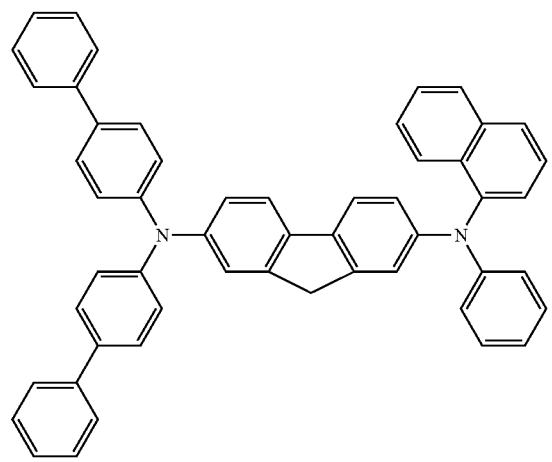
454
-continued
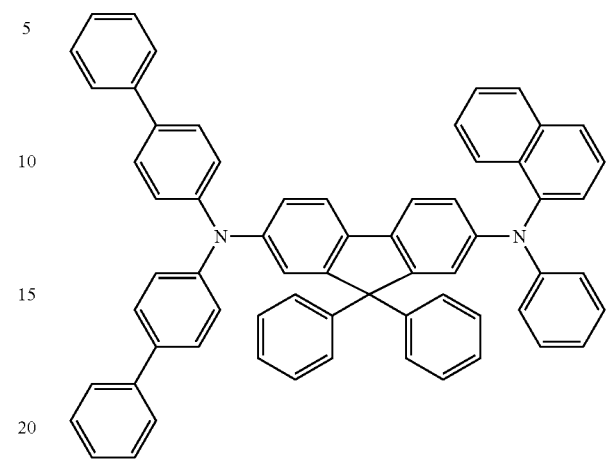
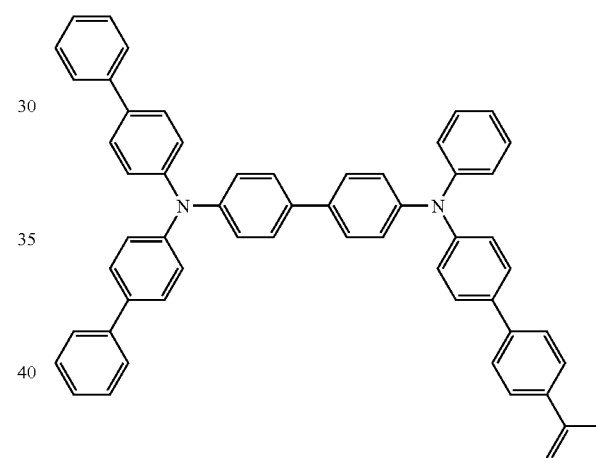
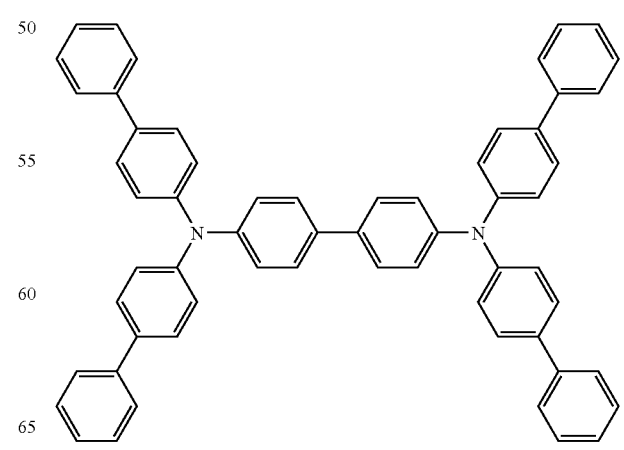

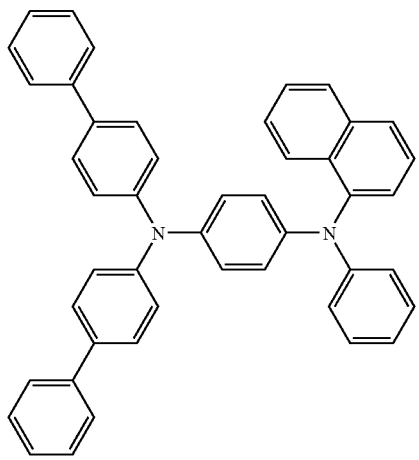
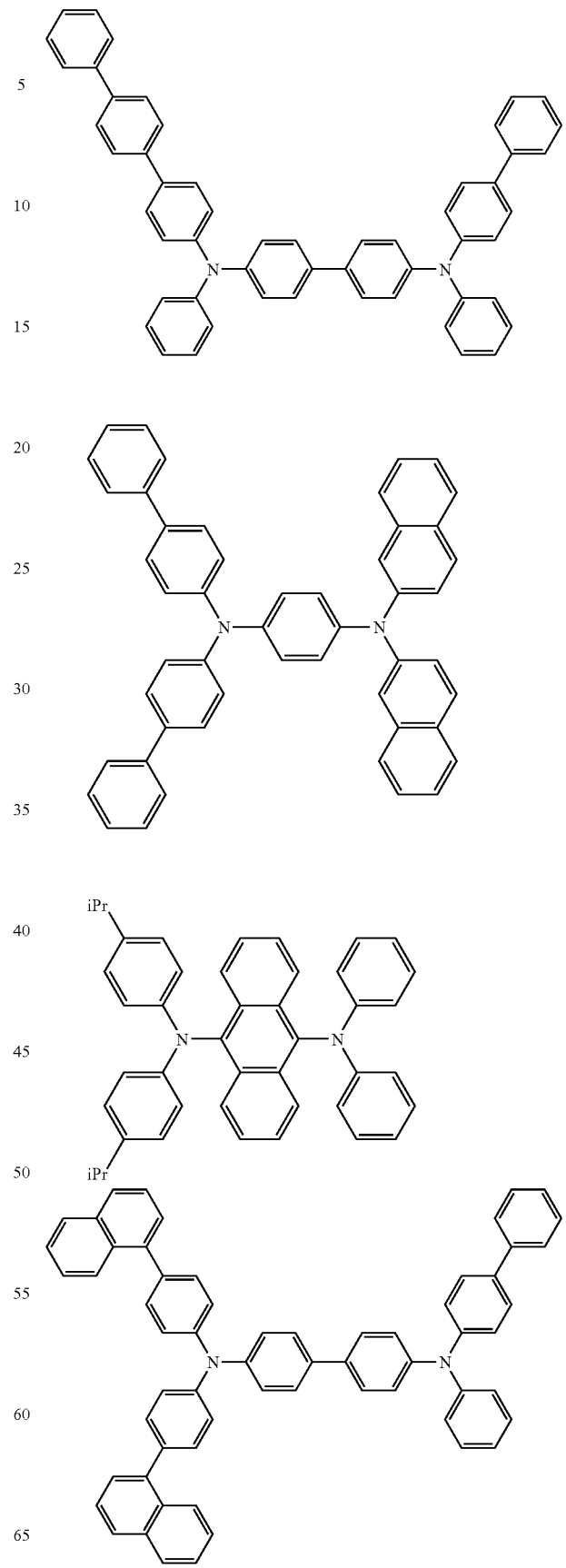

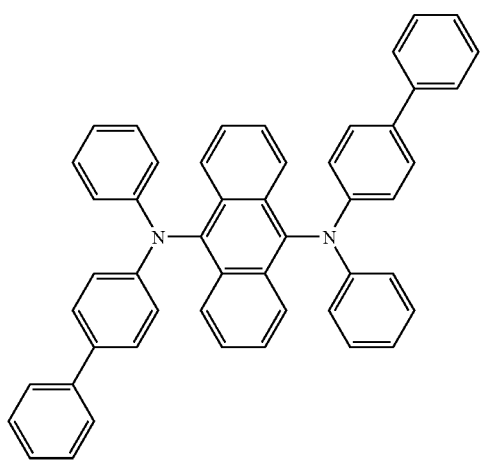

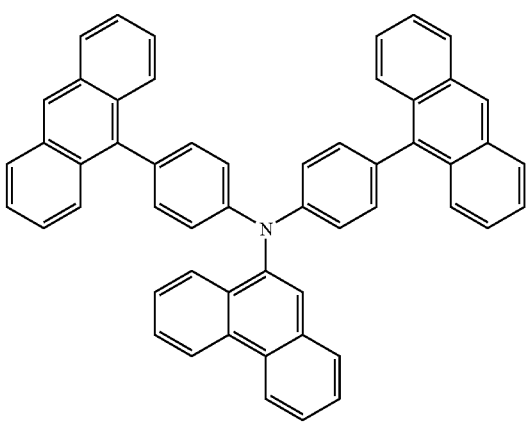

In addition, an aromatic amine represented by the following general formula (II) is also suitably used in the formation of the hole injecting layer or hole transporting layer.

[Chem 148]

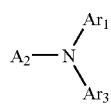
(II)

In the general formula (II), the definition of $Ar_1$ to $Ar_3$ is the same as that of $Ar^1$ to $Ar^4$ in the general formula (I). Specific examples of the compound represented by the general formula (II) are shown below. However, the present invention is not limited to these examples.

[Chem 149]

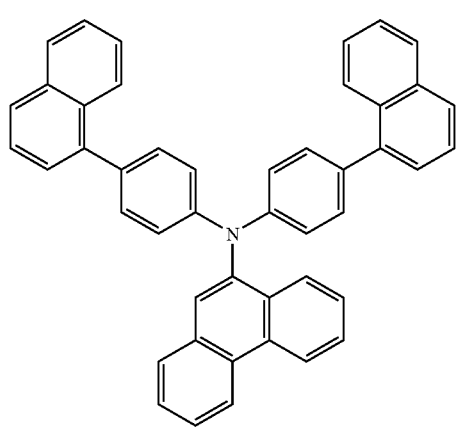

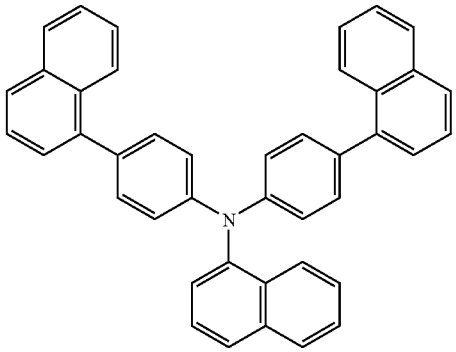

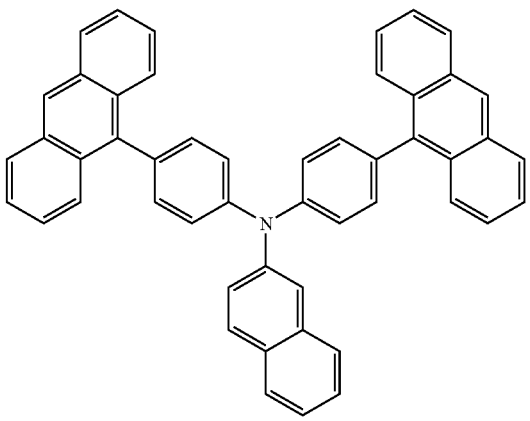

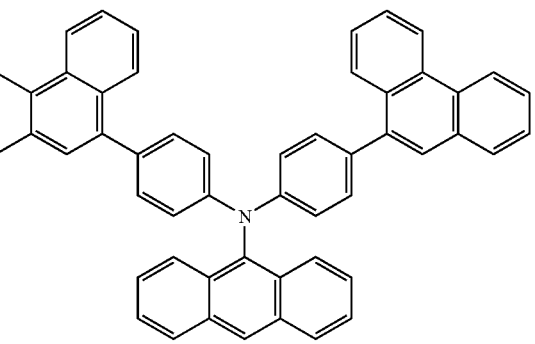

459
-continued
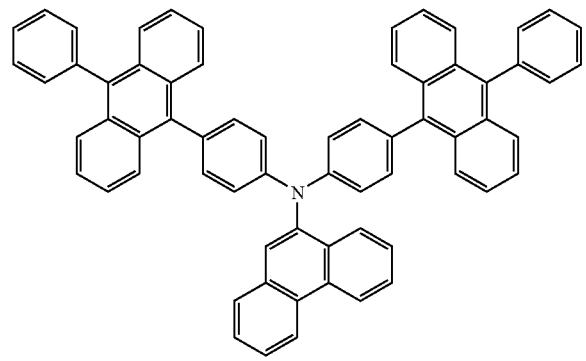
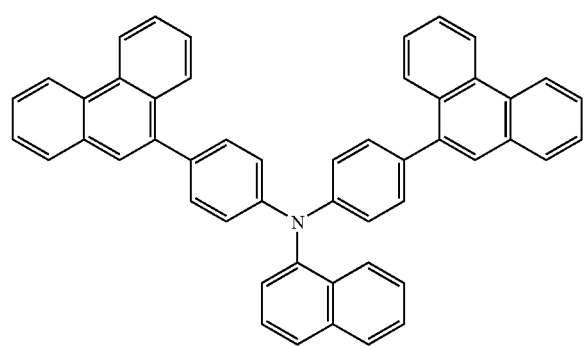
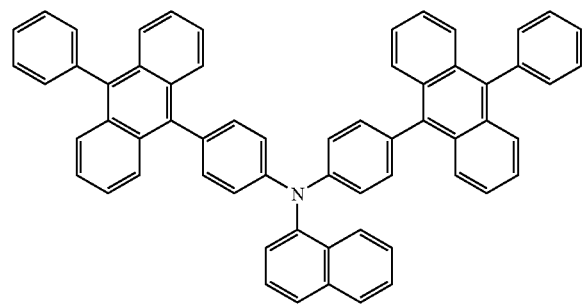
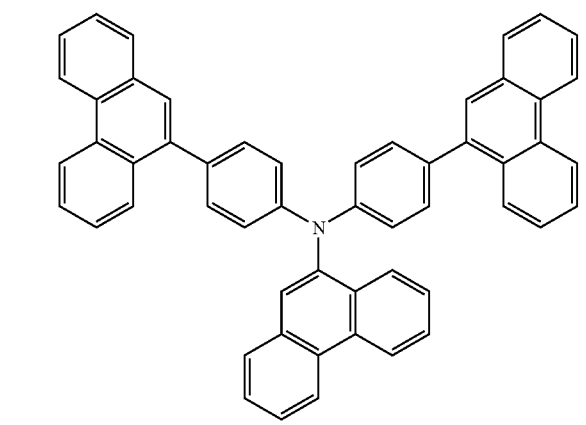
460
-continued
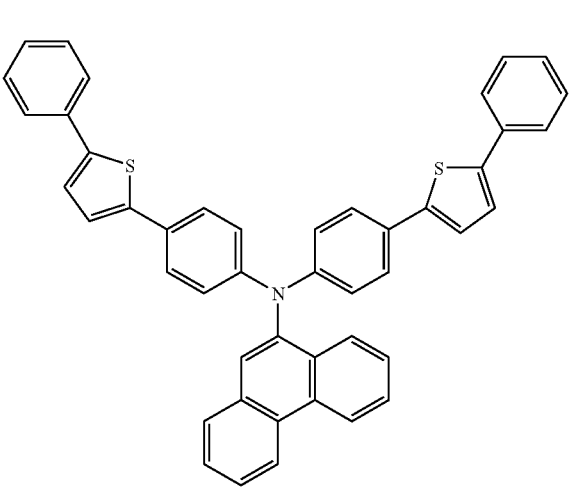
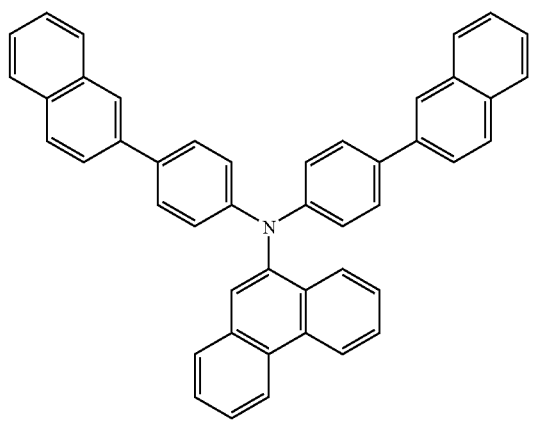

461
-continued

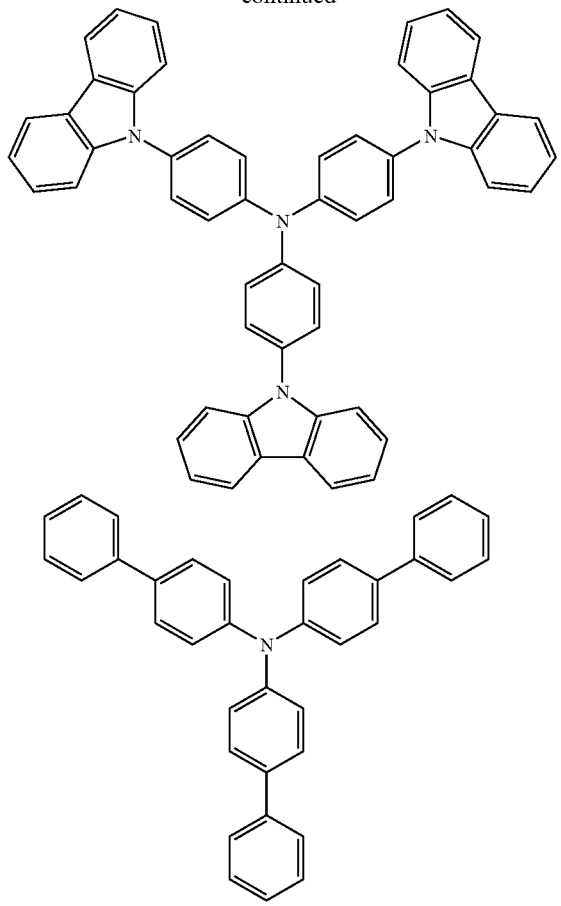

The compound of the present invention can be used in each of the hole injecting layer, the hole transporting layer, the electron injecting layer, and the electron transporting layer because the compound can transport both a hole and an electron.

In the present invention, the anode in the organic EL device has the function of injecting holes into the hole transporting layer or the light emitting layer. It is effective that the anode has a work function of 4.5 eV or greater. Specific examples of the material for the anode used in the present invention include indium tin oxide alloys (ITO), tin oxide (NESA), gold, silver, platinum, and copper. In addition, as the cathode, a material having a small work function is preferred in view to inject an electron into an electron injecting layer or a light emitting layer. Examples of the cathode material are not particularly limited, and specifically, indium, aluminum, magnesium, an magnesium-indium alloy, a magnesium-aluminum alloy, an aluminum-lithium alloy, an aluminum-scandium-lithium alloy, and a magnesium-silver alloy may be used.

The method of forming the layers in the organic EL device of the present invention is not particularly limited. A conventionally known process such as the vacuum vapor deposition process or the spin coating process can be used. The organic thin film layer which is used in the organic EL device of the present invention and includes the compound represented by general formula (1) described above can be formed in accordance with a known process such as the vacuum vapor deposition process or the molecular beam epitaxy process (MBE process) or, using a solution prepared by dissolving the compounds into a solvent, in accordance with a coating process such as the dipping process, the spin coating process, the casting process, the bar coating process, or the roll coating process.

The thickness of each organic layer in the organic EL device of the present invention is not particularly limited. In general, an excessively thin layer tends to have defects such as pin holes, whereas an excessively thick layer requires a high applied voltage to decrease the efficiency. Therefore, a thickness in the range of several nanometers to 1 μm is preferable.

EXAMPLES

Next, the present invention is described in detail by way of examples, but the present invention is not limited to the following examples. Note that, in the synthesis examples below, DMF refers to dimethylformamide, THF refers to tetrahydrofuran, DME refers to dimethoxyethane, NBS refers to N-bromosuccine imide, Ph refers to a phenyl group, AcOEt refers to ethyl acetate, and NMP refers to N-methylpyrrolidone.

Synthesis Example 1-1

Synthesis of Compound 1-1

(1) Synthesis of Compound A-1

[Chem 150]

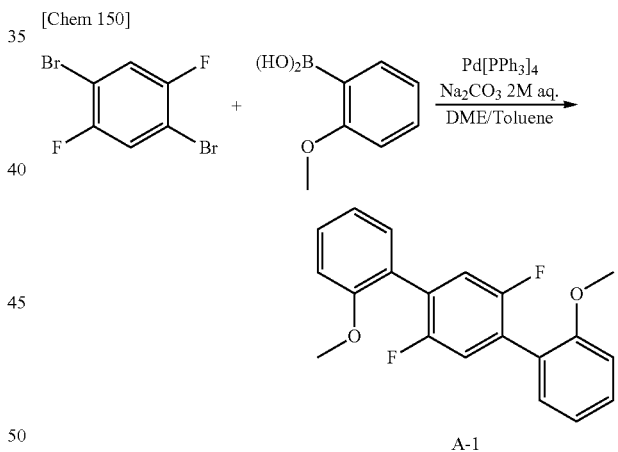

1,4-dibromo-2,5-difluorobenzene (49.3 g, 181.5 mmol), 2-methoxyphenylboronic acid (66.2 g, 435.6 mmol), a 2 M aqueous solution of $Na_2CO_3$ (363 mL, 726 mmol), DME (360 mL), toluene (360 mL), and $Pd[PPh_3]_4$ (21 g, 18.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 38.5 g in 65% yield.

FD-MS $C_{20}H_{16}F_2O_2$: theoretical value 326, observed value 326

(2) Synthesis of Compound A-2

[Chem 151]

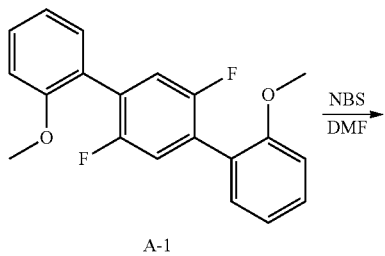

A-1

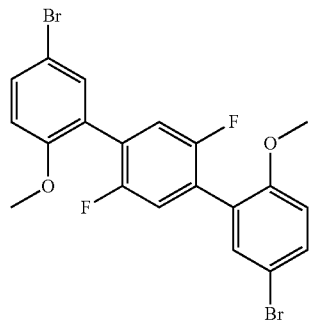

A-2

Compound A-1 (36.6 g, 112.1 mmol), NBS (39.9 g, 224 mmol), and DMF (1,000 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 38 g in 70% yield.

FD-MS $C_{20}H_{14}Br_2F_2O_2$: theoretical value 484, observed value 484

(3) Synthesis of Compound A-3

[Chem 152]

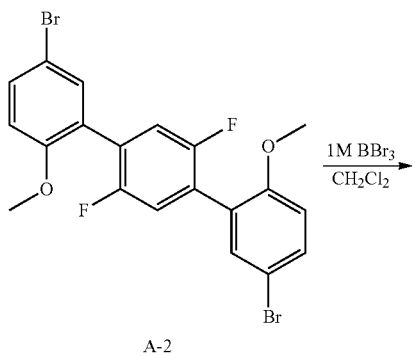

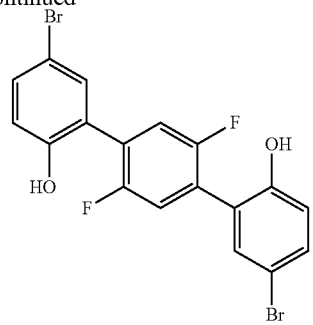

A-3

Compound A-2 (37.2 g, 76.7 mmol), a 1-M solution of $BBr_3$ in $CH_2Cl_2$ (180 mL, 180 mmol), and $CH_2Cl_2$ (500 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 28 g in 80% yield.

FD-MS $C_{18}H_{10}Br_2F_2O_2$: theoretical value 456, observed value 456

Synthesis of Compound A-4

[Chem 153]

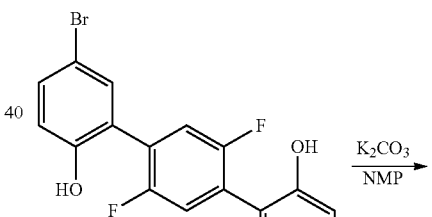

A-3

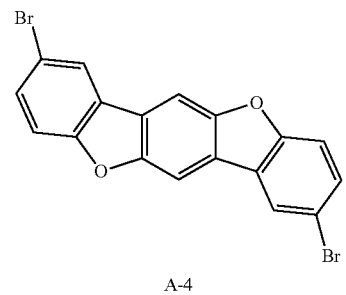

A-4

Compound A-3 (27.4 g, 60 mmol), $K_2CO_3$ (18.2 g, 132 mmol), and NMP (250 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 20 g in 80% yield.

FD-MS $C_{18}H_8Br_2O_2$: theoretical value 416, observed value 416

(5) Synthesis of Compound 1-1

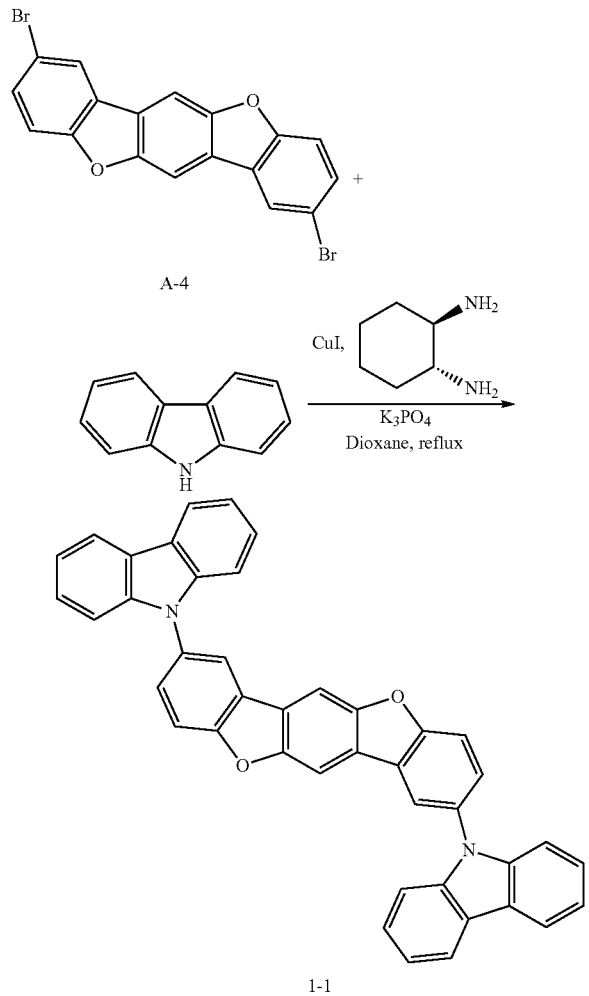

1-1

Compound A-4 (3 g, 7.2 mmol), carbazole (2.9 g, 17.3 mmol), CuI (1.4 g, 7.2 mmol), transcyclohexane 1,2-diamine (2.5 g, 21.6 mmol), $K_3PO_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 1-1) was obtained. The powder was purified by sublimation, whereby a white solid was obtained in an amount of 2.2 g in 52% yield.

FD-MS $C_{42}H_{24}N_2O_2$: theoretical value 588, observed value 588

Synthesis Example 1-2

Synthesis of Compound 1-17

(1) Synthesis of Compound A-5

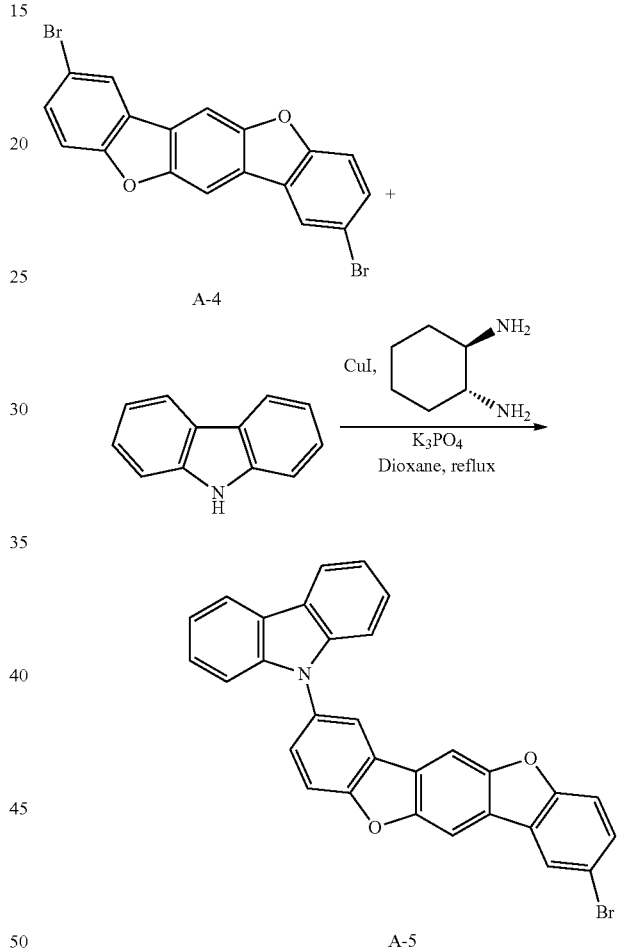

A-5

Compound A-4 (3 g, 7.2 mmol), carbazole (1.5 g, 7.2 mmol), CuI (1.4 g, 7.2 mmol), transcyclohexane 1,2-diamine (2.5 g, 21.6 mmol), $K_3PO_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 2.2 g in 60% yield.

FD-MS $C_{30}H_{16}BrNO_2$: theoretical value 502, observed value 502

(2) Synthesis of Compound 1-17

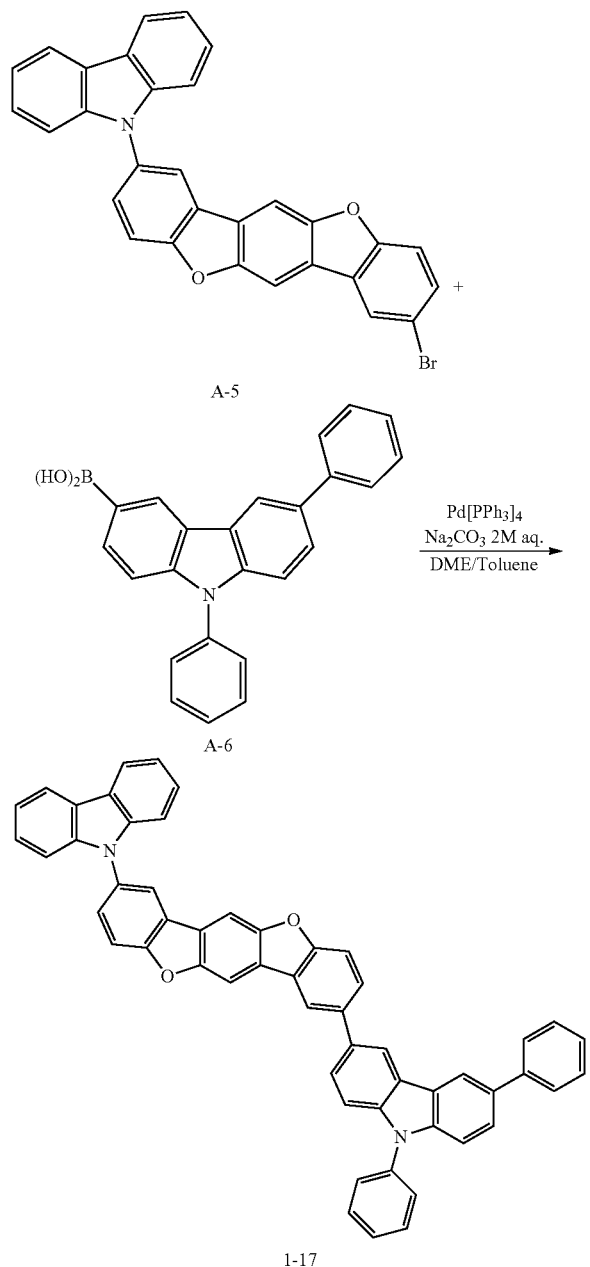

Synthesis Example 1-3

Synthesis of Compound 1-18

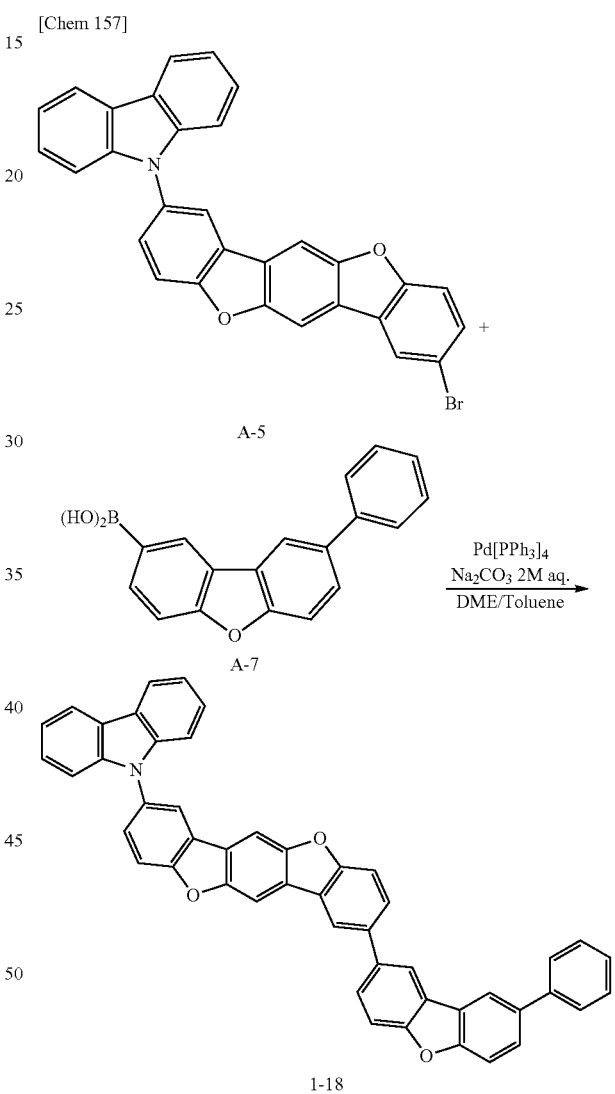

Compound A-5 (3.0 g, 6.0 mmol), Compound A-6 (2.4 g, 6.6 mmol), a 2 M aqueous solution of Na$_2$CO$_3$ (6 mL, 12 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 1-17) was obtained. The powder was purified by sublimation, whereby a white solid was obtained in an amount of 2.0 g in 45% yield.

FD-MS C$_{54}$H$_{32}$N$_2$O$_2$: theoretical value 740, observed value 740

Compound A-5 (3.3 g, 6.6 mmol), Compound A-7 (2.1 g, 7.3 mmol), a 2 M aqueous solution of Na$_2$CO$_3$ (6 mL, 13 mmol), DME (12 mL), toluene (12 mL), and Pd[PPh$_3$]$_4$ (0.38 g, 0.33 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 1-18) was obtained. The powder was purified by sublimation, whereby a white solid was obtained in an amount of 2.3 g in 52% yield.

FD-MS $C_{48}H_{27}NO_3$: theoretical value 665, observed value 665

Synthesis Example 1-4

Synthesis of Compound 1-34

(1) Synthesis of Compound A-8

[Chem 158]

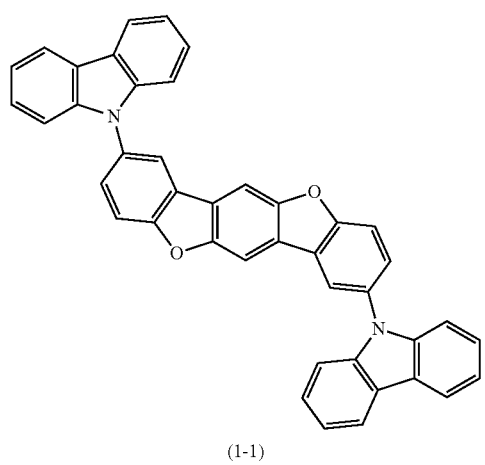

(1-1)

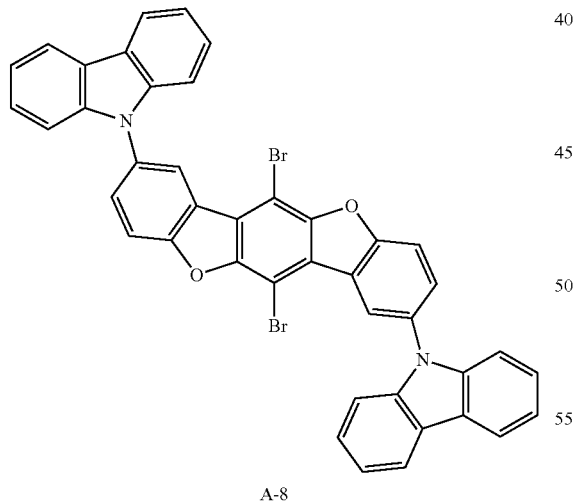

A-8

Compound (1-1) (10 g, 17 mmol) and $CH_2Cl_2$ (100 mL) were loaded into a three-necked flask and bromine (5.4 g, 34 mmol) was dropped thereto under an Ar atmosphere at 0° C. After that, the mixture was stirred at room temperature for 8 hours. After the completion of the reaction, the sample was transferred to a separating funnel and water (50 mL) was added thereto, followed by extraction with $CH_2Cl_2$. An organic layer was washed with a saturated $NaNO_2$ aqueous solution (50 mL) and dried with $MgSO_4$, followed by filtration and concentration. The sample was purified by a column chromatography, whereby a white solid was obtained in an amount of 7.9 g in 62% yield.

FD-MS $C_{42}H_{22}Br_2N_2O_2$: theoretical value 746, observed value 746

(2) Synthesis of Compound 1-34

[Chem 159]

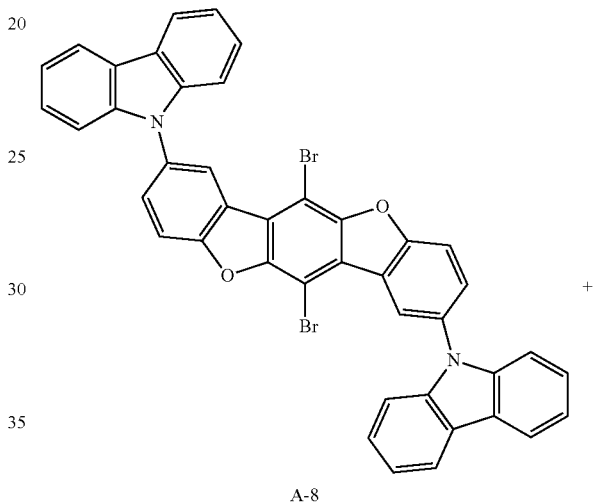

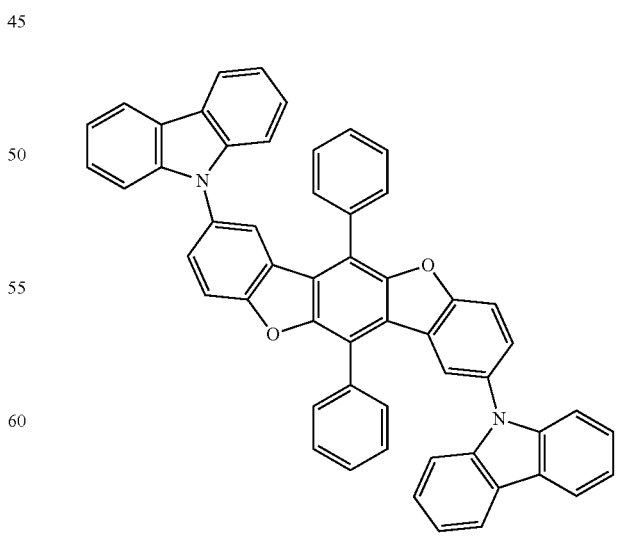

1-34

Compound A-8 (3.7 g, 4.9 mmol), phenylboronic acid (1.32 g, 10.8 mmol), a 2 M aqueous solution of $Na_2CO_3$ (5 mL, 9.8 mmol), DME (10 mL), toluene (10 mL), and $Pd[PPh_3]_4$ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-34) was obtained. The powder was purified by sublimation, whereby a white solid was obtained in an amount of 1.8 g in 50% yield.

FD-MS $C_{54}H_{32}N_2O_2$: theoretical value 740, observed value 740

Synthesis Example 1-5

Synthesis of Compound 1-46

(1) Synthesis of Compound A-9

[Chem 160]

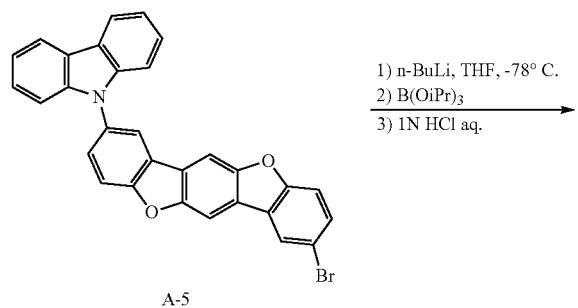

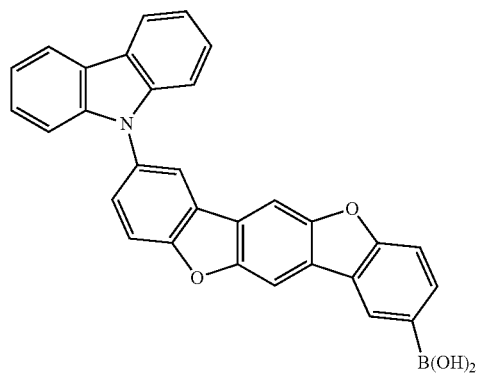

Compound A-5 (10 g, 20 mmol) and THF (200 mL) were loaded into a three-necked flask, and the mixture was cooled to −78° C. Then, n-BuLi (1.65-M solution in n-hexane, 13.3 mL, 22 mmol) was added dropwise to the flask, and the resultant mixture was stirred at −78° C. for 20 minutes. Tri-isopropyl boronate (11.3 g, 60 mmol) was added to the resultant, and the mixture was stirred at −78° C. for 1 hour. After that, the resultant was left to stand overnight at room temperature. Then, 1N HCl (40 mL) was charged into the resultant, and the mixture was stirred at room temperature for 1 hour. The resultant sample was concentrated, and was then transferred to a separating funnel. Water (50 mL) was charged into the funnel, and the mixture was extracted with $CH_2Cl_2$. The extract was dried with $MgSO_4$, and was then filtrated and concentrated. The resultant sample was purified by recrystallization (toluene-hexane), whereby a white solid was obtained in an amount of 5.6 g in 600 yield.

(2) Synthesis of Compound 1-46

[Chem 161]

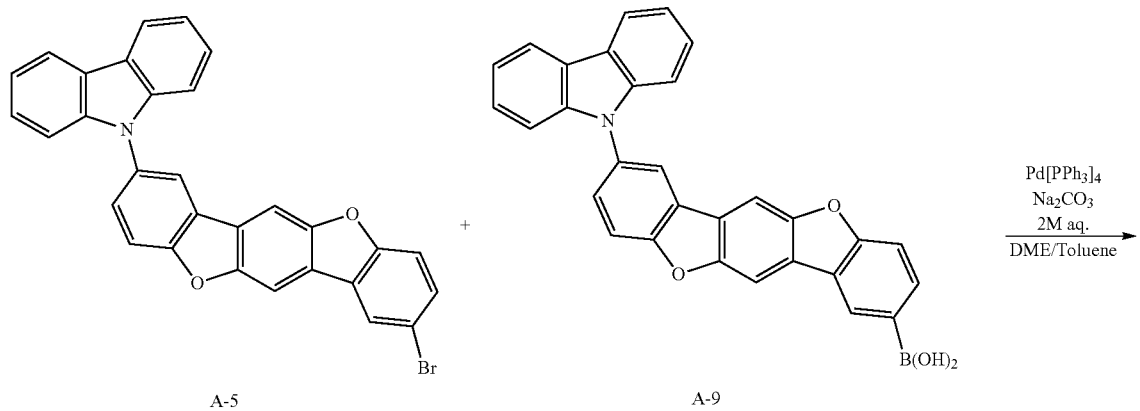

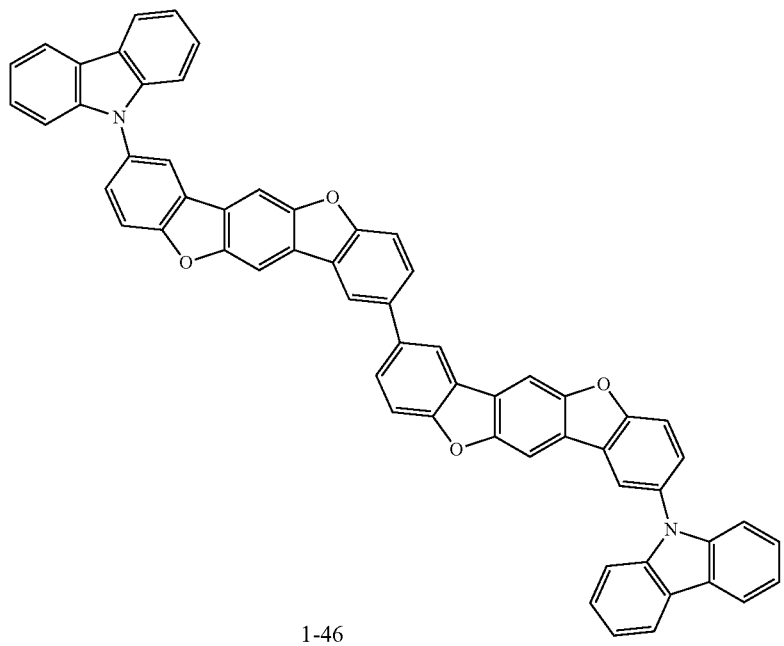

1-46

Compound A-5 (3.1 g, 6.2 mmol), Compound A-9 (3.2 g, 6.8 mmol), a 2 M aqueous solution of $Na_2CO_3$ (6.2 mL, 12.4 mmol), DME (12 mL), toluene (12 mL), and $Pd[PPh_3]_4$ (0.36 g, 0.31 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-46) was obtained. The powder was purified by sublimation, whereby a white solid was obtained in an amount of 2.1 g in 40% yield.

FD-MS $C_{60}H_{32}N_2O_4$: theoretical value 844, observed value 844

Synthesis Example 1-6

Synthesis of Compound 1-49

[Chem 162]

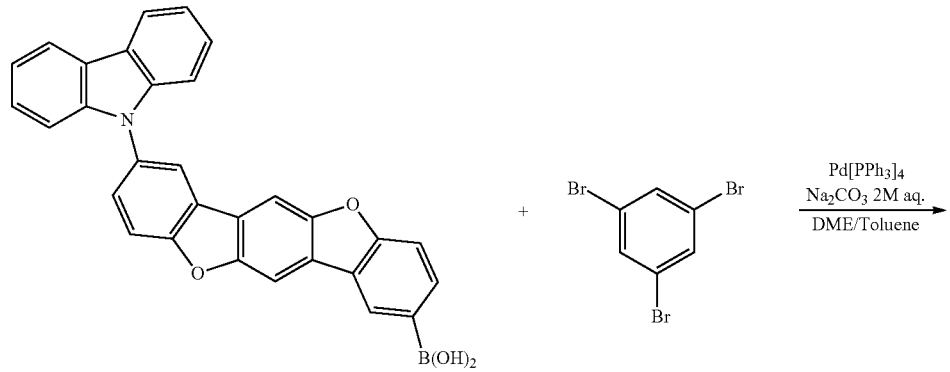

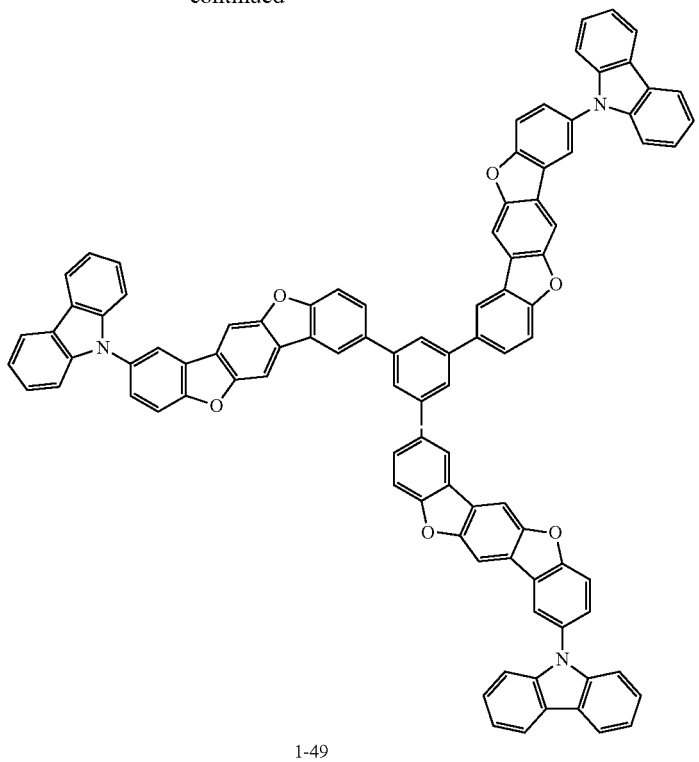

1-49

Compound A-9 (10.2 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-49) was obtained. The powder was purified by sublimation, whereby a white solid was obtained in an amount of 1.6 g in 16% yield.

FD-MS $C_{96}H_{51}N_3O_6$: theoretical value 1,342 observed value 1,342

Synthesis Example 1-7

Synthesis of Compound 1-68

[Chem 163]

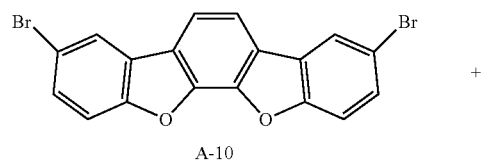

A-10

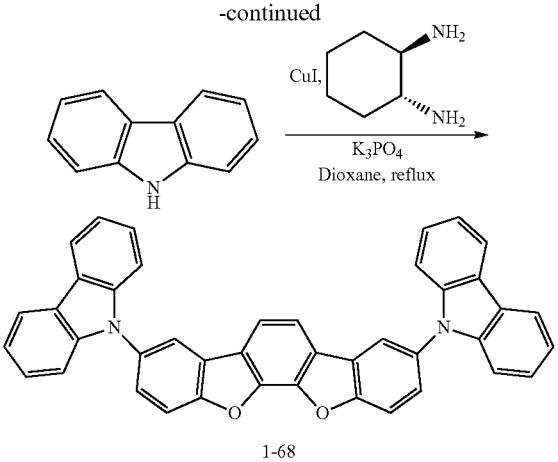

1-68

Compound A-10 (3 g, 7.2 mmol), carbazole (3.0 g, 14.4 mmol), CuI (1.4 g, 7.2 mmol), transcyclohexane 1,2-diamine (2.5 g, 21.6 mmol), $K_3PO_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 1-68) was obtained. The powder was purified by sublimation, whereby a white solid was obtained in an amount of 2.2 g in 52% yield.

FD-MS $C_{42}H_{24}N_2O_2$: theoretical value 588, observed value 588

Synthesis Example 1-8

Synthesis of Compound 1-74

[Chem 164]

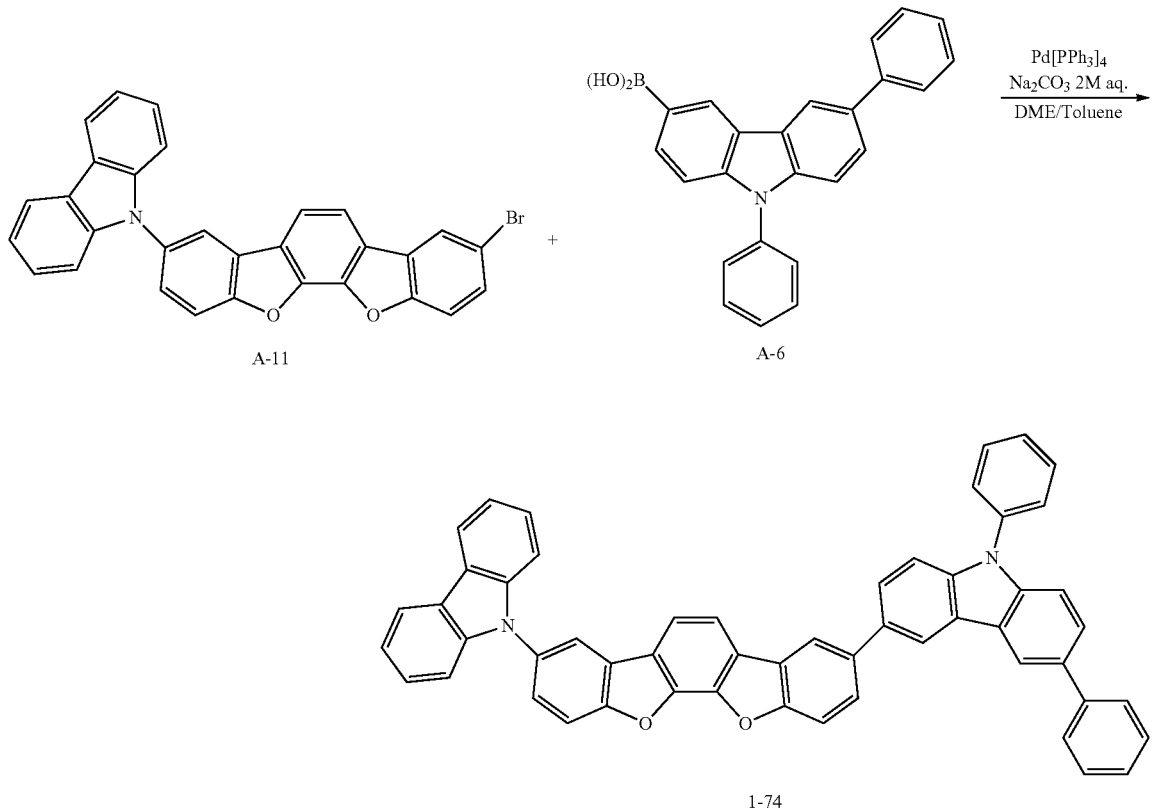

Compound A-11 (3.7 g, 4.9 mmol), Compound A-6 (2.0 g, 5.4 mmol), a 2 M aqueous solution of $Na_2CO_3$ (5 mL, 9.8 mmol), DME (10 mL), toluene (10 mL), and $Pd[PPh_3]_4$ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-74) was obtained. The powder was purified by sublimation, whereby a white solid was obtained in an amount of 1.8 g in 50% yield.

FD-MS $C_{54}H_{32}N_2O_2$: theoretical value 740, observed value 740

Synthesis Example 1-9

Synthesis of Compound 1-85

[Chem 165]

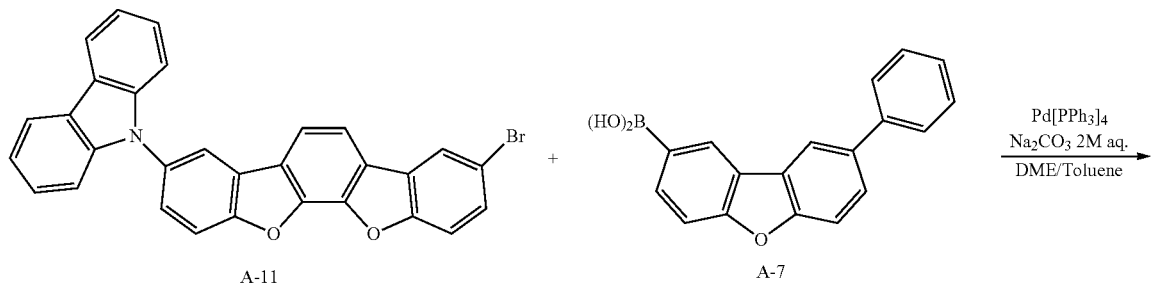

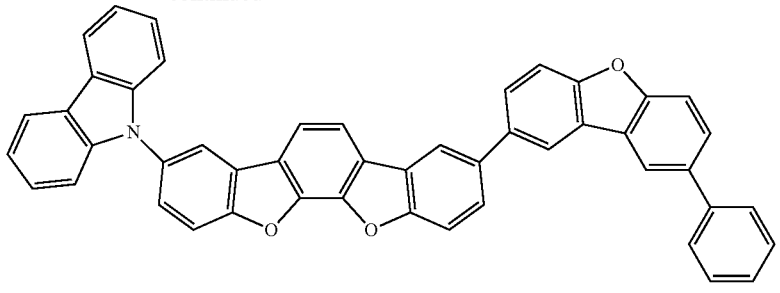

1-85

Compound A-11 (3.0 g, 6.0 mmol), Compound A-7 (1.9 g, 6.6 mmol), a 2 M aqueous solution of $Na_2CO_3$ (6 mL, 12 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-85) was obtained. The powder was purified by sublimation, whereby a white solid was obtained in an amount of 2.2 g in 55% yield.

FD-MS $C_{48}H_{27}NO_3$: theoretical value 665, observed value 665

Synthesis Example 1-10

Synthesis of Compound 1-87

[Chem 166]

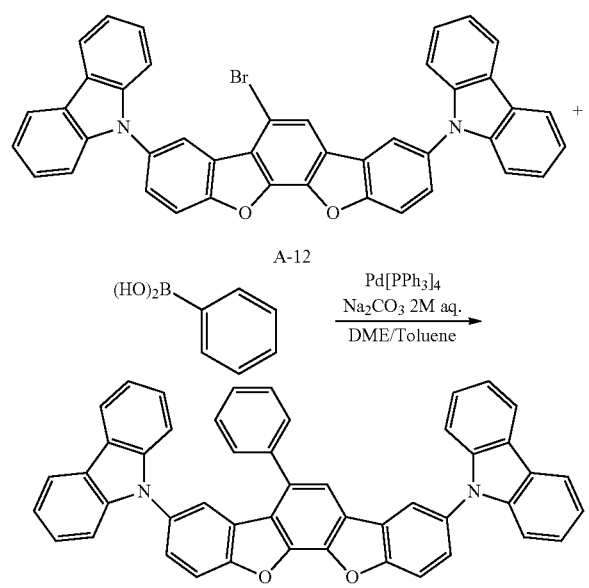

Compound A-12 (3.3 g, 5.0 mmol), phenylboronic acid (0.67 g, 5.5 mmol), a 2 M aqueous solution of $Na_2CO_3$ (5 mL, 10 mmol), DME (10 mL), toluene (10 mL), and $Pd[PPh_3]_4$ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-87) was obtained. The powder was purified by sublimation, whereby a white solid was obtained in an amount of 1.5 g in 45% yield.

FD-MS $C_{48}H_{28}N_2O_2$: theoretical value 664, observed value 664

Synthesis Example 1-11

Synthesis of Compound 1-113

(1) Synthesis of Compound A-13

[Chem 167]

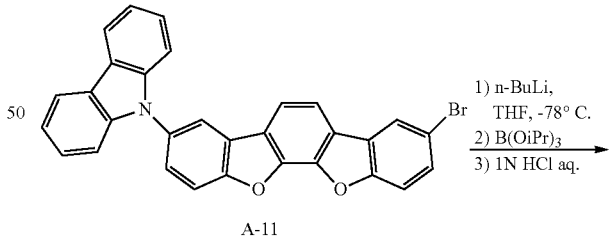

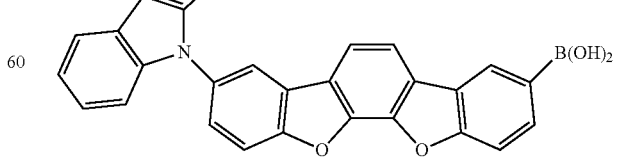

Compound A-11 (109 g, 20 mmol) and THF (200 mL) were loaded into a three-necked flask, and the mixture was cooled to −78° C. Then, n-BuLi (1.65-M solution in n-hexane, 13.3 mL, 22 mmol) was added dropwise to the flask, and the resultant mixture was stirred at −78° C. for 20 minutes. Triisopropyl boronate (11.3 g, 60 mmol) was added to the resultant, and the mixture was stirred at −78° C. for 1 hour. After that, the resultant was left to stand overnight at room temperature. Then, 1N HCl (40 mL) was charged into the resultant, and the mixture was stirred at room temperature for 1 hour. The resultant sample was concentrated, and was then transferred to a separating funnel. Water (50 mL) was charged into the funnel, and the mixture was extracted with $CH_2Cl_2$. The extract was dried with $MgSO_4$, and was then filtrated and concentrated. The resultant sample was purified by recrystallization (toluene-hexane), whereby a white solid was obtained in an amount of 5.0 g in 540 yield.

2) Synthesis of Compound 1-113

Compound A-11 (3.0 g, 6.0 mmol), Compound A-13 (3.1 g, 6.6 mmol), a 2 M aqueous solution of $Na_2CO_3$ (6.0 mL, 12 mmol), DME (12 mL), toluene (12 mL), and $Pd[PPh_3]_4$ (0.35 g, 0.30 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-113) was obtained. The powder was purified by sublimation, whereby a white solid was obtained in an amount of 2.8 g in 56% yield.

FD-MS $C_{60}H_{32}N_2O_4$: theoretical value 844, observed value 844

[Chem 168]

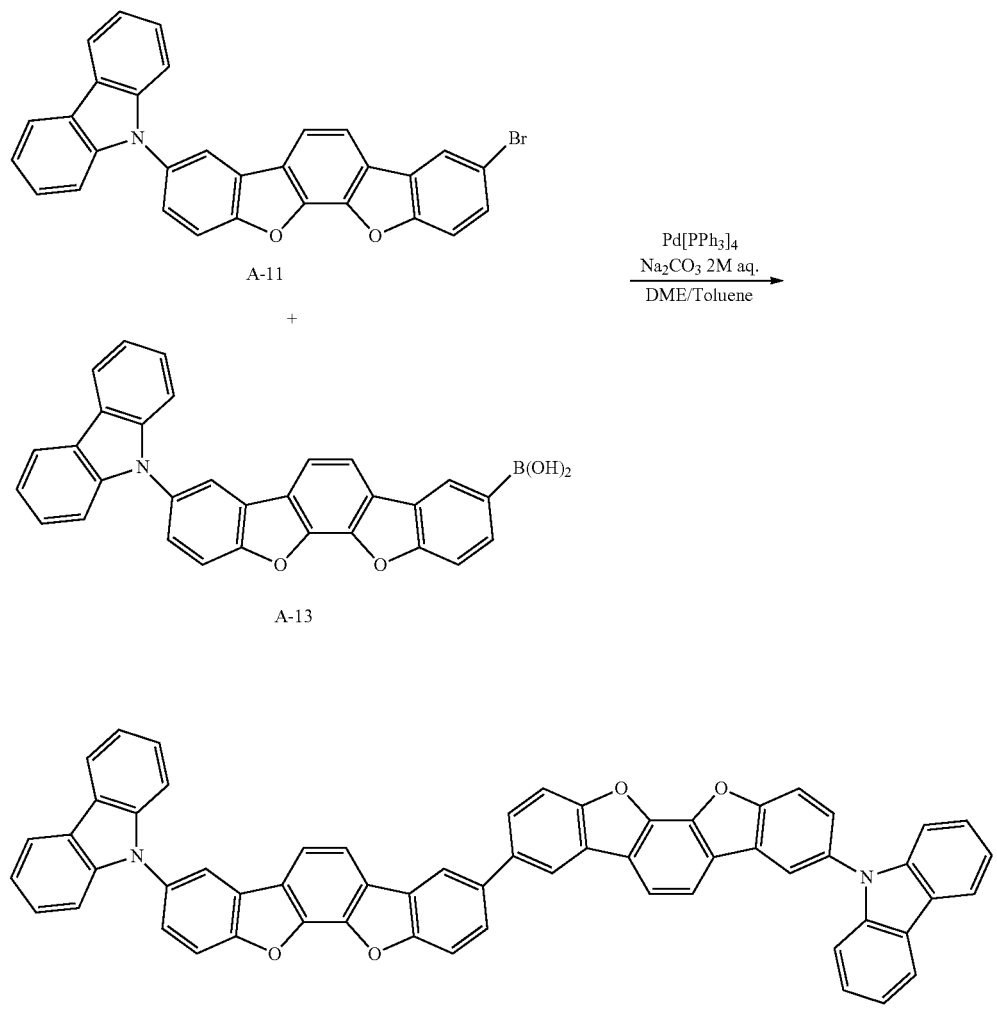

Synthesis Example 1-12

Synthesis of Compound 1-116

[Chem 169]

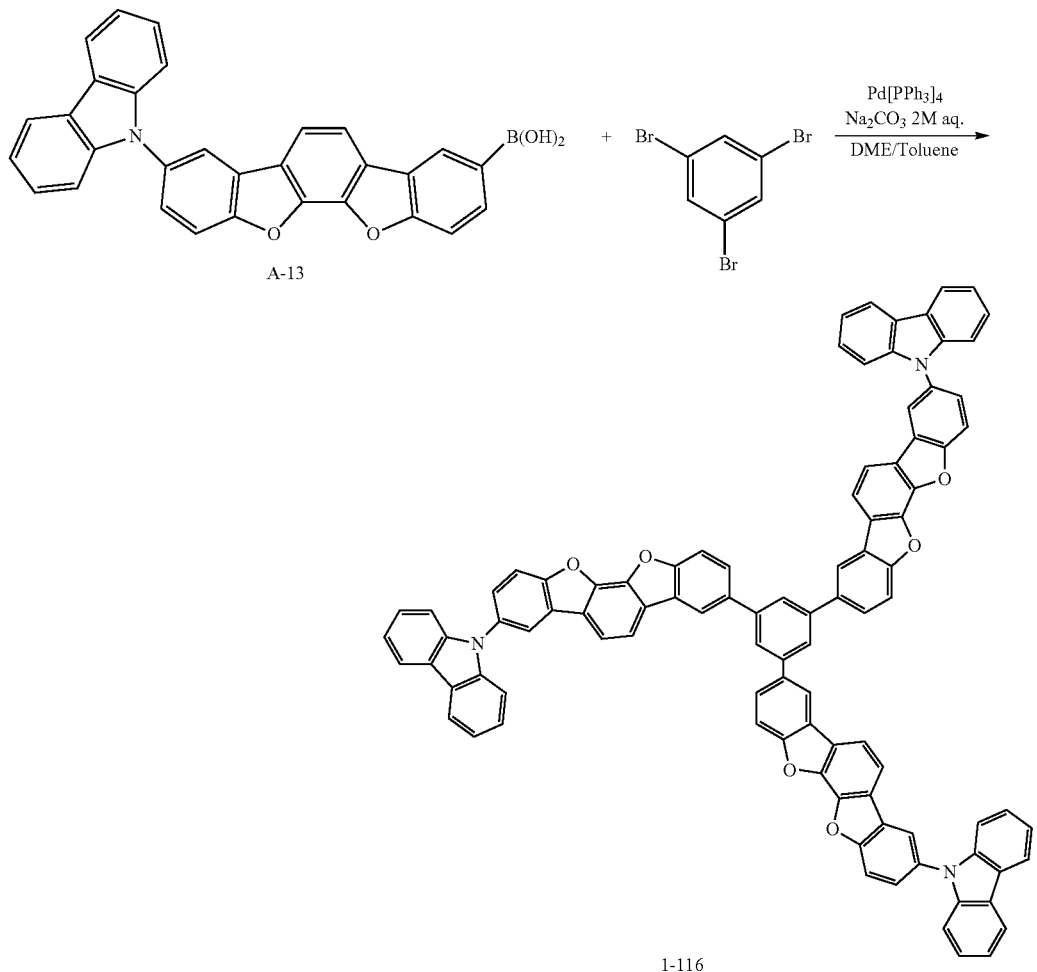

Compound A-13 (10.2 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 1-116) was obtained. The powder was purified by sublimation, whereby a white solid was obtained in an amount of 1.3 g in 13% yield.

FD-MS $C_{96}H_{51}N_3O_6$: theoretical value 1,342, observed value 1,342

Synthesis Example 1-13

Synthesis of Compound 1-138

(1) Synthesis of Compound A-15

[Chem 170]

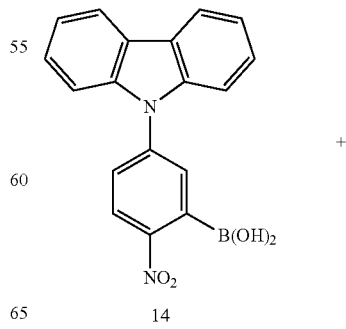

14

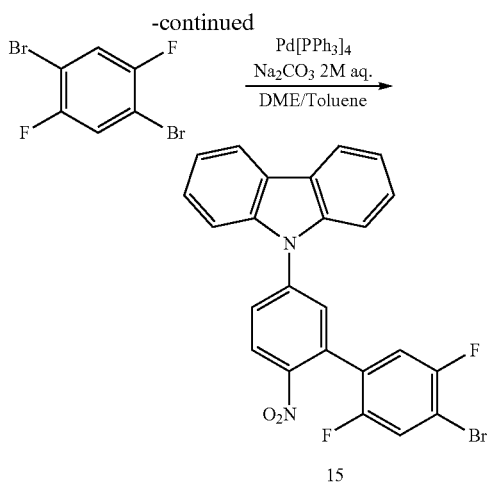

Compound A-14 (24.6 g, 74 mmol), 1,4-dibromo-2,5-difluorobenzene (20 g, 74 mmol), and a 2 M aqueous solution of $Na_2CO_3$ (75 mL, 150 mmol), DME (150 mL), toluene (150 mL), and $Pd[PPh_3]_4$ (4.3 g, 3.7 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 21 g in 60% yield.

FD-MS $C_{24}H_{13}BrF_2N_2O_2$: theoretical value 479, observed value 479

(2) Synthesis of Compound A-17

[Chem 171]

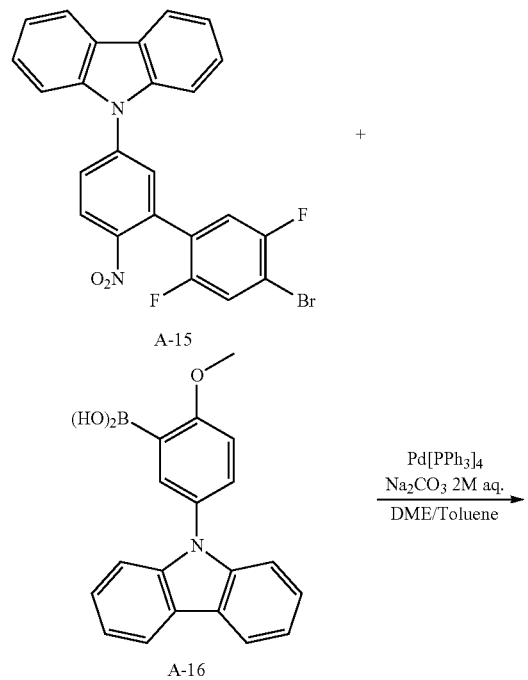

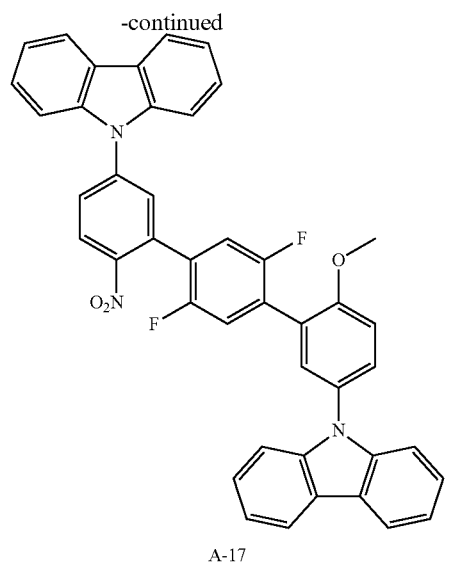

Compound A-15 (20.1 g, 42 mmol), Compound A-16 (14.6 g, 46 mmol), a 2 M aqueous solution of $Na_2CO_3$ (42 mL, 84 mmol), DME (85 mL), toluene (85 mL), and $Pd[PPh_3]_4$ (2.4 g, 2.1 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 15.5 g in 55% yield.

FD-MS $C_{43}H_{27}F_2N_3O_3$: theoretical value 671, observed value 671

(3) Synthesis of Compound A-18

[Chem 172]

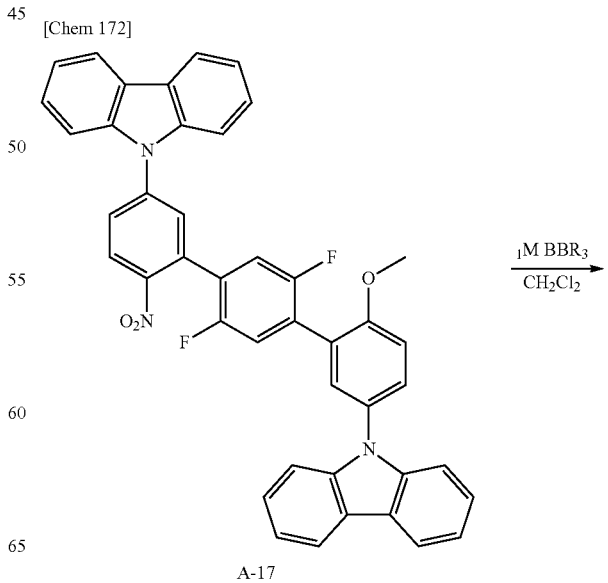

-continued

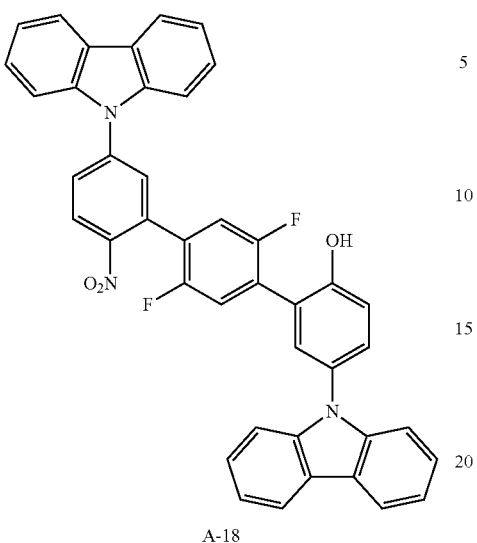

A-18

Compound A-17 (15.0 g, 22.3 mmol), a 1-M solution of in CH$_2$Cl$_2$ (100 mL, 100 mmol), and CH$_2$Cl$_2$ (200 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of NaHCO$_3$. The resultant sample was transferred to a separating funnel, and was extracted with CH$_2$Cl$_2$. The resultant sample was purified by column chromatography, whereby a white solid was obtained in an amount of 12.5 g in 85% yield.

FD-MS C$_{42}$H$_{25}$F$_2$N$_3$O$_3$: theoretical value 657, observed value 657

(4) Synthesis of Compound A-19

[Chem 173]

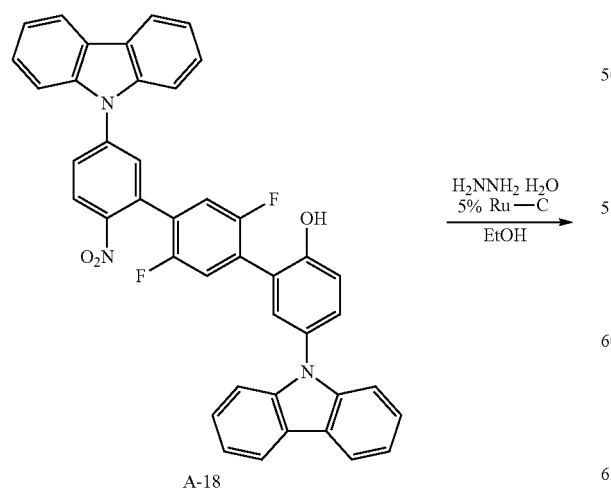

A-18

-continued

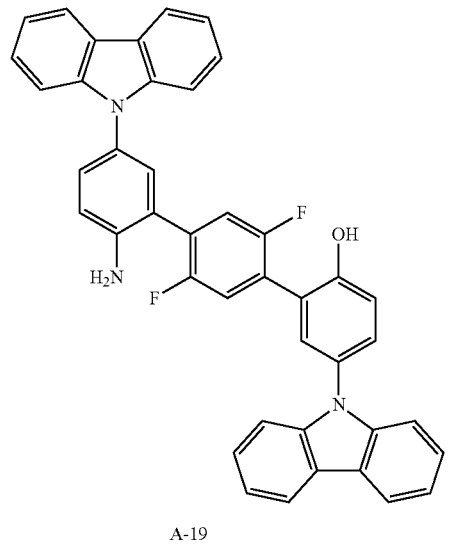

A-19

Compound A-18 (12.0 g, 18.2 mmol), 5% Ru—C (0.73 g), and ethanol (68 mL) were loaded into a three-necked flask, and the mixture was stirred under an Ar atmosphere at 70° C. Hydrazine monohydrate (5.5 g, 110 mmol) was dissolved in ethanol (6 mL) and dropped thereto. After that, the reaction mixture was refluxed for 8 hours. After the completion of the reaction, the resultant was cooled to room temperature. The sample was filtrated under reduced pressure, and the filtrate was concentrated. The sample was purified by silica gel column chromatography, whereby a white solid was obtained in an amount of 9.7 g in 85% yield.

FD-MS C$_{42}$H$_{27}$F$_2$N$_3$O: theoretical value 627, observed value 627

(5) Synthesis of Compound A-20

[Chem 174]

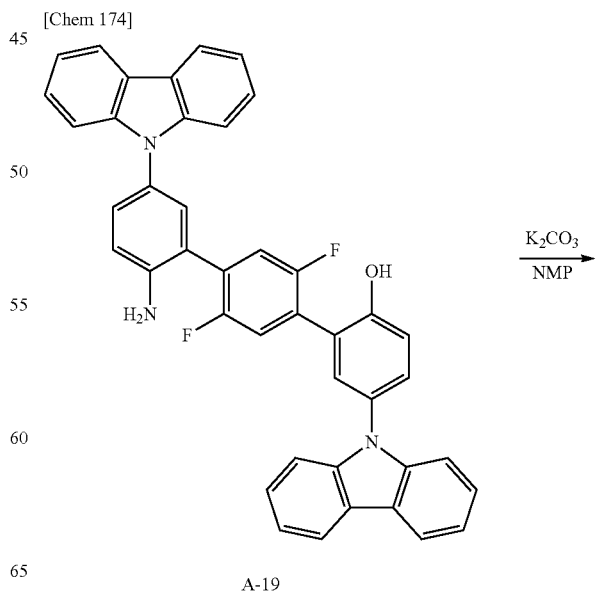

A-19

-continued

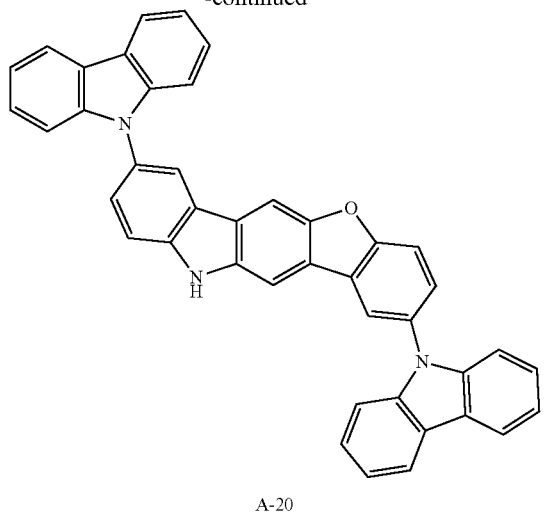

A-20

-continued

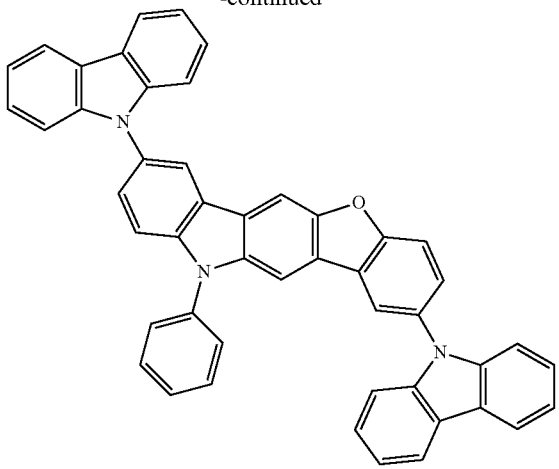

1-138

Compound A-19 (9.7 g, 15.5 mmol), $K_2CO_3$ (4.7 g, 34.1 mmol), and NMP (50 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 7.3 g in 80% yield.

FD-MS $C_{42}H_{25}N_3O$: theoretical value 587, observed value 587

(6) Synthesis of Compound 1-138

[Chem 175]

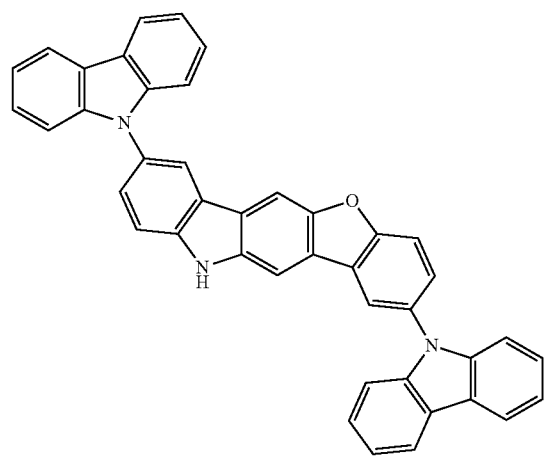

A-20

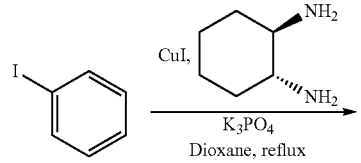

Compound A-20 (5.0 g, 8.5 mmol), iodobenzene (1.7 g, 8.5 mmol), CuI (1.6 g, 8.5 mmol), transcyclohexane 1,2-diamine (2.9 g, 25.5 mmol), $K_3PO_4$ (7.2 g, 34 mmol), and 1,4-dioxane (9 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 1-138) was obtained. The powder was purified by sublimation, whereby a white solid was obtained in an amount of 2.8 g in 50% yield.

FD-MS $C_{48}H_{29}N_3O$: theoretical value 663, observed value 663

Synthesis Example 1-14

Synthesis of Compound 1-140

[Chem 176]

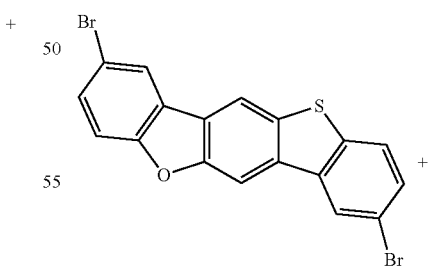

A-21

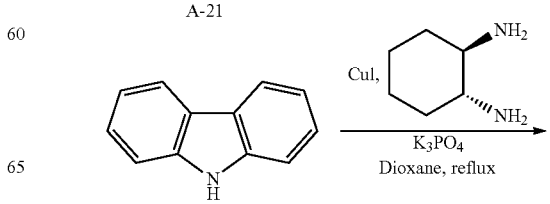

-continued

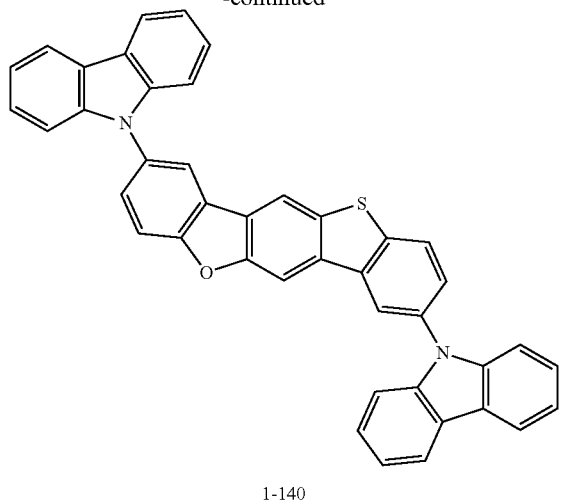

1-140

Compound A-21 (2.8 g, 7.3 mmol), carbazole (2.4 g, 14.6 mmol), CuI (1.4 g, 7.3 mmol), transcyclohexane 1,2-diamine (2.5 g, 21.9 mmol), K$_3$PO$_4$ (6.2 g, 29.2 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 1-140) was obtained. The powder was purified by sublimation, whereby a white solid was obtained in an amount of 2.3 g in 52% yield.

FD-MS C$_{42}$H$_{24}$N$_2$OS: theoretical value 604, observed value 604

Synthesis Example 1-15

Synthesis of Compound 1-148

(1) Synthesis of Compound A-23

[Chem 177]

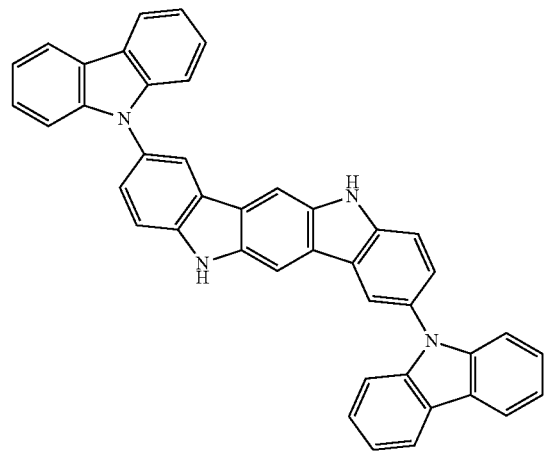

A-22

-continued

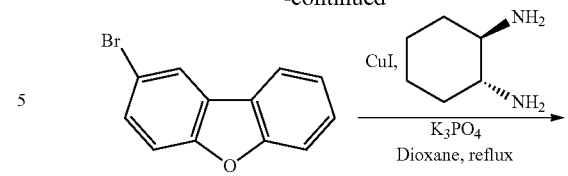

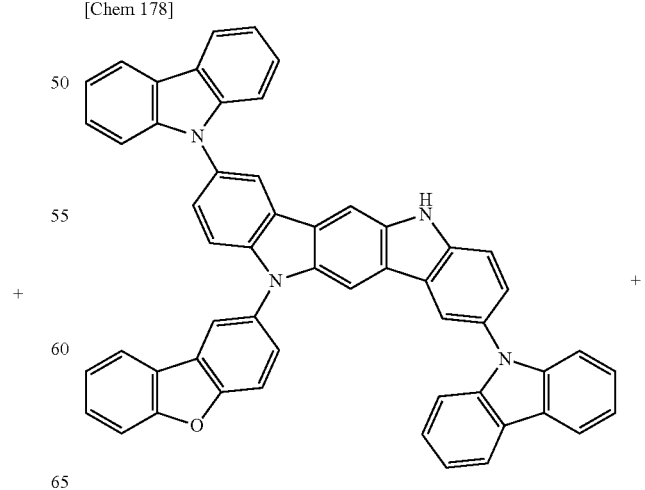

A-23

Compound A-22 (5.0 g, 8.5 mmol), 2-bromobenzofuran (2.1 g, 8.5 mmol), CuI (1.6 g, 8.5 mmol), transcyclohexane 1,2-diamine (2.9 g, 25.5 mmol), K$_3$PO$_4$ (7.2 g, 34 mmol), and 1,4-dioxane (9 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by column chromatography, whereby a white solid was obtained in an amount of 2.4 g in 37% yield.

FD-MS C$_{54}$H$_{32}$N$_4$O: theoretical value 752, observed value 752

(2) Synthesis of Compound 1-148

[Chem 178]

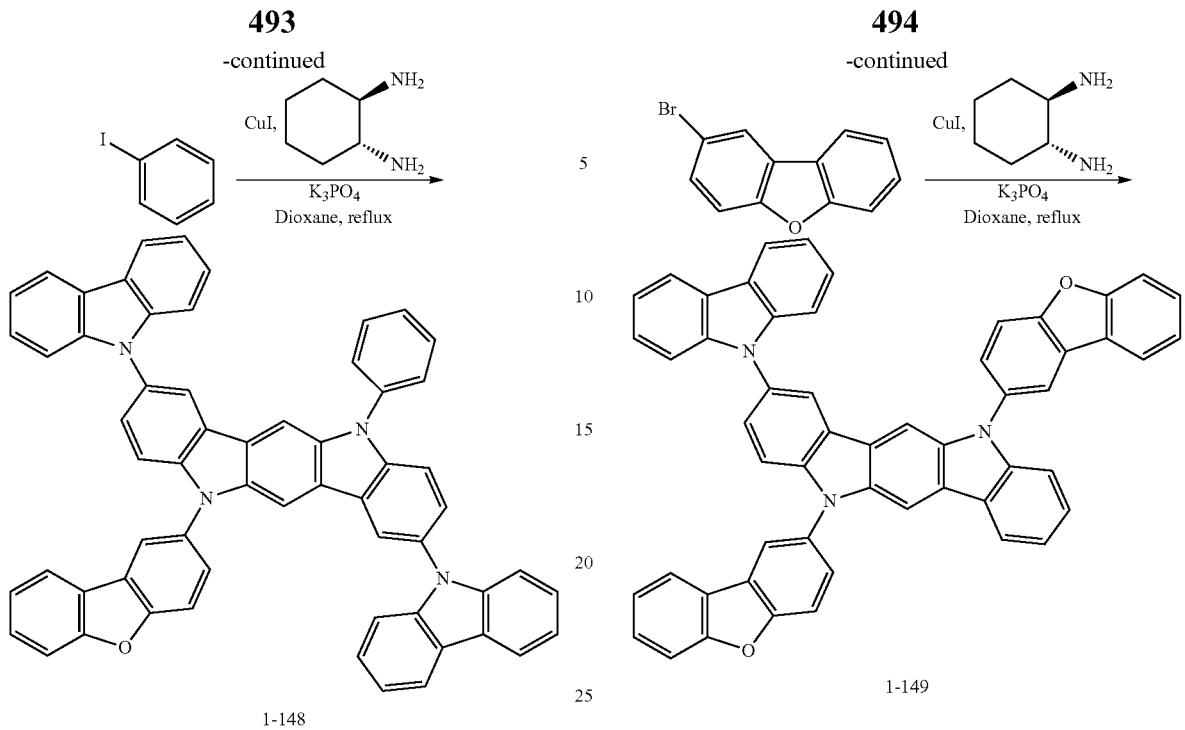

1-148

1-149

Compound A-23 (2.4 g, 3.2 mmol), iodobenzene (0.65 g, 3.2 mmol), CuI (0.61 g, 3.2 mmol), transcyclohexane 1,2-diamine (1.1 g, 9.6 mmol), K$_3$PO$_4$ (2.7 g, 12.8 mmol), and 1,4-dioxane (4 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 1-148) was obtained. The powder was purified by sublimation, whereby a white solid was obtained in an amount of 1.4 g in 53% yield.

FD-MS C$_{60}$H$_{36}$N$_4$O: theoretical value 828, observed value 828

Compound A-24 (4.2 g, 10 mmol), 2-bromobenzofuran (5.0 g, 20 mmol), CuI (1.9 g, 10 mmol), transcyclohexane 1,2-diamine (3.4 g, 30 mmol), K$_3$PO$_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 1-149) was obtained. The powder was purified by sublimation, whereby a white solid was obtained in an amount of 2.6 g in 35% yield.

FD-MS C$_{54}$H$_{31}$N$_3$O$_2$: theoretical value 753, observed value 753

Synthesis Example 1-16

Synthesis of Compound 1-149

[Chem 179]

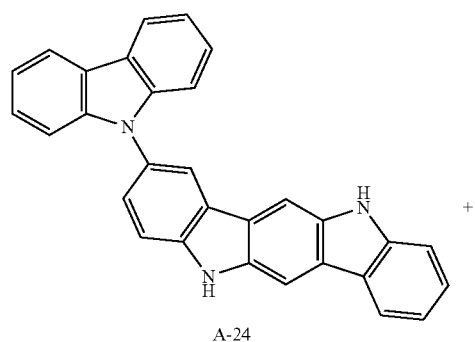

A-24

Synthesis Example 1-17

Synthesis of Compound 1-163

[Chem 180]

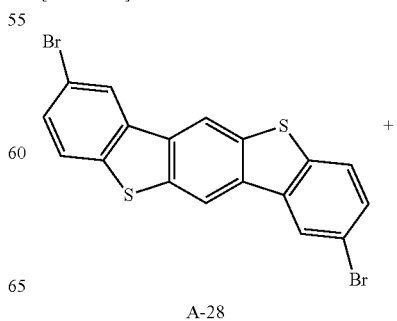

A-28

-continued

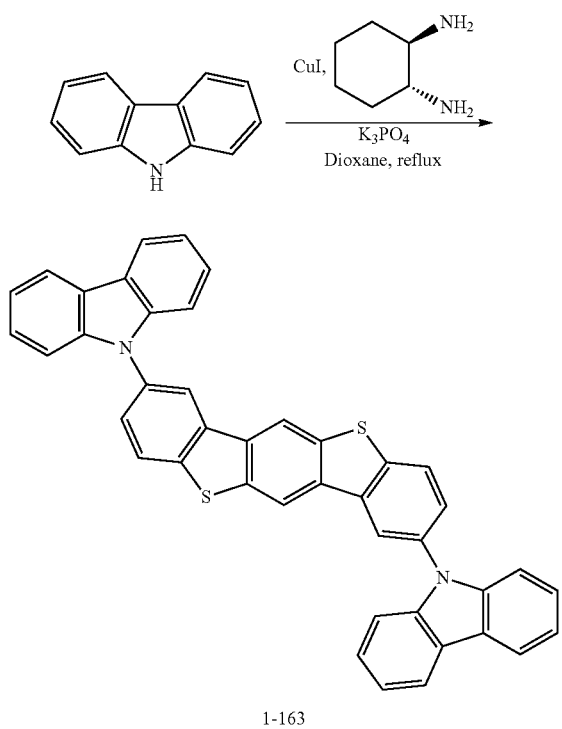

1-163

Compound A-28 (3.5 g, 7.9 mmol), carbazole (2.7 g, 16 mmol), CuI (1.5 g, 7.9 mmol), transcyclohexane 1,2-diamine (2.7 g, 23.7 mmol), K$_3$PO$_4$ (6.7 g, 31.6 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 1-163) was obtained. The powder was purified by sublimation, whereby a white solid was obtained in an amount of 2.2 g in 45% yield.

FD-MS C$_{42}$H$_{24}$N$_2$S$_2$: theoretical value 620, observed value 620

Synthesis Example 1-18

Synthesis of Compound 1-169

[Chem 181]

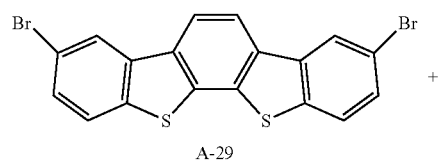

A-29

-continued

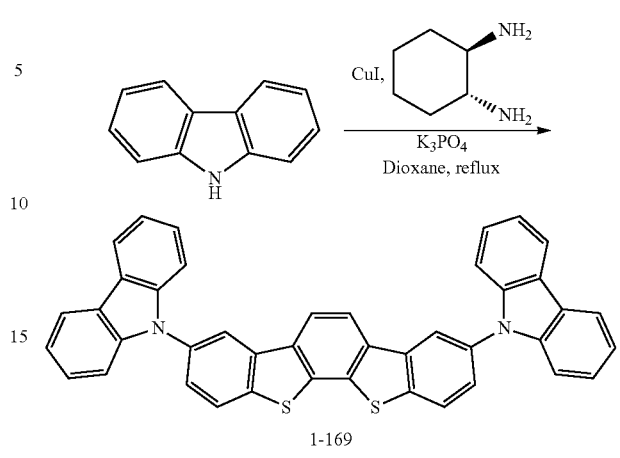

1-169

Compound A-29 (3.5 g, 7.9 mmol), carbazole (2.7 g, 16 mmol), CuI (1.5 g, 7.9 mmol), transcyclohexane 1,2-diamine (2.7 g, 23.7 mmol), K$_3$PO$_4$ (6.7 g, 31.6 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 1-169) was obtained. The powder was purified by sublimation, whereby a white solid was obtained in an amount of 2.3 g in 47% yield.

FD-MS C$_{42}$H$_{24}$N$_2$S$_2$: theoretical value 620, observed value 620

Synthesis Example 1-19

Synthesis of Compound 1-191

(1) Synthesis of Compound A-28

[Chem 182]

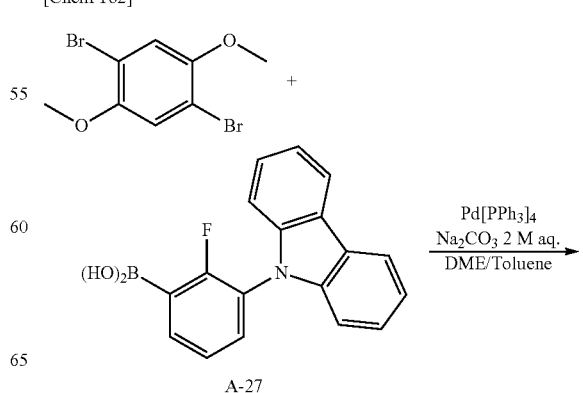

A-27

497
-continued

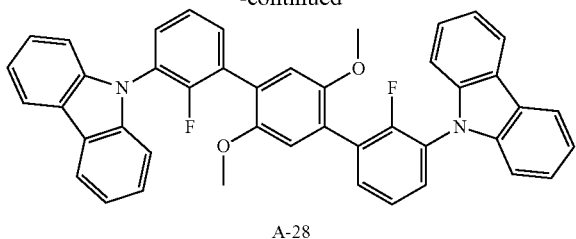

A-28

1,4-dibromo-2,5-dimethoxybenzene (4.4 g, 15.0 mmol), Compound A-27 (11.0 g, 36.0 mmol), and a 2 M aqueous solution of $Na_2CO_3$ (30 mL, 60.0 mmol), DME (30 mL), toluene (30 mL), and $Pd[PPh_3]_4$ (0.87 g, 0.75 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (150 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 9.5 g in 97% yield.

FD-MS $C_{44}H_{30}F_2N_2O_2$: theoretical value 656, observed value 656
[Chem 183]

(2) Synthesis of Compound A-29

[Chem 184]

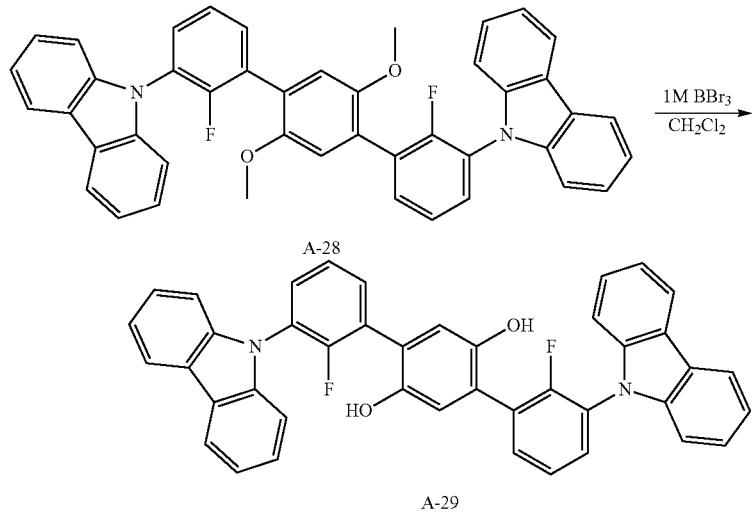

Compound A-28 (9.5 g, 14.5 mmol), a 1-M solution of $BBr_3$ in $CH_2Cl_2$ (90 mL, 90.0 mmol), and $CH_2Cl_2$ (100 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 8.0 g in 88% yield.

498

FD-MS $C_{42}H_{26}F_2N_2O_2$: theoretical value 628, observed value 628
[Chem 185]

(3) Synthesis of Compound 1-191

[Chem 186]

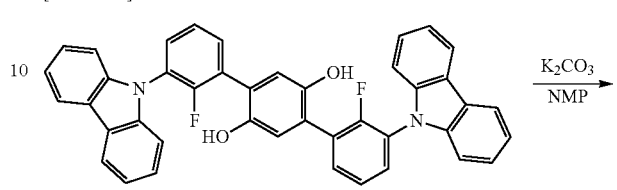

A-29

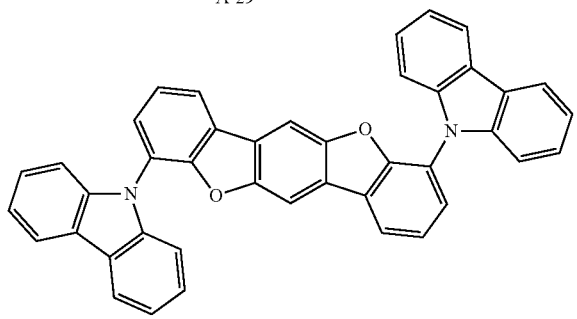

1-191

Compound A-29 (8.0 g, 12.7 mmol), $K_2CO_3$ (7.0 g, 50.9 mmol), and NMP (240 mL) were loaded into a three-necked flask, and the mixture was stirred under an Ar atmosphere at 200° C. for 3 hours.

After the completion of the reaction, the resultant was cooled to room temperature. Toluene (500 mL) was charged into the resultant sample. The mixture was transferred to a separating funnel, and was washed with water. The washed product was dried with $MgSO_4$, and was then filtrated and concentrated. The resultant sample was purified by silica gel column chromatography. The purified product was concentrated to dryness, and was then recrystallized twice, whereby a white powder (Compound 1-191) was obtained. The powder was purified by sublimation, whereby a white solid was obtained in an amount of 2.4 g in 31% yield.

FD-MS $C_{42}H_{24}N_2O_2$: theoretical value 588, observed value 588

An apparatus and measurement conditions adopted for field desorption mass spectrometry (FD-MS) in each of Synthesis Examples 1-1 to 1-19 are shown below.
Apparatus: HX110 (manufactured by JEOL Ltd.)
Conditions: accelerating voltage 8 kV
scan range m/z=50 to 1,500
emitter kind: carbon
emitter current: 0 mA→2 mA/min→40 mA (held for 10 minutes)

Example 1-1

(Production of Organic EL Device)

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound 1-A was deposited from the vapor onto the surface of the glass substrate on the side where a transparent electrode line was formed so as to cover the transparent electrode, whereby a hole transporting layer having a thickness of 30 nm was obtained.

Compound 1-1 as a host for phosphorescence and Ir(Ph-ppy)3 as a dopant for phosphorescence were co-deposited from the vapor onto the hole transporting layer, whereby a phosphorescent layer having a thickness of 30 nm was obtained. The concentration of Ir(Ph-ppy)$_3$ was 5 masse.

Subsequently, Compound 1-B having a thickness of 10 nm, Compound 1-C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

[Chem 187]

Compound 1-A

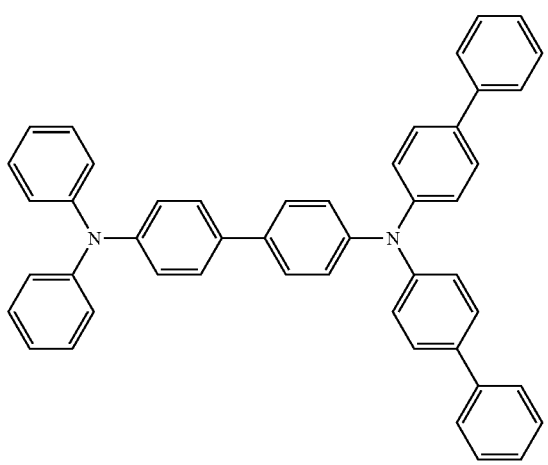

Compound 1-B

Compound 1-C

Ir(Ph-ppy)3(facial body)

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m$^2$ was determined. Further, the lifetime of the device at a luminance of 20,000 cd/m$^2$ was determined. Table 1 shows the results.

Examples 1-2 to 1-19

Organic EL devices were each produced in the same manner as in Example 1-1 except that a host material listed in Table 1 was used instead of Host Compound 1-1 in Example 1-1, and the devices were each evaluated in the same manner as in Example 1-1. Table 1 shows the results of the evaluation for light emitting performance.

Comparative Examples 1-1 to 1-3

Organic EL devices were each produced in the same manner as in Example 1-1 except that the following compounds (1-a) to (1-c) described in EP 0908787 A was used as a host material instead of Host Compound 1-1 in Example 1-1, and the devices were each evaluated in the same manner as in Example 1-1. Table 1 shows the results of the evaluation for light emitting performance.

Comparative Examples 1-4 to 1-9

Organic EL devices were each produced in the same manner as in Example 1 except that the following compounds (1-d) to (1-i) described in WO 2006-122630 was used as a host material instead of Host Compound 1-1 in Example 1-1, and the devices were each evaluated in the same manner as in Example 1-1. Table 1 shows the results of the evaluation for light emitting performance.

Comparative Examples 1-10 and 1-11

An organic EL device was produced in the same manner as in Example 1-1 except that the following compound (1-j) or (1-k) described in WO 2007-063754 was used as a host material instead of Host Compound 1-1 in Example 1-1, and the device was evaluated in the same manner as in Example 1-1. Table 1 shows the results of the evaluation for light emitting performance.

[Chem 188]

(1-a)

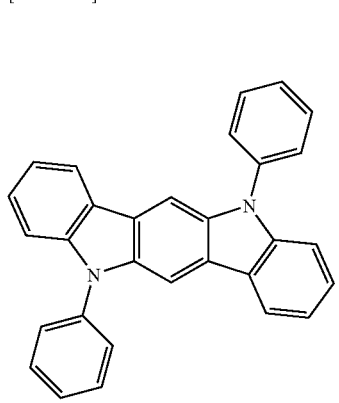

(1-b)

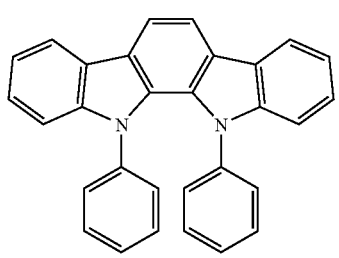

(1-c)

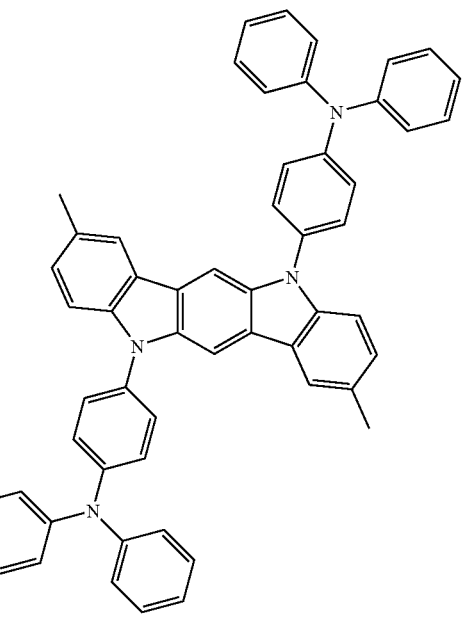

(1-d)

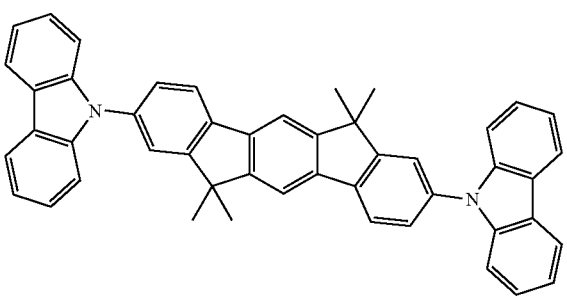

(1-e)

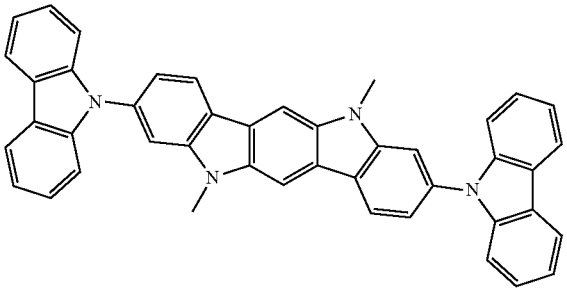

(1-f)

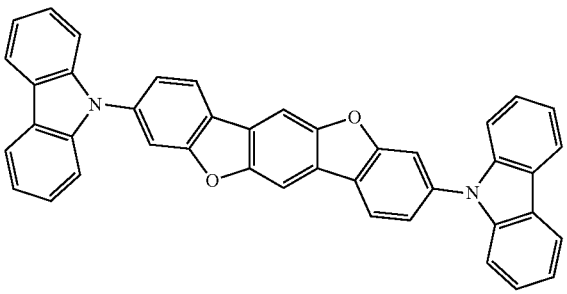

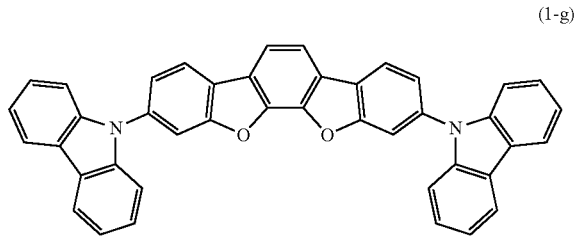
(1-g)

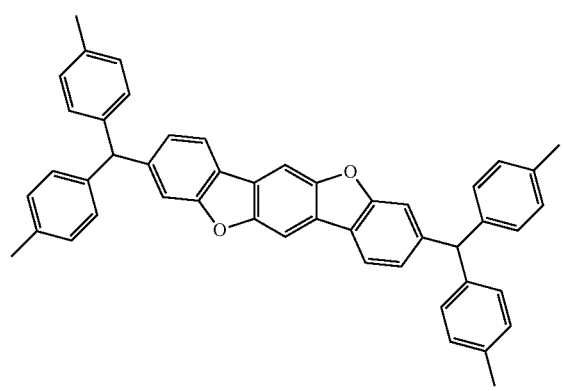
(1-h)

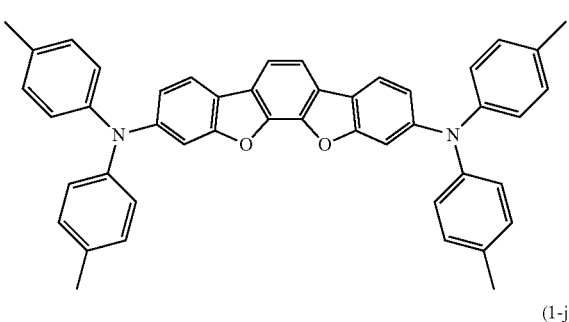
(1-i)

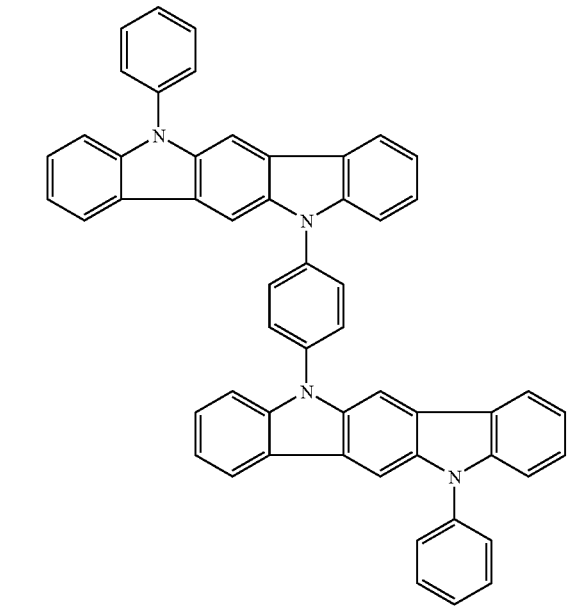
(1-j)

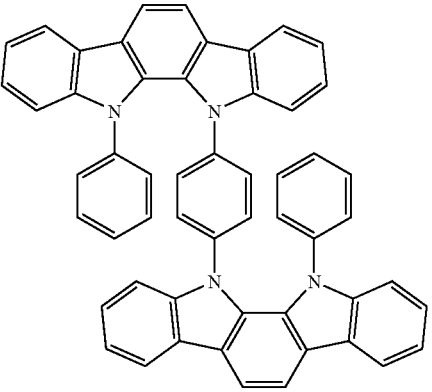
(1-k)

TABLE 1

| | Host compound | Voltage (V) @20 mA/cm$^2$ | Efficiency (cd/A) @1,000 cd/m$^2$ | Life time (hr) @20,000 cd/m$^2$ |
|---|---|---|---|---|
| Example 1-1 | (1-1) | 4.8 | 58.1 | 400 |
| Example 1-2 | (1-17) | 4.9 | 60.9 | 390 |
| Example 1-3 | (1-18) | 5.0 | 60.2 | 400 |
| Example 1-4 | (1-34) | 4.8 | 57.4 | 450 |
| Example 1-5 | (1-46) | 4.6 | 58.3 | 500 |
| Example 1-6 | (1-49) | 4.7 | 57.8 | 500 |
| Example 1-7 | (1-68) | 4.8 | 60.7 | 300 |
| Example 1-8 | (1-74) | 5.0 | 62.9 | 300 |
| Example 1-9 | (1-85) | 5.0 | 63.3 | 300 |
| Example 1-10 | (1-87) | 5.1 | 63.3 | 350 |
| Example 1-11 | (1-113) | 4.8 | 62.1 | 300 |
| Example 1-12 | (1-116) | 4.6 | 59.9 | 300 |
| Example 1-13 | (1-138) | 4.5 | 42.2 | 170 |
| Example 1-14 | (1-140) | 4.7 | 61.6 | 360 |
| Example 1-15 | (1-148) | 4.9 | 41.5 | 140 |
| Example 1-16 | (1-149) | 5.0 | 41.8 | 140 |
| Example 1-17 | (1-163) | 4.7 | 60.4 | 300 |
| Example 1-18 | (1-169) | 4.7 | 60.6 | 280 |
| Example 1-19 | (1-191) | 5.0 | 60.2 | 520 |
| Comparative Example 1-1 | (1-a) | 4.6 | 26.5 | 50 |
| Comparative Example 1-2 | (1-b) | 4.7 | 26.1 | 30 |
| Comparative Example 1-3 | (1-c) | 4.2 | 17.6 | 30 |
| Comparative Example 1-4 | (1-d) | 4.9 | 36.3 | 20 |
| Comparative Example 1-5 | (1-e) | 4.3 | 27.4 | 40 |
| Comparative Example 1-6 | (1-f) | 5.6 | 35.9 | 120 |
| Comparative Example 1-7 | (1-g) | 5.6 | 36.1 | 100 |
| Comparative Example 1-8 | (1-h) | 4.8 | 38.5 | 10 |
| Comparative Example 1-9 | (1-i) | 4.9 | 39.6 | 10 |
| Comparative Example 1-10 | (1-j) | 4.3 | 17.3 | 30 |
| Comparative Example 1-11 | (1-k) | 4.5 | 17.9 | 20 |

Synthesis Example 2-1

Synthesis of Compound 2-1

(1) Synthesis of Compound B-1

[Chem 189]

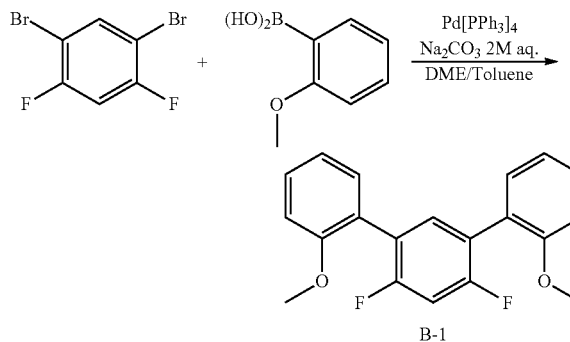

1,3-dibromo-4,6-difluorobenzene (50.0 g, 183.9 mmol), 2-methoxyphenylboronic acid (67.1 g, 441.4 mmol), and a 2 M aqueous solution of $Na_2CO_3$ (368 mL, 736 mmol), DME (370 mL), toluene (370 mL), and $Pd[PPh_3]_4$ (21.3 g, 18.4 mmol) were loaded in to a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 40.2 g in 67% yield.

FD-MS $C_{20}H_{16}F_2O_2$: theoretical value 326, observed value 326

(2) Synthesis of Compound B-2

[Chem 190]

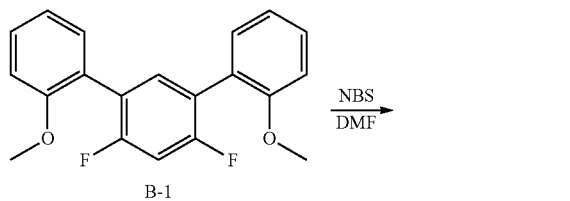

Compound B-1 (40.0 g, 122.6 mmol), NBS (43.6 g, 245 mmol) and DMF (1,100 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 42.1 g in 71% yield.

FD-MS $C_{20}H_{14}Br_2F_2O_2$: theoretical value 484, observed value 484

(3) Synthesis of Compound B-3

[Chem 191]

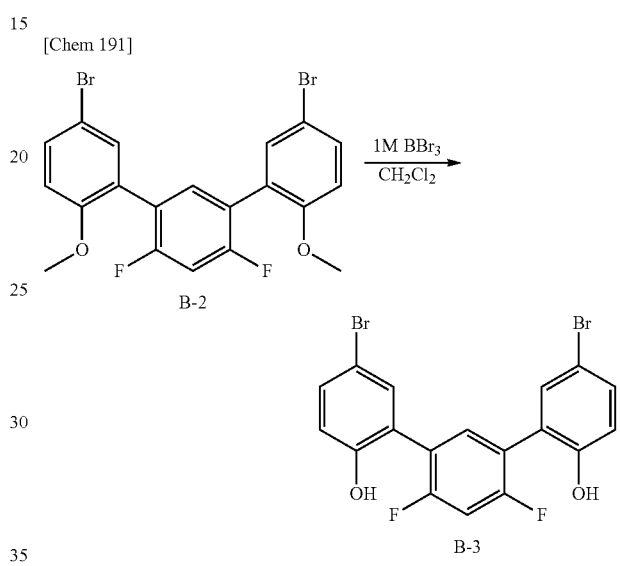

Compound B-2 (40.0 g, 82.6 mmol), a 1-M solution of $BBr_3$ in $CH_2Cl_2$ (194 mL, 194 mmol), and $CH_2Cl_2$ (500 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 30.2 g in 80% yield.

FD-MS $C_{18}H_{10}Br_2F_2O_2$: theoretical value 456, observed value 456

(4) Synthesis of Compound B-4

[Chem 192]

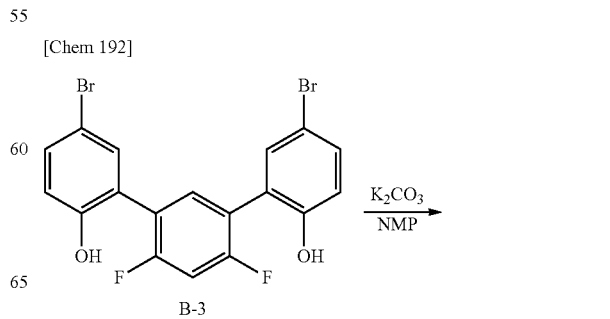

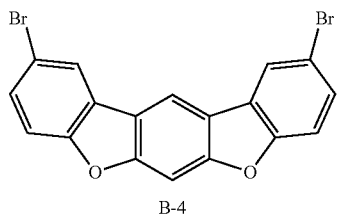

B-4

Compound B-3 (30.0 g, 65.7 mmol), K$_2$CO$_3$ (19.9 g, 144.5 mmol), and NMP (270 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 21.9 g in 80% yield.

FD-MS C$_{18}$H$_8$Br$_2$O$_2$: theoretical value 416, observed value 416

(5) Synthesis of Compound 2-1

[Chem 193]

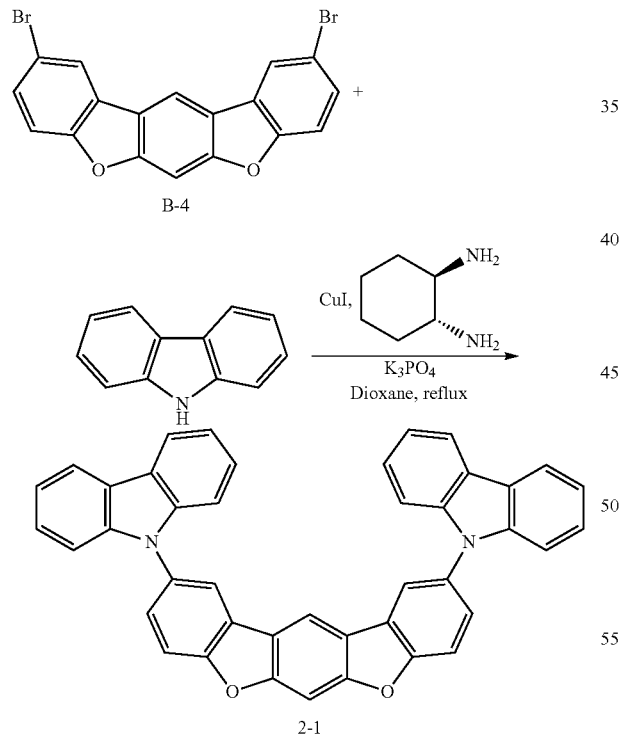

2-1

Compound B-4 (3 g, 7.2 mmol), carbazole (2.9 g, 17.3 mmol), CuI (1.4 g, 7.2 mmol), transcyclohexane 1,2-diamine (2.5 g, 21.6 mmol), K$_3$PO$_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was trans-ferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 2-1) was obtained. The powder was purified by sublimation, whereby a white solid was obtained in an amount of 2.5 g in 60% yield.

FD-MS C$_{42}$H$_{24}$N$_2$O$_2$: theoretical value 588, observed value 588

Synthesis Example 2-2

Synthesis of Compound 2-17

(1) Synthesis of Compound B-5

[Chem 194]

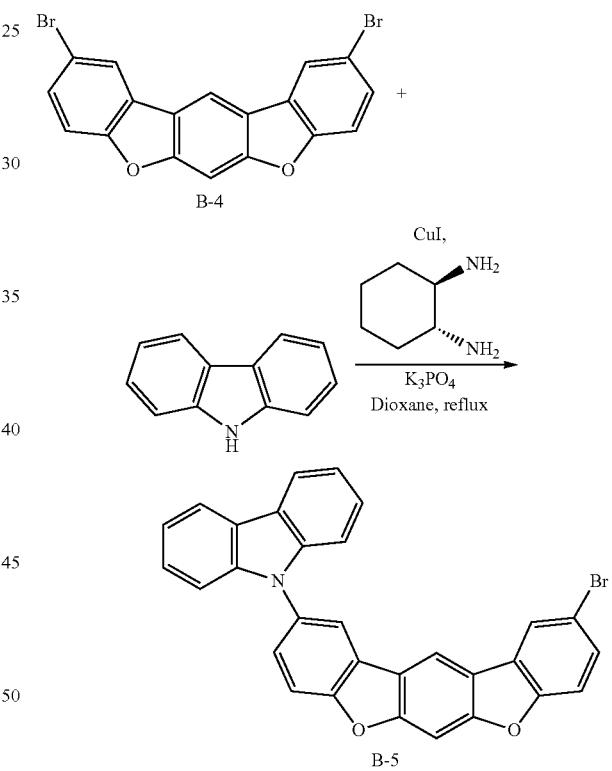

B-5

Compound B-4 (3 g, 7.2 mmol), carbazole (1.5 g, 7.2 mmol), CuI (1.4 g, 7.2 mmol), transcyclohexane 1,2-diamine (2.5 g, 21.6 mmol), K$_3$PO$_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by column chromatography, whereby a white solid was obtained in an amount of 2.0 g in 54% yield.

FD-MS $C_{30}H_{16}BrNO_2$: theoretical value 502, observed value 502

(2) Synthesis of Compound 2-17

[Chem 195]

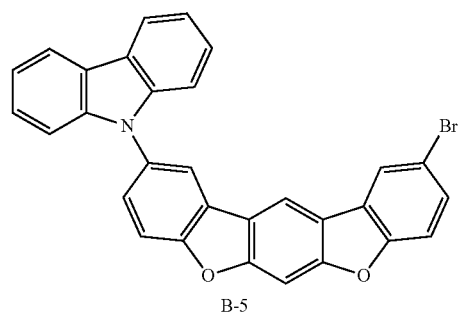

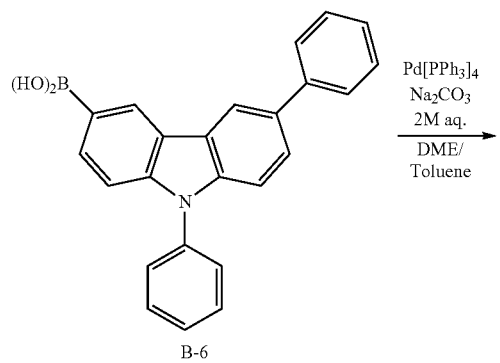

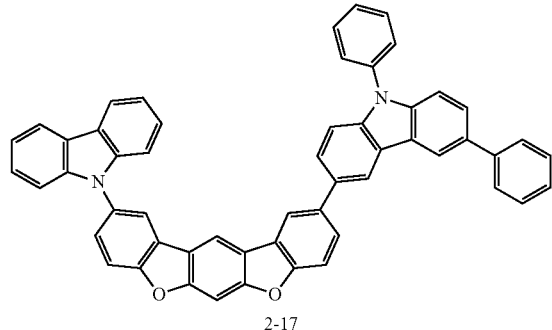

2-17

Compound B-5 (3.0 g, 6.0 mmol), Compound B-6 (2.4 g, 6.6 mmol), a 2 M aqueous solution of $Na_2CO_3$ (6 mL, 12 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 2-17) was obtained. The powder was purified by sublimation, whereby a white solid was obtained in an amount of 2.5 g in 56% yield.

FD-MS $C_{54}H_{32}N_2O_4$: theoretical value 740, observed value 740

Synthesis Example 2-3

Synthesis of Compound 2-18

[Chem 196]

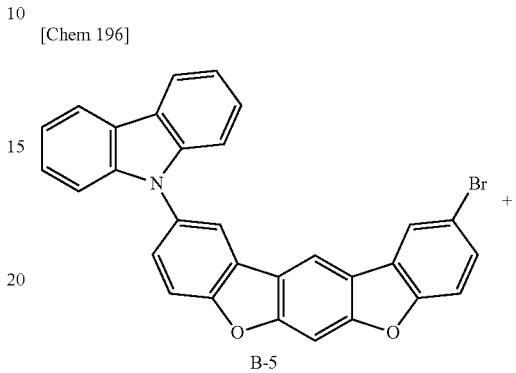

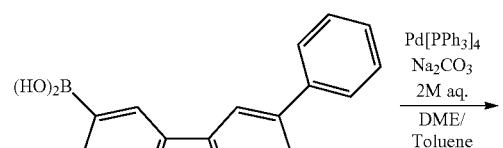

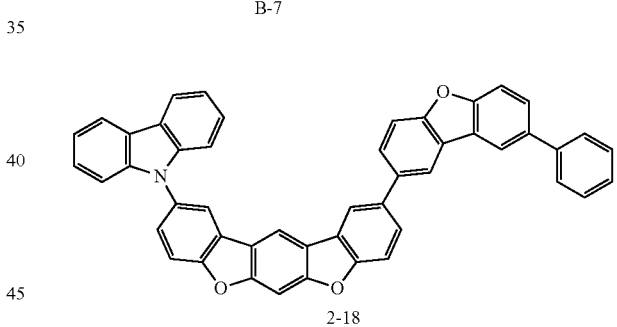

2-18

Compound B-5 (3.0 g, 6.0 mmol), Compound B-7 (1.7 g, 6.0 mmol), a 2 M aqueous solution of $Na_2CO_3$ (6 mL, 12 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 2-18) was obtained. The powder was purified by sublimation, whereby a white solid was obtained in an amount of 2.1 g in 52% yield.

FD-MS $C_{48}H_{27}NO_3$: theoretical value 665, observed value 665

Synthesis Example 2-4

Synthesis of Compound 2-34

(1) Synthesis of Compound B-8

[Chem 197]

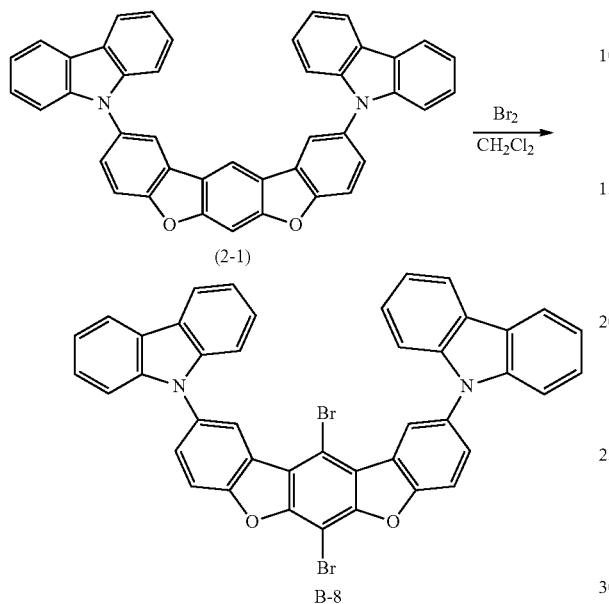

Compound (2-1) (10 g, 17 mmol) and CH$_2$Cl$_2$ (100 mL) were loaded into a three-necked flask and bromine (5.4 g, 34 mmol) was dropped thereto under an Ar atmosphere at 0° C. After that, the mixture was stirred at room temperature for 8 hours. After the completion of the reaction, the sample was transferred to a separating funnel and water (50 mL) was added thereto, followed by extraction with CH$_2$Cl$_2$. An organic layer was washed with a saturated NaNO$_2$ aqueous solution (50 mL) and dried with MgSO$_4$, followed by filtration and concentration. The sample was purified by a column chromatography, whereby a white solid was obtained in an amount of 7.6 g in 60% yield.

FD-MS C$_{42}$H$_{22}$Br$_2$N$_2$O$_2$: theoretical value 746, observed value 746

(2) Synthesis of Compound 2-34

[Chem 198]

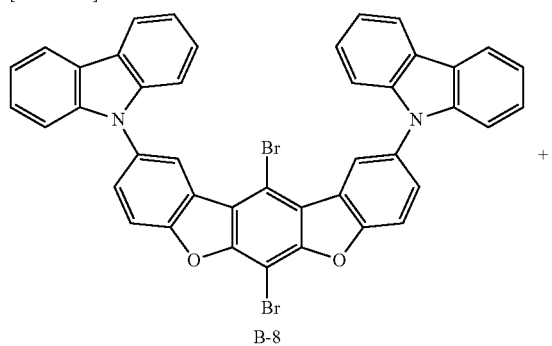

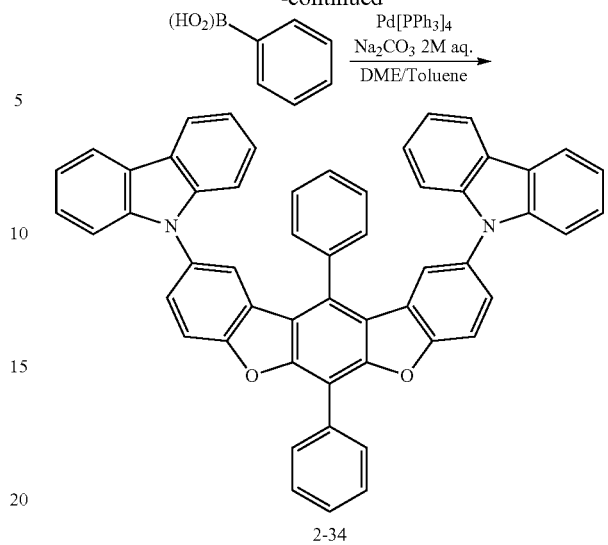

Compound B-8 (3.7 g, 4.9 mmol), phenylboronic acid (1.32 g, 10.8 mmol), a 2 M aqueous solution of Na$_2$CO$_3$ (5 mL, 9.8 mmol), DME (10 mL), toluene (10 mL), and Pd[PPh$_3$]$_4$ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 2-34) was obtained. The powder was purified by sublimation, whereby a white solid was obtained in an amount of 1.5 g in 40% yield.

FD-MS C$_{54}$H$_{32}$N$_2$O$_2$: theoretical value 740, observed value 740

Synthesis Example 2-5

Synthesis of Compound 2-46

(1) Synthesis of Compound B-9

[Chem 199]

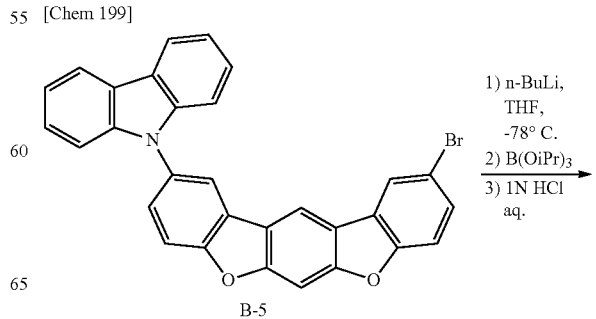

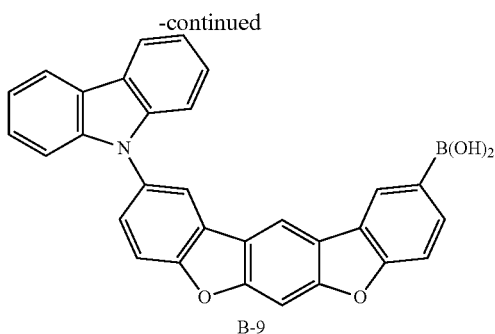

B-9

Compound B-5 (10 g, 20 mmol) and THF (200 mL) were loaded into a three-necked flask, and the mixture was cooled to −78° C. Then, n-BuLi (1.65-M solution in n-hexane, 13.3 mL, 22 mmol) was added dropwise to the flask, and the resultant mixture was stirred at −78° C. for 20 minutes. Triisopropyl boronate (11.3 g, 60 mmol) was added to the resultant, and the mixture was stirred at −78° C. for 1 hour. After that, the resultant was left to stand overnight at room temperature. Then, 1N HCl (40 mL) was charged into the resultant, and the mixture was stirred at room temperature for 1 hour. The resultant sample was concentrated, and was then transferred to a separating funnel. Water (50 mL) was charged into the funnel, and the mixture was extracted with $CH_2Cl_2$. The extract was dried with $MgSO_4$, and was then filtrated and concentrated. The resultant sample was purified by recrystallization (toluene-hexane), whereby a white solid was obtained in an amount of 5.9 g in 63% yield.

(2) Synthesis of Compound 2-46

Compound B-5 (3.0 g, 6.0 mmol), Compound B-9 (3.1 g, 6.6 mmol), a 2 M aqueous solution of $Na_2CO_3$ (6 mL, 12 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 2-46) was obtained. The powder was purified by sublimation, whereby a white solid was obtained in an amount of 2.1 g in 41% yield.

FD-MS $C_{60}H_{32}N_2O_4$: theoretical value 844, observed value 844

[Chem 200]

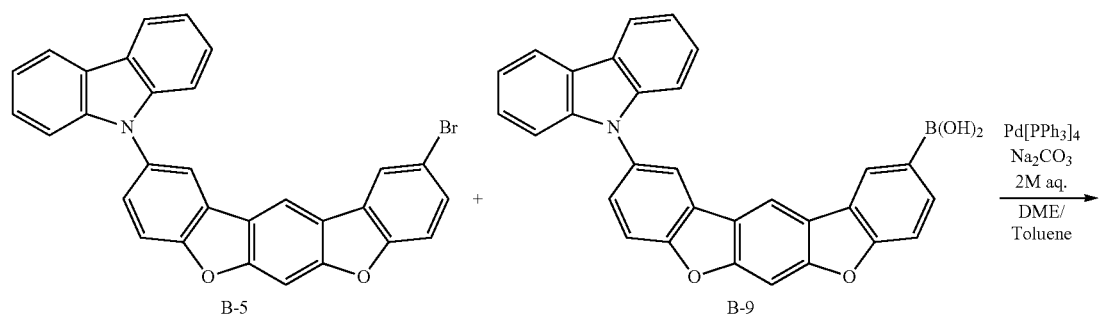

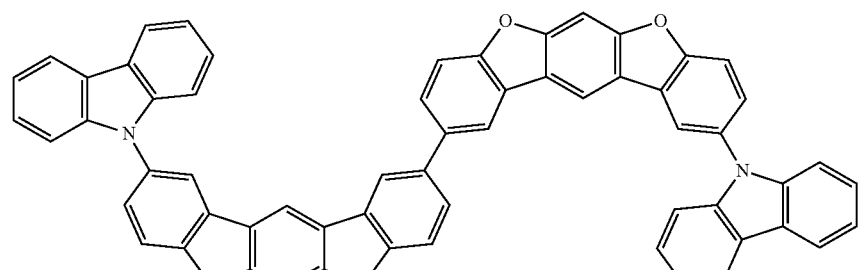

2-46

Synthesis Example 2-6

Synthesis of Compound 2-49

[Chem 201]

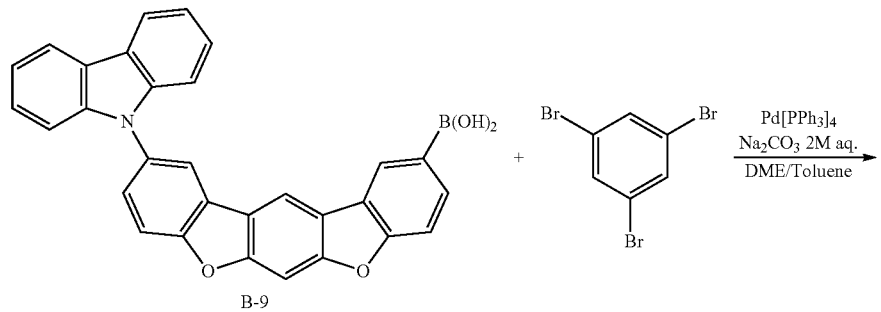

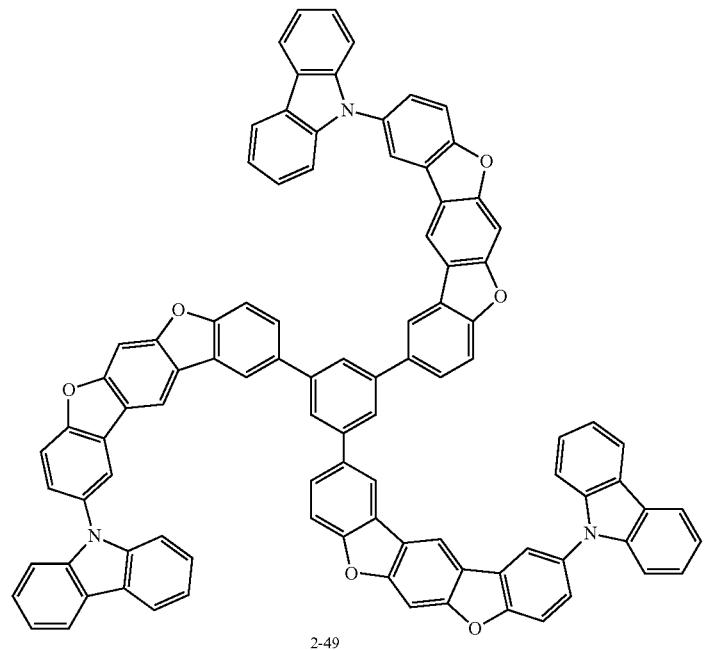

Compound B-9 (10.2 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 2-49) was obtained. The powder was purified by sublimation, whereby a white solid was obtained in an amount of 1.4 g in 14% yield.

FD-MS $C_{96}H_{51}N_3O_6$: theoretical value 1,342, observed value 1,342

Synthesis Example 2-7

Synthesis of Compound 2-68

[Chem 202]

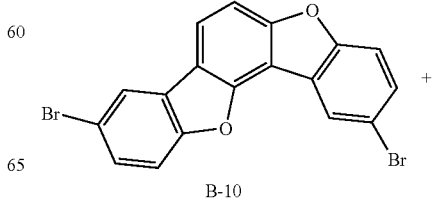

-continued

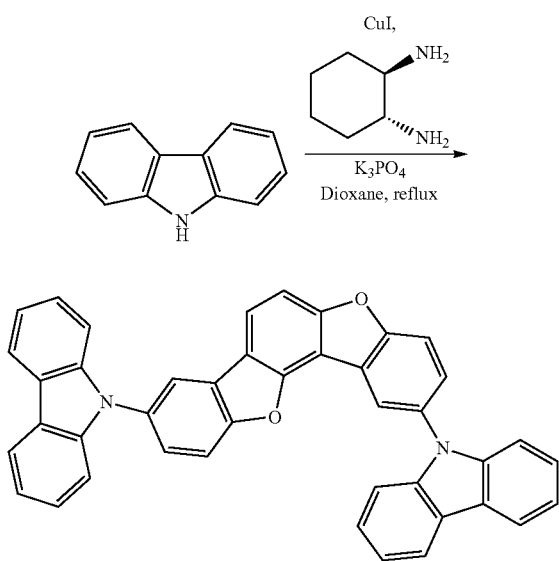

2-68

Compound B-10 (3 g, 7.2 mmol), carbazole (3.0 g, 14.4 mmol), CuI (1.4 g, 7.2 mmol), transcyclohexane 1,2-diamine (2.5 g, 21.6 mmol), K$_3$PO$_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 2-68) was obtained. The powder was purified by sublimation, whereby a white solid was obtained in an amount of 1.9 g in 46% yield.

FD-MS C$_{42}$H$_{24}$N$_2$O$_2$: theoretical value 588, observed value 588

Synthesis Example 2-8

Synthesis of Compound 2-74

[Chem 203]

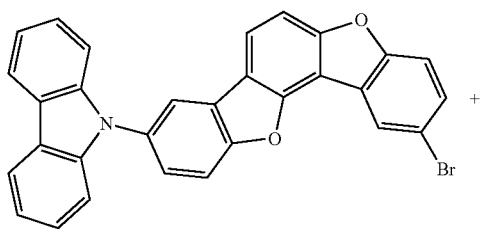

B-11

-continued

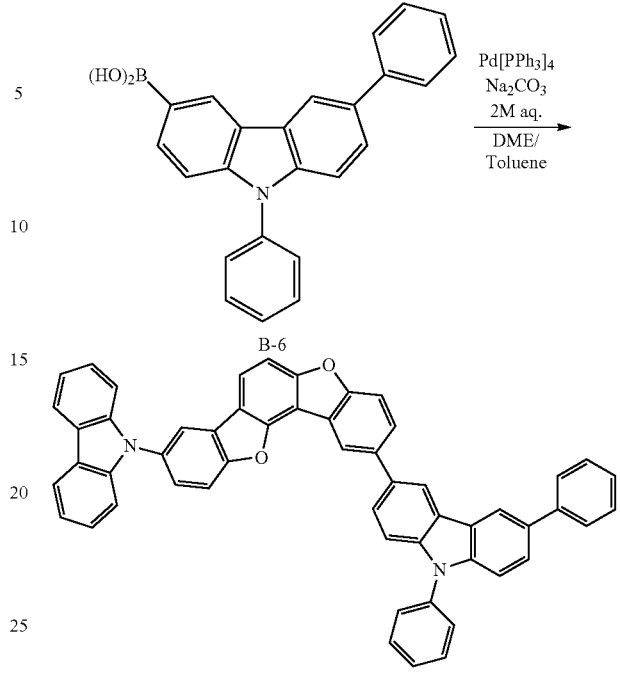

2-74

Compound B-11 (3.0 g, 6.0 mmol), Compound B-6 (2.4 g, 6.6 mmol), a 2 M aqueous solution of Na$_2$CO$_3$ (6 mL, 12 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 2-74) was obtained. The powder was purified by sublimation, whereby a white solid was obtained in an amount of 1.8 g in 40% yield.

FD-MS C$_{54}$H$_{32}$N$_2$O$_2$: theoretical value 740, observed value 740

Synthesis Example 2-9

Synthesis of Compound 2-85

[Chem 204]

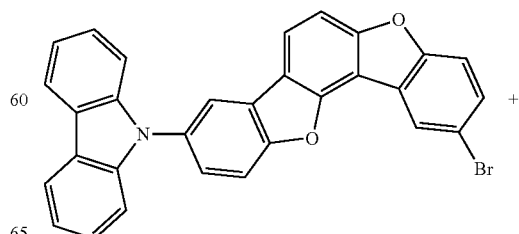

B-11

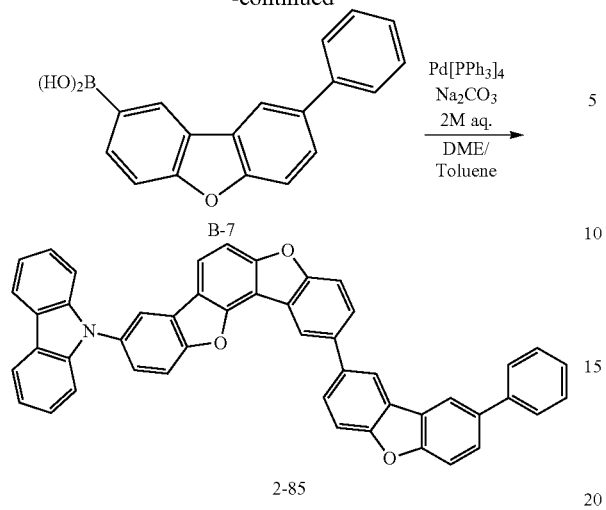

B-7

2-85

Compound B-11 (3.0 g, 6.0 mmol), Compound B-7 (1.9 g, 6.6 mmol), a 2 M aqueous solution of Na$_2$CO$_3$ (6 mL, 12 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 2-85) was obtained. The powder was purified by sublimation, whereby a white solid was obtained in an amount of 2.1 g in 52% yield.

FD-MS C$_{48}$H$_{27}$NO$_3$: theoretical value 665, observed value 665

Synthesis Example 2-10

Synthesis of Compound 2-87

[Chem 205]

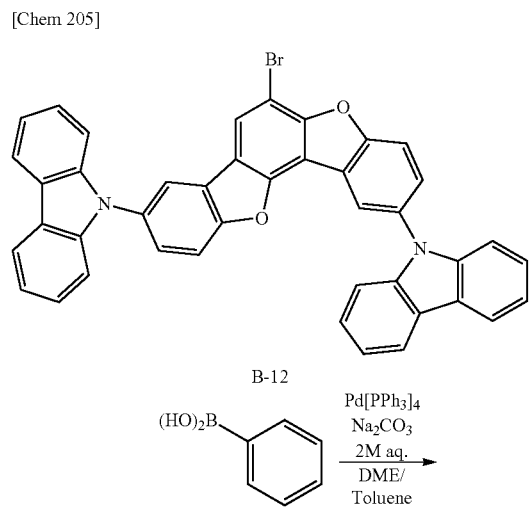

B-12

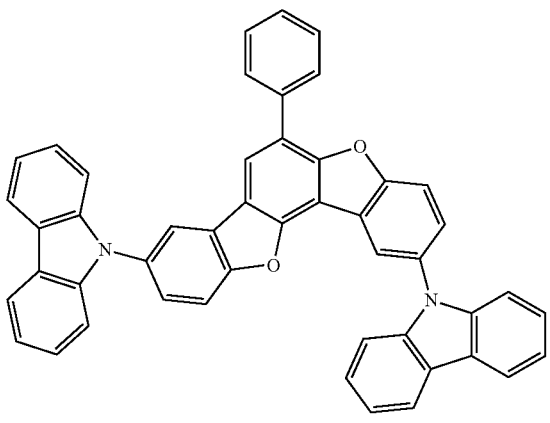

2-87

Compound B-12 (3.3 g, 5.0 mmol), phenylboronic acid (0.67 g, 5.5 mmol), a 2 M aqueous solution of Na$_2$CO$_3$ (5 mL, 10 mmol), DME (10 mL), toluene (10 mL), and Pd[PPh$_3$]$_4$ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 2-87) was obtained. The powder was purified by sublimation, whereby a white solid was obtained in an amount of 1.3 g in 40% yield.

FD-MS C$_{48}$H$_{28}$N$_2$O$_2$: theoretical value 664, observed value 664

Synthesis Example 2-11

Synthesis of Compound 2-113

(1) Synthesis of Compound B-13

[Chem 206]

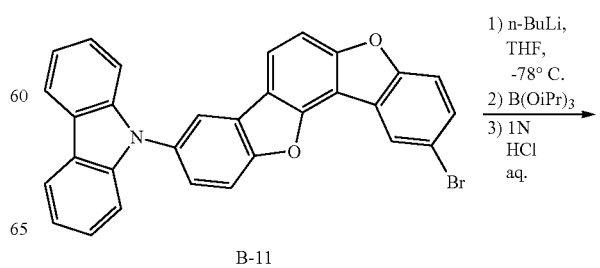

B-11

1) n-BuLi, THF, -78° C.
2) B(OiPr)$_3$
3) 1N HCl aq.

-continued

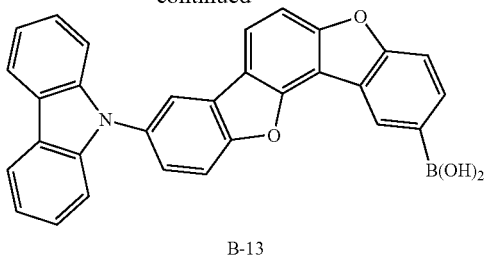

B-13

Compound B-11 (10 g, 20 mmol) and THF (200 mL) were loaded into a three-necked flask, and the mixture was cooled to −78° C. Then, n-BuLi (1.65-M solution in n-hexane, 13.3 mL, 22 mmol) was added dropwise to the flask, and the resultant mixture was stirred at −78° C. for 20 minutes. Triisopropyl boronate (11.3 g, 60 mmol) was added to the resultant, and the mixture was stirred at −78° C. for 1 hour. After that, the resultant was left to stand overnight at room temperature. Then, 1N HCl (40 mL) was charged into the resultant, and the mixture was stirred at room temperature for 1 hour. The resultant sample was concentrated, and was then transferred to a separating funnel. Water (50 mL) was charged into the funnel, and the mixture was extracted with CH$_2$Cl$_2$. The extract was dried with MgSO$_4$, and was then filtrated and concentrated. The resultant sample was purified by recrystallization (toluene-hexane), whereby a white solid was obtained in an amount of 6.3 g in 670 yield.

(2) Synthesis of Compound 2-113

Compound B-11 (3.0 g, 6.0 mmol), Compound B-13 (3.1 g, 6.6 mmol), a 2 M aqueous solution of Na$_2$CO$_3$ (6.0 mL, 12 mmol), DME (12 mL), toluene (12 mL), and Pd[PPh$_3$]$_4$ (0.35 g, 0.30 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 113) was obtained. The powder was purified by sublimation, whereby a white solid was obtained in an amount of 2.7 g in 53% yield.

FD-MS C$_{60}$H$_{32}$N$_2$O$_4$: theoretical value 844, observed value 844

[Chem 207]

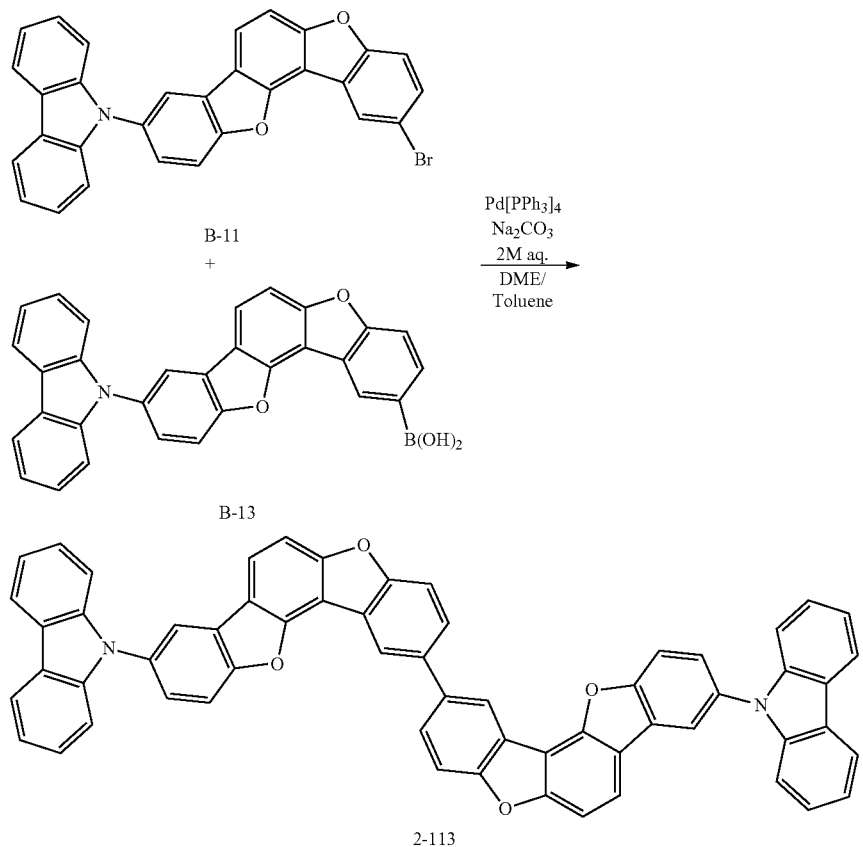

2-113

Synthesis Example 2-12

Synthesis of Compound 2-116

[Chem 208]

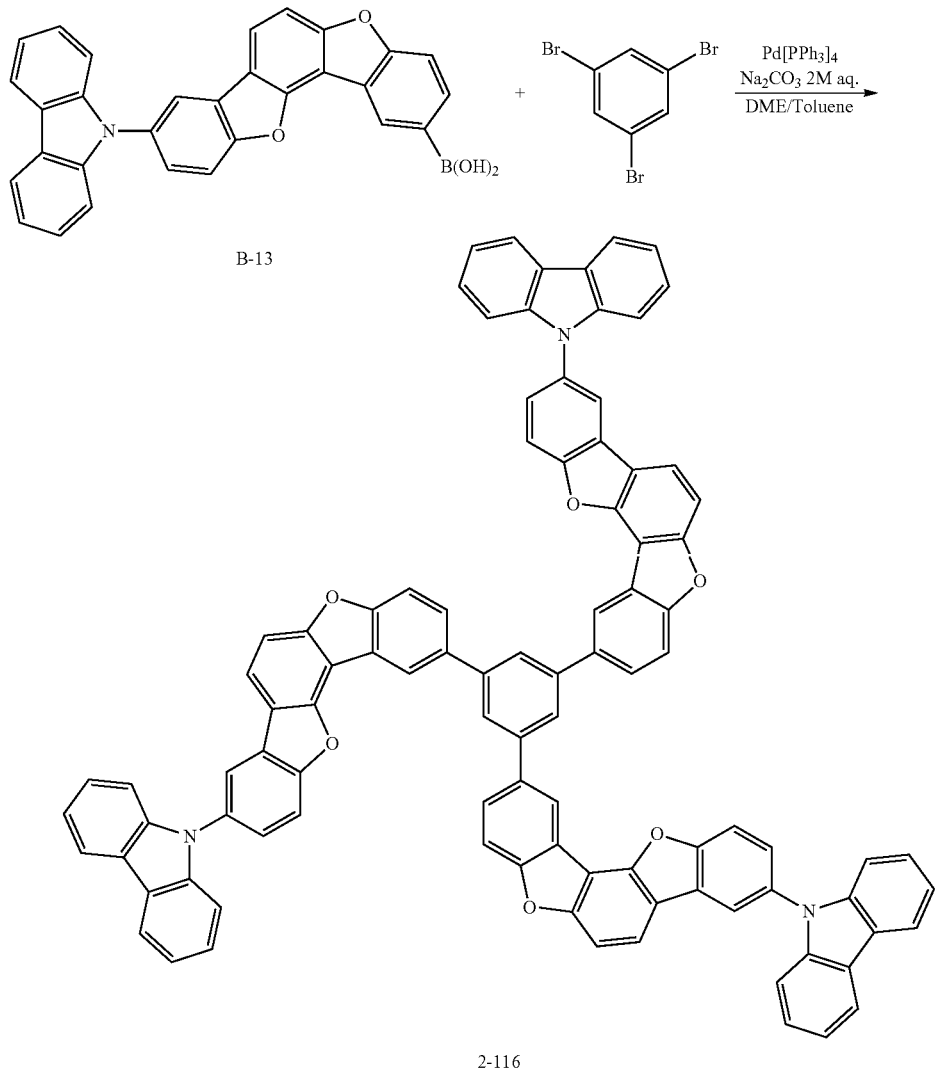

B-13

2-116

Compound B-13 (10.2 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and Pd[PPh$_3$]$_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 2-116) was obtained. The powder was purified by sublimation, whereby a white solid was obtained in an amount of 1.7 g in 17% yield.

FD-MS $C_{96}H_{51}N_3O_6$: theoretical value 1,342, observed value 1,342

Synthesis Example 2-13

Synthesis of Compound 2-138

(1) Synthesis of Compound B-15

[Chem 209]

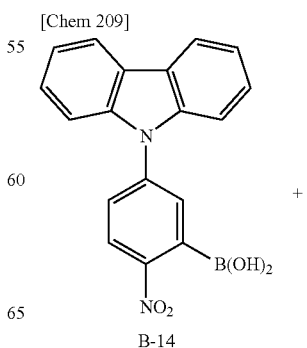

B-14

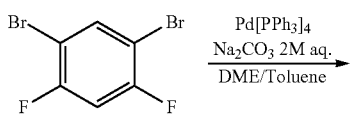

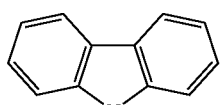

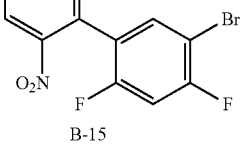

B-15

Compound B-14 (24.6 g, 74 mmol), 1,3-dibromo-4,6-difluorobenzene (20 g, 74 mmol), and a 2 M aqueous solution of $Na_2CO_3$ (75 mL, 150 mmol), DME (150 mL), toluene (150 mL), and $Pd[PPh_3]_4$ (4.3 g, 3.7 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 20 g in 56% yield.

FD-MS $C_{24}H_{13}BrF_2N_2O_2$: theoretical value 479, observed value 479

(2) Synthesis of Compound B-17

[Chem 210]

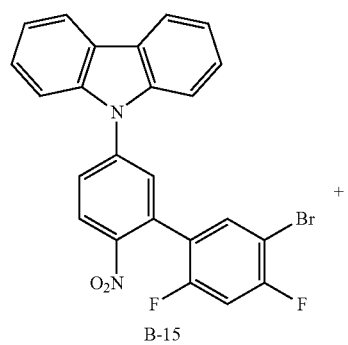

B-15

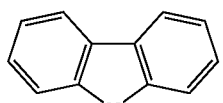

B-16

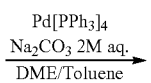

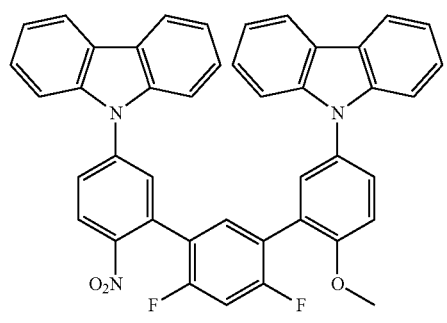

B-17

Compound B-15 (20.0 g, 42 mmol), Compound B-16 (14.6 g, 46 mmol), and a 2 M aqueous solution of $Na_2CO_3$ (42 mL, 84 mmol), DME (85 mL), toluene (85 mL), and $Pd[PPh_3]_4$ (2.4 g, 2.1 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 13.3 g in 47% yield.

FD-MS $C_{43}H_{27}F_2N_3O_3$: theoretical value 671, observed value 671

(3) Synthesis of Compound B-18

[Chem 211]

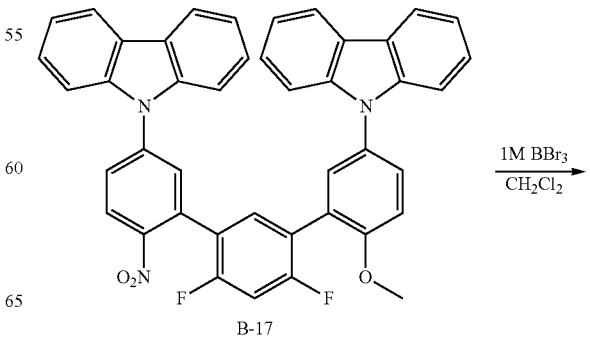

B-17

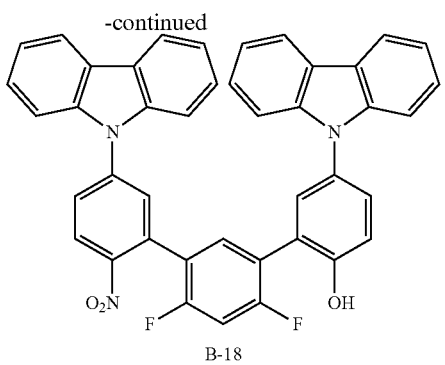

B-18

Compound B-17 (13.0 g, 19.4 mmol), a 1-M solution of BBr₃ in CH₂Cl₂ (100 mL, 100 mmol), and CH₂Cl₂ (200 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of NaHCO₃. The resultant sample was transferred to a separating funnel, and was extracted with CH₂Cl₂. The resultant sample was purified by column chromatography, whereby a white solid was obtained in an amount of 10.6 g in 83% yield.

FD-MS $C_{42}H_{25}F_2N_3O_3$: theoretical value 657, observed value 657

(4) Synthesis of Compound B-19

[Chem 212]

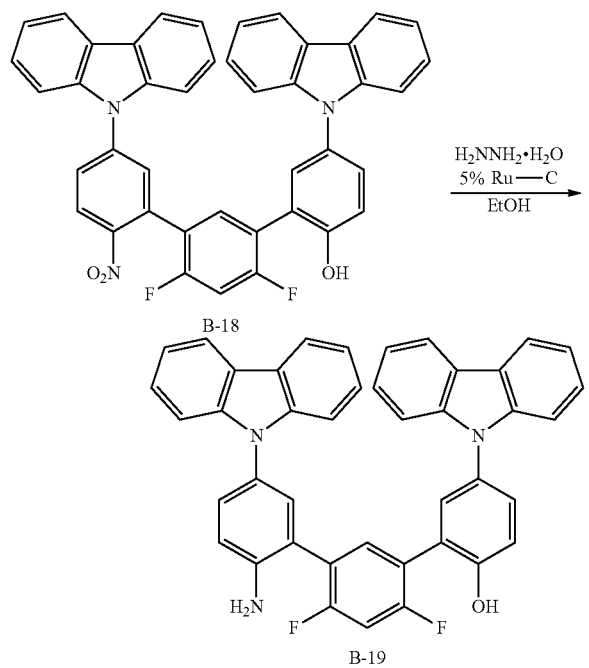

Compound B-18 (10.0 g, 15.2 mmol), 5% Ru—C (0.61 g), and ethanol (57 mL) were loaded into a three-necked flask, and the mixture was stirred under an Ar atmosphere at 70° C. Hydrazine monohydrate (4.6 g, 91.9 mmol) was dissolved in ethanol (5 mL) and dropped thereto. After that, the reaction mixture was refluxed for 8 hours. After the completion of the reaction, the resultant was cooled to room temperature. The sample was filtrated under reduced pressure, and the filtrate was concentrated. The sample was purified by silica gel column chromatography, whereby a white solid was obtained in an amount of 8.0 g in 84% yield.

FD-MS $C_{42}H_{27}F_2N_3O$: theoretical value 627, observed value 627

(5) Synthesis of Compound B-20

[Chem 213]

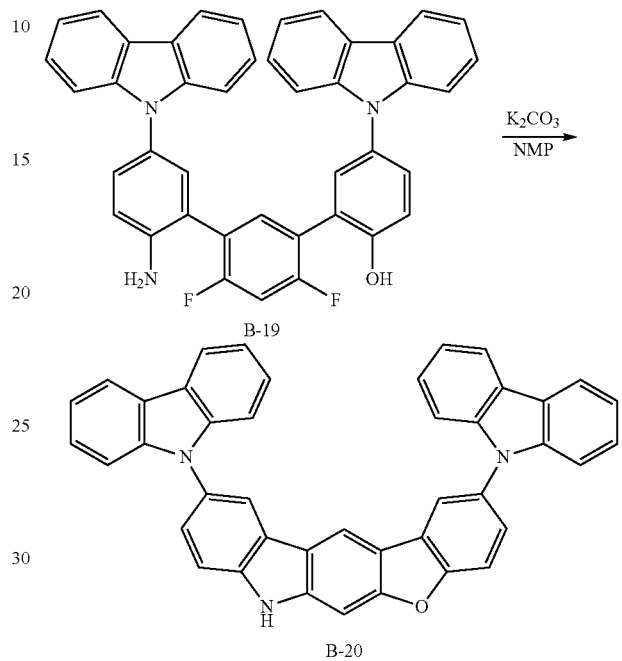

Compound B-19 (8.0 g, 12.7 mmol), K₂CO₃ (3.9 g, 28.1 mmol), and NMP (50 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (50 mL) was charged into the funnel. Then, the mixture was extracted with CH₂Cl₂. The resultant sample was purified by column chromatography, whereby a white solid was obtained in an amount of 6.0 g in 80% yield.

FD-MS $C_{42}H_{25}N_3O$: theoretical value 587, observed value 587

(6) Synthesis of Compound 2-138

[Chem 214]

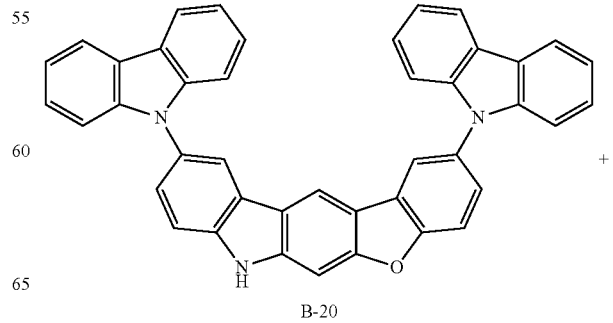

-continued

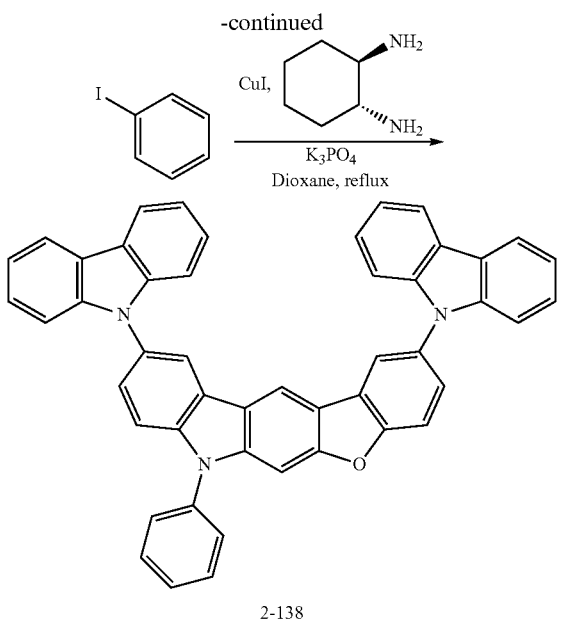

2-138

Compound B-20 (5.0 g, 8.5 mmol), iodobenzene (1.7 g, 8.5 mmol), CuI (1.6 g, 8.5 mmol), transcyclohexane 1,2-diamine (2.9 g, 25.5 mmol), K$_3$PO$_4$ (7.2 g, 34 mmol), and 1,4-dioxane (9 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 2-138) was obtained. The powder was purified by sublimation, whereby a white solid was obtained in an amount of 2.7 g in 47% yield.

FD-MS C$_{48}$H$_{29}$N$_3$O: theoretical value 663, observed value 663

Synthesis Example 2-14

Synthesis of Compound 2-140

[Chem 215]

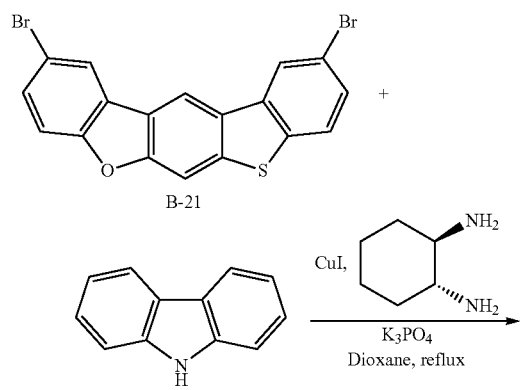

B-21

-continued

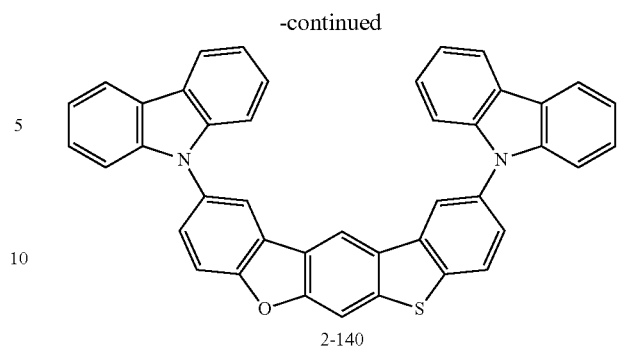

2-140

Compound B-21 (2.8 g, 7.3 mmol), carbazole (2.4 g, 14.6 mmol), CuI (1.4 g, 7.3 mmol), transcyclohexane 1,2-diamine (2.5 g, 21.9 mmol), K$_3$PO$_4$ (6.2 g, 29.2 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated to dryness, and was then recrystallized twice, whereby a white powder (Compound 2-140) was obtained. The powder was purified by sublimation, whereby a white solid was obtained in an amount of 2.4 g in 55% yield.

FD-MS C$_{42}$H$_{24}$N$_2$OS: theoretical value 604, observed value 604

Synthesis Example 2-15

Synthesis of Compound 2-148

(1) Synthesis of Compound B-23

[Chem 216]

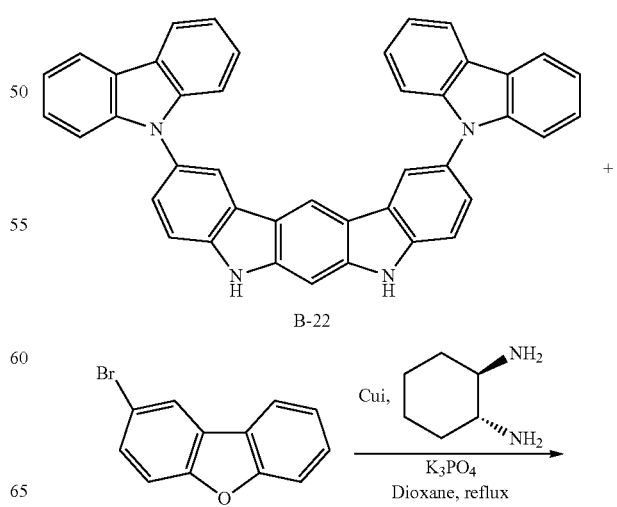

B-22

531
-continued

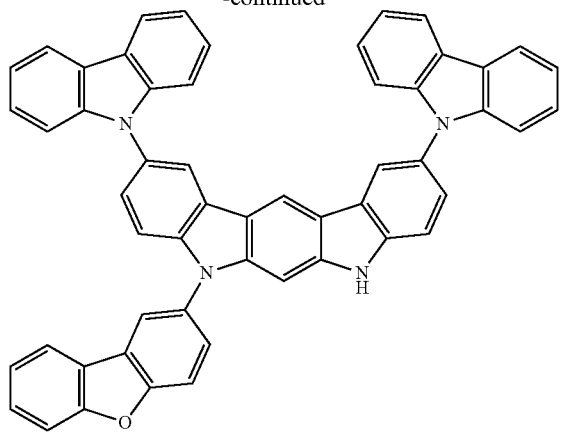

B-23

Compound B-22 (5.0 g, 8.5 mmol), 2-bromodibenzofuran (2.1 g, 8.5 mmol), CuI (1.6 g, 8.5 mmol), transcyclohexane 1,2-diamine (2.9 g, 25.5 mmol), $K_3PO_4$ (7.2 g, 34 mmol), and 1,4-dioxane (9 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 2.9 g in 45% yield.

FD-MS $C_{54}H_{32}N_4O$: theoretical value 752, observed value 752

(2) Synthesis of Compound 2-148

[Chem 217]

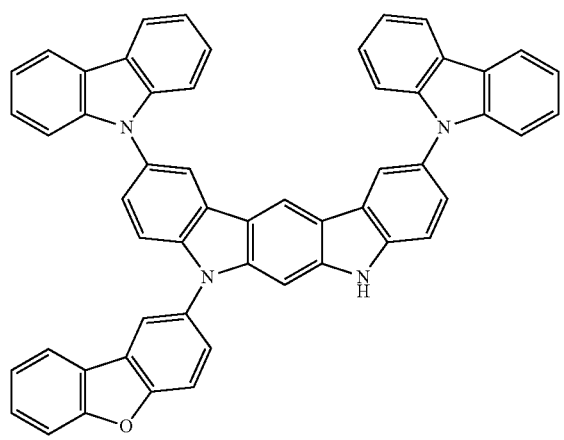

B-23

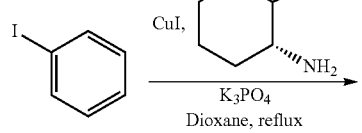

532
-continued

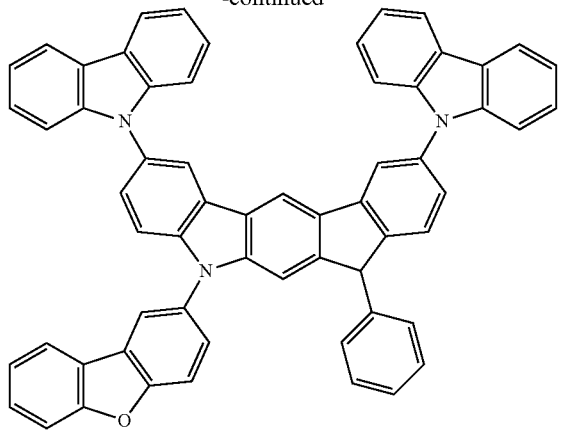

2-148

Compound B-23 (2.9 g, 3.9 mmol), iodobenzene (0.8 g, 3.9 mmol), CuI (0.74 g, 3.9 mmol), transcyclohexane 1,2-diamine (1.3 g, 11.7 mmol), $K_3PO_4$ (3.3 g, 15.6 mmol), and 1,4-dioxane (4 mL) were loaded into a three-necked flask, and the mixture was refluxed under an argon atmosphere for 10 hours.

After the completion of the reaction, the resultant was cooled to room temperature. The resultant sample was transferred to a separating funnel, and 50 mL of water was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 2-148) was obtained. The powder was purified by sublimation, whereby a white solid was obtained in an amount of 1.4 g in 43% yield.

FD-MS $C_{60}H_{36}N_4O$: theoretical value 828, observed value 828

Synthesis Example 2-16

Synthesis of Compound 2-149

[Chem 218]

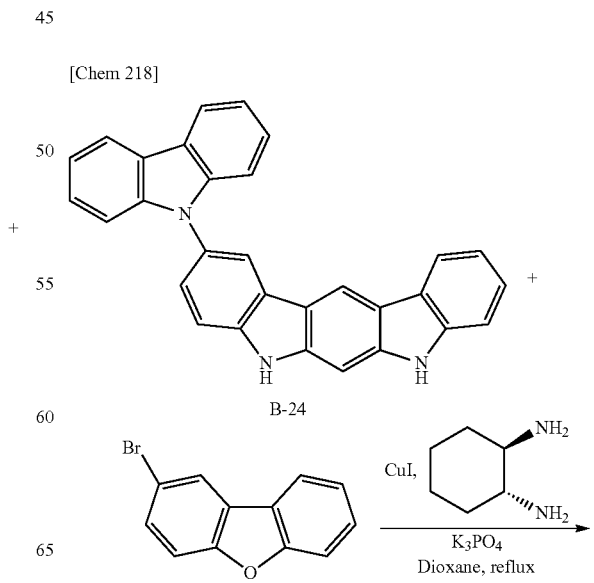

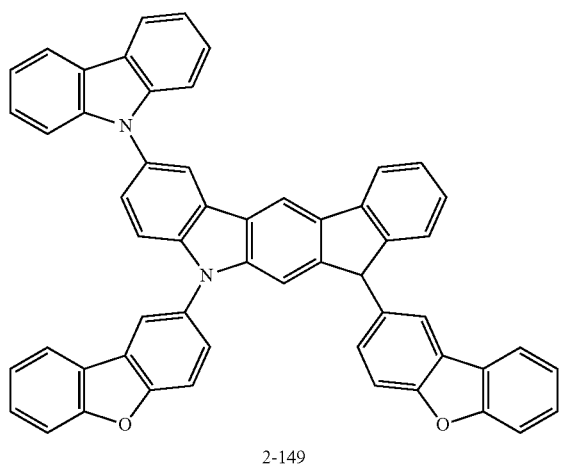

2-149

Compound B-24 (4.2 g, 10 mmol), 2-bromodibenzofuran (5.0 g, 20 mmol), CuI (1.9 g, 10 mmol), transcyclohexane 1,2-diamine (3.4 g, 30 mmol), $K_3PO_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 2-149) was obtained. The powder was purified by sublimation, whereby a white solid was obtained in an amount of 2.1 g in 28% yield.

FD-MS $C_{54}H_{31}N_3O_2$: theoretical value 753, observed value 753

Synthesis Example 2-17

Synthesis of Compounds 2-157 and 2-163

(1) Synthesis of Compound B-26

[Chem 219]

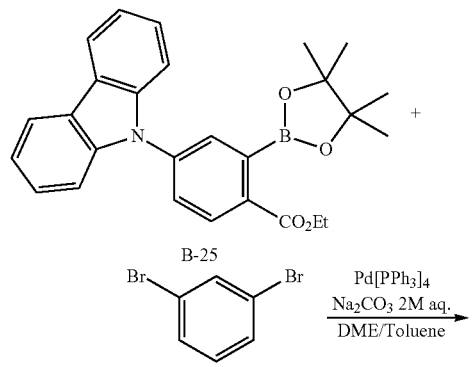

Compound B-25 (29.1 g, 66 mmol), 1,3-dibromobenzene (7.1 g, 30 mmol), a 2 M aqueous solution of $Na_2CO_3$ (60 mL, 120 mmol), DME (60 mL), toluene (60 mL), and $Pd[PPh_3]_4$ (1.7 g, 1.5 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 9.1 g in 43% yield.

FD-MS $C_{48}H_{36}N_2O_4$: theoretical value 704, observed value 704

(2) Synthesis of Compound B-27

[Chem 220]

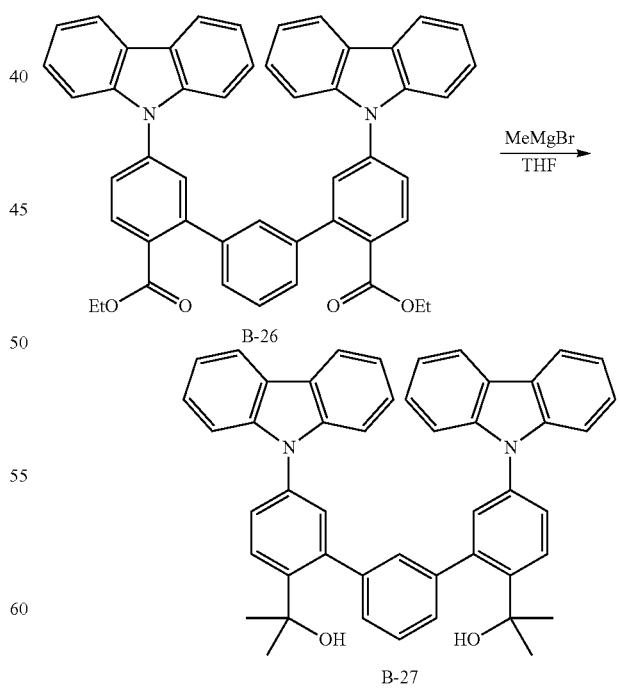

Compound B-26 (9.0 g, 12.8 mmol) and THF (45 mL) were loaded into a three-necked flask, and the mixture was stirred at 0° C. MeMgBr (0.97M THF solution, 59 mL, 57 mmol) was dropped thereto. After stirred at 0° C. for 3 hours, the mixture was left to stand at room temperature overnight. The sample was transferred to a separating funnel, and a saturated NH₄Cl aqueous solution (50 mL) was added, followed by extraction with AcOEt. The sample was dried with MgSO₄, followed by filtration and concentration. The sample was purified by silica gel column chromatography, whereby a white solid was obtained in an amount of 6.9 g in 80% yield.

FD-MS $C_{48}H_{40}N_2O_2$: theoretical value 676, observed value 676

(3) Synthesis of Compounds 2-157 and 2-163

[Chem 221]

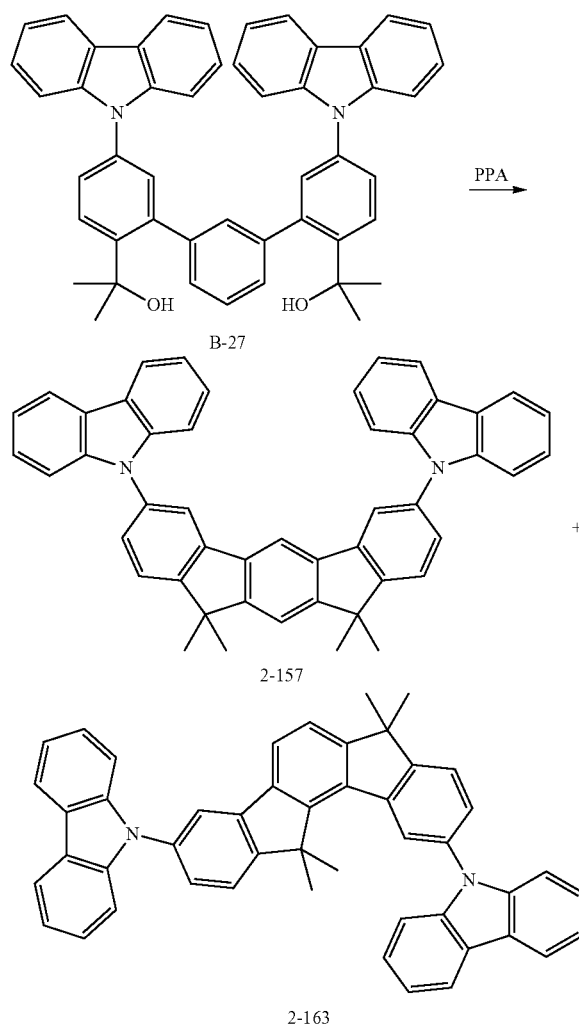

Compound B-27 (5 g, 7.4 mmol) and polyphosphoric acid (10 g) were loaded into a three-necked flask, and the mixture was stirred at 40° C. for 8 hours.

After the completion of the reaction, the mixture was cooled to room temperature. The sample was dissolved in water (100 mL) and CH₂Cl₂ (100 mL) and transferred to a separating funnel, followed by extraction with CH₂Cl₂. The resultant was dried with MgSO₄, followed by filtration and concentration. The sample was purified by silica gel chromatography. After concentration to dryness, recrystallization was carried out twice, whereby a white powder (Compounds 2-157 and 2-163) was obtained. The obtained powder was purified by sublimation, whereby a white solid was obtained. The obtained amount and yield of Compound 2-157 were 2.4 g and 51%, respectively. The obtained amount and yield of Compound 2-163 were 1.2 g and 25%, respectively.

FD-MS $C_{48}H_{36}N_2$: theoretical value 640, observed value 640 for both of Compounds (2-157 and 2-163)

Synthesis Example 2-18

Synthesis of Compound 2-169

[Chem 222]

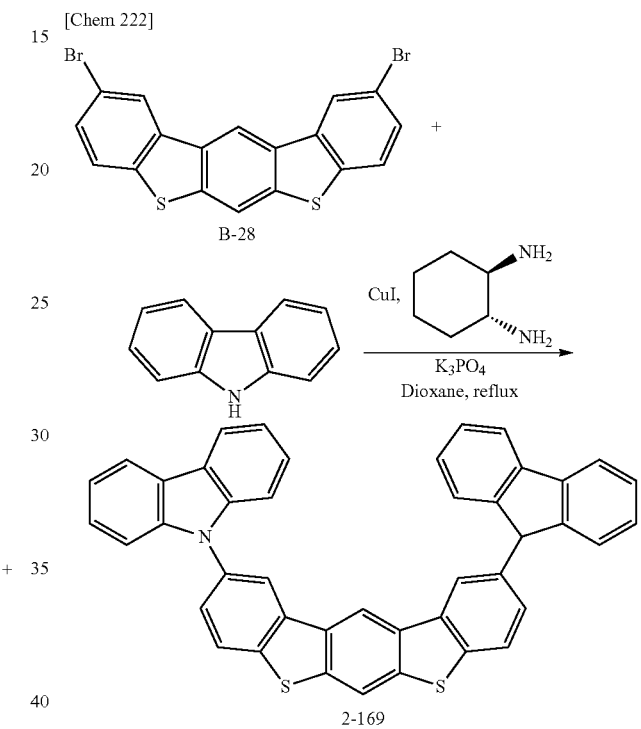

Compound B-28 (3.5 g, 7.9 mmol), carbazole (2.7 g, 16 mmol), CuI (1.5 g, 7.9 mmol), transcyclohexane 1,2-diamine (2.7 g, 23.7 mmol), K₃PO₄ (6.7 g, 31.6 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and 50 mL of water was charged into the funnel. Then, the mixture was extracted with CH₂Cl₂. The resultant sample was purified by silica gel column chromatography. The purified product was concentrated to dryness, and was then recrystallized twice, whereby a white powder (Compound 2-169) was obtained. The powder was purified by sublimation, whereby a white solid was obtained in an amount of 1.9 g in 40% yield.

FD-MS $C_{42}H_{24}N_2S_2$: theoretical value 620, observed value 620

An apparatus and measurement conditions adopted for field desorption mass spectrometry (FD-MS) in each of Synthesis Examples 2-1 to 2-18 are shown below.
Apparatus: HX110 (manufactured by JEOL Ltd.)
Conditions: accelerating voltage 8 kV
scan range m/z=50 to 1,500
emitter kind: carbon
emitter current: 0 mA→2 mA/min→40 mA (held for 10 minutes)

Example 2-1

(Production of Organic EL Device)

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound 2-A was deposited from the vapor onto the surface of the glass substrate on the side where a transparent electrode line was formed so as to cover the transparent electrode, whereby a hole transporting layer having a thickness of 30 nm was obtained.

Compound 2-1 as a host for phosphorescence and Ir(Ph-ppy)3 as a dopant for phosphorescence were co-deposited from the vapor onto the hole transporting layer, whereby a phosphorescent layer having a thickness of 30 nm was obtained. The concentration of Ir(Ph-ppy)3 was 5 mass %.

Subsequently, Compound 2-B having a thickness of 10 nm, Compound 2-C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

[Chem 223]

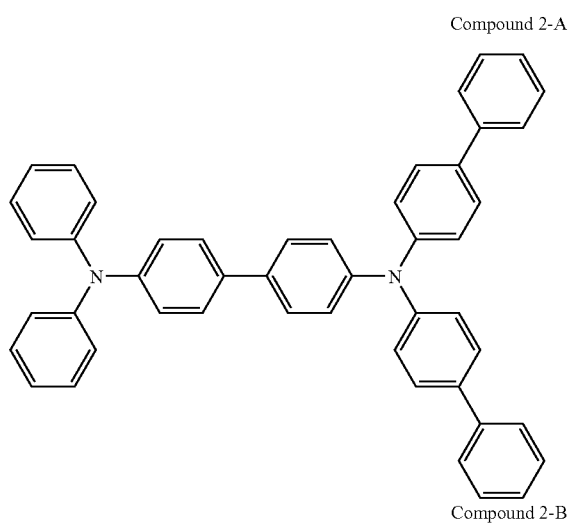

Compound 2-A

Compound 2-B

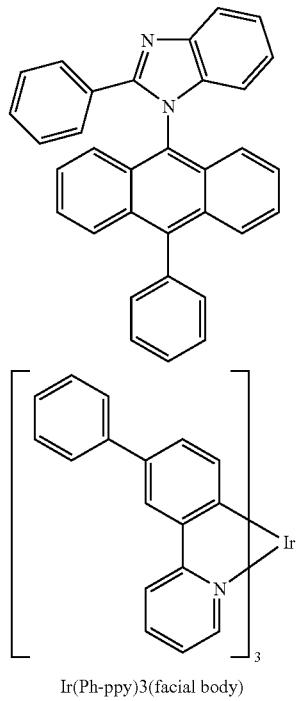

Compound 2-C

Ir(Ph-ppy)3(facial body)

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m$^2$ was determined. Further, the lifetime of the device at a luminance of 20,000 cd/m$^2$ was determined. Table 2 shows the results.

Examples 2-2 to 2-19

Organic EL devices were each produced in the same manner as in Example 2-1 except that a host material listed in Table 2 was used instead of Host Compound 2-1 in Example 2-1, and the devices were each evaluated in the same manner as in Example 2-1. Table 2 shows the results of the evaluation for light emitting performance.

Comparative Examples 2-1 to 2-3

Organic EL devices were each produced in the same manner as in Example 2-1 except that the following compounds (2-a) to (2-c) described in EP 0908787 A was used as a host material instead of Host Compound 2-1 in Example 2-1, and the devices were each evaluated in the same manner as in Example 2-1. Table 2 shows the results of the evaluation for light emitting performance.

Comparative Examples 2-4 to 2-9

Organic EL devices were each produced in the same manner as in Example 2-1 except that the following compounds (2-d) to (2-i) described in WO 2006-122630 was used as a host material instead of Host Compound 2-1 in Example 2-1, and the devices were each evaluated in the same manner as in Example 2-1. Table 2 shows the results of the evaluation for light emitting performance.

Comparative Examples 2-10 and 2-11

An organic EL device was produced in the same manner as in Example 2-1 except that the following compound (2-j) or (2-k) described in WO 2007-063754 was used as a host material instead of Host Compound 2-1 in Example 2-1, and the device was evaluated in the same manner as in Example 2-1. Table 1 shows the results of the evaluation for light emitting performance.

[Chem 224]

(2-a)

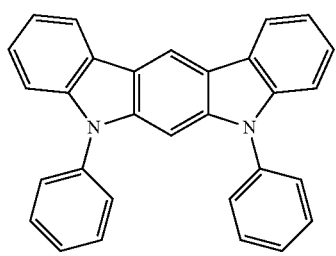

(2-b)

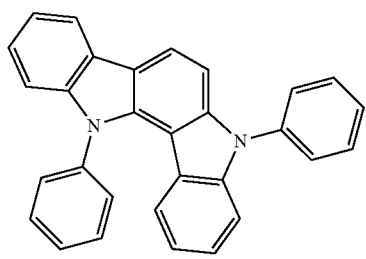

(2-c)

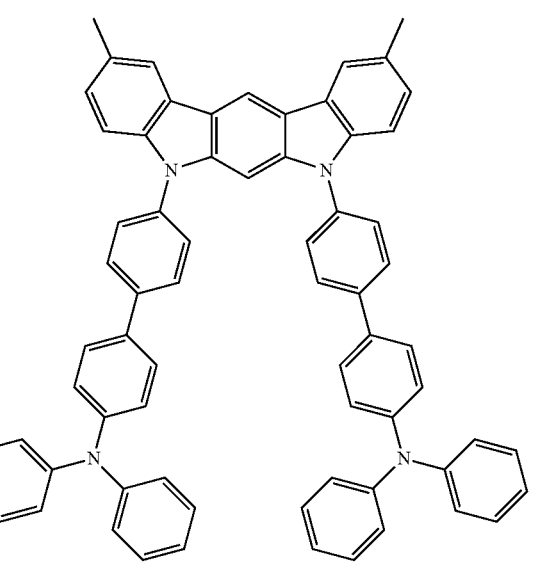

(2-d)

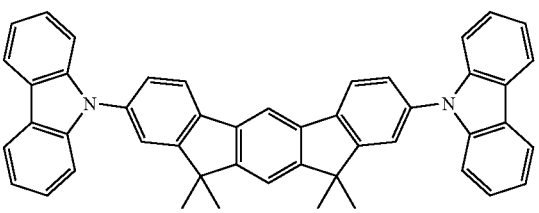

(2-e)

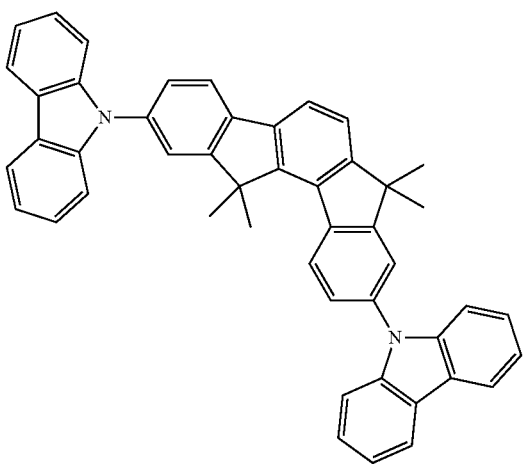

(2-f)

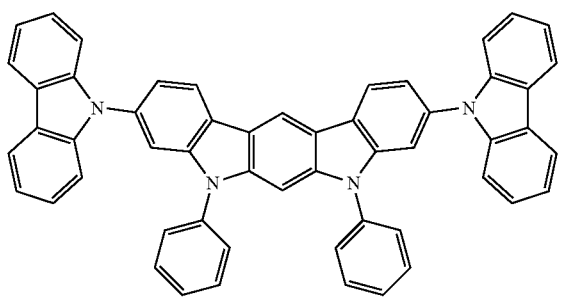

(2-g)

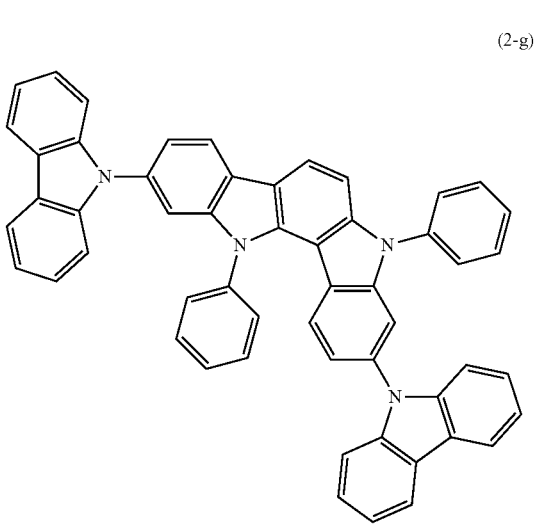

-continued

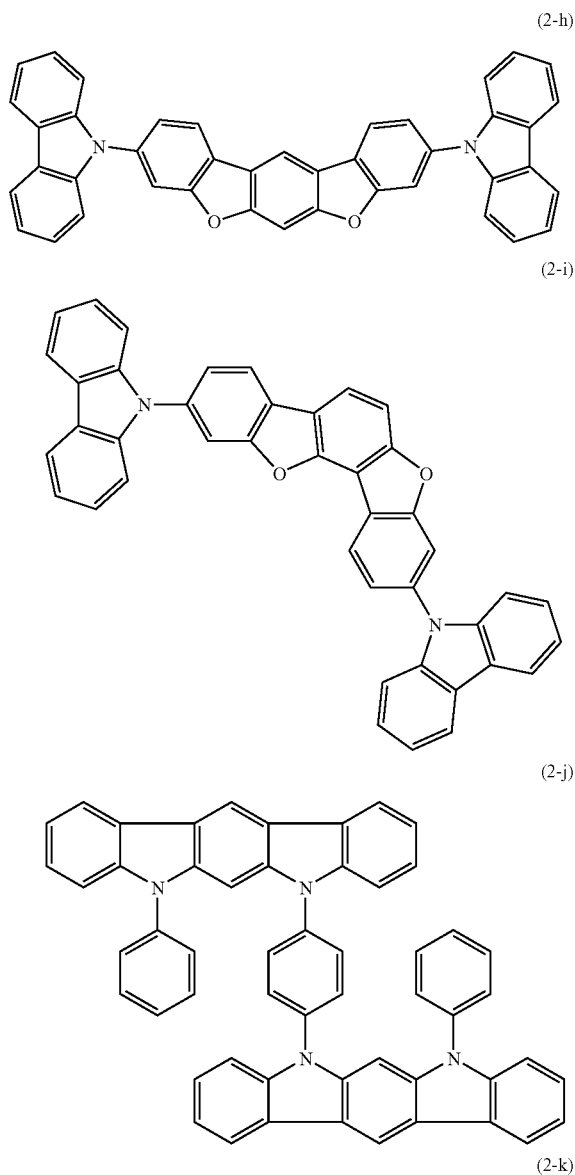

TABLE 2

| Host compound | | Voltage (V) @20 mA/cm² | Efficiency (cd/A) @1,000 cd/m² | Life time (hr) @20,000 cd/m² |
|---|---|---|---|---|
| Example 2-1 | (2-1) | 5.6 | 60.1 | 250 |
| Example 2-2 | (2-17) | 5.8 | 61.2 | 200 |
| Example 2-3 | (2-18) | 5.9 | 62.4 | 200 |
| Example 2-4 | (2-34) | 5.6 | 59.8 | 300 |
| Example 2-5 | (2-46) | 5.4 | 60.5 | 300 |
| Example 2-6 | (2-49) | 5.3 | 59.3 | 300 |
| Example 2-7 | (2-68) | 5.9 | 60.9 | 280 |
| Example 2-8 | (2-74) | 6.1 | 61.1 | 200 |
| Example 2-9 | (2-85) | 6.2 | 62.1 | 200 |
| Example 2-10 | (2-87) | 5.9 | 61.8 | 220 |
| Example 2-11 | (2-113) | 5.9 | 62.0 | 300 |
| Example 2-12 | (2-116) | 5.6 | 59.5 | 280 |
| Example 2-13 | (2-138) | 4.8 | 53.1 | 140 |
| Example 2-14 | (2-140) | 5.7 | 60.7 | 200 |
| Example 2-15 | (2-148) | 4.5 | 51.3 | 130 |
| Example 2-16 | (2-149) | 4.4 | 52.2 | 100 |
| Example 2-17 | (2-157) | 5.2 | 58.1 | 150 |
| Example 2-18 | (2-163) | 5.4 | 58.3 | 150 |
| Example 2-19 | (2-169) | 5.6 | 59.4 | 180 |
| Comparative Example 2-1 | (2-a) | 4.7 | 28.9 | 60 |
| Comparative Example 2-2 | (2-b) | 4.7 | 28.1 | 60 |
| Comparative Example 2-3 | (2-c) | 4.3 | 18.5 | 30 |
| Comparative Example 2-4 | (2-d) | 5.5 | 38.1 | 70 |
| Comparative Example 2-5 | (2-e) | 5.6 | 35.9 | 60 |
| Comparative Example 2-6 | (2-f) | 4.8 | 17.1 | 50 |
| Comparative Example 2-7 | (2-g) | 4.7 | 17.6 | 50 |
| Comparative Example 2-8 | (2-h) | 6.1 | 48.2 | 70 |
| Comparative Example 2-9 | (2-i) | 6.2 | 48.7 | 80 |
| Comparative Example 2-10 | (2-j) | 4.5 | 18.1 | 30 |
| Comparative Example 2-11 | (2-k) | 4.7 | 17.4 | 40 |

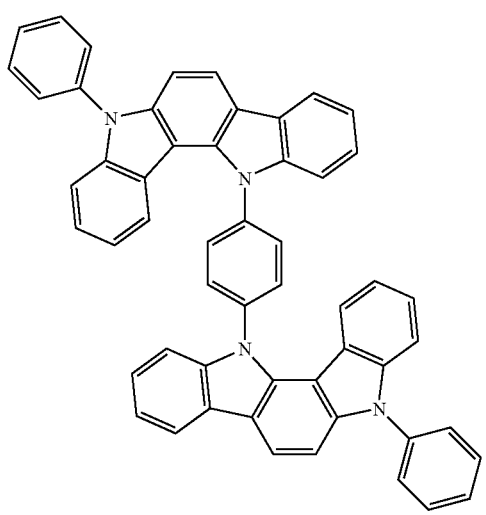

Synthesis Example 3-1

Synthesis of Compound 3-1

(1) Synthesis of Compound C-1

[Chem 225]

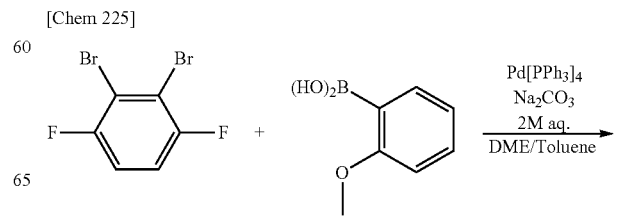

(3) Synthesis of Compound C-3

[Chem 227]

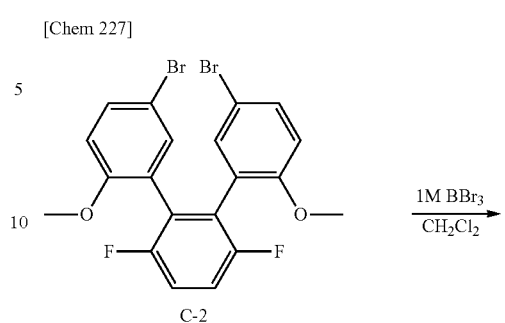

1,2-dibromo-3,6-difluorobenzene (50.0 g, 183.9 mmol), 2-methoxyphenylboronic acid (67.1 g, 441.4 mmol), a 2 M aqueous solution of $Na_2CO_3$ (368 mL, 736 mmol), DME (370 mL), toluene (370 mL), and $Pd[PPh_3]_4$ (21.3 g, 18.4 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 30.6 g in 51% yield.

FD-MS $C_{20}H_{16}F_2O_2$: theoretical value 326, observed value 326

(2) Synthesis of Compound C-2

[Chem 226]

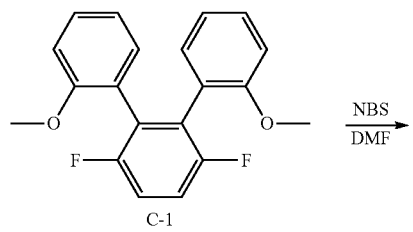

Compound C-1 (30.0 g, 91.9 mmol), NBS (32.8 g, 184 mmol), and DMF (820 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 32 g in 72% yield.

FD-MS $C_{20}H_{14}Br_2F_2O_2$: theoretical value 484, observed value 484

Compound C-2 (32.0 g, 66.1 mmol), a 1-M solution of $BBr_3$ in $CH_2Cl_2$ (155 mL, 155 mmol), and $CH_2Cl_2$ (430 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 24.1 g in 80% yield.

FD-MS $C_{18}H_{10}Br_2F_2O_2$: theoretical value 456, observed value 456

(4) Synthesis of Compound C-4

[Chem 228]

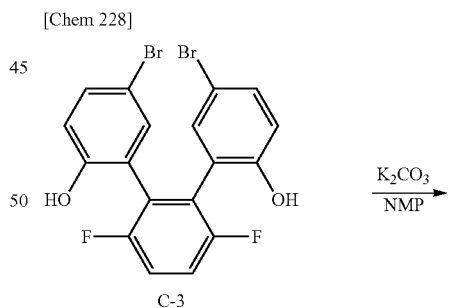

Compound C-3 (24.1 g, 52.8 mmol), $K_2CO_3$ (16.0 g, 116 mmol), and NMP (220 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 18.7 g in 85% yield.

FD-MS $C_{18}H_8Br_2O_2$: theoretical value 416, observed value 416

(5) Synthesis of Compound 3-1 ness, and was then recrystallized twice, whereby a white powder (Compound 3-1) was obtained. The powder was purified by sublimation, whereby a white solid was obtained in an amount of 1.7 g in 39% yield.

FD-MS $C_{42}H_{24}N_2O_2$: theoretical value 588, observed value 588

Synthesis Example 3-2

Synthesis of Compound 3-17

(1) Synthesis of Compound C-5

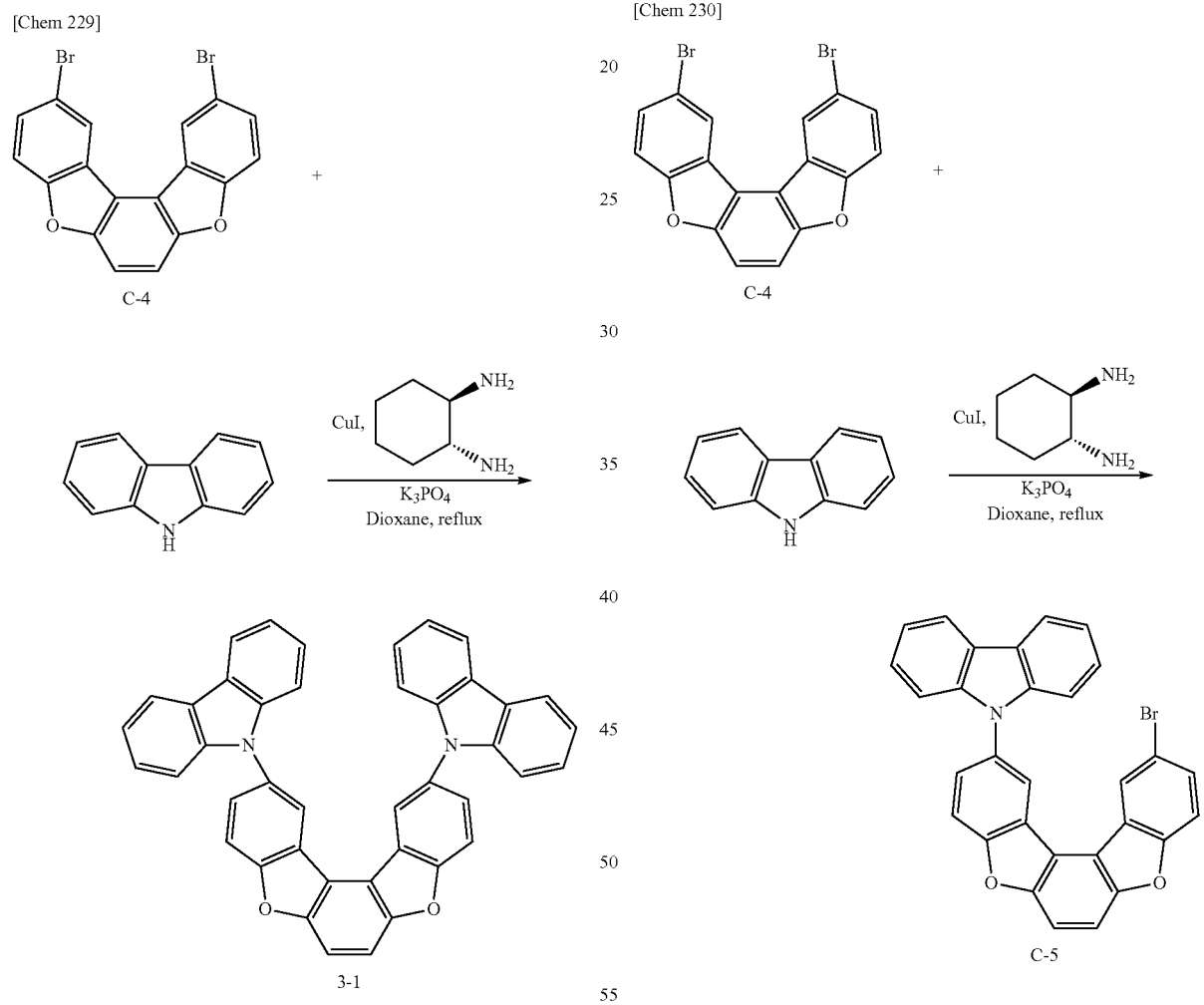

Compound C-4 (3 g, 7.2 mmol), carbazole (2.9 g, 17.3 mmol), CuI (1.4 g, 7.2 mmol), transcyclohexane 1,2-diamine (2.5 g, 21.6 mmol), $K_3PO_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dry- Compound C-4 (3 g, 7.2 mmol), carbazole (1.5 g, 7.2 mmol), CuI (1.4 g, 7.2 mmol), transcyclohexane 1,2-diamine (2.5 g, 21.6 mmol), $K_3PO_4$ (6.1 g, 28.8 mmol), and 1,4-dioxane (8 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 2.2 g in 60% yield.

FD-MS $C_{30}H_{16}BrNO_2$: theoretical value 502, observed value 502

(2) Synthesis of Compound 3-17

[Chem 231]

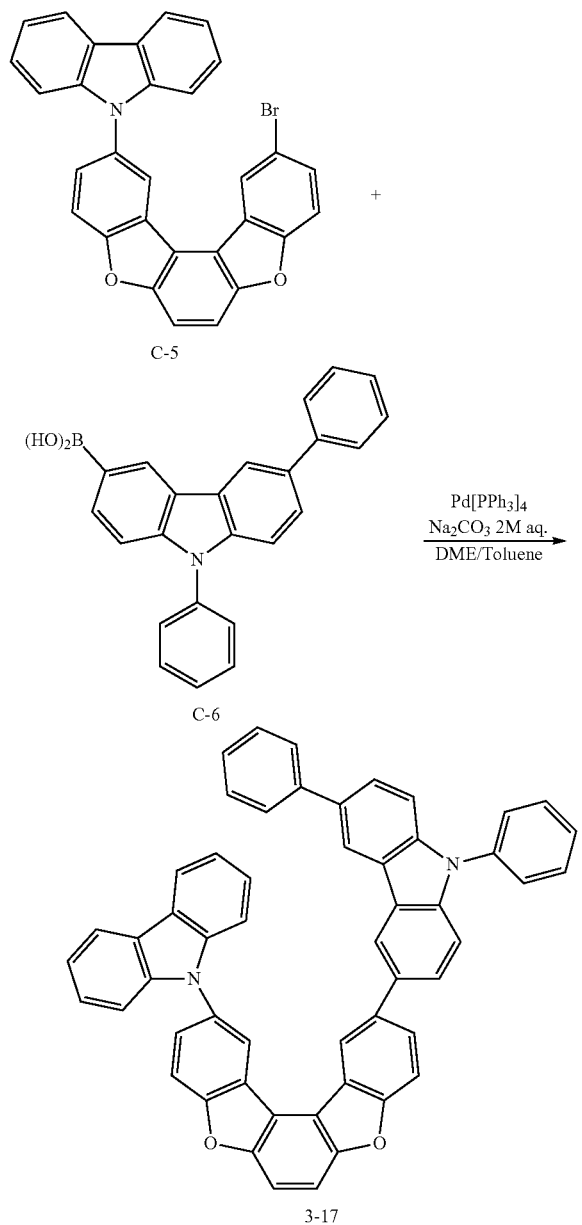

Compound C-5 (3.0 g, 6.0 mmol), Compound C-6 (2.4 g, 6.6 mmol), a 2 M aqueous solution of $Na_2CO_3$ (6 mL, 12 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 3-17) was obtained. The powder was purified by sublimation, whereby a white solid was obtained in an amount of 1.3 g in 30% yield.

FD-MS $C_{54}H_{30}N_2O_2$: theoretical value 740, observed value 740

Synthesis Example 3-3

Synthesis of Compound 3-18

[Chem 232]

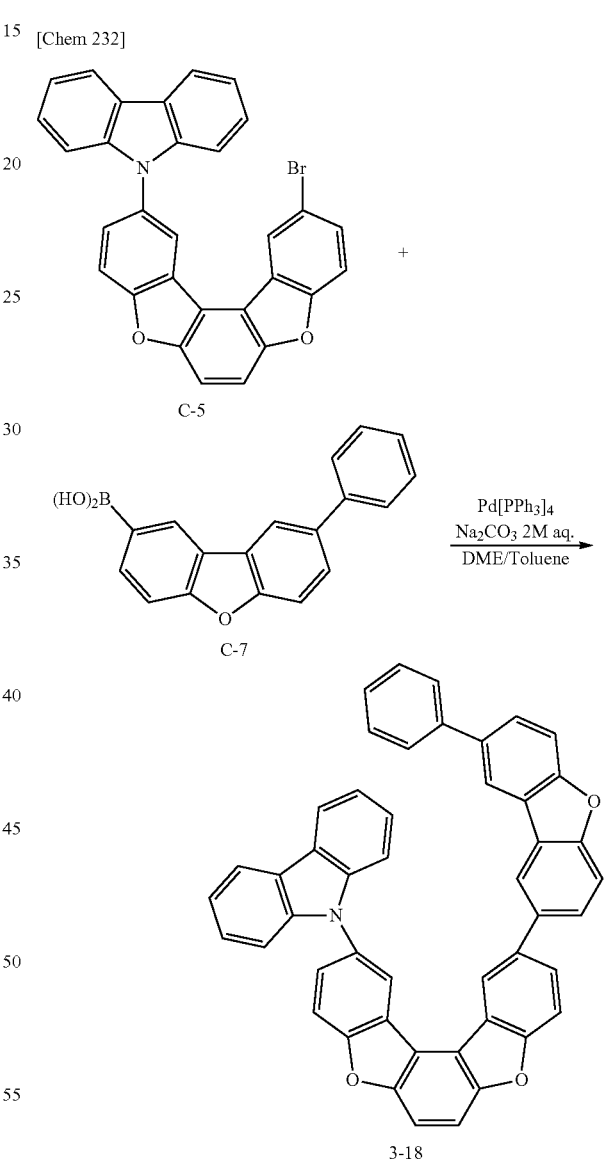

Compound C-5 (3.3 g, 6.6 mmol), Compound C-7 (2.1 g, 7.3 mmol), a 2 M aqueous solution of $Na_2CO_3$ (6 mL, 13 mmol), DME (13 mL), toluene (1 mL), and $Pd[PPh_3]_4$ (0.38 g, 0.33 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH₂Cl₂. The extract was dried with MgSO₄, and was then filtrated and concentrated. The resultant sample was purified by silica gel column chromatography. The purified product was concentrated to dryness, and was then recrystallized twice, whereby a white powder (Compound 3-18) was obtained. The powder was purified by sublimation, whereby a white solid was obtained in an amount of 1.4 g in 31% yield.

FD-MS $C_{48}H_{27}NO_3$: theoretical value 665, observed value 665

Synthesis Example 3-4

Synthesis of Compound 3-34

(1) Synthesis of Compound C-8

[Chem 233]

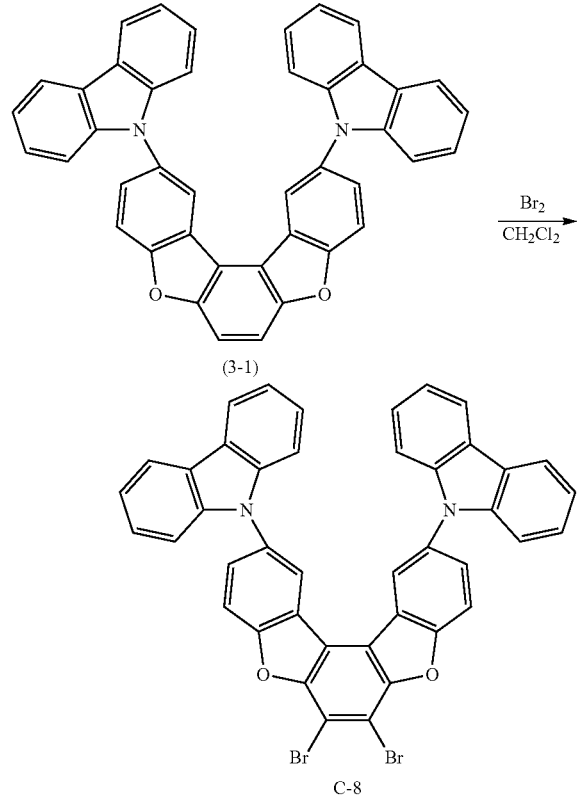

Compound (3-1) (10 g, 17 mmol) and CH₂Cl₂ (100 mL) were loaded into a three-necked flask and bromine (5.4 g, 34 mmol) was dropped thereto under an Ar atmosphere at 0° C. After that, the mixture was stirred at room temperature for 8 hours. After the completion of the reaction, the sample was transferred to a separating funnel and water (50 mL) was added thereto, followed by extraction with CH₂Cl₂. An organic layer was washed with a saturated NaNO₂ aqueous solution (50 mL) and dried with MgSO₄, followed by filtration and concentration. The sample was purified by a column chromatography, whereby a white solid was obtained in an amount of 3.7 g in 29% yield.

FD-MS $C_{42}H_{22}Br_2N_2O_2$: theoretical value 746, observed value 746

(2) Synthesis of Compound 3-34

[Chem 234]

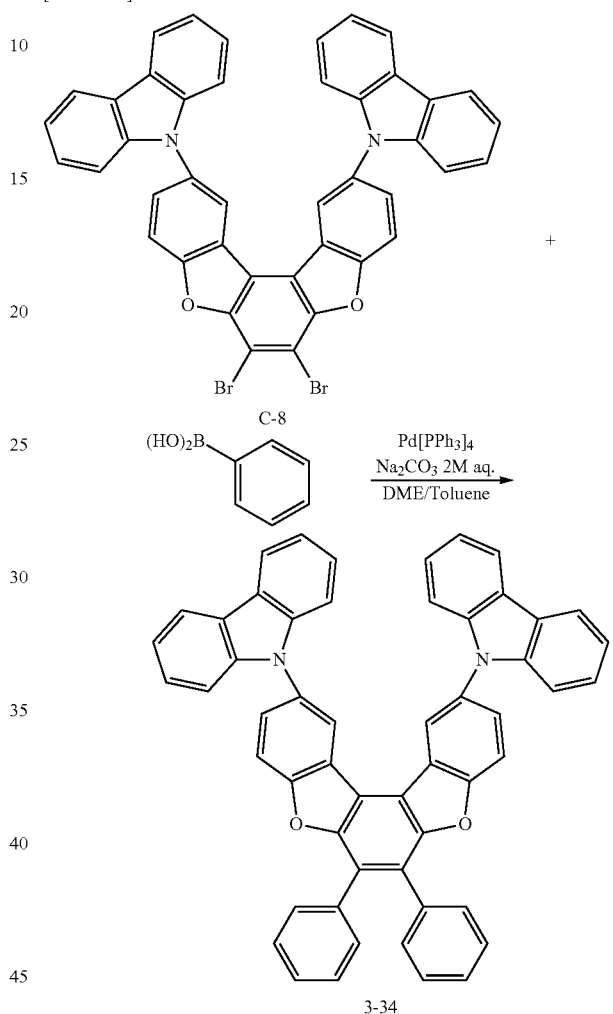

Compound C-8 (3.7 g, 4.9 mmol), phenylboronic acid (1.32 g, 10.8 mmol), a 2 M aqueous solution of Na₂CO₃ (5 mL, 9.8 mmol), DME (10 mL), toluene (10 mL), and Pd[PPh₃]₄ (0.29 g, 0.25 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH₂Cl₂. The extract was dried with MgSO₄, and was then filtrated and concentrated. The resultant sample was purified by silica gel column chromatography. The purified product was concentrated to dryness, and was then recrystallized twice, whereby a white powder (Compound 3-34) was obtained. The powder was purified by sublimation, whereby a white solid was obtained in an amount of 1.2 g in 32% yield.

FD-MS $C_{54}H_{32}N_2O_2$: theoretical value 740, observed value 740

Synthesis Example 3-5

Synthesis of Compound 3-46

(1) Synthesis of Compound C-9

[Chem 235]

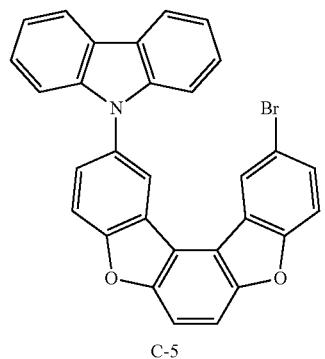

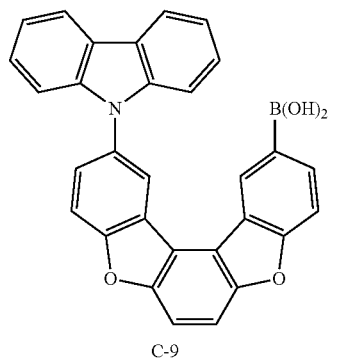

Compound C-5 (10 g, 20 mmol) and THF (200 mL) were loaded into a three-necked flask, and the mixture was cooled to −78° C. Then, n-BuLi (1.65-M solution in n-hexane, 13.3 mL, 22 mmol) was added dropwise to the flask, and the resultant mixture was stirred at −78° C. for 1 hour. Triisopropyl boronate (11.3 g, 60 mmol) was added to the resultant, and the mixture was stirred at −78° C. for 20 minutes. After that, the resultant was left to stand overnight at room temperature. Then, 1N HCl (40 mL) was charged into the resultant, and the mixture was stirred at room temperature for 1 hour. The resultant sample was concentrated, and was then transferred to a separating funnel. Water (50 mL) was charged into the funnel, and the mixture was extracted with CH$_2$Cl$_2$. The extract was dried with MgSO$_4$, and was then filtrated and concentrated. The resultant sample was purified by recrystallization (toluene-hexane), whereby a white solid was obtained in an amount of 5.1 g in 55% yield.

(2) Synthesis of Compound 3-46

[Chem 236]

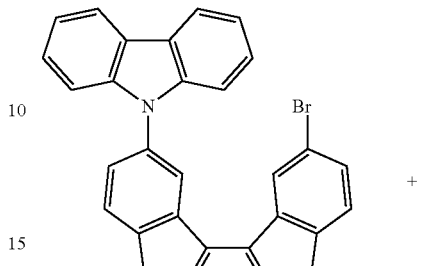

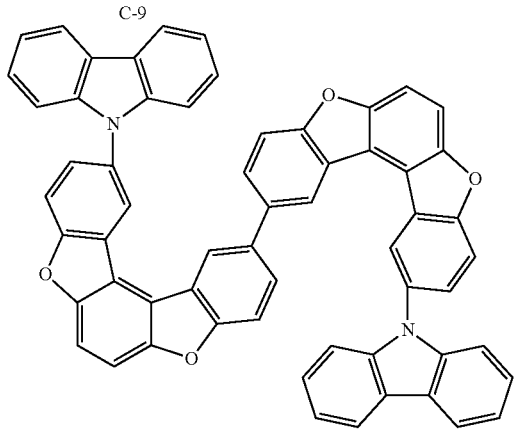

Compound C-5 (3.1 g, 6.2 mmol), Compound C-9 (3.2 g, 6.8 mmol), a 2 M aqueous solution of Na$_2$CO$_3$ (6.2 mL, 12.4 mmol), DME (12 mL), toluene (12 mL), and Pd[PPh$_3$]$_4$ (0.36 g, 0.31 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated to dryness, and was then recrystallized twice, whereby a white powder (Compound 3-46) was obtained. The powder was purified by sublimation, whereby a white solid was obtained in an amount of 1.1 g in 20% yield.

FD-MS $C_{60}H_{32}N_2O_4$: theoretical value 844, observed value 844

Synthesis Example 3-6

Synthesis of Compound 3-49

[Chem 237]

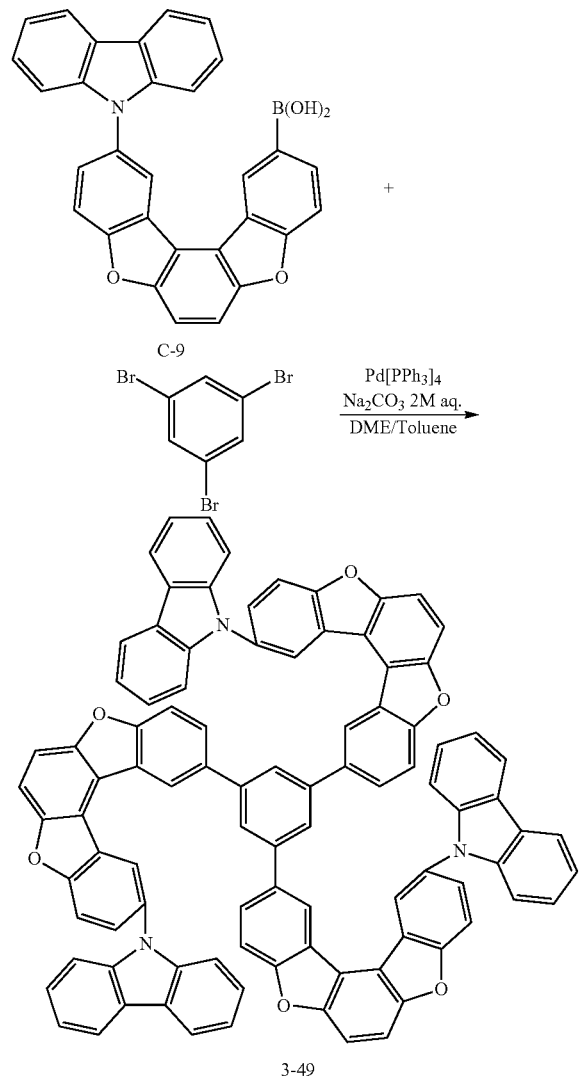

3-49

Compound C-9 (10.2 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated to dryness, and was then recrystallized twice, whereby a white powder (Compound 3-49) was obtained. The powder was purified by sublimation, whereby a white solid was obtained in an amount of 1.5 g in 15% yield.

FD-MS $C_{96}H_{51}N_3O_6$: theoretical value 1,342, observed value 1,342

Synthesis Example 3-7

Synthesis of Compound 3-71

(1) Synthesis of Compound C-11

[Chem 238]

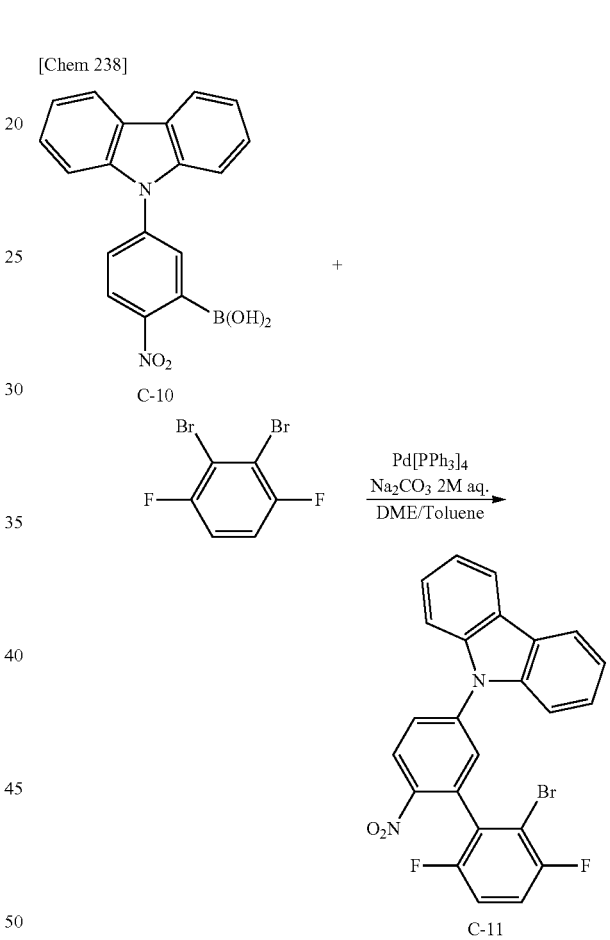

Compound C-10 (24.6 g, 74 mmol), 1,2-dibromo-3,6-difluorobenzene (20 g, 74 mmol), a 2 M aqueous solution of $Na_2CO_3$ (75 mL, 150 mmol), DME (150 mL), toluene (150 mL), and $Pd[PPh_3]_4$ (4.3 g, 3.7 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 14.3 g in 41% yield.

FD-MS C$_{24}$H$_{13}$BrF$_2$N$_2$O$_2$: theoretical value 479, observed value 479

(2) Synthesis of Compound C-13

[Chem 239]

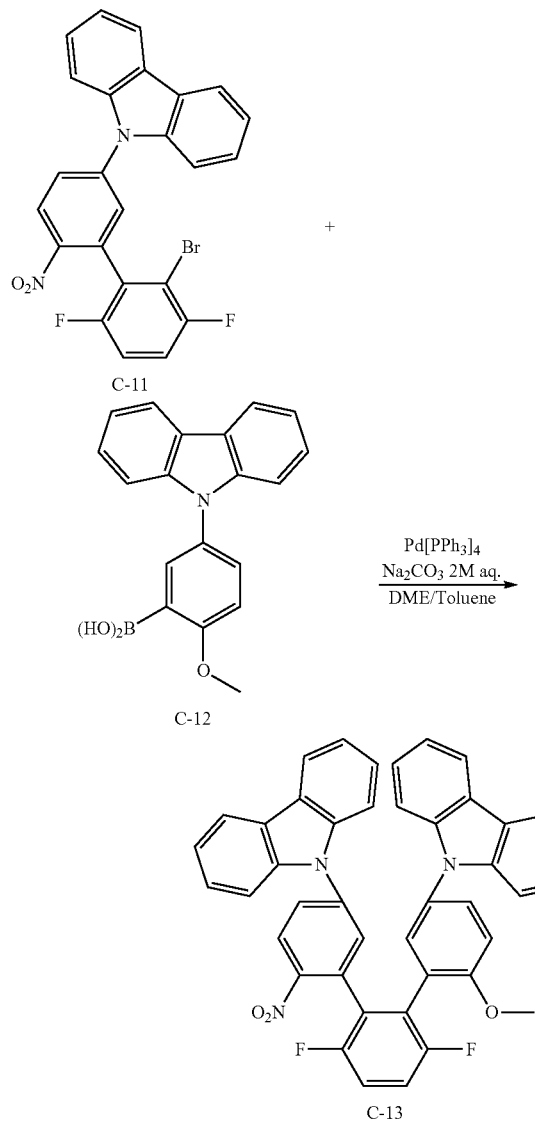

Compound C-11 (14.0 g, 29.2 mmol), Compound C-12 (10.2 g, 32 mmol), a 2 M aqueous solution of Na$_2$CO$_3$ (30 mL, 60 mmol), DME (60 mL), toluene (60 mL), and Pd[PPh$_3$]$_4$ (1.7 g, 1.5 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with CH$_2$Cl$_2$. The extract was dried with MgSO$_4$, and was then filtrated and concentrated. The resultant sample was purified by silica gel column chromatography, whereby a white solid was obtained in an amount of 6.9 g in 35% yield.

FD-MS C$_{43}$H$_{27}$F$_2$N$_3$O$_2$: theoretical value 671, observed value 671

(3) Synthesis of Compound C-14

[Chem 240]

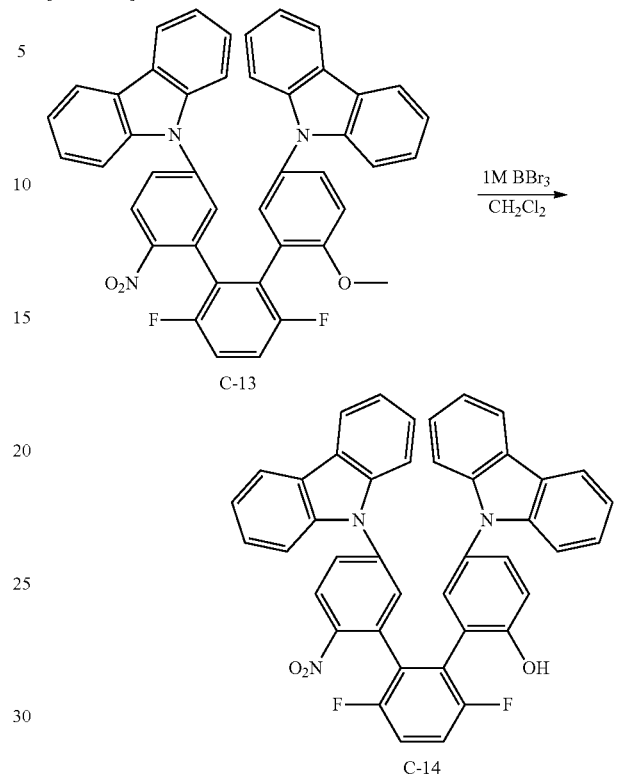

Compound C-13 (6.9 g, 10.3 mmol), a 1-M solution of BBr$_3$ in CH$_2$Cl$_2$ (50 mL, 50 mmol), and CH$_2$Cl$_2$ (100 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of NaHCO$_3$. The resultant sample was transferred to a separating funnel, and was extracted with CH$_2$Cl$_2$. The resultant sample was purified by column chromatography, whereby a white solid was obtained in an amount of 5.8 g in 85% yield.

FD-MS C$_{42}$H$_{25}$F$_2$N$_3$O$_3$: theoretical value 657, observed value 657

(4) Synthesis of Compound C-15

[Chem 241]

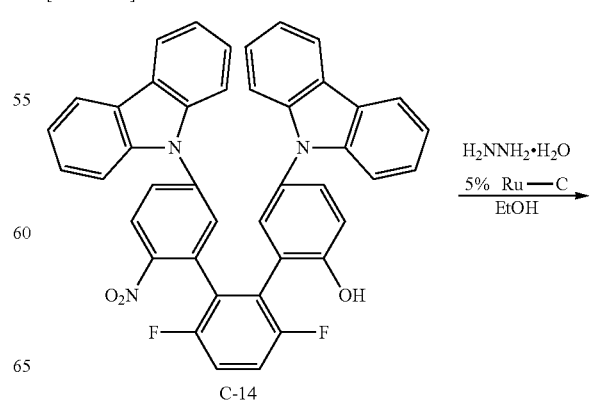

-continued

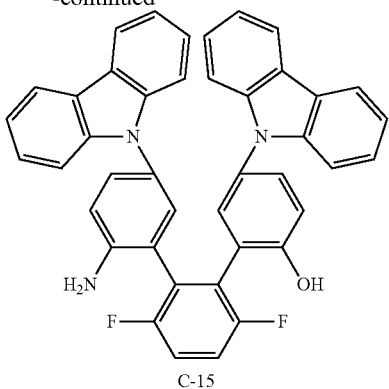

C-15

Compound C-14 (5.8 g, 8.8 mmol), 5% Ru—C (0.35 g), and ethanol (33 mL) were loaded into a three-necked flask, and the mixture was stirred under an Ar atmosphere at 70° C. Hydrazine monohydrate (2.7 g, 53.2 mmol) was dissolved in ethanol (3 mL) and dropped thereto. After that, the reaction mixture was refluxed for 8 hours. After the completion of the reaction, the resultant was cooled to room temperature. The sample was filtrated under reduced pressure, and the filtrate was concentrated. The sample was purified by silica gel column chromatography, whereby a white solid was obtained in an amount of 4.7 g in 85% yield.

FD-MS $C_{42}H_{27}F_2N_3O$: theoretical value 627, observed value 627

(5) Synthesis of Compound C-16

[Chem 242]

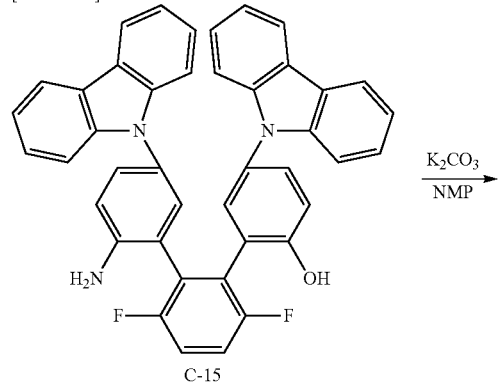

C-16

Compound C-15 (4.7 g, 7.5 mmol), $K_2CO_3$ (2.3 g, 16.5 mmol), and NMP (24 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 3.6 g in 81% yield.

FD-MS $C_{42}H_{25}N_3O$: theoretical value 587, observed value 587

(6) Synthesis of Compound (1-71)

[Chem 243]

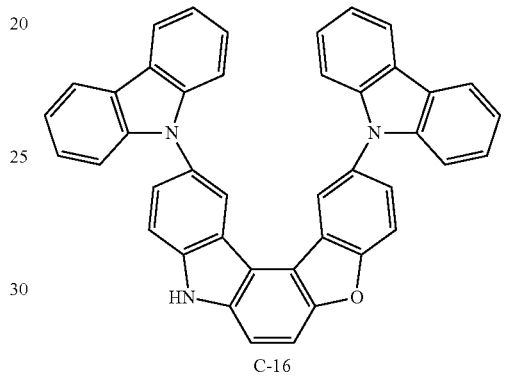

C-16

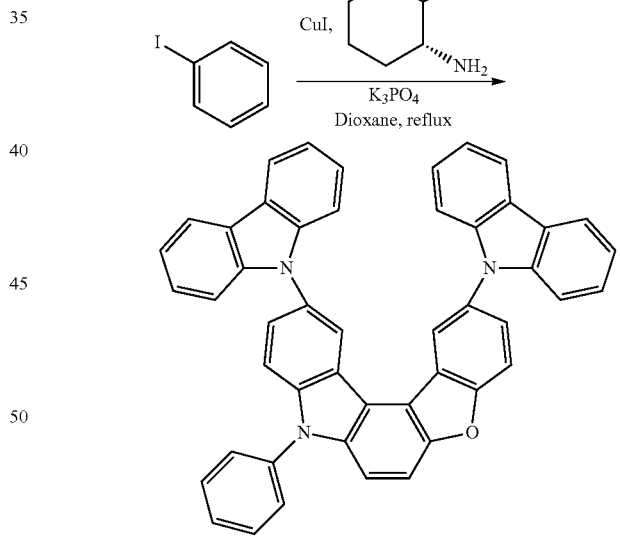

3-71

Compound C-16 (3.0 g, 5.1 mmol), iodobenzene (1.0 g, 5.1 mmol), CuI (0.96 g, 5.1 mmol), transcyclohexane 1,2-diamine (1.7 g, 15.3 mmol), $K_3PO_4$ (4.3 g, 20.4 mmol), and 1,4-dioxane (6 mL) were loaded into a three-necked flask, and the mixture was refluxed under an Ar atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$.

The resultant sample was purified by silica gel column chromatography. The purified product was concentrated to dryness, and was then recrystallized twice, whereby a white powder (Compound 3-71) was obtained. The powder was purified by sublimation, whereby a white solid was obtained in an amount of 1.7 g in 50% yield.

FD-MS $C_{48}H_{29}N_{30}$: theoretical value 663, observed value 663

Synthesis Example 3-8

Synthesis of Compound 3-73

[Chem 244]

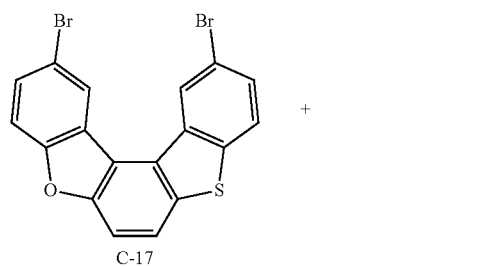

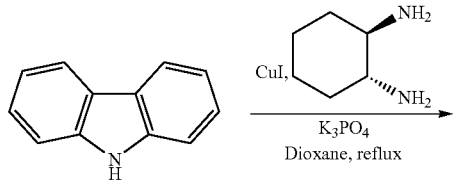

3-73

Compound C-17 (2.8 g, 7.3 mmol), carbazole (2.4 g, 14.6 mmol), CuI (1.4 g, 7.3 mmol), transcyclohexane 1,2-diamine (2.5 g, 21.9 mmol), $K_3PO_4$ (6.2 g, 29.2 mmol), and 1,4-dioxane (8 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 3-73) was obtained. The powder was purified by sublimation, whereby a white solid was obtained in an amount of 1.4 g in 32% yield.

FD-MS $C_{42}H_{24}N_2OS$: theoretical value 604, observed value 604

Synthesis Example 3-9

Synthesis of Compound 3-75

(1) Synthesis of Compound C-19

[Chem 245]

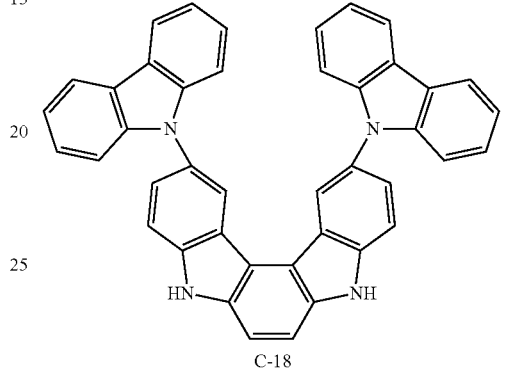

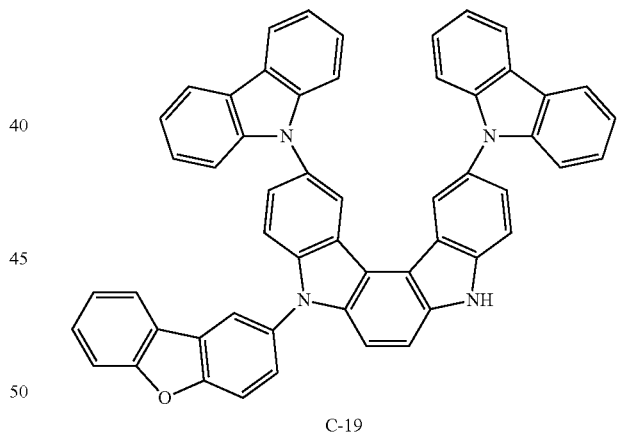

C-19

Compound C-18 (5.0 g, 8.5 mmol), 2-bromodibenzofuran (2.1 g, 8.5 mmol), CuI (1.6 g, 8.5 mmol), transcyclohexane 1,2-diamine (2.9 g, 25.5 mmol), $K_3PO_4$ (7.2 g, 34 mmol), and 1,4-dioxane (9 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography, whereby a white solid was obtained in an amount of 3.4 g in 52% yield.

FD-MS $C_{54}H_{32}N_4O$: theoretical value 752, observed value 752

(2) Synthesis of Compound 3-75

[Chem 246]

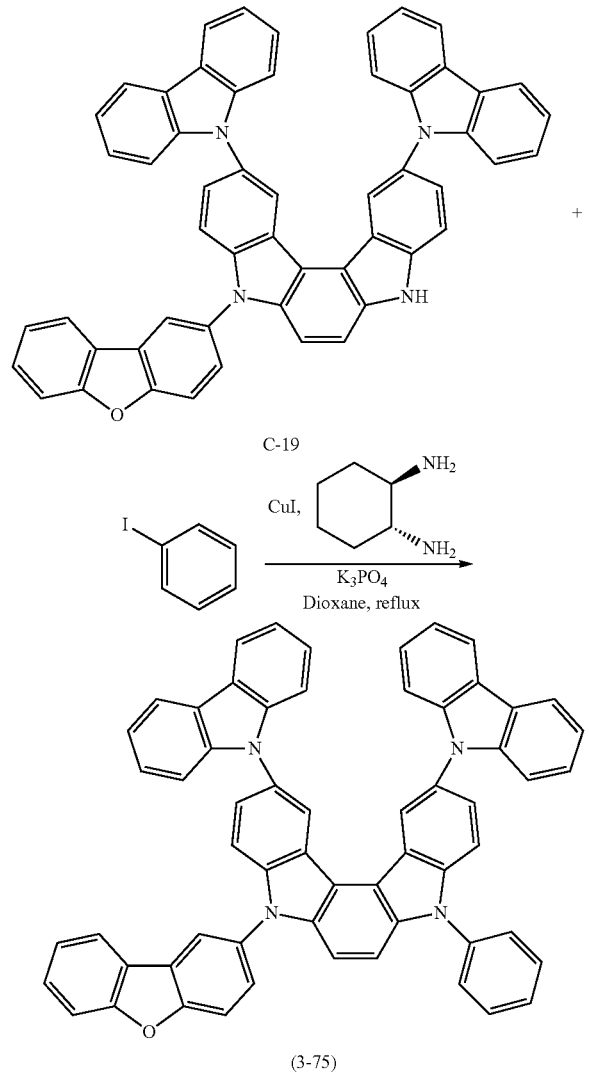

(3-75)

Compound C-19 (3.0 g, 4.0 mmol), iodobenzene (0.8 g, 4.0 mmol), CuI (0.77 g, 4.0 mmol), transcyclohexane 1,2-diamine (1.3 g, 12.1 mmol), $K_3PO_4$ (2.4 g, 16.1 mmol), and 1,4-dioxane (4 mL) were loaded into a three-necked flask, and the mixture was refluxed under an argon atmosphere for 10 hours.

After the completion of the reaction, the resultant was cooled to room temperature. The resultant sample was transferred to a separating funnel, and 50 mL of water was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 3-75) was obtained. The powder was purified by sublimation, whereby a white solid was obtained in an amount of 1.8 g in 54% yield.

FD-MS $C_{60}H_{36}N_4O$: theoretical value 828, observed value 828

Synthesis Example 3-10

Synthesis of Compound 3-76

[Chem 247]

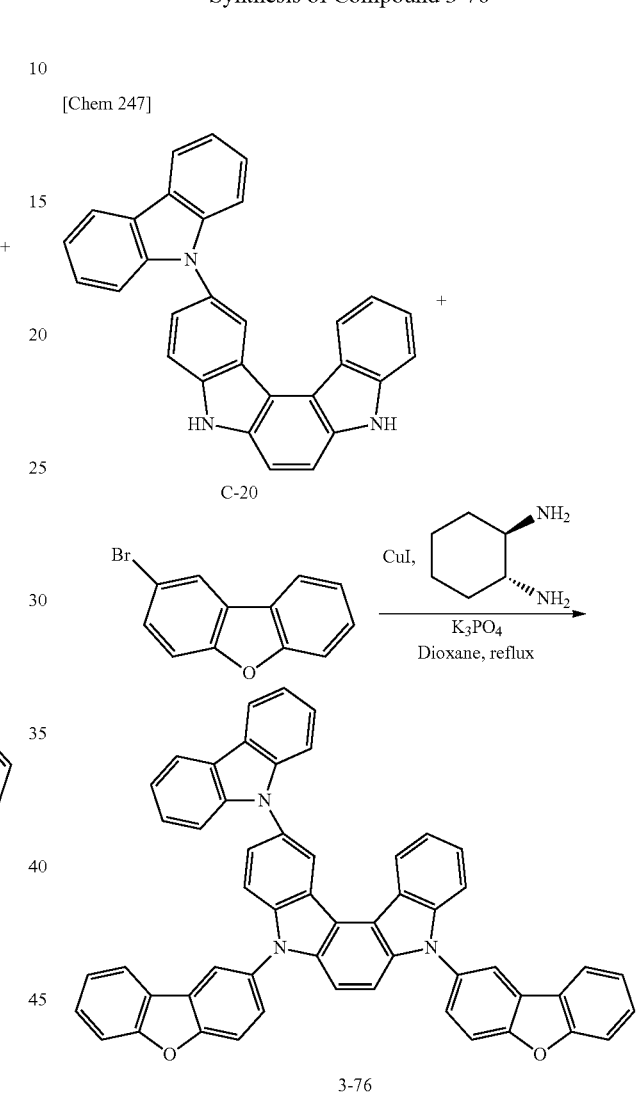

3-76

Compound C-20 (4.2 g, 10 mmol), 2-bromodibenzofuran (5.0 g, 20 mmol), CuI (1.9 g, 10 mmol), transcyclohexane 1,2-diamine (3.4 g, 30 mmol), $K_3PO_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 3-76) was obtained. The powder was purified by sublimation, whereby a white solid was obtained in an amount of 2.2 g in 30% yield.

FD-MS $C_{54}H_{31}N_3O_2$: theoretical value 753, observed value 753

Synthesis Example 3-11

Synthesis of Compound 3-79

(1) Synthesis of Compound C-22

[Chem 248]

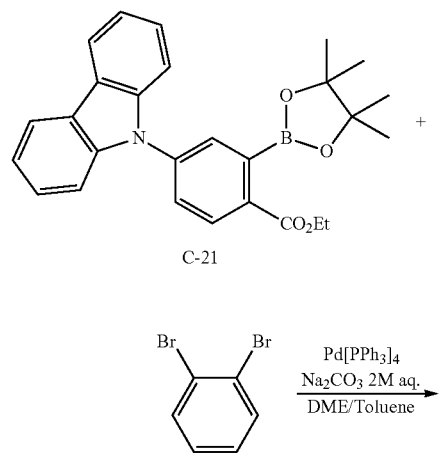

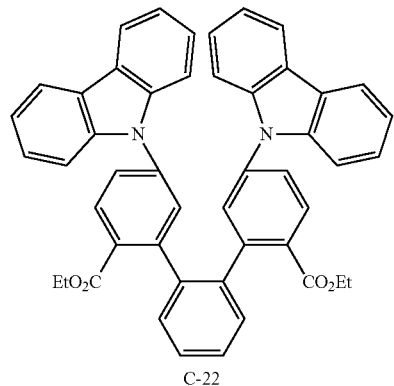

Compound C-21 (29.1 g, 66 mmol), 1,2-dibromobenzene (7.1 g, 30 mmol), a 2 M aqueous solution of $Na_2CO_3$ (60 mL, 120 mmol), DME (60 mL), toluene (60 mL), and $Pd[PPh_3]_4$ (1.7 g, 1.5 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 7.6 g in 36% yield.

FD-MS $C_{48}H_{36}N_2O_4$: theoretical value 704, observed value 704

(2) Synthesis of Compound C-23

[Chem 249]

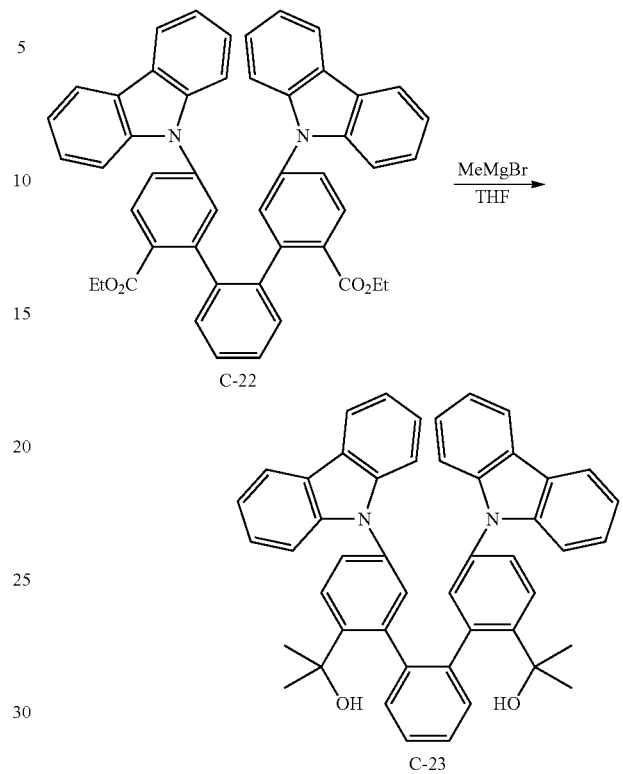

Compound C-22 (7.6 g, 10.8 mmol) and THF (38 mL) were loaded into a three-necked flask, and the mixture was stirred at 0° C. MeMgBr (0.97M THF solution, 50 mL, 49 mmol) was dropped thereto. After stirred at 0° C. for 3 hours, the mixture was left to stand at room temperature overnight. The sample was transferred to a separating funnel, and a saturated $NH_4Cl$ aqueous solution (50 mL) was added, followed by extraction with AcOEt. The sample was dried with $MgSO_4$, followed by filtration and concentration. The sample was purified by silica gel column chromatography, whereby a white solid was obtained in an amount of 5.8 g in 80% yield.

FD-MS $C_{48}H_{40}N_2O_2$: theoretical value 676, observed value 676

(3) Synthesis of Compound 3-79

[Chem 250]

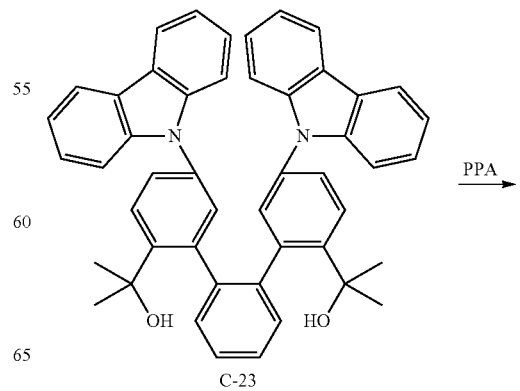

-continued

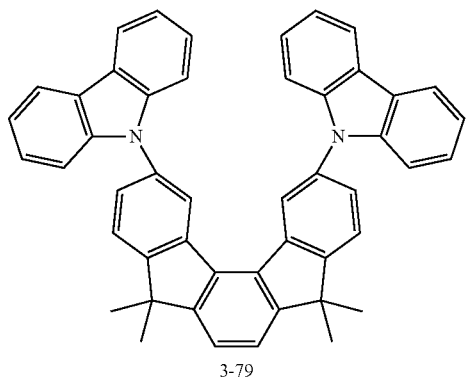

3-79

Compound C-23 (5 g, 7.4 mmol) and polyphosphoric acid (10 g) were loaded into a three-necked flask, and the mixture was stirred at 40° C. for 8 hours.

After the completion of the reaction, the mixture was cooled to room temperature. The sample was dissolved in water (100 mL) and $CH_2Cl_2$ (100 mL) and transferred to a separating funnel, followed by extraction with $CH_2Cl_2$. The resultant was dried with $MgSO_4$, followed by filtration and concentration. The sample was purified by silica gel chromatography. After concentration to dryness, recrystallization was carried out twice, whereby a white powder (Compound 3-79) was obtained. The obtained powder was purified by sublimation, whereby a white solid was obtained in an amount of 2.4 g in 50% yield.

FD-MS $C_{48}H_{36}N_2$: theoretical value 640, observed value 640

Synthesis Example 3-12

Synthesis of Compound 3-85

[Chem 251]

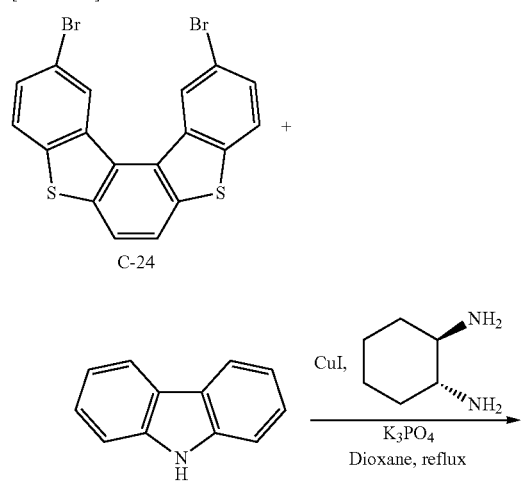

-continued

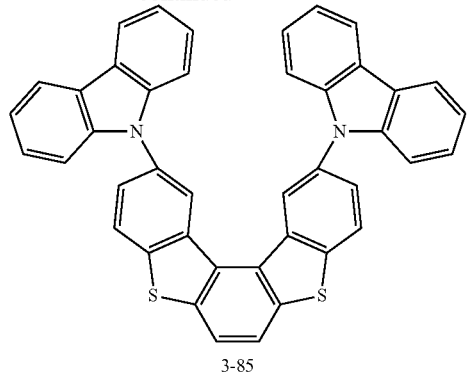

3-85

Compound C-24 (36 g, 8.0 mmol), carbazole (2.9 g, 17.6 mmol), CuI (1.5 g, 8.0 mmol), transcyclohexane 1,2-diamine (2.7 g, 24.0 mmol), $K_3PO_4$ (6.8 g, 32.0 mmol), and 1,4-dioxane (a mL) were loaded into a three-necked flask, and the mixture was refluxed under an argon atmosphere for 10 hours.

After the completion of the reaction, the resultant was cooled to room temperature. The resultant sample was transferred to a separating funnel, and 50 mL of water was charged into the funnel. Then, the mixture was extracted with $CH_2Cl_2$. The resultant sample was purified by silica gel column chromatography. The purified product was concentrated to dryness, and was then recrystallized twice, whereby a white powder (Compound 3-85) was obtained. The powder was purified by sublimation, whereby a white solid was obtained in an amount of 1.2 g in 25% yield.

FD-MS $C_{42}H_{24}N_2S_2$: theoretical value 620, observed value 620

An apparatus and measurement conditions adopted for field desorption mass spectrometry (FD-MS) in each of Synthesis Examples 3-1 to 3-12 are shown below.

Apparatus: HX110 (manufactured by JEOL Ltd.)
Conditions: accelerating voltage 8 kV
scan range m/z=50 to 1,500
emitter kind: carbon
emitter current: 0 mA→2 mA/min→40 mA (held for 10 minutes)

Example 3-1

(Production of Organic EL Device)

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound 3-A mentioned below was deposited from the vapor onto the surface of the glass substrate on the side where a transparent electrode line was formed so as to cover the transparent electrode, whereby a hole transporting layer having a thickness of 30 nm was obtained.

Compound 3-1 as a host for phosphorescence and Ir(Ph-ppy)$_3$ as a dopant for phosphorescence were co-deposited from the vapor onto the hole transporting layer, whereby a phosphorescent layer having a thickness of 30 nm was obtained. The concentration of Ir(Ph-ppy)$_3$ was 5 mass %.

Subsequently, Compound 3-B mentioned below having a thickness of 10 nm, Compound 3-C mentioned below having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

[Chem 252]

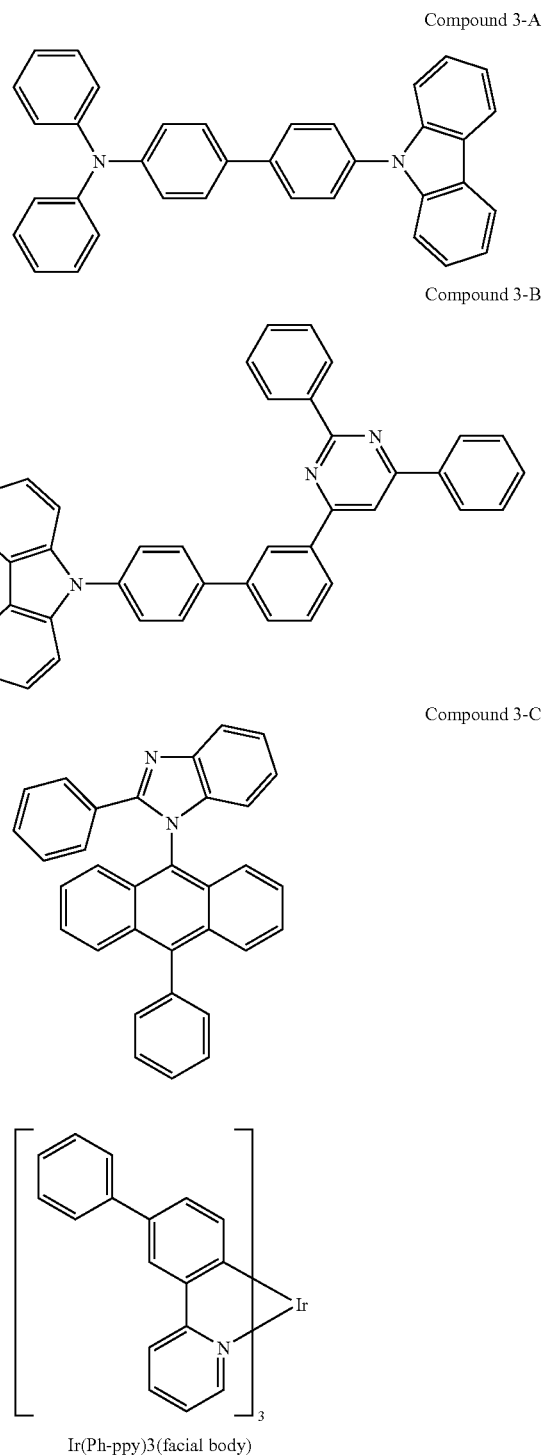

Compound 3-A

Compound 3-B

Compound 3-C

Ir(Ph-ppy)3(facial body)

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 $cd/m^2$ was determined. Further, the lifetime of the device at a luminance of 20,000 $cd/m^2$ was determined. Table 1 shows the results.

Examples 3-2 to 3-12

Organic EL devices were each produced in the same manner as in Example 3-1 except that a host material listed in Table 3 was used instead of Host Compound 3-1 in Example 3-1, and the devices were each evaluated in the same manner as in Example 3-1. Table 3 shows the results of the evaluation for light emitting performance.

Comparative Examples 3-1 and 3-2

Organic EL devices were each produced in the same manner as in Example 3-1 except that the following compounds (3-a) to (3-b) described in EP 0908787 A was used as a host material instead of Host Compound 3-1 in Example 3-1, and the devices were each evaluated in the same manner as in Example 3-1. Table 3 shows the results of the evaluation for light emitting performance.

Comparative Examples 3-3 to 3-5

Organic EL devices were each produced in the same manner as in Example 3-1 except that the following compounds (3-c) to (3-e) described in WO 2006-122630 was used as a host material instead of Host Compound 3-1 in Example 3-1, and the devices were each evaluated in the same manner as in Example 3-1. Table 3 shows the results of the evaluation for light emitting performance.

Comparative Example 3-6

An organic EL device was produced in the same manner as in Example 3-1 except that the following compound (3-f) described in WO 2007-063754 was used as a host material instead of Host Compound in Example 3-1, and the device was evaluated in the same manner as in Example 3-1. Table 3 shows the results of the evaluation for light emitting performance.

[Chem 253]

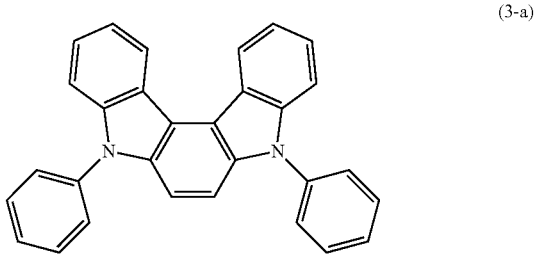

(3-a)

-continued

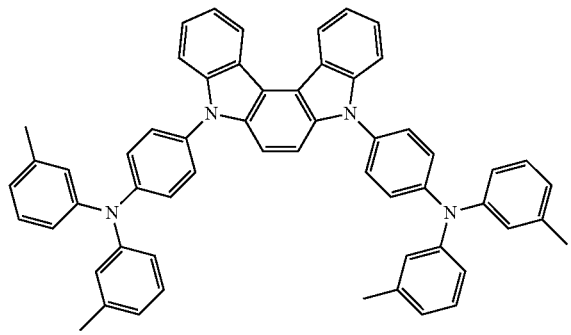
(3-b)

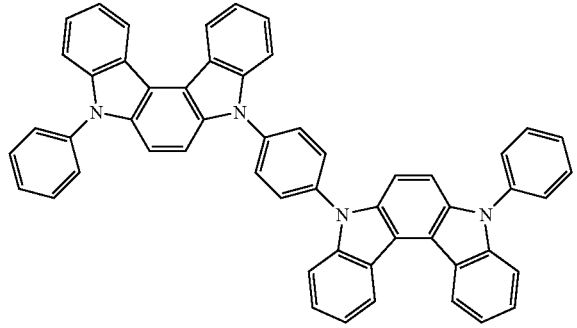
(3-f)

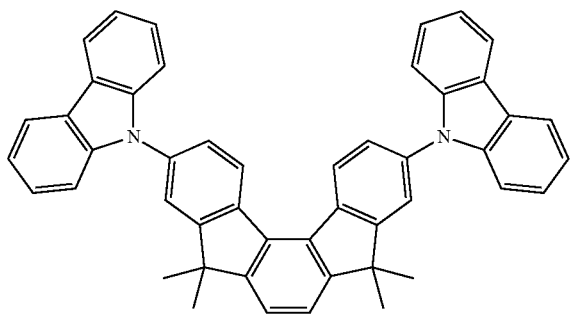
(3-c)

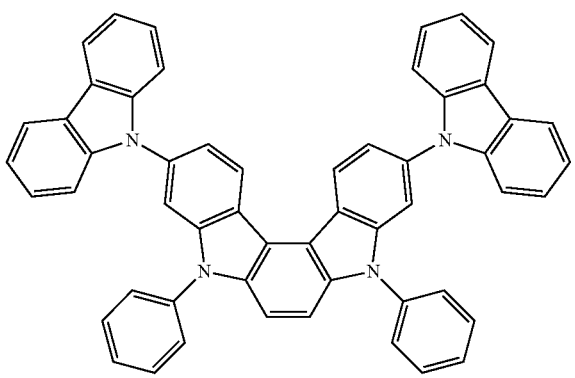
(3-d)

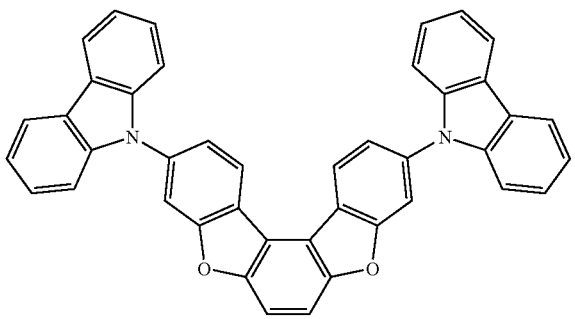
(3-e)

TABLE 3

| | Host compound | Voltage (V) @20 mA/cm² | Efficiency (cd/A) @1,000 cd/m² | Life time (hr) @20,000 cd/m² |
|---|---|---|---|---|
| Example 3-1 | (3-1) | 6.0 | 62.3 | 200 |
| Example 3-2 | (3-17) | 6.2 | 60.5 | 220 |
| Example 3-3 | (3-18) | 6.3 | 63.8 | 250 |
| Example 3-4 | (3-34) | 6.1 | 62.5 | 300 |
| Example 3-5 | (3-46) | 6.0 | 61.5 | 250 |
| Example 3-6 | (3-49) | 5.8 | 59.7 | 230 |
| Example 3-7 | (3-71) | 4.7 | 49.8 | 200 |
| Example 3-8 | (3-73) | 5.7 | 58.1 | 150 |
| Example 3-9 | (3-75) | 4.8 | 50.6 | 180 |
| Example 3-10 | (3-76) | 4.8 | 51.2 | 150 |
| Example 3-11 | (3-79) | 4.8 | 45.3 | 100 |
| Example 3-12 | (3-85) | 5.5 | 53.4 | 120 |
| Comparative Example 3-1 | (3-a) | 4.5 | 23.1 | 50 |
| Comparative Example 3-2 | (3-b) | 4.5 | 14.4 | 10 |
| Comparative Example 3-3 | (3-c) | 4.8 | 34.1 | 70 |
| Comparative Example 3-4 | (3-d) | 4.8 | 17.6 | 70 |
| Comparative Example 3-5 | (3-e) | 6.1 | 40.1 | 80 |
| Comparative Example 3-6 | (3-f) | 4.9 | 17.9 | 45 |

Example 4-1

(Production of Organic EL Device)

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound 4-A was deposited from the vapor onto the surface of the glass substrate on the side where a transparent electrode line was formed so as to cover the transparent electrode, whereby a hole transporting layer having a thickness of 30 nm was obtained.

(4-62) as a host for phosphorescence and Ir(Ph-ppy)3 as a dopant for phosphorescence were co-deposited from the vapor onto the hole transporting layer, whereby a phosphorescent layer having a thickness of 30 nm was obtained. The concentration of Ir(Ph-ppy)3 was 10 mass %.

Subsequently, Compound (1-191) having a thickness of 10 nm, Compound 4-C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (cd/A) of the device at a luminance of 1,000 cd/m² was determined. Further, the lifetime of the device at a luminance of 20,000 cd/m² was determined. Table 4 shows the results.

Examples 4-2 and 4-3

Organic EL devices were each produced in the same manner as in Example 4-1 except that a host material listed in Table 4 was used instead of Host Compound (4-62) in Example 4-1, and the devices were each evaluated in the same manner as in Example 4-1. Table 4 shows the results of the evaluation for light emitting performance.

Comparative Example 4-1

An organic EL device was produced in the same manner as in Example 4-1 except that: CBP was used instead of Host Compound (4-62) in Example 4-1; and BAlq was used instead of Electron Transportable Compound (1-191) in Example 4-1. Then, the device was evaluated in the same manner as in Example 4-1. Table 4 shows the results of the evaluation for light emitting performance.

[Chem 254]

Compound 4-A

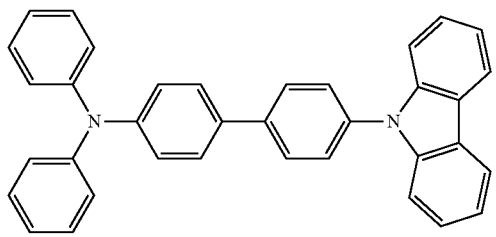

Compound 4-B

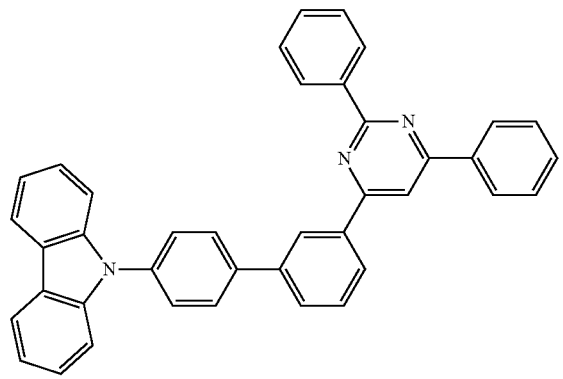

Compound 4-C

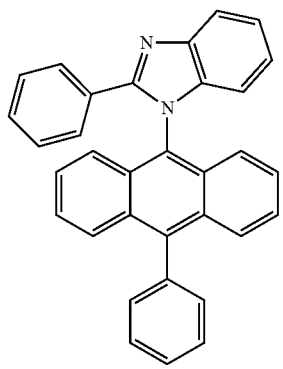

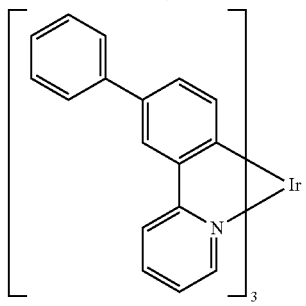

Ir(Ph-ppy)3(facial body)

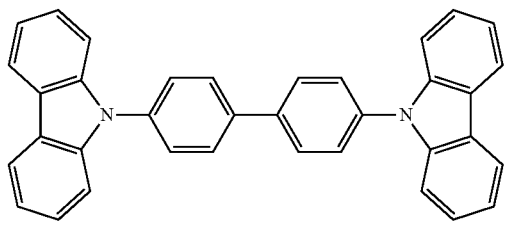

CBP

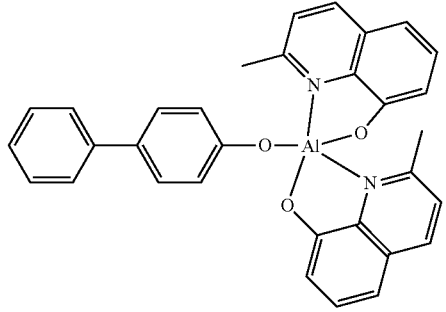

BAlq

TABLE 4

| | Host compound | Electron transportable compound | Voltage (V) @20 mA/cm² | Efficiency (cd/A) @1,000 cd/m² | Lifetime (hr) @20,000 cd/m² |
|---|---|---|---|---|---|
| Example 4-1 | (4-62) | (1-191) | 4.5 | 64.9 | 580 |
| Example 4-2 | (4-1) | (1-191) | 4.0 | 63.7 | 600 |
| Example 4-3 | CBP | (1-191) | 5.1 | 45.1 | 120 |
| Comparative Example 4-1 | CBP | BAlq | 6.5 | 45.1 | 30 |

Each of the organic EL devices of the comparative examples showed a lower current efficiency, was driven at a higher voltage, and had a shorter lifetime than those of each of the organic EL devices of the examples.

INDUSTRIAL APPLICABILITY

As described above in detail, the utilization of the polycyclic compound of the present invention represented in the general formula (1) or (2) can provide an organic EL device which shows high luminous efficiency, is free of any pixel defect, and has a long lifetime. Accordingly, the organic EL device of the present invention is extremely useful as, for example, a light source for various electronic instruments. In addition, the material can be effectively used also as a material for an organic electron device, and is extremely useful in an organic solar cell, organic semiconductor laser, a sensor using organic matter, or an organic TFT.

The invention claimed is:

1. A polycyclic compound represented by the following general formulae (7) or (8):

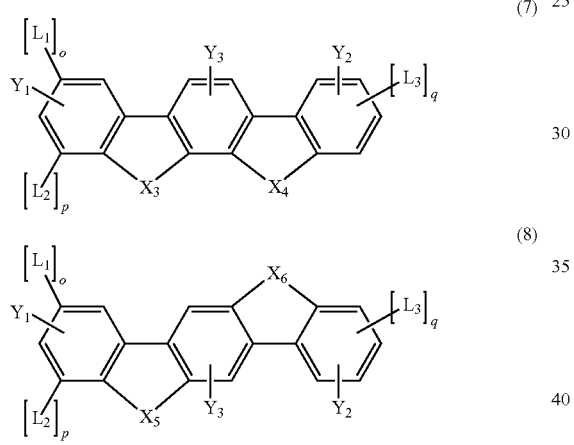

(7)

(8)

where:

X$_3$, X$_4$, X$_5$, and X$_6$ each independently represent oxygen (O), sulfur (S), or N—R$_1$, R$_1$ represents a substituted or unsubstituted alkyl group having 1 to 20 carbon atoms, a substituted or unsubstituted cycloalkyl group having 3 to 20 carbon atoms forming the ring, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both X$_3$ and X$_4$ or both X$_5$ and X$_6$ represent N—R$_1$, at least one R$_1$ represents a substituted or unsubstituted monovalent fused aromatic heterocyclic group having 8 to 24 atoms forming the aromatic ring;

o, p, and q each independently represent 0 or 1, provided that o+p is 1 or more;

L$_1$, L$_2$, and L$_3$ each independently represent a structure which is selected from the following formulae (21) to (39) and may have a substituent:

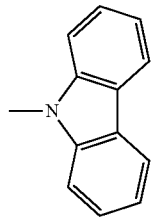

(21)

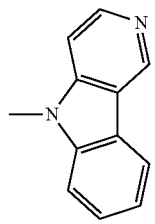

(22)

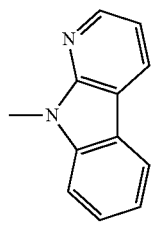

(23)

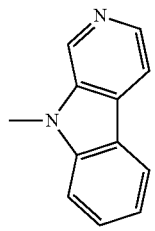

(24)

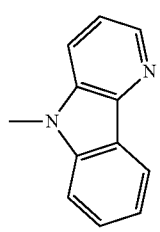

(25)

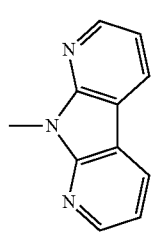

(26)

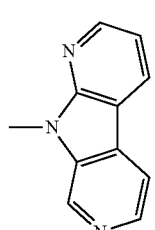

(27)

-continued

(28) 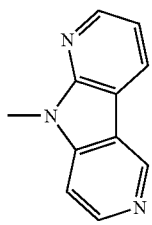

(29) 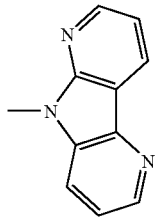

(30) 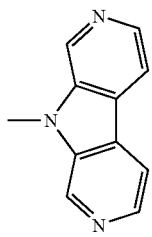

(31) 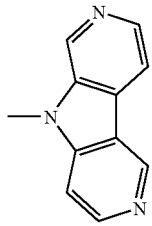

(32) 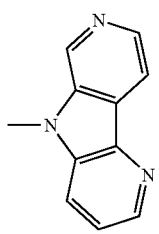

(33) 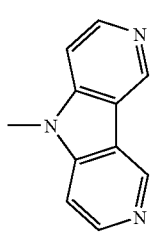

(34) 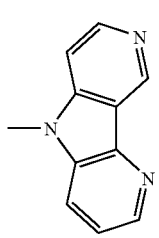

(35) 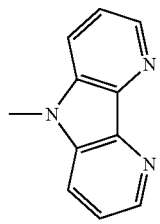

(36) 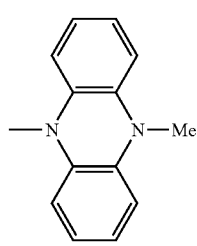

(37) 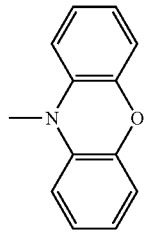

(38) 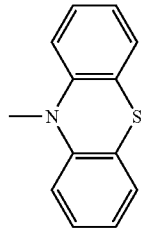

(39) 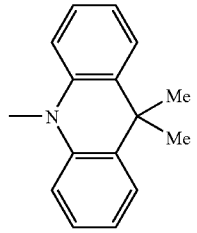

and $Y_1$, $Y_2$, and $Y_3$ each independently represent a substituted or unsubstituted alkyl group having 1 to 20 carbon atoms, a substituted or unsubstituted cycloalkyl group having 3 to 20 carbon atoms forming the ring, a substituted or unsubstituted alkoxy group having 1 to 20 carbon atoms, a substituted or unsubstituted aralkyl group having 7 to 24 carbon atoms, a substituted or unsubstituted organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring which is bonded with a carbon atom, a number of $Y_1$'s is 0, 1, 2, or 3, a number of $Y_2$'s is 0, 1, 2, 3, or 4, and a number of $Y_3$'s is 0, 1, or 2.

2. The polycyclic compound according to claim 1, which is represented by any one of the following general formulae (7-1), (7-2), (8-1), and (8-2):

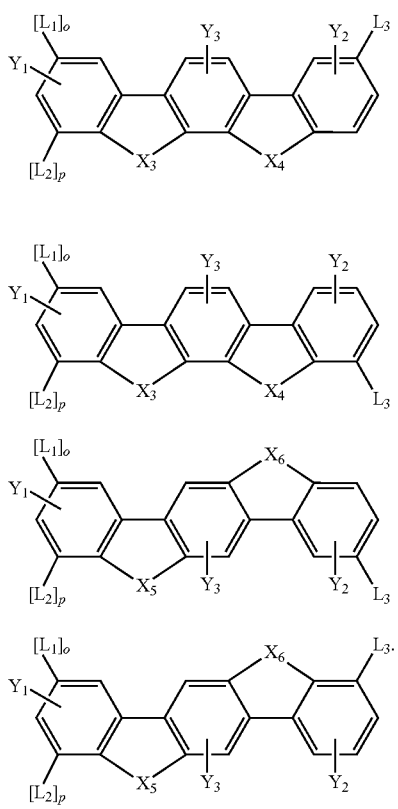

(7-1)

(7-2)

(8-1)

(8-2)

3. The polycyclic compound according to claim 1, which is represented by the following general formula (19):

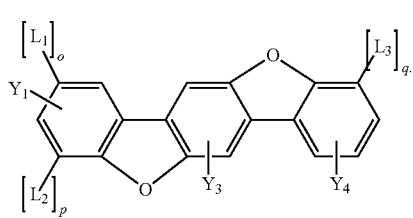

(19)

4. The polycyclic compound according to claim 1, wherein a total number of substituents represented by $Y_1$, $Y_2$, and $Y_3$ in the general formulae (7) and (8) is 2 or less.

5. The polycyclic compound according to claim 1, wherein a number of substituents represented by $Y_1$ and $Y_2$ in the general formulae (7) and (8) is 0.

6. The polycyclic compound according to claim 1, wherein a number of substituents represented by $Y_3$ in the general formulae (7) and (8) is 0.

7. The polycyclic compound according to claim 1, wherein o+p+q is 2 or less in the general formulae (7) and (8).

8. The polycyclic compound according to claim 1, wherein o+p is 1 in the general formulae (7) and (8).

9. The polycyclic compound according to claim 1, wherein both $X_3$ and $X_4$ or $X_5$ and $X_6$ represent N—$R_1$ in the general formulae (7) and (8).

10. The polycyclic compound according to claim 1, wherein both $X_3$ and $X_4$ represent N—$R_1$ in the general formula (7) and both $R_1$'s represent substituted or unsubstituted fused aromatic heterocycles each having 8 to 24 atoms forming the aromatic ring, and both $X_5$ and $X_6$ represent N—$R_1$ in the general formula (8) and both $R_1$'s represent substituted or unsubstituted fused aromatic heterocycles each having 8 to 24 atoms forming the aromatic ring.

11. The polycyclic compound according to claim 1, wherein $X_3$ and $X_4$ or $X_5$ and $X_6$ each represent N—$R_1$ in the general formulae (7) and (8) and N—$R_1$ of $X_3$ and N—$R_1$ of $X_4$ or N—$R_1$ of $X_5$ and N—$R_1$ of $X_6$ are different from each other.

12. The polycyclic compound according to claim 1, wherein at least one of $X_3$ and $X_4$ in the general formula (7) represents an oxygen atom, and at least one of $X_5$ and $X_6$ in the general formula (8) represents an oxygen atom.

13. The polycyclic compound according to claim 12, wherein both $X_3$ and $X_4$ or both $X_5$ and $X_6$ in the general formulae (7) and (8) represent oxygen atoms.

14. An organic electroluminescence device, comprising one or more organic thin film layers containing a light emitting layer between a cathode and an anode, wherein at least one of the organic thin film layers contains the polycyclic compound according to claim 1.

15. The organic electroluminescence device according to claim 14, wherein the light emitting layer contains the polycyclic compound as a host material.

16. The organic electroluminescence device according to claim 14, wherein the light emitting layer further contains a phosphorescent material.

17. The organic electroluminescence device according to claim 14, wherein the light emitting layer contains a host material and a phosphorescent material, and the phosphorescent material comprises an orthometalated complex of an iridium (Ir), osmium (Os), or platinum (Pt) metal.

18. The organic electroluminescence device according to claim 14, further comprising an electron injecting layer between the light emitting layer and the cathode, wherein the electron injecting layer contains a nitrogen-containing ring derivative.

19. The organic electroluminescence device according to claim 14, further comprising an electron transporting layer between the light emitting layer and the cathode, wherein the electron transporting layer contains the polycylic compound.

20. The organic electroluminescence device according to claim 14, further comprising a hole transporting layer between the light emitting layer and the anode, wherein the hole transporting layer contains the polycyclic compound.

21. The organic electroluminescence device according to claim 14, further comprising a reducing dopant at an interfacial region between the cathode and the organic thin film layer.

22. The organic electroluminescence device according to claim 19, wherein the light emitting layer includes a material for an organic electroluminescence device which is a compound having a π-conjugated heteroacene skeleton crosslinked with a carbon atom, a nitrogen atom, an oxygen atom, or a sulfur atom as a host material.

23. The organic electroluminescence device according to claim 19, wherein the light emitting layer contains, as a host material, a material for an organic electroluminescence device represented by any one of the following general formulae (40) to (43):

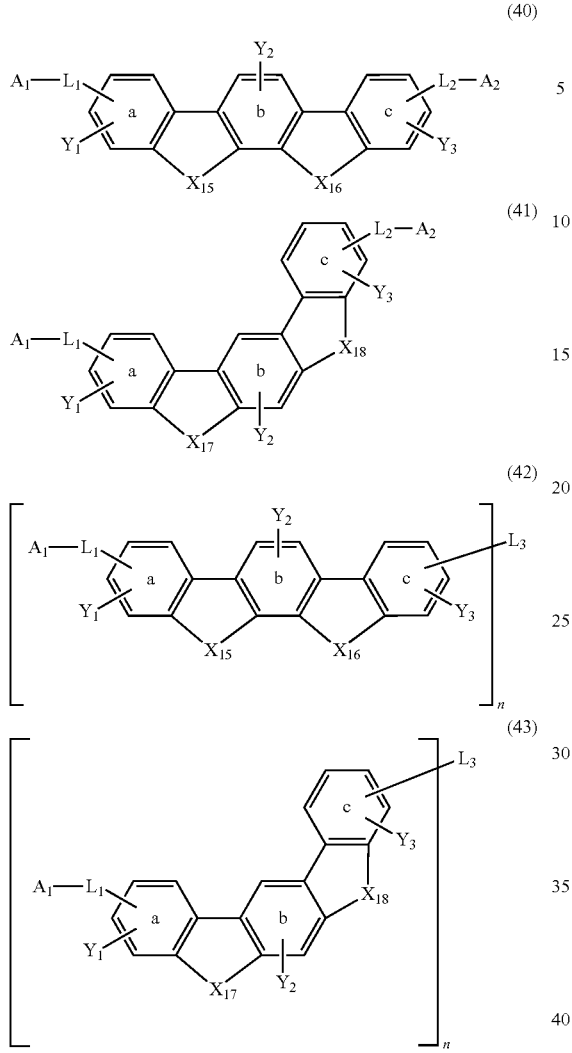

where:
- $X_{15}$, $X_{16}$, $X_{17}$, and $X_{18}$ each independently represent oxygen (O), sulfur (S), N—$R_1$, or $CR_2R_3$, $R_1$, $R_2$, and $R_3$ each independently represent an alkyl group having 1 to 20 carbon atoms, a substituted or unsubstituted cycloalkyl group having 3 to 20 carbon atoms forming the ring, an aralkyl group having 7 to 24 carbon atoms, an organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group having 3 to 24 atoms forming the aromatic ring, provided that when both $X_{15}$ and $X_{16}$ or both $X_{17}$ and $X_{18}$ represent N—$R_1$, at least one $R_1$ represents a substituted or unsubstituted monovalent fused aromatic heterocyclic group having 8 to 24 atoms forming the aromatic ring;
- n represents 2, 3, or 4, and the material comprises a dimer using $L_3$ as a linking group for n=2, a trimer using $L_3$ as a linking group for n=3, or a tetramer using $L_3$ as a linking group for n=4;
- $L_1$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring a through a carbon-carbon bond;
- $L_2$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring c through a carbon-carbon bond, provided that when both $X_{15}$ and $X_{16}$ or both $X_{17}$ and $X_{18}$ represent $CR_2R_3$ and both $L_1$ and $L_2$ represent substituted or unsubstituted divalent aromatic hydrocarbon groups having 6 to 24 carbon atoms forming the aromatic ring, a case where $L_1$ and $L_2$ are simultaneously linked at para position with respect to a benzene ring b is excluded;
- when n represents 2, $L_3$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with the benzene ring c through a carbon-carbon bond, when n represents 3, $L_3$ represents an alkanetriyl group having 1 to 20 carbon atoms, a substituted or unsubstituted cycloalkanetriyl group having 3 to 20 carbon atoms forming the ring, a trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group which has 3 to 24 atoms and which is linked with the benzene ring c through a carbon-carbon bond, and when n represents 4, $L_3$ represents an alkanetetrayl group having 1 to 20 carbon atoms, a substituted or unsubstituted cycloalkanetetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group which has 3 to 24 atoms forming the aromatic ring and which is linked with the benzene ring c through a carbon-carbon bond, provided that when both $X_{15}$ and $X_{16}$ or both $X_{17}$ and $X_{18}$ represent $CR_2R_3$ and both $L_1$ and $L_3$ represent substituted or unsubstituted divalent, trivalent, or tetravalent aromatic hydrocarbon groups having 6 to 24 carbon atoms forming the aromatic ring, a case where $L_1$ and $L_3$ are simultaneously linked at para position with respect to the benzene ring b is excluded;
- $A_1$ represents a hydrogen atom, a substituted or unsubstituted cycloalkyl group having 3 to 20 carbon atoms forming the ring, an organsilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_1$ through a carbon-carbon bond, provided that when $L_1$ represents an alkyl or alkylene group having 1 to 20 carbon atoms, a case where $A_1$ represents a hydrogen atom is excluded;

$A_2$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_2$ through a carbon-carbon bond, provided that when $L_2$ represents an alkyl or alkylene group having 1 to 20 carbon atoms, a case where $A_2$ represents a hydrogen atom is excluded;

$Y_1$, $Y_2$, and $Y_3$ each represent an alkyl group having 1 to 20 carbon atoms, a substituted or unsubstituted cycloalkyl group having 3 to 20 carbon atoms forming the ring, an alkoxy group having 1 to 20 carbon atoms, an aralkyl group having 7 to 24 carbon atoms, an organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group which has 3 to 24 atoms forming the aromatic ring and which is linked with the benzene ring a, b, or c through a carbon-carbon bond, a number of each of $Y_1$ and $Y_3$ is 0, 1, 2, or 3, and a number of $Y_2$ is 0, 1, or 2, provided that when both $X_{15}$ and $X_{16}$ or both $X_{17}$ and $X_{18}$ represent oxygen (O), sulfur (S), or $CR_2R_3$, both $L_1$ and $L_2$ represent single bonds, and both $A_1$ and $A_2$ represent hydrogen atoms, a case where a benzene ring b has one or two $Y_2$'s, which represent a methyl group or an unsubstituted phenyl group is excluded; and $A_1$, $A_2$, $L_1$, $L_2$, and $L_3$ are each free of any carbonyl group.

24. The organic electroluminescence device according to claim 19, wherein the light emitting layer contains, as a host material, a material for an organic electroluminescence device represented by any one of the following general formulae (44) to (47):

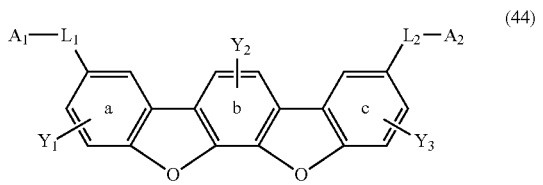
(44)

(45)

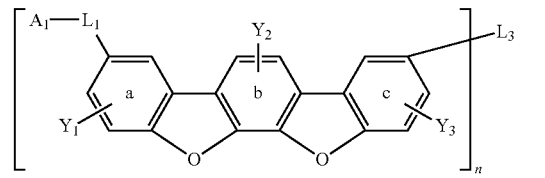
(46)

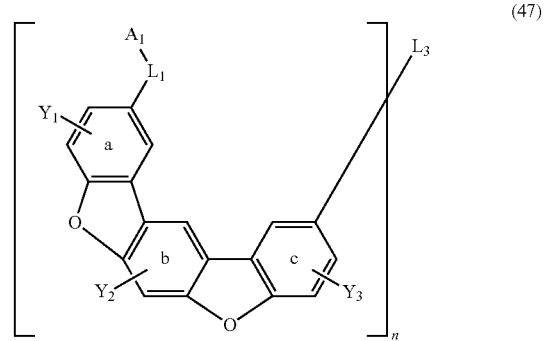
(47)

where:
n represents 2, 3, or 4, and the material comprises a dimer using $L_3$ as a linking group for n=2, a trimer using $L_3$ as a linking group for n=3, or a tetramer using $L_3$ as a linking group for n=4;

$L_1$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring a through a carbon-carbon bond;

$L_2$ represents a single bond, an alkylene group having 1 to 20 carbon atoms, a substituted or unsubstituted cycloalkylene group having 3 to 20 carbon atoms forming the ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with a benzene ring c through a carbon-carbon bond;

when n represents 2, $L_3$ represents a single bond, an alkylene group having 1 to 20 carbon atoms, a substituted or unsubstituted cycloalkylene group having 3 to 20 carbon atoms forming the aromatic ring, a divalent organosilyl group having 2 to 20 carbon atoms which is bonded with a silicon atom, a substituted or unsubstituted divalent aromatic hydrocarbon group having 6 to 24 carbon atoms forming the aromatic ring, or a substituted or unsubstituted divalent aromatic heterocyclic group which has 3 to 24 atoms forming the aromatic ring and which is linked with the benzene ring c through a carbon-carbon bond, when n represents 3, $L_3$ represents an alkanetriyl group having 1 to 20 carbon atoms, a substituted or unsubstituted cycloalkanetriyl group having 3 to 20 carbon atoms forming the ring, a trivalent organosilyl group having 1 to 20 carbon atoms which is bonded with a silicon atom, a substituted or unsubstituted trivalent aromatic hydrocarbon group having 6 to 24 carbon atoms forming the aromatic ring, or a substituted or unsubstituted trivalent aromatic heterocyclic group which has 3 to 24 atoms and which is linked with the benzene ring c through a carbon-carbon bond, or when n represents 4, $L_3$ represents an alkanetetrayl group having 1 to 20 carbon atoms, a substituted or unsubstituted cycloalkanetetrayl group having 3 to 20 carbon atoms forming the ring, a silicon atom, a substituted or unsubstituted tetravalent aromatic hydrocarbon group having 6 to 24 carbon atoms forming the aromatic ring, or a substituted or unsubstituted tetravalent aromatic heterocyclic group which has 3 to 24 atoms forming the aromatic ring and which is linked with the benzene ring c through a carbon-carbon bond;

$A_1$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_1$ through a carbon-carbon bond, provided that when $L_1$ represents an alkyl or alkylene group having 1 to 20 carbon atoms, a case where $A_1$ represents a hydrogen atom is excluded;

$A_2$ represents a hydrogen atom, a substituted or unsubstituted cycloalkyl group having 3 to 20 carbon atoms forming the ring, an organosilyl group having 3 to 20 carbon atoms, a substituted or unsubstituted aromatic hydrocarbon group having 6 to 24 carbon atoms forming the aromatic ring, or an aromatic heterocyclic group which has 3 to 24 atoms forming the aromatic ring and which is linked with $L_2$ through a carbon-carbon bond, provided that when $L_2$ represents an alkyl or alkylene group having 1 to 20 carbon atoms, a case where $A_2$ represents a hydrogen atom is excluded;

$Y_1$, $Y_2$, and $Y_3$ each represent an alkyl group having 1 to 20 carbon atoms, a substituted or unsubstituted cycloalkyl group having 3 to 20 carbon atoms forming the ring, an alkoxy group having 1 to 20 carbon atoms, an aralkyl group having 7 to 24 carbon atoms, an organosilyl group having 3 to 20 carbon atoms, a substituted or unsubstituted aromatic hydrocarbon group having 6 to 24 carbon atoms forming the aromatic ring, or a substituted or unsubstituted aromatic heterocyclic group which has 3 to 24 atoms forming the aromatic ring and which is linked with the benzene ring a, b, or c through a carbon-carbon bond, a number of each of $Y_1$ and $Y_3$ is 0, 1, 2, or 3, and a number of $Y_2$ is 0, 1, or 2, provided that when both $L_1$ and $L_2$ represent single bonds, and both $A_1$ and $A_2$ represent hydrogen atoms, a case where a benzene ring b has one or two $Y_2$'s, which represent a methyl group or an unsubstituted phenyl group is excluded; and $A_1$, $A_2$, $L_1$, $L_2$, and $L_3$ are each free of any carbonyl group.

* * * * *